US006262334B1

(12) United States Patent
Endege et al.

(10) Patent No.: US 6,262,334 B1
(45) Date of Patent: Jul. 17, 2001

(54) HUMAN GENES AND EXPRESSION PRODUCTS: II

(75) Inventors: Wilson O. Endege, Norwood; Kathleen E. Steinmann, Winchester; Jon H. Astle, Taunton; Christopher C. Burgess, Westwood; Eddie Carroll, III, Norwood; Theodore J. Catino, Attleboro; Poornima Dwivedi, Medfield; Donna M. Ford, Plainville; Marcia E. Lewis, Cohasset; Gary A. Molino, Norfolk; John E. Monahan, Walpole; Robert Schlegel, Auburndale, all of MA (US)

(73) Assignee: Bayer Corporation, East Walpole, MA (US)

( * ) Notice: Subject to any disclaimer, the term of this patent is extended or adjusted under 35 U.S.C. 154(b) by 0 days.

(21) Appl. No.: 09/385,982

(22) Filed: Aug. 30, 1999

Related U.S. Application Data

(63) Continuation-in-part of application No. 09/328,111, filed on Jun. 8, 1999.

(60) Provisional application No. 60/117,393, filed on Jan. 27, 1999, and provisional application No. 60/098,639, filed on Aug. 31, 1998.

(51) Int. Cl.[7] .......................... A01K 67/00; C07H 21/02; C07H 21/04; C12N 15/00

(52) U.S. Cl. ................................ 800/8; 800/13; 536/23.1; 536/24.1; 435/320.1; 514/44

(58) Field of Search ................................ 536/23.1, 24.1; 435/320.1; 514/44; 800/13

(56) References Cited

U.S. PATENT DOCUMENTS

| | | | | |
|---|---|---|---|---|
| 4,824,776 | * | 4/1989 | Heller | 435/6 |
| 5,648,478 | * | 7/1997 | Henderson | 536/241 |
| 5,686,240 | * | 11/1997 | Schuchman et al. | 435/6 |

OTHER PUBLICATIONS

Hillier et al, "Generation and analysis of 280,000 human expressed sequence tags", Genome Research, vol. 6, No.9, 1996, pp. 807–828.*

Marra M et al, vd25a10.s1 Knowles Solter mouse 2 cell Mus musculus cDNA clone, GenCore version 4.5, Accession AA415444, The WashU–HHMI Mouse EST project, Oct. 16, 1997.*

Tanaka et al, "Construction of a normalized directionally cloned cDNA library from adult heart and analysis of 3040 clones by partial sequencing", Genomics 35, 1996, pp. 231–235.*

* cited by examiner

*Primary Examiner*—John S. Brusca
*Assistant Examiner*—Stephen Siu
(74) *Attorney, Agent, or Firm*—Palmer & Dodge LLP

(57) ABSTRACT

This invention relates to novel human genes, to proteins expressed by the genes, and to variants of the proteins. The invention also relates to diagnostic assays and therapeutic agents related to the genes and proteins, including probes, antisense constructs, and antibodies. The subject nucleic acids have been found to be differentially regulated in tumor cells, particularly in colon cancer tissue.

15 Claims, 1 Drawing Sheet

Differential Expression Analysis

HUMAN GENES AND EXPRESSION PRODUCTS: II

RELATED APPLICATION INFORMATION

This application is based on Provisional Application Nos. 60/117,393, filed Jan. 27, 1999, and 60/098,639, filed Aug. 31, 1998, which are incorporated herein by reference in their entirety. This application is a continuation-in-part of application Ser. No. 09/328,111, filed on Jun. 8, 1999, which is incorporated by reference herein, in its entirety.

FIELD OF THE INVENTION

The present invention provides nucleic acid sequences and proteins encoded thereby, as well as probes derived from the nucleic acid sequences, antibodies directed to the encoded proteins, and diagnostic methods for detecting cancerous cells, especially colon cancer cells.

BACKGROUND OF THE INVENTION

Colorectal carcinoma is a malignant neoplastic disease. There is a high incidence of colorectal carcinoma in the Western world, particularly in the United States. Tumors of this type often metastasize through lymphatic and vascular channels. Many patients with colorectal carcinoma eventually die from this disease. In fact, it is estimated that 62,000 persons in the United States alone die of colorectal carcinoma annually.

However, if diagnosed early, colon cancer may be treated effectively by surgical removal of the cancerous tissue. Colorectal cancers originate in the colorectal epithelium and typically are not extensively vascularized (and therefore not invasive) during the early stages of development. Colorectal cancer is thought to result from the clonal expansion of a single mutant cell in the epithelial lining of the colon or rectum. The transition to a highly vascularized, invasive and ultimately metastatic cancer which spreads throughout the body commonly takes ten years or longer. If the cancer is detected prior to invasion, surgical removal of the cancerous tissue is an effective cure. However, colorectal cancer is often detected only upon manifestation of clinical symptoms, such as pain and black tarry stool. Generally, such symptoms are present only when the disease is well established, often after metastasis has occurred, and the prognosis for the patient is poor, even after surgical resection of the cancerous tissue. Early detection of colorectal cancer therefore is important in that detection may significantly reduce its morbidity.

Invasive diagnostic methods such as endoscopic examination allow for direct visual identification, removal, and biopsy of potentially cancerous growths such as polyps. Endoscopy is expensive, uncomfortable, inherently risky, and therefore not a practical tool for screening populations to identify those with colorectal cancer. Non-invasive analysis of stool samples for characteristics indicative of the presence of colorectal cancer or precancer is a preferred alternative for early diagnosis, but no known diagnostic method is available which reliably achieves this goal. A reliable, non-invasive, and accurate technique for diagnosing colon cancer at an early stage would help save many lives.

SUMMARY OF THE INVENTION

The present invention provides nucleic acid sequences and proteins encoded thereby, as well as probes derived from the nucleic acid sequences, antibodies directed to the encoded proteins, and diagnostic methods for detecting cancerous cells, especially colon cancer cells. The sequences disclosed herein have been found to be differentially expressed in samples obtained from colon cancer cell lines and/or colon cancer tissue. The 544 sequences that were obtained were analyzed by "blasting" the sequences against the publicly available databases; based upon the Blast search results it was found that SEQ ID Nos: 1–35 contained novel sequences, SEQ ID Nos: 36–168 contained EST sequences and SEQ ID Nos: 169–544 contained known sequences.

In one aspect, the invention provides an isolated nucleic acid comprising a nucleotide sequence which hybridizes under stringent conditions to a sequence of SEQ ID Nos. 1–544 or a sequence complementary thereto. In a related embodiment, the nucleic acid is at least about 80% or about 100% identical to a sequence corresponding to at least about 12, at least about 15, at least about 25, or at least about 40 consecutive nucleotides up to the full length of one of SEQ ID Nos. 1–544 or a sequence complementary thereto or up to the full length of the gene of which said sequence is a fragment. In certain embodiments, a nucleic acid of the present invention includes at least about five, at least about ten, or at least about twenty nucleic acids from a region designated as novel in Table 2. In certain other embodiments, a nucleic acid of the present invention includes at least about five, at least about ten, or at least about twenty nucleotides which are not included in corresponding clones whose accession numbers are listed in Table 2.

In another aspect, the invention provides an isolated nucleic acid comprising a nucleotide sequence which hybridizes under stringent conditions to a sequence of SEQ ID Nos. 1–168, preferably SEQ ID Nos. 1–35, or a sequence complementary thereto. In a related embodiment, the nucleic acid is at least about 80% or about 100% identical to a sequence corresponding to at least about 12, at least about 15, at least about 25, or at least about 40 consecutive nucleotides up to the full length of one of SEQ ID Nos. 1–168, preferably SEQ ID Nos. 1–35 or a sequence complementary thereto or up to the full length of the gene of which said sequence is a fragment. In certain embodiments, a nucleic acid of the present invention includes at least about five, at least about ten, or at least about twenty nucleic acids from a region designated as novel in Table 2. In certain other embodiments, a nucleic acid of the present invention includes at least about five, at least about ten, or at least about twenty nucleotides which are not included in corresponding clones whose accession numbers are listed in Table 2.

In one embodiment, the invention provides a nucleic acid comprising a nucleotide sequence which hybridizes under stringent conditions to a sequence of SEQ ID Nos. 1–168, preferably SEQ ID Nos. 1–35, or a sequence complementary thereto, and a transcriptional regulatory sequence operably linked to the nucleotide sequence to render the nucleotide sequence suitable for use as an expression vector. In another embodiment, the nucleic acid may be included in an expression vector capable of replicating in a prokaryotic or eukaryotic cell. In a related embodiment, the invention provides a host cell transfected with the expression vector.

In another embodiment, the invention provides a transgenic animal having a transgene of a nucleic acid comprising a nucleotide sequence which hybridizes under stringent conditions to a sequence of SEQ ID Nos. 1–168, preferably SEQ ID Nos 1–35, or a sequence complementary thereto incorporated in cells thereof. The transgene modifies the level of expression of the nucleic acid, the stability of a mRNA transcript of the nucleic acid, or the activity of the encoded product of the nucleic acid.

In yet another embodiment, the invention provides substantially pure nucleic acid which hybridizes under stringent conditions to a nucleic acid probe corresponding to at least about 12, at least about 15, at least about 25, or at least about 40 consecutive nucleotides up to the full length of one of SEQ ID Nos. 1–168, preferably SEQ ID Nos 1–35, or a sequence complementary thereto or up to the fill length of the gene of which said sequence is a fragment. The invention also provides an antisense oligonucleotide analog which hybridizes under stringent conditions to at least 12, at least 25, or at least 50 consecutive nucleotides of one of SEQ ID Nos. 1–544 up to the full length of one of SEQ ID Nos. 1–544 or a sequence complementary thereto or up to the full length of the gene of which said sequence is a fragment, and which is resistant to cleavage by a nuclease, preferably an endogenous endonuclease or exonuclease.

In another embodiment, the invention provides a probe/primer comprising a substantially purified oligonucleotide, said oligonucleotide containing a region of nucleotide sequence which hybridizes under stringent conditions to at least about 12, at least about 15, at least about 25, or at least about 40 consecutive nucleotides of sense or antisense sequence selected from SEQ ID Nos. 1–168 up to the full length of one of SEQ ID Nos. 1–168 or a sequence complementary thereto or up to the full length of the gene of which said sequence is a fragment. In preferred embodiments, the probe selectively hybridizes with a target nucleic acid. In another embodiment, the probe may include a label group attached thereto and able to be detected. The label group may be selected from radioisotopes, fluorescent compounds, enzymes, and enzyme co-factors. The invention further provides arrays of at least about 10, at least about 25, at least about 50, or at least about 100 different probes as described above attached to a solid support.

In yet another embodiment, the invention pertains to a method of determining the phenotype of a cell, comprising detecting the differential expression, relative to a normal cell, of at least one nucleic acid which hybridizes under stringent conditions to one of SEQ ID Nos. 1–544, wherein the nucleic acid is differentially expressed by at least a factor of two, at least a factor of five, at least a factor of twenty, or at least a factor of fifty.

In another aspect, the invention provides polypeptides encoded by the subject nucleic acids. In one embodiment, the invention pertains to a polypeptide including an amino acid sequence encoded by a nucleic acid comprising a nucleotide sequence which hybridizes under stringent conditions to a sequence of SEQ ID Nos. 1–168 or a sequence complementary thereto, or a fragment comprising at least about 25, or at least about 40 amino acids thereof. Further provided are antibodies immunoreactive with these polypeptides.

In still another aspect, the invention provides diagnostic methods. In one embodiment, the invention pertains to a method for determining the phenotype of cells from a patient by providing a nucleic acid probe comprising a nucleotide sequence having at least 12, at least about 15, at least about 25, or at least about 40 consecutive nucleotides represented in a sequence of SEQ ID Nos. 1–544 up to the full length of one of SEQ ID Nos. 1–544 or a sequence complementary thereto or up to the full length of the gene of which said sequence is a fragment, obtaining a sample of cells from a patient, providing a second sample of cells substantially all of which are non-cancerous, contacting the nucleic acid probe under stringent conditions with mRNA of each of said first and second cell samples, and comparing (a) the amount of hybridization of the probe with mRNA of the first cell sample, with (b) the amount of hybridization of the probe with mRNA of the second cell sample, wherein a difference of at least a factor of two, at least a factor of five, at least a factor of twenty, or at least a factor of fifty in the amount of hybridization with the mRNA of the first cell sample as compared to the amount of hybridization with the mRNA of the second cell sample is indicative of the phenotype of cells in the first cell sample. Determining the phenotype includes determining the genotype, as the term is used herein.

In another embodiment, the invention provides a test kit for identifying an transformed cells, comprising a probe/primer as described above, for measuring a level of a nucleic acid which hybridizes under stringent conditions to a nucleic acid of SEQ ID Nos. 1–544 in a sample of cells isolated from a patient. In certain embodiments, the kit may further include instructions for using the kit, solutions for suspending or fixing the cells, detectable tags or labels, solutions for rendering a nucleic acid susceptible to hybridization, solutions for lysing cells, or solutions for the purification of nucleic acids.

In another embodiment, the invention provides a method of determining the phenotype of a cell, comprising detecting the differential expression, relative to a normal cell, of at least one protein encoded by a nucleic acid which hybridizes under stringent conditions to one of SEQ ID Nos. 1–544, wherein the protein is differentially expressed by at least a factor of two, at least a factor of five, at least a factor of twenty, or at least a factor of fifty. In one embodiment, the level of the protein is detected in an immunoassay. The invention also pertains to a method for determining the presence or absence of a nucleic acid which hybridizes under stringent conditions to one of SEQ ID Nos. 1–168 in a cell, comprising contacting the cell with a probe as described above. The invention further provides a method for determining the presence or absence of a subject polypeptide encoded by a nucleic acid which hybridizes under stringent conditions to one of SEQ ID Nos. 1–168 in a cell, comprising contacting the cell with an antibody as described above. In yet another embodiment, the invention provides a method for determining the presence of an aberrant mutation (e.g., deletion, insertion, or substitution of nucleic acids) or aberrant methylation in a gene which hybridizes under stringent conditions to a sequence of SEQ ID Nos. 1–168 or a sequence complementary thereto, comprising collecting a sample of cells from a patient, isolating nucleic acid from the cells of the sample, contacting the nucleic acid sample with one or more primers which specifically hybridize to a nucleic acid sequence of SEQ ID Nos. 1–544 under conditions such that hybridization and amplification of the nucleic acid occurs, and comparing the presence, absence, or size of an amplification product to the amplification product of a normal cell.

In one embodiment, the invention provides a test kit for identifying transformed cells, comprising an antibody specific for a protein encoded by a nucleic acid which hybridizes under stringent conditions to any one of SEQ Nos. 1–544. In certain embodiments, the kit further includes instructions for using the kit. In certain embodiments, the kit may further include instructions for using the kit, solutions for suspending or fixing the cells, detectable tags or labels, solutions for rendering a polypeptide susceptible to the binding of an antibody, solutions for lysing cells, or solutions for the purification of polypeptides.

In yet another aspect, the invention provides pharmaceutical compositions including the subject nucleic acids. In one embodiment, an agent which alters the level of expression in a cell of a nucleic acid which hybridizes under stringent conditions to one of SEQ ID Nos. 1–544 or a sequence complementary thereto is identified by providing a cell, treating the cell with a test agent, determining the level of expression in the cell of a nucleic acid which hybridizes under stringent conditions to one of SEQ ID Nos. 1–544 or a sequence complementary thereto, and comparing the level of expression of the nucleic acid in the treated cell with the level of expression of the nucleic acid in an untreated cell, wherein a change in the level of expression of the nucleic acid in the treated cell relative to the level of expression of the nucleic acid in the untreated cell is indicative of an agent which alters the level of expression of the nucleic acid in a cell. The invention further provides a pharmaceutical composition comprising an agent identified by this method. In another embodiment, the invention provides a pharmaceutical composition which includes a polypeptide encoded by a nucleic acid having a nucleotide sequence that hybridizes under stringent conditions to one of SEQ ID Nos. 1–544 or a sequence complementary thereto. In one embodiment, the invention pertains to a pharmaceutical composition comprising a nucleic acid including a sequence which hybridizes under stringent conditions to one of SEQ ID Nos. 1–544 or a sequence complementary thereto.

BRIEF DESCRIPTION OF THE FIGURE

The FIGURE depicts an exemplary assay result for determining differential expression of gene products in cells.

DETAILED DESCRIPTION OF THE INVENTION

Figure 1:
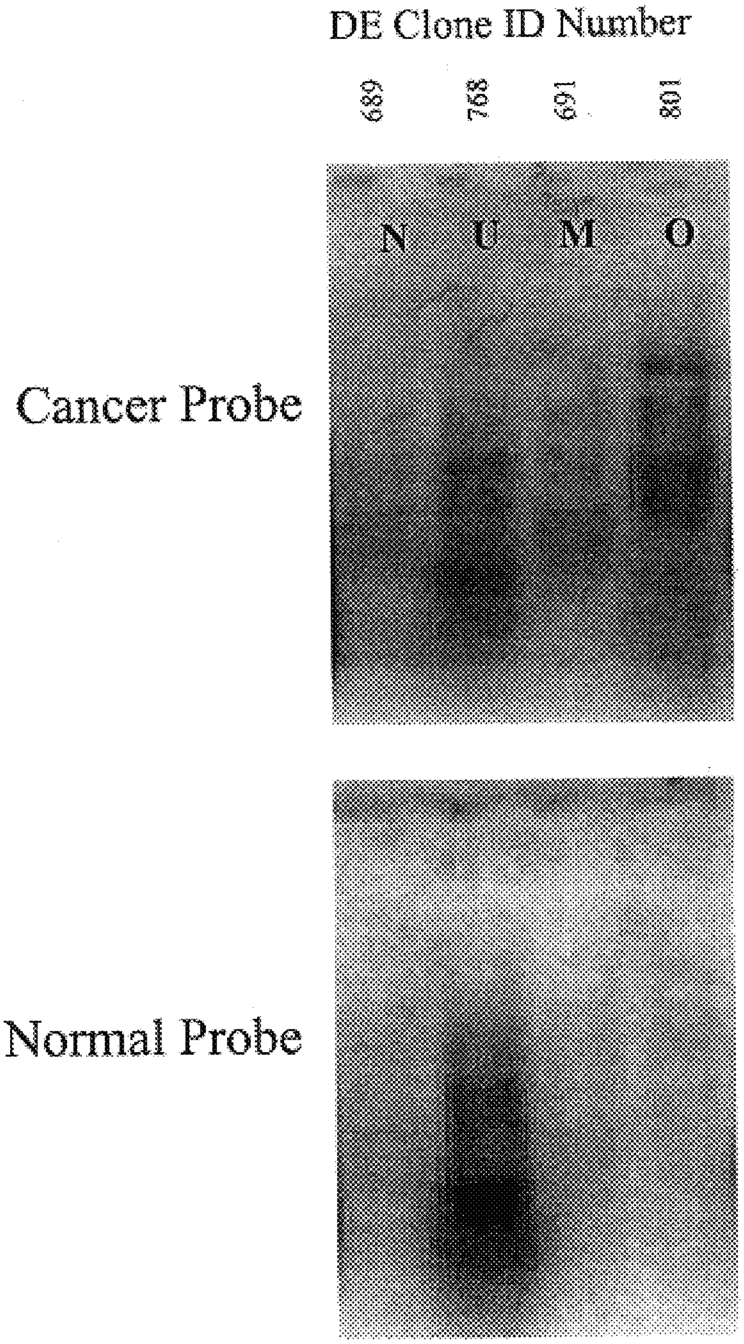

The invention relates to nucleic acids having the disclosed nucleotide sequences (SEQ ID Nos. 1–544), as well as full length cDNA, mRNA, and genes corresponding to these sequences, and to polypeptides and proteins encoded by these nucleic acids and genes, and portions thereof.

Also included are polypeptides and proteins encoded by the nucleic acids of SEQ ID Nos. 1–544. The various nucleic acids that can encode these polypeptides and proteins differ because of the degeneracy of the genetic code, in that most amino acids are encoded by more than one triplet codon. The identity of such codons is well known in this art, and this information can be used for the construction of the nucleic acids within the scope of the invention.

Nucleic acids encoding polypeptides and proteins that are variants of the polypeptides and proteins encoded by the nucleic acids and related cDNA and genes are also within the scope of the invention. The variants differ from wild-type protein in having one or more amino acid substitutions that either enhance, add, or diminish a biological activity of the wild-type protein. Once the amino acid change is selected, a nucleic acid encoding that variant is constructed according to the invention.

The following detailed description discloses how to obtain or make full-length cDNA and human genes corresponding to the nucleic acids, how to express these nucleic acids and genes, how to identify structural motifs of the genes, how to identify the function of a protein encoded by a gene corresponding to an nucleic acid, how to use nucleic acids as probes in mapping and in tissue profiling, how to use the corresponding polypeptides and proteins to raise antibodies, and how to use the nucleic acids, polypeptides, and proteins for therapeutic and diagnostic purposes.

The sequences investigated herein have been found to be differentially expressed in samples obtained from colon cancer cell lines and/or colon cancer tissue. However, it is also believed that these sequences may also have utility with other types of cancer. In particular, Table 3 provides nucleic acid sequences which are over-expressed in both cancer cell line SW 480 as well colon cancer tissue obtained from various patients.

Accordingly, certain aspects of the present invention relate to nucleic acids differentially expressed in tumor tissue, especially colon cancer cell lines, polypeptides encoded by such nucleic acids, and antibodies immunoreactive with these polypeptides, and preparations of such compositions. Moreover, the present invention provides diagnostic and therapeutic assays and reagents for detecting and treating disorders involving, for example, aberrant expression of the subject nucleic acids.

I. General

This invention relates in part to novel methods for identifying and/or classifying cancerous cells present in a human tumors, particularly in solid tumors, e.g., carcinomas and sarcomas, such as, for example, breast or colon cancers. The method uses genes that are differentially expressed in cancer cell lines and/or cancer tissue compared with related normal cells, such as normal colon cells, and thereby identifies or classifies tumor cells by the upregulation and/or downregulation of expression of particular genes, an event which is implicated in tumorigenesis.

Upregulation or increased expression of certain genes such as oncogenes, act to promote malignant growth. Downregulation or decreased expression of genes such as tumor suppressor genes also promotes malignant growth. Thus, alteration in the expression of either type of gene is a potential diagnostic indicator for determining whether a subject is at risk of developing or has cancer, e.g., colon cancer.

Accordingly, in one aspect, the invention also provides biomarkers, such as nucleic acid markers, for human tumor cells, e.g., for colon cancer cells. The invention also provides proteins encoded by these nucleic acid markers.

The invention also features methods for identifying drugs useful for treatment of such cancer cells, and for treatment of a cancerous condition, such as colon cancer. Unlike prior methods, the invention provides a means for identifying cancer cells at an early stage of development, so that premalignant cells can be identified prior to their spreading throughout the human body. This allows early detection of potentially cancerous conditions, and treatment of those cancerous conditions prior to spread of the cancerous cells throughout the body, or prior to development of an irreversible cancerous condition.

II. Definitions

For convenience, the meaning of certain terms and phrases used in the specification, examples, and appended claims, are provided below.

The term “an aberrant expression”, as applied to a nucleic acid of the present invention, refers to level of expression of that nucleic acid which differs from the level of expression of that nucleic acid in healthy tissue, or which differs from the activity of the polypeptide present in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in the activity; for example, an aberrant polypeptide can interact with a different target peptide. A cell can have an aberrant expression level of a gene due to overexpression or underexpression of that gene.

The term "agonist", as used herein, is meant to refer to an agent that mimics or upregulates (e.g., potentiates or supplements) the bioactivity of a protein. An agonist can be a wild-type protein or derivative thereof having at least one bioactivity of the wild-type protein. An agonist can also be a compound that upregulates expression of a gene or which increases at least one bioactivity of a protein. An agonist can also be a compound which increases the interaction of a polypeptide with another molecule, e.g., a target peptide or nucleic acid.

The term "allele", which is used interchangeably herein with "allelic variant", refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide, or several nucleotides, and can include substitutions, deletions, and/or insertions of nucleotides. An allele of a gene can also be a form of a gene containing mutations.

The term "allelic variant of a polymorphic region of a gene" refers to a region of a gene having one of several nucleotide sequences found in that region of the gene in other individuals.

"Antagonist" as used herein is meant to refer to an agent that downregulates (e.g., suppresses or inhibits) at least one bioactivity of a protein. An antagonist can be a compound which inhibits or decreases the interaction between a protein and another molecule, e.g., a target peptide or enzyme substrate. An antagonist can also be a compound that downregulates expression of a gene or which reduces the amount of expressed protein present.

The term "antibody" as used herein is intended to include whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Nonlimiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal, or other purified preparations of antibodies and recombinant antibodies.

The phenomenon of "apoptosis" is well known, and can be described as a programmed death of cells. As is known, apoptosis is contrasted with "necrosis", a phenomenon when cells die as a result of being killed by a toxic material, or other external effect. Apoptosis involves chromatic condensation, membrane blebbing, and fragmentation of DNA, all of which are generally visible upon microscopic examination.

A disease, disorder, or condition "associated with" or "characterized by" an aberrant expression of a nucleic acid refers to a disease, disorder, or condition in a subject which is caused by, contributed to by, or causative of an aberrant level of expression of a nucleic acid.

As used herein the term "bioactive fragment of a polypeptide" refers to a fragment of a full-length polypeptide, wherein the fragment specifically agonizes (mimics) or antagonizes (inhibits) the activity of a wild-type polypeptide. The bioactive fragment preferably is a fragment capable of interacting with at least one other molecule, e.g., protein, small molecule, or DNA, which a full length protein can bind.

"Biological activity" or "bioactivity" or "activity" or "biological function", which are used interchangeably, herein mean an effector or antigenic function that is directly or indirectly performed by a polypeptide (whether in its native or denatured conformation), or by any subsequence thereof. Biological activities include binding to polypeptides, binding to other proteins or molecules, activity as a DNA binding protein, as a transcription regulator, ability to bind damaged DNA, etc. A bioactivity can be modulated by directly affecting the subject polypeptide. Alternatively, a bioactivity can be altered by modulating the level of the polypeptide, such as by modulating expression of the corresponding gene.

The term "biomarker" refers a biological molecule, e.g., a nucleic acid, peptide, hormone, etc., whose presence or concentration can be detected and correlated with a known condition, such as a disease state.

"Cells," "host cells", or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric polypeptide" or "fusion polypeptide" is a fusion of a first amino acid sequence encoding one of the subject polypeptides with a second amino acid sequence defining a domain (e.g., polypeptide portion) foreign to and not substantially homologous with any domain of the subject polypeptide. A chimeric polypeptide may present a foreign domain which is found (albeit in a different polypeptide) in an organism which also expresses the first polypeptide, or it may be an "interspecies," "intergenic," etc., fusion of polypeptide structures expressed by different kinds of organisms. In general, a fusion polypeptide can be represented by the general formula $(X)_n$-$(Y)_m$-$(Z)_n$, wherein Y represents a portion of the subject polypeptide, and X and Z are each independently absent or represent amino acid sequences which are not related to the native sequence found in an organism, or which are not found as a polypeptide chain contiguous with the subject sequence, where m is an integer greater than or equal to one, and each occurrence of n is, independently, 0 or an integer greater than or equal to 1 (n and m are preferably no greater than 5 or 10).

A "delivery complex" shall mean a targeting means (e.g., a molecule that results in higher affinity binding of a nucleic acid, protein, polypeptide or peptide to a target cell surface and/or increased cellular or nuclear uptake by a target cell). Examples of targeting means include: sterols (e.g., cholesterol), lipids (e.g., a cationic lipid, virosome or liposome), viruses (e.g., adenovirus, adeno-associated virus, and retrovirus), or target cell-specific binding agents (e.g., ligands recognized by target cell specific receptors). Preferred complexes are sufficiently stable in vivo to prevent significant uncoupling prior to internalization by the target cell. However, the complex is cleavable under appropriate conditions within the cell so that the nucleic acid, protein, polypeptide or peptide is released in a functional form.

As is well known, genes or a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a polypeptide" may thus refer to one or more genes within a particular individual. Moreover, certain differences in nucleotide sequences may exist between individual organisms, which are called aalleles. Such allelic differences may or may not result in differences in amino acid sequence of the encoded polypeptide yet still encode a polypeptide with the same biological activity.

The term "equivalent" is understood to include nucleotide sequences encoding functionally equivalent polypeptides. Equivalent nucleotide sequences will include sequences that differ by one or more nucleotide substitutions, additions or deletions, such as allelic variants; and will, therefore, include sequences that differ from the nucleotide sequence of the nucleic acids shown in SEQ ID NOs: 1–544 due to the degeneracy of the genetic code.

As used herein, the terms "gene", "recombinant gene", and "gene construct" refer to a nucleic acid of the present invention associated with an open reading frame, including both exon and (optionally) intron sequences.

A "recombinant gene" refers to nucleic acid encoding a polypeptide and comprising exon sequences, though it may optionally include intron sequences which are derived from, for example, a related or unrelated chromosomal gene. The term "intron" refers to a DNA sequence present in a given gene which is not translated into protein and is generally found between exons.

The term "growth" or "growth state" of a cell refers to the proliferative state of a cell as well as to its differentiative state. Accordingly, the term refers to the phase of the cell cycle in which the cell is, e.g., G0, G1, G2, prophase, metaphase, or telophase, as well as to its state of differentiation, e.g., undifferentiated, partially differentiated, or fully differentiated. Without wanting to be limited, differentiation of a cell is usually accompanied by a decrease in the proliferative rate of a cell.

"Homology" or "identity" or "similarity" refers to sequence similarity between two peptides or between two nucleic acid molecules, with identity being a more strict comparison. Homology and identity can each be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. An "unrelated" or "non-homologous" sequence shares less than 40% identity, though preferably less than 25% identity, with one of the sequences of the present invention.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in *Methods in Enzymology*, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173–187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

Databases with individual sequences are described in *Methods in Enzymology*, ed. Doolittle, supra. Databases include Genbank, EMBL, and DNA Database of Japan (DDBJ).

Preferred nucleic acids have a sequence at least 70%, and more preferably 80% identical and more preferably 90% and even more preferably at least 95% identical to an nucleic acid sequence of a sequence shown in one of SEQ ID NOS: 1–544. Nucleic acids at least 90%, more preferably 95%, and most preferably at least about 98–99% identical with a nucleic sequence represented in one of SEQ ID NOS: 1–544 are of course also within the scope of the invention. In preferred embodiments, the nucleic acid is mammalian.

The term "interact" as used herein is meant to include detectable interactions (e.g., biochemical interactions) between molecules, such as interaction between protein-protein, protein-nucleic acid, nucleic acid-nucleic acid, and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The terms "modulated" and "differentially regulated" as used herein refer to both upregulation (i.e., activation or stimulation (e.g., by agonizing or potentiating)) and down-regulation (i.e., inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant.

The designation "N", where it appears in the accompanying Sequence Listing, indicates that the identity of the corresponding nucleotide is unknown. "N" should therefore not necessarily be interpreted as permitting substitution with any nucleotide, e.g., A, T, C, or G, but rather as holding the place of a nucleotide whose identity has not been conclusively determined.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

The term "nucleotide sequence complementary to the nucleotide sequence of SEQ ID NO. x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a non-coding strand.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

As used herein, the term "promoter" means a DNA sequence that regulates expression of a selected DNA sequence operably linked to the promoter, and which effects expression of the selected DNA sequence in cells. The term encompasses "tissue specific" promoters, i.e., promoters which effect expression of the selected DNA sequence only in specific cells (e.g., cells of a specific tissue). The term also covers so-called "leaky" promoters, which regulate expression of a selected DNA primarily in one tissue, but cause expression in other tissues as well. The term also encompasses non-tissue specific promoters and promoters that constitutively expressed or that are inducible (i.e., expression levels can be controlled).

The terms "protein", "polypeptide", and "peptide" are used interchangeably herein when referring to a gene product.

The term "recombinant protein" refers to a polypeptide of the present invention which is produced by recombinant DNA techniques, wherein generally, DNA encoding a polypeptide is inserted into a suitable expression vector which is in turn used to transform a host cell to produce the heterologous protein. Moreover, the phrase "derived from", with respect to a recombinant gene, is meant to include within the meaning of "recombinant protein" those proteins having an amino acid sequence of a native polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays of the invention to identify compounds that modulate a bioactivity.

As used herein, the term "specifically hybridizes" or "specifically detects" refers to the ability of a nucleic acid molecule of the invention to hybridize to at least a portion of, for example; approximately 6, 12, 15, 20, 30, 50, 100, 150, 200, 300, 350, 400, 500, 750, or 1000 contiguous nucleotides of a nucleic acid designated in any one of SEQ ID Nos: 1–544, or a sequence complementary thereto, or naturally occurring mutants thereof, such that it has less than 15%, preferably less than 10%, and more preferably less than 5% background hybridization to a cellular nucleic acid (e.g., mRNA or genomic DNA) encoding a different protein. In preferred embodiments, the oligonucleotide probe detects only a specific nucleic acid, e.g., it does not substantially hybridize to similar or related nucleic acids, or complements thereof.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of the polypeptide.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of the target gene is disrupted.

As used herein, the term "transgene" means a nucleic acid sequence (or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extra-chromosomally replicating DNA. In the typical transgenic animals described herein, the transgene causes cells to express a recombinant form of one of the subject polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

III. Nucleic Acids of the Present Invention

As described below, one aspect of the invention pertains to isolated nucleic acids, variants, and/or equivalents of such nucleic acids.

Nucleic acids of the present invention have been identified as differentially expressed in tumor cells, e.g., colon cancer-derived cell lines (relative to the expression levels in normal tissue, e.g., normal colon tissue and/or normal non-colon tissue), such as SEQ ID Nos. 1–544, preferably SEQ ID Nos. 1–168, even more preferably SEQ ID Nos. 1–35, or a sequence complementary thereto. In certain embodiments, the subject nucleic acids are differentially expressed by at least a factor of two, preferably at least a factor of five, even more preferably at least a factor of twenty, still more preferably at least a factor of fifty. Preferred nucleic acids include sequences identified as differentially expressed both in colon cancer cell tissue and colon cancer cell lines. In preferred embodiments, nucleic acids of the present invention are upregulated in tumor cells, especially colon cancer tissue and/or colon cancer-derived cell lines. In another embodiment, nucleic acids of the present invention are downregulated in tumor cells, especially colon cancer tissue and/or colon cancer-derived cell lines.

Table 1 indicates those sequences which are over- or underexpressed in a colon cancer-derived cell line relative to normal tissue, and further designates those sequences which are also differentially regulated in colon cancer tissue. The designation O indicates that the corresponding sequence was overexpressed, M indicates possible overexpression, N indicates no differential expression, and U indicates underexpression.

Genes which are upregulated, such as oncogenes, or downregulated, such as tumor suppressors, in aberrantly proliferating cells may be targets for diagnostic or therapeutic techniques. For example, upregulation of the cdc2 gene induces mitosis. Overexpression of the myt1 gene, a mitotic deactivator, negatively regulates the activity of cdc2. Aberrant proliferation may thus be induced either by upregulating cdc2 or by downregulating myt1. Similarly, downregulation of tumor suppressors such as p53 and Rb have been implicated in tumorigenesis.

Particularly preferred polypeptides are those that are encoded by nucleic acid sequences at least about 70%, 75%, 80%, 90%, 95%, 97%, or 98% similar to a nucleic acid sequence of SEQ ID Nos. 1–544. Preferably, the nucleic acid includes all or a portion (e.g., at least about 12, at least about 15, at least about 25, or at least about 40 nucleotides) of the nucleotide sequence corresponding to the nucleic acid of SEQ ID Nos. 1–168, preferably SEQ ID Nos. 1–35, or a sequence complementary thereto.

Still other preferred nucleic acids of the present invention encode a polypeptide comprising at least a portion of a polypeptide encoded by one of SEQ ID Nos. 1–544. For example, preferred nucleic acid molecules for use as probes/primers or antisense molecules (i.e., noncoding nucleic acid molecules) can comprise at least about 12, 20, 30, 50, 60, 70, 80, 90, or 100 base pairs in length up to the length of the complete gene. Coding nucleic acid molecules can comprise, for example, from about 50, 60, 70, 80, 90, or 100 base pairs up to the length of the complete gene.

Another aspect of the invention provides a nucleic acid which hybridizes under low, medium, or high stringency conditions to a nucleic acid sequence represented by one of SEQ ID Nos. 1–168, preferably SEQ ID Nos. 1–35, or a sequence complementary thereto. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–12.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In a preferred embodiment, a nucleic acid of the present invention will bind to one of SEQ ID Nos. 1–168, preferably SEQ ID Nos. 1–35, or a sequence complementary thereto, under moderately stringent conditions, for example at about 2.0×SSC and about 40° C. In a particularly preferred embodiment, a nucleic acid of the present invention will bind to one of SEQ ID Nos. 1–168, preferably SEQ ID Nos. 1–35, or a sequence complementary thereto, under high stringency conditions.

In one embodiment, the invention provides nucleic acids which hybridize under low stringency conditions of 6×SSC at room temperature followed by a wash at 2×SSC at room temperature.

In another embodiment, the invention provides nucleic acids which hybridize under high stringency conditions of 2×SSC at 65° C. followed by a wash at 0.2×SSC at 65° C.

Nucleic acids having a sequence that differs from the nucleotide sequences shown in one of SEQ ID Nos. 1–168, preferably SEQ ID Nos. 1–35, or a sequence complementary thereto, due to degeneracy in the genetic code, are also within the scope of the invention. Such nucleic acids encode functionally equivalent peptides (i.e., a peptide having equivalent or similar biological activity) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a polypeptide. However, it is expected that DNA sequence polymorphisms that do lead to changes in the amino acid sequences of the subject polypeptides will exist among mammals. One skilled in the art will appreciate that these variations in one or more nucleotides (e.g., up to about 3–5% of the nucleotides) of the nucleic acids encoding polypeptides having an activity of a polypeptide may exist among individuals of a given species due to natural allelic variation.

Also within the scope of the invention are nucleic acids encoding splicing variants of proteins encoded by a nucleic acid of SEQ ID Nos. 1–544, preferably SEQ ID Nos. 1–168, even more preferably SEQ ID Nos. 1–35, or a sequence complementary thereto, or natural homologs of such proteins. Such homologs can be cloned by hybridization or PCR, as further described herein.

The polynucleotide sequence may also encode for a leader sequence, e.g., the natural leader sequence or a heterologous leader sequence, for a subject polypeptide. For example, the desired DNA sequence may be fused in the same reading frame to a DNA sequence which aids in expression and secretion of the polypeptide from the host cell, for example, a leader sequence which functions as a secretory sequence for controlling transport of the polypeptide from the cell. The protein having a leader sequence is a preprotein and may have the leader sequence cleaved by the host cell to form the mature form of the protein.

The polynucleotide of the present invention may also be fused in frame to a marker sequence, also referred to herein as "Tag sequence" encoding a "Tag peptide", which allows for marking and/or purification of the polypeptide of the present invention. In a preferred embodiment, the marker sequence is a hexahistidine tag, e.g., supplied by a PQE-9 vector. Numerous other Tag peptides are available commercially. Other frequently used Tags include myc-epitopes (e.g., see Ellison et al. (1991) *J Biol Chem* 266:21150–21157) which includes a 10-residue sequence from c-myc, the pFLAG system (International Biotechnologies, Inc.), the pEZZ-protein A system (Pharmacia, N.J.), and a 16 amino acid portion of the *Haemophilus influenza* hemagglutinin protein. Furthermore, any polypeptide can be used as a Tag so long as a reagent, e.g., an antibody interacting specifically with the Tag polypeptide is available or can be prepared or identified.

As indicated by the examples set out below, nucleic acids can be obtained from mRNA present in any of a number of eukaryotic cells, e.g., and are preferably obtained from metazoan cells, more preferably from vertebrate cells, and even more preferably from mammalian cells. It should also be possible to obtain nucleic acids of the present invention from genomic DNA from both adults and embryos. For example, a gene can be cloned from either a cDNA or a genomic library in accordance with protocols generally known to persons skilled in the art. cDNA can be obtained by isolating total mRNA from a cell, e.g., a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene can also be cloned using established polymerase chain reaction techniques in accordance with the nucleotide sequence information provided by the invention.

In certain embodiments, a nucleic acid, probe, vector, or other construct of the present invention includes at least about five, at least about ten, or at least about twenty nucleic acids from a region designated as novel in Table 2. In certain other embodiments, a nucleic acid of the present invention includes at least about five, at least about ten, or at least about twenty nucleic acids which are not included in the clones whose accession numbers are listed in Table 2.

The invention includes within its scope a polynucleotide having the nucleotide sequence of nucleic acid obtained from this biological material, wherein the nucleic acid hybridizes under stringent conditions (at least about 4×SSC at 65° C., or at least about 4×SSC at 42° C.; see, for example, U.S. Pat. No. 5,707,829, incorporated herein by reference) with at least 15 contiguous nucleotides of at least one of SEQ ID Nos. 1–544. By this is intended that when at least 15 contiguous nucleotides of one of SEQ ID Nos. 1–544 is used as a probe, the probe will preferentially hybridize with a gene or mRNA (of the biological material) comprising the complementary sequence, allowing the identification and retrieval of the nucleic acids of the biological material that uniquely hybridize to the selected probe. Probes from more than one of SEQ ID Nos. 1–544 will hybridize with the same gene or mRNA if the cDNA from which they were derived corresponds to one mRNA. Probes of more than 15 nucleotides can be used, but 15 nucleotides represents enough sequence for unique identification.

Because the present nucleic acids represent partial mRNA transcripts, two or more nucleic acids of the invention may represent different regions of the same mRNA transcript and the same gene. Thus, if two or more of SEQ ID Nos. 1–544 are identified as belonging to the same clone, then either sequence can be used to obtain the full-length mRNA or gene.

Nucleic acid-related polynucleotides can also be isolated from cDNA libraries. These libraries are preferably prepared from mRNA of human colon cells, more preferably, human colon cancer specific tissue, designated as the DE clones in the appended Tables. In another embodiment the nucleic acids are isolated from libraries prepared from normal colon specific tissue, designated herein as PA clones in the appended Tables. In yet another embodiment, this invention discloses nucleic acid sequences that can be isolated from both libraries prepared from a human colon adenocarcinoma cell line, SW480, as well as from libraries prepared from either normal colon specific tissue or from colon cancer specific tissue. These sequences are listed in Table 3. Alignment of SEQ ID Nos. 1–544, as described above, can indicated that a cell line or tissue source of a related protein or polynucleotide can also be used as a source of the nucleic acid-related cDNA.

Techniques for producing and probing nucleic acid sequence libraries are described, for example, in Sambrook et al., "Molecular Cloning: A Laboratory Manual" (New York, Cold Spring Harbor Laboratory, 1989). The eDNA can be prepared by using primers based on a sequence from SEQ ID Nos. 1–544. In one embodiment, the cDNA library can be made from only poly-adenylated mRNA. Thus, poly-T primers can be used to prepare cDNA from the mRNA. Alignment of SEQ ID Nos. 1–544 can result in identification of a related polypeptide or polynucleotide. Some of the polynucleotides disclosed herein contains repetitive regions that were subject to masking during the search procedures. The information about the repetitive regions is discussed below.

Constructs of polynucleotides having sequences of SEQ ID Nos. 1–544 can be generated synthetically. Alternatively, single-step assembly of a gene and entire plasmid from large numbers of oligodeoxyribonucleotides is described by Stemmer et al., *Gene* (*Amsterdam*) (1995) 164(1):49–53. In this method, assembly PCR (the synthesis of long DNA sequences from large numbers of oligodeoxyribonucleotides (oligos)) is described. The method is derived from DNA shuffling (Stemmer, *Nature* (1994) 370:389–391), and does not rely on DNA ligase, but instead relies on DNA polymerase to build increasingly longer DNA fragments during the assembly process. For example, a 1.1-kb fragment containing the TEM-1 beta-lactamase-encoding gene (bla) can be assembled in a single reaction from a total of 56 oligos, each 40 nucleotides (nt) in length. The synthetic gene can be PCR amplified and cloned in a vector containing the tetracycline-resistance gene (Tc-R) as the sole selectable marker. Without relying on ampicillin (Ap) selection, 76% of the Tc-R colonies were Ap-R, making this approach a general method for the rapid and cost-effective synthesis of any gene.

IV. Identification of Functional and Structural Motifs of Novel Genes Using Art-Recognized Methods Translations of the nucleotide sequence of the nucleic acids, cDNAs, or full genes can be aligned with individual known sequences. Similarity with individual sequences can be used to determine the activity of the polypeptides encoded by the polynucleotides of the invention. For example, sequences that show similarity with a chemokine sequence may exhibit chemokine activities. Also, sequences exhibiting similarity with more than one individual sequence may exhibit activities that are characteristic of either or both individual sequences.

The full length sequences and fragments of the polynucleotide sequences of the nearest neighbors can be used as probes and primers to identify and isolate the full length sequence of the nucleic acid. The nearest neighbors can indicate a tissue or cell type to be used to construct a library for the full-length sequences of the nucleic acid.

Typically, the nucleic acids are translated in all six frames to determine the best alignment with the individual sequences. The sequences disclosed herein in the Sequence Listing are in a 5' to 3' orientation and translation in three frames can be sufficient (with a few specific exceptions as described in the Examples). These amino acid sequences are referred to, generally, as query sequences, which will be aligned with the individual sequences.

Nucleic acid sequences can be compared with known genes by any of the methods disclosed above. Results of individual and query sequence alignments can be divided into three categories: high similarity, weak similarity, and no similarity. Individual alignment results ranging from high similarity to weak similarity provide a basis for determining polypeptide activity and/or structure.

Parameters for categorizing individual results include: percentage of the alignment region length where the strongest alignment is found, percent sequence identity, and p value.

The percentage of the alignment region length is calculated by counting the number of residues of the individual sequence found in the region of strongest alignment. This number is divided by the total residue length of the query sequence to find a percentage. An example is shown below:

```
Query sequence:        ASNPERRMIPVTRVGLIRYM
                           |    ||| |||| |||
Individual sequence:  YMMTEYLA IPV.RVGLPRYM
                      1   5    10     15
```

The region of alignment begins at amino acid 9 and ends at amino acid 19. The total length of the query sequence is 20 amino acids. The percent of the alignment region length is 11/20 or 55%.

Percent sequence identity is calculated by counting the number of amino acid matches between the query and individual sequence and dividing total number of matches by the number of residues of the individual sequence found in the region of strongest alignment. For the example above, the percent identity would be 10 matches divided by 11 amino acids, or approximately 90.9%.

P value is the probability that the alignment was produced by chance. For a single alignment, the p value can be calculated according to Karlin et al., *Proc. Natl. Acad. Sci.* 87: 2264 (1990) and Karlin et al., *Proc. Natl. Acad. Sci.* 90: (1993). The p value of multiple alignments using the same query sequence can be calculated using an heuristic approach described in Altschul et al., *Nat. Genet.* 6: 119 (1994). Alignment programs such as BLAST program can calculate the p value.

The boundaries of the region where the sequences align can be determined according to Doolittle, Methods in Enzymology, supra; BLAST or FASTA programs; or by determining the area where the sequence identity is highest.

Another factor to consider for determining identity or similarity is the location of the similarity or identity. Strong local alignment can indicate similarity even if the length of alignment is short. Sequence identity scattered throughout the length of the query sequence also can indicate a similarity between the query and profile sequences.

High Similarity

For the alignment results to be considered high similarity, the percent of the alignment region length, typically, is at least about 55% of total length query sequence; more typically, at least about 58%; even more typically; at least about 60% of the total residue length of the query sequence. Usually, percent length of the alignment region can be as much as about 62%; more usually, as much as about 64%; even more usually, as much as about 66%.

Further, for high similarity, the region of alignment, typically, exhibits at least about 75% of sequence identity; more typically, at least about 78%; even more typically; at least about 80% sequence identity. Usually, percent sequence identity can be as much as about 82%; more usually, as much as about 84%; even more usually, as much as about 86%.

The p value is used in conjunction with these methods. If high similarity is found, the query sequence is considered to have high similarity with a profile sequence when the p value is less than or equal to about $10^{-2}$; more usually; less than or equal to about $10^{-3}$; even more usually; less than or equal to about $10^{-4}$. More typically, the p value is no more than about $10^{-5}$; more typically; no more than or equal to about $10^{-10}$; even more typically; no more than or equal to about $10^{-15}$ for the query sequence to be considered high similarity.

Weak Similarity

For the alignment results to be considered weak similarity, there is no minimum percent length of the alignment region nor minimum length of alignment. A better showing of weak similarity is considered when the region of alignment is, typically, at least about 15 amino acid residues in length; more typically, at least about 20; even more typically; at least about 25 amino acid residues in length. Usually, length of the alignment region can be as much as about 30 amino acid residues; more usually, as much as about 40; even more usually, as much as about 60 amino acid residues.

Further, for weak similarity, the region of alignment, typically, exhibits at least about 35% of sequence identity; more typically, at least about 40%; even more typically; at least about 45% sequence identity. Usually, percent sequence identity can be as much as about 50%; more usually, as much as about 55%; even more usually, as much as about 60%.

If low similarity is found, the query sequence is considered to have weak similarity with a profile sequence when the p value is usually less than or equal to about $10^{-2}$; more usually; less than or equal to about $10^{-3}$; even more usually; less than or equal to about $10^{-4}$. More typically, the p value is no more than about $10^{-5}$; more usually; no more than or equal to about $10^{-10}$; even more usually; no more than or equal to about $10^{-15}$ for the query sequence to be considered weak similarity.

Similarity Determined by Sequence Identity

Sequence identity alone can be used to determine similarity of a query sequence to an individual sequence and can indicate the activity of the sequence. Such an alignment, preferably, permits gaps to align sequences. Typically, the query sequence is related to the profile sequence if the sequence identity over the entire query sequence is at least about 15%; more typically, at least about 20%; even more typically, at least about 25%; even more typically, at least about 50%. Sequence identity alone as a measure of similarity is most useful when the query sequence is usually, at least 80 residues in length; more usually, 90 residues; even more usually, at least 95 amino acid residues in length. More typically, similarity can be concluded based on sequence identity alone when the query sequence is preferably 100 residues in length; more preferably, 120 residues in length; even more preferably, 150 amino acid residues in length.

Determining Activity from Alignments with Profile and Multiple Aligned Sequences Translations of the nucleic acids can be aligned with amino acid profiles that define either protein families or common motifs. Also, translations of the nucleic acids can be aligned to multiple sequence alignments (MSA) comprising the polypeptide sequences of members of protein families or motifs. Similarity or identity with profile sequences or MSAs can be used to determine the activity of the polypeptides encoded by nucleic acids or corresponding cDNA or genes. For example, sequences that show an identity or similarity with a chemokine profile or MSA can exhibit chemokine activities.

Profiles can designed manually by (1) creating a MSA, which is an alignment of the amino acid sequence of members that belong to the family and (2) constructing a statistical representation of the alignment. Such methods are described, for example, in Birney et al., *Nucl. Acid Res.* 24(14 : 2730–2739 (1996).

MSAs of some protein families and motifs are publicly available. For example, these include MSAs of 547 different families and motifs. These MSAs are described also in Sonnhammer et al., *Proteins* 28: 405–420 (1997). Other sources are also available in the world wide web. A brief description of these MSAs is reported in Pascarella et al., *Prot. Eng.* 9(3): 249–251 (1996).

Techniques for building profiles from MSAs are described in Sonnhammer et al., supra; Birney et al., supra; and *Methods in Enzymology*, vol. 266: "Computer Methods for Macromolecular Sequence Analysis," 1996, ed. Doolittle, Academic Press, Inc., a division of Harcourt Brace & Co., San Diego, Calif., USA.

Similarity between a query sequence and a protein family or motif can be determined by (a) comparing the query sequence against the profile and/or (b) aligning the query sequence with the members of the family or motif.

Typically, a program such as Searchwise can be used to compare the query sequence to the statistical representation of the multiple alignment, also known as a profile. The program is described in Birney et al., supra. Other techniques to compare the sequence and profile are described in Sonnhammer et al., supra and Doolittle, supra.

Next, methods described by Feng et al., *J. Mol. Evol.* 25: 351–360 (1987) and Higgins et al., *CABIOS* 5: 151–153 (1989) can be used align the query sequence with the members of a family or motif, also known as a MSA. Computer programs, such as PILEUP, can be used. See Feng et al., infra.

The following factors are used to determine if a similarity between a query sequence and a profile or MSA exists: (1) number of conserved residues found in the query sequence, (2) percentage of conserved residues found in the query sequence, (3) number of frameshifts, and (4) spacing between conserved residues.

Some alignment programs that both translate and align sequences can make any number of frameshifts when translating the nucleotide sequence to produce the best alignment. The fewer frameshifts needed to produce an alignment, the stronger the similarity or identity between the query and profile or MSAs. For example, a weak similarity resulting from no frameshifts can be a better indication of activity or structure of a query sequence, than a strong similarity resulting from two frameshifts. Preferably, three or fewer frameshifts are found in an alignment; more preferably two or fewer frameshifts; even more preferably, one or fewer frameshifts; even more preferably, no frameshifts are found in an alignment of query and profile or MSAs.

Conserved residues are those amino acids that are found at a particular position in all or some of the family or motif members. For example, most known chemokines contain four conserved cysteines. Alternatively, a position is considered conserved if only a certain class of amino acids is found in a particular position in all or some of the family members. For example, the N-terminal position may contain a positively charged amino acid, such as lysine, arginine, or histidine.

Typically, a residue of a polypeptide is conserved when a class of amino acids or a single amino acid is found at a particular position in at least about 40% of all class members; more typically, at least about 50%; even more typically, at least about 60% of the members. Usually, a residue is conserved when a class or single amino acid is found in at least about 70% of the members of a family or motif; more usually, at least about 80%; even more usually, at least about 90%; even more usually, at least about 95%.

A residue is considered conserved when three unrelated amino acids are found at a particular position in the some or all of the members; more usually, two unrelated amino acids. These residues are conserved when the unrelated amino acids are found at particular positions in at least about 40% of all class member; more typically, at least about 50%; even more typically, at least about 60% of the members. Usually, a residue is conserved when a class or single amino acid is found in at least about 70% of the members of a family or motif; more usually, at least about 80%; even more usually, at least about 90%; even more usually, at least about 95%.

A query sequence has similarity to a profile or MSA when the query sequence comprises at least about 25% of the conserved residues of the profile or MSA; more usually, at least about 30%; even more usually; at least about 40%. Typically, the query sequence has a stronger similarity to a profile sequence or MSA when the query sequence comprises at least about 45% of the conserved residues of the profile or MSA; more typically, at least about 50%; even more typically; at least about 55%.

V. Probes and Primers

The nucleotide sequences determined from the cloning of genes from tumor cells, especially colon cancer cell lines and tissues will further allow for the generation of probes and primers designed for identifying and/or cloning homologs in other cell types, e.g., from other tissues, as well as homologs from other mammalian organisms. Nucleotide sequences useful as probes/primers may include all or a portion of the sequences listed in SEQ ID Nos. 1–544 or sequences complementary thereto or sequences which hybridize under stringent conditions to all or a portion of SEQ ID Nos. 1–544. For instance, the present invention also provides a probe/primer comprising a substantially purified oligonucleotide, which oligonucleotide comprising a nucleotide sequence that hybridizes under stringent conditions to at least approximately 12, preferably 25, more preferably 40, 50, or 75 consecutive nucleotides up to the full length of the sense or anti-sense sequence selected from the group consisting of SEQ ID Nos. 1–544, preferably SEQ ID Nos. 1–168, even more preferably SEQ ID Nos. 1–35, or a sequence complementary thereto, or naturally occurring mutants thereof. For instance, primers based on a nucleic acid represented in SEQ ID Nos. 1–544, preferably SEQ ID Nos. 1–168, even more preferably SEQ ID Nos. 1–35, or a sequence complementary thereto, can be used in PCR reactions to clone homologs of that sequence.

In yet another embodiment, the invention provides probes/primers comprising a nucleotide sequence that hybridizes under moderately stringent conditions to at least approximately 12, 16, 25, 40, 50 or 75 consecutive nucleotides up to the full length of the sense or antisense sequence selected from the group consisting of SEQ ID Nos. 1–544, preferably SEQ ID Nos. 1–168, even more preferably SEQ ID Nos. 1–35, or naturally occurring mutants thereof.

In particular, these probes are useful because they provide a method for detecting mutations in wild-type genes of the present invention. Nucleic acid probes which are complementary to a wild-type gene of the present invention and can form mismatches with mutant genes are provided, allowing for detection by enzymatic or chemical cleavage or by shifts in electrophoretic mobility.

Likewise, probes based on the subject sequences can be used to detect transcripts or genomic sequences encoding the same or homologous proteins, for use, for example, in prognostic or diagnostic assays. In preferred embodiments, the probe further comprises a label group attached thereto and able to be detected, e.g., the label group is selected from radioisotopes, fluorescent compounds, chemiluminescent compounds, enzymes, and enzyme co-factors.

Full-length cDNA molecules comprising the disclosed nucleic acids are obtained as follows. A subject nucleic acid or a portion thereof comprising at least about 12, 15, 18, or 20 nucleotides up to the full length of a sequence represented in SEQ ID Nos. 1–544, preferably SEQ ID Nos. 1–168, even more preferably SEQ ID Nos. 1–35, or a sequence complementary thereto, may be used as a hybridization probe to detect hybridizing members of a cDNA library using probe design methods, cloning methods, and clone selection techniques as described in U.S. Pat. No. 5,654,173, "Secreted Proteins and Polynucleotides Encoding Them," incorporated herein by reference. Libraries of cDNA may be made from selected tissues, such as normal or tumor tissue, or from tissues of a mammal treated with, for example, a pharmaceutical agent. Preferably, the tissue is the same as that used to generate the nucleic acids, as both the nucleic acid and the cDNA represent expressed genes. Most preferably, the cDNA library is made from the biological material described herein in the Examples. Alternatively, many cDNA libraries are available commercially. (Sambrook et al., *Molecular Cloning: A Laboratory Manual, 2nd Ed.* (Cold Spring Harbor Press, Cold Spring Harbor, N.Y. 1989). The choice of cell type for library construction may be made after the identity of the protein encoded by the nucleic acid-related gene is known. This will indicate which tissue and cell types are likely to express the related gene, thereby containing the mRNA for generating the cDNA.

Members of the library that are larger than the nucleic acid, and preferably that contain the whole sequence of the native message, may be obtained. To confirm that the entire cDNA has been obtained, RNA protection experiments may be performed as follows. Hybridization of a full-length cDNA to an mRNA may protect the RNA from RNase degradation. If the cDNA is not full length, then the portions of the mRNA that are not hybridized may be subject to RNase degradation. This may be assayed, as is known in the art, by changes in electrophoretic mobility on polyacrylamide gels, or by detection of released monoribonucleotides. Sambrook et al., *Molecular Cloning: A Laboratory Manual, 2nd Ed.* (Cold Spring Harbor Press, Cold Spring Harbor, N.Y. 1989). In order to obtain additional sequences 5' to the end of a partial cDNA, 5' RACE (PCR Protocols: A Guide to Methods and Applications (Academic Press, Inc. 1990)) may be performed.

Genomic DNA may be isolated using nucleic acids in a manner similar to the isolation of full-length cDNAs. Briefly, the nucleic acids, or portions thereof, may be used as probes to libraries of genomic DNA. Preferably, the library is obtained from the cell type that was used to generate the nucleic acids. Most preferably, the genomic DNA is obtained from the biological material described herein in the Example. Such libraries may be in vectors suitable for carrying large segments of a genome, such as P1 or YAC, as described in detail in Sambrook et al., 9.4–9.30. In addition, genomic sequences can be isolated from human BAC libraries, which are commercially available from Research Genetics, Inc., Huntville, Ala., USA, for example. In order to obtain additional 5' or 3' sequences, chromosome walking may be performed, as described in Sambrook et al., such that adjacent and overlapping fragments of genomic DNA are isolated. These may be mapped and pieced together, as is known in the art, using restriction digestion enzymes and DNA ligase.

Using the nucleic acids of the invention, corresponding full length genes can be isolated using both classical and PCR methods to construct and probe cDNA libraries. Using either method, Northern blots, preferably, may be performed on a number of cell types to determine which cell lines express the gene of interest at the highest rate.

Classical methods of constructing cDNA libraries are taught in Sambrook et al., supra. With these methods, cDNA can be produced from mRNA and inserted into viral or expression vectors. Typically, libraries of mRNA comprising poly(A) tails can be produced with poly(T) primers. Similarly, cDNA libraries can be produced using the instant sequences as primers.

PCR methods may be used to amplify the members of a cDNA library that comprise the desired insert. In this case, the desired insert may contain sequence from the full length cDNA that corresponds to the instant nucleic acids. Such PCR methods include gene trapping and RACE methods.

Gene trapping may entail inserting a member of a cDNA library into a vector. The vector then may be denatured to produce single stranded molecules. Next, a substrate-bound probe, such a biotinylated oligo, may be used to trap cDNA inserts of interest. Biotinylated probes can be linked to an avidin-bound solid substrate. PCR methods can be used to amplify the trapped cDNA. To trap sequences corresponding to the full length genes, the labeled probe sequence may be based on the nucleic acids of the invention, e.g., SEQ ID Nos. 1-1 68, preferably SEQ ID Nos. 1–35, or a sequence complementary thereto. Random primers or primers specific to the library vector can be used to amplify the trapped cDNA. Such gene trapping techniques are described in Gruber et al., PCT WO 95/04745 and Gruber et al., U.S. Pat. No. 5,500,356. Kits are commercially available to perform gene trapping experiments from, for example, Life Technologies, Gaithersburg, Maryland, USA.

"Rapid amplification of cDNA ends," or RACE, is a PCR method of amplifying cDNAs from a number of different RNAs. The cDNAs may be ligated to an oligonucleotide linker and amplified by PCR using two primers. One primer may be based on sequence from the instant nucleic acids, for which full length sequence is desired, and a second primer may comprise a sequence that hybridizes to the oligonucleotide linker to amplify the cDNA. A description of this method is reported in PCT Pub. No. WO 97/19110.

In preferred embodiments of RACE, a common primer may be designed to anneal to an arbitrary adaptor sequence ligated to cDNA ends (Apte and Siebert, *Biotechniques* 15:890–893, 1993; Edwards et al., *Nuc. Acids Res.* 19:5227–5232, 1991). When a single gene-specific RACE primer is paired with the common primer, preferential amplification of sequences between the single gene specific primer and the common primer occurs. Commercial cDNA pools modified for use in RACE are available.

Another PCR-based method generates full-length cDNA library with anchored ends without specific knowledge of the cDNA sequence. The method uses lock-docking primers (I–VI), where one primer, poly TV (I–III) locks over the polyA tail of eukaryotic mRNA producing first strand synthesis and a second primer, polyGH (IV–VI) locks onto the polyC tail added by terminal deoxynucleotidyl transferase (TdT). This method is described in PCT Pub. No. WO 96/40998.

The promoter region of a gene generally is located 5' to the initiation site for RNA polymerase II. Hundreds of promoter regions contain the "TATA" box, a sequence such as TATTA or TATAA, which is sensitive to mutations. The promoter region can be obtained by performing 5' RACE using a primer from the coding region of the gene. Alternatively, the cDNA can be used as a probe for the genomic sequence, and the region 5' to the coding region is identified by "walking up."

If the gene is highly expressed or differentially expressed, the promoter from the gene may be of use in a regulatory construct for a heterologous gene.

Once the full-length cDNA or gene is obtained, DNA encoding variants can be prepared by site-directed mutagenesis, described in detail in Sambrook et al., 15.3–15.63. The choice of codon or nucleotide to be replaced can be based on the disclosure herein on optional changes in amino acids to achieve altered protein structure and/or function.

As an alternative method to obtaining DNA or RNA from a biological material, nucleic acid comprising nucleotides having the sequence of one or more nucleic acids of the invention can be synthesized. Thus, the invention encompasses nucleic acid molecules ranging in length from 12 nucleotides (corresponding to at least 12 contiguous nucleotides which hybridize under stringent conditions to or are at least 80% identical to a nucleic acid represented by one of SEQ ID Nos. 1–544, preferably SEQ ID Nos. 1–168, even more preferably SEQ ID Nos. 1–35, or a sequence complementary thereto) up to a maximum length suitable for one or more biological manipulations, including replication and expression, of the nucleic acid molecule. The invention includes but is not limited to (a) nucleic acid having the size of a full gene, and comprising at least one of SEQ ID Nos. 1–544, preferably SEQ ID Nos. 1–168, even more preferably SEQ ID Nos. 1–35, or a sequence complementary thereto; (b) the nucleic acid of (a) also comprising at least one additional gene, operably linked to permit expression of a fusion protein; (c) an expression vector comprising (a) or (b); (d) a plasmid comprising (a) or (b); and (e) a recombinant viral particle comprising (a) or (b). Construction of (a) can be accomplished as described below in part IV.

The sequence of a nucleic acid of the present invention is not limited and can be any sequence of A, T, G, and/or C (for DNA) and A, U, G, and/or C (for RNA) or modified bases thereof, including inosine and pseudouridine. The choice of sequence will depend on the desired function and can be dictated by coding regions desired, the intron-like regions desired, and the regulatory regions desired.

VI. Vectors Carrying Nucleic Acids of the Present Invention

The invention further provides plasmids and vectors, which can be used to express a gene in a host cell. The host cell may be any prokaryotic or eukaryotic cell. Thus, a nucleotide sequence derived from any one of SEQ ID Nos. 1–544, preferably SEQ ID Nos. 1–168, even more preferably SEQ ID Nos. 1–35, or a sequence complementary thereto, encoding all or a selected portion of a protein, can be used to produce a recombinant form of an polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures well known in the art.

Vectors that allow expression of a nucleic acid in a cell are referred to as expression vectors. Typically, expression vectors contain a nucleic acid operably linked to at least one transcriptional regulatory sequence. Regulatory sequences are art-recognized and are selected to direct expression of the subject nucleic acids. Transcriptional regulatory sequences are described in Goeddel; Gene Expression Technology: Methods in Enzymology 185, Academic Press, San Diego, Calif. (1990). In one embodiment, the expression vector includes a recombinant gene encoding a peptide having an agonistic activity of a subject polypeptide, or alternatively, encoding a peptide which is an antagonistic form of a subject polypeptide.

The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The nucleic acid or full-length gene is inserted into a vector typically by means of DNA ligase attachment to a cleaved restriction enzyme site in the vector. Alternatively, the desired nucleotide sequence may be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence.

Nucleic acids or full-length genes are linked to regulatory sequences as appropriate to obtain the desired expression properties. These may include promoters (attached either at the 5' end of the sense strand or at the 3' end of the antisense strand), enhancers, terminators, operators, repressors, and inducers. The promoters may be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art may be used.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to the nucleic acid is identified, its expression can be regulated in the cell to which the gene is native. For example, an endogenous gene of a cell can be regulated by an exogenous regulatory sequence as disclosed in U.S. Pat. No. 5,641,670, "Protein Production and Protein Delivery." A number of vectors exist for the expression of recombinant proteins in yeast (see, for example, Broach et al. (1983) in Experimental Manipulation of Gene Expression, ed. M. Inouye, Academic Press, p. 83, incorporated by reference herein). In addition, drug resistance markers such as ampicillin can be used. In an illustrative embodiment, a polypeptide is produced recombinantly utilizing an expression vector generated by subcloning one of the nucleic acids represented in one of SEQ ID Nos. 1–544, preferably SEQ ID Nos. 1–168, even more preferably SEQ ID Nos. 1–35, or a sequence complementary thereto.

The preferred mammalian expression vectors contain both prokaryotic sequences, to facilitate the propagation of the vector in bacteria, and one or more eukaryotic transcription units that are expressed in eukaryotic cells. The various methods employed in the preparation of plasmids and transformation of host organisms are well known in the art. For other suitable expression systems for both prokaryotic and eukaryotic cells, as well as general recombinant procedures, see *Molecular Cloning: A Laboratory Manual, 2nd Ed.,* ed. by Sambrook, Fritsch and Maniatis (Cold Spring Harbor Laboratory Press: 1989) Chapters 16 and 17. When it is desirable to express only a portion of a gene, e.g., a truncation mutant, it may be necessary to add a start codon (ATG) to the oligonucleotide fragment containing the desired sequence to be expressed. It is well known in the art that a methionine at the N-terminal position can be enzyrnatically cleaved by the use of the enzyme methionine aminopeptidase (MAP). MAP has been cloned from *E. coli* (Ben-Bassat et al. (1987) J. Bacteriol. 169:751–757) and Salmonella typhimurium and its in vitro activity has been demonstrated on recombinant proteins (Miller et al. (1987) PNAS 84:2718–1722). Therefore, removal of an N-terminal methionine, if desired, can be achieved either in vivo by expressing polypeptides in a host which produces MAP (e.g., *E. coli* or CM89 or S. cerevisiae), or in vitro by use of purified MAP (e.g., procedure of Miller et al., supra).

Moreover, the nucleic acid constructs of the present invention can also be used as part of a gene therapy protocol to deliver nucleic acids such as antisense nucleic acids. Thus, another aspect of the invention features expression vectors for in vivo or in vitro transfection with an antisense oligonucleotide.

In addition to viral transfer methods, non-viral methods can also be employed to introduce a subject nucleic acid, e.g., a sequence represented by one of SEQ ID Nos. 1–544, preferably SEQ ID Nos. 1–168, even more preferably SEQ ID Nos. 1–35, or a sequence complementary thereto, into the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject nucleic acid by the targeted cell. Exemplary targeting means of this type include liposomal derived systems, polylysine conjugates, and artificial viral envelopes.

A nucleic acid of any of SEQ ID Nos. 1–544, preferably SEQ ID Nos. 1–168, even more preferably SEQ ID Nos. 1–35, or a sequence complementary thereto, the corresponding cDNA, or the full-length gene may be used to express the partial or complete gene product. Appropriate nucleic acid constructs are purified using standard recombinant DNA techniques as described in, for example, Sambrook et al., (1989) Molecular Cloning: A Laboratory Manual, 2nd ed. (Cold Spring Harbor Press, Cold Spring Harbor, New York), and under current regulations described in United States Dept. of HHS, National Institute of Health (NIH) Guidelines for Recombinant DNA Research. The polypeptides encoded by the nucleic acid may be expressed in any expression system, including, for example, bacterial, yeast, insect, amphibian and mammalian systems. Suitable vectors and host cells are described in U.S. Pat. No. 5,654,173.

Bacteria. Expression systems in bacteria include those described in Chang et al., *Nature* (1978) 275:615, Goeddel et al., *Nature* (1979) 281:544, Goeddel et al., *Nucleic Acids Res.* (1980) 8:4057; EP 0 036,776, U.S. Pat. No. 4,551,433, DeBoer et al., *Proc. Natl. Acad. Sci.* (*USA*) (1983) 80:2125, and Siebenlist et al., *Cell* (1980) 20:269.

Yeast. Expression systems in yeast include those described in Hinnen et al., *Proc. Natl. Acad. Sci.* (*USA*) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459, Roggenkamp et al., *Mol. Gen. Genet.* (1986) 202:302) Das et al., *J. Bacteriol.* (1984) 158:1165; De Louvencourt et al., *J. Bacteriol.* (1983) 154:737, Van den Berg et al., *Bio/Technology* (1990)8:135; Kunze et al., *J. Basic Microbiol.* (1985)25:141; Cregg et al., *Mol. Cell. Biol.* (1985) 5:3376, U.S. Pat. Nos. 4,837,148 and 4,929,555; Beach and Nurse, *Nature* (1981) 300:706; Davidow et al., *Curr. Genet.* (1985) 10:380, Gaillardin et al., *Curr. Genet.* (1985) 10:49, Ballance et al., *Biochem. Biophys. Res. Commun.* (1983) 112:284289; Tilburn et al., *Gene* (1983) 26:205221, Yelton et al., *Proc. Natl. Acad. Sci.* (*USA*) (1984) 81:14701474, Kelly and Hynes, *EMBO J.* (1985) 4:475479; EP 0 244,234, and WO 91/00357.

Insect Cells. Expression of heterologous genes in insects is accomplished as described in U.S. Pat. No. 4,745,051, Friesen et al. (1986) "The Regulation of Baculovirus Gene Expression" in: The Molecular Biology Of Baculoviruses (W. Doerfler, ed.), EP 0 127,839, EP 0 155,476, and Vlak et al., *J. Gen. Virol.* (1988) 69:765776, Miller et al., *Ann. Rev. Microbiol.* (1988) 42:177, Carbonell et al., *Gene* (1988) 73:409, Maeda et al., *Nature* (1985) 315:592594, Lebacq Verheyden et al., *Mol. Cell. Biol.* (1988) 8:3129; Smith et al., *Proc. Natl. Acad. Sci.* (*USA*) (1985) 82:8404, Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:4755, Miller et al., Generic Engineering (Setlow, J. K. et al. eds.), Vol. 8 (Plenum Publishing, 1986), pp. 277279, and Maeda et al., *Nature,* (1985) 315:592–594.

Mammalian Cells. Mammalian expression is accomplished as described in Dijkema et al., *EMBO J.* (1985) 4:761, Gorman et al., *Proc. Natl. Acad. Sci.* (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

VII. Therapeutic Nucleic Acid Constructs

One aspect of the invention relates to the use of the isolated nucleic acid, e.g., SEQ ID Nos. 1–544, preferably SEQ ID Nos. 1–168, even more preferably SEQ ID Nos. 1–35, or a sequence complementary thereto, in antisense therapy. As used herein, antisense therapy refers to administration or in situ generation of oligonucleotide molecules or their derivatives which specifically hybridize (e.g., bind) under cellular conditions with the cellular mRNA and/or genomic DNA, thereby inhibiting transcription and/or translation of that gene. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA. Alternatively, the antisense construct is an oligonucleotide probe which is generated ex vivo and which, when introduced into the cell, causes inhibition of expression by hybridizing with the mRNA and/or genomic sequences of a subject nucleic acid. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958–976; and Stein et al. (1988) Cancer Res 48:2659–2668. With respect to antisense DNA, oligodeoxyribonucleotides derived from the translation initiation site, e.g., between the −10 and +10 regions of the nucleotide sequence of interest, are preferred.

Antisense approaches involve the design of oligonucleotides (either DNA or RNA) that are complementary to mRNA. The antisense oligonucleotides will bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a gene could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are typically less efficient inhibitors of translation but could also be used in accordance with the invention. Whether designed to hybridize to the 5', 3', or coding region of subject mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or the blood-brain barrier (see, e.g., PCT Publication No. WO 89/10134, published Apr. 25, 1988), hybridization-triggered cleavage agents (See, e.g., Krol et al., 1988, BioTechniques 6:958–976), or intercalating agents (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytriethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–12148), or a chimeric RNA-DNA analogue (Inoue et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olgonucleotides can be prepared by use of controlled pore glass polymer supports (Sarin et al., 1988, Proc. Natl. Acad. Sci. U.S.A. 85:7448–7451), etc.

While antisense nucleotides complementary to a coding region sequence can be used, those complementary to the transcribed untranslated region and to the region comprising the initiating methionine are most preferred.

The antisense molecules can be delivered to cells which express the target nucleic acid in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation on endogenous mRNAs. Therefore, a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous transcripts and thereby prevent translation of the target mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue (e.g., for brain, herpesvirus vectors may be used), in which case administration may be accomplished by another route (e.g., systemically).

In another aspect of the invention, ribozyme molecules designed to catalytically cleave target mRNA transcripts can be used to prevent translation of target mRNA and expression of a target protein (See, e.g., PCT International Publication WO90/11364, published Oct. 4, 1990; Sarver et al., 1990, Science 247:1222–1225 and U.S. Pat. No. 5,093,246). While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. Preferably the ribozyme is engineered so that the cleavage recognition site is located near the 5' end of the target mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. W088/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene.

As in the antisense approach, the ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous messages and inhibit translation. Because ribozymes, unlike antisense molecules, are catalytic, a lower intracellular concentration is required for efficiency.

Antisense RNA, DNA, and ribozyme molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

VIII. Polypeptides of the Present Invention

The present invention makes available isolated polypeptides which are isolated from, or otherwise substantially free of other cellular proteins, especially other signal transduction factors and/or transcription factors which may normally be associated with the polypeptide. Subject polypeptides of the present invention include polypeptides encoded by the nucleic acids of SEQ ID Nos. 1–544, preferably SEQ ID Nos. 1–168, even more preferably SEQ ID Nos. 1–35, or a sequence complementary thereto, or polypeptides encoded by genes of which a sequence in SEQ ID Nos. 1–544, preferably SEQ ID Nos. 1–168, even more preferably SEQ ID Nos. 1–35, or a sequence complementary thereto, is a fragment. Polypeptides of the present invention include those proteins which are differentially regulated in tumor cells, especially colon cancer-derived cell lines (relative to normal cells, e.g., normal colon tissue and non-colon tissue). In preferred embodiments, the polypeptides are upregulated in tumor cells, especially colon cancer cancer-derived cell lines. In other embodiments, the polypeptides are downregulated in tumor cells, especially colon cancer-derived cell lines. Proteins which are upregulated, such as oncogenes, or downregulated, such as tumor suppressors, in aberrantly proliferating cells may be targets for diagnostic or therapeutic techniques. For example, upregulation of the cdc2 gene induces mitosis. Overexpression of the myt1 gene, a mitotic deactivator, negatively regulates the activity of cdc2. Aberrant proliferation may thus be induced either by upregulating cdc2 or by downregulating myt1.

The term "substantially free of other cellular proteins" (also referred to herein as "contaminating proteins") or "substantially pure or purified preparations" are defined as encompassing preparations of polypeptides having less than about 20% (by dry weight) contaminating protein, and preferably having less than about 5% contaminating protein. Functional forms of the subject polypeptides can be prepared, for the first time, as purified preparations by using a cloned nucleic acid as described herein. Full length proteins or fragments corresponding to one or more particular motifs and/or domains or to arbitrary sizes, for example, at least about 5, 10, 25, 50, 75, or 100 amino acids in length are within the scope of the present invention.

For example, isolated polypeptides can be encoded by all or a portion of a nucleic acid sequence shown in any of SEQ ID Nos. 1–544, preferably SEQ ID Nos. 1–168, even more preferably SEQ ID Nos. 1–35, or a sequence complementary thereto. Isolated peptidyl portions of proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") protein.

Another aspect of the present invention concerns recombinant forms of the subject proteins. Recombinant polypeptides preferred by the present invention, in addition to native proteins, as described above are encoded by a nucleic acid, which is at least 60%, more preferably at least 80%, and more preferably 85%, and more preferably 90%, and more preferably 95% identical to an amino acid sequence encoded by SEQ ID Nos. 1–544. Polypeptides which are encoded by a nucleic acid that is at least about 98–99% identical with the sequence of SEQ ID Nos. 1–544 are also within the scope of the invention. Also included in the present invention are peptide fragments comprising at least a portion of such a protein.

In a preferred embodiment, a polypeptide of the present invention is a mammalian polypeptide and even more preferably a human polypeptide. In particularly preferred embodiment, the polypeptide retains wild-type bioactivity. It will be understood that certain post-translational modifications, e.g., phosphorylation and the like, can increase the apparent molecular weight of the polypeptide relative to the unmodified polypeptide chain.

The present invention further pertains to recombinant forms of one of the subject polypeptides. Such recombinant polypeptides preferably are capable of functioning in one of either role of an agonist or antagonist of at least one biological activity of a wild-type ("authentic") polypeptide of the appended sequence listing. The term "evolutionarily related to", with respect to amino acid sequences of proteins, refers to both polypeptides having amino acid sequences which have arisen naturally, and also to mutational variants of human polypeptides which are derived, for example, by combinatorial mutagenesis.

In general, polypeptides referred to herein as having an activity (e.g., are "bioactive") of a protein are defined as polypeptides which include an amino acid sequence encoded by all or a portion of the nucleic acid sequences shown in one of SEQ ID Nos. 1–544, preferably SEQ ID Nos. 1–168, even more preferably SEQ ID Nos. 1–35, or a sequence complementary thereto, and which mimic or antagonize all or a portion of the biological/biochemical activities of a naturally occurring protein. According to the present invention, a polypeptide has biological activity if it is a specific agonist or antagonist of a naturally occurring form of a protein.

Assays for determining whether a compound, e.g, a protein or variant thereof, has one or more of the above biological activities are well known in the art. In certain embodiments, the polypeptides of the present invention have activities such as those outlined above.

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a polypeptide (see, for example, EP Publication No: 0259149; and Evans et al. (1989) Nature 339:385; Huang et al. (1988) J. Virol. 62:3855; and Schlienger et al. (1992) J. Virol. 66:2). In addition to utilizing fusion proteins to enhance immunogenicity, it is widely appreciated that fusion proteins can also facilitate the expression of proteins, and, accordingly, can be used in the expression of the polypeptides of the present invention (see, for example, Current Protocols in Molecular Biology, eds. Ausubel et al. (N.Y.: John Wiley & Sons, 1991)). In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a $Ni^{2+}$ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of nucleic acid fragments can be carried out using anchor primers which give rise to complementary overhangs between two consecutive nucleic acid fragments which can subsequently be annealed to generate a chimeric nucleic acid sequence (see, for example, Current Protocols in Molecular Biology, eds. Ausubel et al. John Wiley & Sons: 1992).

The present invention further pertains to methods of producing the subject polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant polypeptide is a fusion protein containing a domain which facilitates its purification, such as GST fusion protein.

Moreover, it will be generally appreciated that, under certain circumstances, it may be advantageous to provide homologs of one of the subject polypeptides which function in a limited capacity as one of either an agonist (mimetic) or an antagonist, in order to promote or inhibit only a subset of the biological activities of the naturally occurring form of the protein. Thus, specific biological effects can be elicited by treatment with a homolog of limited function, and with fewer side effects relative to treatment with agonists or antagonists which are directed to all of the biological activities of naturally occurring forms of subject proteins.

Homologs of each of the subject polypeptide can be generated by mutagenesis, such as by discrete point mutation(s), or by truncation. For instance, mutation can give rise to homologs which retain substantially the same, or merely a subset, of the biological activity of the polypeptide from which it was derived. Alternatively, antagonistic forms of the polypeptide can be generated which are able to inhibit the function of the naturally occurring form of the protein, such as by competitively binding to a receptor.

The recombinant polypeptides of the present invention also include homologs of the wild-type proteins, such as versions of those proteins which are resistant to proteolytic cleavage, for example, due to mutations which alter ubiquitination or other enzymatic targeting associated with the protein.

Polypeptides may also be chemically modified to create derivatives by forming covalent or aggregate conjugates with other chemical moieties, such as glycosyl groups, lipids, phosphate, acetyl groups and the like. Covalent derivatives of proteins can be prepared by linking the chemical moieties to functional groups on amino acid sidechains of the protein or at the N-terminus or at the C-terminus of the polypeptide.

Modification of the structure of the subject polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally occurring form of the protein, or to produce specific antagonists thereof, are considered functional equivalents of the polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e., isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, $2^{nd}$ ed., Ed. by L. Stryer, W H Freeman and Co.: 1981). Whether a change in the amino acid sequence of a peptide results in a functional homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner. The variant may be designed so as to retain biological activity of a particular region of the protein. In a non-limiting example, Osawa et al., 1994, *Biochemistry and Molecular International* 34:1003–1009, discusses the actin binding region of a protein from several different species. The actin binding regions of the these species are considered homologous based on the fact that they have amino acids that fall within "homologous residue groups." Homologous residues are judged according to the following groups (using single letter amino acid designations): STAG; ILVMF; HRK; DEQN; and FYW. For example, an S, a T, an A or a G can be in a position and the function (in this case actin binding) is retained.

Additional guidance on amino acid substitution is available from studies of protein evolution. Go et al., 1980, *Int. J. Peptide Protein Res.* 15:211–224, classified amino acid residue sites as interior or exterior depending on their accessibility. More frequent substitution on exterior sites was confirmed to be general in eight sets of homologous protein families regardless of their biological functions and the presence or absence of a prosthetic group. Virtually all types of amino acid residues had higher mutabilities on the exterior than in the interior. No correlation between mutability and polarity was observed of amino acid residues in the interior and exterior, respectively. Amino acid residues were classified into one of three groups depending on their polarity: polar (Arg, Lys, His, Gln, Asn, Asp, and Glu); weak polar (Ala, Pro, Gly, Thr, and Ser), and nonpolar (Cys, Val, Met, Ile, Leu, Phe, Tyr, and Trp). Amino acid replacements during protein evolution were very conservative: 88% and 76% of them in the interior or exterior, respectively, were within the same group of the three. Inter-group replacements are such that weak polar residues are replaced more often by nonpolar residues in the interior and more often by polar residues on the exterior.

Querol et al., 1996, *Prot. Eng.* 9:265–271, provides general rules for amino acid substitutions to enhance protein thermostability. New glycosylation sites can be introduced as discussed in Olsen and Thomsen, 1991, *J. Gen. Microbiol.* 137:579–585. An additional disulfide bridge can be introduced, as discussed by Perry and Wetzel, 1984, *Science* 226:555–557; Pantoliano et al., 1987, *Biochemistry* 26:2077–2082; Matsumura et al., 1989, *Nature* 342:291–293; Nishikawa et al., 1990, *Protein Eng.* 3:443–448; Takagi et al., 1990, *J. Biol. Chem.* 265:6874–6878; Clarke et al., 1993, *Biochemistry* 32:4322–4329; and Wakarchuk et al., 1994, *Protein Eng.* 7:1379–1386.

An additional metal binding site can be introduced, according to Toma et al., 1991, *Biochemistry* 30:97–106, and Haezerbrouck et al., 1993, *Protein Eng.* 6:643–649. Substitutions with prolines in loops can be made according to Masul et al., 1994, *Appl. Env. Microbiol.* 60:3579–3584; and Hardy et al., *FEBS Lett.* 317:89–92.

Cysteine-depleted muteins are considered variants within the scope of the invention. These variants can be constructed according to methods disclosed in U.S. Pat. No. 4,959,314, which discloses how to substitute other amino acids for cysteines, and how to determine biological activity and effect of the substitution. Such methods are suitable for proteins according to this invention that have cysteine residues suitable for such substitutions, for example to eliminate disulfide bond formation.

To learn the identity and function of the gene that correlates with an nucleic acid, the nucleic acids or corresponding amino acid sequences can be screened against profiles of protein families. Such profiles focus on common structural motifs among proteins of each family. Publicly available profiles are described above. Additional or alternative profiles are described below.

In comparing a new nucleic acid with known sequences, several alignment tools are available. Examples include PileUp, which creates a multiple sequence alignment, and is described in Feng et al., *J. Mol. Evol. (*1987) 25:351–360. Another method, GAP, uses the alignment method of Needleman et al., *J. Mol. Biol.* (1970) 48:443–453. GAP is best suited for global alignment of sequences. A third method, BestFit, functions by inserting gaps to maximize the number of matches using the local homology algorithm of Smith and Waterman, *Adv. Appl. Math.* (1981) 2:482–489.

Examples of such profiles are described below.

Chemokines

Chemokines are a family of proteins that have been implicated in lymphocyte trafficking, inflammatory diseases, angiogenesis, hematopoiesis, and viral infection. See, for example, Rollins, *Blood* (1997) 90(3):909–928, and Wells et al., *J. Leuk. Biol.* (1997) 61:545–550. U.S. Pat. No. 5,605, 817 discloses DNA encoding a chemokine expressed in fetal spleen. U.S. Pat. No. 5,656,724 discloses chemokine-like proteins and methods of use. U.S. Pat. No. 5,602,008 discloses DNA encoding a chemokine expressed by liver.

Mutants of the encoded chemokines are polypeptides having an amino acid sequence that possesses at least one amino acid substitution, addition, or deletion as compared to native chemokines. Fragments possess the same amino acid sequence of the native chemokines; mutants may lack the amino and/or carboxyl terminal sequences. Fusions are mutants, fragments, or the native chemokines that also include amino and/or carboxyl terminal amino acid extensions.

The number or type of the amino acid changes is not critical, nor is the length or number of the amino acid deletions, or amino acid extensions that are incorporated in the chemokines as compared to the native chemokine amino acid sequences. A polynucleotide encoding one of these variant polypeptides will retain at least about 80% amino acid identity with at least one known chemokine. Preferably, these polypeptides will retain at least about 85% amino acid sequence identity, more preferably, at least about 90%; even more preferably, at least about 95%. In addition, the variants will exhibit at least 80%; preferably about 90%; more preferably about 95% of at least one activity exhibited by a native chemokine. Chemokine activity includes immunological, biological, receptor binding, and signal transduction functions of the native chemokine.

Chemotaxis. Assays for chemotaxis relating to neutrophils are described in Walz et al., *Biochem. Biophys. Res. Commun.* (1987) 149:755, Yoshimura et al., *Proc. Natl. Acad. Sci.* (*USA*) (1987) 84:9233, and Schroder et al., *J. Immunol.* (1987) 139:3474; to lymphocytes, Larsen et al., Science (1989) 243:1464, Carr et al., *Proc. Natl. Acad. Sci.* (*USA*) (1994) 91:3652; to tumor-infiltrating lymphocytes, Liao et al., *J. Exp. Med* (1995). 182:1301; to hemopoietic progenitors, Aiuti et al., *J. Exp. Med.* (1997) 185:111; to monocytes, Valente et al., *Biochem.* (1988) 27:4162; and to natural killer cells, Loetscher et al., *J. Immunol.* (1996) 156:322, and Allavena et al., *Eur. J. Immunol.* (1994) 24:3233.

Assays for determining the biological activity of attracting cosinophils are described in Dahinden et al., *J. Exp. Med.* (1994) 179:751, Weber et al., *J. Immunol.* (1995) 154:4166, and Noso et al., *Biochem. Biophys. Res. Commun.* (1994) 200:1470; for attracting dendritic cells, Sozzani et al., *J. Immunol.* (1995) 155:3292; for attracting basophils, in Dahinden et al., *J. Exp. Med.* (1994) 179:751, Alam et al., *J. Immunol.* (1994) 152:1298, Alam et al., *J. Exp. Med.* (1992) 176:781; and for activating neutrophils, Maghazaci et al., *Eur. J. Immunol.* (1996) 26:315, and Taub et al., *J. Immunol.* (1995) 155:3877. Native chemokines can act as mitogens for fibroblasts, assayed as described in Mullenbach et al., *J. Biol Chem.* (1986) 261:719.

Receptor Binding. Native chemokines exhibit binding activity with a number of receptors. Description of such receptors and assays to detect binding are described in, for example, Murphy et al., *Science* (1991) 253:1280; Combadiere et al., *J. Biol. Chem.* (1995) 270:29671; Daugherty et al., *J. Exp. Med.* (1996) 183:2349; Samson et al., *Biochem.* (1996) 35:3362; Raport et al., *J. Biol. Chem.* (1996) 271:17161; Combadiere et al., *J. Leukoc. Biol.* (1996) 60:147; Baba et al., *J. Biol. Chem.* (1997) 23:14893; Yosida et al., *J. Biol. Chem.* (1997) 272:13803; Arvannitakis et al., *Nature* (1997) 385:347, and many other assays are known in the art.

Kinase Activiation. Assays for kinase activation are described by Yen et al., *J. Leukoc. Biol.* (1997) 61:529; Dubois et al., *J. Immunol.* (1996) 156:1356; Turner et al., *J. Immunol.* (1995) 155:2437. Assays for inhibition of angiogenesis or cell proliferation are described in Maione et al., *Science* (1990) 247:77. Glycosaminoglycan production can be induced by native chemokines, assayed as described in Castor et al., *Proc. Natl. Acad. Sci.* (*USA*) (1983) 80:765. Chemokine-mediated histamine release from basophils is assayed as described in Dahinden et al., *J. Exp. Med.* (1989) 170:1787; and White et al., *Immunol. Lett.* (1989) 22:151. Heparin binding is described in Luster et al., *J. Exp. Med.* (1995) 182:219.

Dimerization Activity. Chemokines can possess dimerization activity, which can be assayed according to Burrows et al., *Biochem.* (1994) 33:12741; and Zhang et al., *Mol. Cell. Biol.* (1995) 15:4851. Native chemokines can play a role in the inflammatory response of viruses. This activity can be assayed as described in Bleul et al., *Nature* (1996) 382:829; and Oberlin et al., *Nature* (1996) 382:833. Exocytosis of monocytes can be promoted by native chemokines. The assay for such activity is described in Uguccioni et al., *Eur. J. Immunol.* (1995) 25:64. Native chemokines also can inhibit hemapoietic stem cell proliferation. The method for testing for such activity is reported in Graham et al., *Nature* (1990) 344:442.

Death Domain Proteins Several protein families contain death domain motifs (Feinstein and Kimchi, *TIBS Letters* (1995) 20:242–244). Some death domain-containing proteins are implicated in cytotoxic intracellular signaling (Cleveland and Ihle, *Cell* (1995) 81:479–482, Pan et al, *Science* (1997) 276:111–113, Duan and Dixit, *Nature* (1997) 385:86–89, and Chinnaiyan et al, *Science* (1996) 274:990–992). U.S. Pat. No. 5,563,039 describes a protein homologous to TRADD (Tumor Necrosis Factor Receptor-1 Associated Death Domain containing protein), and modifications of the active domain of TRADD that retain the functional characteristics of the protein, as well as apoptosis assays for testing the function of such death domain containing proteins. U.S. Pat. No. 5,658,883 discloses biologically active TGF-B1 peptides. U.S. Pat. No. 5,674,734 discloses protein RIP which contains a C-terminal death domain and an N-terminal kinase domain.

Leukemia Inhibitory Factor (LIF) An LIF profile is constructed from sequences of leukemia inhibitor factor, CT-1 (cardiotrophin-1), CNTF (ciliary neurotrophic factor), OSM (oncostatin M), and IL-6 (interleukin-6). This profile encompasses a family of secreted cytokines that have pleiotropic effects on many cell types including hepatocytes, osteoclasts, neuronal cells and cardiac myocytes, and can be used to detect additional genes encoding such proteins. These molecules are all structurally related and share a common co-receptor gp130 which mediates intracellular signal transduction by cytoplasmic tyrosine kinases such as src.

Novel proteins related to this family are also likely to be secreted, to activate gp130 and to function in the development of a variety of cell types. Thus new members of this family would be candidates to be developed as growth or survival factors for the cell types that they stimulate. For more details on this family of cytokines, see Pennica et al, *Cytokine and Growth Factor Reviews* (1996) 7:81–91. U.S. Pat. No. 5,420,247 discloses LIF receptor and fusion proteins. U.S. Pat. No. 5,443,825 discloses human LIF.

Angiopoietin Angiopoietin-1 is a secreted ligand of the TIE-2 tyrosine kinase; it functions as an angiogenic factor critical for normal vascular development. Angiopoietin-2 is a natural antagonist of angiopoietin-1and thus functions as an anti-angiogenic factor. These two proteins are structurally similar and activate the same receptor. (Folkman and D'Amore, *Cell* (1996) 87:1153–1155, and Davis et al., *Cell* (1996) 87:1161–1169.)

The angiopoietin molecules are composed of two domains, a coiled-coil region and a region related to fibrinogen. The fibrinogen domain is found in many molecules including ficolin and tesascin, and is well defined structurally with many members.

Receptor Protein-Tyrosine Kinases Receptor Protein-Tyrosine Kinases or RPTKs are described in Lindberg, *Annu. Rev. Cell Biol.* (1994) 10:251–337.

Growth Factors: Epidermal Growth Factor (EGF) and Fibroblast Growth Factor (FGF) For a discussion of growth factor superfamilies, see *Growth Factors: A Practical Approach*, Appendix A1 (Ed. McKay and Leigh, Oxford University Press, NY, 1993) pp. 237–243.

The alignments (pretty box) for EGF and FGF are shown in FIGS. 1 and 2, respectively. U.S. Pat. No. 4,444,760 discloses acidic brain fibroblast growth factor, which is active in the promotion of cell division and wound healing. U.S. Pat. No. 5,439,818 discloses DNA encoding human recombinant basic fibroblast growth factor, which is active in wound healing. U.S. Pat. No. 5,604,293 discloses recombinant human basic fibroblast growth factor, which is useful for wound healing. U.S. Pat. No. 5,410,832 discloses brain-derived and recombinant acidic fibroblast growth factor, which act as mitogens for mesoderm and neuroectoderm-derived cells in culture, and promote wound healing in soft tissue, cartilaginous tissue and musculo-skeletal tissue. U.S. Pat. No. 5,387,673 discloses biologically active fragments of FGF that retain activity.

Proteins of the TNF Family A profile derived from the TNF family is created by aligning sequences of the following TNF family members: nerve growth factor (NGF), lymphotoxin, Fas ligand, tumor necrosis factor (TNF ), CD40 ligand, TRAIL, ox40 ligand, 4-1BB ligand, CD27 ligand, and CD30 ligand. The profile is designed to identify sequences of proteins that constitute new members or homologues of this family of proteins.

U.S. Pat. No. 5,606,023 discloses mutant TNF proteins; U.S. Pat. No. 5,597,899 and U.S. Pat. No. 5,486,463 disclose TNF muteins; and U.S. Pat. No. 5,652,353 discloses DNA encoding TNF-α muteins.

Members of the TNF family of proteins have been show in vitro to multimerize, as described in Burrows et al., *Biochem.* (1994) 33:12741 and Zhang et al., *Mol. Cell. Biol.* (1995) 154851 and bind receptors as described in Browning et al., *J. Immunol.* (1994) 147:1230, Androlewicz et al., *J. Biol. Chem.*(1992) 267:2542, and Crowe et al., *Science* (1994) 264:707.

In vivo, TNFs proteolytically cleave a target protein as described in Kriegel et al., *Cell* (1988) 53:45 and Mohler et al., *Nature* (1994) 370:218 and demonstrate cell proliferation and differentiation activity. T-cell or thymocyte proliferation is assayed as described in Armitage et al., *Eur. J. Immunol.* (1992) 22:447; Current Protocols in Immunology, ed. J. E. Coligan et al., 3.1–3.19; Takai et al., *J. Immunol.* (1986) 137:3494–3500, Bertagnoli et al., *J. Immunol.* (1990) 145:1706–1712, Bertagnoli et al., *J. Immunol.* (1991) 133:327–340, Bertagnoli et al., *J. Immunol.* (1992) 149:3778–3783, and Bowman et al., *J. Immunol.* (1994) 152:1756–1761. B cell proliferation and Ig secretion are assayed as described in Maliszewski, *J. Immunol.* (1990) 144:3028–3033, and Assays for B Cell Function: In vitro antibody production, Mond and Brunswick, Current Protocols in Immunol., Coligan Ed vol 1 pp 3.8.1–3.8.16, John Wiley and Sons, Toronto 1994, Kehrl et al., *Science* (1987) 238:1144 and Boussiotis et al., *PNAS USA* (1994) 91:7007.

Other in vivo activities include upregulation of cell surface antigens, upregulation of costimulatory molecules, and cellular aggregation/adhesion as described in Barrett et al., *J. Immunol.* (1991) 146:1722; Bjorck et al., *Eur. J. Immunol.* (1993) 23:1771; Clark et al., *Annu Rev. Immunol.* (1991) 9:97; Ranheim et al., *J. Exp. Med.* (1994) 177:925; Yellin, *J. Immunol.* (1994) 153:666; and Gruss et al., *Blood* (1994) 84:2305.

Proliferation and differentiation of hematopoietic and lymphopoietic cells has also been shown in vivo for TNFs, using assays for embryonic differentiation and hematopoiesis as described in Johansson et al., *Cellular Biology* (1995) 15:141–151, Keller et al., *Mol. Cell. Biol.* (1993) 13:473–486, McClanahan et al., *Blood* (1993) 81:2903–2915 and using assays to detect stem cell survival and differentiation as described in Culture of Hematopoietic Cells, Freshney et al. eds, pp 1–21, 23–29, 139–162, 163–179, and 265–268, Wiley-Liss, Inc., New York, N.Y., 1994, and Hirajama et al., *PNAS USA* (1992) 89:5907–5911.

In vivo activities of TNFs also include lymphocyte survival and apoptosis, assayed as described in Darzynkewicz et al., *Cytometry* (1992) 13:795–808; Gorczca et al., *Leukemia* (1993) 7:659–670; Itoh et al., Cell (1991) 66:233–243; Zacharduk, *J. Immunol.* (1990) 145:4037–4045; Zamai et al., *Cytometry* (1993) 14:891–897; and Gorczyca et al., *Int'l J. Oncol.* (1992) 1:639–648.

Some members of the TNF family are cleaved from the cell surface; others remain membrane bound. The three-dimensional structure of TNF is discussed in Sprang and Eck, Tumor Necrosis Factors; supra.

TNF proteins include a transmembrane domain. The protein is cleaved into a shorter soluble version, as described in Kriegler et al., *Cell* (1988) 53:45–53, Perez et al., *Cell* (1990) 63:251–258, and Shaw et al., *Cell* (1986) 46:659–667. The transmembrane domain is between amino acid 46 and 77 and the cytoplasmic domain is between position 1 and 45 on the human form of TNFα-(. The 3-dimensional motifs of TNF include a sandwich of two pleated β-sheets. Each sheet is composed of anti-parallel α-strands. α-Strands facing each other on opposite sites of the sandwich are connected by short polypeptide loops, as described in Van Ostade et al., *Protein Engineering* (1994) 7(1):5–22, and Sprang et al., Tumor Necrosis Factors; supra.

Residues of the TNF family proteins that are involved in the β-sheet secondary structure have been identified as described in Van Ostade et al., *Protein Engineering* (1994) 7(1):5–22, and Sprang et al., Tumor Necrosis Factors; supra.

TNF receptors are disclosed in U.S. Pat. No. 5,395,760. A profile derived from the TNF receptor family is created by aligning sequences of the TNF receptor family, including Apo1/Fas, TNFR I and II, death receptor3 (DR3), CD40, ox40, CD27, and CD30. Thus, the profile is designed to identify, from the nucleic acids of the invention, sequences of proteins that constitute new members or homologs of this family of proteins.

Tumor necrosis factor receptors exist in two forms in humans: p55 TNFR and p75 TNFR, both of which provide intracellular signals upon binding with a ligand. The extracellular domains of these receptor proteins are cysteine rich. The receptors can remain membrane bound, although some forms of the receptors are cleaved forming soluble receptors. The regulation, diagnostic, prognostic, and therapeutic value of soluble TNF receptors is discussed in Aderka, *Cytokine and Growth Factor Reviews,* (1996) 7(3):231–240.

PDGF Family U.S. Pat. No. 5,326,695 discloses platelet derived growth factor agonists; bioactive portions of PDGF-B are used as agonists. U.S. Pat. No. 4,845,075 discloses biologically active B-chain homodimers, and also includes variants and derivatives of the PDGF-B chain. U.S. Pat. No. 5,128,321 discloses PDGF analogs and methods of use. Proteins having the same bioactivity as PDGF are disclosed, including A and B chain proteins.

Kinase (Including MKK) Family U.S. Pat. No. 5,650,501 discloses serine/threonine kinase, associated with mitotic and meiotic cell division; the protein has a kinase domain in its N-terminal and 3 PEST regions in the C-terminus. U.S. Pat. No. 5,605,825 discloses human PAK65, a serine protein kinase.

The foregoing discussion provides a few examples of the protein profiles that can be compared with the nucleic acids of the invention. One skilled in the art can use these and other protein profiles to identify the genes that correlate with the nucleic acids.

IX. Determinin2 the Function of the Encoded Expression Products

Ribozymes, antisense constructs, dominant negative mutants, and triplex formation can be used to determine function of the expression product of an nucleic acid-related gene.

A. Ribozymes

Trans-cleaving catalytic RNAs (ribozymes) are RNA molecules possessing endoribonuclease activity. Ribozymes are specifically designed for a particular target, and the target message must contain a specific nucleotide sequence. They are engineered to cleave any RNA species site-specifically in the background of cellular RNA. The cleavage event renders the mRNA unstable and prevents protein expression. Importantly, ribozymes can be used to inhibit expression of a gene of unknown function for the purpose of determining its function in an in vitro or in vivo context, by detecting the phenotypic effect.

One commonly used ribozyme motif is the hammerhead, for which the substrate sequence requirements are minimal. Design of the hammerhead ribozyme is disclosed in Usman et al., *Current Opin. Strict. Biol.* (1996) 6:527–533. Usman also discusses the therapeutic uses of ribozymes. Ribozymes can also be prepared and used as described in Long et al., *FASEB J.* (1993) 7:25; Symons, *Ann. Rev. Biochem.* (1992) 61:641; Perrotta et al., *Biochem.* (1992) 31:16–17; Ojwang et al., *Proc. Natl. Acad. Sci.* (*USA*) (1992) 89:10802–10806; and U.S. Pat. No. 5,254,678. Ribozyme cleavage of HIV-I RNA is described in U.S. Pat. No. 5,144,019; methods of cleaving RNA using ribozymes is described in U.S. Pat. No. 5,116,742; and methods for increasing the specificity of ribozymes are described in U.S. Pat. No. 5,225,337 and Koizumi et al., *Nucleic Acid Res.* (1989) 17:7059–7071. Preparation and use of ribozyme fragments in a hammerhead structure are also described by Koizumi et al., *Nucleic Acids Res.* (1989) 17:7059–7071. Preparation and use of ribozyme fragments in a hairpin structure are described by Chowrira and Burke, *Nucleic Acids Res.* (1992) 20:2835. Ribozymes can also be made by rolling transcription as described in Daubendiek and Kool, *Nat. Biotechnol.* (1997) 15(3):273–277.

The hybridizing region of the ribozyme may be modified or may be prepared as a branched structure as described in Horn and Urdea, *Nucleic Acids Res.* (1989) 17:6959–67. The basic structure of the ribozymes may also be chemically altered in ways familiar to those skilled in the art, and chemically synthesized ribozymes can be administered as synthetic oligonucleotide derivatives modified by monomeric units. In a therapeutic context, liposome mediated delivery of ribozymes improves cellular uptake, as described in Birikh et al., *Eur. J. Biochem.* (1997) 245:1–16.

Using the nucleic acid sequences of the invention and methods known in the art, ribozymes are designed to specifically bind and cut the corresponding mRNA species. Ribozymes thus provide a means to inhibit the expression of any of the proteins encoded by the disclosed nucleic acids or their full-length genes. The full-length gene need not be known in order to design and use specific inhibitory ribozymes. In the case of a nucleic acid or cDNA of unknown function, ribozymes corresponding to that nucleotide sequence can be tested in vitro for efficacy in cleaving the target transcript. Those ribozymes that effect cleavage in vitro are further tested in vivo. The ribozyme can also be used to generate an animal model for a disease, as described in Birikh et al., *Eur. J. Biochem.* (1997) 245:1–16. An effective ribozyme is used to determine the function of the gene of interest by blocking its transcription and detecting a change in the cell. Where the gene is found to be a mediator in a disease, an effective ribozyme is designed and delivered in a gene therapy for blocking transcription and expression of the gene.

Therapeutic and functional genomic applications of ribozymes proceed beginning with knowledge of a portion of the coding sequence of the gene to be inhibited. Thus, for many genes, a partial nucleic acid sequence provides adequate sequence for constructing an effective ribozyme. A target cleavage site is selected in the target sequence, and a ribozyme is constructed based on the 5' and 3' nucleotide sequences that flank the cleavage site. Retroviral vectors are engineered to express monomeric and multimeric hammerhead ribozymes targeting the mRNA of the target coding sequence. These monomeric and multimeric ribozymes are tested in vitro for an ability to cleave the target mRNA. A cell line is stably transduced with the retroviral vectors expressing the ribozymes, and the transduction is confirmed by Northern blot analysis and reverse-transcription polymerase chain reaction (RT-PCR). The cells are screened for inactivation of the target mRNA by such indicators as reduction of expression of disease markers or reduction of the gene product of the target mRNA.

B. Antisense

Antisense nucleic acids are designed to specifically bind to RNA, resulting in the formation of RNA-DNA or RNA-RNA hybrids, with an arrest of DNA replication, reverse transcription or messenger RNA translation. Antisense polynucleotides based on a selected nucleic acid sequence can interfere with expression of the corresponding gene. Antisense polynucleotides are typically generated within the cell by expression from antisense constructs that contain the antisense nucleic acid strand as the transcribed strand. Antisense nucleic acids will bind and/or interfere with the translation of nucleic acid-related mRNA. The expression products of control cells and cells treated with the antisense construct are compared to detect the protein product of the gene corresponding to the nucleic acid. The protein is isolated and identified using routine biochemical methods.

One rationale for using antisense methods to determine the function of the gene corresponding to a nucleic acid is the biological activity of antisense therapeutics. Antisense therapy for a variety of cancers is in clinical phase and has been discussed extensively in the literature. Reed reviewed antisense therapy directed at the Bc1-2 gene in tumors; gene transfer-mediated overexpression of Bcl-2 in tumor cell lines conferred resistance to many types of cancer drugs. (Reed, J. C., *N.C.I.* (1997) 89:988–990). The potential for clinical development of antisense inhibitors of ras is discussed by Cowsert, L. M., *Anti-Cancer Drug Design* (1997) 12:359–371. Additional important antisense targets include leukemia (Geurtz, A. M., *Anti-Cancer Drug Design* (1997) 12:341–358); human C-ref kinase (Monia, B. P., *Anti-Cancer Drug Design* (1997) 12:327–339); and protein kinase C (McGraw et al., *Anti-Cancer Drug Design* (1997) 12:315–326.

Given the extensive background literature and clinical experience in antisense therapy, one skilled in the art can use selected nucleic acids of the invention as additional potential therapeutics. The choice of nucleic acid can be narrowed by first testing them for binding to "hot spot" regions of the genome of cancerous cells. If a nucleic acid is identified as binding to a "hot spot", testing the nucleic acid as an antisense compound in the corresponding cancer cells clearly is warranted.

Ogunbiyi et al., *Gastroenterology* (1997) 113(3):761–766 describe prognostic use of allelic loss in colon cancer; Barks et al., *Genes, Chromosomes, and Cancer* (1997) 19(4):278–285 describe increased chromosome copy number detected by FISH in malignant melanoma; Nishizake et al., *Genes, Chromosomes, and Cancer* (1997) 19(4):267–272 describe genetic alterations in primary breast cancer and their metastases and direct comparison using modified comparative genome hybridization; and Elo et al., *Cancer Research* (1997) 57(16):3356–3359 disclose that loss of heterozygosity at 16z24.1-q24.2 is significantly associated with metastatic and aggressive behavior of prostate cancer.

C. Dominant Negative Mutations

As an alternative method for identifying function of the nucleic acid-related gene, dominant negative mutations are readily generated for corresponding proteins that are active as homomultimers. A mutant polypeptide will interact with wild-type polypeptides (made from the other allele) and form a non-functional multimer. Thus, a mutation is in a substrate-binding domain, a catalytic domain, or a cellular localization domain. Preferably, the mutant polypeptide will be overproduced. Point mutations are made that have such an effect. In addition, fusion of different polypeptides of various lengths to the terminus of a protein can yield dominant negative mutants. General strategies are available for making dominant negative mutants. See Herskowitz, *Nature* (1987) 329:219–222. Such a technique can be used for creating a loss-of-function mutation, which is useful for determining the function of a protein.

D. Triplex Formation

Endogenous gene expression can also be reduced by inactivating or "knocking out" the gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional gene (or a completely unrelated DNA sequence) flanked by DNA homologous to the endogenous gene (either the coding regions or regulatory regions of the gene) can be used, with or without a selectable marker and/or a negative selectable marker, to transfect cells that express that gene in vivo. Insertion of the DNA construct, via targeted homologous recombination, results in inactivation of the gene.

Alternatively, endogenous gene expression can be reduced by targeting deoxyribonucleotide sequences complementary to the regulatory region of the target gene (i.e., the gene promoter and/or enhancers) to form triple helical structures that prevent transcription of the gene in target cells in the body. (See generally, Helene, C. 1991, Anticancer Drug Des., 6(6):569–84; Helene, C., et al., 1992, Ann, N.Y. Accad. Sci., 660:27–36; and Maher, L. J., 1992, Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base-pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

X. Diagnostic & Prognostic Assays and Drug Screening Methods

The present invention provides method for determining whether a subject is at risk for developing a disease or condition characterized by unwanted cell proliferation by detecting the disclosed biomarkers, i.e., the disclosed nucleic acid markers (SEQ ID Nos: 1–544) and/or polypeptide markers for colon cancer encoded thereby.

In clinical applications, human tissue samples can be screened for the presence and/or absence of the biomarkers identified herein. Such samples could consist of needle biopsy cores, surgical resection samples, lymph node tissue, or serum. For example, these methods include obtaining a biopsy, which is optionally fractionated by cryostat sectioning to enrich tumor cells to about 80% of the total cell population. In certain embodiments, nucleic acids extracted from these samples may be amplified using techniques well known in the art. The levels of selected markers detected would be compared with statistically valid groups of metastatic, non-metastatic malignant, benign, or normal colon tissue samples.

In one embodiment, the diagnostic method comprises determining whether a subject has an abnormal mRNA and/or protein level of the disclosed markers, such as by Northern blot analysis, reverse transcription-polymerase chain reaction (RT-PCR), in situ hybridization, immunoprecipitation, Western blot hybridization, or immunohistochemistry. According to the method, cells are obtained from a subject and the levels of the disclosed biomarkers, protein or mRNA level, is determined and compared to the level of these markers in a healthy subject. An abnormal level of the biomarker polypeptide or mRNA levels is likely to be indicative of cancer such as colon cancer.

Accordingly, in one aspect, the invention provides probes and primers that are specific to the unique nucleic acid markers disclosed herein. Accordingly, the nucleic acid probes comprise a nucleotide sequence at least 12 nucleotides in length, preferably at least 15 nucleotides, more preferably, 25 nucleotides, and most preferably at least 40 nucleotides, and up to all or nearly all of the coding sequence which is complementary to a portion of the coding sequence of a marker nucleic acid sequence, which nucleic acid sequence is represented by SEQ ID Nos: 1–544 or a sequence complementary thereto.

In one embodiment, the method comprises using a nucleic acid probe to determine the presence of cancerous cells in a tissue from a patient. Specifically, the method comprises:

1. providing a nucleic acid probe comprising a nucleotide sequence at least 12 nucleotides in length, preferably at least 15 nucleotides, more preferably, 25 nucleotides, and most preferably at least 40 nucleotides, and up to all or nearly all of the coding sequence which is complementary to a portion of the coding sequence of a nucleic acid sequence represented by SEQ ID Nos: 1–544 or a sequence complementary thereto and is differentially expressed in tumors cells, such as colon cancer cells;
2. obtaining a tissue sample from a patient potentially comprising cancerous cells;
3. providing a second tissue sample containing cells substantially all of which are non-cancerous;
4. contacting the nucleic acid probe under stringent conditions with RNA of each of said first and second tissue samples (e.g., in a Northern blot or in situ hybridization assay); and
5. comparing (a) the amount of hybridization of the probe with RNA of the first tissue sample, with (b) the amount of hybridization of the probe with RNA of the second tissue sample; wherein a statistically significant difference in the amount of hybridization with the RNA of the first tissue sample as compared to the amount of hybridization with the RNA of the second tissue sample is indicative of the presence of cancerous cells in the first tissue sample.

In one aspect, the method comprises in situ hybridization with a probe derived from a given marker nucleic acid sequence, which nucleic acid sequence is represented by SEQ ID Nos: 1–544 or a sequence complementary thereto. The method comprises contacting the labeled hybridization probe with a sample of a given type of tissue potentially containing cancerous or pre-cancerous cells as well as normal cells, and determining whether the probe labels some cells of the given tissue type to a degree significantly different (e.g., by at least a factor of two, or at least a factor of five, or at least a factor of twenty, or at least a factor of fifty) than the degree to which it labels other cells of the same tissue type.

Also within the invention is a method of determining the phenotype of a test cell from a given human tissue, e.g., whether the cell is (a) normal, or (b) cancerous or precancerous, by contacting the mRNA of a test cell with a nucleic acid probe at least 12 nucleotides in length, preferably at least 15 nucleotides, more preferably at least 25 nucleotides, and most preferably at least 40 nucleotides, and up to all or nearly all of a sequence which is complementary to a portion of the coding sequence of a nucleic acid sequence represented by SEQ ID Nos: 1–544 or a sequence complementary thereto, and which is differentially expressed in tumor cells as compared to normal cells of the given tissue type; and determining the approximate amount of hybridization of the probe to the mRNA, an amount of hybridization either more or less than that seen with the mRNA of a normal cell of that tissue type being indicative that the test cell is cancerous or pre-cancerous.

Alternatively, the above diagnostic assays may be carried out using antibodies to detect the protein product encoded by the marker nucleic acid sequence, which nucleic acid sequence is represented by SEQ ID Nos: 1–544 or a sequence complementary thereto. Accordingly, in one embodiment, the assay would include contacting the proteins of the test cell with an antibody specific for the gene product of a nucleic acid represented by SEQ ID Nos: 1–544 or a sequence complementary thereto, the marker nucleic acid being one which is expressed at a given control level in normal cells of the same tissue type as the test cell, and determining the approximate amount of immunocomplex formation by the antibody and the proteins of the test cell, wherein a statistically significant difference in the amount of the immunocomplex formed with the proteins of a test cell as compared to a normal cell of the same tissue type is an indication that the test cell is cancerous or pre-cancerous.

Another such method includes the steps of: providing an antibody specific for the gene product of a marker nucleic acid sequence represented by SEQ ID Nos 1–544, the gene product being present in cancerous tissue of a given tissue type (e.g., colon tissue) at a level more or less than the level of the gene product in non-cancerous tissue of the same tissue type; obtaining from a patient a first sample of tissue of the given tissue type, which sample potentially includes cancerous cells; providing a second sample of tissue of the same tissue type (which may be from the same patient or from a normal control, e.g. another individual or cultured cells), this second sample containing normal cells and essentially no cancerous cells; contacting the antibody with protein (which may be partially purified, in lysed but unfractionated cells, or in situ) of the first and second samples under conditions permitting immunocomplex formation between the antibody and the marker nucleic acid sequence product present in the samples; and comparing (a) the amount of immunocomplex formation in the first sample, with (b) the amount of immunocomplex formation in the second sample, wherein a statistically significant difference in the amount of immunocomplex formation in the first sample less as compared to the amount of immunocomplex formation in the second sample is indicative of the presence of cancerous cells in the first sample of tissue.

The subject invention further provides a method of determining whether a cell sample obtained from a subject possesses an abnormal amount of marker polypeptide which comprises (a) obtaining a cell sample from the subject, (b) quantitatively determining the amount of the marker polypeptide in the sample so obtained, and (c) comparing the amount of the marker polypeptide so determined with a known standard, so as to thereby determine whether the cell sample obtained from the subject possesses an abnormal amount of the marker polypeptide. Such marker polypeptides may be detected by immunohistochemical assays, dot-blot assays, ELISA and the like.

Immunoassays are commonly used to quantitate the levels of proteins in cell samples, and many other immunoassay techniques are known in the art. The invention is not limited to a particular assay procedure, and therefore is intended to include both homogeneous and heterogeneous procedures. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In another embodiment, the level of the encoded product, i.e., the product encoded by SEQ ID Nos 1–544 or a sequence complementary thereto, in a biological fluid (e.g., blood or urine) of a patient may be determined as a way of monitoring the level of expression of the marker nucleic acid sequence in cells of that patient. Such a method would include the steps of obtaining a sample of a biological fluid from the patient, contacting the sample (or proteins from the sample) with an antibody specific for a encoded marker polypeptide, and determining the amount of immune complex formation by the antibody, with the amount of immune complex formation being indicative of the level of the marker encoded product in the sample. This determination is particularly instructive when compared to the amount of immune complex formation by the same antibody in a control sample taken from a normal individual or in one or more samples previously or subsequently obtained from the same person.

In another embodiment, the method can be used to determine the amount of marker polypeptide present in a cell, which in turn can be correlated with progression of a hyperproliferative disorder, e.g., colon cancer. The level of the marker polypeptide can be used predictively to evaluate whether a sample of cells contains cells which are, or are predisposed towards becoming, transformed cells. Moreover, the subject method can be used to assess the phenotype of cells which are known to be transformed, the phenotyping results being useful in planning a particular therapeutic regimen. For instance, very high levels of the marker polypeptide in sample cells is a powerful diagnostic and prognostic marker for a cancer, such as colon cancer. The observation of marker polypeptide level can be utilized in decisions regarding, e.g., the use of more aggressive therapies.

As set out above, one aspect of the present invention relates to diagnostic assays for determining, in the context of cells isolated from a patient, if the level of a marker polypeptide is significantly reduced in the sample cells. The term "significantly reduced" refers to a cell phenotype wherein the cell possesses a reduced cellular amount of the marker polypeptide relative to a normal cell of similar tissue origin. For example, a cell may have less than about 50%, 25%, 10%, or 5% of the marker polypeptide that a normal control cell. In particular, the assay evaluates the level of marker polypeptide in the test cells, and, preferably, compares the measured level with marker polypeptide detected in at least one control cell, e.g., a normal cell and/or a transformed cell of known phenotype.

Of particular importance to the subject invention is the ability to quantitate the level of marker polypeptide as determined by the number of cells associated with a normal or abnormal marker polypeptide level. The number of cells with a particular marker polypeptide phenotype may then be correlated with patient prognosis. In one embodiment of the invention, the marker polypeptide phenotype of the lesion is determined as a percentage of cells in a biopsy which are found to have abnormally high/low levels of the marker polypeptide. Such expression may be detected by immunohistochemical assays, dot-blot assays, ELISA and the like.

Where tissue samples are employed, immunohistochemical staining may be used to determine the number of cells having the marker polypeptide phenotype. For such staining, a multiblock of tissue is taken from the biopsy or other tissue sample and subjected to proteolytic hydrolysis, employing such agents as protease K or pepsin. In certain embodiments, it may be desirable to isolate a nuclear fraction from the sample cells and detect the level of the marker polypeptide in the nuclear fraction.

The tissue samples are fixed by treatment with a reagent such as formalin, glutaraldehyde, methanol, or the like. The samples are then incubated with an antibody, preferably a monoclonal antibody, with binding specificity for the marker polypeptides. This antibody may be conjugated to a label for subsequent detection of binding. Samples are incubated for a time sufficient for formation of the immuno-complexes. Binding of the antibody is then detected by virtue of a label conjugated to this antibody. Where the antibody is unlabeled, a second labeled antibody may be employed, e.g., which is specific for the isotype of the anti-marker polypeptide antibody. Examples of labels which may be employed include radionuclides, fluorescers, chemiluminescers, enzymes and the like.

Where enzymes are employed, the substrate for the enzyme may be added to the samples to provide a colored or fluorescent product. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In one embodiment, the assay is performed as a dot blot assay. The dot blot assay finds particular application where tissue samples are employed as it allows determination of the average amount of the marker polypeptide associated with a single cell by correlating the amount of marker polypeptide in a cell-free extract produced from a predetermined number of cells.

It is well established in the cancer literature that tumor cells of the same type (e.g., breast and/or colon tumor cells) may not show uniformly increased expression of individual oncogenes or uniformly decreased expression of individual tumor suppressor genes. There may also be varying levels of expression of a given marker gene even between cells of a given type of cancer, further emphasizing the need for reliance on a battery of tests rather than a single test. Accordingly, in one aspect, the invention provides for a battery of tests utilizing a number of probes of the invention, in order to improve the reliability and/or accuracy of the diagnostic test.

In one embodiment, the present invention also provides a method wherein nucleic acid probes are immobilized on a DNA chip in an organized array. Oligonucleotides can be bound to a solid support by a variety of processes, including lithography. For example a chip can hold up to 250,000 oligonucleotides (GeneChip, Affymetrix). These nucleic acid probes comprise a nucleotide sequence at least about 12 nucleotides in length, preferably at least about 15 nucleotides, more preferably at least about 25 nucleotides, and most preferably at least about 40 nucleotides, and up to all or nearly all of a sequence which is complementary to a portion of the coding sequence of a marker nucleic acid sequence represented by SEQ ID Nos: 1–544 and is differentially expressed in tumor cells, such as colon cancer cells. The present invention provides significant advantages over the available tests for various cancers, such as colon cancer, because it increases the reliability of the test by providing an array of nucleic acid markers on a single chip.

The method includes obtaining a biopsy, which is optionally fractionated by cryostat sectioning to enrich tumor cells to about 80% of the total cell population. The DNA or RNA is then extracted, amplified, and analyzed with a DNA chip to determine the presence of absence of the marker nucleic acid sequences.

In one embodiment, the nucleic acid probes are spotted onto a substrate in a two-dimensional matrix or array. Samples of nucleic acids can be labeled and then hybridized to the probes. Double-stranded nucleic acids, comprising the labeled sample nucleic acids bound to probe nucleic acids, can be detected once the unbound portion of the sample is washed away.

The probe nucleic acids can be spotted on substrates including glass, nitrocellulose, etc. The probes can be bound to the substrate by either covalent bonds or by non-specific interactions, such as hydrophobic interactions. The sample nucleic acids can be labeled using radioactive labels, fluorophores, chromophores, etc.

Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. No. 5,593,839; U.S. Pat. No. 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734.

Further, arrays can be used to examine differential expression of genes and can be used to determine gene function. For example, arrays of the instant nucleic acid sequences can be used to determine if any of the nucleic acid sequences are differentially expressed between normal cells and cancer cells, for example. High expression of a particular message in a cancer cell, which is not observed in a corresponding normal cell, can indicate a cancer specific protein.

In yet another embodiment, the invention contemplates using a panel of antibodies which are generated against the marker polypeptides of this invention, which polypeptides are encoded by SEQ ID Nos: 1–544. Such a panel of antibodies may be used as a reliable diagnostic probe for colon cancer. The assay of the present invention comprises contacting a biopsy sample containing cells, e.g., colon cells, with a panel of antibodies to one or more of the encoded products to determine the presence or absence of the marker polypeptides.

The diagnostic methods of the subject invention may also be employed as follow-up to treatment, e.g., quantitation of the level of marker polypeptides may be indicative of the effectiveness of current or previously employed cancer therapies as well as the effect of these therapies upon patient prognosis.

Accordingly, the present invention makes available diagnostic assays and reagents for detecting gain and/or loss of marker polypeptides from a cell in order to aid in the diagnosis and phenotyping of proliferative disorders arising from, for example, tumorigenic transformation of cells.

The diagnostic assays described above can be adapted to be used as prognostic assays, as well. Such an application takes advantage of the sensitivity of the assays of the invention to events which take place at characteristic stages in the progression of a tumor. For example, a given marker gene may be up- or downregulated at a very early stage, perhaps before the cell is irreversibly committed to developing into a malignancy, while another marker gene may be characteristically up or down regulated only at a much later stage. Such a method could involve the steps of contacting the mRNA of a test cell with a nucleic acid probe derived from a given marker nucleic acid which is expressed at different characteristic levels in cancerous or precancerous cells at different stages of tumor progression, and determining the approximate amount of hybridization of the probe to the mRNA of the cell, such amount being an indication of the level of expression of the gene in the cell, and thus an indication of the stage of tumor progression of the cell; alternatively, the assay can be carried out with an antibody specific for the gene product of the given marker nucleic acid, contacted with the proteins of the test cell. A battery of such tests will disclose not only the existence and location of a tumor, but also will allow the clinician to select the mode of treatment most appropriate for the tumor, and to predict the likelihood of success of that treatment.

The methods of the invention can also be used to follow the clinical course of a tumor. For example, the assay of the invention can be applied to a tissue sample from a patient; following treatment of the patient for the cancer, another tissue sample is taken and the test repeated. Successful treatment will result in either removal of all cells which demonstrate differential expression characteristic of the cancerous or precancerous cells, or a substantial increase in expression of the gene in those cells, perhaps approaching or even surpassing normal levels.

In yet another embodiment, the invention provides methods for determining whether a subject is at risk for developing a disease, such as a predisposition to develop cancer, for example colon cancer, associated with an aberrant activity of any one of the polypeptides encoded by nucleic acids of SEQ ID Nos: 1–544, wherein the aberrant activity of the polypeptide is characterized by detecting the presence or absence of a genetic lesion characterized by at least one of (i) an alteration affecting the integrity of a gene encoding a marker polypeptides, or (ii) the mis-expression of the encoding nucleic acid. To illustrate, such genetic lesions can be detected by ascertaining the existence of at least one of (i) a deletion of one or more nucleotides from the nucleic acid sequence, (ii) an addition of one or more nucleotides to the nucleic acid sequence, (iii) a substitution of one or more nucleotides of the nucleic acid sequence, (iv) a gross chromosomal rearrangement of the nucleic acid sequence, (v) a gross alteration in the level of a messenger RNA transcript of the nucleic acid sequence, (vii) aberrant modification of the nucleic acid sequence, such as of the methylation pattern of the genomic DNA, (vii) the presence of a non-wild type splicing pattern of a messenger RNA transcript of the gene, (viii) a non-wild type level of the marker polypeptide, (ix) allelic loss of the gene, and/or (x) inappropriate post-translational modification of the marker polypeptide.

The present invention provides assay techniques for detecting lesions in the encoding nucleic acid sequence. These methods include, but are not limited to, methods involving sequence analysis, Southern blot hybridization, restriction enzyme site mapping, and methods involving detection of absence of nucleotide pairing between the nucleic acid to be analyzed and a probe.

Specific diseases or disorders, e.g., genetic diseases or disorders, are associated with specific allelic variants of polymorphic regions of certain genes, which do not necessarily encode a mutated protein. Thus, the presence of a specific allelic variant of a polymorphic region of a gene in a subject can render the subject susceptible to developing a specific disease or disorder. Polymorphic regions in genes, can be identified, by determining the nucleotide sequence of genes in populations of individuals. If a polymorphic region is identified, then the link with a specific disease can be determined by studying specific populations of individuals, e.g, individuals which developed a specific disease, such as colon cancer. A polymorphic region can be located in any region of a gene, e.g., exons, in coding or non coding regions of exons, introns, and promoter region.

In an exemplary embodiment, there is provided a nucleic acid composition comprising a nucleic acid probe including a region of nucleotide sequence which is capable of hybridizing to a sense or antisense sequence of a gene or naturally occurring mutants thereof, or 5' or 3' flanking sequences or intronic sequences naturally associated with the subject genes or naturally occurring mutants thereof. The nucleic acid of a cell is rendered accessible for hybridization, the probe is contacted with the nucleic acid of the sample, and the hybridization of the probe to the sample nucleic acid is detected. Such techniques can be used to detect lesions or allelic variants at either the genomic or mRNA level, including deletions, substitutions, etc., as well as to determine mRNA transcript levels.

A preferred detection method is allele specific hybridization using probes overlapping the mutation or polymorphic site and having about 5, 10, 20, 25, or 30 nucleotides around the mutation or polymorphic region. In a preferred embodiment of the invention, several probes capable of hybridizing specifically to allelic variants are attached to a solid phase support, e.g., a "chip". Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) (see, e.g., Landegran et al. (1988) *Science* 241:1077–1080; and Nakazawa et al. (1994) *PNAS* 91:360–364), the latter of which an be particularly useful for detecting point mutations in the gene (see Abravaya et al. (1995) *Nuc Acid Res* 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a nucleic acid sequence under conditions such that hybridization and amplification of the nucleic acid (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in, or allelic variants, of a gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

Another aspect of the invention is directed to the identification of agents capable of modulating the differentiation and proliferation of cells characterized by aberrant proliferation. In this regard, the invention provides assays for determining compounds that modulate the expression of the marker nucleic acids (SEQ ID Nos: 1–544) and/or alter for example, inhibit the bioactivity of the encoded polypeptide.

Several in vivo methods can be used to identify compounds that modulate expression of the marker nucleic acids (SEQ ID Nos: 1–544) and/or alter for example, inhibit the bioactivity of the encoded polypeptide.

Drug screening is performed by adding a test compound to a sample of cells, and monitoring the effect. A parallel sample which does not receive the test compound is also monitored as a control. The treated and untreated cells are then compared by any suitable phenotypic criteria, including but not limited to microscopic analysis, viability testing, ability to replicate, histological examination, the level of a particular RNA or polypeptide associated with the cells, the level of enzymatic activity expressed by the cells or cell lysates, and the ability of the cells to interact with other cells or compounds. Differences between treated and untreated cells indicates effects attributable to the test compound.

Desirable effects of a test compound include an effect on any phenotype that was conferred by the cancer-associated marker nucleic acid sequence. Examples include a test compound that limits the overabundance of mRNA, limits production of the encoded protein, or limits the functional effect of the protein. The effect of the test compound would be apparent when comparing results between treated and untreated cells.

The invention thus also encompasses methods of screening for agents which inhibit expression of the nucleic acid markers (SEQ ID Nos: 1–544) in vitro, comprising exposing a cell or tissue in which the marker nucleic acid mRNA is detectable in cultured cells to an agent in order to determine whether the agent is capable of inhibiting production of the mRNA; and determining the level of mRNA in the exposed cells or tissue, wherein a decrease in the level of the mRNA after exposure of the cell line to the agent is indicative of inhibition of the marker nucleic acid mRNA production.

Alternatively, the screening method may include in vitro screening of a cell or tissue in which marker protein is detectable in cultured cells to an agent suspected of inhibiting production of the marker protein; and determining the level of the marker protein in the cells or tissue, wherein a decrease in the level of marker protein after exposure of the cells or tissue to the agent is indicative of inhibition of marker protein production.

The invention also encompasses in vivo methods of screening for agents which inhibit expression of the marker nucleic acids, comprising exposing a mammal having tumor cells in which marker mRNA or protein is detectable to an agent suspected of inhibiting production of marker mRNA or protein; and determining the level of marker mRNA or protein in tumor cells of the exposed mammal. A decrease in the level of marker mRNA or protein after exposure of the mammal to the agent is indicative of inhibition of marker nucleic acid expression.

Accordingly, the invention provides a method comprising incubating a cell expressing the marker nucleic acids (SEQ ID Nos: 1–544) with a test compound and measuring the mRNA or protein level. The invention further provides a method for quantitatively determining the level of expression of the marker nucleic acids in a cell population, and a method for determining whether an agent is capable of increasing or decreasing the level of expression of the marker nucleic acids in a cell population. The method for determining whether an agent is capable of increasing or decreasing the level of expression of the marker nucleic acids in a cell population comprises the steps of (a) preparing cell extracts from control and agent-treated cell populations, (b) isolating the marker polypeptides from the cell extracts, (c) quantifying (e.g., in parallel) the amount of an immunocomplex formed between the marker polypeptide and an antibody specific to said polypeptide. The marker polypeptides of this invention may also be quantified by assaying for its bioactivity. Agents that induce increased the marker nucleic acid expression may be identified by their ability to increase the amount of immunocomplex formed in the treated cell as compared with the amount of the immunocomplex formed in the control cell. In a similar manner, agents that decrease expression of the marker nucleic acid may be identified by their ability to decrease the amount of the immunocomplex formed in the treated cell extract as compared to the control cell.

mRNA levels can be determined by Northern blot hybridization. mRNA levels can also be determined by methods involving PCR. Other sensitive methods for measuring mRNA, which can be used in high throughput assays, e.g., a method using a DELFIA endpoint detection and quantification method, are described, e.g., in Webb and Hurskainen (1996) *Journal of Biomolecular Screening* 1:119. Marker protein levels can be determined by immunoprecipitations or immunohistochemistry using an antibody that specifically recognizes the protein product encoded by SEQ ID Nos: 1–544.

Agents that are identified as active in the drug screening assay are candidates to be tested for their capacity to block cell proliferation activity. These agents would be useful for treating a disorder involving aberrant growth of cells, especially colon cells.

A variety of assay formats will suffice and, in light of the present disclosure, those not expressly described herein will nevertheless be comprehended by one of ordinary skill in the art. For instance, the assay can be generated in many different formats, and include assays based on cell-free systems, e.g., purified proteins or cell lysates, as well as cell-based assays which utilize intact cells.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

A. Use of Nucleic Acids as Probes in Mapping and in Tissue Profiling Probes

Polynucleotide probes as described above, e.g., comprising at least 12 contiguous nucleotides selected from the nucleotide sequence of an nucleic acid as shown in SEQ ID Nos. 1–544, preferably SEQ ID Nos. 1–168, even more preferably SEQ ID Nos. 1–35, or a sequence complementary thereto, are used for a variety of purposes, including identification of human chromosomes and determining transcription levels. Additional disclosure about preferred regions of the nucleic acid sequences is found in the accompanying tables.

The nucleotide probes are labeled, for example, with a radioactive, fluorescent, biotinylated, or chemiluminescent label, and detected by well known methods appropriate for the particular label selected. Protocols for hybridizing nucleotide probes to preparations of metaphase chromosomes are also well known in the art. A nucleotide probe will hybridize specifically to nucleotide sequences in the chromosome preparations which are complementary to the nucleotide sequence of the probe. A probe that hybridizes specifically to a nucleic acid should provide a detection signal at least 5-, 10-, or 20-fold higher than the background hybridization provided with other unrelated sequences.

In a non-limiting example, commercial programs are available for identifying regions of chromosomes commonly associated with disease, such as cancer. Nucleic acids of the invention can be used to probe these regions. For example, if, through profile searching, a nucleic acid is identified as corresponding to a gene encoding a kinase, its ability to bind to a cancer-related chromosomal region will suggest its role as a kinase in one or more stages of tumor cell development/ growth. Although some experimentation would be required to elucidate the role, the nucleic acid constitutes a new material for isolating a specific protein that has potential for developing a cancer diagnostic or therapeutic.

Nucleotide probes are used to detect expression of a gene corresponding to the nucleic acid. For example, in Northern blots, mRNA is separated electrophoretically and contacted with a probe. A probe is detected as hybridizing to an mRNA species of a particular size. The amount of hybridization is quantitated to determine relative amounts of expression, for example under a particular condition. Probes are also used to detect products of amplification by polymerase chain reaction. The products of the reaction are hybridized to the probe and hybrids are detected. Probes are used for in situ hybridization to cells to detect expression. Probes can also be used in vivo for diagnostic detection of hybridizing sequences. Probes are typically labeled with a radioactive isotope. Other types of detectable labels may be used such as chromophores, fluorophores, and enzymes.

Expression of specific mRNA can vary in different cell types and can be tissue specific. This variation of mRNA levels in different cell types can be exploited with nucleic acid probe assays to determine tissue types. For example, PCR, branched DNA probe assays, or blotting techniques utilizing nucleic acid probes substantially identical or complementary to nucleic acids of SEQ ID Nos. 1–544, preferably SEQ ID Nos. 1–168, even more preferably SEQ ID Nos. 1–35, or a sequence complementary thereto, can determine the presence or absence of target cDNA or mRNA.

Examples of a nucleotide hybridization assay are described in Urdea et al., PCT WO92/02526 and Urdea et al., U.S. Pat. No. 5,124,246, both incorporated herein by reference. The references describe an example of a sandwich nucleotide hybridization assay.

Alternatively, the Polymerase Chain Reaction (PCR) is another means for detecting small amounts of target nucleic acids, as described in Mullis et al., *Meth. Enzymol.* (1987) 155:335–350; U.S. Pat. No. 4,683,195; and U.S. Pat. No. 4,683,202, all incorporated herein by reference. Two primer polynucleotides nucleotides hybridize with the target nucleic acids and are used to prime the reaction. The primers may be composed of sequence within or 3' and 5' to the polynucleotides of the Sequence Listing. Alternatively, if the primers are 3' and 5' to these polynucleotides, they need not hybridize to them or the complements. A thermostable polymerase creates copies of target nucleic acids from the primers using the original target nucleic acids as a template. After a large amount of target nucleic acids is generated by the polymerase, it is detected by methods such as Southern blots. When using the Southern blot method, the labeled probe will hybridize to a polynucleotide of the Sequence Listing or complement.

Furthermore, mRNA or cDNA can be detected by traditional blotting techniques described in Sambrook et al., "Molecular Cloning: A Laboratory Manual" (New York, Cold Spring Harbor Laboratory, 1989). mRNA or cDNA generated from mRNA using a polymerase enzyme can be purified and separated using gel electrophoresis. The nucleic acids on the gel are then blotted onto a solid support, such as nitrocellulose. The solid support is exposed to a labeled probe and then washed to remove any unhybridized probe. Next, the duplexes containing the labeled probe are detected. Typically, the probe is labeled with radioactivity.

Mapping

Nucleic acids of the present invention are used to identify a chromosome on which the corresponding gene resides. Using fluorescence in situ hybridization (FISH) on normal metaphase spreads, comparative genomic hybridization allows total genome assessment of changes in relative copy number of DNA sequences. See Schwartz and Samad, *Current Opinions in Biotechnology* (1994) 8:70–74; Kallioniemi et al., *Seminars in Cancer Biology* (1993) 4:41–46; Valdes and Tagle, *Methods in Molecular Biology* (1997) 68:1, Boultwood, ed., Human Press, Totowa, N.J.

Preparations of human metaphase chromosomes are prepared using standard cytogenetic techniques from human primary tissues or cell lines. Nucleotide probes comprising at least 12 contiguous nucleotides selected from the nucleotide sequence of SEQ ID Nos. 1–544, preferably SEQ ID Nos. 1–168, even more preferably SEQ ID Nos. 1–35, or a sequence complementary thereto, are used to identify the corresponding chromosome. The nucleotide probes are labeled, for example, with a radioactive, fluorescent, biotinylated, or chemiluminescent label, and detected by well known methods appropriate for the particular label selected. Protocols for hybridizing nucleotide probes to preparations of metaphase chromosomes are also well known in the art. A nucleotide probe will hybridize specifically to nucleotide sequences in the chromosome preparations that are complementary to the nucleotide sequence of the probe. A probe that hybridizes specifically to a target gene provides a detection signal at least 5-, 10-, or 20-fold higher than the background hybridization provided with unrelated coding sequences.

Nucleic acids are mapped to particular chromosomes using, for example, radiation hybrids or chromosome-specific hybrid panels. See Leach et al, *Advances in Genetics,* (1995) 33:63–99; Walter et al., *Nature Genetics* (1994) 7:22–28; Walter and Goodfellow, *Trends in Genetics* (1992) 9:352. Panels for radiation hybrid mapping are available from Research Genentics, Inc., Huntsville, Alabama, USA. Databases for markers using various panels are available via the world wide web at http:/F/shgc-www.stanford.edu; and other locations. The statistical program RHMAP can be used to construct a map based on the data from radiation hybridization with a measure of the relative likelihood of one order versus another. RHMAP is available via the world wide web at http://www.sph.umich.edu/group/statgen/software.

Such mapping can be useful in identifying the function of the target gene by its proximity to other genes with known function. Function can also be assigned to the target gene when particular syndromes or diseases map to the same chromosome.

Tissue Profiling

The nucleic acids of the present invention can be used to determine the tissue type from which a given sample is derived. For example, a metastatic lesion is identified by its developmental organ or tissue source by identifying the expression of a particular marker of that organ or tissue. If a nucleic acid is expressed only in a specific tissue type, and a metastatic lesion is found to express that nucleic acid, then the developmental source of the lesion has been identified. Expression of a particular nucleic acid is assayed by detection of either the corresponding mRNA or the protein product. Immunological methods, such as antibody staining, are used to detect a particular protein product. Hybridization methods may be used to detect particular mRNA species, including but not limited to in situ hybridization and Northern blotting.

Use of Polymorphisms

A nucleic acid will be useful in forensics, genetic analysis, mapping, and diagnostic applications if the corresponding region of a gene is polymorphic in the human population. A particular polymorphic form of the nucleic acid may be used to either identify a sample as deriving from a suspect or rule out the possibility that the sample derives from the suspect. Any means for detecting a polymorphism in a gene are used, including but not limited to electrophoresis of protein polymorphic variants, differential sensitivity to restriction enzyme cleavage, and hybridization to an allele-specific probe.

B. Use of Nucleic Acids and Encoded Polypeptides to Raise Antibodies

Expression products of a nucleic acid, the corresponding mRNA or cDNA, or the corresponding complete gene are prepared and used for raising antibodies for experimental, diagnostic, and therapeutic purposes. For nucleic acids to which a corresponding gene has not been assigned, this provides an additional method of identifying the corresponding gene. The nucleic acid or related cDNA is expressed as described above, and antibodies are prepared. These antibodies are specific to an epitope on the encoded polypeptide, and can precipitate or bind to the corresponding native protein in a cell or tissue preparation or in a cell-free extract of an in vitro expression system.

Immunogens for raising antibodies are prepared by mixing the polypeptides encoded by the nucleic acids of the present invention with adjuvants. Alternatively, polypeptides are made as fusion proteins to larger immunogenic proteins. Polypeptides are also covalently linked to other larger immunogenic proteins, such as keyhole limpet hemocyanin. Immunogens are typically administered intradermally, subcutaneously, or intramuscularly. Immunogens are administered to experimental animals such as rabbits, sheep, and mice, to generate antibodies. Optionally, the animal spleen cells are isolated and fused with myeloma cells to form hybridomas which secrete monoclonal antibodies. Such methods are well known in the art. According to another method known in the art, the nucleic acid is administered directly, such as by intramuscular injection, and expressed in vivo. The expressed protein generates a variety of protein-specific immune responses, including production of antibodies, comparable to administration of the protein.

Preparations of polyclonal and monoclonal antibodies specific for nucleic acid-encoded proteins and polypeptides are made using standard methods known in the art. The antibodies specifically bind to epitopes present in the polypeptides encoded by a nucleic acid of SEQ ID Nos. 1–544, preferably SEQ ID Nos. 1–168, even more preferably SEQ ID Nos. 1–35, or a sequence complementary thereto. In another embodiment, the antibodies specifically bind to epitopes present in a polypeptide encoded by SEQ ID Nos. 1–544. Typically, at least about 6, 8, 10, or 12 contiguous amino acids are required to form an epitope. However, epitopes which involve non-contiguous amino acids may require more, for example, at least about 15, 25, or 50 amino acids. A short sequence of a nucleic acid may then be unsuitable for use as an epitope to raise antibodies for identifying the corresponding novel protein, because of the potential for cross-reactivity with a known protein. However, the antibodies may be useful for other purposes, particularly if they identify common structural features of a known protein and a novel polypeptide encoded by a nucleic acid of the invention.

Antibodies that specifically bind to human nucleic acid-encoded polypeptides should provide a detection signal at least about 5-, 10-, or 20-fold higher than a detection signal provided with other proteins when used in Western blots or other immunochemical assays. Preferably, antibodies that specifically bind nucleic acid T-encoded polypeptides do not detect other proteins in immunochemical assays and can immunoprecipitate nucleic acid-encoded proteins from solution.

To test for the presence of serum antibodies to the nucleic acid-encoded polypeptide in a human population, human antibodies are purified by methods well known in the art. Preferably, the antibodies are affinity purified by passing antiserum over a column to which a nucleic acid-encoded protein, polypeptide, or fusion protein is bound. The bound antibodies can then be eluted from the column, for example using a buffer with a high salt concentration.

In addition to the antibodies discussed above, genetically engineered antibody derivatives are made, such as single chain antibodies.

Antibodies may be made by using standard protocols known in the art (See, for example, Antibodies: A Laboratory Manual ed. by Harlow and Lane (Cold Spring Harbor Press: 1988)). A mammal, such as a mouse, hamster, or rabbit can be immunized with an immunogenic form of the peptide (e.g., a mammalian polypeptide or an antigenic fragment which is capable of eliciting an antibody response, or a fusion protein as described above).

In one aspect, this invention includes monoclonal antibodies that show a subject polypeptide is highly expressed in colorectal tissue or tumor tissue, especially colon cancer tissue or colon cancer-derived cell lines. Therefore, in one embodiment, this invention provides a diagnostic tool for the analysis of expression of a subject polypeptide in general, and in particular, as a diagnostic for colon cancer.

Techniques for conferring immunogenicity on a protein or peptide include conjugation to carriers or other techniques well known in the art. An immunogenic portion of a protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a protein of a mammal, e.g., antigenic determinants of a protein encoded by one of SEQ ID Nos. 1–544 or closely related homologs (e.g., at least 90% identical, and more preferably at least 95% identical).

Following immunization of an animal with an antigenic preparation of a polypeptide, antisera can be obtained and, if desired, polyclonal antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a polypeptide of the present invention and monoclonal antibodies isolated from a culture comprising such hybridoma cells.

The term antibody as used herein is intended to include fragments thereof which are also specifically reactive with one of the subject polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for a polypeptide conferred by at least one CDR region of the antibody. In preferred embodiments, the antibodies, the antibody further comprises a label attached thereto and able to be detected, (e.g., the label can be a radioisotope, fluorescent compound, chemiluminescent compound, enzyme, or enzyme co-factor).

Antibodies can be used, e.g., to monitor protein levels in an individual for determining, e.g., whether a subject has a disease or condition, such as colon cancer, associated with an aberrant protein level, or allowing determination of the efficacy of a given treatment regimen for an individual afflicted with such a disorder. The level of polypeptides may be measured from cells in bodily fluid, such as in blood samples.

Another application of antibodies of the present invention is in the immunological screening of cDNA libraries constructed in expression vectors such as gt11, gt18-23, ZAP, and ORF8. Messenger libraries of this type, having coding sequences inserted in the correct reading frame and orientation, can produce fusion proteins. For instance, gt11 will produce fusion proteins whose amino termini consist of β-galactosidase amino acid sequences and whose carboxyl termini consist of a foreign polypeptide. Antigenic epitopes of a protein, e.g., other orthologs of a particular protein or other paralogs from the same species, can then be detected with antibodies, as, for example, reacting nitrocellulose filters lifted from infected plates with antibodies. Positive phage detected by this assay can then be isolated from the infected plate. Thus, the presence of homologs can be detected and cloned from other animals, as can alternate isoforms (including splicing variants) from humans.

In another embodiment, a panel of monoclonal antibodies may be used, wherein each of the epitope's involved functions are represented by a monoclonal antibody. Loss or perturbation of binding of a monoclonal antibody in the panel would be indicative of a mutational attention of the protein and thus of the corresponding gene.

C. Differential Expression

The present invention also provides a method to identify abnormal or diseased tissue in a human. For nucleic acids corresponding to profiles of protein families as described above, the choice of tissue may be dictated by the putative biological function. The expression of a gene corresponding to a specific nucleic acid is compared between a first tissue that is suspected of being diseased and a second, normal tissue of the human. The normal tissue is any tissue of the human, especially those that express the target gene including, but not limited to, brain, thymus, testis, heart, prostate, placenta, spleen, small intestine, skeletal muscle, pancreas, and the mucosal lining of the colon.

The tissue suspected of being abnormal or diseased can be derived from a different tissue type of the human, but preferably it is derived from the same tissue type; for example an intestinal polyp or other abnormal growth should be compared with normal intestinal tissue. A difference between the target gene, mRNA, or protein in the two tissues which are compared, for example in molecular weight, amino acid or nucleotide sequence, or relative abundance, indicates a change in the gene, or a gene which regulates it, in the tissue of the human that was suspected of being diseased.

The target genes in the two tissues are compared by any means known in the art. For example, the two genes are sequenced, and the sequence of the gene in the tissue suspected of being diseased is compared with the gene sequence in the normal tissue. The target genes, or portions thereof, in the two tissues are amplified, for example using nucleotide primers based on the nucleotide sequence shown in the Sequence Listing, using the polymerase chain reaction. The amplified genes or portions of genes are hybridized to nucleotide probes selected from a corresponding nucleotide sequence shown SEQ ID No. 1–544. A difference in the nucleotide sequence of the target gene in the tissue suspected of being diseased compared with the normal nucleotide sequence suggests a role of the nucleic acid-encoded proteins in the disease, and provides a lead for preparing a therapeutic agent. The nucleotide probes are labeled by a variety of methods, such as radiolabeling, biotinylation, or labeling with fluorescent or chemiluminescent tags, and detected by standard methods known in the art.

Alternatively, target mRNA in the two tissues is compared. $PolyA^+RNA$ is isolated from the two tissues as is known in the art. For example, one of skill in the art can readily determine differences in the size or amount of target mRNA transcripts between the two tissues using Northern blots and nucleotide probes selected from the nucleotide sequence shown in the Sequence Listing. Increased or decreased expression of a target mRNA in a tissue sample suspected of being diseased, compared with the expression of the same target mRNA in a normal tissue, suggests that the expressed protein has a role in the disease, and also provides a lead for preparing a therapeutic agent.

Any method for analyzing proteins is used to compare two nucleic acid-encoded proteins from matched samples. The sizes of the proteins in the two tissues are compared, for example, using antibodies of the present invention to detect nucleic acid-encoded proteins in Western blots of protein extracts from the two tissues. Other changes, such as expression levels and subcellular localization, can also be detected immunologically, using antibodies to the corresponding protein. A higher or lower level of nucleic acid-encoded protein expression in a tissue suspected of being diseased, compared with the same nucleic acid-encoded protein expression level in a normal tissue, is indicative that the expressed protein has a role in the disease, and provides another lead for preparing a therapeutic agent.

Similarly, comparison of gene sequences or of gene expression products, e.g., mRNA and protein, between a human tissue that is suspected of being diseased and a normal tissue of a human, are used to follow disease progression or remission in the human. Such comparisons of genes, mRNA, or protein are made as described above.

For example, increased or decreased expression of the target gene in the tissue suspected of being neoplastic can indicate the presence of neoplastic cells in the tissue. The degree of increased expression of the target gene in the neoplastic tissue relative to expression of the gene in normal tissue, or differences in the amount of increased expression of the target gene in the neoplastic tissue over time, is used to assess the progression of the neoplasia in that tissue or to monitor the response of the neoplastic tissue to a therapeutic protocol over time.

The expression pattern of any two cell types can be compared, such as low and high metastatic tumor cell lines, or cells from tissue which have and have not been exposed to a therapeutic agent. A genetic predisposition to disease in a human is detected by comparing an target gene, mRNA, or protein in a fetal tissue with a normal target gene, mRNA, or protein. Fetal tissues that are used for this purpose include, but are not limited to, amniotic fluid, chorionic villi, blood, and the blastomere of an in vitro-fertilized embryo. The comparable normal target gene is obtained from any tissue. The mRNA or protein is obtained from a normal tissue of a human in which the target gene is expressed. Differences such as alterations in the nucleotide sequence or size of the fetal target gene or mRNA, or alterations in the molecular weight, amino acid sequence, or relative abundance of fetal target protein, can indicate a germline mutation in the target gene of the fetus, which indicates a genetic predisposition to disease.

D. Use of Nucleic Acids, and Encoded Polypeptides to Screen for Peptide Analogs and Antagonists Polypeptides encoded by the instant nucleic acids, e.g., SEQ ID Nos. 1–544, preferably SEQ ID Nos. 1–168, even more preferably SEQ ID Nos. 1–35, or a sequence complementary thereto, and corresponding full length genes can be used to screen peptide libraries to identify binding partners, such as receptors, from among the encoded polypeptides.

A library of peptides may be synthesized following the methods disclosed in U.S. Pat. No. 5,010,175, and in PCT WO 91/17823. As described below in brief, one prepares a mixture of peptides, which is then screened to identify the peptides exhibiting the desired signal transduction and receptor binding activity. In the ’175 method, a suitable peptide synthesis support (e.g., a resin) is coupled to a mixture of appropriately protected, activated amino acids. The concentration of each amino acid in the reaction mixture is balanced or adjusted in inverse proportion to its coupling reaction rate so that the product is an equimolar mixture of amino acids coupled to the starting resin. The bound amino acids are then deprotected, and reacted with another balanced amino acid mixture to form an equimolar mixture of all possible dipeptides. This process is repeated until a mixture of peptides of the desired length (e.g., hexamers) is formed. Note that one need not include all amino acids in each step: one may include only one or two amino acids in some steps (e.g., where it is known that a particular amino acid is essential in a given position), thus reducing the complexity of the mixture. After the synthesis of the peptide library is completed, the mixture of peptides is screened for binding to the selected polypeptide. The peptides are then tested for their ability to inhibit or enhance activity. Peptides exhibiting the desired activity are then isolated and sequenced.

The method described in WO 91/17823 is similar. However, instead of reacting the synthesis resin with a mixture of activated amino acids, the resin is divided into twenty equal portions (or into a number of portions corresponding to the number of different amino acids to be added in that step), and each amino acid is coupled individually to its portion of resin. The resin portions are then combined, mixed, and again divided into a number of equal portions for reaction with the second amino acid. In this manner, each reaction may be easily driven to completion. Additionally, one may maintain separate “subpools” by treating portions in parallel, rather than combining all resins at each step. This simplifies the process of determining which peptides are responsible for any observed receptor binding or signal transduction activity.

In such cases, the subpools containing, e.g., 1–2,000 candidates each are exposed to one or more polypeptides of the invention. Each subpool that produces a positive result is then resynthesized as a group of smaller subpools (sub-subpools) containing, e.g., 20–100 candidates, and reassayed. Positive sub-subpools may be resynthesized as individual compounds, and assayed finally to determine the peptides that exhibit a high binding constant. These peptides can be tested for their ability to inhibit or enhance the native activity. The methods described in WO 91/7823 and U.S. Pat. No. 5,194,392 (herein incorporated by reference) enable the preparation of such pools and subpools by automated techniques in parallel, such that all synthesis and resynthesis may be performed in a matter of days.

Peptide agonists or antagonists are screened using any available method, such as signal transduction, antibody binding, receptor binding, mitogenic assays, chemotaxis assays, etc. The methods described herein are presently preferred. The assay conditions ideally should resemble the conditions under which the native activity is exhibited in vivo, that is, under physiologic pH, temperature, and ionic strength. Suitable agonists or antagonists will exhibit strong inhibition or enhancement of the native activity at concentrations that do not cause toxic side effects in the subject. Agonists or antagonists that compete for binding to the native polypeptide may require concentrations equal to or greater than the native concentration, while inhibitors capable of binding irreversibly to the polypeptide may be added in concentrations on the order of the native concentration.

The end results of such screening and experimentation will be at least one novel polypeptide binding partner, such as a receptor, encoded by a nucleic acid of the invention, and at least one peptide agonist or antagonist of the novel binding partner. Such agonists and antagonists can be used to modulate, enhance, or inhibit receptor function in cells to which the receptor is native, or in cells that possess the receptor as a result of genetic engineering. Further, if the novel receptor shares biologically important characteristics with a known receptor, information about agonist/antagonist binding may help in developing improved agonists/antagonists of the known receptor.

E. Pharmaceutical Compositions and Therapeutic Uses

Pharmaceutical compositions can comprise polypeptides, antibodies, or polynucleotides of the claimed invention. The pharmaceutical compositions will comprise a therapeutically effective amount of either polypeptides, antibodies, or polynucleotides of the claimed invention.

The term “therapeutically effective amount” as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject’s size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician.

For purposes of the present invention, an effective dose will be from about 0.01 mg/ kg to 50 mg/kg or 0.05 mg/kg to about 10 mg/kg of the DNA constructs in the individual to which it is administered.

A pharmaceutical composition can also contain a pharmaceutically acceptable carrier. The term “pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the nucleic acid compositions of the invention can be (1) administered directly to the subject; (2) delivered ex vivo, to cells derived from the subject; or (3) delivered in vitro for expression of recombinant proteins.

Direct delivery of the compositions will generally be accomplished by injection, either subcutaneously, intraperitoneally, intravenously or intramuscularly, or delivered to the interstitial space of a tissue. The compositions can also be administered into a tumor or lesion. Other modes of administration include oral and pulmonary administration, suppositories, and transdermal applications, needles, and gene guns or hyposprays. Dosage treatment may be a single dose schedule or a multiple dose schedule.

Methods for the ex vivo delivery and reimplantation of transformed cells into a subject are known in the art and described in e.g., International Publication No. WO 93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Once a subject gene has been found to correlate with a proliferative disorder, such as neoplasia, dysplasia, and hyperplasia, the disorder may be amenable to treatment by administration of a therapeutic agent based on the nucleic acid or corresponding polypeptide.

Preparation of antisense polypeptides is discussed above. Neoplasias that are treated with the antisense composition include, but are not limited to, cervical cancers, melanomas, colorectal adenocarcinomas, Wilms' tumor, retinoblastoma, sarcomas, myosarcomas, lung carcinomas, leukemias, such as chronic myelogenous leukemia, promyelocytic leukemia, monocytic leukemia, and mycloid leukemia, and lymphomas, such as histiocytic lymphoma. Proliferative disorders that are treated with the therapeutic composition include disorders such as anhydric hereditary ectodermal dysplasia, congenital alveolar dysplasia, epithelial dysplasia of the cervix, fibrous dysplasia of bone, and mammary dysplasia. Hyperplasias, for example, endometrial, adrenal, breast, prostate, or thyroid hyperplasias or pseudoepitheliomatous hyperplasia of the skin, are treated with antisense therapeutic compositions. Even in disorders in which mutations in the corresponding gene are not implicated, downregulation or inhibition of nucleic acid-related gene expression can have therapeutic application. For example, decreasing nucleic acid-related gene expression can help to suppress tumors in which enhanced expression of the gene is implicated.

Both the dose of the antisense composition and the means of administration are determined based on the specific qualities of the therapeutic composition, the condition, age, and weight of the patient, the progression of the disease, and other relevant factors. Administration of the therapeutic antisense agents of the invention includes local or systemic administration, including injection, oral administration, particle gun or catheterized administration, and topical administration. Preferably, the therapeutic antisense composition contains an expression construct comprising a promoter and a polynucleotide segment of at least about 12, 22, 25, 30, or 35 contiguous nucleotides of the antisense strand of a nucleic acid. Within the expression construct, the polynucleotide segment is located downstream from the promoter, and transcription of the polynucleotide segment initiates at the promoter.

Various methods are used to administer the therapeutic composition directly to a specific site in the body. For example, a small metastatic lesion is located and the therapeutic composition injected several times in several different locations within the body of tumor. Alternatively, arteries which serve a tumor are identified, and the therapeutic composition injected into such an artery, in order to deliver the composition directly into the tumor. A tumor that has a necrotic center is aspirated and the composition injected directly into the now empty center of the tumor. The antisense composition is directly administered to the surface of the tumor, for example, by topical application of the composition. X-ray imaging is used to assist in certain of the above delivery methods.

Receptor-mediated targeted delivery of therapeutic compositions containing an antisense polynucleotide, subgenomic polynucleotides, or antibodies to specific tissues is also used. Receptor-mediated DNA delivery techniques are described in, for example, Findeis et al., *Trends in Biotechnol.* (1993) 11:202–205; Chiou et al., (1994) Gene Therapeutics: Methods And Applications Of Direct Gene Transfer (J. A. Wolff, ed.); Wu & Wu, *J. Biol. Chem.* (1988) 263:621–24; Wu et al., *J. Biol. Chem.* (1994) 269:542–46; Zenke et al., *Proc. Natl. Acad. Sci.* (*USA*) (1990) 87:3655–59; Wu et al., *J. Biol. Chem.* (1991) 266:338–42. Preferably, receptor-mediated targeted delivery of therapeutic compositions containing antibodies of the invention is used to deliver the antibodies to specific tissue.

Therapeutic compositions containing antisense subgenomic polynucleotides are administered in a range of about 100 ng to about 200 mg of DNA for local administration in a gene therapy protocol. Concentration ranges of about 500 ng to about 50 mg, about 1 mg to about 2 mg, about 5 mg to about 500 mg, and about 20 mg to about 100 mg of DNA can also be used during a gene therapy protocol. Factors such as method of action and efficacy of transformation and expression are considerations which will affect the dosage required for ultimate efficacy of the antisense subgenomic nucleic acids. Where greater expression is desired over a larger area of tissue, larger amounts of antisense subgenomic nucleic acids or the same amounts readministered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect. A more complete description of gene therapy vectors, especially retroviral vectors, is contained in U.S. Ser. No. 08/869,309, which is expressly incorporated herein, and in section F below.

For genes encoding polypeptides or proteins with anti-inflammatory activity, suitable use, doses, and administration are described in U.S. Pat. No. 5,654,173, incorporated herein by reference. Therapeutic agents also include antibodies to proteins and polypeptides encoded by the subject nucleic acids, as described in U.S. Pat. No. 5,654,173.

F. Gene Therapy

The therapeutic nucleic acids of the present invention may be utilized in gene delivery vehicles. The gene delivery vehicle may be of viral or non-viral origin (see generally, Jolly, *Cancer Gene Therapy* (1994) 1:51–64; Kimura, *Human Gene Therpay* (1994) 5:845–852; Connelly, *Human Gene Therapy* (1995) 1:185–193; and Kaplitt, *Nature Genetics* (1994) 6:148–153). Gene therapy vehicles for delivery of constructs including a coding sequence of a therapeutic of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 0 415 731; WO 90/07936; WO 94/03622; WO 93/25698; WO 93/25234; U.S. Pat. No. 5, 219,740; WO 93/11230; WO 93/10218; Vile and Hart, *Cancer Res.* (1993) 53:3860–3864; Vile and Hart, *Cancer Res.* (1993) 53:962–967; Ram et al., *Cancer Res.* (1993) 53:83–88; Takamiya et al., *J. Neurosci. Res.* (1992) 33:493–503; Baba et al., *J. Neurosurg.* (1993) 79:729–735; U.S. Pat. no. 4,777,127; GB Patent No. 2,200,651; and EP 0 345 242. Preferred recombinant retroviruses include those described in WO 91/02805.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

The present invention also employs alphavirus-based vectors that can function as gene delivery vehicles. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and PCT Publication Nos. WO 92/10578; WO 94/21792; WO 95/27069; WO 95/27044; and WO 95/07994.

Gene delivery vehicles of the present invention can also employ parvovirus such as adeno-associated virus (AAV) vectors. Representative examples include the AAV vectors disclosed by Srivastava in WO 93/09239, Samulski et al., *J. Vir.* (1989) 63:3822–3828; Mendelson et al., *Virol.* (1988) 166:154–165; and Flotte et al., *PNAS* (1993) 90:10613–10617.

Representative examples of adenoviral vectors include those described by Berkner, *Biotechniques* (1988) 6:616–627; Rosenfeld et al., *Science* (1991) 252:431– 434; WO 93/19191; Kolls et al., *PNAS* (1994) 91:215–219; Kass-Eisler et al., *PNAS* (1993) 90:11498–11502; Guzman et al., *Circulation* (1993) 88:2838–2848; Guzman et al., *Cir. Res.* (1993) 73:1202–1207; Zabner et al., *Cell* (1993) 75:207–216; Li et al., *Hum. Gene Ther.* (1993) 4:403–409; Cailaud et al., *Eur. J. Neurosci.* (1993) 5:1287–1291; Vincent et al., *Nat. Genet.* (1993) 5:130–134; Jaffe et al., *Nat. Genet.* (1992) 1:372–378; and Levrero et al., *Gene* (1991) 101:195–202. Exemplary adenoviral gene therapy vectors employable in this invention also include those described in WO 94/12649, WO 93/03769; WO 93/19191; WO 94/28938; WO 95/11984 and WO 95/00655. Administration of DNA linked to killed adenovirus as described in Curiel, *Hum. Gene Ther.* (1992) 3:147–154 may be employed.

Other gene delivery vehicles and methods may be employed, including polycationic condensed DNA linked or unlinked to killed adenovirus alone, for example Curiel, *Hum. Gene Ther.* (1992) 3:147–154; ligand linked DNA, for example see Wu, *J. Biol. Chem.* (1989) 264:16985–16987; eukaryotic cell delivery vehicles cells, for example see U.S. Ser. No. 08/240,030, filed May 9, 1994, and U.S. Ser. No. 08/404,796; deposition of photopolymerized hydrogel materials; hand-held gene transfer particle gun, as described in U.S. Pat. No. 5,149,655; ionizing radiation as described in U.S. Pat. No. 5,206,152 and in WO92/11033; nucleic charge neutralization or fusion with cell membranes. Additional approaches are described in Philip, *Mol. Cell Biol.* (1994) 14:2411–2418, and in Woffendin, *Proc. Natl. Acad. Sci.* (1994) 91:1581–1585.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422, 120, PCT Nos. WO 95/13796, WO 94/23697, and WO 91/14445, and EP No. 0 524 968.

Further non-viral delivery suitable for use includes mechanical delivery systems such as the approach described in Woffendin et al., *Proc. Natl. Acad. Sci. USA* (1994) 91(24):11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

G. Transoenic Animals

One aspect of the present invention relates to transgenic non-human animals having germline and/or somatic cells in which the biological activity of one or more genes are altered by a chromosomally incorporated transgene.

In a preferred embodiments, the transgene encodes a mutant protein, such as dominant negative protein which antagonizes at least a portion of the biological function of a wild-type protein.

Yet another preferred transgenic animal includes a transgene encoding an antisense transcript which, when transcribed from the transgene, hybridizes with a gene or a mRNA transcript thereof, and inhibits expression of the gene.

In one embodiment, the present invention provides a desired non-human animal or an animal (including human) cell which contains a predefined, specific and desired alteration rendering the non-human animal or animal cell predisposed to cancer. Specifically, the invention pertains to a genetically altered non-human animal (most preferably, a mouse), or a cell (either non-human animal or human) in culture, that is defective in at least one of two alleles of a tumor-suppressor gene. The inactivation of at least one of these tumor suppressor alleles results in an animal with a higher susceptibility to tumor induction or other proliferative or differentiative disorders, or disorders marked by aberrant signal transduction, e.g., from a cytokine or growth factor. A genetically altered mouse of this type is able to serve as a useful model for hereditary cancers and as a test animal for carcinogen studies. The invention additionally pertains to the use of such non-human animals or animal cells, and their progeny in research and medicine.

Furthermore, it is contemplated that cells of the transgenic animals of the present invention can include other transgenes, e.g., which alter the biological activity of a second tumor suppressor gene or an oncogene. For instance, the second transgene can functionally disrupt the biological activity of a second tumor suppressor gene, such as p53, p73, DCC, $p21^{cip1}$, $p27^{kip1}$, Rb, Mad or E2F. Alternatively, the second transgene can cause overexpression or loss of regulation of an oncogene, such as ras, myc, a cdc25 phosphatase, Bc1-2, Bc1-6, a transforming growth factor, neu, int-3, polyoma virus middle T antigen, SV40 large T antigen, a papillomaviral E6 protein, a papillomaviral E7 protein, CDK4, or cyclin D1.

A preferred transgenic non-human animal of the present invention has germline and/or somatic cells in which one or more alleles of a gene are disrupted by a chromosomally incorporated transgene, wherein the transgene includes a marker sequence providing a detectable signal for identifying the presence of the transgene in cells of the transgenic animal, and replaces at least a portion of the gene or is inserted into the gene or disrupts expression of a wild-type protein.

Still another aspect of the present invention relates to methods for generating non-human animals and stem cells having a functionally disrupted endogenous gene. In a preferred embodiment, the method comprises the steps of:

(i) constructing a transgene construct including (a) a recombination region having at least a portion of the gene, which recombination region directs recombination of the transgene with the gene, and (b) a marker sequence which provides a detectable signal for identifying the presence of the transgene in a cell;

(ii) transfering the transgene into stem cells of a non-human animal;

(iii) selecting stem cells having a correctly targeted homologous recombination between the transgene and the gene;

(iv) transfering cells identified in step (iii) into a non-human blastocyst and implanting the resulting chimeric blastocyst into a non-human female; and (v) collecting offspring harboring an endogenous gene allele having the correctly targeted recombination.

Yet another aspect of the invention provides a method for evaluating the carcinogenic potential of an agent by (i) contacting a transgenic animal of the present invention with a test agent, and (ii) comparing the number of transformed cells in a sample from the treated animal with the number of transformed cells in a sample from an untreated transgenic animal or transgenic animal treated with a control agent. The difference in the number of transformed cells in the treated animal, relative to the number of transformed cells in the absence of treatment with a control agent, indicates the carcinogenic potential of the test compound.

Another aspect of the invention provides a method of evaluating an anti-proliferative activity of a test compound. In preferred embodiments, the method includes contacting a transgenic animal of the present invention, or a sample of cells from such animal, with a test agent, and determining the number of transformed cells in a specimen from the transgenic animal or in the sample of cells. A statistically significant decrease in the number of transformed cells, relative to the number of transformed cells in the absence of the test agent, indicates the test compound is a potential anti-proliferative agent.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press:1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

As mentioned above, the sequences described herein are believed to have particular utility in regards to colon cancer. However, they may also be useful with other types of cancers and other disease states.

The present invention will now be illustrated by reference to the following examples which set forth particularly advantageous embodiments. However, it should be noted that these embodiments are illustrative and are not to be construed as restricting the invention in any way.

XI. EXAMPLES

A. Identification of Differentially Expressed Sequences

Description of the Libraries

SEQ ID Nos: 1–544 were derived from libraries designated as DE and PA as described below. The DE library is a normalized, colon cancer specific, subtracted cDNA library. The DE library is specific for sequences expressed in colon cancer [proximal and distal Dukes' B, microsatellite instability negative (MSI−)] but not expressed in normal tissues, including normal colon tissue. The PA library is a normalized, colon specific, subtracted cDNA library. The PA library is specific for sequences expressed in normal colon tissue but not expressed in other normal tissues.

Construction of a Colon Cancer Specific Library

A subtracted colon cancer specific library was made by subtracting pooled proximal, stage B, $MSI^-$ and distal, Stage B, $MSI^-$ tumor tissue cDNA against a combination of pooled driver normal cDNA made from colon, peripheral blood leukocytes (PBL), liver, spleen, lung, kidney, heart, small intestine, skeletal muscle, and prostate tissue cDNAs. The following RNA samples were obtained from Origene Technologies, Inc., Rockville, Md., and were used to synthesize the pooled driver cDNA: #HT-1015 normal colon total RNA, #HT-1005 liver total RNA, #HT-1004 spleen total RNA, #HT-1009 lung total RNA, #HT-1003 kidney total RNA, #HT-1006 peripheral blood leukocyte total RNA, #HT-prostate total RNA, #HM-1002 heart muscle poly A+RNA, #HM-1007 intestine poly A+RNA, and #HM-1008 skeletal muscle poly A+RNA. First-strand cDNA was prepared for each using 1 microgram of RNA. A biased pool of first-strand cDNA was prepared containing 50% normal colon first-strand cDNA reaction and 5.56% of each of the remaining tissue first-strand cDNA reactions by volume. Eight individual amplification reactions, each containing 1 microliter of the biased first-strand cDNA reaction pool, were performed for 18 cycles. The double stranded cDNA product from all eight amplification reactions were pooled and purified for subsequent use in subtractive hybridization. The colon cancer specific subtracted library was called DE and individual clones derived from this library were referred to with a number prefixed by DE.

Normalized subtracted DE colon cancer specific and pooled normal human tissue specific cDNA libraries (same as components of driver cDNA above) were generated according published procedures (Daitchenko et al., 1996 PNAS 93:6025–6030, Gurskaya et al., 1996 Analytical Biochemistry 240:90–97) using Clontech Laboratories, Inc., PCR-Select cDNA subtraction kit, PT1117-1. A forty-five fold mass excess of driver cDNA (450 nanograms) was used for each subtraction experiment. Subtractive hybridization of tester with driver cDNAs was performed twice, each time for about 8–12 hours. Subtracted cancer specific DE cDNA was ligated into the pCR2.1-TOPO plasmid vector (Invitrogen Corporation, Carlsbad Calif.) and chemically transformed into ultracompetent Epicurian *E. coli* XL10-Gold cells (Stratagene, La Jolla, Calif.). A reverse library was also constructed wherein the tester and driver samples were switched; this library was designated as MD.

Construction of a Normal Colon Specific Library

This normal colon tissue specific library was made using Clontech Laboratories Inc PCR-Select kit, K1804-1, following instructions from the users manual (PT1117-1).

Four, 100 μl, SMART PCR cDNA amplification reactions for each normal, non-cancerous, patient sample, were performed, starting with 1 μl from their respective first strand cDNA reactions. Each sample was amplified for only 18 cycles using the following PCR conditions; 95 C-10 sec, 68 C 5 min. using a 9600 Perkin Elmer instrument. The following are Bayer Diagnostic sample identification numbers for the cDNA samples that were amplified: NPB(−)27347, NPB(−)27859, NPB(−)28147, NPB(−)28162, NDB(−)28800, NDB(−)29243, NDB(−)29244 and NDB(−)42472. These are normal colon tissue samples obtained from the same patients providing the proximal stage B MSI− and distal stage B MSI− cancer samples, which were used to prepare the DE library described above. Equal volumes of the eight normal colon cDNAs were pooled. A subtracted normal colon tissue specific library was made by subtracting the normal colon cDNA pool against a combination of pooled driver normal cDNA made from peripheral blood leukocytes (PBL), liver, spleen, lung, kidney, heart, small intestine, skeletal muscle, and prostate tissue cDNAs. The following are the RNA samples that were used to synthesize the pooled driver cDNA: #HT-1005 liver total RNA, #HT-1004 spleen total RNA, #HT-1009 lung total RNA, #HT-1003 kidney total RNA, #HT-1006 peripheral blood leukocyte total RNA, #HT-prostate total RNA, #HM-1002 heart muscle poly A+RNA, #HM-1007 intestine poly A+RNA, and #HM-1008 skeletal muscle poly A+RNA. First-strand cDNA was prepared for each using 1 microgram of RNA. A pool of first strand cDNA reactions was then made consisting of equal volumes of the nine driver tissue first-strand cDNA reactions. Eight individual amplification reactions, each containing 1 microliter of the first-strand cDNA reaction pool, were performed for 18 cycles. The double stranded cDNA product from all eight amplification reactions was pooled and purified for subsequent use in subtractive hybridization. The normal colon tissue specific subtracted library was called PA and individual clones derived from this library were referred to with a number prefixed by PA.

The normalized subtracted PA normal colon specific cDNA library and a subtracted normal human tissue specific cDNA library, consisting of the human tissues listed above were generated according published procedures (Daitchenko et al., 1996 PNAS 93:6025–6030, Gurskaya et al., 1996 Analytical Biochemistry 240:90–97) using Clontech Laboratories, Inc., PCR-Select cDNA subtraction kit, PTI 117–1. Library construction and cloning were carried out as described above for the colon cancer specific library. Out of the 1152 clones that were analyzed for differential expression, approximately 69% were differentially expressed.

Each EST isolated from each of the above libraries represents a sequence from a partial mRNA transcript, since the cDNA used for making the subtracted library was restricted with RsaI, a four base cutter restriction endonuclease that generates fragments with an average size of about 600 base pairs.

Validation of Differential Expression in Colon Cancer

To validate that the differentially expressed sequences found in this library were specific to colon cancer, the clones were screened with cDNAs prepared from a colon cancer specific library, Delaware (DE), and a normal tissue specific library Maryland (MD). cDNA clones were analyzed for differential expression following the procedure developed by von Stein et al., 1997, Nucleic Acids Research 25(13):2598–2602 and using probes synthesized according to a published method (Jin et al., 1997, Biotechniques 23:1083–1086). Out of the 1248 clones that were analyzed for differential expression approximately 83% were differentially expressed.

Sequencing and Analysis of Differentially Expressed Clones

The nucleotide sequence of the inserts from clones shown to be differentially expressed was determined by single-pass sequencing from either the T7 or M13 promoter sites using fluorescently labeled dideoxynucleotides via the Sanger sequencing method. Sequences were analyzed according to methods described in the text (XI., Examples; B. Results of Public Database Search).

Each nucleic acid represents sequence from at least a partial mRNA transcript. The nucleic acids of the invention were assigned a sequence identification number (see attachments). The nucleic acid sequences are provided in the attached Sequence Listing.

An example of an experiment to identify differentially expressed clones is shown in the FIGURE, "Differential Expression Analysis". The inserts from subtracted clones were amplified, electrophoresed, and blotted on to membranes as described above. The gel was hybridized with RSAI cut DE and MD cDNA probes as described above.

In the FIGURE, individual clones are designated by a number at the top of each lane; the blots are aligned so that the same clone is represented in the same vertical lane in both the upper ("Cancer Probe") and lower ("Normal Probe") blot. Lanes labeled "O" indicate clones that are overexpressed, i.e., show a darker, more prominent band in the upper blot ("Cancer Probe") relative to that observed, in the same lane, in the lower blot ("Normal Probe"). The Lane labeled "U" indicates a clone that is underexpressed, i.e., shows a darker, more prominent band in the lower blot ("Normal Probe") relative to that observed, in the same lane, in the upper blot ("Cancer Probe"). The lane labeled "M", indicates a clone that is marginally overexpressed in cancer and normal cells.

B. Results of Public Databases Searches

The nucleotide sequence of SEQ ID Nos. 1–544 were aligned with individual sequences that were publicly available. Genbank and divisions of GenBank, such as dbEST, CGAP, and Unigene were the primary databases used to perform the sequence similarity searches. The patent database, GENESEQ, was also utilized.

A total of 544 sequences were analyzed. The sequences were first masked to identify vector-derived sequences, which were subsequently removed. The remaining sequence information was used to create the Sequence Listing (SEQ ID Nos. 1–544). Each of these sequences was used as the query sequence to perform a Blast 2 search against the databases listed above. The Blast 2 search differs from the traditional Blast search in that it allows for the introduction of gaps in order to produce an optimal aligrunent of two sequences.

A proprietary algorithm was developed to utilize the output from the Blast 2 searches and categorize the sequences based upon high similarity (e value<1e-40) or identity to entries contained in the GenBank and dbEST databases. Three categories were created as follows: 1) matches to known human genes, 2) matches to human EST sequences, and 3) no significant match to either 1 or 2, and therefore a potentially novel human sequence.

Those skilled in the art will recognize, or be able to ascertain, using not more than routine experimentation, many equivalents to the specific embodiments of the invention described herein. Such specific embodiments and equivalents are intended to be encompassed by the following claims.

All patents, published patent applications, and publications cited herein are incorporated by reference as if set forth fully herein.

TABLE 1

| SEQ ID NO | clone name | Tissue Probe | SEQ ID NO | clone name | Tissue Probe |
|---|---|---|---|---|---|
| 1 | de0020t7 | U | 273 | de0214t7 | ND |
| 2 | de0041t7 | N | 274 | de0215t7 | ND |
| 3 | de0056t7 | U | 275 | de0218t7 | ND |
| 4 | de0064t7 | N | 276 | de0221t7 | ND |
| 5 | de0092t7 | U | 277 | de0223t7 | O |
| 6 | de0142t7 | N | 278 | de0227t7 | ND |
| 7 | de0153t7 | M | 279 | de0229t7 | O |
| 8 | de0163t7 | U | 280 | de0230t7 | ND |
| 9 | de0188t7 | N | 281 | de0232t7 | ND |
| 10 | de0190t7 | U | 282 | de0234t7 | ND |
| 11 | de0201t7 | M | 283 | de0235t7 | ND |
| 12 | de0225t7 | U | 284 | de0237t7 | ND |
| 13 | de0246t7 | U | 285 | de0238t7 | ND |
| 14 | de0257t7 | N | 286 | de0239t7 | N |
| 15 | de0285t7 | O | 287 | de0241t7 | N |
| 16 | de0529t7 | U | 288 | de0242t7 | O |
| 17 | de0629t7 | U | 289 | de0244t7 | N |
| 18 | de0727t7 | O | 290 | de0247t7 | O |
| 19 | de0787t7 | U | 291 | de0252t7 | ND |
| 20 | de0810t7 | N | 292 | de0255t7 | N |
| 21 | de0833t7 | N | 293 | de0256t7 | ND |
| 22 | pa0107t7 | U | 294 | de0260t7 | N |
| 23 | pa0130t7 | U | 295 | de0261t7 | N |
| 24 | pa0149t7 | U | 296 | de0263t7 | N |
| 25 | pa0185t7 | U | 297 | de0264t7 | ND |
| 26 | pa0203t7 | U | 298 | de0265t7 | ND |
| 27 | pa0277t7 | U | 299 | de0266t7 | O |
| 28 | pa0287t7 | U | 300 | de0267t7 | N |
| 29 | pa0293t7* | U | 301 | de0268t7 | ND |
| 30 | pa0341t7 | U | 302 | de0272t7 | ND |
| 31 | pa0357t7 | N | 303 | de0273t7 | ND |
| 32 | pa0361t7 | U | 304 | de0274t7 | N |
| 33 | pa0404t7 | U | 305 | de0276t7 | O |
| 34 | pa0408t7 | U | 306 | de0277t7 | M |
| 35 | pa0425t7 | N | 307 | de0279t7 | N |
| 36 | de0001t7 | N | 308 | de0280t7 | ND |
| 37 | de0002t7 | N | 309 | de0281t7 | N |
| 38 | de0036t7 | N | 310 | de0282t7 | ND |
| 39 | de0038t7 | M | 311 | de0284t7 | ND |
| 40 | de0040t7 | N | 312 | de0286t7 | ND |
| 41 | de0043t7 | O | 313 | de0339t7 | ND |
| 42 | de0044t7 | N | 314 | de0483t7 | ND |
| 43 | de0045t7 | N | 315 | de0484t7 | M |
| 44 | de0050t7 | N | 316 | de0491t7 | ND |
| 45 | de0052t7 | N | 317 | de0499t7 | ND |
| 46 | de0054t7 | N | 318 | de0507t7 | M |
| 47 | de0055t7 | N | 319 | de0511t7 | O |
| 48 | de0059t7 | O | 320 | de0519t7 | ND |
| 49 | de0060t7 | N | 321 | de0520t7 | N |
| 50 | de0063t7 | U | 322 | de0522t7 | ND |
| 51 | de0066t7 | O | 323 | de0524t7 | M |
| 52 | de0067t7 | O | 324 | de0530t7 | ND |
| 53 | de0079t7 | N | 325 | de0531t7 | ND |
| 54 | de0085t7 | N | 326 | de0532t7 | M |
| 55 | de0089t7 | N | 327 | de0534t7 | N |
| 56 | de0095t7 | N | 328 | de0542t7 | ND |
| 57 | de0099t7 | N | 329 | de0556t7 | M |
| 58 | de0105t7 | N | 330 | de0557t7 | ND |
| 59 | de0112t7 | N | 331 | de0559t7 | U |
| 60 | de0114t7 | N | 332 | de0562t7 | ND |
| 61 | de0121t7 | N | 333 | de0566t7 | U |
| 62 | de0122t7 | N | 334 | de0567t7 | N |
| 63 | de0124t7 | N | 335 | de0568t7 | ND |
| 64 | de0139t7 | M | 336 | de0570t7 | ND |
| 65 | de0143t7 | N | 337 | de0571t7 | ND |
| 66 | de0166t7 | U | 338 | de0574t7 | ND |
| 67 | de0168t7 | N | 339 | de0581t7 | ND |
| 68 | de0171t7 | N | 340 | de0583t7 | U |
| 69 | de0178t7 | N | 341 | de0587t7 | ND |
| 70 | de0180t7 | O | 342 | de0588t7 | ND |
| 71 | de0181t7 | N | 343 | de0591t7 | ND |
| 72 | de0199t7 | N | 344 | de0592t7 | ND |
| 73 | de0200t7 | N | 345 | de0597t7 | U |
| 74 | de0202t7 | N | 346 | de0598t7 | ND |
| 75 | de0205t7 | N | 347 | de0599t7 | ND |
| 76 | de0207t7 | U | 348 | de0602t7 | N |

TABLE 1-continued

| SEQ ID NO | clone name | Tissue Probe | SEQ ID NO | clone name | Tissue Probe |
|---|---|---|---|---|---|
| 77 | de0212t7 | N | 349 | de0605t7 | ND |
| 78 | de0217t7 | N | 350 | de0608t7 | ND |
| 79 | de0220t7 | U | 351 | de0610t7 | ND |
| 80 | de0228t7 | N | 352 | de0616t7 | O |
| 81 | de0236t7 | O | 353 | de0619t7 | U |
| 82 | de0243t7 | N | 354 | de0620t7 | ND |
| 83 | de0253t7 | O | 355 | de0622t7 | ND |
| 84 | de0258t7 | N | 356 | de0623t7 | ND |
| 85 | de0259t7 | N | 357 | de0624t7 | O |
| 86 | de0262t7 | N | 358 | de0625t7 | ND |
| 87 | de0270t7 | N | 359 | de0628t7 | ND |
| 88 | de0275t7 | N | 360 | de0630t7 | ND |
| 89 | de0287t7 | N | 361 | de0631t7 | ND |
| 90 | de0288t7 | N | 362 | de0632t7 | N |
| 91 | de0306t7 | N | 363 | de0634t7 | ND |
| 92 | de0490t7 | N | 364 | de0639t7 | ND |
| 93 | de0501t7 | M | 365 | de0642t7 | ND |
| 94 | de0516t7 | N | 366 | de0649t7 | ND |
| 95 | de0589t7 | N | 367 | de0650t7 | N |
| 96 | de0596t7 | U | 368 | de0656t7 | N |
| 97 | de0600t7 | N | 369 | de0657t7 | ND |
| 98 | de0609t7 | U | 370 | de0660t7 | ND |
| 99 | de0611t7 | N | 371 | de0661t7 | O |
| 100 | de0617t7 | U | 372 | de0662t7 | O |
| 101 | de0633t7 | N | 373 | de0664t7 | ND |
| 102 | de0643t7 | N | 374 | de0665t7 | ND |
| 103 | de0647t7 | M | 375 | de0667t7 | ND |
| 104 | de0652t7 | N | 376 | de0669t7 | ND |
| 105 | de0666t7 | N | 377 | de0676t7 | ND |
| 106 | de0695t7 | U | 378 | de0686t7 | N |
| 107 | de0705t7 | N | 379 | de0687t7 | ND |
| 108 | de0706t7 | M | 380 | de0689t7 | N |
| 109 | de0708t7 | N | 381 | de0691t7 | M |
| 110 | de0724t7 | N | 382 | de0693t7 | ND |
| 111 | de0735t7 | N | 383 | de0703t7 | ND |
| 112 | de0740t7 | N | 384 | de0704t7 | M |
| 113 | de0742t7 | N | 385 | de0707t7 | O |
| 114 | de0747t7 | N | 386 | de0709t7 | O |
| 115 | de0764t7 | N | 387 | de0710t7 | ND |
| 116 | de0777t7 | O | 388 | de0712t7 | N |
| 117 | de0781t7 | N | 389 | de0715t7 | ND |
| 118 | de0793t7 | U | 390 | de0719t7 | N |
| 119 | de0794t7 | N | 391 | de0722t7 | ND |
| 120 | de0798t7 | N | 392 | de0723t7 | ND |
| 121 | de0800t7 | O | 393 | de0725t7 | N |
| 122 | de0816t7 | N | 394 | de0728t7 | ND |
| 123 | de0818t7 | N | 395 | de0729t7 | ND |
| 124 | de0835t7 | N | 396 | de0731t7 | ND |
| 125 | pa0078t7 | U | 397 | de0732t7 | ND |
| 126 | pa0080t7 | N | 398 | de0737t7 | ND |
| 127 | pa0088t7 | U | 399 | de0739t7 | M |
| 128 | pa0089t7 | U | 400 | de0741t7 | ND |
| 129 | pa0095t7 | U | 401 | de0744t7 | N |
| 130 | pa0158t7 | U | 402 | de0746t7 | ND |
| 131 | pa0159t7 | U | 403 | de0749t7 | N |
| 132 | pa0187t7 | N | 404 | de0750t7 | ND |
| 133 | pa0190t7 | U | 405 | de0756t7 | ND |
| 134 | pa0192t7 | U | 406 | de0759t7 | ND |
| 135 | pa0209t7 | U | 407 | de0761t7 | O |
| 136 | pa0215t7 | N | 408 | de0762t7 | ND |
| 137 | pa0218t7 | N | 409 | de0766t7 | ND |
| 138 | pa0220t7 | N | 410 | de0768t7 | U |
| 139 | pa0238t7 | N | 411 | de0769t7 | ND |
| 140 | pa0249t7 | U | 412 | de0772t7 | ND |
| 141 | pa0256t7 | N | 413 | de0776t7 | ND |
| 142 | pa0258t7 | U | 414 | de0779t7 | ND |
| 143 | pa0272t7 | N | 415 | de0785t7 | ND |
| 144 | pa0283t7 | N | 416 | de0786t7 | ND |
| 145 | pa0295t7 | N | 417 | de0788t7 | ND |
| 146 | pa0309t7 | U | 418 | de0789t7 | ND |
| 147 | pa0314t7 | N | 419 | de0792t7 | ND |
| 148 | pa0317t7 | N | 420 | de0796t7 | ND |
| 149 | pa0319t7 | N | 421 | de0797t7 | ND |
| 150 | pa0323t7 | N | 422 | de0801t7 | O |
| 151 | pa0333t7 | N | 423 | de0804t7 | ND |
| 152 | pa0336t7 | N | 424 | de0805t7 | ND |

TABLE 1-continued

| SEQ ID NO | clone name | Tissue Probe | SEQ ID NO | clone name | Tissue Probe |
|---|---|---|---|---|---|
| 153 | pa0353t7 | N | 425 | de0806t7 | ND |
| 154 | pa0363t7 | N | 426 | de0807t7 | N |
| 155 | pa0364t7 | N | 427 | de0811t7 | O |
| 156 | pa0366t7 | U | 428 | de0812t7 | ND |
| 157 | pa0382t7 | N | 429 | de0817t7 | N |
| 158 | pa0383t7 | N | 430 | de0820t7 | ND |
| 159 | pa0388t7 | N | 431 | de0821t7 | ND |
| 160 | pa0389t7 | N | 432 | de0822t7 | ND |
| 161 | pa0405t7 | N | 433 | de0823t7 | N |
| 162 | pa0406t7 | N | 434 | de0824t7 | N |
| 163 | pa0409t7 | U | 435 | de0825t7 | ND |
| 164 | pa0411t7 | N | 436 | de0826t7 | ND |
| 165 | pa0417t7 | N | 437 | de0827t7 | ND |
| 166 | pa0421t7 | U | 438 | de0829t7 | ND |
| 167 | pa0429t7 | U | 439 | de0830t7 | ND |
| 168 | pa0432t7 | U | 440 | de0837t7 | N |
| 169 | de0004t7 | U | 441 | de0840t7 | ND |
| 170 | de0008t7 | ND | 442 | de0848t7 | ND |
| 171 | de0009t7 | ND | 443 | pa0079t7 | N |
| 172 | de0010t7 | ND | 444 | pa0081t7 | ND |
| 173 | de0011t7 | ND | 445 | pa0082t7 | ND |
| 174 | de0012t7 | ND | 448 | pa0083t7 | ND |
| 175 | de0013t7 | ND | 447 | pa0084t7 | ND |
| 176 | de0014t7 | ND | 448 | pa0085t7 | ND |
| 177 | de0016t7 | ND | 449 | pa0086t7 | M |
| 178 | de0017t7 | ND | 450 | pa0090t7 | N |
| 179 | de0018t7 | M | 451 | pa0091t7 | ND |
| 180 | de0019t7 | ND | 452 | pa0092t7 | N |
| 181 | de0023t7 | O | 453 | pa0096t7 | ND |
| 182 | de0024t7 | N | 454 | pa0100t7 | ND |
| 183 | de0029t7 | ND | 455 | pa0101t7 | U |
| 184 | de0030t7 | ND | 456 | pa0103t7 | ND |
| 185 | de0032t7 | ND | 457 | pa0104t7 | ND |
| 186 | de0033t7 | O | 458 | pa0114t7 | ND |
| 187 | de0034t7 | ND | 459 | pa0115t7 | ND |
| 188 | de0035t7 | ND | 460 | pa0118t7 | ND |
| 189 | de0042t7 | ND | 461 | pa0120t7 | ND |
| 190 | de0047t7 | ND | 462 | pa0129t7 | ND |
| 191 | de0048t7 | N | 463 | pa0131t7 | U |
| 192 | de0049t7 | ND | 464 | pa0133t7 | ND |
| 193 | de0051t7 | O | 465 | pa0135t7 | N |
| 194 | de0053t7 | ND | 466 | pa0140t7 | O |
| 195 | de0065t7 | ND | 467 | pa0142t7 | ND |
| 196 | de0068t7 | N | 468 | pa0143t7 | ND |
| 197 | de0069t7 | ND | 469 | pa0146t7 | ND |
| 198 | de0071t7 | N | 470 | pa0147t7 | ND |
| 199 | de0072t7 | ND | 471 | pa0148t7 | ND |
| 200 | de0076t7 | U | 472 | pa0151t7 | ND |
| 201 | de0077t7 | ND | 473 | pa0157t7 | ND |
| 202 | de0078t7 | ND | 474 | pa0164t7 | ND |
| 203 | de0080t7 | ND | 475 | pa0167t7 | N |
| 204 | de0082t7 | ND | 476 | pa0171t7 | U |
| 205 | de0086t7 | ND | 477 | pa0174t7 | ND |
| 206 | de0087t7 | ND | 478 | pa0175t7 | ND |
| 207 | de0088t7 | ND | 479 | pa0179t7 | N |
| 208 | de0093t7 | N | 480 | pa0182t7 | ND |
| 209 | de0094t7 | ND | 481 | pa0184t7 | ND |
| 210 | de0097t7 | O | 482 | pa0186t7 | U |
| 211 | de0098t7 | ND | 483 | pa0189t7 | ND |
| 212 | de0100t7 | ND | 484 | pa0207t7 | ND |
| 213 | de0101t7 | ND | 485 | pa0210t7 | ND |
| 214 | de0102t7 | ND | 486 | pa0212t7 | ND |
| 215 | de0106t7 | ND | 487 | pa0214t7 | ND |
| 216 | de0109t7 | U | 488 | pa0216t7 | ND |
| 217 | de0110t7 | N | 489 | pa0217t7 | M |
| 218 | de0111t7 | N | 490 | pa0219t7 | N |
| 219 | de0113t7 | ND | 491 | pa0223t7 | ND |
| 220 | de0115t7 | O | 492 | pa0224t7 | ND |
| 221 | de0117t7 | ND | 493 | pa0228t7 | ND |
| 222 | de0118t7 | U | 494 | pa0229t7 | U |
| 223 | de0119t7 | ND | 495 | pa0231t7 | ND |
| 224 | de0123t7 | ND | 496 | pa0232t7 | ND |
| 225 | de0125t7 | ND | 497 | pa0240t7 | ND |
| 226 | de0126t7 | ND | 498 | pa0252t7 | ND |
| 227 | de0129t7 | ND | 499 | pa0260t7 | U |
| 228 | de0130t7 | U | 500 | pa0261t7 | N |

TABLE 1-continued

| SEQ ID NO | clone name | Tissue Probe | SEQ ID NO | clone name | Tissue Probe |
|---|---|---|---|---|---|
| 229 | de0131t7 | O | 501 | pa0262t7 | ND |
| 230 | de0132t7 | ND | 502 | pa0264t7 | N |
| 231 | de0134t7 | O | 503 | pa0265t7 | N |
| 232 | de0135t7 | ND | 504 | pa0268t7 | ND |
| 233 | de0137t7 | M | 505 | pa0276t7 | ND |
| 234 | de0138t7 | ND | 506 | pa0279t7 | ND |
| 235 | de0140t7 | ND | 507 | pa0280t7 | ND |
| 236 | de0141t7 | ND | 508 | pa0282t7 | ND |
| 237 | de0145t7 | ND | 509 | pa0285t7 | ND |
| 238 | de0146t7 | O | 510 | pa0299t7 | ND |
| 239 | de0148t7 | ND | 511 | pa0300t7 | U |
| 240 | de0149t7 | ND | 512 | pa0301t7 | ND |
| 241 | de0151t7 | O | 513 | pa0302t7 | ND |
| 242 | de0152t7 | ND | 514 | pa0305t7 | N |
| 243 | de0154t7 | ND | 515 | pa0306t7 | ND |
| 244 | de0156t7 | ND | 516 | pa0307t7 | ND |
| 245 | de0157t7 | U | 517 | pa0311t7 | ND |
| 246 | de0158t7 | ND | 518 | pa0316t7 | ND |
| 247 | de0159t7 | N | 519 | pa0318t7 | ND |
| 248 | de0162t7 | ND | 520 | pa0321t7 | M |
| 249 | de0169t7 | U | 521 | pa0325t7 | N |
| 250 | de0170t7 | O | 522 | pa0326t7 | ND |
| 251 | de0174t7 | ND | 523 | pa0332t7 | ND |

TABLE 1-continued

| SEQ ID NO | clone name | Tissue Probe | SEQ ID NO | clone name | Tissue Probe |
|---|---|---|---|---|---|
| 252 | de0176t7 | ND | 524 | pa0339t7 | ND |
| 253 | de0177t7 | O | 525 | pa0346t7 | O |
| 254 | de0182t7 | ND | 526 | pa0349t7 | ND |
| 255 | de0183t7 | ND | 527 | pa0351t7 | U |
| 256 | de0184t7 | ND | 528 | pa0355t7 | ND |
| 257 | de0186t7 | ND | 529 | pa0358t7 | ND |
| 258 | de0187t7 | M | 530 | pa0360t7 | N |
| 259 | de0189t7 | ND | 531 | pa0362t7 | ND |
| 260 | de0191t7 | M | 532 | pa0368t7 | U |
| 261 | de0192t7 | ND | 533 | pa0369t7 | ND |
| 262 | de0193t7 | ND | 534 | pa0373t7 | ND |
| 263 | de0195t7 | N | 535 | pa0380t7 | ND |
| 264 | de0196t7 | N | 536 | pa0393t7 | ND |
| 265 | de0197t7 | N | 537 | pa0395t7 | ND |
| 266 | de0198t7 | ND | 538 | pa0396t7 | ND |
| 267 | de0203t7 | ND | 539 | pa0397t7 | ND |
| 268 | de0208t7 | ND | 540 | pa0410t7 | N |
| 269 | de0209t7 | N | 541 | pa0415t7 | ND |
| 270 | de0210t7 | N | 542 | pa0416t7 | ND |
| 271 | de0211t7 | ND | 543 | pa0424t7 | ND |
| 272 | de0213t7 | ND | 544 | pa0430t7 | ND |

*In the provisional application (60/098,639) filed August 31, 1998, clone PA0293t7 was labeled clone PA0023t7 in error. That mistake has been corrected here to reflect the accurate clone name.

TABLE 2

| SEQ ID NO | Clone name | "Novel" Region 1 Start/Stop | "Novel" Region 2 Start/Stop | GenBank Identifier for top 5 matching EST sequences | | | | |
|---|---|---|---|---|---|---|---|---|
| 36.00 | de0001t7 | 439–607 | | g835668 | g857149 | g1321047 | g1968601 | g1476832 |
| 40.00 | de0040t7 | 1–201 | | g2166831 | g4136486 | g1747976 | g1180529 | g2265195 |
| 41.00 | de0043t7 | 467–615 | | g5129477 | g1801229 | g1845053 | g1544683 | g1694347 |
| 43.00 | de0045t7 | 1–228 | | g2322205 | g1139955 | g4267203 | g2165927 | g3039227 |
| 45.00 | de0052t7 | 455–628 | | g1523492 | g1548890 | g1523465 | g1809433 | g5132985 |
| 50.00 | de0063t7 | 1–114 | 452–624 | g2197338 | g5754794 | g2694448 | g2070840 | g3419233 |
| 51.00 | de0066t7 | 301–631 | | g2162184 | g749398 | g1239250 | g839454 | g1966148 |
| 52.00 | de0067t7 | 391–623 | | g1521548 | g848102 | g1349419 | g1196287 | g771178 |
| 54.00 | de0085t7 | 415–565 | | g1367045 | g1367136 | g2337716 | g841637 | g795336 |
| 63.00 | de0124t7 | 411–605 | | g1809451 | g1757444 | g3181138 | g2905518 | g1157799 |
| 64.00 | de0139t7 | 424–612 | | g3899105 | g3431615 | g3246439 | g1312989 | g1182375 |
| 65.00 | de0143t7 | 479–598 | | g1239204 | g1067288 | g1080541 | g4876470 | g1188553 |
| 68.00 | de0171t7 | 443–611 | | g867521 | g1636718 | g2162333 | g2342197 | g1466482 |
| 69.00 | de0178t7 | 485–603 | | g1371240 | g2055704 | g2208007 | g1686872 | g1740908 |
| 71.00 | de0181t7 | 1–153 | | g1188057 | g1018287 | g1447796 | g1025264 | g1069169 |
| 73.00 | de0200t7 | 1–218 | 384–581 | g1972267 | g1989383 | g964966 | g2883986 | g483738 |
| 74.00 | de0202t7 | 448–599 | | g2115372 | g1959491 | g1329334 | g1198642 | g1957432 |
| 75.00 | de0205t7 | 1 to 75 | | g779809 | g2167738 | g2537620 | g2656428 | |
| 77.00 | de0212t7 | 1–185 | | g4265939 | g1548503 | g1687914 | g1716864 | g877386 |
| 80.00 | de0228t7 | 411–594 | | g3446139 | g3745043 | g1126367 | g2163321 | g1195781 |
| 82.00 | de0243t7 | 253–604 | | g2001999 | g1071313 | g966668 | g26974 | |
| 83.00 | de0253t7 | 1–133 | | g2111781 | g1663818 | g574791 | g1406232 | g1663812 |
| 85.00 | de0259t7 | 241–602 | | g2216159 | g5177204 | g1969363 | g1388290 | g1389464 |
| 86.00 | de0262t7 | 351–583 | | g1025700 | g2019225 | g2080424 | g1547366 | g728148 |
| 88.00 | de0275t7 | 455–592 | | g5665082 | g5553136 | g5552975 | g389141 | g1665092 |
| 89.00 | de0287t7 | 364–630 | | g2026446 | g4622337 | g2021046 | g2056125 | g5037418 |
| 92.00 | de0490t7 | 1–264 | 482–653 | g1812285 | g2816130 | g2818085 | g2819140 | g1194260 |
| 96.00 | de0596t7 | 362–655 | | g1155862 | g1991972 | g1996949 | g1149020 | g3307331 |

TABLE 2-continued

| SEQ ID NO | Clone name | "Novel" Region 1 Start/Stop | "Novel" Region 2 Start/Stop | GenBank Identifier for top 5 matching EST sequences | | | | |
|---|---|---|---|---|---|---|---|---|
| 97.00 | de0600t7 | 1 to 71 | | g883470 | g1880085 | g3162627 | g3162628 | g918039 |
| 98.00 | de0609t7 | 434–582 | | g5037002 | g1404408 | g2816378 | g759987 | g2969638 |
| 102.00 | de0643t7 | 433–605 | | g1382697 | g5236495 | g5235876 | g5177792 | g4453929 |
| 105.00 | de0666t7 | 385–586 | | g2932996 | g1010052 | g2616680 | g3277252 | g2252166 |
| 106.00 | de0695t7 | 401–644 | | g4897106 | g1741190 | g1501550 | g3932286 | g781364 |
| 107.00 | de0705t7 | 431–599 | | g5176918 | g1551249 | g4739742 | g2540062 | g2583382 |
| 108.00 | de0706t7 | 407–620 | | g826820 | g870098 | g1685556 | g1687983 | g685342 |
| 110.00 | de0724t7 | 127–192 | 423–603 | g2036407 | g1969842 | g616903 | g1218717 | g1745366 |
| 113.00 | de0742t7 | 1 to 49 | | g2596046 | g3277962 | g4665052 | g895453 | g1521473 |
| 116.00 | de0777t7 | 270–610 | | g2358992 | g1692100 | g1979572 | g1720777 | g1547963 |
| 117.00 | de0781t7 | 457–608 | | g1982258 | g1379170 | g1496197 | g1981084 | g1982434 |
| 118.00 | de0793t7 | 435–577 | | g1860678 | g1991856 | g946392 | g4703537 | g5741112 |
| 119.00 | de0794t7 | 342–584 | | g4394682 | g3418148 | g3424422 | g1398292 | g4985474 |
| 120.00 | de0798t7 | 1 to 65 | 384–585 | g1570282 | g4817443 | g3891031 | g2028723 | g2357411 |
| 121.00 | de0800t7 | 270–568 | | g2358992 | g1892100 | g1979572 | g1720777 | g1692006 |
| 122.00 | de0816t7 | 485–550 | | g2014274 | g2189652 | g1087845 | g2013302 | g643722 |
| 123.00 | de0818t7 | 387–573 | | g4190027 | g4900502 | g3601481 | g4070577 | g4112474 |
| 124.00 | de0835t7 | 330–570 | | g2029304 | g2029457 | g1544689 | g1947895 | g2986865 |
| 129.00 | pa0095t7 | 1–370 | | g5340876 | g771049 | g791906 | g677786 | |
| 132.00 | pa0187t7 | 388–593 | | g2029457 | g2029304 | g1544689 | g1947895 | g2986865 |
| 134.00 | pa0192t7 | 444–618 | | g4897608 | g1815096 | g2051120 | g3426889 | g4690585 |
| 139.00 | pa0238t7 | 364–586 | | g4728995 | g4971678 | g1615267 | g1501282 | g5447095 |
| 140.00 | pa0249t7 | 124–588 | | g2061363 | g2060961 | g2060863 | g1135265 | g2060372 |
| 142.00 | pa0258t7 | 254–595 | | g2784639 | g2276958 | g968701 | g1670101 | g2329615 |
| 143.00 | pa0272t7 | 1 to 98 | | g2198976 | g1961065 | g2188645 | g1965162 | g1852287 |
| 148.00 | pa0317t7 | 457–612 | | g5113829 | g2080750 | g3739118 | g3753615 | g2933157 |
| 153.00 | pa0353t7 | 357–620 | | g2029457 | g2029304 | g2986865 | g1544689 | g1947895 |
| 156.00 | pa0366t7 | 354–760 | | g5339118 | g775873 | g610250 | g3886660 | g2052048 |
| 157.00 | pa0382t7 | 395–668 | | g3886319 | g968094 | g2216376 | g4126052 | g1747689 |
| 159.00 | pa0388t7 | 492–739 | | g1636721 | g2006249 | g5035641 | g3430502 | g778670 |
| 160.00 | pa0389t7 | 1–177 | | g1321159 | g1320039 | g1371307 | g2070781 | g1350314 |
| 161.00 | pa0405t7 | 119–214 | | g4824527 | g4852801 | g1368093 | g1392201 | g1350038 |
| 164.00 | pa0411t7 | 289–345 | | g4810371 | g2369264 | g3163382 | g3839554 | g1950020 |
| 166.00 | pa0421t7 | 233–745 | | g5747013 | g4150749 | g1482715 | g1137706 | g3900569 |

TABLE 3

The following list of clones indicates those found in either the DE or PA libraries and the SW480 library

| SEQ ID NO | clone name |
|---|---|
| 185 | de0032t7 |
| 186 | de0033t7 |
| 193 | de0051t7 |
| 196 | de0068t7 |
| 240 | de0149t7 |
| 241 | de0151t7 |
| 247 | de0159t7 |
| 72 | de0199t7 |
| 279 | de0229t7 |
| 281 | de0232t7 |
| 283 | de0235t7 |
| 306 | de0277t7 |
| 310 | de0282t7 |
| 318 | de0507t7 |
| 328 | de0542t7 |
| 331 | de0559t7 |
| 342 | de0588t7 |
| 359 | de0628t7 |
| 375 | de0667t7 |
| 379 | de0687t7 |
| 407 | de0761t7 |

TABLE 3-continued

The following list of clones indicates those found in either the DE or PA libraries and the SW480 library

| SEQ ID NO | clone name |
|---|---|
| 410 | de0768t7 |
| 427 | de0811t7 |
| 466 | pa0140t7 |
| 470 | pa0147t7 |
| 481 | pa0184t7 |
| 493 | pa0228t7 |
| 494 | pa0229t7 |
| 140 | pa0249t7 |
| 506 | pa0279t7 |
| 510 | pa0299t7 |
| 515 | pa0306t7 |
| 517 | pa0311t7 |
| 518 | pa0316t7 |
| 536 | pa0393t7 |
| 539 | pa0397t7 |
| 544 | pa0430t7 |

We claim:

1. An isolated nucleic acid molecule consisting of a nucleotide sequence selected from the group consisting of SEQ ID Nos. 8, 13, 18–19, 41, 51, and 319.

2. An isolated nucleic acid molecule consisting of a nucleotide sequence at least 80% identical to a sequence selected from the group consisting of SEQ ID Nos. 8, 13, 18–19, 41, 51, and 319.

3. An expression vector, capable of replicating in at least one of a prokaryotic cell and eukaryotic cell, consisting of vector sequences and the nucleic acid of claim 1.

4. The expression vector of claim 3, further consisting of a transcriptional regulatory sequence operably linked to said nucleotide sequence so as to render said expression vector capable of replicating in said at least one of a prokaryotic cell and eukaryotic cell.

5. A host cell transfected with the expression vector of claim 3.

6. A probe/primer consisting of a nucleotide sequence of 30 consecutive nucleotides of a sequence selected from the group consisting of SEQ ID Nos. 8, 13, 18–19, 41, 51, and 319.

7. The probe/primer of claim 6, wherein said probe/primer is labeled with a label group.

8. The probe/primer of claim 7, wherein said label group being selected from radioisotopes, fluorescent compounds, enzymes, and enzyme co-factors.

9. A test kit for determining the phenotype of transformed cells, conprising the probe/primer of claim 7 and suitable packaging materials therefore.

10. A pharmaceutical composition comprising a nucleic acid molecule consisting of a sequence selected from the group consisting of SEQ ID Nos. 8, 13, 18–19, 41, 51, and 319.

11. An isolated nucleic acid molecule consisting of a nucleotide sequence complementary to a nucleotide sequence selected from the group consisting of SEQ ID Nos. 8, 13, 18–19, 41, 51, and 319.

12. An isolated nucleic acid molecule consisting of a nucleotide sequence complementary to a nucleotide sequence which is at least 80% identical to a sequence selected from the group consisting of SEQ ID Nos. 8, 13, 18–19, 41, 51, and 319.

13. A probe/primer consisting of a nucleotide sequence complementary to 30 consecutive nucleotides of a sequence selected from the group consisting of SEQ ID Nos. 8, 13, 18–19, 41, 51, and 319.

14. A test kit for determining the phenotype of transformed cells, comprising the probe/primer of claim 13 and suitable packaging materials therefore.

15. A pharmaceutical composition comprising a nucleic acid molecule consisting of a nucleotide sequence complementary to a nucleotide sequence selected from the group consisting of SEQ ID Nos. 8, 13, 18–19, 41, 51, and 319.

* * * * *

SEQUENCE LISTING

<160> NUMBER OF SEQ ID NOS: 544

<210> SEQ ID NO 1
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 1
gcgtggtcng gccgaggtac agtctcggct cactgcaatc tctgcctgcc cagntcaagc 60
gattctccat catgttggcc aggctggtct caaattcctg aggtgatctg cccacctctg 120
cctgccaaag tgctgggatt acaggtgttg agcgatagtg ctcggcctat tatttctttt 180
taaatctttg gtagaattaa tcactgaaac tatntgtgct ttttttgnng gaaaaattat 240
ttattttaaa gacagggtct tgntctgttg cctgtgctgg antgcagtgg tgcaatctca 300
gtttactgca accttgtgcc aacctactgn caagtgatcc tactgnctca cctccnagta 360
ncttggatta caggcacgcg ccaccatgcc cngntaggtn ttgnattttt aggagaaacn 420
gggtttcatn atattggnca gcnnggcttg agcttctgaa ctcaantgat ccnccncctc 480
ggcctnccaa acactgggat tacaggcgtg agccctcccc tgntgatacg nagnggtttt 540
aanaagattn tcttcaantt ngtttaaaaa ttctaatttn ngaccatttt tnctgcccgc 600
ggcgnnaaag gcnaatcn 618

<210> SEQ ID NO 2
<211> LENGTH: 640
<212> TYPE: DNA
<213> ORGANISM: Homo sapiens
<220> FEATURE:
<221> NAME/KEY: misc_feature
<222> LOCATION: (1)...(640)
<223> OTHER INFORMATION: n = A,T,C or G

<400> SEQUENCE: 2
actttttttt tttttttttt tttttgagac agggtcttgc tttgtcacct gggctgaagt 60
gcagtggcat gatcatggct cactgcagcc tcaacctcct aggctcaagt gattctctca 120
cctcctcctc ttgagtagat gggacttaca ggcgcatgcc accacatgca gataattttt 180 gtatttttttg tanaaacagg gttttgccat gttacccaaa ctggtcccaa gctcctgggc 240
tcaagagatc tgcctgcccc aacctcccaa agtgctggga attacaggca ttgagccacc 300
acacccagcc tgattgtttc ttctcataac tcaactctac tgntgatcct ctttaatgaa 360
ttttantttc aagtcattct acttttccac tccaaaattt tgatttgggt cttttaaata 420
aattttattt attggaattc tttatttggg gagaaggtat catatattcc tttanttctt 480
ttggcgngct ttcttttaac tctttgatat ttataatagc tgntttgaaa gctttttntg 540
gtaagtccaa cattngggnc ctcaangctt ttttaatgct gcttttttttc ccctattatg 600 gnaaacttcc agttatttta tgctaataag gttcggaaaa 640

<210> SEQ ID NO 3
<211> LENGTH: 635
<212> TYPE: DNA
<213> ORGANISM: Homo sapiens
<220> FEATURE:
<221> NAME/KEY: misc_feature -continued
<222> LOCATION: (1)...(635)
<223> OTHER INFORMATION: n = A,T,C or G

<400> SEQUENCE: 3

```
acactagcat aaatgaagat taagaaataa gtctttccag attattttta ctcaagaatt     60

tgtttcagtg ctaggcaagg atgatcaatt ttagtttgca tatgaagact caaagggaga    120

tgattaaaag cacgtaactc tttgactcac ccctagaagg tctttgatga ggcccagcaa    180

tctggaaaat tatgatataa tattacacaa tgattattta acaatatttt agaagtaact    240

gccatttggg ggtcacagaa caatactaat ctcaattatg ttacccatca acaaattgaa    300

tataattaaa ttattttcaa aatatatggg ttgagattat tttccaatta aaattgccag    360

gtgaggaaca gcacttttcc attcgctgct gaatgtgatg aaatactgga tagtcataga    420

gggtctaccc agatgtccct ttgggagaag tgttgtgggg gaaaatgggc tggttgtgtg    480

cacccaaact accctttaag aacttggtgc tggagccatt aaaaataatt gngctggtct    540

tataaatatg aaaaactttg ggaaatcctt gtgacatcga tgcanttggg ttgggaagtt    600

cctgataaaa atatctaaaa atacacccat tgaaa                               635
```

<210> SEQ ID NO 4
<211> LENGTH: 627
<212> TYPE: DNA
<213> ORGANISM: Homo sapiens
<220> FEATURE:
<221> NAME/KEY: misc_feature
<222> LOCATION: (1)...(627)
<223> OTHER INFORMATION: n = A,T,C or G

<400> SEQUENCE: 4

```
acgcggggac taagacctca aaagcacagg cgacaaaaat aaaaatagac aaatgggaat     60

taactaagaa gtttctacac aacaaaagaa ataatcaaca gagtaaacag ataatttcca    120

gaacggaaga aaatatgtgc aaactattca tccagcagtg gacaaatacc cagtatatac    180

aagaaactca aacaacaaca ataaaagaca aatcatcccc ttaaaaggag ggcaaaagac    240

aagaacagac atttttcaaa agaagatata caaatgacta acaggtatat taaaaatgca    300

caacatcact aatcatcaga gaaatgcaaa ttaaaaccac aatgagatat catcttaccc    360

cagtcaaaat ggctactatt aaagagtcaa aaaataatag atcttggcca ggacatggat    420

aaaagagaac tcttacatac tggtggtagg aatgcaaatt aacacagcct ctatagaaaa    480

cagtatngag attgctcaag aactaaaaat agagctatca tttgcccanc atnccctgnt    540

gggttctacc caangaaaag aaatcatggt caaaaaaaaa aaaaaaaaaa aaagtncttg    600

gcgggaccct aaggggattc acccctn                                        627
```

<210> SEQ ID NO 5
<211> LENGTH: 411
<212> TYPE: DNA
<213> ORGANISM: Homo sapiens
<220> FEATURE:
<221> NAME/KEY: misc_feature
<222> LOCATION: (1)...(411)
<223> OTHER INFORMATION: n = A,T,C or G

<400> SEQUENCE: 5

```
cgaggtacgc ggcctggcca acatggtgaa accccgtctc taccaaagat acaaaaaatt     60

agccaggtgt ggtggcatgt gcctgtagtc ccagctactc aggaggatga ggcaggggaa    120

tcacttaaac ctgggaggcg gagattgcag tgagccaaga tcgcgctatt gcactctagc    180
```

-continued

```
ctgggtgaca gagcaagact ccgtctcaaa aaataataat aataaaatga aaataatcag    240

ctgggtgtgg tggcatgtgc ctgtagtccc agctactcag gaggatgagg caggggaatc    300

acttaaacct gggaggcgga gattgcagtg agccaagatc gcgctattgc actccagcct    360

gatgacagac ctagactccg tctccaaaaa aaaaaaanaa aaaaaaaaag t             411


<210> SEQ ID NO 6
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 6

accaagtcac cagacacaag taaatatggg ccttggggct tcttttcttg ctgacgcata     60

ttcacacagg cagcgtgtgc tgtgtgtgtt tacaactgtg tttcttagtc ttctattcag    120

agtaataaca gcatgacttc cctaagatct gattcagaga attgaaatat gccctgagaa    180

aacataagag gtttttctgg agaagtgtcc caagggtaat attaattgtt caaggatgtt    240

tcggaaaaag ttgcaatcat cactgtggca aatgaatcta gggagaggaa gcatgagtta    300

tttaatgtca gttactcctt tccgtaggtt tttgcctttt tttggacttt acacacagcc    360

catttgctat gaaactatca gctcaaatag cangctttca ngcaggccaa caatggcaga    420

ctgcattctt nctactttnt ccaatcatat ttatcaagtc ccattgggag aatactttca    480

gtagngctca aantacccgc ntncaattgg aactgcangg aaccnttcag aaataacnct    540

tnaagaaaga aataaccctt canggaanac cctttnggnt tcactctann tggggttnac    600

aagaaa                                                               606


<210> SEQ ID NO 7
<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 7

ccgtggcccc ggccgaaggt ccnctgganc cccgggtggt aattggctgg aggtaaatgg     60

tggtaangta ttaaccattt ctatggaaat gnccctttgg ggccctcctg gattttaaaa    120

tggtcccctg gtttggacnt ttctattaaa gaaatggnca ttttacctaa aatgccnggt    180

ctaccttatt aaagancaaa tngnntattn gaccttaaaa taggcatttt tcctaatcat    240

aatctggccg gcttaacccc aatcaagata attgggtgcc cnttatgaat ttgaagttag    300

tgatagcctc cttgtaaggt gctaccctna tggggataga gaccccagct actantaatt    360

ngggaaaatg gttaaggtat ttgggaaaag tactctttta aaaacatatt ggccacagaa    420

ancctaggct gaattacnng gattgataat tttgnaanta atttcntana atgggcnngc    480

tggatgaaaa aatggcctcc tcnttttccc tggaaccagc ngctttttgc ctaaacntta    540

nccttttttaa gttgaaccta gggaccacct aatnggcntc acaattccct ttttcctttc   600

cttttttttt gcccaagggn                                                620


<210> SEQ ID NO 8
<211> LENGTH: 263
```

-continued

<212> TYPE: DNA
<213> ORGANISM: Homo sapiens

<400> SEQUENCE: 8

```
gcgtgggtcg cggccgaggt accacttttc ttattgcaac tcaacaagtg gcaattggtg     60
atgaaaagtc aagtggggaa cccagtctgt ggggaacaaa tggaataact tacctgtcac    120
cttgtctaac cgggatgcaa atcctcaagt ggtattaaaa agcatacagt gttttataac    180
tgtagttgtg tggaaagtaa ctggtctcca agaacagaaa ttactcagcg cacttgggtg    240
aatgcccaag aaataatact tgt                                            263
```

<210> SEQ ID NO 9
<211> LENGTH: 590
<212> TYPE: DNA
<213> ORGANISM: Homo sapiens
<220> FEATURE:
<221> NAME/KEY: misc_feature
<222> LOCATION: (1)...(590)
<223> OTHER INFORMATION: n = A,T,C or G

<400> SEQUENCE: 9

```
acaacagggt tcttgcatca agcttcatgc tttcccagac atttactcaa gggaacgtgg     60
gagagggagg aggaggaggg gagctgggag tgataagcag atgttacaca tgtttttcct    120
ggaaagatca ccccactttt tctaatttcc cagaattaaa agaatgtatt ttatctgtat    180
taccatggaa attactagta acactggatt tttttccctc ttttctaaag tttccaaaaa    240
ctttcaaaag tgttcaaaga aattttcttg aacaatttta atatgtttga tttctcattt    300
ggggctggaa tatttgtatt ctttttaatt tttttacttc atttattaga agaagtttct    360
aatatgtgta ggaatacaat tttaaatgta agattatata gatgtagata tagatagata    420
gatatatgta gatatatnga tttatgtcnc aatatcactn taaggcattc ttcttccatc    480
cttttatatc tncccaaact ggtntnatgg gacctgtcct gcctgtaggt aaaanccttn    540
taatttccct gaaaggctac cnctttctan ggggncaacc aattgggagn               590
```

<210> SEQ ID NO 10
<211> LENGTH: 609
<212> TYPE: DNA
<213> ORGANISM: Homo sapiens
<220> FEATURE:
<221> NAME/KEY: misc_feature
<222> LOCATION: (1)...(609)
<223> OTHER INFORMATION: n = A,T,C or G

<400> SEQUENCE: 10

```
cgaggtacgt tttcaatgt tttaaaaaat tgaaagggag tataatgttt cataacacat      60
gggaaattat gtgcagctca aatttcaagt atccataaat aaagttttat tggaacacag    120
ctacgctcac tcattagata ttgtctatgg ctgtttttgt gcaaaatggc aganttgggt    180
tcagagttag caacagagag cttgtagcct gcaagcctag agtatttact atctggattt    240
ctacagaaaa aaaaaattat tgccccctgc catacagtct gactgatagc ctgagaaagt    300
atgcattaaa agaaagttac ctaccctgac cccatgagaa tgaatttgaa aagaaccnag    360
atgtggtaga agcagatagg ctatgaaagt ttcagaaggg tancatcact gtgggcnagg    420
atattcaaga aaagacttca nggaaaatgt nggggtttga actggncttg agtaggagtt    480
naacttangg gaactggntt taggtngcca ctttaaggct gtcaaanatc atggcccaac    540
attcantttg gcccaaattc cccangngcc ttaaaaattt ggacatggct tgggttgggg    600
```

-continued gncaccctt 609

<210> SEQ ID NO 11
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 11
acgcgggatg tagtcagagg aggccctgac atctgcaggg cagcatgggt caaaccaaaa 60
agacttttct gaggttgggc gcagtggctc acgcctgtaa tcccaacact ttggaaggcc 120
agtaggggcg gatcacctga ggtcaggaga ttcgagacca tcctggctaa cacggtgaaa 180
ccccatctct actaaaaaaa atacgaaaaa aattagccag gcgtggtgac gggtgcctgt 240
agtcccagct actagggagg ctgaggcagg agaatggtgt gaacccggga ggcagagctt 300
gcagtgagcc gagatcaggc cactgcactc cagcctgggc cacaagagcg agactctgtc 360
ttaaaaaaaa caaacaaaca aacacacaca cacacacaan aagacaaaaa taattagcag 420
ggaatgctgg tgcatgcctg tatcccaact ctcaggaggt tgaagcagga gaatcacctt 480
gacccatnag caatgttcat gaacttagnc cngccntgga cttcancaag gcaccgagta 540
aganttcntt tnaaaaaaaa aannnaaaaa aaagtcct 578

<210> SEQ ID NO 12
<211> LENGTH: 581
<212> TYPE: DNA
<213> ORGANISM: Homo sapiens
<220> FEATURE:
<221> NAME/KEY: misc_feature
<222> LOCATION: (1)...(581)
<223> OTHER INFORMATION: n = A,T,C or G

<400> SEQUENCE: 12 acttttttttt ttttttttt ttttttttt gggacggagt cttgctctgt tgcccaggct 60
ggagtgcagt ggcgccatct tggctcacta caagctccgc ctcccgggtt cacaccattc 120
tcctgtctta gcctcccagc gcccgccacc gcacccggct aattttttgt atttttagta 180
gagacagggt ttcaccatgt tagccaggat ggtctcgatc tcctgacctc gtggcccacc 240
tgccttggcc tccaaaagtg ctggaattac agtcgtgagc caccacgccc ggcctaaacc 300
atttctcttg acaacactct ggattttatt tctggccaga taccatttat caattttacc 360
atcaagaata agataatcaa aataataatc aagttttata ttagacttat gaagattctt 420
gcacctttga aattacagct atctcactag ttnattctcc tctctcatat tttattacng 480
acntccagga agacaaccaa cacctttaaa agttggctga gcatttttta nggagaccct 540
taggtaanag ggncctnggc gggaacccct taggggnaat n 581

<210> SEQ ID NO 13
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 13
ggtactggaa caactataag acccctgttc agattaagga atttggtgca gtttcaaaag 60

-continued

```
tagacttttc tcctcagcct ccatataatt atgctgtcac agcttcctca agaattcaca    120

tttatggccg atactcccaa gaacctataa aaaccttttc tcgatttaaa gacacagcat    180

actgtgctac ttttcgacaa gatggtagat tgcttgtggc tggcagtgaa gatggtggag    240

ttcaactttt tgatataagt gggagggctc ccctcaggca gtttgaaggc catacaaaag    300

cagttcatac agtagatttt acagctgaca aatatcacgt ggtctctggg gctgatgatt    360

atacagttaa attatgggat attccaaact ccaaagaaat ttttgacatt taaaggaaca    420

ctctgattat gtgangtgtg gatgtgctag caaactttaa tccggatctc tttataacca    480

gggacatatg atcatactgn gaagatgttg gatgcncgaa ccnattgaaa agtggtcttt    540

ccgttgagca tggccnncag tngaaantgn cctacttttc cccttggaag gctttggggt    600

annangg                                                              607
```

```
<210> SEQ ID NO 14
<211> LENGTH: 599
<212> TYPE: DNA
<213> ORGANISM: Homo sapiens
<220> FEATURE:
<221> NAME/KEY: misc_feature
<222> LOCATION: (1)...(599)
<223> OTHER INFORMATION: n = A,T,C or G

<400> SEQUENCE: 14

ggtactttca aaatataaca attttcgttc tcccatataa caggggggcta acaagaaaac     60

caaaaataaa taaaaagaga aaatttaaaa ataagtaaaa aataaaaaaa tatttttaaa    120

aagcagcctg ggcaagagaa gtgggtgggt ttaggagaat ccctttcgaa aaattcagag    180

cattattatt aatcgttctt aaattaaatg cagggccaag catgctgcac gtggaatctg    240

gacaattttt tgataaactt taaggctgct aaataattta cagaaactgt gaatgcattt    300

tcattttacg aggcaaaaga gaaaatattc aagattgcat agcaatttta ttttttgaaa    360

tggttatcct aaagaatttc cttaaattca gattttgcaa aattcctact ctncaagtca    420

tcaagtgaac actaaaagca actttctcgt gaatcagtgg acttttacga ggcatgcatt    480

tttcataaat ctaggccaag tgacctaatt gngattaaat cttaatcatc ctgngattct    540

ggctattaan atgggtttaa ancngtaaaa atnctttnaa aaagccgtta cttnccgan     599
```

```
<210> SEQ ID NO 15
<211> LENGTH: 457
<212> TYPE: DNA
<213> ORGANISM: Homo sapiens
<220> FEATURE:
<221> NAME/KEY: misc_feature
<222> LOCATION: (1)...(457)
<223> OTHER INFORMATION: n = A,T,C or G

<400> SEQUENCE: 15

ggtacttttt tttttttttt ttttttttc gaaatgaaca aatatttatt tatcttttat     60

aacaagtaag gcaatgttgc ttaaaggaag acaaacaaac ataaaagatt ccgttgacaa    120

tgcatttttt catntgttcg gcacaatgct tttgtcataa tggagatgtg acagcaaact    180

ttccaggaca ttcagtcttc ggnggcagca cttagggcan atgactggcc gctcaaattc    240

tctatnttgt ttcaggacag tggaaaagct tatanatgag gccaaagcac caggtaggtg    300

gaaggttctt gtatcggttc gaaccccgac agcgcgccaa cagacaacac naggcagtgg    360

ggagcaacat gctgttttaa tganccgcctg ggtgcangcg tgctgaggct gaaaatggca    420
```

-continued

```
taacccccgc gtcctgccng gcgggcgttc aaanggn                               457


<210> SEQ ID NO 16
<211> LENGTH: 643
<212> TYPE: DNA
<213> ORGANISM: Homo sapiens
<220> FEATURE:
<221> NAME/KEY: misc_feature
<222> LOCATION: (1)...(643)
<223> OTHER INFORMATION: n = A,T,C or G

<400> SEQUENCE: 16

ggtacaatct agctgaaatc atatacaagt aagtaggtgt ggacttttac tgctgagcta       60

aagtttatgt ttatatatgt tttattcttt aagctaaaca aacattcaga taacattcta      120

tgcatttttt gaagcatagg gttagtaatg aggacttaga ttttttaatt aaacaattca      180

gtaactatat aaaaagaaaa ggagtccctt atgaataaat attaaaatta aaagaaatag      240

gcaactataa aagtaagtat ttttaataat ggcattgatt ttagtaagaa atcaattagg      300

ctgggctgga aagaaaaact ggcttaatat aaagtagttt taatatggca aatattcttc      360

ttaaaattgn ggccctggaa tatcatttct gcctattgct gatgctaagg natcaactgn      420

gccaagtatt gggctgntcc acaggtggga angagtagca acattttgng gatttttttt      480

ttttttaaa accggagaat acccggccag gggntcaagn ctgnatccac antttgggag       540

nttagccgga naanccttgg anccggagna aaggttnaan gagncaaaat gngccatggn      600

ttccanctgg ggacccgggg gnaactcttt taaaccnaaa aat                        643


<210> SEQ ID NO 17
<211> LENGTH: 336
<212> TYPE: DNA
<213> ORGANISM: Homo sapiens
<220> FEATURE:
<221> NAME/KEY: misc_feature
<222> LOCATION: (1)...(336)
<223> OTHER INFORMATION: n = A,T,C or G

<400> SEQUENCE: 17

ggtactttga taaatgtaga aagattattt aattctggct tggtaccgtg gctcatgcct       60

ataatcccag cacttcagga ggctgaggtg ggtggatcac ttgagctcag gagtttgaga      120

ccaggcgaaa ccctgtctcc acaaaaaatg caaaaattgc tggacatggt ggcacatgcc      180

tgtagtccca gctacttgga aggctgaggc aggaggatag cttgagccca ggaggtcaag      240

gttgcagtga gccgagattg tgccactgca ctccagcctg ggcaacagag caagaccctg      300

cctcaaattt aaaaaaaaaa aannaaaaaa aaaagt                                336


<210> SEQ ID NO 18
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 18

ggtacactct tcttcgcctt tgagtgccgc tacctggctg ttcagctgtc tcctgccatc       60

cctgtatttg ctgccatgct cttccttttc tccatggcta cactgttgag gaccagtttc      120

agtgaccctg gagtgattcc tcgggcgcta ccagatgaag cagctttcat agaaatggag      180

atagaagcta ccaatggtgc ggtgccccag ggccagcgac caccgcctcg tatcaagaat      240
```

-continued ttccagataa acaaccagat tgtgaaactg aaatactgtt acacatgcaa gatcttccgg 300
cctcccgggc ctccattgca gcatctgtga caactgtgtg gagcgcttcg accatcactg 360
cccctgggta gggaaatgtg ttggaaaaga ggaactaccg ntacttctac ctcttcatcc 420
tttctctttt ccctccttac aaactaaggc tttngctttc aacatcgcta tgtgggccct 480
aaaatctttg aaaattggct ttttggaana cattgaaaga aactcctgga aactggtcta 540
gaaagnccta attgcttctt tacactttgg nccnncnggg actgatggga tttcanactt 600
tcttgggact ttna 614

<210> SEQ ID NO 19
<211> LENGTH: 296
<212> TYPE: DNA
<213> ORGANISM: Homo sapiens
<220> FEATURE:
<221> NAME/KEY: misc_feature
<222> LOCATION: (1)...(296)
<223> OTHER INFORMATION: n = A,T,C or G

<400> SEQUENCE: 19 acttttttttt tttttttttt tttttttgg gatggagtct cactntgttg ccaaggctgg 60
agtgcagtgg cataatttcg gctcacttca acctctgcct cccgggttca agcaattctg 120
cgtcagcctc cggaggagct aggactacag gcatgcacca ccatgcccaa ctaatttttg 180
natttttagt agagatggag tttcaccata ttgaccaggc taggctggtc ttgaactcct 240
agcctnaggt gatctgccca cctnagcccc ccaaagtacc tcggccgtga ccacgc 296

<210> SEQ ID NO 20
<211> LENGTH: 565
<212> TYPE: DNA
<213> ORGANISM: Homo sapiens
<220> FEATURE:
<221> NAME/KEY: misc_feature
<222> LOCATION: (1)...(565)
<223> OTHER INFORMATION: n = A,T,C or G

<400> SEQUENCE: 20
accaattata atgcattatt atgaaatatt taaaatgggg aatccaagat gacatagttt 60
ttaactcatc cacatactgg aagtttagag aaactcagaa tttcttattt ctttttcttt 120
ttcctccata gcataaaagc tttgctaata agaataaata tatatattgg agttttagtg 180
tttgatcctg tgatcagttg taaccatgtg tcataaaact ctctcacaga ttccatcttt 240
cccaaatctt ctgatcataa cacagattgc catatagact tcccttgtaa ggagaatatg 300
ctggccataa ggcaagcana agtgaacttg cagtttcact tcttggaaat taatgcattt 360
gcattgactt ctataannta atctctcctg aattttttttg cttagtcaac ttactgtgtg 420
caaagncaac agnaaattgt ctttggttna acttttaaca ggncaattta taaattggtt 480
tgaagaagcn tcccnaaatt ttttattgaa ggctgaattc aagcctccnt taaaatggnc 540
atngnataan gggaatttat tgtng 565

<210> SEQ ID NO 21
<211> LENGTH: 582
<212> TYPE: DNA
<213> ORGANISM: Homo sapiens
<220> FEATURE:
<221> NAME/KEY: misc_feature
<222> LOCATION: (1)...(582)
<223> OTHER INFORMATION: n = A,T,C or G -continued

<400> SEQUENCE: 21
ggtactggaa caactataag acccctgttc agattaagga atttggcgca gtttcaaaag 60
tagacttttc tcctcagcct ccatataatt atgctgtcac agcttcctca agaattcaca 120
tttatggccg atactcccaa gaacctataa aaaccttttc tcgatttaaa gacacagcat 180
actgtgctac ttttcgacaa gatggtagat tgcttgtggc tggcagtgaa gatggtggag 240
ttcaactttt tgatataagt gggagggctc ccctcaggca gtttgaaggc catcaaaagc 300
agttcataca gtagatttta cagctgacaa atatcacgtg gtctctgggg ctgatgatta 360
tacnagttaa atttatgggg atattncaaa cttccaaaga aaattttgnc catttaaaag 420
aacactctng antatggnga aggtgnggnt tgtgcctaac caaacttaat tccgggatct 480
tttttatnta ccnggattcn tttggatctt ncnggtaaaa aanggttgga tnccccnaac 540
nnattgaaaa nngttctntc cnnttgacct nggccanccn ng 582

<210> SEQ ID NO 22
<211> LENGTH: 349
<212> TYPE: DNA
<213> ORGANISM: Homo sapiens

<400> SEQUENCE: 22
actttttttt tttttttttt ttttttgaga tggagtcttg ctcttgttgc ccaggctgga 60
gcaacctccg cctcctgggt tcaagtgatt ctcctgcctc aacctcccga gtagctggga 120
ttacaggtgc ccgccaccat gccgagctaa tttttgtatc cctagtaaag acggagtttt 180
gccatgttgg ccaggctggt ctcgaactcc taacttcatg atctgctcac catggcctcc 240
caaagtgctg ggattacagg cgtgagccac tgtgcccaac cctcttttcc tttttcaaat 300
gtcaatggaa agttgattgg aaaggacaat ttggctacct tttggtacc 349

<210> SEQ ID NO 23
<211> LENGTH: 576
<212> TYPE: DNA
<213> ORGANISM: Homo sapiens
<220> FEATURE:
<221> NAME/KEY: misc_feature
<222> LOCATION: (1)...(576)
<223> OTHER INFORMATION: n = A,T,C or G

<400> SEQUENCE: 23
acctgttctt ggagccaatg tgactgcttt cattgaatca cagaatggac atacagaagt 60
tttggaactt ttggataatg gtgcaggcgc tgattctttc aagaatgatg gagtctactc 120
caggtatttt acagcatata cagaaaatgg cagatatagc ttaaaagttc gggctcatgg 180
aggagcaaac actgccaggc taaaattacg gcctccactg aatagagccg cgtacatacc 240
aggctgggta gtgaacgggg aaattgaagc aaacccgcca agacctgaaa ttgatgagga 300
tactcagacc accttggagg atttcagccg aacagcatcc ggaggtgcat ttgtggtatc 360
acaagtccca agccttcctt gcctgaccaa tacccaccaa gtcaaatcac agaccttgat 420
gccacagttc attaggataa gattattctt acatggacag caccaggaga taattttgat 480
gttggaaaag ttcaacgtta tatcataaga ataatgccag tattcttgac taagagacag 540
ttttgatgat ctcttaagta aatactctga ntgccn 576

<210> SEQ ID NO 24
<211> LENGTH: 618
<212> TYPE: DNA
<213> ORGANISM: Homo sapiens -continued
<220> FEATURE:
<221> NAME/KEY: misc_feature
<222> LOCATION: (1)...(618)
<223> OTHER INFORMATION: n = A,T,C or G

<400> SEQUENCE: 24
acttaaaata aagttaacaa ttacaacaga cccaatcaca gacaatacca gcgtagaaat 60
attaactcca gaattatgac ttttatcagg agtaggagta ggagtaggag taggtgtagg 120
atcaatgtca tcaggatttg cttgagggat aaacaaagtt acttgtgcaa tgttggatac 180
ttttgatgtc aaattgcttt tatctatact tttaatggca ataaatatgt gggttgcatt 240
ttcttctgag atattttctg gtttaaatgc aaagctttcc ttggagttgg cctcctttgg 300
tgacagatca gtagtattta cttgaagagc atcatcaaaa ctgtctctta gatcaagaat 360
acttgcactt attcttatga tataacgttg aacttttcca acatcaaaat tatctcctgg 420
tgctgtccat gtaagaataa tcttatcctc atgaactgtg gcatcaaggt ctgtgatttg 480
acttggtggg tattggtcag caagggaagg cttgggactt gtgatccaca aatgccctcc 540
ggatgctgtc ggctgaaatc ctccangtgg ctgagtatcc tcatcaattc aggtcttggc 600
nggttgcttc aattnccc 618

<210> SEQ ID NO 25
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 25
acataccacg ctgggtagtg aacggggaaa ttgaagcaaa cccgccaaga cctgaaattg 60
atgaggatac tcagaccacc ttggaggatt tcagccgaac agcatccgga ggtgcatttg 120
tggtntcaca agtcccaagc cttcccttgc ctgaccaata cccaccaagt caaatcacag 180
accttgatgc cacagntcat gaggataana ttattcttac atggacagca ccaggagata 240
attttgatgt tggaaaagtt caacgntata tcataagaat aagtgcaagt attcttgatc 300
taagagacag ttntgatgat gctcttcaag taaatactac tgatctgtca ccaaaggagg 360
ccaactccaa ngaaagcttt gcntttaaac cagaaaatat ctcagaagaa aatgcaaccc 420
acatatttat tgccnttnaa agtatagata nagcaatttg acatcnaagt ntccacattg 480
nacaagtnac tttggttatc cctcagcaaa tctgatgaca ttggatctac tctactctac 540
ttctanttct gaaaaaggat aatccggngt aaattttccc tggattgctg ggatg 595

<210> SEQ ID NO 26
<211> LENGTH: 361
<212> TYPE: DNA
<213> ORGANISM: Homo sapiens
<220> FEATURE:
<221> NAME/KEY: misc_feature
<222> LOCATION: (1)...(361)
<223> OTHER INFORMATION: n = A,T,C or G

<400> SEQUENCE: 26
actttttttt tttttttttt ttttttctga gcatattata tctaattttt gaaggttgta 60
ttttctccct tgttttaatt ttctgcanat actttttttct tttttacttt ccccaattag 120
tttgtttctg actttcttcc tcaatctctc ctgaaccatt gtttntttttt aagatcagag 180

-continued

```
cagattctta ggaactttta aaactgtatg tgggtgggat tgtcacctan agtgcttttt    240

tggagagtaa ttggatggng tgataattaa ttttatgtgt caatttgaca gggtcttggg    300

gtgtccagtt atttggttaa acattatttc tgggtgtgcc taaaagggtg tcccgcgtac    360

c                                                                    361


<210> SEQ ID NO 27
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 27

acctgttctt ggagccaatg tgactgcttt cattgaatca cagaatggga catacagaag     60

ttttggaact tttggataat ggtgcaggcg ctgattcttt caagaatgat ggagtctact    120

ccaggtattt tacagcatat acagaaaatg gcagatatag cttaaaagtt cgggctcatg    180

gaggagcaaa cactgccagg ctaaaattac ggcctccact gaatagagcc gcgtacatac    240

caagctgggt agtgaacggg gaaattgaag caaacccgcc aagacctgaa attgatgagg    300

atactcagac caccttggag gatttcagcc gaacagcatc ccgaggtgca tttgtggtat    360

cacaaagtcc caaacctttc cttgcctgac caatacccac caagtcaaat cacagacctt    420

gatgccacaa gtcattagga taaaatattc ttacatggan gcccangaaa taattttgat    480

gttngnaaag ntcaccgtnt ntataanaat aaggccagtt ttttgactaa aaaaagtttg    540

aagagctttc aagaaancta tgatttgncc caaggggccc tccaggaagn ttgttttacc    600

caaaattttn a                                                         611


<210> SEQ ID NO 28
<211> LENGTH: 443
<212> TYPE: DNA
<213> ORGANISM: Homo sapiens
<220> FEATURE:
<221> NAME/KEY: misc_feature
<222> LOCATION: (1)...(443)
<223> OTHER INFORMATION: n = A,T,C or G

<400> SEQUENCE: 28

cgtgcccaaa gcttggcaag ttttcggctt taaccacgca caccaccacc accaccatnc     60

taaataactt actgcatcct caaagcctgt tttatgggga ttgcatggtt ttatttgaaa    120

tcacgcctgt aatcccanca ctttgggagg ccaaggcagg cagatcacaa ggtcaggaga    180

tcgagaccaa tctggctaca cggtgaaacc ctgtctctat taaaaaaaat acaaaacaat    240

tagccaggca tggtggcagg cgcctgtagt cccanctact cgggaggctg angcaagana    300

atggcgtgaa acttggaggc ggagcttgca atgagccgag atcgcacttg ctgcacttna    360

acctgggcaa caaaacgaga cttcatntct nttttnnaaa nnnaannnnn nnnnnnnnng    420

tcctttggcc cgaccacnct tan                                            443


<210> SEQ ID NO 29
<211> LENGTH: 403
<212> TYPE: DNA
<213> ORGANISM: Homo sapiens
<220> FEATURE:
<221> NAME/KEY: misc_feature
<222> LOCATION: (1)...(403)
<223> OTHER INFORMATION: n = A,T,C or G
```

-continued

<400> SEQUENCE: 29
ggtacttttt tttttttttt ttttttttg gagtgcatat catcacccca acttcggttt 60
tttacatttt aatttgtatt gnttttaatt tattttgagg caatgtctca ctatgttgcc 120
caggctggtc tcaaatgaaa acaatgctat caatcacatt cttgcatagg atatgtgtca 180
gtaatcctcc aaaatgaaca tganaaatgg aattgtcaag tcatagatta agtgcatata 240
acttttgaat agatagtata aattttttcc ccaaatgaga attttatatt ctcactggca 300
acatgaaaat agccatctct ctataatctt atcaaccctc gatagtgtca ttttttaatt 360
tataattatg agtgaaaatg gtcctgcccn ggcgggcgct cga 403

<210> SEQ ID NO 30
<211> LENGTH: 615
<212> TYPE: DNA
<213> ORGANISM: Homo sapiens
<220> FEATURE:
<221> NAME/KEY: misc_feature
<222> LOCATION: (1)...(615)
<223> OTHER INFORMATION: n = A,T,C or G

<400> SEQUENCE: 30
ggtacagtgg tagcatccaa atgggcaaac gtagtagcag gggcagggtc agtcaagtca 60
tcagcaggca catagatagc ctgtactttg taatattctt cccacccttg agaatggact 120
ttgtaagatc cgccccctgc ccacaaaaaa atttctccta actccactgc ctatcccaaa 180
cctataagaa ctaatgataa tcccaccacc ctttgctgac tctcttttca aactcagcct 240
gcctgcgccc aggtgattaa aaagctttat tgctcaccca aagcctgttt ggtggtctct 300
tcacacagac gcgcgtgaca gaaaccactt gaagcccggg cgcggtggct caggcctgta 360
atcccagcac tttgggaggc tgaggtgggt ggattacctg aggtcangag ttcgagacca 420
gcctgaccaa catggtaaaa ccctgtctct actaaaaatc aaaaaaaanta accnngggtg 480 gtggnnggca cctgtaattc agttcttggg accttangca ngaaaatcct tgaacttgga 540
ggcggaggtg catanttgaa acaaaccttg nctcaacctg gnaacaaaat aaaaatccgn 600
tnaaaaaana aaaaa 615

<210> SEQ ID NO 31
<211> LENGTH: 485
<212> TYPE: DNA
<213> ORGANISM: Homo sapiens
<220> FEATURE:
<221> NAME/KEY: misc_feature
<222> LOCATION: (1)...(485)
<223> OTHER INFORMATION: n = A,T,C or G

<400> SEQUENCE: 31
acgcggggat aagctacaac ataaacacat ctaggttctt gttcttagaa tacagcatga 60
agaatttgct ttcttctttc ttcctaacat tttcatgtga gatccagaaa ggacacattg 120
tctctggcca ttcgaagaaa gaaagaaaga aagaaaaaaa aggtatttag agacagagag 180
agaaaaaggc tgaaatgggt tcgctgggtt ctaaaaatcc gcaaaccaaa caagcccaag 240
ttcttctttt gggacttgac tcagctggga agtctactct cctttataaa ttaaagcttg 300
ctaaggatat taccaccatc cctacaatag gtttcaatgt ggaaatgatc gagttggaaa 360
ggaatctttc actcacagtc tgggatgttg gaggacagga aaaaatgaga actgtttggg 420
gctgttctgt gagaacccna tnggctngtg tatgtgtgga cagtccttcg gcccgaaccc 480

-continued

```
cttan                                                                485

<210> SEQ ID NO 32
<211> LENGTH: 780
<212> TYPE: DNA
<213> ORGANISM: Homo sapiens
<220> FEATURE:
<221> NAME/KEY: misc_feature
<222> LOCATION: (1)...(780)
<223> OTHER INFORMATION: n = A,T,C or G

<400> SEQUENCE: 32

cgaggtacgc gggtgtctag accttatgtc aaaataagcc caattgtatt aaagagtatt     60

aaattgtatt aagaataaaa acacatggcc gggcacggtg gctcacgcct gtaatcccag    120

cactttggga ggacgagatg ggcggattac aaggtcagga gattgagacc atcctggcta    180

acatggtgaa accccgtctc tactaaaaat acaaaaaaaa aattgtccag ccgtggtggc    240

aggtgcctct agtcccacta ctccagagct gaggcaggag aatgatgtga acccgggagg    300

canagcttgn agtgagccng agatctcgcc actgcactcc ggcctaggcg acagagcgag    360

actctgtctc anaaaaaaat aatgantaaa aaaanaagtc ctgcccggcc ggcgntcnaa    420

nggcgaattt cancacatgg cngcngttac tatggatccn actcggtcca anctggcgta    480

atcatggcat agnttttnct gtggnaaatg gtatccgtnc aantcnccna attcaaccgg    540

agcttaannn ntaacctggg gcnatnnnnn nctacttcat tattgcntnc ntatggcgct    600

tncattggaa ctnttgcnct gnntatnatc gcccnccngg aaagnnttnn ntgggncctt    660

ctctgttann atctnnggct tngttgggag gntnctntna gnggntngtt tnatnggtcc    720

ngnaaatttc agcctangnc antnagcctn ttgnttaatc tccnactnna aaaaataang    780

<210> SEQ ID NO 33
<211> LENGTH: 742
<212> TYPE: DNA
<213> ORGANISM: Homo sapiens
<220> FEATURE:
<221> NAME/KEY: misc_feature
<222> LOCATION: (1)...(742)
<223> OTHER INFORMATION: n = A,T,C or G

<400> SEQUENCE: 33

acataccagg ctgggtagtg aacggggaaa ttgaagcaaa cccgccaaga cctgaaattg     60

atgaggatac tcagaccacc ttggaggatt tcagccgaac agcatccgga ggtgcatttg    120

tggtatcaca agtcccaagc cttcccttgc ctgaccaata cccaccaagt caaatcacag    180

accttgatgc cacagttcat gaggataaga ttattcttac atggacagca ccaggagata    240

attttgatgt tggaaaagtt caacgttata tcataagaat aagtgcaagt attcttgatc    300

taagagacag ttttgatgat gctcttcaag taaatctact gatctgcacc aaaggaggcc    360

aacttcaagg aaagctttgc atttaaccan aaaatattta taagaaaatg cacccacata    420

ttataccatt aaaagttnga taaaacantt tgcctcaaaa gtttccacca tggacaagta    480

acttggttat cctnagcaat cttgtgcctt gattactcnn ctctattcta tcctgtnaaa    540

gcntaatctg agtaaaattt nccctggntt gtggattggc tngtnatgta atttnttaag    600

nctggcngac cnctaggnaa tnnccttggg cgttangncc gtngccantt gtattngtaa    660

tttctngaat gtnntcnncn nnntaccngt aagnatgggn tnggnnatnn atnttttncn    720

tnttnatnnn cntnnannnn tg                                             742
```

-continued

<210> SEQ ID NO 34
<211> LENGTH: 763
<212> TYPE: DNA
<213> ORGANISM: Homo sapiens
<220> FEATURE:
<221> NAME/KEY: misc_feature
<222> LOCATION: (1)...(763)
<223> OTHER INFORMATION: n = A,T,C or G

<400> SEQUENCE: 34
ggtcaaatga ggaataatga ggaaacaaaa ccatacatac aagagggatg gcacagacct 60
tgtgacaaag tggtcctgaa atttctggag gggaaatgaa taagaataac cgagatagtt 120
atgcttggag gaagaggaag atcaaggtgt cctaacctac cagaaactaa gacttatgaa 180
accttagtca ttaaaatatg tagtattagt tcagaaatag taaataaatc aatgtaactg 240
aatggaacct gggaacaaat atagctacat gtaagatctg ggtatatgct ggaggtgaca 300
taacaaatga agagaaacaa tggactattc aaagctgtgt tgctatcttt attggcaaca 360
aatatgggaa aaaatnaaat gagatcctat tcacatgaat gacaaaaata aatgccatat 420
tgattaaacc taaatatgac aaggaaggcc tcaaatttta gaaaaaaatg ccaaattnta 480
cncattggga gataattcat taacaagacc aanaaccnta aggaaagatg ntaatttnga 540
tatattaaga tttactatgt ttataaatca aggatagtcc cgcttaagan actttctttt 600
atttttaatt aatattatta atatttgana cttgcttgnt tnggtgaacc ggtaatttgg 660
tattnacctt ctccggttan gattnnctaa nccntgtgnt nngttgnncc ncncnatttt 720
tntacagttn ttgcgcgnta ttncnggnng cccccnnngn ngg 763

<210> SEQ ID NO 35
<211> LENGTH: 767
<212> TYPE: DNA
<213> ORGANISM: Homo sapiens
<220> FEATURE:
<221> NAME/KEY: misc_feature
<222> LOCATION: (1)...(767)
<223> OTHER INFORMATION: n = A,T,C or G

<400> SEQUENCE: 35
acaggggaat ggaatggaat ggaatgcaat ggaatggaat catccgtaat ggaattgaaa 60
ggaatggaat ggaatggaat ggaatggaat ggaatggaat ggaatcaact cgattgcaat 120
cgaatggaat ggaattgaac taacccgaat agaatcgaat ggaatggaat ggaacggaac 180
ggaatggaat ggaatggaat ggaatggaat ggaatggaat ggaacggaac ggaatggaat 240
ggaatggaat ggaatggaat ggaatcaacg cgagtgcagg ggaatggaat ggaatggaat 300
gcaatggaat ggaatcttcc ggaatggaat ggaatggaat ggaatggaat ggaatgaaat 360
gcaatggatt caactcgatt gcaatggaat ggaatanaat ggaatggaat ggaatggagt 420
ggaataattc naatagaatg gaatggaatg gaatggaacg gaatggaccg gatggaacca 480
attgtaatgg aatggaattg atggaatgga atggaatcac cctagtcaan ggaatgtatg 540
gaccggattc aatgaatgga tattccgnat ggatggatgg gaatgaattg atgattggat 600
ggatggatca ccatccatga agattgatga tggatgatgc cacccatgat gattatgnat 660
tagngtnata tctncatnna ggatgntncn attatgngnt gatgacatga ntannccnnc 720
nctttnancn tattttttg ggncccccctc ccagttgntt taaannn 767

<210> SEQ ID NO 36
<211> LENGTH: 608
<212> TYPE: DNA

-continued

<213> ORGANISM: Homo sapiens
<220> FEATURE:
<221> NAME/KEY: misc_feature
<222> LOCATION: (1)...(608)
<223> OTHER INFORMATION: n = A,T,C or G

<400> SEQUENCE: 36
acatatagtc aacgaaatat tcaaagaata actttatata ctcttgttct ttaaattcta 60
tcctctcttt cagaattctt ccatttaagt ttgggtattt tcctagtttc aacagatgaa 120
cagaagactt cattgaacat tttgacagta agctactaga gaccaattat caactggtgc 180
tacacatgct gtgttatctc ccttactatt aaactataac cctctcttgc tattttgttt 240
catgcatcac caaccaaact tcattttttc taataaaaaa taaatatata aagaagacac 300
tgacaggcat atattcacaa gatctcaact tcttaaaaca taagtatggg tatatttatt 360
tctctcaaat gcatacnaga caataattac ncagcaacca atcttttgtt caacaatgat 420
ttgantcata agcatttgga aattacataa tttcatatca atanccctgt tttttnaata 480
cagaagtaaa aaanccccaa taaccaatct taaatttcna ttatcccctt acctccaacc 540
tttnaaaggt cccaccgggc cttttccnac attaatttgg tnaaactggg gttnaaaacc 600 gcctnccn 608

<210> SEQ ID NO 37
<211> LENGTH: 245
<212> TYPE: DNA
<213> ORGANISM: Homo sapiens

<400> SEQUENCE: 37
acagacatgg cggcggcttt tcggaaggcg gctaagtccc ggcagcggga acacagagag 60
cgaagccagc ctggctttcg aaaacatctg ggcctgctgg agaaaaagaa agattacaaa 120
cttcgtgcag atgactaccg taaaaaacaa gaatacctca aagctcttcg gaagaaggct 180
cttgaaaaaa atccagatga attctactac aaaatgactc gggttaaact ccaggatgga 240
gtacc 245

<210> SEQ ID NO 38
<211> LENGTH: 630
<212> TYPE: DNA
<213> ORGANISM: Homo sapiens
<220> FEATURE:
<221> NAME/KEY: misc_feature
<222> LOCATION: (1)...(630)
<223> OTHER INFORMATION: n = A,T,C or G

<400> SEQUENCE: 38
actacactga attcaccccc actgaaaaag atgagtatgc ctgccgtgtg aaccatgtga 60
ctttgtcaca gcccaagata gttaagtggg atcgagacat gtaagcagca tcatggaggt 120
ttgaagatgc cgcatttgga ttggatgaat tccaaattct gcttgcttgc tttttaatat 180
tgatatgctt atacacttac actttatgca caaaatgtag ggttataata atgttaacat 240
ggacatgatc ttctttataa ttctactttg agtgctgtct ccatgtttga tgtatctgag 300
caggttgctc cacaggtagc tctaggaggg ctggcaactt anaggtgggg agcagagaat 360
tctcttatcc aacatcaaca tcttggtcag atttgaactc ttcaatctct ttgcactcaa 420
agcttgttna gatagtttaa gccgtgcata aattnacttc caaatttaca tactctgctt 480
anaaatttgg ggggaaaaat taaaaaatnt aattggccag gatnttggna atttgttata 540
atgaatgaaa cattttngna ttaaaaatca nattacttnt aanctttgat aaantaaggc 600

-continued atggntgggg gtaattgggt tttttgttcc 630

<210> SEQ ID NO 39
<211> LENGTH: 626
<212> TYPE: DNA
<213> ORGANISM: Homo sapiens
<220> FEATURE:
<221> NAME/KEY: misc_feature
<222> LOCATION: (1)...(626)
<223> OTHER INFORMATION: n = A,T,C or G

<400> SEQUENCE: 39
acagtggtcc ttttcagagt tggacttcta gactcacctg ttctcactcc ctgttttaat 60
tcaacccagc catgcaatgc caaataatag aattgctccc taccagctga acagggagga 120
gtctgtgcag tttctgacac ttgttgttga acatggctaa atacaatggg tatcgctgag 180
actaagttgt agaaattaac aaatgtgctg cttggttaaa atggctacac tcatctgact 240
cattctttat tctattttag ttggtttgta tcttgcctaa ggtgcgtagt ccaactcttg 300
gtattaccct cctaatagtc atactagtag tcatactccc tggtgtagtg tattctctaa 360
aagctttaaa tgtctgcatg cagccagcca tcaaatagtg aatggtctct ctttggctgg 420
aattacaaaa ctcaaagaaa tgtgtcatca ggagaacatc ataacccatg aaggataaaa 480
gccccaaatg gnggtactga taataacact aatgcnttaa gatttggtca ccctctcnct 540
aagggagccc attgagccna nggngctaaa gcctcatact ccacctgaat ggttaggaga 600
aaatttatcc caaaaaaaaa aaaaan 626

<210> SEQ ID NO 40
<211> LENGTH: 645
<212> TYPE: DNA
<213> ORGANISM: Homo sapiens
<220> FEATURE:
<221> NAME/KEY: misc_feature
<222> LOCATION: (1)...(645)
<223> OTHER INFORMATION: n = A,T,C or G

<400> SEQUENCE: 40
cgaggtacgc gggcaggaca tttaaaaggt ttcagcagaa atcttatgat tatgtctgac 60
ttgcagtatt ttatttgcct ctttgacggc tttttttttt tttttttttg agacagagtc 120
tcacactgca ctccagcctg ggtgacagag tgagagactc cgtctcaaaa atgaatgaat 180
gaatgaatga atgaatgaac aaacgaacaa ggtggtttaa tgtcagaaaa cttcctaagc 240
atttgctccc caaacctttc atgtttttca agaagccttt attacataaa ggggaataga 300
attaaaatgt ttctttataa gaaaaatata catatttgtg ttcttggccc cattaaaact 360
aatcagtagt cctttggcca aaaaatagtc aacaaganaa ctgggtatga ntccnggcnt 420
tactcctgnt cataagtgng gatgcntgtg tctganccna actgnctcaa ctngagctct 480
tggggtataa caanaaaccc gngttttcat gaaacccctg ggccnttata aaaggtttcc 540
cttggggggc ccaatgctta ttntngattn gggttccaaa annntngcaat tggnataggt 600 gcttgaaata accccctttt agtnnaattc cnaccaaaac cntgn 645

<210> SEQ ID NO 41
<211> LENGTH: 616
<212> TYPE: DNA
<213> ORGANISM: Homo sapiens
<220> FEATURE:
<221> NAME/KEY: misc_feature
<222> LOCATION: (1)...(616)

-continued

<223> OTHER INFORMATION: n = A,T,C or G

<400> SEQUENCE: 41
acgcggggct cttcacgagg tggaaacaag atggaggatt cggcctcggc ctcgctgtct 60
tctgcagccg ctactggaac ctccacctcg actccagcgg ccccgacagc acggaagcag 120
ctggataaag aacaggttag aaaggcagtg gacgctctct tgacgcattg caagtccagg 180
aaaaacaatt atgggttgct tttgaatgag aatgaaagtt tatttttaat ggtggtatta 240
tggaaaattc caagtaaaga actgagggtc agattgacct tgcctcatag tattcgatca 300
gattcagaag atatctgttt atttacgaag gatgaaccca attcaactcc tgaaaagaca 360
gaacaagttt tatagaaagc ttttaaacaa gcatggaatt aaaaccggtt ctnaagatat 420
ctcctccaac tctaaanaan gaatataaat cctatgaacc aagctcgcct tttaacagtt 480
tgattcttcn tactgatcca aaataagcgg ttttacctcc ttattgggag acattntttta 540 aaaaagaaag tccatntntg naaccttttt ccaaaatttn tcagananac atgctgnttg 600
gngacggctt aaaatt 616

<210> SEQ ID NO 42
<211> LENGTH: 259
<212> TYPE: DNA
<213> ORGANISM: Homo sapiens
<220> FEATURE:
<221> NAME/KEY: misc_feature
<222> LOCATION: (1)...(259)
<223> OTHER INFORMATION: n = A,T,C or G

<400> SEQUENCE: 42
ngtacggtcg gtggcagtgc tattctgaga tctgtagatg cttagaatat cagtattttg 60
gatgttgctg cattttacaa tttatttgga gtcttccttn attttcctcc agatatatga 120
aaatatgcaa tacctgctta tatcatgtag aaaagcttag caattattaa tttttctnta 180
tttcatttta tttgaccaaa gtcggtgctt cacttgactc antgtgtttt aggtgttngt 240
ntttntacct ttccggtca 259

<210> SEQ ID NO 43
<211> LENGTH: 509
<212> TYPE: DNA
<213> ORGANISM: Homo sapiens
<220> FEATURE:
<221> NAME/KEY: misc_feature
<222> LOCATION: (1)...(509)
<223> OTHER INFORMATION: n = A,T,C or G

<400> SEQUENCE: 43
acgagtgtat ttttgatggg aaggccatgc taaatctata aaacagatgt ttcctctccc 60
aacagtggtc accagtagtt tcaacttttt ccccccagta gcatcaacca aacttagcat 120
agtgattttt aactctttgc tcccacacgc actcatccca acttccccgc ttgccccact 180
ccctgggggg aaataaccct gcctttaaaa taaatagcaa ccaagtgctc agttctatgg 240
aaagtatgaa tatttatttc aggctttcga tcccaatcga tttcaaaaaa caaagtctga 300
tttctctcct cagagcagct gaggcctcca tgttacgatg gtttcatgga gattgaagga 360
gcacatttca tcaggcttag cacaaagtcc ctgatgccca ccatgtccca gccttagnaa 420
aggaaagaaa cagaattcac caccatgggg ctgaacgaat gccacaccta atgtaaatga 480
ncagctaacc ttggccaaat tgtggtttt 509

-continued

<210> SEQ ID NO 44
<211> LENGTH: 544
<212> TYPE: DNA
<213> ORGANISM: Homo sapiens
<220> FEATURE:
<221> NAME/KEY: misc_feature
<222> LOCATION: (1)...(544)
<223> OTHER INFORMATION: n = A,T,C or G

<400> SEQUENCE: 44 tttttttaaaa gtgtcactna ntctttaann anatncatta ccattttttt tncaaantaa 60
attacggttt taaanggaan acacatggna atntananaa ncaccgnnga annttaanta 120
cctngggngc gancanactn anggcgaatt cgaaccaatg ggggcngnaa cnaggggatc 180
ccagctnggt accaaaattg gcgtnatgat cgcaatagcg gtacctgtgn naaanggtta 240
ttcnntngta aaancagann tcntnnaagn nngaccaaaa aangtaaatc ctggggtgcc 300
taatgannga tntaaancna ttaattgggn tgcccacctg cnantttatc gttcaaaaac 360
ccgttaaacn ngtgnaaaaa tgaatngcca acccntngga aaagccgnat cntttgggng 420
cttttccttt ttggtcctna cncttcctan nngnnngttt gggnncggnt nagttcntaa 480
aggcgnaaaa catttacaaa aataggggaa ancccgaaaa acatttaccc nagccacctt 540 ntcn 544

<210> SEQ ID NO 45
<211> LENGTH: 630
<212> TYPE: DNA
<213> ORGANISM: Homo sapiens
<220> FEATURE:
<221> NAME/KEY: misc_feature
<222> LOCATION: (1)...(630)
<223> OTHER INFORMATION: n = A,T,C or G

<400> SEQUENCE: 45
ggtactctct atcactgaca aatgcaggct ggattcttat tatatacaga gatggctcaa 60
aaatggggtt tcagatcttt gtgacgaaat agaatactgt ttcatatttg aatcagaggg 120
cttcttgttc tgagaaatag gttcaaaatc attggaacca ggaacaagaa tagcttattg 180
ttatctgtga taacactgtt ttctaaacac aaggattttc ttttttatta atatgcaaca 240
tagacattgc cataacagaa taataaacca catgtggggt tttaaaaatg aaatttggct 300
aataggagca attcagctat ttttctatca agaaattggg tggggtggga tagaaagaaa 360
aaccgggttc aaccccactt ctgcccccta accagctata tggcctggat ggagcattca 420
acctttaata agggtcaatt tcntctgttn aaaagacccc aaacctggaa atcacnttng 480
cctctccctg aaaataanaa ggctngattt ttggaataan aaacataatg nangctnggc 540
ccaatggctc gccccgtaat ccaccctttg gaggccangc ggncggacac ttgaggtagg 600
agttgaacca cccgccacct gggaacccnn 630

<210> SEQ ID NO 46
<211> LENGTH: 622
<212> TYPE: DNA
<213> ORGANISM: Homo sapiens
<220> FEATURE:
<221> NAME/KEY: misc_feature
<222> LOCATION: (1)...(622)
<223> OTHER INFORMATION: n = A,T,C or G

<400> SEQUENCE: 46
tttttgactc ccaaagtcat tttatttaac aaaggggtca aggcagagga aagtttccct 60

-continued

```
taatatcccc acaactgctc cacatgtctt ctgtggaaac acttcaccag gaactagctc    120

aacactcttg ctaacaattt agtgtctata caggaaggct ggtgtctctg ttacaggtgg    180

cccgttcctt aaagccttta gggttaatcg cagctgcact gagtggccaa gcagaccctg    240

ttgggatgtg aaagcagttt gttaacaggg cccctggccg ggcccagagg ctgtcagact    300

cancaagtaa cactgaatgt ccaaaaatac ggctgtgtta aactaacaag ccaatccttc    360

tgctcagatc tctggataga aatgattttt cttttatcta tgggggaatg caatttcatc    420

acaacccctt acataaacgc tcctgaaacc ctttcagtag acagcatttc aattcaaaaa    480

ccaaaagtga aactatcttt gaaaacangg acctggctgg gaaaccatgc acacctcggc    540

gaacactttt cccccccacg aacttggact ttntgggaag gtggcgggtt tttggcnaaa    600

acattcttga agcntaggaa gg                                              622
```

<210> SEQ ID NO 47
<211> LENGTH: 253
<212> TYPE: DNA
<213> ORGANISM: Homo sapiens

<400> SEQUENCE: 47

```
ggtactttgg tttgaaaaca acacttagag cctccagata acttttaaga cttatttagc     60

tttgtgggtg gtattttcat gcaaataagt aagggtgggt tttatatttt gtagaagttt    120

tcggtcctat tttaatgctc tttgtatggc agtatgtata tattgtgtta agttcctcaa    180

gaatctcctt aaaaactttg aagttaatac ttttgtgcaa ctgtgttttg aataaagcca    240

tgacagtgtt aaa                                                        253
```

<210> SEQ ID NO 48
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 48

```
acttacatat cctacatttg actacattat ttccaaacca agtattccat ccaaaggaac     60

atactgctat catagagacc aaggagggac tgtttaaagt tgccaaggtg aagcgagctg    120

agaggctttg tcctcgtgcc agtaactctg aaatttctct taattcctgc tgtccaggca    180

gcagaatgcc atggtttccc caagtaggta gctgctttag cagttaaagc ccaaatgtct    240

gttctgttga tcaagaggtc tctgaatttc tgaagtggtg tttcgtttct ggtgactgag    300

ttaatccttt acaatncctc ttgtaaagtg tgctaataga aagaatccac ctttcaaagc    360

tgcagaacca naccgtgccc taaattgacc aaccgtanct gatgtgcctn angaagtctt    420

ttgccaactg ccctgtgaan acccctnctt ccccccagct ngtggcttgc acactgaaca    480

tttaaactgn gcaaagccgt gtagttataa nacagtaaat cccaaggctt ggttaantgc    540

tgggnnaaaa ctggttggat anacttaact taaaacccct tacataaacn tnggaactcn    600

aagaaaa                                                               607
```

<210> SEQ ID NO 49
<211> LENGTH: 421
<212> TYPE: DNA
<213> ORGANISM: Homo sapiens

<400> SEQUENCE: 49

-continued

```
ggtaccactg gatgaggggc cgggacatac tgactgcccc tttgacccca caagaatcta     60
tgatacagcc ttggctctct ggatcccttc tttgctcatg tctgcagggg aggctgctct    120
atctggttac tgctgtgtgg ctgcactcac tctacgtgga gttgggccct gcaggaagga    180
cggacttcag gggcagctag aggaaatgac agagcttgaa tctcctaaat gtaaaaggca    240
ggaaaatgag cagctactgg atcaaaatca agaaatccgg gcatcacaga gaagttgggt    300
ttaggacagg tgctgttccc gagactcagt cctaaagggt ttttttccca ctaagcaagg    360
ggccctgacc tcgggatgag ataacaaatt gtaataaaag taacttctct tttctttcaa    420
a                                                                    421
```

<210> SEQ ID NO 50
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 50

```
ggtacttcag tattgcattc tattcctctt aatgttttta tgggatctcc agggaaagag     60
gaaaatgaaa accgtgatct aacagctgag tctaagaaaa tatatatggg aaaacaggaa    120
tctaaagact ccttcaaaca gttagcaaag ttggtcacat ctggtgctga aagtggaaat    180
ctaaatacct ctccatcatc taaccaaaca agaaattctg agaaatttga aaagccagag    240
aatgaaattg aagcccagtt gatatgtgaa cccccaatca atggatcctc aactccaaat    300
ccaaagatag catcttctgt cactgctgga gttgccagtt cactctcaga aaaaatagcc    360
gacagcattg gaaataaccg gcaaaatgca ccattgactt ccattcaaat tcgtttattc    420
aaacatgatc aagaaacgtt ggatgacttt aaaaaanatg ccntaaggac anttgtgatt    480
tgcaggtggg aagatnaaca gttcatatcc actgaatgaa atgcatcttg tggaaganct    540
catgnatnaa ggttaatggc tgaaatgaaa actccaaaag aaaccaaaaa ataccggccc    600
ctttgaaatt cagggannce tatg                                           624
```

<210> SEQ ID NO 51
<211> LENGTH: 632
<212> TYPE: DNA
<213> ORGANISM: Homo sapiens
<220> FEATURE:
<221> NAME/KEY: misc_feature
<222> LOCATION: (1)...(632)
<223> OTHER INFORMATION: n = A,T,C or G

<400> SEQUENCE: 51

```
ggtacgcggg ggaaacggaa gtgagcggcg gggtcgactg acggtaacgg ggcagagagg     60
ctgttcgcag agctgcggaa gatgaatgcc agaggacttg gatctgagct aaaggacagt    120
attccagtta ctgaactttc agcaagtgga ccttttgaaa gtcatgatct tcttcggaaa    180
ggtttttctt gtgtgaaaaa tgaacttttg cctagtcatc cccttgaatt atcaagaaaa    240
aaatttccag ctcaaccnaa gataaaatga atttttttccc cctgaagaaa cattcagggc    300
tattttgctt cccttaaaat accagaatgg gattcaaggg cagtgccacc aggtcaaccg    360
ctttcatttc tttcaagcct caaatctttc acttgaatgt ttgaagggta atggatgaag    420
acctattgga attgagggat atctttaatg atccgcccca aaccgaatcc ttggaaaagc    480
```

-continued caccccttgat ggtggaatat aaccttggtt actgaatatg tgcctgtcat ggaaccgagg 540
ccgcatctgg ttatagcatc tttgacctgc cggccgcccc aaaggcgaat ccacncctgc 600
ggccgttcta tggaccaact cggnccaact gn 632

<210> SEQ ID NO 52
<211> LENGTH: 623
<212> TYPE: DNA
<213> ORGANISM: Homo sapiens
<220> FEATURE:
<221> NAME/KEY: misc_feature
<222> LOCATION: (1)...(623)
<223> OTHER INFORMATION: n = A,T,C or G

<400> SEQUENCE: 52
acttttaatg gtgggaattt acagtagaag catcctttgc tgagttatac attcctttat 60
caatctcttt tgatacaaca tttaaaacaa gtagcttcaa gaaaccactg gtgttttgag 120
gatagtattt ctaaatagca ttcaggaaca gagtattatt gcacagatct gaagatcaaa 180
aaaaagctca aggaaataca gatcggaagt gctgatgagt tatatttatt gaaaacccaa 240
cttttaagga agtgctaaga tcagtcaccc atgtgaataa gaagccagga aaggaaagat 300
ggggaaagcc canatcacca ggcttctatt aaggaggaaa gcaacagang aaacagtgaa 360
agggaacaga aaggggtagc caagtgttac aaaaaanccg actggataac caaactncaa 420
aaagngtatg ttggggagaa ctgaaangga aaacaaaata cttgactaat cntaagtaga 480
aaaaagcagn tagagaaaac caaatatttc tggncctgtc acatacaact tcaaataccc 540
ttatanaatc caaaaatgat gtgtgtaagg naaaatttat tgccntccga aaaataantt 600
tntccaatnt gaaacaaatc aac 623

<210> SEQ ID NO 53
<211> LENGTH: 627
<212> TYPE: DNA
<213> ORGANISM: Homo sapiens
<220> FEATURE:
<221> NAME/KEY: misc_feature
<222> LOCATION: (1)...(627)
<223> OTHER INFORMATION: n = A,T,C or G

<400> SEQUENCE: 53
ggtacgcggg gtcgcatgcg ctgtggctaa tgccgtaggc tctttcaggg ctgagccatc 60
ctgcgtgtct tgcgctcggt ggaaatgccc agccgaggga cgcgaccaga ggacagctct 120
gtgctgatcc ccaccgacaa ttcgaccccca cacaaggagg atctaagcag caagattaaa 180
gaacaaaaaa ttgtggtgga tgaactttct aaccttaaga agaataggaa agtatatagg 240
caacaacaga acagcaatat attctttctt gcagaccgaa cagaaatgct gtctgagagc 300
aagaatatat tggatgaact gaaaaaagaa taccaagaaa tagaaaactt agacaagacc 360
aaaatcaaga aatagtcaac ctgatttcac ataacaatgt gtggcatttg ttgttctgta 420
aacttttctg ctgagcattt cagtcaagat ttaaaagagg acttactata taatcttaaa 480
cagcggggac ccaatagtag taaacaattg gtaaagtctg atgttaacta ccagtgntta 540
ttttctgntc acgtnctaca cttgangggg gtttgactac ccancctgtg gaagaagaaa 600
gaagcaatgn ggttctatgg atggaga 627

<210> SEQ ID NO 54
<211> LENGTH: 565
<212> TYPE: DNA
<213> ORGANISM: Homo sapiens -continued
<220> FEATURE:
<221> NAME/KEY: misc_feature
<222> LOCATION: (1)...(565)
<223> OTHER INFORMATION: n = A,T,C or G

<400> SEQUENCE: 54
ttttccttga gtgctccctt ttatgtcatt ttattttctt ttatgcagac cagtgggggg 60
aaaatcccat agattcttct ggaaactgtc aagatgctgg gaagatgaat gcaaaactta 120
catagattgg gatgtccaca gtttggattt tcaaggtatg gcttttgcag gatgacgtga 180
tcaacccaaa cttctgcttg atctggtttg tcctgaactc ctgccacttg ccgccaacca 240
gggcctctgc tctgatctca tacttcacca ggcgtgccgn tcgcaggctg acgtggttgt 300
gctcgtagac cgcagaggga gattccaggt ctgtgtgctt tattctctgc atgtaaaaac 360
tataagaggt agtatcatgt ttgagtccct ttatcttaaa gaagaatcca tatagagcaa 420
tcgttttcga ataagttgna ttctctgngt ctggcactgt gtccagtgct ctcanaggat 480
gcangggaga anaccaaaaa gtntctgagc agtctcacat gggaaataaa atgtgtcccc 540
ggtaccttgg ccgngaacac nctaa 565

<210> SEQ ID NO 55
<211> LENGTH: 451
<212> TYPE: DNA
<213> ORGANISM: Homo sapiens

<400> SEQUENCE: 55
acagagatga caagagaaag gcacaaatga ccggagtcag ggattgtggt gagggctcca 60
catgaagaca gcatgttgga ggagaccaag ttgggaaggg tgacatgtca tacatcaaaa 120
gttgccccaa gatagcaggt tataatgggc tagagagaaa ttagagggaa catctcttcc 180
ttcacttgaa caacaccaaa aatagaagac cagagaatag aaggatggtg acaaatccca 240
aaaaggaaat ggaggaggag ttcgtggaag ggcagaaaca ctttaatcct agagggaggg 300
tgaggcactg ttgaaaagag aagcaaactt tggcaggggt ggccattctg ccttgctgag 360
tcatgggctg agatacggaa gtcactttca atcattttct acttctccca gggcactcag 420
acaaaatcag tgcaaggtat atggaagtac c 451

<210> SEQ ID NO 56
<211> LENGTH: 623
<212> TYPE: DNA
<213> ORGANISM: Homo sapiens
<220> FEATURE:
<221> NAME/KEY: misc_feature
<222> LOCATION: (1)...(623)
<223> OTHER INFORMATION: n = A,T,C or G

<400> SEQUENCE: 56
ggtacgcggg gcttccgaga cgcactgggg gccggatgta gaatcctgct tatctgtgaa 60
atgcagttaa cacatcagct ggacctattt cccgaatgca gggtaaccct tctgttattt 120
aaagatgtaa aaaatgcggg agacttgaga agaaaggcca tggaaggcac catcgatgga 180
tcactgataa atcctacagt gtttcactct tgttgcccag gctggagtgc aatggcgcga 240
tcttggctca cggcaacctc tgcctcccgg gttcaagcaa ttgtcctgcc tcagcctcct 300
gagttgctgg gattacagat tgttgatcca tttcagatac ttgtggcagc aaacaaagca 360
gttcacctct acaaactggg aaaaatgaag acaagaactc tatctactga aattattttc 420
aacctttccc caaataacaa tatttcagag ctttgaaaaa atttggtatc tcaacaaatg 480

-continued

```
acacttcaat tctaantgnt tacattgaan aagggagaaa acnataaatc angaatacct    540

aatatcttca gtngaanggc atcaaggttc tcttgaaaac ttnccggaat aatgaatntn    600

ccnaagtcca aaanattttt aac                                              623
```

<210> SEQ ID NO 57
<211> LENGTH: 622
<212> TYPE: DNA
<213> ORGANISM: Homo sapiens
<220> FEATURE:
<221> NAME/KEY: misc_feature
<222> LOCATION: (1)...(622)
<223> OTHER INFORMATION: n = A,T,C or G

<400> SEQUENCE: 57

```
cgaggtactt tttttttttg tttttttttt tttggtttct gtcctttaat tttttaacag     60

aatatacaga gccacacaat acgatttcaa tttcaaatta tgggagatca tattcaaata    120

tgcttaggtt tgacaagttg ctgttacaat actgagaact ttcatgaaaa cggtatttaa    180

caatttttaa gataatcaaa tatctttttg ctacgtgggc caacgcatta atactaactt    240

gtttaaaaat gcagtctttt agacttcaaa ttattataaa acaatatcaa gatcatatag    300

atatacttcc tgattactca aaactcgttc cattctgatg gaggctgaag gtaaatgtta    360

ttatacatta gaacatttca tgaaaccact tctcctttgc acttacctgt aaaagtcaaa    420

aattaaacca caatttccta agacataact atttctagaa tacattggtg taatcataaa    480

agactacnag taaattatca tttttatcta acacttttta ccacacacat ctttcctaaa    540

aggaccnaaa aaaattggga atttggattc cttacataac aggactcata cttctgattt    600

aataaattnc actcttttca ag                                               622
```

<210> SEQ ID NO 58
<211> LENGTH: 471
<212> TYPE: DNA
<213> ORGANISM: Homo sapiens
<220> FEATURE:
<221> NAME/KEY: misc_feature
<222> LOCATION: (1)...(471)
<223> OTHER INFORMATION: n = A,T,C or G

<400> SEQUENCE: 58

```
ggtacttttt ttttgtttgt tttctagact taataaaagc ttaggattaa ttagaagaag     60

caatctagtt aaatttccca tttgtatttt attttcttga atactttttt catagttatt    120

tgtttaaaaa gatttaaaaa tcattgcact ttggtcagaa aaataataaa tatatcttat    180

aaatgtttga ttcccttcct tgctattttt attcagtaga tttttgtttg gcatcatgtt    240

gaagcacccg aaagataaat gatttttaaa aggctataga gtccaaagga atattctttt    300

acaccaattc ttcctttaaa aatctctgag gaatttgttt tcgccttact ttttttttctt    360

ctgtcacaat gctaagtggt atccgaggtt cttaatatga gatttaaaat cttaaaatgn    420

ttcttatttt cagcacttac atcatttggt acctgccngg cggccgntcg a              471
```

<210> SEQ ID NO 59
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 59

-continued

```
ggtacataca caatcactca actggaacaa tcaaaaccat ctatgagtgt ggttattaaa     60
aaataaaatt acgttcatac aatggtagaa aatgaaatgt ttttattaat ttgattatta    120
atacaaaacc acacatatat gaattatata acctagtgtt atatatttaa aaatctttat    180
gcttgcaact gaaatgtctc tactccaagg gaagtttctg atttttaatt ttcttatttt    240
aaggaatcta ttatattcac aatgattaaa atgccttaca cataggcaaa aagcagaccc    300
aatcccagca aacagaaaaa ccataagtct atcatatcac catatgtttc accatatagt    360
tttgaaaaat aatcctattt gcagtttggt atgtcttcat atttatactt attatcaaag    420
tgattgcata ttgaggcaca gagcttaaag aggaaatata tattacttat aggggaacca    480
gacactgaaa caaggaatat caatcaatgg cttcaaacna aaaaaaaann nnnnnnnnnn    540
nnnnnnggaa aaggaaaagt cctgncccgg cggncgttca aagggcnaat tcaaccactg    600
ggggccgtac ttatggac                                                  618
```

```
<210> SEQ ID NO 60
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 60

actttttaaa ccctcccaac cagccctttc tcaatattca tcaaatctaa aacatttagg     60
gggcaaaatt ctaacatgtt catggtatct tgcaaatagt aaaagcttta ttctgaagga    120
ttataaacta gttttctcca ttttaactag cactattttg tggaaattag aaacctcttt    180
tatttctctt cccaaaagta atacttatta taaggctgta gtatcaggtt aaggatacag    240
ataaataaag ttcacttata tcttcttaca aatgtctggg ttttaatatg gttaatcact    300
tatatacaaa tattacaact ttttagtgca agtttttgga agaaaacttt ttgataaaac    360
actgtgattg atgtgacttt atttttaatt taaacgatga ggtggccaga agaaagatgg    420
gtctaaaatt tctcccatga aagatgtaaa actatggctt ttttaaaatc aaaatttcat    480
ctttaaaata atgggttgaa atctggatng gatctgaaca gaataatcac atttaggatc    540
tatataaatc tcaactggag tntaactgaa ggaaataccn ngattttaag aaatatnttc    600
aaaaan                                                               606
```

```
<210> SEQ ID NO 61
<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 61

ggtacattct ggtatgaaaa catctcaaaa tgtaacaaca caagagtttg ggtcaagacg     60
acccacccag gaggctgtaa aaactggttt gaactagaac tgtggaatgg aactagttta    120
aaatatgaag cagctctaaa caccaagctt agagacattt gccctattag aaaacaaaaa    180
tcattaaagc tacaaaataa caagtgcaaa catgctgaac ctgtttccag ggagtgacat    240
tcccttctgc caacaggtcc caaactcaca cccacaaggt gtaactctct ttcctgttcc    300
```

-continued

```
actagatttc ctttctctca tctcaaaggt cctcagaaat gacaatggaa aacgtatgaa    360

ttgttgaaat ttaccctgtg gaccaattcc tgaagagata acagccacaa ctctgagatg    420

attaagacat gcagtgttta cttgatgact ttctgnattt ctagaaaccc tcaaagcatt    480

aaactgncta tttcaaaatc taaacttnct agcactttta ttatttggag taagcnnacc    540

gaagacaatt tactggccca caggaataac cacgcttact tgtcaccata agtttacggn    600

atggacattc actggaaaac                                                620
```

<210> SEQ ID NO 62
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 62

```
gccgaggtac ataaatctgt gatcccattt cttattgcac cattcaggaa cactttatat     60

aaatgagtgg ctttttattt catattatta gtagtatcat ggttccatta caggcctatt    120

aacatcatac attgtcatta gtctttgaag aaaaaatatg taaatatata tgtgtaacat    180

gagaatttct ctctaaagca gggcttaaaa ttttttggaa aagtttgaca aagcatacca    240

catgaattca gatttacctc aatgctaaga attatgttta gttaggaaaa aggaaagtca    300

ttttgacctc aggtagaaaa atagattgct ttgagtttta tgtagcttta gactttaaaa    360

agttagaatt tattctgtaa ctaaaaatta tttgaaaaaa ttatgcctct ggtttaatta    420

ttggtgatta cacactcttt ctcttaccct tgngtattga actatgtcca taatcaagtt    480

gatgtggatc ctgaaaaatg gtatgaacat ctgatgggat tggcacatta ttttaaaant    540

agcatctgac acttcaaaac tgtcantgng atgggttcac cataccacgg ntgaccntac    600

attaaatttt nacn                                                      614
```

<210> SEQ ID NO 63
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 63

```
ggtacatata agagtaatta gttttattct ctctttttta taaaatcggg tttcagatga     60

gatgtttatc ttagactatt ttagggaaaa attttacatg tttgagatgg tggagtaaaa    120

agactgttaa acatttcttt taaaaaatta tttttacatt acaacaatat atttatgatg    180

tgttcagatc aaaaatttaa cttctgtgtc ccagatctac tttcaaagtg agattttcac    240

ttgtcagctt aaatttctga ctagaactaa catttgtgta tttttgtgct tagtcggaat    300

acaaatttca cagtggattt ttgaagtttg tccttaaatt ggataaaatc aagtgattaa    360

agttactaaa gagataaaaa tggtaatttc catttttaaa agtaatttgg ttgtgtttat    420

agttatttgt acttcgagtc tcccttcacc atttccgacg gcatctacng ctcaacattt    480

tttggtaccc cangctttca cggacttcac gtcattattg gctcaacttt cctcactatc    540

tacttcatcc gccactaata tttcctttac atccaacatc ctttgacttt naagccgccg    600

ctgatnctgc attttn                                                    616
```

-continued

<210> SEQ ID NO 64
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 64
ggtacagata tcattncttg tgtatgccat gacttgaaaa agtttgggaa gctctttanc 60
aatatcagct aanaggatat gaaatcacag gtgatagcag ttgtcattca gtaatttcct 120
acaagcagca ccccaaagga aatatagtcc taatctttac tatccacttc taaatttaat 180
gtgaatttca tacatgttat tagttgtttc ctttataatt ttataaaaat tattcatcgg 240
gagtttaact tccacttcca tgctatcgga tgtgttgggc tccatgcaag aacttggaag 300
aaaaacaggc aggaatgcat ttgcataatg acccagatca tcattttctg caactgagaa 360
ttatatttca tcattgcttc tagaagtctg caattcttta cttttctttg gtgcattatt 420
atctangtgc ccatcactgg ataatgtgga gtgactagag aagtcatnta tcactggaag 480
gncctgcccn ggcggccgtt caaaaggnca antccagcan nctggcggcc gttctaatgg 540
gntccaactt ngggnccaan cttggngnan tcatggcnta acnngttccn gggggggaaat 600 gntntccctc ac 612

<210> SEQ ID NO 65
<211> LENGTH: 599
<212> TYPE: DNA
<213> ORGANISM: Homo sapiens
<220> FEATURE:
<221> NAME/KEY: misc_feature
<222> LOCATION: (1)...(599)
<223> OTHER INFORMATION: n = A,T,C or G

<400> SEQUENCE: 65
acaagctaca aaatagcatc tctttcatgg tatgtttgag tgtgtaattt tagtttcttt 60
tctggttgta tttgtggtag tcagatgtgt tggattgatt ccaactggac agagtaagga 120
attccagcat cctcttcctg cttgctcgtg ttaccccaca gatcaaaccc tcaattctag 180
ttggggatgc tgtctagccc cacaccatga ctgaagcctt aagcactgtt gcgcctccat 240
gtgctttggg tcagcaaccc cagtggtatt ctaccagagc attgtgggaa ggcagatgta 300
tagtcaggtc ccaacagcaa attgttgggt gtgagagttc taaagtatag gggtgaaggg 360
aaagagaang atatgaactc ctctgacctt aaccacattc atttaacttt tatgcctact 420
taacaagaga acctggagaa aactatcgna ttcaagagat taatcaaaat cagggtttan 480
ccagccatga ccgaaancnc cttccttaac ctcatcttgn anggctgnaa naattcannc 540
ctaggatggt taanccagaa ccccngatga ttaantgtcc aaccttnatt tncatantn 599

<210> SEQ ID NO 66
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 66

-continued

```
ncatgacctt tagtggaaga ttatttggtc atcaaatacc catatccaag tttccatggg     60

gcctgggaat ttcctttcac ttggatagaa agtatatatt aggaaagtcc agttaataag    120

tatttttatt taaaaaaaaa aaaaaaggaa aaaagaatca gcagaagtca agttgtctta    180

agtcttaagg ctttctggat ttcttccttg gaggaggtca ggatcttccc aaggcctggg    240

tcctcgaata ttcttccagt catcaaactt ggagtctttg attttctcat attccgactc    300

taaagatatt ttattctctt tcagtttttt ttcaagctca ggatccattt tactcttcac    360

agcatcatat cggatttgag aaaactcacg aagaccaaaa gaaccttcaa caatcagcaa    420

caacatgggg actccatacc cagagtcttg gtcttgcgaa aagcacgcnt naaccgcggg    480

tgccaacatg agtgaactct ttcatcggtt naaactccaa cnggcctacg caaactccca    540

atttacaggt tangctttta ccaaacaagt ncctnggcgg gacnccctag gggaattcgc    600

cactgggggg t                                                          611
```

<210> SEQ ID NO 67
<211> LENGTH: 639
<212> TYPE: DNA
<213> ORGANISM: Homo sapiens
<220> FEATURE:
<221> NAME/KEY: misc_feature
<222> LOCATION: (1)...(639)
<223> OTHER INFORMATION: n = A,T,C or G

<400> SEQUENCE: 67

```
nagaattcgn gcttncnagc ggtcgnccgg gcaggtacac tttacttaaa aactattaac     60

agtttttcat gttgcactgg tggtaatttt gaacttggaa ttactgggtg ggaattccag    120

gaaccacaga gtattgattt ttgctgccaa aatgctcttg aagcagatgt ccctgtgctc    180

ccctggctgc ttctggctga aggggggagg tgtagactga agcttgggca ctcatgtgtg    240

tcccctccca gtccccatcc tagtggggcc agtctcatta ggcagccata gataagcctg    300

gaacttggct gcattagtga cttgatcctg gtatgaaatg catactgggt ataaagntgc    360

tcaagnattt tatttccttg gccacaactt ccatagatgc caatggtttg atagcctcag    420

tttctnaacg atgtcttttg gttacagtgc tcacttantg ngagtcaaga aatgcttgag    480

ttaccagaaa cttcttantc aggttgagta acnttttacn ttcatgngta nctnnggcgc    540

gaacaccctt anggggaatt ccacacactt ggnggccgta ctaanggatc caacttgggn    600

ccaacttggg ggaaaaangg cnaantggtt ccttgngaa                           639
```

<210> SEQ ID NO 68
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 68

```
tcgaccggcc gcccggccng gnccttcccc atcactnnac tggnacnatc aaaaccntct     60

atgantgngg gtattaaaaa ataaaattac gttcatacna tggtagaaaa tgaaatgntt    120

ttattaattt gattattaat acaaaaccac acatatatga attatataac ctagtgntat    180

atatttaaaa atctttatgc ttgcaactga aatgtctcta ctccaaggga agtttctgat    240

ttttaatttt cttattttaa ggaatctatt atattcacaa tgattaaaat gccttacaca    300

taggcnaaaa gcagacccaa tcccagcaaa cagaaaaacc ntaagtctat catatcacca    360
```

-continued tatgtttcac cntatagttt tgaaaaataa tcctatttgc agtttggnat gncttcatat 420
ttatacttat tatccaagtg atgcntattg angnccnaag ctttaagang gaattttntt 480
cctatngggg acccnaccct tgacccgaat tcatcaangg ntttaaccca aaaaaaaann 540
aaaaaaaaat ggnaangggg ctcccttnaa ancccccca acctntttnt ttaacnagnc 600
tnagcctttc a 611

<210> SEQ ID NO 69
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 69
accaaagcat tacccgcatg gtagagaaca cactcgatta aaaatgttaa gctatctgaa 60
aaataaaatg tgcaagtctt caggatggca caaaacaaag gtcaatgctt cttggggcac 120
atttcttaga gggcttgctg agtgtgtaaa tataatcgac ttttgtttgt gttacatgac 180
ttctgtgact tcattgaaaa tctgcacaat tcagtttcag ctctggatta cttcagttga 240
cctttgtgaa ggtttttatc tgtgtagaat gggtgtttga cttgttttaa cctattaaat 300
ttttattttc tttcactctg tattaaaagt aaaacttact aaaagaaaag aagtttgtgt 360
tcacattaaa tgggtttggt ttggcttctt ttaatcaggc tttctgaaca ttgagatatc 420
ctgaacttag agctcttcaa tcctaagaat ttcatgaaaa gnctntnact ttgaacccaa 480
accanaatac ctcggccgga caccctaagg cgaattccag ccactggcng gccgtactaa 540
nggatccanc ttggtnccaa cttggggnaa catggcnaac tggttccggg gaaatggatc 600 cccncn 606

<210> SEQ ID NO 70
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 70
ncgtggncgc ggccgaggtn cttttttttt tttttttttt ttttttttnn aaaangggta 60
accttaaagg tttantggcc ccccaaangn aacctggggt taatggcttc nnattttaaa 120
tttttggaaa ttaaaaaaat tacnagtttt aaatagccna tggctggnta tgttttcana 180
aaacatgatt agactaattc attaatgggg gcttcaagct tttccttatt ggctccanaa 240
aattcacccn ccttttgncc cttcttaaaa aactggaatg ttggcatgca tttgacttca 300
cactctgaag caacatcctg acagtcatcc ncatntactt caaggaatat ccgttggaat 360
acttttcana aagggaatga aagaaaggct tgatcatttt gcaagggccc caccacgtgg 420
gcgganaaat cacttctaca ggttattacc tgganngtca aagntttctg naaaacanct 480
tgctctcaac tggtttacca tttggtgctg gagctnacaa ccggtttaag gcccttggna 540
anggtccaag ncccaanaaa ctttcccggt ccttccggng gccttnaagg gaatccnccc 600
tgggggcgtt t 611

-continued

<210> SEQ ID NO 71
<211> LENGTH: 588
<212> TYPE: DNA
<213> ORGANISM: Homo sapiens
<220> FEATURE:
<221> NAME/KEY: misc_feature
<222> LOCATION: (1)...(588)
<223> OTHER INFORMATION: n = A,T,C or G

<400> SEQUENCE: 71

```
nctgggaacn ccgaaggtgg aaggccnttt cataacattt cttgtggatc aaaccaccgg     60

gacacctttt ttnccatcaa caggactagc gtcttgtcag tcttggtgac agtgacattg    120

aangtggggg cccaccggtg ctcttggtac tttcccaaga ggtcctcatc ctgagacggt    180

ctctacccat gtttaaccca aagagtgcag gccaggttcc ttatccttct gatgaaggat    240

gagagaactc atttagaagt cagagcaaac tagggtctca gtattgagaa acgcacctgc    300

canggaatca cagagacatc ggggtgcccg cgatggcctc atgaaccatg cctngacggn    360

attcaggaac cctgcaaacg tgctttttga ctcattggnc agtgtgaatt ttacacaagg    420

naaacctggt cnaaggcatt ngggaattgc tccaacnnat acttcctntt aggaacccaa    480

ggaancaggt tcncgaattt tgaaaactgg gtntgaagtt ctttcttcct ttgggnacaa    540

ggccttaaca aanancttgn ggnttccaaa tggncctggc cccacacc                 588
```

<210> SEQ ID NO 72
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 72

```
ggtacaaact tagaagaaaa ttggaagata gaaacaagat agaaaatgaa aatattgtca     60

agagtttcag atagaaaatg aaaaacaagc taagacaagt attggagaag tatagaagat    120

agaaaaatat aaagccaaaa attggataaa atagcactga aaaaatgagg aaattattgg    180

taaccaattt attttaaaag cccatcaatt taatttctgg tggtgcagaa gttagaaggt    240

aaagcttgag aagatgaggg tgtttacgta gaccagaacc aatttagaag aatacttgaa    300

gctagaaggg gaagttggtt aaaaatcaca tcaaaaagct actaaaagga ctggtgtaat    360

ttaaaaaaaa ctaaggcaga aggcttttgg aagagttaga agaatttgga aggccttaaa    420

tatagtagct tagtttgaaa aatgtgaagg actttcgtaa cggaagtaat tcaagatcaa    480

gagtaattac ccacttaatg gttttgcctt ngacttttgg gttaagaata tttttaaatc    540

ctgnggctnc cttaattggc cgnttgncca ngggttccnn aaatgggttc n              591
```

<210> SEQ ID NO 73
<211> LENGTH: 581
<212> TYPE: DNA
<213> ORGANISM: Homo sapiens
<220> FEATURE:
<221> NAME/KEY: misc_feature
<222> LOCATION: (1)...(581)
<223> OTHER INFORMATION: n = A,T,C or G

<400> SEQUENCE: 73

```
acgcgggtat ctgtaatttt tataattcat caattctgga atgctatata taatatttaa     60

aagacttttt aaatgtgttt aatttcatca tcgtaaaaag ggatcatctc agagagaaca    120
```

gcagtattct gcgtattttt aaaaatgctc tagagtaaca tttgaagtaa ttcactgtag 180
tgtatgccag tcctagaaat aattttttta atttctggtg tctgtttcta atacactaac 240
caagttttca aaatatattt acaaagatgc atctttaccc attattttaa aatgattaag 300
gaggatagtt gcttcaggta acaagctaat ttttcaaata ttaggccctt acagaactat 360
ttagtcaaaa agtaagatat tcctttaaaa tatataaccc aaagctttca gttaaaccat 420
gatatatcac aaatactatt aaaatggtaa agagaaaatg caattgcant taatgatgcc 480
caaatngtaa aatatngaga ttcaaaagct gggnctttat ttaggnggga tnccaatgnn 540
aatgatactg gcctggnttt acctttacct tttaaaaaan a 581

<210> SEQ ID NO 74
<211> LENGTH: 599
<212> TYPE: DNA
<213> ORGANISM: Homo sapiens
<220> FEATURE:
<221> NAME/KEY: misc_feature
<222> LOCATION: (1)...(599)
<223> OTHER INFORMATION: n = A,T,C or G

<400> SEQUENCE: 74
cgaggtactt tttccgcaca tgccttgtgc ctatctgagt attgatgcca tggatgtggc 60
cggagaacag cagctggatg tggaacacaa cctgttcaag caacgactag ataaagatgg 120
catccccgtg agctcagagg ctgagcggca tgagcttggg aaagtcgagg tgacggtgtt 180
tgaccctgac tccctggacc ctgatcgctg tgagagctgc tatggtgctg aggcagaaga 240
tatcaagtgc tgtaacacct gtgaagatgt gcgggaggca tatcgcccgt anaagctggg 300
ccttcaagaa cccagatact attgagcagt gccggcgaag agggcttcag ccagaagatg 360
caggaaccag aagaatgaag ctgccangtg tatggctttc ttggaaagtc aaataaggtg 420
gcccgaaact ttcactttgc ccttggggaa ganctttcca gcantcccat gtcacntcat 480
tgacttggca aactttggnc ttgacaaccn tnaccatgac ccactacatc ancacctgtc 540
atttngggga ggactttcna gccttgggaa accccctngac cccccaatgg taattggcc 599

<210> SEQ ID NO 75
<211> LENGTH: 594
<212> TYPE: DNA
<213> ORGANISM: Homo sapiens
<220> FEATURE:
<221> NAME/KEY: misc_feature
<222> LOCATION: (1)...(594)
<223> OTHER INFORMATION: n = A,T,C or G

<400> SEQUENCE: 75
acatcaaatt ataaatgcaa aacaggttca gatttcatct tttgtgattt cttttaaata 60
ctattcattt ttatttaaat gcacagtatt tcccctatat tttagtcctt ccattcctag 120
agacaaacca gttatttggt ggtgggaagt agctgaagca aagaaggaaa agtaatacct 180
ttaacctcac tagcttcaag agtagacatt cttactagct caatttaaat aattgatttt 240
aaataggaag aaaagaggat atatttaaga tacatagaaa ttatgatgtg aagtattcat 300
gagaatctgt agattccatc aaaataagta ggaactcatc taaaattgtt ggatttaaag 360
aggcactttt ggttatgatt caaatatggg gaatttgaga aatattcatt ttgnccactg 420
gatggtcact attttactaa aanggnagct ttttatgggg ggactgngac tgaggtctta 480
aagactgaaa gaagttgggg ggttcatttt cngtaccacc ttcnnggacc atttggacct 540

-continued ttggccggga acacccctaa ggngnaattn cngnccctgg gggccgtcta atgg 594

<210> SEQ ID NO 76
<211> LENGTH: 585
<212> TYPE: DNA
<213> ORGANISM: Homo sapiens
<220> FEATURE:
<221> NAME/KEY: misc_feature
<222> LOCATION: (1)...(585)
<223> OTHER INFORMATION: n = A,T,C or G

<400> SEQUENCE: 76
acgcgggggg cggagtagca agtggccatg gggagcctca gcggtctgcg cctggtagca 60
ggaagctgtt ttaggttatg tgaaagagat gtttcctcat ctctaaggct taccagaagc 120
tctgatttga agagaataaa tggattttgc acaaaaccac aggaaagtcc cggagctcca 180
tcccgcactt acaacagagt gcctttacac aaacctacgg attggcagaa aaagatcctc 240
atatggtcag gtcgcttcaa aaaggaagat gaaatcccag agactgtctc gttggagatg 300
cttgatgctg caaagaacaa gatgcgagtg aagatcagct atctaatgat tgccctgacg 360
gtggtaggat gcatcttcat ggttattgag ggcaagaagg ctgcccaaga cacgagactt 420
ttaccaagct tgaacttana aaagaaagct cgtcttgaaa gangaagcnc tntgaaggcc 480
aaaacagagt acanaagttt ccnngttggc ttggattttg aaaattcnng aattntntat 540
aacgggcttn tttaaaaagg atnggnttan gnacctttnt taaat 585

<210> SEQ ID NO 77
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 77
ggtacgcggg agtcatattt atgaaaaaag gtttgtgttt tactcttgct agtgagaaag 60
tgggacaaaa tatacttttg aaataaaatg ctatatggca cctaattatt ttttctttta 120
aaatgcctta agttgcagtc tcattttgat aatcatttgc ttccagtgtt taaaaattaa 180
aaaaagaatg gggagaaggt tatgagaaga gcattattaa gtttccaaat ttaatttgaa 240
ttccaaattc acctagcaat aaaatctaat ttttaaaaag tatataaata taaaatgtat 300
aaatgatgga tagatttttg tattgatttg caaaatgcag attatatttg ataggctata 360
gtatgtagat attcctttta ggaatattac agctgtaaat tatatgagac ttgccagtca 420
aatgctattt ggtttaaaaa aattattgca atctcaagtt aatggaatat ttttaaatcc 480
cacattcaga gttaaaacct ngttttcaat gggtttttan tgtggcactt gnttatagat 540
taatttttaa taacctgttn ggaancnggg ccttttaact ggtccttggg g 591

<210> SEQ ID NO 78
<211> LENGTH: 252
<212> TYPE: DNA
<213> ORGANISM: Homo sapiens

<400> SEQUENCE: 78
actgagaagt attttcagtg attcgaccca gaccagattt caacacatgg ttcccataca 60
ggaaggactg ctctgcacca ggctttatcc aaactttata cttggcataa ggtgcaaggt 120
aatccagagc tgtgacgtgc aaccgaaact tgtgggtttt agtgaatttt ccaaagcagg 180

-continued tccccagcga caccagcttg tccccggaaa tattggcggc cagcttcata atcttctcac 240
tcacatagta cc 252

<210> SEQ ID NO 79
<211> LENGTH: 571
<212> TYPE: DNA
<213> ORGANISM: Homo sapiens
<220> FEATURE:
<221> NAME/KEY: misc_feature
<222> LOCATION: (1)...(71)
<223> OTHER INFORMATION: n = A,T,C or G

<400> SEQUENCE: 79
gctcgggcaa gcactttaac cttttaagcc caaccagatg agttgcctgc agttttggag 60
gccttcagag catttcacta gacctctgtc tgtgtcggtc cagtgtcttt agccaagctt 120
tgattaaaga tgacttcctt gtttgctcaa gaaattcgcc tttctaaaag acatgaagaa 180
atagtatcac aaagattaat gttacttcaa caaatggaga ataaattggg tgatcaacac 240
acagaaaagg catctcaact ccaaactgtt gagactgctt ttaaaaggaa ccttagtctt 300
ttaaaggata tagaagcagc agaaaagtca ctacagacca ggattcaccc acttccacgg 360
cctgaggtgg tttctcttga actcgttact gggcatcagt agaagaatat attcccaaat 420
ngggacaagt tcttttagga agacccctta tccttttgct ggtgaaaatc aaaatgaagc 480
nnaaaatccc ttcaaaatga ggccaacgan taactttttt aaatggcttt tcaaaaagcc 540
ntgttaatta ancttnantg taaaggnttt t 571

<210> SEQ ID NO 80
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 80
acctcttcct gttcgaatgg gttatccagt aaaaaagggc gtgcccatgg caaaggaggg 60
aaatctagaa cttttaaaga ttcccaattt tctgcatttg actcctgtag caattaaaaa 120
gcactgtgaa gcccttaaag atttttgcac tgagtggcca gccgcactgg acagtgacga 180
gaaatgtgag aagcattttc caattgaaat tgacagcact gattatgttt catcaggacc 240
atctgttcgg aaccccagag cacgagtagt agtctcaaga gtaaagcttt ccagtttgaa 300
tttagatgat cacgcaaaga agaaattaat taaacttgta ggagagcgat actgcaagac 360
cacagatgtg cttaccatca aaacagatag gtgcccttta aggaggcaga attaccatta 420
tgccagtgta tctactaaca gtgttatatc atgagtcttg gaatactgaa gaatgggaaa 480
aaagttagac tgaagccgac ttggagaatn tatatgggaa aatactatca gaaagaaata 540
tctggnaacc cttttccgat gaaagtgctg anaaaatntg gaattaataa gaagn 595

<210> SEQ ID NO 81
<211> LENGTH: 601
<212> TYPE: DNA
<213> ORGANISM: Homo sapiens
<220> FEATURE:
<221> NAME/KEY: misc_feature
<222> LOCATION: (1)...(601)
<223> OTHER INFORMATION: n = A,T,C or G -continued

<400> SEQUENCE: 81

```
acgcggggga aaacaagatg gaggattcgg cctcggcctc gctgtcttct gcagccgcta     60
ctggaacctc cacctcgact ccagcggccc cgacagcacg gaagcagctg gataaagaac    120
aggttagaaa ggcagtggac gctctcttga cgcattgcaa gtccaggaaa aacaattatg    180
ggttgctttt gaatgagaat gaaagtttat ttttaatggt ggtattatgg aaaattccaa    240
gtaaagaact gagggtcaga ttgaccttgc ctcatagtat tcgatcagat tcagaagata    300
tctgtttatt tacgaaggat gaacccaatt caactcctga aaagacagaa cagttttata    360
gaaagctttt aaacaagcat ggaattaaaa ccgtttctca gattatctnc cttcaaactc    420
taaagaanga atataaatcc tatgaagccc aacttccgnc ttctgagcag ttttgaattc    480
ttncttactg atgccagaat tangcngntc ttacccttac tcattgggag acatttctat    540
caaagaaaga aagttcagta tctgtaaacc ntttgtccaa gaatttttca ggagagatca    600
a                                                                    601
```

<210> SEQ ID NO 82
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 82

```
cgaggtactt tgaatatgga gtagtttaca gctatttttt tttcttactg gtaatcttaa     60
ctaatatgat tcccttatta gagagcctct cactccccca cccccaaaaa tgtctactat    120
tcatgacagt aaccaattat tctggacaaa ttgcttcttt ttaatttgag ctatctgcca    180
tggactttct aaaatggaaa cacagcctga gtgtatctta gggagagttt gattgaaaaa    240
atccaaatca ctatccatat agatcatgga tataaagaga tacctgattt ttattaaaaa    300
gatacttttt caaatttaag agttaatctt ggaaatttgg aacaagtaaa ggggcaagta    360
aaccttttga tgaaatataa aaggactcat tgcatgaagt gactatcaaa ttctgngatg    420
tgnggcttct taaaaatatt ctcagggctt tgggggcctg ccanatggta cctgcccggc    480
ggccgtcaaa agggcgaatt ccncacactg ggggccgtac taggggggtcc caacttggac   540
ccaacctggn gnaaataang gcataantgg tccnggggga aatggtnncc gttccattnc    600
cccann                                                               606
```

<210> SEQ ID NO 83
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G

<400> SEQUENCE: 83

```
gcgtggtcgg gccgaggtac acgttcgtca tggcggctgg ccctggacct gggtaggggg     60
tccgggttca gtggtaatag cggcggagat gggggagcct ccgcttggct tctttcacac    120
gggttgcttc ggaggaatcc gccgtgcaaa tctgtccgcc cccttggcca ctgatccccc    180
gaagagcttc tgtcgccgct ctaggaatac agacattgaa gtttgggaca agatatttat    240
ctaacttctg tgtcaaaatt agcgacctgc tatggcaatg aagaaagaaa ctgaatttgt    300
```

-continued cattttcacc tgaagaaaaa tgatagacaa aaatcaaacc tgtggtgtag gacaggattc 360
tgtgccctat atgatttgct gattcacata ctcgaagaat ggtttggtgt ggaacanttg 420
gaggactatt tgaattttgc aaactatctc ttgngggttt tacaccacta atacttttaa 480
tacttcctta ctttactatc tttcttctct accttactaa taatttctta cacattatta 540
agaagaaaga tgttttgaaa gaagcctact ntcataatta tnggatggtn caagggaaac 600
anggcactnt ntg 613

<210> SEQ ID NO 84
<211> LENGTH: 605
<212> TYPE: DNA
<213> ORGANISM: Homo sapiens
<220> FEATURE:
<221> NAME/KEY: misc_feature
<222> LOCATION: (1)...(605)
<223> OTHER INFORMATION: n = A,T,C or G

<400> SEQUENCE: 84
ggtactatct gctgctggca aatggggttg ctctgggtga cagggatctg ctgacccaat 60
gctatggttt gttccagtca atgagttgag aaggctaaag ccttggttcc tatcattctt 120
catcactaca ttggaccaca cattggcatt cagggcttgg acaattcgct ttactcctgt 180
agattctggg aagtcatcat cctcctcagg caactcctct ggactaagtt ctaccaattc 240
aaagccatgt ttgaggcacc attcttgagc tttttgtcgg tttataccat cttcagacac 300
tctatcgcag accaagatca tcacctcagg taaccatgct tttgccagtg gaagccatga 360
ggagacacta tcaaggcccg atttttgtgt gctgtcaaag taaaccacaa atgcttggac 420
agattctgca atctctgcag taaccagaaa tttgttgggc accccacata gattgagtct 480
gctgaaaagt atttattatc aatggncccn ggataaaact acacattatt tggaagtact 540
ttcncaataa gaacttntgg tccaaggtat ttttggaccn aanggnctct tgaaaaaacg 600
gagga 605

<210> SEQ ID NO 85
<211> LENGTH: 603
<212> TYPE: DNA
<213> ORGANISM: Homo sapiens
<220> FEATURE:
<221> NAME/KEY: misc_feature
<222> LOCATION: (1)...(603)
<223> OTHER INFORMATION: n = A,T,C or G

<400> SEQUENCE: 85
acagggaatg aagactcgaa gaggagatgt cactttcctg gaagatgttt taaatgagat 60
tcaattaagg atgctacaga acatggcttc aattaagaca actaaagaac tcaagaaccc 120
acaagagact gcagagaggg tcgggctcgc agcactcatt attcaggact tcaaaggttt 180
actcttatct gactacaagt tcagctggga tcgtgttttc cagagtcgcg gggacacagg 240
tagagtaaac tgcanagctg cctgtctgtg acttccaagg ctaggtcata aaaggagata 300
aagcttcttc tggctgggtg ggctgcttgc tcttgaacct tcagtctatg cacgcaacat 360
gcctttccag ccttctgtgg ttgtagagtg natagaaagc aattggatca ctatngacag 420
cggggtaaaa cttgaggaag caacctccgc caggnggtac atggaggagnc cctgaannaa 480 aggaanaaaa gggcacangg gcttaatcct gtcttggaat gcttncctnt gcaatggnnc 540
atttcaatgg ccnagccaat tatgccatcc ctgcnttaan accatgggcc ttcnttgnca 600

-continued ttn 603

<210> SEQ ID NO 86
<211> LENGTH: 583
<212> TYPE: DNA
<213> ORGANISM: Homo sapiens
<220> FEATURE:
<221> NAME/KEY: misc_feature
<222> LOCATION: (1)...(583)
<223> OTHER INFORMATION: n = A,T,C or G

<400> SEQUENCE: 86
actgtaggta tttattaata atagcaatga agatgaaaga gtgatgtatc agagaggtgg 60
agataaaatc agtaaaactt agacactaaa tgatagggga aggtggagga gaggaatgag 120
cctagaaaac ttagaatata atggttctaa aattaaccaa agtaagggac acaggcatta 180
gagtaggttt tgcagagaat gaatgtttta agacacacac aggtgtctct gggacaacca 240
agaaaagtgc aacaggcaga tggattgagg agtctggcta aagataagga tttaggaact 300
gctgaattaa aattacccaa gcgtgagaag tggtgttgtg attaagagag aaaaaaaaaa 360
tggaggtctg aggaatacct ttaanggatt aatgaanang cccaaaggtg ggggggtggt 420
caggagtgac ccaaatgtag aagtcaggga ataaacttta aagtngggt gtcaaaatgc 480 naatccgaaa aaaagtnagt nccttggccg gaccccctag gcgaatccac ccctggngcc 540
gtctanggat ccacttgncc aacttgggaa nntggctnct ttt 583

<210> SEQ ID NO 87
<211> LENGTH: 332
<212> TYPE: DNA
<213> ORGANISM: Homo sapiens

<400> SEQUENCE: 87
acgcgggggc attgctagaa gccggcagga gtgactctcg gcatggagga cccatctcct 60
agcacacgtg cccactgaag tggcaccaac agaagtttgg cttgaactaa aggacatttt 120 attttttta ctttagcaca taatttgtat atttgaaaat aatatatatt attttaccta 180
ttagattctg atttgatata caaaggacta agatattttc ttcttgaaga gacttttcga 240
ttagtcctca tatatttatc tactaaaata gagtgtttac catgaacagt gtgttgcttc 300
agactattac aaagacaact ggggcaggta cc 332

<210> SEQ ID NO 88
<211> LENGTH: 592
<212> TYPE: DNA
<213> ORGANISM: Homo sapiens
<220> FEATURE:
<221> NAME/KEY: misc_feature
<222> LOCATION: (1)...(592)
<223> OTHER INFORMATION: n = A,T,C or G

<400> SEQUENCE: 88
cgaggtacgc ggggacaacc agctgactcc cgtagaggaa gacactgtgg aggccagttc 60
tggagctatt gcagcctcgg ttgcccggcc cgggacccga acccgaaaaa gttatcgtca 120
gaatgtcggg caaagaccga attgaaatct ttccctcgcg aatggcacag accatcatga 180
aggctcgttt aaagggagca cagacaggtc gaaacctcct gaagaaaaaa tctgatgcct 240
taactcttcg atttcgacag atcctaaaga agatnataga gactaaaatg ttgatgggcc 300
aagtgatgag agaagctgcc ttttcactag ctgaagccaa gttcacagca ggtgacttca 360
gcactacagg tattccaaat gtcaataaag ccccagtgaa gattcnagcn aagaaagata 420

-continued tgtacnagtg gtactttgnc ngtatttgaa cattccntga aggactgcng gttttnactg 480
cttgggttaa cccaagtggg gacnnnttgc ttaaattaaa gaggaatttt gcccaancnt 540
gggacttctg gnggaattac ttttttggaa actttttggn accttggagn aa 592

<210> SEQ ID NO 89
<211> LENGTH: 630
<212> TYPE: DNA
<213> ORGANISM: Homo sapiens
<220> FEATURE:
<221> NAME/KEY: misc_feature
<222> LOCATION: (1)...(630)
<223> OTHER INFORMATION: n = A,T,C or G

<400> SEQUENCE: 89
acgcgggggt ctttgggccg gcgcgaacca tggccggcat ggtggacttc caggatgagg 60
agcaggtcaa gtccttttg gagaacatgg aggtggagtg caactaccac tgctaccacg 120
agaaggaccc ggacggttgc tatcggctgg tggactattt ggaagggatc cggaagaatt 180
ttgatgaggc tgccaaggtg ttgaagttta actgtgaaga gaaccagcac agtgatagct 240
gctacaaact gggggcctac tatgtgactg gaaaaggtgg tctgacccaa gacctgaaag 300
ctgccccagg tgctttttga tggcgtgtga gaaacctgga aagaaatcaa tagcancatg 360
tcacaacgtt ggccttctgg cacatgatgg acagggtaat gaagatggcn acctgacttt 420
ggaaaaggca aggactacta ccaaaggcct gngatggngg ntatctttca gtgcttnaaa 480
cctaatgcat ttttcttcag gggggcccaag ctttccaagg acatggcctt gcctgtnaat 540
cttcattaaa gccttgacct ggtcatattt ggccttgcca tgcaatccat ttacttggcc 600
ggacacctan gggaatcacc actggggcgt 630

<210> SEQ ID NO 90
<211> LENGTH: 653
<212> TYPE: DNA
<213> ORGANISM: Homo sapiens
<220> FEATURE:
<221> NAME/KEY: misc_feature
<222> LOCATION: (1)...(653)
<223> OTHER INFORMATION: n = A,T,C or G

<400> SEQUENCE: 90
ggtaccactt cactccagcc tggcgacaga gtggaactcc gtctcaaaaa ataaaataaa 60
ataaaataaa gcaaaaatat aaaatgttaa aaaaaaaaca aaaaaaggga aaaaggaagc 120
tgattgcctt ggtgagtcaa cactgggtat tttctgacca ctatttgaaa caaaaaaagga 180 aaccactgat attctatgca aagatctgtt cctggaaggc actctgcgga gacaccagga 240
gaacttttat caatccttca ttgatttgaa gtaaaagtgc taaagcaatg gttggtgggt 300
ggcaacccat tagcagatca caaaatcact gtagtgggta actaaacaag aggaaacaca 360
agacggcatc ctgtgtaact ggggttaagc attactctct gaaactcatg gcatcagttt 420
cctcttaggc tcttcccaca aagtataatc atgttcattt cagtttacaa tcccttgcag 480
tcccatcgat ttgtgagaat atcccaagtc atncacagng gagnctggaa atggtcntan 540
ttgtcctgcc cggcngccgt tcnaanggcg aattcaacac actggcngcc gttctaatgg 600
atccaactcg naccaacctg gnggaacatg gctactggtt ctggngnaaa tgn 653

<210> SEQ ID NO 91
<211> LENGTH: 657
<212> TYPE: DNA

-continued

<213> ORGANISM: Homo sapiens
<220> FEATURE:
<221> NAME/KEY: misc_feature
<222> LOCATION: (1)...(657)
<223> OTHER INFORMATION: n = A,T,C or G

<400> SEQUENCE: 91

```
acttttttttt tttttttttt ttttttttg ggagaaaagc ctnactccgt tgcccacgtt     60
ggagtgcagt ggcgtggnca tagcttattg catgcagcct naacctccca ggctnaagca    120
atnctccnac ctnnncgtgc tgnnttnntg gaactacnca tncacncnat tatgcccanc    180
tngtngttgt naatttaaag tganaccatg cncncaggnn gnatggcntt nnntancnan    240
catgcatgct cagctgtgta gtgcacgcac aggataaatg gaagggggat ttgatcaggg    300
tttttgtcac atnagcattn naaatccgna ngactgccnt gtgtctgcct ttgnaagggc    360
ctgggagtat tctgtgtagc ctttgnaaat aagggnaaaa tgngcncctg ccaaagaagt    420
cnttgctact ntgggtgngt caaaatntcc ctgtaacttg tcaatggnca caagcttggn    480
ggngtntttg ggntcttggn tgtcnttttn acgtctattg nccatgtggt tcctatatga    540
cacantcctc ntnataatcc ntganaattg ctaanntgcn cttttttttt ttttnanatt    600
nattttgctn ttaaantagc ttaanncttt ntttatcctn gggcanccna anncaat       657
```

<210> SEQ ID NO 92
<211> LENGTH: 653
<212> TYPE: DNA
<213> ORGANISM: Homo sapiens
<220> FEATURE:
<221> NAME/KEY: misc_feature
<222> LOCATION: (1)...(653)
<223> OTHER INFORMATION: n = A,T,C or G

<400> SEQUENCE: 92

```
accataaaac cattaaaagc aataaataac tagagtcatg tgagatgttt caaagactgc     60
tggaggtttc tgtaaaccag ggtaatcaga aatattaccc ttgtagatag ccctctcata    120
ccagtaaata caaagagtta aaattccaat gccacagtgt aacagttaac aatctatttt    180
gtaattttaa atattactac attaattcac cctgagaata cagaggaaac atttaataca    240
agacattctg atatgntttt ttttcccatt gnatttgctt tcttctggnt ttcatcagcc    300
ctttaagggc acagatattt taatttaaag ggtgatttgg atatgctttt ttggtaactg    360
agatttatgc cacagtcaga tactggtgat agaaaagccc aaaaaggntt gnagaaaaga    420
ggcaagcagc aatccccagg cagaaaagac ngaaagtctt gaaaaagaag aggagtaaaa    480
attttttaa gctgntcaat gccctgtatt tgggnacaag tacctttatt ttcctttagc    540
tganggnant cagagtaacc gaattggnag nnnactattt tcnctggnaa ggaaaataga    600
atttggnaat cccnggaang gtnctngaaa tnnagcccca tccatttgnn gng           653
```

<210> SEQ ID NO 93
<211> LENGTH: 640
<212> TYPE: DNA
<213> ORGANISM: Homo sapiens
<220> FEATURE:
<221> NAME/KEY: misc_feature
<222> LOCATION: (1)...(640)
<223> OTHER INFORMATION: n = A,T,C or G

<400> SEQUENCE: 93

```
acagagaaac cacaggttgc cctttccaca gctggataga cttatccaaa acggcaggat     60
ggttctgtat taatcttttt ggaaagcatg tctgtattaa gattgcaaaa catacagata    120
```

-continued

```
gctaccacaa attaggtcaa acgactgatc aagttgtaac atctgtgagg tcaaattcca    180

aagtgcctag atacacattt atacaacaga ccataagagc tgaattcttt acaaatgtct    240

ttatgggcat gtaaaattga ctctgcattt ctgcatgtgt gcattccata agagagacca    300

gtctgcactg agtcatatat actccaactt gaaaaagtaa gtgnaacaac tggntaatca    360

tgcaagtctg gttgnaatat aacaatgact ggnaaaacat gaattcttcg cacagtagta    420

ataggngcac tnatttaaaa ccctnccgaa aaacctgnat ttggtgcaan atctgantt     480

aagnggtagt aacttgacnt ttaaaaatag tttgaacnat ttanaaaggn aagccaactt    540

ttacttaaaa gaatcccaag tggnaaaanc tggntttcaa tggaatgaac tnggtgngac    600

ctnccctaat nngaccttga gcctatnagc taatntangg                          640
```

<210> SEQ ID NO 94
<211> LENGTH: 658
<212> TYPE: DNA
<213> ORGANISM: Homo sapiens
<220> FEATURE:
<221> NAME/KEY: misc_feature
<222> LOCATION: (1)...(658)
<223> OTHER INFORMATION: n = A,T,C or G

<400> SEQUENCE: 94

```
acgcgggcca agcttttttt ttaatttggt gttttctccc atcctttccc tttaaccctc     60

agtatcaagc acaaaaattg atggactgat aaaagaacta tcttagaact cagaagaaga    120

aagaatcaaa ttcataggat aagtcaatac cttaatggtg gtagagcctt tacctgtagc    180

ttgaaagggg aaagattgga ggtaagagag aaaatgaaag aacacctctg ggtccttctg    240

tccagttttc aagcactagt cttactcagc tatccattat agttttgccc ttaagaaagt    300

catgattaac ttatgaaaaa attatttggg gacaggaatg tgataccttc cttggntttt    360

ttttgcaanc ctcaaatcct aacttcctgc cccacaatgg tgagcaggtt cccctgatac    420

ttcttttctt taatgattta actatnaact tgnataaata acttataggg gatagggaaa    480

attcctgaat tccagaatgc catctgntaa aaaagaatnn aaatgggaag tnggactnaa    540

aaggagccaa cagcatgctg cggtggnngn cacttctttg cnctatccca ggaaggaagg    600

tccccatttg gaaaggggtt cttnctcact ggnaccggtt tgacntnatt ggnacncc      658
```

<210> SEQ ID NO 95
<211> LENGTH: 392
<212> TYPE: DNA
<213> ORGANISM: Homo sapiens
<220> FEATURE:
<221> NAME/KEY: misc_feature
<222> LOCATION: (1)...(392)
<223> OTHER INFORMATION: n = A,T,C or G

<400> SEQUENCE: 95

```
actcagactt gatcgattaa tgaagtggtt attttggcct ttgcttgata ttatcaactc     60

actggtaaca acagtattca tgctcatcgt atctgtgttg gcactgatac cagaaaccac    120

aacattgaca gttggtggag gggtgtttgc acttgtgaca gcagtatgct gtcttgccga    180

cggggccctt atttaccgga agcttctgtt caatcccagc ggtccttacc agaaaaagcc    240

tgtgcatgaa aaaaaaagaa gttttgtaat tttatattac ttnttaagtt tgatactaag    300

tattaaacat atttctgnat tcttccaaaa aaaanaaant aatnaantta naancttttta   360

aanatanaaa taaaataata angaccattg ag                                  392
```

-continued

<210> SEQ ID NO 96
<211> LENGTH: 655
<212> TYPE: DNA
<213> ORGANISM: Homo sapiens
<220> FEATURE:
<221> NAME/KEY: misc_feature
<222> LOCATION: (1)...(655)
<223> OTHER INFORMATION: n = A,T,C or G

<400> SEQUENCE: 96
ggtacaggtt tttatgtgaa catacatttt cattttctgg gataaatgct caaaagggca 60
actgttgggt tgtatggtaa acacatatat ttttgtaaga aactacccta ctctttttcc 120
agagtggctc tactttttac atacagccac tcatacaatt cagacagcaa tgtatgattg 180
atccagtttc ttcacatcct caccagcatt tggtattact actatttttt atcttaacca 240
ttcacataga tgtgtgtaat gataccacat gtggttttaa tttgcatttc caatggctaa 300
tgatgttgag tatctttttg tgtgctaatt tgccatctat gtatcctctt cggtgaaatg 360
tcttcatgtc ttttgnctat tttctattta agncatttgg tctttttact attgagtttg 420
agagggtttt tatatatcct agataaaaat cctctggtan anatgtgggt gcctggaatt 480
ttaacataac ttctacccan ggaaaataag taaaatttcc acccttgctg gcnagcctta 540
cttaatnccg gccttaangg tccttctaga gaattaagaa gatttgaggt ttaaatanaa 600
tcagggcntt aaaaagtaat cctaaaatcn ggtttaagca agccatatcc tgggg 655

<210> SEQ ID NO 97
<211> LENGTH: 224
<212> TYPE: DNA
<213> ORGANISM: Homo sapiens

<400> SEQUENCE: 97
acaagtttaa ggtaggacgc agcattttat agtgttacgt ccttcctccc cacattcctg 60
tgaggcggaa caagaacaat tacttgaccc tggaggaaga cgacgccttg tggtcaggga 120
gagaacagca gttcatgctg gctgcctcgt ctttccaggc ctgctgctgc ccaggcttct 180
actgaccttg ttaggtctga ttctagaaaa tgaaggcagg tacc 224

<210> SEQ ID NO 98
<211> LENGTH: 582
<212> TYPE: DNA
<213> ORGANISM: Homo sapiens
<220> FEATURE:
<221> NAME/KEY: misc_feature
<222> LOCATION: (1)...(582)
<223> OTHER INFORMATION: n = A,T,C or G

<400> SEQUENCE: 98
ggtaccacca tgcctggttt attgttttat ttttttggca gagatgggtc tcactgtgtt 60
gcccaggctg atctcaaact cctggcctca agcgatcctc ccatctcagc ctcccaaagt 120
gctgggatta cagacctgag ccaccacacc tgggcaacag agtgaaacct gtccctgttt 180
tcctgctctt actctcacct ctgaggcctc ctctgcctgg aagagattac agggaaattc 240
caggcagccc ttgtcaattg tttttatgaa ttctttacct gttcctttta aagacaagga 300
aactgaggcc caaagttcta agttgtttgg caaatggagt ctcctaccct cagctcctgc 360
aaggacctgg gggaccccca ggtccagcag ccacatgatt ctgcacagac agggacctag 420
agcacatctg gatttaagcc caccctggca actggctgct agagactncc aagatgccga 480
taataggatc tgccnttaaa aaatctggat tctggcctgc ntaantgcta cttcatttgg 540

-continued

```
ctacaaagnt ttaaggngga accnttaaaa ccttccccaa aa                        582


<210> SEQ ID NO 99
<211> LENGTH: 619
<212> TYPE: DNA
<213> ORGANISM: Homo sapiens
<220> FEATURE:
<221> NAME/KEY: misc_feature
<222> LOCATION: (1)...(619)
<223> OTHER INFORMATION: n = A,T,C or G

<400> SEQUENCE: 99

ggtacagtgg tccttttcag agttggactt ctagactcac ctgttctcac tccctgtttt      60

aattcaaccc agccatgcaa tgccaaataa tagaattgct ccctaccagc tgaacaggga     120

ggagtctgtg cagtttctga cacttgttgt tgaacatggc taaatacaat gggtatcgct     180

gagactaagt tgtagaaatt aacaaatgtg ctgcttggtt aaaatggcta cactcatctg     240

actcattctt tattctattt tagttggttt gtatcttgcc taaggtgcgt agtccaactc     300

ttggtattac cctcctaata gtcatactag tagtcatact ccctggtgta gtgtattctc     360

taaaagcttt aaatgtctgc atgcagccag ccatcaaata gtgaatggtc tctctttggc     420

tggaattaca aaactcagag aaaatgtgcc catcangaga acatcataac ccatggaagg     480

atnaaagccc caaatggngg naactgataa tagccctaat ggctttaaga atttgggcac     540

actnttacct aggngaaccc atttganccn angggggctta aaggcttntt acttcaactg     600

aaagttnagg gaaaaaaan                                                  619


<210> SEQ ID NO 100
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 100

acgcggggga agcaaaggag agggaagctg gaagcacctt tggcccggga cagaaatctg      60

gagagcttgg ctacctccat cctcctcagg ccggagcagg cttcctgaga gagtccaggt     120

cgtaggagtt ttacgactta gaaaagcggg ctgcagattc cttcctgggt gtttggttca     180

agccctggct ccagcctcac tctcagtctt cccgggagtt cgtgggattt ggaccttaga     240

ttattagtat tattttgagg gcctcctgtg tgtaagcact ggttgtgcgc agatggctgt     300

gcagagggcc atgaggtaga ggctggggaa atgagggctt ggaggtgctt gaggtatggt     360

ctttacctac gtgaaatgtt ggaggttgag atgaaaactc ttgctttgaa atcttcatgg     420

aggactacat catttcaatc ctgaatctgg ctcaattcta ttaatcactt aatacctgga     480

ttaaaaaacg nttaantggg ccaggcncaa tgggtcacgc ctgnaatccc agccntttgg     540

gaggccaagg cangccggat acnttagggc ngnanttnaa accancttgg caaattggga     600

aacccgcntt tntn                                                       614


<210> SEQ ID NO 101
<211> LENGTH: 625
<212> TYPE: DNA
<213> ORGANISM: Homo sapiens
<220> FEATURE:
<221> NAME/KEY: misc_feature
<222> LOCATION: (1)...(625)
```

-continued

<223> OTHER INFORMATION: n = A,T,C or G

<400> SEQUENCE: 101

```
ggtactttgc ctacggcagc aacctgctga cagagaggat ccacctccga aacccctcgg     60
cggcgttctt ctgtgtggcc cgcctgcagg caagaagggg ttaaaagtgg aatgtatgtt    120
gtaatagaag ttaaagttgc gactcaagaa ggaaaagaaa taacctgtcg aagttatctg    180
atgacaaatt acgaaagtgc tcccnnatcc ccacagtata aaaagattat ttgcatgggt    240
gcaaaagaaa atggtttgcc gntggagtat caagagaagt taaaagcaat agaaccaaat    300
gactatacag gaaaggtctc agaagaaatt gaaagacatc atcaaaaagg ggnaaacaca    360
aactctttag aaccatancn gaatatatct taagggtatt cctatgtgcc taatataata    420
tatttttaac acttgagaac cagggatttt gggggattct ccaacgtttg ttcaatttta    480
agaantggtt tgaaggagtt ttttacttgg gtnattcntg gttttaggat tttnnanngn    540
aanntggntt nggngtttgn nnttttaann gggntntttt ngggtcttna aatttttcca    600
anaaaanngtn gnttccttcc cggnn                                          625
```

<210> SEQ ID NO 102
<211> LENGTH: 605
<212> TYPE: DNA
<213> ORGANISM: Homo sapiens
<220> FEATURE:
<221> NAME/KEY: misc_feature
<222> LOCATION: (1)...(605)
<223> OTHER INFORMATION: n = A,T,C or G

<400> SEQUENCE: 102

```
ggtacaagaa agaaaaaata taaaaacaag tctgctgagt gtcgggagtt ggtgagggat     60
atcctaccat attgtgacgg agtccaaata gaaaacatgc agcaacagtt ctcctgcttt    120
atcagctccc tggaaaataa accagtaacc ctggtagtgc agtaaccatt tggttaacag    180
gacaaacttc ctgatggaca cagatagtaa ttcactgcat ttcccttctc taacttctct    240
cttcacacca attcctttc tttcctttaa gatgggtttc atcctgttga caaaagattt    300
ggttttattt gtaaagtaaa gcagataata tcctgattga agtattcaat gatttaattg    360
aggatgcttg gggatcaaac tttgtaaaaa ggtcaattaa gctagttagc agagactatc    420
agtggcttgc agaaaaaaaa ntcngatata tggtttggta aaangcccaa aggataaccg    480
ngaaaaatcc tanggatacc gggacctaat taatcaaagc canaggggga ccttggttaa    540
anccnttact tnggggangg gctnaanggn ggntccaaac naaattggtt cccaacgggc    600
ccggg                                                                 605
```

<210> SEQ ID NO 103
<211> LENGTH: 251
<212> TYPE: DNA
<213> ORGANISM: Homo sapiens

<400> SEQUENCE: 103

```
acgcgggatt ttacattcca tcttttctga agattgtcct acaatttgga ttttgatcat     60
gacaaagaag attaaaattt cattagcatg aatgcaattt gttaaagcag actgatttgt    120
ttctaagata tttttggttt ttttaaaact gataataatg ctgaattatc ttaagtgaga    180
tgttaagccc actttgttct tttaatgtaa tggagcttat gggtagaaga ccatgtctac    240
taattacaaa a                                                          251
```

-continued

<210> SEQ ID NO 104
<211> LENGTH: 293
<212> TYPE: DNA
<213> ORGANISM: Homo sapiens
<220> FEATURE:
<221> NAME/KEY: misc_feature
<222> LOCATION: (1)...(293)
<223> OTHER INFORMATION: n = A,T,C or G

<400> SEQUENCE: 104
ttaatcttgc acaaatggca ttttattaaa gaaaatctaa tttacaaagc tttgtaaatt 60
ttaagaaaaa cattcataga tcataaacaa aaatttcaat atgcaatatt caaatttaca 120
agaaaataag cacaaacttt tagacagtgc agttattgct gcactccttt aattccttat 180
ccagagccca aaaaatgtag acaaacccta aaaatgtagc agaagcattt ccgcacactg 240
gtgtccagaa tctagtttgt gcanaaatgt ttccactaga tttatagagt acc 293

<210> SEQ ID NO 105
<211> LENGTH: 586
<212> TYPE: DNA
<213> ORGANISM: Homo sapiens
<220> FEATURE:
<221> NAME/KEY: misc_feature
<222> LOCATION: (1)...(586)
<223> OTHER INFORMATION: n = A,T,C or G

<400> SEQUENCE: 105
acatcatttc tgccatgtgg gacattttct tgggaatata caagtaatac tccatgtagc 60
ctgacaggtc ctcaatggtc acatcatcca cgaagactcg agcttgctca gaacaggatc 120
ggggagagcc agacagagtt ctggcgtgca gcgactgaga gtagtcctca agtgtggatc 180
ttcgttctgg agccaaggga gggacactct gcgggcctga aaaggaatac acttccatat 240
catgccatct cttacactgg cattccttgc ctatgcatgt gcatggcttg ccctggttta 300
gcttggaaac tgattgaaag tcagagagat cactggcttt gagacttgct tgggggactt 360
gggtagccgt cagaggagtc ttccttctta ctctctgatg ggagccttgg aacagaaagt 420
tctcaaangc tnaacgactg gccctggggt gaatagcatc gagagaagta naccttcttc 480
ctgnactgaa ctnttaaggg gatgaaattc ccagccaatg gtggccttan gnnangcaan 540
ntggcttttg gcttgaatta ctggntggaa aaaacctttg gccntt 586

<210> SEQ ID NO 106
<211> LENGTH: 644
<212> TYPE: DNA
<213> ORGANISM: Homo sapiens
<220> FEATURE:
<221> NAME/KEY: misc_feature
<222> LOCATION: (1)...(644)
<223> OTHER INFORMATION: n = A,T,C or G

<400> SEQUENCE: 106
ggtacnttga ttgctcanat ataangaaat ggcccaatga acgtggntgn gggaggggaa 60
anangaaaca gagctagnca tatgtgaatt gntctgtgnn ataaacatgt taaaacanac 120
aaanatggnt atttttcttt ncctccggac agtgcacatt atcatntgaa ctacctgggg 180
attctntatc anaactggtc ttgttgaata tttatactta attgaaataa ttccttanng 240
gaggcntgtt taaaacgtat taacaggana ttgtgtntna nacatttaat gaaanacgaa 300
attccacnag aatganntaa gtcactttcc aagtgggtgt cattttgtta aaccctngtt 360
tacctgtttt gctattntta ccntttcatt tggaangatg ntttgagntc gtanttacca 420

-continued

```
gggnaaagac gggttncttc ctngctgnnn cttnagccnn tgctaaaaag cnttaatttt    480

ntgcnattng gnncttcctg ctggtaatcn tggaaaaant gggnnaantc cagctttntt    540

tnttggcngc ccaaaaangg attcnnantn gnnannnaac ctttggttcc ntaannaana    600

aaangtatnc anaangaacc ttgncatgcc ngccnntnta aang                     644
```

```
<210> SEQ ID NO 107
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 107

ggtacagact tgccctttga aatctatacc tctggataca ttagaggcat tttattaaca     60

aaggcccttc taaatgtgct atttatttga caataactat cagatttgcc ttaattttgt    120

gtttatagca tttatcaaaa cgtatcctca tagactttat gcagattaat atggtcaatt    180

gatttggata aaagaaagta atttcagggt ttgtttttaa gccaggacaa gaagtgcaaa    240

tgcctctttg aagcaattta ggctaaactg attttgaaat ttcaaaatgt tttattttac    300

tttgttttat taagccagga caagaagtgc aaatgccctc ttttgaagca attcaggcta    360

ggtaaacccg attttggcca tttcaaaacc gtttaattta ctttggttta atatcagagt    420

cttataaaac tgntgncaaa aatttctgaa ggctttngaa aagggttggt agtggaccct    480

gcccgggcgg ccgntcnaag gcgaattcag ccactggcgg ncgtactagg gatnccactc    540

ggacccanct tggcggaatc atgggcataa ctggttcctg ngtgaaatgg gatccgttac    600

aattcccaca acatanng                                                  618
```

```
<210> SEQ ID NO 108
<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 108

ggtaccaaag gagaatttgg agagctggct aaattatttg aagaaagaat tgccaacagt     60

ggtgttcaga gcctcaacaa aaccaaagga taaagggaag ataaccaagc gtgtgaaggc    120

aaagaagaat gctgctccat tcagaagtga agtctgcttt gggaaagagg gcctttggaa    180

acttcttgga ggttttcagg aaacttgcag caaagccatt cgggttggag taattggttt    240

cccaaatgtg gggaaaagca gcattatcaa tagcttaaaa caagaacaga tgtgtaatgt    300

tggtgtatcc atggggctta caaggagcat gcaagttgtc ccctttggac aaacagatca    360

caatcataga tagccccgac cttcatcgaa tctncactta attccttctt tgngccttgn    420

ttttgcnaag ttcanccaag gttttgaagt antaaaancc gatggaagct tgccantgcc    480

atcctttcca agcttgatgc ttgacaggta gtancttgnc cgggccggcc gttcnaaagg    540

gcgaattcaa cacactggcn gccgtactat ggatccgagc ttggnccaaa cttgcgtaat    600

catggcatnc tggttcctgg                                                620
```

```
<210> SEQ ID NO 109
<211> LENGTH: 317
```

-continued

<212> TYPE: DNA
<213> ORGANISM: Homo sapiens
<220> FEATURE:
<221> NAME/KEY: misc_feature
<222> LOCATION: (1)...(317)
<223> OTHER INFORMATION: n = A,T,C or G

<400> SEQUENCE: 109
tttgtatttt tagtagaggc agtgtttcac cgtgttagcc aggatggtct cgatctcctg 60
acctcgtgat ccacccacct cgacctccca aagtgctggg attacaggcg tgagccacca 120
cgcccggcct cttttttttt tagctgccaa tctttttgaa ggaatattct tacctctact 180
ttgtcacctt ctactggctc cttaactaaa atctgccatt tggctctctg gttaacagtc 240
ccttcctgta aagtctaaaa tcttaattct aaatccacag tttaattcac aagctagtac 300
cttggccgng accacgc 317

<210> SEQ ID NO 110
<211> LENGTH: 603
<212> TYPE: DNA
<213> ORGANISM: Homo sapiens
<220> FEATURE:
<221> NAME/KEY: misc_feature
<222> LOCATION: (1)...(603)
<223> OTHER INFORMATION: n = A,T,C or G

<400> SEQUENCE: 110
ggtacattca ggatccctcg gccaaggact ggaccagaag aacacttggg aatcttgggt 60
ccacttatca aaggtgaagt tggtgatatc ctgactgtgg tattcaagaa taatgccagc 120
cgcccctact ctgtgcatgc tcatggagtg ctagaatcta ctactgtctg gccactggct 180
gctgagcctg gtgaggtggt cacttatcag tggaacatcc cagagaggtc tggccctggg 240
cccaatgact ctgcttgtgt ttcctggatc tattattctg cagtggatcc catcaaggac 300
atgtatagtg gcctggtggg gcccttggct atctgccaaa agggcatcct ggaaccccat 360
ggaagaccga gtgacctgga tcnggaattt gcattggtgg tcctgaattt tgatgaaaat 420
aancctggna tttggaagga aatgtgcaac catgggtcca agaatccagc cnnattaacc 480
taccggatga acctttnttg gaaaccataa aatgcctgca atcaatggga actttttcca 540
accttanggg cttaccatga ccttgcccgg ccggccnttt aaanggccaa ttccaccccc 600
tgg 603

<210> SEQ ID NO 111
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 111
acatttaagt tcccatgtta cagaatccca tattgtgact atttcctcaa aactaactgc 60
tagtaaagaa ccatcttcgg agaaacaaca gttagttgct tgatacttgt gataactacc 120
aacaaagtca caggtccagc caacagcttt tttgtatatg tcagagtcat ctgttaatat 180
ccatactttg aagtaaccat ctttgctagc tgtaaccaag gtgggctgtt cagatttttc 240
tgcattacag aaacagagag ctgtaatgca gtcttcgtgt ggcatgttaa ttttagtgtt 300
aagaataaac ccttgtgttt tcttattata catccacagt ttcatttgca attcaagctc 360

-continued

```
aagtttcctt ttcttgccgc tggtccactg gtgcaagcca gttaccaaag cagccaatgc    420

aagccttggt aagtcaattt ggatcaganc ataatcanta atatatcctg ctggataata    480

ctaaattgga tactggntat cactntggag agaataaact gcaggtggcn ggntttcatt    540

caaaccaagc tttagtcttg gacaatcatn aaccagngaa atactcctat ntttn         595
```

<210> SEQ ID NO 112
<211> LENGTH: 523
<212> TYPE: DNA
<213> ORGANISM: Homo sapiens
<220> FEATURE:
<221> NAME/KEY: misc_feature
<222> LOCATION: (1)...(523)
<223> OTHER INFORMATION: n = A,T,C or G

<400> SEQUENCE: 112

```
acaagagcta ttagagatgc tgccatatgg atgggcaaaa ctgagccaat cccacttagg     60

aatggaaggc ttggacatgg aagggaggat ataaacgagg agttggagaa aaacgcaagc    120

ccagtttttg ctagagtgga aatgaaagtg ggaatgaggg tcttgttttt agtcctctaa    180

ggaccaggaa gcaattttaa aacttccttg gtttttctga aagcagcata ttcaaaatgc    240

cagcaaaaac tcctaacaac tgcaaaacca aaagaggatc aaagctcacc aacatccctt    300

cttattgctg aaaggctcta aaattcagga tgccctgttc ccttgtaaaa gggaaaataa    360

ttaaagtctg atttatggta atcataccac atcacacttc taaaaaaata tttcaagtgt    420

gtgaccaggg gaccgtttga ccnccatttt attaaccttc actttantgg gaaaaataaa    480

accttttcca gggccatttn atnccaggac ttttagtagg ggg                      523
```

<210> SEQ ID NO 113
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 113

```
acagtgtaaa taactaagtt gttaactgtc aagtccagtt atgtattctg taagttgtgt     60

tctagtcttt gactaaaatt tatcatctct tataatggga cttaatcttt ctctaaaagc    120

atataagagc ttgtcaatag agcaatcaat caaaaagatt ttgtgattca taacattgaa    180

gttagtctgg ttaagagttt tggtttagac ttcatttata ttttccttac taatatctaa    240

tatttaatga ataatgatca attttttata aagttattaa tatgatcagg gaaacctttg    300

ggacttctga caggcatctg gtgaagagac aattcaagcc ttagtgacta tttagaatag    360

ccagtgatca ctagctaatt ctcatatcca tgcctttttt gccctggtta cagtcttaaa    420

agaggtaaaa cagcaaatat ttttttaag ggaactataa ccctangaat tcctgaaaag     480

aatttcaaaa aaaataagac cctgtggcca tggngnccaa acntaagacc tactatggct    540

atattggtcc attaaaaata aattactact aatccaaa                            578
```

<210> SEQ ID NO 114
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G -continued

<400> SEQUENCE: 114
acggtagtaa gaaacctttg agatctttct gacttttcaa aattagagaa agcaaatggg 60
atggatagat tttttttttc ttttcaaggg gggcaggaag gtaatggttt gagtagcctt 120
tgtttaaaaa aaaactaaat atatttaaaa ggccacattt atattttttt cacaagaacc 180
acataataaa ttccacttct tgacctgaat ttggaaatcc gaaattacta atccaggcca 240
ggtgtggtgg ctcatgcctg taatcccagc actttgagag gccgaggtgg gcagatcact 300
tgaggcctgg agttcaagac caccttggcg aacacggtga aaccccgtct ctacgaaaaa 360
aaaaanatat aaaaaaagta ctggttatta accaaccagc ttagaaaaat aatcatggtn 420
gacacnttan ttcattcttc taaaagcctg ttgatctggg ccttcctgtt gccagcattt 480
cccctttttc aaaaatgggg ggccttttct ttaattnnac ctcgtggngn aananaattt 540
gaagggcccc aggaagttnt ttgggcnctt tgaagcgttt tncacncgtn tagattctnt 600
gattaaatcc tcc 613

<210> SEQ ID NO 115
<211> LENGTH: 190
<212> TYPE: DNA
<213> ORGANISM: Homo sapiens

<400> SEQUENCE: 115
ggtacattgc cactgagtaa agagtggcac cagccacggt ggtaggtgga agaaacatag 60
atcccaatga ggacacaaag acgagaccca ggcccactcc caggggtgca cccatgttca 120
gaaacttttc actgggcgca cacatggcca cagtggagag gcctcccaca atgccagctg 180
tgtacttttt 190

<210> SEQ ID NO 116
<211> LENGTH: 610
<212> TYPE: DNA
<213> ORGANISM: Homo sapiens
<220> FEATURE:
<221> NAME/KEY: misc_feature
<222> LOCATION: (1)...(610)
<223> OTHER INFORMATION: n = A,T,C or G

<400> SEQUENCE: 116
ggtactcttg gtttatcaat gggacgttcc agcaatccac acaagagctc tttatcccca 60
acatcactgt gaataatagc ggatcctata tgtgccaagc ccataactca gccactggcc 120
tcaataggac cacagtcacg atgatcacag tctctggaag tgctcctgtc ctctcagctg 180
tggccaccgt cggcatcacg attggagtgc tggccagggt ggctctgata tagcagccct 240
ggtgtatttt cgatatttca ggaagactgg cagattggac cagaccctga attcttctag 300
ctcctncaat cccattttat cccatggaac cactaaaaac aaggtctgct ctgctcctga 360
gccctatatg ctggagatgg acaactcaat gaaaatttaa agggaaaacc cttangcctg 420
aaggtgtgtg ccacttcaga gactttacct taacttgaga cngntcaaac ttgcaaacca 480
tggngnggaa atttgccgaa ctttacactt tgggcaggtt ttttcccaga agtcanaaca 540
agaactcctn ntcttganaa gggttttanc ccctttnaat ggccttgctt atgctgcctt 600
tttcgtttgg 610

<210> SEQ ID NO 117
<211> LENGTH: 608
<212> TYPE: DNA

-continued

<213> ORGANISM: Homo sapiens
<220> FEATURE:
<221> NAME/KEY: misc_feature
<222> LOCATION: (1)...(608)
<223> OTHER INFORMATION: n = A,T,C or G

<400> SEQUENCE: 117
ggtacgcggg gggtattatt tgtgccaacc aatgatgctt ttaagggaat gactagtgaa 60
gaaaaagaaa ttctgatacg ggacaaaaat gctcttcaaa acatcattct ttatcacctg 120
acaccaggag ttttcattgg aaaaggattt gaacctggtg ttactaacat tttaaagacc 180
acacaaggaa gcaaaatctt tctgaaagaa gtaaatgata cacttctggt gaatgaattg 240
aaatcaaaag aatctgacat catgacaaca aatggtgtaa ttcatgttgt agataaactc 300
ctctatccag cagacacacc tgttggaaat gatcaactgc tggaaatact taataaatta 360
atcaaatcat ccaaattaag tttgttcgtg gtagcacctt caaagaaaat ccccgtgact 420
gctatagacc cacactaacc aaaggtcaaa attgaaaggt gacctgaatt cagactggat 480
taaagaaagg tgaaaccatt actgaaagtg gatncatggg gaagccattt tttaaaaaat 540
nccccaaanc attgatggga attccttnng gaaatacttg aaaggaaccn nnnnagacca 600 atcnttcc 608

<210> SEQ ID NO 118
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 118
actccactta gcaaatgccc tgccagcaaa gtcacagatg actttttttac ccaatcttag 60 gtaaatctgg attatctgcc caaccgtgca agtcaataag ccacccttga aaactgtgtc 120
aagatttgag gaaacaggtc ttaagaacct atccaacaca tgattccata accaatacat 180
cttangttgt tttaggcaaa taggtgtatc tcttgaatca ctgatggatt caatatcaag 240
atctataatt ttcacgttta aaatttactc tgccgaggac attttattgg taaagcataa 300
accagttagt ttgacagaca cnaaaaagaa aacnaaatgt tcacagtcct atcttcgtag 360
ggattcttgg ctataaaaat tggcttcagg ttcaaggtct tagaccactc ttctaaggct 420
nctactggat atantantta ccacttgggg nccaaactta aaacctcntg gactttttcc 480
ccttanggac nangaaaaac caaggggttg tggtttgaac tccntacact tggngnnaaa 540 nctttttcttg gnngnatnta aanattaagg ggcttttn 578

<210> SEQ ID NO 119
<211> LENGTH: 584
<212> TYPE: DNA
<213> ORGANISM: Homo sapiens
<220> FEATURE:
<221> NAME/KEY: misc_feature
<222> LOCATION: (1)...(584)
<223> OTHER INFORMATION: n = A,T,C or G

<400> SEQUENCE: 119
actgtcttag aatattattt atttttttgt atttgtaaat ctgtggacaa aagagggttt 60
cctcactcct tttactcact gggctcatga cagtgaagga gatgctccat ctgcttctcc 120
ccctttctct tgctgtagtc caatgtgcta tgagcatcag cttactttgc cacttagagc 180

-continued aagcaaaacc cagtgcaaga gtctcgttca gctctaaata ggtttgcttt cttttagtta 240
cagtgcccat tttgaaattg cctatacagt cttagtgacc atttaaaccg gacgaactan 300
gcgtttaatt ttcacttctt catgttnaat tngcagttca anatttatag naagatggnt 360
atttcgaaaa nacaaaaaan tggnttttta anaaaanaag tncnttggtc ggcgaancan 420
gcntaagggg cgaatttcca gcncaactgg gcnggcccgt nncntagngg atccccaacc 480
tttggtaccc angcttnggc nntaancaat tggnccanag nttgtttccc tggggtgaaa 540
antngtnatc ccgttcccaa ttcccnnaca ncnnaccnng cccg 584

<210> SEQ ID NO 120
<211> LENGTH: 587
<212> TYPE: DNA
<213> ORGANISM: Homo sapiens
<220> FEATURE:
<221> NAME/KEY: misc_feature
<222> LOCATION: (1)...(587)
<223> OTHER INFORMATION: n = A,T,C or G

<400> SEQUENCE: 120
acgcgggggc cgtagcagcc gccgcccatc cctctttgtg tgctttggaa agccgcggag 60
ctggtggtgg ctacagttgg tgttgggggc ttaggcgagg gacgttaccg ggaagttgca 120
ggcgggagga ctcttcccca tccagtcacc tgacaggtca caaacatgtc agacaaaagt 180
gaattaaagg ctgagttgga acgtaagaag cagcgactgg cccaaatcag agaggaaaag 240
aagagaaaag aagangaagg gaaaaaaaaa gaaacagacc anaataagga agctgttgct 300
cctgtgcaag aagaatcaga tctttgaaaa aaaaaggaga gaagctnaaa gcatttgctt 360
caaagcatgg ggctaacttc agaaatcccc ccattggncc ttcctnctaa tncttncatn 420
ccttcaaaat ctgtggagcc ctttccaagg tgaaacttgn aannccaaga antntggaaa 480
atggcnccct tggggaatct agaccnaggg nccttttttna accttggaat ngnttaaaaa 540
tcacnccaag nttgactttt ccttccttcg anaaaattgg gtcccnn 587

<210> SEQ ID NO 121
<211> LENGTH: 570
<212> TYPE: DNA
<213> ORGANISM: Homo sapiens
<220> FEATURE:
<221> NAME/KEY: misc_feature
<222> LOCATION: (1)...(570)
<223> OTHER INFORMATION: n = A,T,C or G

<400> SEQUENCE: 121
ggtactcttg gtttatcaat gggacgttcc agcaatccac acaagagctc tttatcccca 60
acatcactgt gaataatagc ggatcctata tgtgccaagc ccataactca gccactggcc 120
tcaataggac cacagtcacg atgatcacag tctctggaag tgctcctgtc ctctcagctg 180
tggccaccgt cggcatcacg attggagtgc tggccagggt ggctctgata tagcagccct 240
ggtgtatttt cgatatttca ggaagactgg cagattggac cagaccctga attcttctag 300
ctcctncaat cccattttat cccatggaac cactaanaac aaggtctgct ctgcttctga 360
agncctatat gctggagatg gacaacttaa tgaaanattt aaanggggaa aacccttaag 420
ccttgaggtg tgtgnccact tcanaggact ttaaccttaa ctttgagacc aggtcaacct 480
ggnaanccct tggtggagaa attggccgaa cttcccnact ttggccaggn ttttcccang 540
antgtcaaan caagacttcc ttatcatgnn 570

-continued

<210> SEQ ID NO 122
<211> LENGTH: 551
<212> TYPE: DNA
<213> ORGANISM: Homo sapiens
<220> FEATURE:
<221> NAME/KEY: misc_feature
<222> LOCATION: (1)...(551)
<223> OTHER INFORMATION: n = A,T,C or G

<400> SEQUENCE: 122

```
actatctcta ttcaggatta tgaagttttt cgatgcgaag attcactgga tgaaagaaag     60

ataaaagggg tcattgagct caggaagagc ttactgtctg ccttgagaac ttatgaacca    120

tatggatccc tggttcaaca aatacgaatt ctgctgctgg gtccaattgg agctgggaag    180

tccagctttt tcaactcagt gaggtctgtt ttccaagggc atgtaacgca tcaggctttg    240

gtgggcacta atacaactgg gatatctgag aagtatagga catactctat tagagacggn    300

aaagatggca aatacctgcc cgtttattct gtgtgactca ctggggctga gtgagaaaga    360

aggcggnctg tgcagggatg acatattcta tatctttgac ggtaaccatt cgtgatagat    420

nccagtttaa ttcccatgga atcaaatcaa attaaatcat catgactacc ttggttcccc    480

atcggttgaa gggacngnat tcattggggn ggcattggat ttgatnncna gntttattca    540

atactttctc n                                                         551
```

<210> SEQ ID NO 123
<211> LENGTH: 575
<212> TYPE: DNA
<213> ORGANISM: Homo sapiens
<220> FEATURE:
<221> NAME/KEY: misc_feature
<222> LOCATION: (1)...(575)
<223> OTHER INFORMATION: n = A,T,C or G

<400> SEQUENCE: 123

```
acttaataca tattttcaaa cctgtttgca tttcaaacaa agttagcgtt tttgtaaatc     60

aaatttgata acccgactaa aaatattttc cagctttatt atttaaggag ctgcacagcc    120

tttaaagtgg ggaccaggag gcaggcagag gcagagagac tgaatgcacc caggactgcg    180

cagcagtcta cagcaacatg tcccacaact ttggtgctgg aaacacaagt aatgcacaag    240

acagctgccc tccagtgtca ggatcctgtg aaacagcata tcaaaagatc gccagcttct    300

tataatttac acactttcat ttaggattgc ttttttgaag aaaaatcttt aagaatgcca    360

tttttaattt aatatccaga accctggaat ttaaaaaaac ctaatngaaa ggaaattaac    420

tggtaccatc aaaaatgggg ntgntggttg gancntgtgt gaagttaggg aattctatgg    480

cttttttta a gatgccccgg aaaatttaac cccttaatng cangtttaat ttngaattcn    540

cnccaggtan tgtatgtnng gctcanatta gtanc                               575
```

<210> SEQ ID NO 124
<211> LENGTH: 570
<212> TYPE: DNA
<213> ORGANISM: Homo sapiens
<220> FEATURE:
<221> NAME/KEY: misc_feature
<222> LOCATION: (1)...(570)
<223> OTHER INFORMATION: n = A,T,C or G

<400> SEQUENCE: 124

```
actgagacaa tggttagggt tgttttctta attcttttcc tggtagggca acaagaacca     60

tttccaatct agaggaaagc tccccagcat tgcttgctcc tgggcaaaca ttgctcttga    120
```

-continued

```
gttaagtgac ctaattcccc tgggagacat acgcatcaac tgtggaggtc cgaggggatg    180

agaagggata cccaccacct ttcaagggtc acaagctcac tctctgacaa gtcataatag    240

ggacactgct tctatccctc caatggagag attctggnaa cctttgaaca gcccagagct    300

tgcaanctag ccttacccaa aangactgga aangagacat atctntcaag ctttttttcag    360

gaangcgtnc ctgggaatcc aaggaacttt ttgatgctaa ttanaaangc ttgggactta    420

aaaatgtccn ctanggngtg gcacttttac angtttttgg aangcttnga aggcaganng    480

gggtcnaana ntnaaaanac nnttgacntg ntaatanngg aatantangg cnaatggaaa    540

ctgngttggg ggaggatcaa tttaaagagg                                      570
```

```
<210> SEQ ID NO 125
<211> LENGTH: 593
<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G

<400> SEQUENCE: 125

ggtacagaga tttaaatgaa atcttcgaaa gaataaattt gcttttcagt ccactgtatt     60

ttcaaaattg attatcacca agcttggatg aaagctgtga accacaaacc atttgtttat    120

ttaatagaaa aaagaatgtg tagattatta gcaaagtaat gccttaaaat gtatcttcac    180

acagttgaaa ttttagtata aacttgtata tcaagttgct ttccattatt tattctactt    240

taaaaatata tacaactatg atgttcaaat atgtattctg agccattatg ttcaaacata    300

aatatctggg aaattcaaac tgctgcaaca agttaggaaa ggattaagga aaaatgatga    360

gctacaaatt atgtagttgg aggaagaaaa aaatgttact tagcatttat gtctggatag    420

gtatgtattt tctaatttac atacacatat ccagttgagt atagaccacc atcaaaatgt    480

accagttaca cagagactag actaaaccac cctatttcta tacaggtacc atagtggatt    540

caaaaattta atatctcata gttcccaaaa ttattgnggn aatatgctna ttt            593
```

```
<210> SEQ ID NO 126
<211> LENGTH: 592
<212> TYPE: DNA
<213> ORGANISM: Homo sapiens
<220> FEATURE:
<221> NAME/KEY: misc_feature
<222> LOCATION: (1)...(592)
<223> OTHER INFORMATION: n = A,T,C or G

<400> SEQUENCE: 126

acgcgggggg gccttccggg acgagggcgc gtgggtgagg aaggtcaggt ctaggaactc     60

taactccttg ccactcaaga aatgtcctcc ctttcagaat atgccttccg catgtctcgt    120

ctcagtgccc ggctatttgg tgaagtcacc aggcctacta attccaagtc tatgaaagtg    180

gtgaaactgt ttagtgaact gcccttggcc aagaagaagg agacttatga ttggtatcca    240

aatcaccaca cttacgctga actcatgcag acgctccgat ttcttggact ctacagagat    300

gagcatcagg attttatgga tgagcaaaaa cgactaaaga agcttcgtgg aaaggagaaa    360

ccaaagaaag gagaagggaa aagagcagca aaaaggaaat agtgttggtc ccttcaagag    420

ggagactttc ttcctaatgg ccggaaagaa gaaagtgcat ttattggctt tccacatatt    480

ggaggaatgt catcttccta aatgaagttt atttggagga acacagtcat ttccttggtg    540
```

-continued

```
aaactaatcc ggtacattgn ggttgggttt ttgaacacat ctactgggca aa          592


<210> SEQ ID NO 127
<211> LENGTH: 600
<212> TYPE: DNA
<213> ORGANISM: Homo sapiens
<220> FEATURE:
<221> NAME/KEY: misc_feature
<222> LOCATION: (1)...(600)
<223> OTHER INFORMATION: n = A,T,C or G

<400> SEQUENCE: 127

acagtggtcc ttttcagagt tggacttcta gactcacctg ttctcactcc ctgttttaat    60

tcaacccagc catgcaatgc caaataatag aattgctccc taccagctga acagggagga   120

gtctgtgcag tttctgacac ttgttgttga acatggctaa atacaatggg tatcgctgag   180

actaagttgt agaaattaac aaatgtgctg cttggttaaa atggctacac tcatctgact   240

cattctttat tctattttag ttggtttgta tcttgcctaa ggtgcgtagt ccaactcttg   300

gtattaccct cctaatagtc atactagtag tcatactccc tggtgtagtg tattctctaa   360

aaagctttaa atgtctgcat tgcanccagc catcaaatag tgaatgggct ctcttttggc   420

ntggaattcc aaaacntcag agaaatggtg tcatcaagga gaaccttcat aaccccntga   480

anggattaaa aagccccaaa tgggggggaac tgataatagc acttaaggct ttaagaattg   540

gncacanttt caccttgtga acccattnna cnatngngcc taanngctnc ctnctncaan   600


<210> SEQ ID NO 128
<211> LENGTH: 588
<212> TYPE: DNA
<213> ORGANISM: Homo sapiens
<220> FEATURE:
<221> NAME/KEY: misc_feature
<222> LOCATION: (1)...(588)
<223> OTHER INFORMATION: n = A,T,C or G

<400> SEQUENCE: 128

ggtacttttt tttttttttt tttttttttt tttttttgag acggagtctc actctgtcac    60

ccaggctgga gtgcagtggc atgatcttgg ctcactgcaa gctctgcctc ctgggttcac   120

gccattctcc tgcctcagcc tcctgagtag ctgggactac aggcgtccgc caccacgccc   180

agctaatttt ttgtattttt ggtananaca gggtttcacc gngttagcca ggatggnctc   240

catctcctga cctcgtgatc tgcccacctn ggccttccaa agtgctggga ttacaggcat   300

gagccacggc gcctggccag gatggtatat ttttaactcc ttcactgggc cccacccctg   360

actttctgct ttangaggtc tggggtgagg ctgaanatct gggggccaca cttcgagagc   420

aaccaagact gtaagtgggg ccttccanag cccaatgaag ggaatactta ggtacaggan   480

gtgtctgcat ggncncangt gtggggtttn cttctcggcc ttaaccagaa agtatctctg   540

gttttaattt taaaatgaaa attttaaagg gtgnctgaaa cnaattgg                588


<210> SEQ ID NO 129
<211> LENGTH: 588
<212> TYPE: DNA
<213> ORGANISM: Homo sapiens
<220> FEATURE:
<221> NAME/KEY: misc_feature
<222> LOCATION: (1)...(588)
<223> OTHER INFORMATION: n = A,T,C or G

<400> SEQUENCE: 129

ggtactgccc tctccagatc agcagttcag gagagcacag gaggcaaaac acagattgct    60
```

-continued

```
gggcttattg gtgccatcat cgtgctgatg gtcgttctag ccattggatt tctcctggcg    120

cctctacaaa agtccgtcct ggcagcttta gcattgggaa acttaaaggg aatgctgatg    180

cagtttgctg aaataggcag attgtggcga aaggacaaat atgattgttt aatttggatc    240

atgaccttca tcttcaccat tgtcctggga ctcgggttag gcctggcagc tagtgtggca    300

tttcaactgc taaccatcgt gttcaggacc caatttccaa aatgcagcac gctggctaat    360

attggaagaa ccaacatcta taagaataaa aaagattatt atgatatgta tgagccagaa    420

ggagtgaaaa ttttcagatg tccatctcct atctactttg caaacattgg tttctttagg    480

cggaacttat cgatgctgnt ggctttagtc ccttcgaatt tacgcaagcg cacaaacttt    540

gaggaaaatc cgaaactgcn aagcaagntt gntacaagtg acccaaan                 588
```

```
<210> SEQ ID NO 130
<211> LENGTH: 190
<212> TYPE: DNA
<213> ORGANISM: Homo sapiens

<400> SEQUENCE: 130

ggtacaaaaa aaaccttaca taaattaaga atgaatacat ttacaggcgt aaatgcaaac     60

cgcttccaat tcaaagcaag taacagccca cggtgttctg gccaaagaca tcagctaaga    120

aaggaaactg ggtcctacgg cttggacttt ccaaccctga cagacccgca agaccccgcg    180

tacttttttt                                                           190
```

```
<210> SEQ ID NO 131
<211> LENGTH: 386
<212> TYPE: DNA
<213> ORGANISM: Homo sapiens

<400> SEQUENCE: 131

ggtacagaac tcagaggaaa aaagaaatta aattttagct ttctggagag cagcccctct     60

ctggcaccat caaacacttc tttgtttccc ttcaacttgg aactcttcaa acatcagggg    120

ttgtgagggt ttggccattc ttttatcttg ggtccatgtg agtgacagaa atggtgcggc    180

ctgggaaaga tctccctcct ttacattttc tcttctccct cctcctcctt attctaaaac    240

tgtgcctcca acagaggggc aggggctctt gtagagagat ccctggccca ggacaggaga    300

tgccaaatct aatttatctc actgagggcc tttgagaaaa acgcttcagg gccaggctca    360

gtggctcatg cctatataat cccagt                                         386
```

```
<210> SEQ ID NO 132
<211> LENGTH: 593
<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G

<400> SEQUENCE: 132

actgagacaa tggttagggt tgttttctta attcttttcc tggtagggca acaagaacca     60

tttccaatct agaggaaagc tccccagcat tgcttgctcc tgggcaaaca ttgctcttga    120

gttaagtgac ctaattcccc tgggagacat acgcatcaac tgtggaggtc cgaggggatg    180

agaagggata cccaccacct ttcaagggtc acaagctcac tctctgacaa gtcagaatag    240

ggacactgct tctatccctc caatggagag attctggcaa cctttgaaca gcccagagct    300
```

-continued

```
tgcaacctag cctcacccaa gaagactgga aagagacata tctctcagct ttttcaggag    360

gcgtgcctgg gaatccagga actttttgat gctaattaga aggcctggac taaaaatgtc    420

actatngggt gcactctaca gtttttgaaa tgctaggang cagaagggca aaaataaaaa    480

acatgacctg gttgaaggaa naaaagcaaa gaaacttggg ngggaggaca attaaaaaga    540

gnncctggga tcccctnttc ttaggtccct ctcttacnaa ggacnctntt tat           593
```

<210> SEQ ID NO 133
<211> LENGTH: 588
<212> TYPE: DNA
<213> ORGANISM: Homo sapiens
<220> FEATURE:
<221> NAME/KEY: misc_feature
<222> LOCATION: (1)...(588)
<223> OTHER INFORMATION: n = A,T,C or G

<400> SEQUENCE: 133

```
acagancatt nnnagcnctn gcacaggnta cagaacctna cagacccaaa ggaacatcgg     60

ataggcnaag cgactacagg aggcgtgtgt gcgcttgggc naggtaaaca gggtcagtat    120

tggtcnngtg acaagagnca cgaantctgg ccngacantg angtnaanaa ggttnatnnt    180

ttnacantta tnnnanatat nnnnnaannt attaanctgc ancanntgat tttnacacct    240

anttactaga aaactaanga aagcactnat tagctctgaa tnaantnaca tggnaagcct    300

tttactaatc tncaaanaaa ccttctctgc antatnnnaa agattttatn atacaangng    360

gnnnatcnct cnatcatann gggttctatt ananaaccct gctaantntg cgacttacag    420

aacanccagc ntananatga ntttcatgcc catttgggaa gcatngcccg ggtatcacaa    480

aggaaaccta ctaaagnttt ctgttatacc agccttcntt cntatcantg catgngnana    540

nanaaccntt gaaggttntc cnggggactt tnttctnttn ctttgccc                 588
```

<210> SEQ ID NO 134
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 134

```
tcnagcggcc nnccnggcag gtacantcac annttnnang anctnaacac anactanctg     60

nngtcaaata ttnaacaaaa gcantagatg aanctgctta acattcacgg aaaaacaacc    120

aaaagaaggg aggggtgata aaccanaaaa atgantgacn aaaactaaga gacctcatan    180

gngtctttac aatcnggaat tcagatgcaa ggaacagacn caaanctgtc taaaatgtna    240

cctatgaggc nacanaaagt gacttaaagt ctggtntnan taaaaaatga caacccttat    300

cctagagagt cttacnttat ttaatccana cnttatntaa cgccncngat ttttgnttgg    360

ngctatggng ttnattttnt atcagaanga antgtgggac anatgcatta ctgnttgttn    420

aaagngcttn acagctaatt cacncccnng ggcatggtca aaaaggnaan aaccnggnca    480

tatattgntg anatgaaaaa accacntgtt aaaaaaataa ntgnagccna ntgngttttn    540

natgataacc aaatnttnac nttcagtann ngccttttan aagttggtga actccgaaat    600

ctnctttttt aaaccngg                                                  618
```

<210> SEQ ID NO 135
<211> LENGTH: 374

-continued

<212> TYPE: DNA
<213> ORGANISM: Homo sapiens
<220> FEATURE:
<221> NAME/KEY: misc_feature
<222> LOCATION: (1)...(374)
<223> OTHER INFORMATION: n = A,T,C or G

<400> SEQUENCE: 135 acttttttttt ttttttttt tttttttttg gggatggagt ctcactctgt tgtccaggtt 60
ggagtgcagt ggtgtgatct cggctcactg caacctntgc ctcccaagtg attctcctgg 120
ctcancctcc tgagtagctg ggactacagg catgcactac catgcccggc taatttttgt 180
atttttagta nanacagggt ttcaccatgt tggccaggct ggtcttgatc tcctaatctc 240
aggtgatccg cctgcctcan cctcctaaag tgctgggatt acaggcatga gccactgtgt 300
ntggccaana ncactcgtaa gaaggatggc agtatcacaa aatcaagcca gagatacaga 360
gattacccgc gtcc 374

<210> SEQ ID NO 136
<211> LENGTH: 581
<212> TYPE: DNA
<213> ORGANISM: Homo sapiens
<220> FEATURE:
<221> NAME/KEY: misc_feature
<222> LOCATION: (1)...(581)
<223> OTHER INFORMATION: n = A,T,C or G

<400> SEQUENCE: 136
actccagcct tgctgaagct gcctcaaagg ctgatggttt ggcagttatt ggtgttttga 60
tgaaggttgg tgaggccaac ccaaagctgc agaaagtact tgatgccctc caagcaatta 120
aaaccaaggg caaacgagcc ccattcacaa attttgaccc ctctactctc cttccttcat 180
ccctggattt ctggacctac cctggctctc tgactcatcc tcctctttat gagagtgtaa 240
cttggatcat ctgtaaggag agcatcagtg tcagctcaga gcagctggca caattccgca 300
gccttctatc aaatgttgaa ggtgataacg ctgtccccat gcagcacaac aaccgccaac 360
ccaacctctg aagggcagaa caagtgagag cttcattttg atgattctga gaagaaactt 420
gtncttctca agaacacaac cctgcttctg acataatnca ataaaataat aattttaaaa 480
aataaattat ttcaatatta ncaagacaca tgccttnaat natctgtaaa ctaaaaacta 540
aaatttantc tactgnttaa tcnaanataa taatagcttc a 581

<210> SEQ ID NO 137
<211> LENGTH: 504
<212> TYPE: DNA
<213> ORGANISM: Homo sapiens
<220> FEATURE:
<221> NAME/KEY: misc_feature
<222> LOCATION: (1)...(504)
<223> OTHER INFORMATION: n = A,T,C or G

<400> SEQUENCE: 137
ttttncaaan nnaagttttt tacttccnaa aantnatggc taaggggngg gnggngggng 60
aaaaaagnaa aacaaaaaaa ccccaaaaaa atggggnggn naaaaggggg gganaaaaaa 120
ccnntntttt ntaaantntn acaaggcaag ngcnnangga aaaaaaaaan ncctgnaaaa 180
tcccccncgg nnggggnaaa natnnnggtt tccttttgnt ttnaaacccn ntnangnaag 240
gntntccccc ntncccctna atnaaaaatt tntntnccng ggccnnaacc nccntanggg 300
naaattccac cncnctgggg gccgttanta agggatccna gctnggccca ancttggnga 360

-continued

```
aacatggcaa aactgttcct nnggnaaaat gtttcccctc anaattccca naaaataaaa    420

ccggaacata aagngaaaac cngggggcct aagngggncn cacnccattt attggggtgg    480

cccncgnccc tttcaaangg aaac                                           504
```

<210> SEQ ID NO 138
<211> LENGTH: 386
<212> TYPE: DNA
<213> ORGANISM: Homo sapiens

<400> SEQUENCE: 138

```
acaacaaata acactgtgac tccaacctca caacctgtgc gaaagtctac ctttgatgca     60

gccagtttca ttggaggaat tgtcctggtc ttgggtgtgc aggctgtaat tttctttctt    120

tataaattct gcaaatctaa agaacgaaat taccacactc tgtaaacaga cccattgaat    180

taataaggac tggtgattca tttgtgtaac tcactgaagc caaaatacta tcttttaaga    240

tgtcccacat ggaagacgct attccaggat ctttaaattt ccatggatgc atataggatg    300

tttgggagca tcatccgtga agaaaaaatc aattaaatca ttgtgttcaa caggaatatt    360

taaaataaaa aaaaaaaaaa agtacc                                         386
```

<210> SEQ ID NO 139
<211> LENGTH: 586
<212> TYPE: DNA
<213> ORGANISM: Homo sapiens
<220> FEATURE:
<221> NAME/KEY: misc_feature
<222> LOCATION: (1)...(586)
<223> OTHER INFORMATION: n = A,T,C or G

<400> SEQUENCE: 139

```
ggtactcaag tttataatgt ccccaaacct taagactaga aaatcatccc aagaaaaagg     60

cctatagttg gtttaatttc accctgagaa tactgtgata aaaatcaata tatttcagag    120

ctagtaagta tttaaaaatt agtgtctcaa aaaggggaca tcataaggga aatacagggt    180

ttagaggtct gagctcaagt ggtgtaagac agttctttct tcttcctcct ttaaactctt    240

cactttgctc taacacggaa gatgggggac agtgatcccg aaggtattac taaaatattg    300

cagctttcag taattatgag aagcacagat atcaccagaa aagaaagcaa tcatttggag    360

tactaagaaa cgaaacaatg ttatttggtg gtgtataatt ctacttttct agtagattac    420

tgngtggaat tctgtgaaaa atatttgaga aaangcctgt attgcataaa taaatctttg    480

tatgttgcaa aaaaaaaaaa aaaaaaaagt acctgccggc cgncccaang gcgaattcca    540

cacctgcggc cgtctagngg tccacccggt ccacttgggt atatgg                   586
```

<210> SEQ ID NO 140
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 140

```
acagggagga atttgaagta gatagaaacc gacctggatt actccggtct gaactcagat     60

cacgtaggac tttaatcgtt gaacaaacga acctttaata gcggctgcac catcgggatg    120

tccctgnacc aaccttcaag gccnaaaccc nnntggtgnn tttggnctnt aaatnaggat    180

ggccctgtnt tccntaggta acttgttccg ttggtcaagt tattggatca attgagtata    240
```

-continued gtagttcgct ttgactggtg aagtcttnac cnngtccntt tngngtgggg ttttttttagg 300 naaaagnctt ttggtncatt nntgggggg gnaggggact gaacctttat tntttccaaa 360
tncaccttaa antcagggac aanaaacatt ccaanaacca caatctttta aaaaattaac 420
tngccagtgg gaatgtttaa aaanntnaan ggtctttttt gccttggttt ttgtgggggt 480
ctctcttccc ccccctgggg ttaatttttn aagccgggac ctcncnaana cccctttttt 540
caaagggccc naaaccccccc cccccnaaaa aaaaaaaaaa aaaaaaaanc n 591

<210> SEQ ID NO 141
<211> LENGTH: 592
<212> TYPE: DNA
<213> ORGANISM: Homo sapiens
<220> FEATURE:
<221> NAME/KEY: misc_feature
<222> LOCATION: (1)...(592)
<223> OTHER INFORMATION: n = A,T,C or G

<400> SEQUENCE: 141
ggtacacaaa ccaagacaat atcagggtga caggtgaatg aacttaaatt ctcagtcttg 60
tctattcacc aaaaaagtat actgcctgtt ttttctttaa ttattcaagg ttgatgactt 120
ttaggaacat gttttatact gtatttttta attaaagcaa gtgccttgat gtaattccat 180
gtaaatcatt gcttaaccct cttatgggat gaggatgagt tattaatgta ttgcagccta 240
ctggaaagga gggggagttg gttaatagca gatacttttc ttctagaagc ttatgtttta 300
tgctgtttat tatgtaagat cctgtatgtg tgttgagatt tagaggtttc atttgttttg 360
tctgctaata aattgttact ctaataataa ccnngnnaaa naaannnnnn nnnnnnnnnn 420
nnnannnggt ncctgcccng gcggccgctc gaaagggcga attccancca ctggcnggcg 480
gtactaaggg gatccgnctc gggncccaac ttggcgtaat atnggcatac tggttcccgg 540
gngaaatggt atncgtcaaa ttccccaaat acnaccggaa ncttaagggt aa 592

<210> SEQ ID NO 142
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 142
acaacacctt cattcttaat gcttcttagg gcatcacagg ttttagaaat taatgtattt 60
ttagcattcc acagtaatga tcactttcaa aaactgcaat atacatctgc atgttacact 120
gacatacaac acataagtat tttgtcacac atcaactttt agcctcaaat aatagaatac 180
aaaaagctac actggacata acaccaccga actttttgaat atcccctttt cccaattgtt 240
aacaggtagt actgggatta caggcgtgag cctctgcgcc tggccaagtg gaggttatta 300
ttaaccctat ttaacagata taaaaagaag agattagaga attttatcaa tgttcccact 360
gtcaaataga atataagcaa tgatacaaaa tgttgagtct tcatcctcta actccagatc 420
ctggtatatt gccctacatt tctatacatt aatactaact tatacactga atacaagagt 480
naaaccaact gtcngggctt aatanggnga aaatgctctt gncctaaanc accagggtgg 540
ctnggtttat tcctacatgt ggactaaaan gnaatcatct ttatggcngg aaana 595

<210> SEQ ID NO 143

-continued

<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 143
actactcgat tgtcaacgtc aaggagtcgc aggtcgcctg gttctaggaa taatgggga 60 agtatgtagg agttgaagat tagtccgccg tagtcggtgt actcgtgtga agttggcagg 120
gacggttcct gtcatcttct tgggcttatt tggtgtgctg ttgaaggggg gagactagag 180
aaatggcagg gaacctctta tccggggcag gtaggcgcct gtgggactgg gtgcctctgg 240
cgtgcagaag cttctctctt ggtgtgccta gattgatcgg tataaggctc actctcccgc 300
cccccaaagt ggttgatcgt tggaacgaaa aaagggccat gttcggagtg tatgacaaca 360
tcgggatcct gggaaacttt gaaaagcacc ccaaagaact gatcangggg cccatatgct 420
tcgaggntgg aaanggaatg aattgcaacg ttgtattccn aaagaagaaa atggttggaa 480
gtaaaatgtt ccttatgacc tcncaacctt ataaacncat ccgtttnttt acaaccntta 540
accacatggg aagttcattn aaaaaaactg aaaactttgn aaagnttttt ttnnccttga 600
aaagggaact tacctcgccc 620

<210> SEQ ID NO 144
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G

<400> SEQUENCE: 144
cgaggtactt tttttttttt tttttttttt ggggtcagtg gtgatatccc cctaatcaat 60
tctgattgng ttccttttaa tcttctctca tttctttttt attagactag atagtgattt 120
atctatttta ttaatttttt caaaaaatca cctcctanat ttgttgtttt ttaaggggtt 180
ttatgtctct atctccttca gttcaactct gatcttggnt atttcttgnc ttctgctaga 240
tttggggttt gntttctgnt ggntctctaa gttctttttg ntgngacatt agattgncaa 300
cttaaaatct ttctagctat ttgacgtggg catttaatgc tataaatttc ctggtaacac 360
tgctttcgct gtatnccana naatctggga tggtggggcc ttggtttcaa taanttccaa 420
tacctcttaa gggggnggag ccaanaagan ctaatagggg cagcactgct ctgggctncc 480
atcaanaagg acaaaaactg ggagngaccc tgcttnttca ctgaggnacc ggcccggccg 540
gccgtccnaa ggcgaatcca cncnctggcg gccgtctatg gatccacccg gnccaactgg 600
ggaatatggc aaa 613

<210> SEQ ID NO 145
<211> LENGTH: 345
<212> TYPE: DNA
<213> ORGANISM: Homo sapiens

<400> SEQUENCE: 145
acactgatct acaaaaattt taaaatgagc cgggcgcggt gactcacgcc tgtaatccca 60
gcactttggg aggccaaagc aggcggatca tgaggtcagg agatcaagac catcctggct 120
aacacggtga aaccccgtct ctactaaaaa tacaaaaaat tagccgggtg tggtggcggg 180

```
cacctgtagt cccagctact cgggaggctg aggcaggaga atggcgtgaa gccgggaggt    240

ggagcttgca gtgagccgag atcacaccac tgcactccag cctgggcaac aaagcaagac    300

tctcaaaaaa gaaaaaaatt tttttttaaa tgagctgggt gtacc                    345
```

<210> SEQ ID NO 146
<211> LENGTH: 475
<212> TYPE: DNA
<213> ORGANISM: Homo sapiens
<220> FEATURE:
<221> NAME/KEY: misc_feature
<222> LOCATION: (1)...(475)
<223> OTHER INFORMATION: n = A,T,C or G

<400> SEQUENCE: 146

```
actacaaggt ttagcatttg ctctgctggt cgacattccc ccagtctatg ggttgtatgc     60

atcctttttc ccagccataa tctacctttt cttcggcact tccagacaca tatccgtggg    120

tccgtttccg attctgagta tgatggtggg actagcagtt tcaggagcag tttcaaaagc    180

agtcccagat cgcaatgcaa ctactttggg attgcctaac aactcgaata attcttcact    240

actggatgac gagagggtga gggtggcggc ggcggcatca gtcacagtgc tttctggaat    300

catccagttg gcttttggga ttctgcggat tggatttgta gtgatatacc tgtctgagtt    360

cctcatcagt ggcttcacta ctgctgctgc tgncatgttt tggtttccca actcaaattc    420

atttttcaat tgacagtccc gtcacacact gatccagttt caattttaaa agacc         475
```

<210> SEQ ID NO 147
<211> LENGTH: 629
<212> TYPE: DNA
<213> ORGANISM: Homo sapiens
<220> FEATURE:
<221> NAME/KEY: misc_feature
<222> LOCATION: (1)...(629)
<223> OTHER INFORMATION: n = A,T,C or G

<400> SEQUENCE: 147

```
cgaggtacgc gggatttgaa tcttaaactg tatttttctc ttagtattgc taatgagtaa     60

agaaaagtct cataaggtag ccaaatgaaa aagaatgaaa gggaaagtga aaaattaagg    120

ggacaaaaga tgggatgtga aaagaagaat tctagtttga tggtgactca tattcacgat    180

aggatacaaa gtgtgatttg ttggaaacat gtcccaaatt tctaaaattc tgcttctctg    240

ccaaaagcaa tgtctttctt ggttgatatt tgagttttaa aagggtcaaa tctttctaat    300

tttttgtatc tttagagggc agcactagaa gaaatcagca ggtctaatcc caccagtaag    360

aaaactacca cttcttgatt tttacagatt taaaaaaatc ttttcagtgc ctttcttttt    420

aatgtaaata caaatttaaa cctangctta atatagcgtt tccctttccc caagtgatgt    480

cnaggtcgat gccaaatcaa tgatccnaaa tgatcgnggt naaaataact caaagggttc    540

ttaaggngag tngcatgcca aaaaatacct tgattccggg ggtttggacc tggctttgtt    600

ggggcctntg aaatgccaan ttancccan                                      629
```

<210> SEQ ID NO 148
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G -continued

<400> SEQUENCE: 148

```
acaaaagagc ctgattcttt ttaattccac aaatacctag catctcaaag taacatgtaa     60
acaaacttct atgctgctca atgaatcctt ccaatttcga taataaacta aatagtattg    120
gatctagtat atgactttca tgtgtaagtt atggttctat ccattacttt aacaatatta    180
ctgatgtaac agagaaaaat tttcaactat tgtatttatt taaaacaaac tgacaagttc    240
aagcacctgt cttcagaaaa gccagcagca tttttttttt ttaacatact caaagtaaga    300
tttggcctaa gcccttaata cctttctgaa cagccatgca actaaacacc ctcagggaga    360
tgttacataa gggagagaag aacatggagc aatttgcact ttttccctag ataatattaa    420
caaggnaaag caaatncaga tctttatgaa tgaatggntg gcatggttaa tcacttggac    480
tttttaaact agagncncta tcatattggt aaatagaaan aaaggatttt aataaagctc    540
tncctgcttc aaaattaagg ggacnttttc tgggaggctt tcagggacca taataaggta    600
aaaggggacg gttg                                                      614
```

<210> SEQ ID NO 149
<211> LENGTH: 628
<212> TYPE: DNA
<213> ORGANISM: Homo sapiens
<220> FEATURE:
<221> NAME/KEY: misc_feature
<222> LOCATION: (1)...(628)
<223> OTHER INFORMATION: n = A,T,C or G

<400> SEQUENCE: 149

```
nccgaggnac tttnnttttt tttttttttt ttttnaacag cgncttttca tttttattac     60
tcaaaaaagt ttcatttttt tatttaagct ttctgactct gngcttgggc cttcaacact    120
ttcacaacga ttttctgctc ctcgataagg aaagcccgct tgatcctana aaggaaaata    180
ccaaattaat catttcttta aaatgaactt catttttttat ttagcccaaa aaaggnaaac    240
atggtaaaga accaagcnaa gcaatcaggg aacccaggaa actacnggat acccaaatac    300
ngagtaaaac ttaaaagggg aaattcattt aaagcaggga aatccctcaa tttcatgccn    360
gtagttatct gncctcctct gagcaagaat aactatgaag catcccccag gagaccacnt    420
atgagactta attattggta ggatccagga atagnggnat ttnttgattt gcaaaangtn    480
taaaaaattt taaccctntt ttgaaaattc ccagnaaaaa caccncataa ggggctntgt    540
gttaaaacta aaattaaagg gaagggtttt tccagaaacc ccccccanac cagggtttna    600
accggttang gcanntcncc aaaccnan                                       628
```

<210> SEQ ID NO 150
<211> LENGTH: 509
<212> TYPE: DNA
<213> ORGANISM: Homo sapiens
<220> FEATURE:
<221> NAME/KEY: misc_feature
<222> LOCATION: (1)...(509)
<223> OTHER INFORMATION: n = A,T,C or G

<400> SEQUENCE: 150

```
ttggggaann aaaaaaaaac tttttttttt nggggnnngg ggntgcnanc natncaaaaa     60
tcaaaancnt ntttgggttt taactttttt ttttttgntt gncaaannaa aantaaantt    120
tntttttana tttgctaang ggccngancn gcnnaaaaaa ncctttttttn ggggaanctt    180
nggggcaaat tnnttnancn accctttggg anaacttttn ttagggggggn nnnaaccgnc    240
atttttgccc actttttttcc cttttgntta anggggncct tgggcnggac cncccttagg    300
```

-continued

```
ggnaattcac ccnctggggg gcgttatntt ggatccactc ggnccaactt gggggaaaaa    360

gggaaaacnt tttctggggn aaattttttc ccncnaaatt cccaanaana aaaccggaac    420

nnaaanttaa acccgggggc ccaaggnggg ccnncccntt nttgggtggg ccctgcccnt    480

ttaangggaa attttggccc tttttaaaa                                      509
```

<210> SEQ ID NO 151
<211> LENGTH: 622
<212> TYPE: DNA
<213> ORGANISM: Homo sapiens
<220> FEATURE:
<221> NAME/KEY: misc_feature
<222> LOCATION: (1)...(622)
<223> OTHER INFORMATION: n = A,T,C or G

<400> SEQUENCE: 151

```
ggtacttttt tttttttttt tttttttgc tttggacaaa tttattgaaa catacaggcg      60

gctgttagca gagaaatcat tccatgattg atgtgttaca tttggccact accttgaatg    120

tataatttaa aaattatatt tttcacaact aagcctttgg ccaaaaaagt catttagcac    180

atctttaaag atcaataaga aatggatttt ggacattaaa aagatcaagt cactgaatta    240

aacagtagca acccccatta atctagaatc ccatagtgct gaaggtagag gtgtctgtgc    300

aaagctagtc atttgttaac agcaatcana aaanatgggg gcaggcacac ctgtcaaaag    360

tggcaacana nctggcagga caggacggct gggctggtct ggtcaggtga gcatgtncca    420

aaaacagcag caacagaaaa cccgtccacc angcttgtga agcangtgga tggtcctagc    480

tcatctnttn ttttggnctt ntancacata cactgngggt ttangangnt tctgaggncc    540

accttgccnc cctacctgcc cgggnggccg ttnaaagggg aattccacca ctgggggccg    600

tctaatggga cccacctggg cc                                             622
```

<210> SEQ ID NO 152
<211> LENGTH: 313
<212> TYPE: DNA
<213> ORGANISM: Homo sapiens
<220> FEATURE:
<221> NAME/KEY: misc_feature
<222> LOCATION: (1)...(313)
<223> OTHER INFORMATION: n = A,T,C or G

<400> SEQUENCE: 152

```
acggtggatt agttcttttc agcatgttcc ttctgtatga tacccagaaa gtaatcaagc     60

gtgcagaagt atcaccaatg tatggagttc aaaaatatga tcccattaac tcgatgctga    120

gtatctacat ggatacatta aatatattta tgcgagttgc aactatgctg gcaactggag    180

gcaacagaaa gaaatgaagt gactcagctt ctggcttctc tgctacatca aatatcttgt    240

ttaatggggc agatatgcat taaatagttt gtacgcgggg aaaaaaaaan aaaaaaaaaa    300

aaaaaaaagt acc                                                       313
```

<210> SEQ ID NO 153
<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 153

-continued

```
cgaggtacgc gggagggcaa caagaaccat ttccaatcta gaggaaagct ccccagcatt     60

gcttgctcct gggcaaacat tgctcttgag ttaagtgacc taattcccct gggagacata    120

cgcatcaact gtggaggtcc gaggggatga gaagggatac ccaccacctt tcaagggtca    180

caagctcact ctctgacaag tcagaatagg gacactgctt ctatccctcc aatggagaga    240

ttctggcaac ctttgaacag cccagagctt gcaacctagc ctcacccaag aagactggaa    300

agagacatat ctctcagctt tttcaggagg cgtgcctggg aatccaggaa ctttttgatg    360

ctaattagaa ggcctggact aaaaatgtcc actatggggt gcactctaca gtttttgaaa    420

tgctaggagg caaaaggggc agagagtaaa aaacatgacc tggtagaagg aanaaagcaa    480

aggaaactgg tggggaggat caattagaga ngaggccctg ggatccncnt nttcntaggn    540

ccctctcata cnaaggacac tttttatatg ccttcccaaa ctgntnggga agggtnaaac    600

caaaatccgg ggtanaacct                                                620
```

<210> SEQ ID NO 154
<211> LENGTH: 339
<212> TYPE: DNA
<213> ORGANISM: Homo sapiens

<400> SEQUENCE: 154

```
ggtacctgga ggatatagac ctgaaaacac tggagaagga accaaggact ttcaaagcaa     60

aggagctatg ggaaaaaaat ggagctgtga ttatggccgt gcggaggcca ggctgtttcc    120

tctgtcgaga ggaagctgcg gatctgtcct ccctgaaaag catgttggac cagctgggcc    180

gtccccctct atgcagtggt aaaggagcac atcaggactg aagtgaagga tttccagcct    240

tatttcaaag gagaaatctt ctggatgaaa agaaaaagtt ctatggtcca caaaggcgga    300

agatgatgtt tatgggattt atccgtctgg gagtgtggt                           339
```

<210> SEQ ID NO 155
<211> LENGTH: 450
<212> TYPE: DNA
<213> ORGANISM: Homo sapiens
<220> FEATURE:
<221> NAME/KEY: misc_feature
<222> LOCATION: (1)...(450)
<223> OTHER INFORMATION: n = A,T,C or G

<400> SEQUENCE: 155

```
cgaggtactt tttttttttt tttttttttt tttttcntat ttttgtttaa tttatttaan     60

accacctnct tacaacttnc anagagaaaa tacaaaacaa gaaacanact tggtttnaaa    120

tgcataacca gntgctggan tttaaagcat tactgataac attgttacan aanaatggca    180

nnttactcna gggcacttna gtattcctna ggaataaaca ttgatttctc ttgtcctccc    240

nntgggatgt tctcangtna agtcactgcn cctgcnctta gacatatttt ccatgtnnca    300

naananggag cctgnaaant atgctnacag tnggaataag ccattnctaa ttccatgcca    360

naaccnangg ctaatggnnc attctttttt aataaggtat gtggaaaana ttcntatccc    420

aaanaaaant tgcccggncg gtctntntaa                                     450
```

<210> SEQ ID NO 156
<211> LENGTH: 760
<212> TYPE: DNA
<213> ORGANISM: Homo sapiens
<220> FEATURE:
<221> NAME/KEY: misc_feature
<222> LOCATION: (1)...(760)

-continued

<223> OTHER INFORMATION: n = A,T,C or G

<400> SEQUENCE: 156
cgaggtactg ccccagtgaa aatggaactg aaagagcctg tagctgtcag agaaaggacc 60
acctttcagc actgatcggt tatcgttgtc ctcaaaattt acatggaagg aatgccccac 120
attgataatt tctttggctg tggctgggtt gtaggagaca ctaataggtt tcagagaggt 180
gtcatgtttg gtttcactgg ttttaatatc aacaggggac tggttatttc cattggcaat 240
gggatacagc ttgctccatt gttcaggacc atttttgtca tcatatcccc agtctggact 300
tgccattatc ttctactgag ttttcttttt ctgaaaacaa aaataatacc tggaataact 360
aactgccccc gcgtcctgcc cgggcggcca aaggggcaat tccaccactg gcggccgtac 420
ttatggatcc aactcgtccc ancttggcgt aatatggcat aactgttctg nggnaaatgt 480
atcccttaca attcccncac atcnacccga acctaantgt aancctnggn gcnnataagg 540
actactnctt aatgggtggc tctgncnttt caannggaac cttngcnctn gntatgattg 600
ccaccccgga naggggtggt ttggccttcc ntcttgtann aatcttcncg gnttgttgga 660
anggtnntct taggggatng ttccaatggg gaccgnaanc ttccagccna ggcaccaaan 720
cnttggttta ncccccacnn aaaantanag gggncngggt 760

<210> SEQ ID NO 157
<211> LENGTH: 668
<212> TYPE: DNA
<213> ORGANISM: Homo sapiens
<220> FEATURE:
<221> NAME/KEY: misc_feature
<222> LOCATION: (1)...(668)
<223> OTHER INFORMATION: n = A,T,C or G

<400> SEQUENCE: 157
ggtacccagt agtcattcag gaacaggttg ttcagtttcc atgtagttga gcggttttga 60
gtgagtttct taaacctgag ttgtcgtttg attgcactgt ggtctgagag acagtttgtt 120
ataatttctg ttcttttaca tttgctgagg agtgctttac ttccacctat gtggtcaatt 180
ttggaataag tgagatgtgg tgctaaaaag aatatatatt ctgttgattt gaggtggaga 240
gttctgtaga tgtctattag gtctgcttgg tgcanagctg agtcaattcc tggatatcct 300
tggtaacttt ctgcttgttg ntctgtctaa tattgacagt ggggcgttaa agtctcccat 360
attattgtgt gggagtctaa tctctttgta ggtctctaag gacttgcttt ataaactggg 420
tgctcttgat tgggtgcaat atatttagga tagttagctc ttcttggtga atgganccttt 480 taccaatatg aatggcctcc ttccttttga ccttgtgggt taaagctggt tatngaaact 540
ggatggancc ctgctttttt tggttcattt cttgnagggt cctcagcctt attttancnn 600
gnggctttgn cccncntccg cggcnttaag ggaaccacnc tgngcgtcta ngancactgg 660
caactggg 668

<210> SEQ ID NO 158
<211> LENGTH: 737
<212> TYPE: DNA
<213> ORGANISM: Homo sapiens
<220> FEATURE:
<221> NAME/KEY: misc_feature
<222> LOCATION: (1)...(737)
<223> OTHER INFORMATION: n = A,T,C or G

<400> SEQUENCE: 158
tttttttaag ggtcaatgtt tacatttttt tcatataaat atcaagttgt cagcaccatc 60

-continued tgttgaaaaa aatctttgta atggctaatc ttttatgtca ttagatttga taatagttta 120
agaatttttg ttcctatatt catgagggtt gctttccttt aactttttttg ttttgtaatg 180 tctgtgtcag gntttactat tagaacaata ctagtctagt aaaaaaaaaa anaaacaaaa 240
aactancaag tgtntctccc cttctattta taanaanggn gttacttctt ccttaaatgg 300
nnaaattatg agngaaactt ggagtatcnt tgcnggantg gaagtttcct tgtggaaaga 360
attttatnat nattacattt caatagtncc gcntccctgc ncgggcggnn ntcaaaggcg 420
aatncagcaa attgntggcc gntactnngg accaacntcg gnccatnntg gggnancang 480
tcaanctgtt ctngnnaatt gtncccttcc aatncccaca nanaaccgaa cctaaatgga 540 acccngggc tantaangnc taccnntatt gngnggctnn gcccttnnnt ggaaactgnt 600
cnaccnttat aatggccccc cnggaaggnt tntttggcct tctnntncaa anctggcngg 660
nttntgtgna ggttatctna ntggatgttc cacgggaacn gaanatntan ncagtggacn 720
aaanntnntn ttttnct 737

<210> SEQ ID NO 159
<211> LENGTH: 739
<212> TYPE: DNA
<213> ORGANISM: Homo sapiens
<220> FEATURE:
<221> NAME/KEY: misc_feature
<222> LOCATION: (1)...(739)
<223> OTHER INFORMATION: n = A,T,C or G

<400> SEQUENCE: 159
cgagggtaca ctgtgagaga ataacatgga cttgatatgg catcacactt gttttaaagc 60
aaaaaaaaag aaaaaaagaa aaaaaagaaa gtacagttaa aaagtaagca ttgtagtaaa 120
tagtggattc tctggtgtgt attttttatc tcagtgttga aaattggaaa agaatgggct 180
gaagtctaaa aactggaata atgaaggaca ctaaatgcct ttattgtaga tactatgttt 240
gtaagtctat agctaagcaa cttaagccaa aaaggtcttt caactgaagc tttaatcaac 300
ttattttgga gatgttctct tccttatctc atgcgtcatc cctaaaataa taagatacat 360
gggatcaaat aacccttgcc ttttcaacac aaatcagttg gaaaattatg ggttgagtcc 420
tgttgctgcc atggttctgt tctcaaaatg agtgtgtatg acatcccatc tatgtaatag 480
gctacctttt tggctcttgg aactttgtcc tgccggccgg ccnttaaggc nantcnacca 540
ctggcggccg tactatgggn tccagctcgt ccaaccttgc tatcntggct acttttctgg 600
ngaatgtatc cgtncatccc cacttcancg gagctaangg aancntgggc ctatggggct 660
actccatatg ctngccnctg cnttcnangg aacncgcntc ttaanatgca cccnggaagg 720
gtngtngcct tcnttcttt 739

<210> SEQ ID NO 160
<211> LENGTH: 802
<212> TYPE: DNA
<213> ORGANISM: Homo sapiens
<220> FEATURE:
<221> NAME/KEY: misc_feature
<222> LOCATION: (1)...(802)
<223> OTHER INFORMATION: n = A,T,C or G

<400> SEQUENCE: 160
cgaggtacag cagagacctt cctgcttttt actggggact ccagattttc cccaaacttg 60
cttctgttga gatttttccc tcaccttgcc tctcaggcac aataaatata gttataccac 120

-continued

```
taaaaaaaaa aaaaaaaaag tacgcggggg cccattgttt ttgtaatctc tgaggagaag    180

cagcagcaaa catttgctag tcagacaagt gacagggaat ggattccaaa caccagtgtg    240

taaagctaaa tgatggccac ttcatgcctg tattgggatt tggcacctat gcacctccag    300

aggttccgag aagtaaagct ttggaggtca caaaattagc aatagaagct gggttccgcc    360

atatagattc tgctcattta tncaatatga ggagcaggtt gactggccat ncgaagcaag    420

aatgcagatg gcagtgtgaa gaaagaaaca tatttacctt taaagcttgg tcccttttna    480

tcgaccnaag tggtccgaca agcttggaaa attactngan aaagctcaat nggactatgt    540

gactcttttt aataatttcc anggntttaa acccgtgagg acttttcccc cgntaaatgg    600

aaagtatttt gcnannggac ttgacttccc ggngccntaa gngaattcac cactgggggg    660

gnttagggtc cnnntggnca anttggnaaa ngggtaatnn cntgnaatgt tcctcatccc    720

aantngccgn ataantaacc gggcaaaggg cccaaatggn gccctccttn nngaatnanc    780

cctntannna ancggggggg gg                                              802
```

<210> SEQ ID NO 161
<211> LENGTH: 214
<212> TYPE: DNA
<213> ORGANISM: Homo sapiens
<220> FEATURE:
<221> NAME/KEY: misc_feature
<222> LOCATION: (1)...(214)
<223> OTHER INFORMATION: n = A,T,C or G

<400> SEQUENCE: 161

```
acttttnntt tattcnttat ttttgggacc tgctctcact gtccacccag actggagtgc     60

antggcacca ttatagctna ctgcagcctt gacctnntgg gctcaagtga tcctnctgtc    120

tacacccccc aagnatgntg tgacattatg cttggataat acttgtatnt tangtaaaga    180

cagggtcttt ccnatnnacc nggnagatct naaa                                214
```

<210> SEQ ID NO 162
<211> LENGTH: 304
<212> TYPE: DNA
<213> ORGANISM: Homo sapiens
<220> FEATURE:
<221> NAME/KEY: misc_feature
<222> LOCATION: (1)...(304)
<223> OTHER INFORMATION: n = A,T,C or G

<400> SEQUENCE: 162

```
acttaggaat acaactatat acatatgatt ttatttttaa gaccatatta tatttgggta     60

tctactaata ttttgtataa agcaattttt tgttccatta cgtgactttt tgttttattg    120

tatatgtaat ttaacacaca ataaagggta aagttgcttc cccaaaccac acttttaatc    180

aaaacctaga atcatctgca gtccttgtta aaaatgcagg tttctagaac cctctgaagt    240

tctgattaaa taaatttatt gcaaatcaaa naaaanaaaa aaaaaaaaaa agnccccggg    300

gnta                                                                 304
```

<210> SEQ ID NO 163
<211> LENGTH: 461
<212> TYPE: DNA
<213> ORGANISM: Homo sapiens

<400> SEQUENCE: 163

```
actagagcca gtcatcctta acaaatcttt tcacatttta tttctttcac atgtagtcat     60

cttcaaaaag gaaagatttg gaattttaga aaaggggcaa ctcttctttt tagcattctc    120
```

-continued

```
atcagaaagt cacaaaaatc gatggaatca tttccactgg gaagattgac cttttgtatt    180

tatttgtggg gtaaattaat aagcattcca gatgcttgca gcttcctgca tccaggagat    240

gctgtgttcc ccgtgatgca gctggaaccc aagctgcagc aggagatgca agtttcagga    300

tgttccccac tgagctggag gaatatctac agcagtgatg cttgaaattt tgtatgaatt    360

attttgtcgc ctacccttttt cctccaaaca aaaattagag gattatttaa tccttgggat   420

cttccccttt ttgagaaata aagtttttat caaaaaaaaa a                        461
```

<210> SEQ ID NO 164
<211> LENGTH: 345
<212> TYPE: DNA
<213> ORGANISM: Homo sapiens
<220> FEATURE:
<221> NAME/KEY: misc_feature
<222> LOCATION: (1)...(345)
<223> OTHER INFORMATION: n = A,T,C or G

<400> SEQUENCE: 164

```
ttttttgag acaaggtctt actctgtcac ccaggctgga gtgcagtggc atgatcttgg      60

ctcactgcac cctctgcatc ccaggttcaa gtgattctcc tgtctcagcc tcccttgtag    120

ctgggattac agccacttgc cactgcaacc ggctaatttt tgtattctta gtagagatgg    180

ggttttacca tgttggccag gctggtcttg aactcctgac ctcaagtgat ccacctgcct    240

ccatgtccaa agtgctggga ttacaggcat gagccaccac ccctggccta agtcattaat    300

ttaaaaaatg ttattaggat gancgacctg ccgggcggcc gntaa                    345
```

<210> SEQ ID NO 165
<211> LENGTH: 385
<212> TYPE: DNA
<213> ORGANISM: Homo sapiens
<220> FEATURE:
<221> NAME/KEY: misc_feature
<222> LOCATION: (1)...(385)
<223> OTHER INFORMATION: n = A,T,C or G

<400> SEQUENCE: 165

```
actgaaacag aaactntacc caattgcagt ccatatgttt tctgggatcc cggagttccc     60

tttcaacaat gtaaaataca nacttaggtc aaaagttccc atgtctgaga aaactcaagc    120

caaatcagtt ctcctccaaa gttgacagga tttatgcttt aaaaatagag atacagaatt    180

ctctttggaa agatctacca aattcctgta agaaacagtc tacccaaagt aggggaaagg    240

ctatatgana agttcaaggc acttcttaaa aatatatctt aggttttagg gaaaggaaac    300

agacaagttt ccagacccgt gggtggaatg gatgtagcag atcactgaga ggttacaagc    360

gccgacctng gccgngacac gctan                                          385
```

<210> SEQ ID NO 166
<211> LENGTH: 745
<212> TYPE: DNA
<213> ORGANISM: Homo sapiens
<220> FEATURE:
<221> NAME/KEY: misc_feature
<222> LOCATION: (1)...(745)
<223> OTHER INFORMATION: n = A,T,C or G

<400> SEQUENCE: 166

```
tttttgacga tgtctctcaa caatacctga agtttctcat actcatcatc ccaagtctga     60

aaaacttcaa agcatgctac cataactttt tcaaattctt cataagcaac atgcatcaat    120
```

-continued

```
ttcctagtgc ccaatacttt gagtaattga gaactcaagt ctcttgaaat tgcctccacc    180

aaacgcagtg ccctctgaat aggatatttt gtgtttcgga tctttctcaa atcccgcgta    240

ctttgagaag ctgaggcggc agatcacttg aggccaggag ttcgagacca gtctcgtcaa    300

catggcgaaa ccctgctcta caaaaaaaaa aaaanaanaa aaattagcca gacatggngg    360

cccacatctg tagtcccagc tacttganan gctgaggcat gagaatagct tgacctggaa    420

nggcaaaggt ttantgancc caaactgngc ctggattcca atnnggngga cccagtgana    480

tttgtctcaa aaaaangaaa ggaaaaaaga gcccgncgga aggaaggatg gattgangga    540

aaattgtggc ctccnnnnaa aggnccaang gccctnangt ttctttgaat agtttccctn    600

gccnttctta ngggcctnng ccttttttcn nnctggcgaa cctaggnatt cacatggggg    660

ttangacncc gccnctggga naggaaagtn ctggaagnnc ncntcccaat ancgnntang    720

aacgggcngn ggannaattt tttnc                                          745
```

```
<210> SEQ ID NO 167
<211> LENGTH: 623
<212> TYPE: DNA
<213> ORGANISM: Homo sapiens
<220> FEATURE:
<221> NAME/KEY: misc_feature
<222> LOCATION: (1)...(623)
<223> OTHER INFORMATION: n = A,T,C or G

<400> SEQUENCE: 167

accagccact gcaaaaacat gccaaattgt aaagaccatc gaggctggga agaaactgca     60

tcaactaacg agcaaaataa ccagctaaca tcataatgac aggatcaaat tcacacgtaa    120

cactattaac ctgaaatgta aatggactaa attctccaat taaaagacac agactggcaa    180

attggataaa gagtcaagac ccatcagtgt gctgtattca ggagacccat ctcatgtgca    240

gagacataca taggctcaaa ataaaggaat ggaggaagat ctaccaagca aatggaaaac    300

aaaaaaaggc aagggttgca atcctagtct ctgataaaac agattttaaa ccacaaagat    360

caaaagagac aaagaaggcc attacataat ggtaaaggga tcaattcaca agaagggcta    420

ctattctaaa tatatatgca cccaatacag gacccccaga ttcatgaagc aaatccttga    480

gattnccaaa ggattaactc cncccngtat tatggagact tncacccact ntnacctttc    540

ccgatcttgn cccaaagtac cnggtttccc gaattgactn gtttgncann gggctattaa    600

tttngaattt cncccaaaaa aaa                                            623
```

```
<210> SEQ ID NO 168
<211> LENGTH: 703
<212> TYPE: DNA
<213> ORGANISM: Homo sapiens
<220> FEATURE:
<221> NAME/KEY: misc_feature
<222> LOCATION: (1)...(703)
<223> OTHER INFORMATION: n = A,T,C or G

<400> SEQUENCE: 168

ggtactccct gtttgctgca gaatgtcaga tattttggat gttgcataag agtcctattt     60

gccccagtta attcaacttt tgtctgcctg ttttgtggac tggctggctc tgttagaact    120

ctgtccaaaa agtgcatgga atataacttg taaagcttcc cacaattgac aatatatatg    180

catgtgttta aaccaaatcc agaaagctta aacaatagag ctgcataata gtatttatta    240

aagaatcaca actgtaaaca tgagaataac ttaaggattc tagtttagtt ttttgtaatt    300

gcaaattata tttttgctgc tgatatatta gaataatttt taaatgtcat cttgaaatag    360
```

-continued aaatatgtat tttaagcact cacgcaaagg taaatgagca cgttttaaat gtgtgtgtgc 420
taattttttc cataagaatt gtaaacattg actgaacaaa tacctatatg gattggtaat 480
gacttatgag caanctgctt ggccagacag ttacccaaac tttatatatn tnngaaggta 540
tacactgnga aatctctggc taancgaatg cntccagggg taanngggtn tggntggant 600
aaanaatgcc ctgcaaaaaa aaaaaaaaaa aagccttccg nggccttnaa nggaatcnnc 660
angggnntnn ggccactggc cactggnaaa ngnaacgtct gga 703

<210> SEQ ID NO 169
<211> LENGTH: 609
<212> TYPE: DNA
<213> ORGANISM: Homo sapiens
<220> FEATURE:
<221> NAME/KEY: misc_feature
<222> LOCATION: (1)...(609)
<223> OTHER INFORMATION: n = A,T,C or G

<400> SEQUENCE: 169
acgtccatct tccagctgct tgccagcaaa gatcagtctc tgctgatcag gaggaattcc 60
ttccttatcc tggatcttgg cctttacatt ttctatcgta tccgagggtt caacctcgag 120
ggtgatggtc ttaccagtca gggtcttcac gaagatttgc atcccacctc tgagacggag 180
caccaggtgc agggtggact ctttctggat gttgtagtca gacagggtgc gtccatcttc 240
cagctgtttc ccagcaaaga tcaacctctg ctggtcagga gggatgcctt ccttgtcttg 300
gatctttgcc ttgacattct caatggtgtc actcggctcc acttcgagag tgatggtctt 360
accaagtcag ggtcttcacg aagatctgca tcccacctct aagacggagc accaggtgca 420
gggtggactc tttctggatg ttgtaatcag acanggtgcg ttcatctttc actgnttcca 480
caaaaaacaa cctctgctgg canganggat ccttccttnc ttggactttg cctgacattc 540
tnatggngta ctccgctccc ttcaaaggga tgncttacan tcanggnctt acnaaaattt 600 cntccnctt 609

<210> SEQ ID NO 170
<211> LENGTH: 617
<212> TYPE: DNA
<213> ORGANISM: Homo sapiens
<220> FEATURE:
<221> NAME/KEY: misc_feature
<222> LOCATION: (1)...(617)
<223> OTHER INFORMATION: n = A,T,C or G

<400> SEQUENCE: 170
acaaagaaca tgtagctata ggaaataata gtgtaaatag cagtatataa actggcccat 60
gtaaaataca aaaatattca ctgaagtcag gttttctata aaacagtgtt tattagaggt 120
attttactat gaatcaggca tataatctga atgtagaaac ttttagaaat attaacagca 180
ttcagtcagt gccatgcact tgtgcttcca attatttttt taaagctgct ttgttttgac 240
tcatgtgaaa tagttaaggc ctacattctt atacacatta tccatcttac aaggttaaca 300
attttacact aaaacacagt ttaaattaaa aacgattttg aaaaattaca tctatattta 360
atccctaaga agtgttttaa gctggtaatg cagctcgctg tagctctaag agaggggtta 420
gtcaggaatc tgatcttgag ccataaangg tttcaggcta aacaaagaac aaatttaagt 480
gacagaaaat attataattn caatatactc agttttttgg tataaaatac cctgctagca 540
tgccactggc tatattgngg gcataatata aaatgncggg gggggggatg gancctccaa 600

-continued

```
gncaaanttt ggaccca                                                  617

<210> SEQ ID NO 171
<211> LENGTH: 621
<212> TYPE: DNA
<213> ORGANISM: Homo sapiens
<220> FEATURE:
<221> NAME/KEY: misc_feature
<222> LOCATION: (1)...(621)
<223> OTHER INFORMATION: n = A,T,C or G

<400> SEQUENCE: 171

acagtatggg ggttgtaaat tggcatggaa atttaaagca ggttcttgtt ggtgcacagc     60

acaaattagt tatatatggg gatggtagtt ttttcatctt cagttgtctc tgatgcagct    120

tatacgaaat aattgttgtt ctgttaactg aataccactc tgtaattgca aaaaaaaaaa    180

aagttgcagc tgttttgttg acattctgaa tgcttctaag taaatacaat tttttttatt    240

agtattgttg tccttttcat aggtctgaaa tttttcttct tgaggggaag ctagtctttt    300

gcttttgccc attttgaatc acatgaatta ttacagtgtt tatcctttca tatagttagc    360

taataaaaag cttttgtcta cacaccctgc atatcataat gggggtaaag ttaagttgag    420

atagttttca tccataactg aacatccaaa atcttgatca gttaaaaaat ttcacataac    480

ccacttacat ttaccaactg gaagaataat caatctctca agcatgggat tattagaatc    540

aacantttga aagctgtcct tgaaggctaa taaaaaagnt tgtctaacct ttcatgaggn    600

cttnttntta ctnccttacn g                                              621

<210> SEQ ID NO 172
<211> LENGTH: 399
<212> TYPE: DNA
<213> ORGANISM: Homo sapiens

<400> SEQUENCE: 172

actcaaaatt acacatttgt ttaaataaat atccacacaa attctcagtt acatcaagta     60

gctggtttat atttagatta tctcaagtag gggggaataa ccatgtgtag gaattcatag    120

aaaaataaac aatcagctga agaggtctaa gaaaatgctg acttttaaaa tttcacttat    180

tttccttgaa gttttctacc cttcccatcg atgataaacc aagatcatgt aatggaaaat    240

ttcaaaccag ggctaaattc taaagtaaag cttcaattca agcccttccc ccaagagaat    300

taattttcct gatttctctt tctctcacat ctaaggagaa cattttaggc agttaaattt    360

cagaacttca aggtttcatc agggtcacct ttatgtacc                           399

<210> SEQ ID NO 173
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 173

actttgtgga taagaaaatg gaggaacaca tctgatggag agtgggcatt tgacaacaat     60

ggaacaggta acctgcatgt aaaatcaaaa tataagtgtc tttttaagag ctgaaagctg    120

ctgctggtca ttcattaatg tgtcagacat ttaatcagga tgctggacct tcaaaataac    180

tgaaaaaaga accaagaaaa ggcgtttttg ttttcaacaa actttactaa ataaccctgg    240

aaaggcaatg aacgatctga caatttaagc tctaatgatt taaagctcag ctagaagaaa    300
```

-continued gtgaggcatg acatatactg tcaacggagg gtgaaggagg canatttctg gaaatgcaat 360
gatcccacca tttgcttcaa ngagaaacct gcanacatat tttcangtct tgntaagtna 420
caactgtnta tttgtaatca atcatttngg aaaagtctgc tatgtaactt angncactgt 480
gcccccnacc accgatgaaa aggaaaaacc cctgacacca ggaaaatcct tccatcctca 540
aanaaattaa gngaccaacn tttaaagaaa aaaaatnanc ccncctctnt ttacaaatnt 600
ttcntccaaa tnttcn 616

<210> SEQ ID NO 174
<211> LENGTH: 631
<212> TYPE: DNA
<213> ORGANISM: Homo sapiens
<220> FEATURE:
<221> NAME/KEY: misc_feature
<222> LOCATION: (1)...(631)
<223> OTHER INFORMATION: n = A,T,C or G

<400> SEQUENCE: 174
ggtacgcggg gacacgcacg ccgggcgtgc cagtttataa agggagagag caagcagcga 60
gtcttgaagc tctgtttggt gctttggatc catttccatc ggtccttaca gccgctcgtc 120
agactccagc agccaagatg gtgaagcaga tcgagagcaa gactgctttt caggaagcct 180
tggacgctgc aggtgataaa cttgtagtag ttgacttctc agccacgtgg tgtgggcctt 240
gcaaaatgat caagcctttc tttcattccc tctctgaaaa gtattccaac gtgatattcc 300
ttgaagtaga tgtggatgac tgtcaggatg ttgcttcaaa agtgtgaagt caaatgcatg 360
ccaacattcc agttttttaa gaaagggaca aaaggtgggt gaattttctg gagccaataa 420
ggaaaagctt gaagccacca ttaatgaatt aatctaatca tgttttctga aaacataacc 480
accattggct atttaaaact tgtaattttt ttaattttcc aaaatttaaa tttgaanact 540
taaccccant tgccatntgn gtgacaataa aacattatgc tacccntttt aaaaaaaaaa 600
aaaaaaaaaa agtcctgccc ggcggccctc a 631

<210> SEQ ID NO 175
<211> LENGTH: 261
<212> TYPE: DNA
<213> ORGANISM: Homo sapiens

<400> SEQUENCE: 175
acgaacctac agttttaact gtggatattg ttacgtagcc taaggctcct gttttgcaca 60
gccaaattta aaactgttgg aatggatttt tctttaactg ccgtaattta actttctggg 120
ttgcctttgt ttttggcgtg gctgacttac atcatgtgtt ggggaagggc ctgcccagtt 180
gcactcaggt gacatcctcc agatagtgta gctgaggagg cacctacact cacctgcact 240
aacagagtgg ccgtcctaac c 261

<210> SEQ ID NO 176
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 176
cgaggtactc tgccttttag gagatgaggt aagacatata catagatggc ttttactagc 60

-continued

```
caaggcaatg taaatggact aagattctca tgtgacttga ggttatctga tgaatttatt    120

ctcttcaaaa ccacctacct ttagagggca tgtttaaccc ctctctttat ttaaggaggg    180

agagaaaaac acatgtaacc agaattcaga gtgggttact caacctaaga gaacatacgg    240

agttctcttt gggaaaacaa caagactaca gtgttcactt cgcaccatga agtggcactc    300

ctgttatggc tgtcagagtc ctctcacttc ttatgaaagg atgcatctga ttctgaaatt    360

actgatatat tcgatcagtt anggatgttt taaaaagtga aaacaaatgc cacacataca    420

ctttctagct ttcttgaaat cacccgacac attccaaaaa tagagaattc cctattactt    480

ttagagaaat ttccatatan tcttggtnaa gaanccagtt gngcntattc caatttcagg    540

gtcttggttt ttgcccaaac ccaagtgttt ccntntttta nggcttttca tggccgattt    600

naaaccttnt ttgtgg                                                    616


<210> SEQ ID NO 177
<211> LENGTH: 632
<212> TYPE: DNA
<213> ORGANISM: Homo sapiens
<220> FEATURE:
<221> NAME/KEY: misc_feature
<222> LOCATION: (1)...(632)
<223> OTHER INFORMATION: n = A,T,C or G

<400> SEQUENCE: 177

cgaggtacag gtcagagtct tcttttcttt tctttttgag atggagtctt gctctgttgc     60

cagactggag tgcagtggtg cgatctgggc tcactgcaat ctccacctcc cgggttcaag    120

cgattctcct gcctcagcct cccgagtaac tgggactaca ggtgtgcgcc accaagccca    180

gctcattttt gtatttttag tanagatggg gtttcacggt gttggctagg atggtctcga    240

tctctggtca gaagtctttt ctgtaaatat ccttggtaaa gaagcaattt tagactgtag    300

ctgttgcaaa tgctttaagg aagaagcaaa acaactgtca gtcttcctga aatgaaaaaa    360

ctacaccagg gctgctatat caaagcaacc ccaaccagca cttcaatcat gatgcccaca    420

gtggccccac tgagaaacca agaaaagttn cagatacaaa actgngatgc tcttgctatg    480

gnaatattgc nggcngtanc caagttagaa accaaacaag cntanggccc cgttnttttt    540

tggcgtgatt ttggcaanaa aaaaaactgg gngngtggtg ngggttccca ttgtaccccc    600

aaaaaacttn gggatgggtt aaagcccnng gc                                  632


<210> SEQ ID NO 178
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 178

actttntttt tttttttttt tttttttttg ggatttagtt tttatttcat aatcataaac     60

ttaactctgc aatccagcta ggcatgggag ggaacaagga aaacatggaa cccaaaggga    120

actgcagcga gagcacaaag attctaggat actgcgagca aatggggtgg aggggtgctc    180

tcctgagcta canaaggaat gatctggtgg ttaagataaa aaacaagtca aacttattcg    240

agttgtccac agtcagcaat ggtgatcttc ttgctggtct tgccattcct ggacccaaag    300

cgctccatgg cctccacaat attcatgcct tctttcactt tgccaaacac cacatgcttg    360

ccatccaacc actcaatctt ggcagtgcag atgaaaaact gggaaccatt tgtgttgggt    420
```

-continued

```
ccaacatttg ccatggacaa aatccangac ccgtatgctt taagatgaaa ttctcatttc    480

aaatttcttc ccataaatgg acttgccnca tgccatnttg ggtgtgaagt nccnccttgc    540

ncataaccct ggaatatttt tgaaacagaa ccttttacca atcntttttt catgttaaaa    600

acnaaaattt t                                                         611
```

<210> SEQ ID NO 179
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 179

```
acctcaattt tatcatttta gagtatttgt tagaatagga tctctccaaa atcaaacagg     60

atcaatctgg tcacgtctaa tcctaagaca aaacactatg taaaattttc ctgtatctaa    120

atgttgccct ctaggtaaat ctgtgatatt ttagagactt tcttttgtgg aaaaggtaat    180

ctgataaatg ggaagagatc atcagacaag ttcacaaata accattattt ctgcagaatt    240

cagttgaagt tggtttttttg taaatgctta ttgggaattt ctaaagcact gacttggaga    300

ggccaagagc ctccatcaat ccctgcttgg atagccactc ccgttactac tgctaggtca    360

gggtctacag atgtgttggg atcttttcca aagaactctt gaatgacttg acggatccga    420

ggaataccaa tggagccccc aactaaaacc acctcatcaa tctcagtctt ttncaggtgg    480

ncttcttcaa tctcctgaat gggacctcgg ccgcancacn ctanggcgaa ttccacacct    540

ggcggccgta ctaatggatc caactcgnac caacttgggg aacatggcta gtnttcnngg    600

ggaaatgttt c                                                         611
```

<210> SEQ ID NO 180
<211> LENGTH: 621
<212> TYPE: DNA
<213> ORGANISM: Homo sapiens
<220> FEATURE:
<221> NAME/KEY: misc_feature
<222> LOCATION: (1)...(621)
<223> OTHER INFORMATION: n = A,T,C or G

<400> SEQUENCE: 180

```
acccttaaac tggcaggaca tttttgaaat cacaaatttg cacataaaga atgtcacgaa     60

cagccatgta tccatataca gcaatcaaat aaggaactta tgacctaaag caaaggtaaa    120

ctttcttgaa acttaacatt ctataccaac taggcaacct ctgcccagga tgagagttgg    180

atttttcaaa aacctctaat ttaatagtgc agcatttcgt tttccctgat ggcctgtgtt    240

tcacagcagt ttttaaaaac tgcttgttca actatagctg cagcctatat cccagctatg    300

gaaaaaaaag taaatcttag ttcaattttt gccagttgtt tctgtattta aatttaaaaa    360

aaaacacact tccgctgggc aggtttagag ggttattatc aagtctgtgc ataactaaaa    420

gttcaaagca aattcaattt tgcttaangg aacattgnna aagnacaatt cttggnanta    480

catgcctcgt tgatccattt naancatana aaattcaccc ttgtgtactg gttcaagaaa    540

aaaaccgatt tgacagttaa acatnttaaa anccccaacc tntgaagttc aaccaaactg    600

gantttttgtt cctcgcccga c                                              621
```

<210> SEQ ID NO 181

-continued

<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 181
cgaggtacag accagagaca aagcaagaga agaagcagag actgttggcc cgggccgaga 60
agaaggctgc tggcaaaggg gacgtcccaa cgaanagacc acctgtcctt cgagcaggag 120
ttaacaccgt caccaccttg gtggagaaca agaaagctca nctggtggtg attgcacacg 180
acgtggatcc catcgagctg gttgtcttct tgcctgccct gtgtcgtaaa atgggggccc 240
cttactgcat tatcaangga aaggcaagac tgggacgtct agtccacaag gaagacctgc 300
accactgtcg ccttcacaca ggtgaactcg gaagacaaag gcgctttggc taaactggtg 360
gaagctatca ggaccaatta caatgacnga tacnatgaga tccccctcct ggggtggcaa 420
tgtcctgggt ctaaatctgt ggcttgtatn gccaacttcn aaangcaaag cttaaaaact 480
tgcncttaac tngggtnaat gtactncccg gcggccgttg aanggcaatt caacacattg 540
cggccgtcta atggntcanc ttggnccaac ttgggnaana tggnaaannn ttcttgggna 600 atttnn 606

<210> SEQ ID NO 182
<211> LENGTH: 610
<212> TYPE: DNA
<213> ORGANISM: Homo sapiens
<220> FEATURE:
<221> NAME/KEY: misc_feature
<222> LOCATION: (1)...(610)
<223> OTHER INFORMATION: n = A,T,C or G

<400> SEQUENCE: 182
ggtactcata aaaaaagtct taccccaaaa ttgcaaacaa atacattaaa agattagaag 60
aggtgataga aagcaccaga cattaaacaa aataaaaata ataaaataaa ttcaactcaa 120
aaggtcccca ttcagcaaat actttgtaaa gtatggcctg tatgtaaata gtgctaaatc 180
aaggactttt tagcagaaaa ttgctcggtt cttttatcta aggcttgaat ttgtaaagtg 240
aaggcataaa agttaccaaa cattaagtaa ctcttaaaat ggcacacagg ttttaaagct 300
attggttttt ccttcctaac tctctgaatt tttcccatgg cctttgtaga tcaactattt 360
caaacgtatt ttacaccagc aactctcaac atacttgtct ttcagatatg tcatcagtca 420
tgtctaacag gccaatagcc aaataacnga tttaaaacaa tncttaacta gctagcagga 480
cattactttg gatctgctta ctgcaactga ctatttgtaa gcttaaaatc antttaatcc 540
tgatacagaa acctcatctg cncatacntt actttggcct tcaaccttta aaaatactta 600 atcccccgnc 610

<210> SEQ ID NO 183
<211> LENGTH: 608
<212> TYPE: DNA
<213> ORGANISM: Homo sapiens
<220> FEATURE:
<221> NAME/KEY: misc_feature
<222> LOCATION: (1)...(608)
<223> OTHER INFORMATION: n = A,T,C or G

<400> SEQUENCE: 183
cgaggtactt tttttttttt tttttttttt tttttatttt tttttttttt tttttttttt 60

-continued

```
tttttttggg agncagctnt ttaattaggn tcttaaaaca tttaaaacnc caatttgnga    120

ggataaattc cattcgtcan ancaaacnca aatcgcaggt ancccctggan ctgaggaata    180

nctttgattt ttggnaaaat ttgngagtcc acagctttnt gatcaatntt gcnctgctcc    240

gnaatctcat atttctnttt ttctgngncg aaaatctcac cttcctggng tntgggcttc    300

cgcagcttnt tntttttgaa gtaagcatca ataaaangtt ttgggatttt tacattgctg    360

aaatccattt tgggtgaagg ggcaatgaca aatttntngn gtnttctttt taaaagaacc    420

tcattggggg ccnaaggncc cncccaaatt ataaacccct ttccccctgg tttangnaaa    480

cccccctttg ccctgngggg nccangagga taaanaaagg ccccggggaa gctggcccca    540

ntttttcccg ccgncgaagg gttttgccgg ctaaaanttt tngggcattt nnngggnaat    600

tttggctt                                                              608
```

<210> SEQ ID NO 184
<211> LENGTH: 622
<212> TYPE: DNA
<213> ORGANISM: Homo sapiens
<220> FEATURE:
<221> NAME/KEY: misc_feature
<222> LOCATION: (1)...(622)
<223> OTHER INFORMATION: n = A,T,C or G

<400> SEQUENCE: 184

```
acagccctga tgcaaagttt cagagcatga ccagcaagtg gccagctgtg tgggtcaaga     60

tcagctccag ctgggtctgc ctcctgcttt acgtctggac ccttgtggct ccacttgtcc    120

tcaccagtcg ggacttcagc tgaacctctg agtgccaagg acaccactgg aactcacaaa    180

ggtctccttc accgaaaacc catatacctt ttaagtttgt ttcaactaaa atattaagtg    240

aatgctttgc aagtttgact gtatgcaggt ttatatcaag aaggtgagat tgaataatgc    300

ttgatgcaga atcgaaactt ctcatttatc tgnatattat gtttacttct aaggatatag    360

cacaaaggga acattttttg tttaaagtga actacagctg tgctgtgaag agagttcttt    420

ataaagcctg taggtctttt aactttggtt aaaatgtaag ataggaaaat gttggatatt    480

tgaggcntgc ctaatatatt tatattggag natcctttna aagccaaaaa aaaaaaaaaa    540

aaaaaaaagt nccttggccg gaccncccta aggggaattc cacncactgg gggccgtntt    600

atggatccaa ctcgnaccaa ct                                              622
```

<210> SEQ ID NO 185
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 185

```
acgcggggac agtcccaccc tcacacgatt ctttaccttt cacttcatct tgcccttcat     60

tattgcagcc ctagcagcac tccacctcct attcttgcac gaaacgggat caaacaaccc    120

cctaggaatc acctcccatt ccgataaaat caccttccac ccttactaca caatcaaaga    180

cgccctcggc ttacttctct tccttctctc cttaatgaca ttaacactat tctcaccaga    240

cctcctaggc gacccagaca attataccct agccaacccc ttaaacaccc ctccccacat    300

caagcccgaa tgatatttcc tattcgccta cacaattctt cgatccgtcc taacaaacta    360
```

-continued

```
agaggcgtcc ttgccctatt actatccatc ctcatcctag caataatccc atccttcata    420

tatcccaaca acaaagcata atatttcgnc cactaagcca atactttatt gattctagcc    480

ggagacctct nantntaacc tggatcggag gaaaccagta gctacccttt accaatantg    540

ganaagaaga tcgnaccttg gcgggacacc ttangggaat tcaaccactg gnggcggtat    600

atgggacccn ccng                                                      614
```

<210> SEQ ID NO 186
<211> LENGTH: 627
<212> TYPE: DNA
<213> ORGANISM: Homo sapiens
<220> FEATURE:
<221> NAME/KEY: misc_feature
<222> LOCATION: (1)...(627)
<223> OTHER INFORMATION: n = A,T,C or G

<400> SEQUENCE: 186

```
ggtactgatt ttaaaaacta ataacttaaa actgccacac gcaaaaaaga aaaccaaagt     60

ggtccacaaa acattctcct ttccttctga aggttttacg atgcattgtt atcattaacc    120

agtcttttac tactaaactt aaatggccaa ttgaaacaaa cagttctgag accgttcttc    180

caccactgat taagagtggg gtggcaggta ttagggataa cattcattta gccttctgag    240

ctttctgggc agacttggtg accttgccag ctccagcagc cttcttgtcc actgctttga    300

tgacacccac cgcaactgtc tgtctcatat cacgaacagc aaagcgaccc aaaggnggat    360

agtctgagaa gctctnaaca cacatgggct tgccaggaac catatnaaca atggcagcat    420

caccagactt naagaattta agggcatctt ccacttttta ccaaaacngn gaacaatctt    480

tttcnttact taacnaacnt gcttccatgg gagccgggng naatccaatc aagggcataa    540

cccgggcctt atttggcnng atgggtcang gnaatancct gaccaggaaa cccctgnttc    600

cttgggggga antttgttgn nccccac                                        627
```

<210> SEQ ID NO 187
<211> LENGTH: 256
<212> TYPE: DNA
<213> ORGANISM: Homo sapiens
<220> FEATURE:
<221> NAME/KEY: misc_feature
<222> LOCATION: (1)...(256)
<223> OTHER INFORMATION: n = A,T,C or G

<400> SEQUENCE: 187

```
ggaccttttt tttttttttt tttttttttt ggaaaagaaa ggccttacat atttattact     60

gaatccagcc aaccaacgtg ttcataacag attcagagag gaaaacacgt cgaaatctcc    120

anatagtggt gacattttca gcttgatatg gtaacatgat cgtgaccttc anacagcata    180

aatatgtgtg ccatctcatg tgcaattcct tatanaccca gcttggttct tctccaatgt    240

ctccttttgg agttgt                                                    256
```

<210> SEQ ID NO 188
<211> LENGTH: 523
<212> TYPE: DNA
<213> ORGANISM: Homo sapiens
<220> FEATURE:
<221> NAME/KEY: misc_feature
<222> LOCATION: (1)...(523)
<223> OTHER INFORMATION: n = A,T,C or G

<400> SEQUENCE: 188

```
ggtaccacct acacccaaca agtcaatgag ggacttcttt ttaatttggt aggattttga     60
```

-continued

```
ctggttttgc aacaataggt ctattattag agtcacctat gacaaaaaat aggggttacc    120

tagataatgc caaagtcagc atttgtcctg ggttcccttg tgtgatctgt ttggactatg    180

ttttcttttc ttctcccact tgctcagcag cttgggcttc cattctagct cttttaccaa    240

gatttttgtg tgaccatgtt gacttcattt ggattgccct ctttcaattt ccttgtgaaa    300

acacccttaa ctttctcttt acccttagct gaaatgttta cataacttct ggtgatatct    360

tttcatgatt ttatatctct taaaatggtg atggatgtga cacctcataa aagtgagctt    420

tgaactgtag ataactctta aagaaaatgt cattttanac aattaaaata tttgtgctca    480

aaaaaaaaaa aaaaaaaaaa gtcctgcccg gcggccgtcn aan                      523


<210> SEQ ID NO 189
<211> LENGTH: 622
<212> TYPE: DNA
<213> ORGANISM: Homo sapiens
<220> FEATURE:
<221> NAME/KEY: misc_feature
<222> LOCATION: (1)...(622)
<223> OTHER INFORMATION: n = A,T,C or G

<400> SEQUENCE: 189

acaatttaat ttttctgctt gcccaagaaa caaagcttct gtggaaccat ggaagaagat     60

gaaaatgaga ctggcaaaga acaaatgctg aatctgaaga agaggacaac tttgggcaaa    120

taatctgcat acttttaatt gggaataaga tggaaaatat gaatgctaaa tcaaattttt    180

taaaaaatac accacacgat acaactcaat acaggagtat ttcttctcaa attcttctag    240

caccatcaac attcttcaag tatctgaaat actattaatt aagcaccttt gtattatgaa    300

caaaacaaaa caaggacctc agttcatctc tgtctaggtc agcacctaac aatgtggatc    360

acactcatgg gaaagtgttt tgaggtagtt taaacctttt ggaaggttgg gttttaaact    420

tccctctgtg gaagatatca aaagccccaa gtggtgccaa atggttatgg ttttattttt    480

caattttaat ttgggtttct tccaaaggtg acatttccat acaaggggaa gggggtggaa    540

aaaaaatcaa attttggggg accagggagg ataatnaact gtttgcaatg cttgacaacc    600

tttttttttt gnccaantaa ca                                             622


<210> SEQ ID NO 190
<211> LENGTH: 628
<212> TYPE: DNA
<213> ORGANISM: Homo sapiens
<220> FEATURE:
<221> NAME/KEY: misc_feature
<222> LOCATION: (1)...(628)
<223> OTHER INFORMATION: n = A,T,C or G

<400> SEQUENCE: 190

accactaata gggtgtatct cagaaactga attgaaataa gggaaaatag gattttctgt     60

cctggttttt gaagattgtt cttgattccc ttgattccca ggagagattc tctgacattc    120

acgtgtcagc cactttggca cggaagcctt acagtgtggg gaaccaaaac ttcgtgtctc    180

ctctttcccc gatgccatca gcatagactt gacttcctta aaccgagagt tttgatgtgg    240

ccttggcaac cctaaaatca gctgtgttag gtaacaaaac tcaggctttc tgttgatgac    300

atcgagatgg tgtcacttaa aagagccaag attcctgttt tcagtttgtg gattcatcct    360

gctggtttta ctttagtccc tccatgtcaa agtgggcctg agaaaagctc atacatgcct    420

catgtgaagt gtccaccccc tctgaaaatc tttcttgttc aaaacancna cgacatatct    480
```

-continued

```
tggtaacttt tacggtgact tttggangag gggagtttgg aaattgtaaa atgttatana    540

tggtgcctat ttcctgctga angaaatgtt ttaaaaagnn tntntaancn taatcnaatg    600

gttggggggn gaccttctac cnaanntn                                       628


<210> SEQ ID NO 191
<211> LENGTH: 474
<212> TYPE: DNA
<213> ORGANISM: Homo sapiens
<220> FEATURE:
<221> NAME/KEY: misc_feature
<222> LOCATION: (1)...(474)
<223> OTHER INFORMATION: n = A,T,C or G

<400> SEQUENCE: 191

ggtacagccc tcaatctgtt cttcaagctc aagaacttca agacagctgc cacctttgct     60

cggcgcctac tagaactcgg gcccaagcct gaggtggccc aacagacccg aaaaatcctg    120

tctgcctgtg agaagaatcc cacagatgcc taccagctca attatgacat gcacaacccc    180

tttgacattt gtgctgcatc atatcggccc atctaccgtg gaaagccagt agaaaagtgt    240

ccactcagtg ggcctgcta ttcccctgag ttcaaaggtc aaatctgcag ggtcaccaca    300

gtgacagaga ttggcaaaga tgtgattggt ttaaggatca agtcctctgc agtttcgcta    360

aagccccctt tgtgtgcatg ggtcaagtca ccatatgttc cccccaaaaa atgtgtctat    420

atctccttct aacaacacct tcccctgcac tactcttcaa atctngctct ntgt          474


<210> SEQ ID NO 192
<211> LENGTH: 234
<212> TYPE: DNA
<213> ORGANISM: Homo sapiens

<400> SEQUENCE: 192

acgcgggggt tggtgagtgg gctcctaccg accgaggttt aggcagcgcg gggagctttg     60

cgggttgcca tttgtaactc cggatcctaa aattcctgtc ctgttctctg tctcttctag    120

gttgggggcc gtcccgctcc taaggcagga agatggtggc cgcaaagaag acgaaaaagt    180

cgctggagtc gatcaactct aggctccaac tcgttatgaa aagtgggaag tacc          234


<210> SEQ ID NO 193
<211> LENGTH: 367
<212> TYPE: DNA
<213> ORGANISM: Homo sapiens

<400> SEQUENCE: 193

ggtaccaata ccaccaattt tgtagacatc ctggagaggc aggcgcaagg gcttgtcagt     60

tggacgagtt ggtggtagga tgcagtccag agcctcaagc agcgtggttc cactggcatt    120

gccatcctta cgggtgactt tccatccctt gaaccaaggc atgttagcac ttggctccag    180

catgttgtca ccattccaac cagaaattgg cacaaatgct actgtgtcgg ggttgtagcc    240

aattttctta atgtaagtgc tgacttcctt aacaatttcc tcatatctct tctggctgta    300

gggtggctca gtggaatcca ttttgttaac accgacaatt agttgtttca cacccagtgt    360

cccgcgt                                                              367


<210> SEQ ID NO 194
<211> LENGTH: 613
<212> TYPE: DNA
<213> ORGANISM: Homo sapiens
<220> FEATURE:
<221> NAME/KEY: misc_feature
```

-continued

<222> LOCATION: (1)...(613)
<223> OTHER INFORMATION: n = A,T,C or G

<400> SEQUENCE: 194
ggtactcttg gtttgtcaat gggactttcc agcaatccac ccaagagctc tttatcccca 60
acatcactgt gaataatagt ggatcctata cgtgccaagc ccataactca gacactggcc 120
tcaataggac cacagtcacg acgatcacag tctatgcaga gccacccaaa cccttcatca 180
ccagcaacaa ctccaacccc gtggaggatg aggatgctgt agccttaacc tgtgaacctg 240
agattcagaa cacaacctac ctgtggtggg taaataatca gagcctccgg tcagtcccag 300
gctgcagctg tccaatgaca acaggaccct cactctactc antgtcacaa ggaatgatgt 360
aggaccctat gagtgtggaa tccanaacga attaagtgtt gccacagcga cccagtcatt 420
ctgaatgtcc tctatgncca gacgaacccc catttcccct catacccctan taccgtcaag 480 ggtgaacctt agctttctgc atgcagcttt aaccactgcc agtttcttgn tgatgatgga 540
catcacacca cacaagactn ttatttcaca tactgagaan aaagcgactt ntactgcagg 600
cataactanc ngg 613

<210> SEQ ID NO 195
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G

<400> SEQUENCE: 195
acgcgggcgc cagagtccct gaactctcgc tttcttttta atcccctgca tcggatcacc 60
ggcgtgcccc accatgtcag acgcagccgt agacaccagc tccgaaatca ccaccaagga 120
cttaaaggag aagaaggtga tggtgaggaa gaggatggag atgaagatga ggaagctgag 180
tcagctacgg gcaagcgggc agctgaagat gatgaggatg acgatgtcga taccaagaag 240
cagaagaccg acgaggatga ctagacagca aaaaaggaaa agttaaacta aaaaaaaaaa 300
aggccgccgt gacctattca cccttcactt tccgtctnaa aatctaaacg tggtcacctt 360
caataaaaag gccccccgcc cccngggcag tgccccccca aaataaacgc gctttcacca 420
ccaaccaaac atgaaaattt tccacaaggg anggaaaaaa aaccaaacnt ccaaggcctn 480
ttttttttta aaatactngg ccgcgaccac cctanggcga attccanacc tggcggccgt 540
nttatggatc cnactcggac caacttgggn aatatggcat antggttctt ggngaaatgt 600
atccctccat tcn 613

<210> SEQ ID NO 196
<211> LENGTH: 296
<212> TYPE: DNA
<213> ORGANISM: Homo sapiens
<220> FEATURE:
<221> NAME/KEY: misc_feature
<222> LOCATION: (1)...(296)
<223> OTHER INFORMATION: n = A,T,C or G

<400> SEQUENCE: 196
gcggnggcnn ggccgacgnn ctcatcaatg ttgttcggtc agcccttccc taattacacc 60
tatccnctac acatacatgc acatagacac acncntgaac ncactgaana tatttccttc 120
aggtgtgtgt aaaatatgct gcttggattg aaattcannt gggattgatt agncaagtan 180

-continued cttganacct cacagtaatc ttcacacttn nccttacaca cctatgcagg catgttggga 240
gcangttaca atgttacttc agcccacagt ttatttctat acttgagttc ttaagt 296

<210> SEQ ID NO 197
<211> LENGTH: 222
<212> TYPE: DNA
<213> ORGANISM: Homo sapiens

<400> SEQUENCE: 197
acatggagga gaatgaccag ctcaagaagg gagctgctgt tgacggaggc aagttggatg 60
tcgggaatgc tgaggtgaag ttggaggaag agaacaggag cctgaaggct gacctgcaga 120
agctaaagga cgagctggcc agcactaagc aaaaactaga gaaagctgaa aaccaggttc 180
tggccatgcg gaagcagtct gagggcctca ccaaggagta cc 222

<210> SEQ ID NO 198
<211> LENGTH: 539
<212> TYPE: DNA
<213> ORGANISM: Homo sapiens

<400> SEQUENCE: 198
cgaggtacta catatttcag cactaaggcg gttgcttcac tttatatcta tataaaaaaa 60
gtggtaaaaa tcttttcctt ttgtgcagtt gaacccatcc tacattcaga ttctctcaag 120
cactaataaa atacttattt ggttgaggaa gatttaaggc aagttcgggc ccttccaaag 180
gcactgtgag actccccccc cactccccgt tattgctaca tgtctttata ctcgagtatg 240
tcacagtaga actggtggaa taagcaaaca ctttttttgct agtttataaa gttggaatta 300
gaaaagcatg ccacatttca gcctgattgc aaagtatgtg gtcatttttt tctttgaagt 360
tggatgggct acaaccttta tacattctaa gaaaactcat aggatgttcc tcaaactact 420
tccacagcat caagatcgat ttctgtcaag aaatcatgca atctttcaaa atttacgtaa 480
acaaggaaag aaattaatga aataaatatt acatacaatc tcttaaatta agaatttgt 539

<210> SEQ ID NO 199
<211> LENGTH: 626
<212> TYPE: DNA
<213> ORGANISM: Homo sapiens
<220> FEATURE:
<221> NAME/KEY: misc_feature
<222> LOCATION: (1)...(626)
<223> OTHER INFORMATION: n = A,T,C or G

<400> SEQUENCE: 199
cgaggtacaa gatgtccaaa tattgcgaag atctatttgg ggatctcctg ttgaaacaag 60
cacttgaatc acatccactt gaaccaggca gggctttgcc atccccccaat gacctcaaaa 120 gaaaaatact cataaaaaac aagcggctga aacctgaagt tgaaaaaaaa cagctggaag 180
ctttgagaag catgatggaa gctggagaat ctgcctcccc agcaaacatc ttagaggacg 240
ataatgaaga ggagatcgaa agtgctgacc aagaggagga agctcacccc gaattcaaat 300
ttggaaatga actttctgct gatgacttgg gtcacaagga agctgttgca aatagcgtca 360
agaaggcttc agatgacctt gaacatgaaa acaacaaaaa gggcctggtc actgtagaag 420
atgagcaggc gtggatggca tctttataaat atgtaggtgc tccactaata tccatncata 480
tttgtccaca atgatcaact acgcccacct gtaaaggttc aaggttncat gtggcagaag 540
aaccncatat tcattataca tggcttcttt tatgaatant cggccttggt tcttgaancc 600
cttgcaatga atttgnaatt ntacca 626

-continued

<210> SEQ ID NO 200
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 200
actcataaaa aaagtcttac cccaaaattg caaacaaata cattaaaaga ttagaagagg 60
tgacagaaag caccagacat taaacaaaat aaaaataata aaataaattc aactcaaaag 120
gtccccattc agcaaatact ttgtaaagta tggcctgtat gtaaatagtg ctaaatcaag 180
gactttttag cagaaaattg ctcggttctt ttatctaagg cttgaatttg taaagtgaag 240
gcataaaagt taccaaacat taagtaactc ttaaaatggc acacaggttt taaagctatt 300
ggtttttcct tcctaactct ctgaattttt cccatggcct ttgtagatca actatttcaa 360
acgtatttta caccagcaac tctcaacata cttgtctttc agatatgtca tcagtcatgt 420
ctaacaggca aatagcanaa taacagattt aaaacaatcc ttaactanct agcaggacat 480
ttactttgga ttctgcataa ctgcaaactg acatatttgt aaagctaaaa atcagtttaa 540
tcntgattac agaaactcta tcatgctcat tacttaacta ttgnccttca atcgctattn 600
aaattcactt aatccaat 618

<210> SEQ ID NO 201
<211> LENGTH: 627
<212> TYPE: DNA
<213> ORGANISM: Homo sapiens
<220> FEATURE:
<221> NAME/KEY: misc_feature
<222> LOCATION: (1)...(627)
<223> OTHER INFORMATION: n = A,T,C or G

<400> SEQUENCE: 201
ggtactaggc acaatagaac atacagaaaa cattgtccct gctcttgagg agcttacatt 60
ctaaaagaaa aaatacacct tttttaaaat ggcatttttg tttggtgttt tctgcaaagt 120
acgcggggct ttttcttttt gaggaagacg cggtcgtaag ggctgaggat ttttggtccg 180
cacgctcctg ctcctgactc accgctgttc gctctcgccg aggaacaagt cggtcaggaa 240
gcccgcncgc aacagccatg gcttttaagg ataccggaaa aacacccgtg gagtcggagg 300
tggcaattca ccgaattcga atcaccctaa caagccgcan cgtaaaatcc ttggaaaagg 360
tgtgtgctga cttgataaga ggcncanaag aaaagaatct canagtgaaa ggaccaagtt 420
ngaatgccta ccaagacttt gagaatnact acgaganaaa ctccttgtgg tgaaggtcta 480
agacgtgggn tngnttccag atgagaattc acaagcgact tattgacttc acaagtcctt 540
ntgagattgt tangctgatt acttccttna ntatganccn ngaatttaag ngggangtna 600
ccntncagan gnttagttna ctatttt 627

<210> SEQ ID NO 202
<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G -continued

<400> SEQUENCE: 202
actgcttaac gaaacactat cagcttgttt taaatggatc ttttaaatat caactgtagc 60
ctggttggct aattctttct aatcttcccc attactttcg cctagatttc ccatagatca 120
acaggcatag taaaatgcct catcagaaca cacttctcca cacaattcaa aaagggagct 180
cctgtgggct caaagcaacc atcagtccag caatgcccat gatttatctg aaactgcttc 240
ccaagagaca ggagtgcaga tctgagtagc tgtgctgcca atacagatag gtttagcact 300
agatatttag tgattgtggc aaggaagaat cggtgatgat gggggtggtg ggtgaaggaa 360
gggccagggg atctgaagga tcttcagttg ccttctcctg cttcttcatc ctgctggtcg 420
ctcgtccana gggtgaggtt gtctcgcagc aactgcatga tcagcgtgga gtccttatag 480
gaatcctcgt ttagtgtgtc cagctcagct atggcatcat cgaaggcttg tttggctaaa 540
agcangcttg ctcangtgca ttctggatct catagtagaa caccggagaa ntganggcca 600
ggcccaaccg gatnggatgc 620

<210> SEQ ID NO 203
<211> LENGTH: 577
<212> TYPE: DNA
<213> ORGANISM: Homo sapiens
<220> FEATURE:
<221> NAME/KEY: misc_feature
<222> LOCATION: (1)...(577)
<223> OTHER INFORMATION: n = A,T,C or G

<400> SEQUENCE: 203
ggtacttttt tttttttttt tttttttttt tttttttttt tttttttttt tgaaaaagtc 60
atggaggcca tggggttggc ttgaaaccag ctttgggggg ttcgattcct tcctttttttg 120 tctaaatttt atgtatacgg gttcttcnaa tgtgtggtag ggtgggggc atccatatag 180 tcactccagg tttatggagg gttcttctac tattaggact tttcgcttcn aagcgaaggc 240
ttctcaaatc atgaaaatta ttaatattac tgctgttaga naaatgaatg ancctacaga 300
tgataggatg tttcatgtgg ggtatgcatc ggggtantcc gagtaacgtc ggggcattcc 360
ggataggccn agaaagtgtt ntgggaanaa agttagattt accccgatga atatgatagt 420
gaaatggatt ttggcgtagg tttggtctag ggtgtancct gagaataggg gaaatccgtg 480
aatgaaacct cctatgatgg caaatacact cctattgnta ggacataatg ngaagtgagc 540
tacaaccgta atacctgccc nggcnggccc ttannan 577

<210> SEQ ID NO 204
<211> LENGTH: 629
<212> TYPE: DNA
<213> ORGANISM: Homo sapiens
<220> FEATURE:
<221> NAME/KEY: misc_feature
<222> LOCATION: (1)...(629)
<223> OTHER INFORMATION: n = A,T,C or G

<400> SEQUENCE: 204
cgaggtactt gttttttttt ttttttttga gacggagtct cagtctgtca cccaggctag 60
agtgcagtgg cacgacatcg gctcactgca acctccgcct cccgggttca agtgattctc 120
ctgcctcaac ctcccgagta gctgggacta caggcatgtg ccaccacgcc tgactaattt 180
ttgtattttt agtanagatg ggatttcatt atgttggcca gctggtcttg aacttctgag 240
ctcaggtgat ccacccgcct tagcctncca gagtgctagg ataacaggca tgagccgtcg 300
cgcctggcca aaatagcata atgttttaag aaagtttacg aatttgtctt gggccacatt 360

-continued naaaaccatc atgggccaag ggttggacaa gctagcctta ggtcatgtca gaatgcaatt 420
taacaggaat ttcaagcnaa acttacaaaa aattaaatcc acaaaaaaaa tatcatttgg 480
taaatgcact gnctacacac tttactncta agtccattca accatgacga ccctttacat 540
aaaaattagg gcattctccc aagttctaaa gatgatttct aaaacattac caangnctaa 600
agtctaattc ccacaaanca ttttttttn 629

<210> SEQ ID NO 205
<211> LENGTH: 424
<212> TYPE: DNA
<213> ORGANISM: Homo sapiens
<220> FEATURE:
<221> NAME/KEY: misc_feature
<222> LOCATION: (1)...(424)
<223> OTHER INFORMATION: n = A,T,C or G

<400> SEQUENCE: 205
ggtacaaatg cttttatatt cagcccctgt aaagccatca gatgtttgaa agtttttaaa 60
cacgaaccaa agggtttaat tttaagaact tagctaggaa tgggtgaaat cctacccaat 120
taatagagtt ctgcaaatta gtaacaaagt gtaaaatgaa aggaagggtc ccttggagat 180
gtgaaattct tctattgaga gtcctgtctt ctttattcaa gaagtttgta gccattttca 240
gaattcactc aagaaccaac ttcttaattt agatatcagc gaacaagtca tggcaaaaaa 300
tacacaaaga gaaacaccac cacatcgaaa aggatgaaaa gccagaggtc caaccagtan 360
gagtgtttgg gaagcccatt tgccccagac tgaggcctca catcgaagtt ctgcctcccc 420
gcgt 424

<210> SEQ ID NO 206
<211> LENGTH: 633
<212> TYPE: DNA
<213> ORGANISM: Homo sapiens
<220> FEATURE:
<221> NAME/KEY: misc_feature
<222> LOCATION: (1)...(633)
<223> OTHER INFORMATION: n = A,T,C or G

<400> SEQUENCE: 206
ggtaccaatg gtgcctcctg gaatcaagta tctttacctt aggaataacc agattgacca 60
tattgatgaa aaggcctttg agaatgtaac tgatctgcag tggctcattc tagatcacaa 120
ccttctagaa aactccaaga taaaagggag agttttctct aaattgaaac aactgaagaa 180
gctgcatata aaccacaaca acctgacaga gtctgtgggc ccacttccca aatctctgga 240
ggatctgcag cttactcata acaagatcac aaagctgggc tcttttgaag gattggtaaa 300
cctgaccttc atccatctcc agcacaatcg gctgaaagag gatgctgttt cagctgcttt 360
taaaggtctt aaatcactcg aataccttga cttgagcttc aatcagatag ccagactgcc 420
ttctggtctc cctgtctctc ttctaactct ctacttagac aacaataaga tcagcaacat 480
ccctgatgaa gtatttcaag cgtttaatgc tttgcagtat ctgcgtttat ctcacaacga 540
actggctgat agtggaatac ctggaaattc tttcaatggn gccatcctgg gtgaacctgg 600
acttgcctat accagcntaa aacataccac cgg 633

<210> SEQ ID NO 207
<211> LENGTH: 623
<212> TYPE: DNA
<213> ORGANISM: Homo sapiens
<220> FEATURE:

-continued

<221> NAME/KEY: misc_feature
<222> LOCATION: (1)...(623)
<223> OTHER INFORMATION: n = A,T,C or G

<400> SEQUENCE: 207
ggtacttttt tttttttttt tttttttttt ttagaaacta tggctcttta ttttcatgtg 60
gataattcaa acaaagtcat tagtagtctt tgttcaattt ttttttaaaa aacaaaaaaa 120
ccctcaaata aaaaatcttg ggcttaaaag aactctatca caggagcctg gttggaggat 180
tcctagtttt atacatgaga aatagaatgc agatttctct gaagagtgtt taaagaagga 240
atggtagttg agggggctta tttcccaggc tcaaagtgat ttaggggtgg tgtcacagtg 300
ctaggtatag ggtgatggac agtgatcact gccgagggcc ttggaacgga tcttgctgtc 360
acacaatgca ggtaacagag agtgggacaa caaaaagtaa tcaaggcgcc aaccaacatt 420
cttggatcga gcattcatat ataagtccaa aaggtgtang cataaggtgt gttggggtan 480
aagtgcctaa agctgcaacc agtggcacan cctgcagtaa ttccccgaac cttggccttt 540
tggggcgtga anccnccatt cttttggtnc cctnggggtg cnaaggcaat ttttnatgtg 600
cccattgagg gttcaaacac aca 623

<210> SEQ ID NO 208
<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 208
acgatgtcta gtgatgagtt tgctaataca atgccagtca ggccacctac ggtgaaaaga 60
aagatgaatc ctagggctca gagcactgca gcagatcatt tcatattgct tccgtggagt 120
gtggcgagtc agctaaatac tttgacgccg gtggggatag cgatgattat ggtagcggag 180
gtgaaatatg ccccgcgtac ttgctttgaa agattaccta ctattttatg ataaaatgta 240
gttgtctcca gagcttaaat ataatttgta aagcacttgg tttaaatttc tctctaccta 300
taaacagttt agcattaagg gtttctatta atgacacaga attattggcc aagtgtaatt 360
tcttaaaatt tagcattact ttaaatagcc agcatgtaat acaagtaact acactacctc 420
atatctacat gattttcaag ttgtaatgca gatggacaga taaaaaagat ttacgttgnc 480
ttttggccat aagtgggaaa agttttctgn atattgcata gcattacaca tttatgccta 540
ttttacatta acttctaaag aagtttttct aagaaaangg ttcaggcaat attttttgag 600
gctgccgaan aaaaatgant 620

<210> SEQ ID NO 209
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 209
ggtactggta caaaaacagg cacataaacc aatgaaacag aatagaaagc ccagaaataa 60
tgcttcaccc ccacaaccat ctgatcttca acaaaataaa caaaaacgag ccatggggaa 120
aggactccct attcaataaa tggtgctggg ataactagtt aaccatatgc agaagattaa 180

```
agctggaccc cttccttaca aaataaggag ctggacccct tatacaaaaa tcaactcaag    240

atggattaaa gccttaaatg tgaaactata aaaccctgga agacaacata ggcgattcca    300

ttctagacat cagaactggc aaagatttca tgaggaagac accaaaagca attgcaacaa    360

aagcaaaaat tgacaactgg gatataatta agtttaagag cttctgcaca gcaaaagaga    420

gactatcagc agagtaaaca gaccacctac agaatgggag aaaatatttg caaactatgc    480

atgtgacaaa ggtctaatat ctagcatcta taagtactta aacaaatttc aacagaaaac    540

caacacccca ttaaaaagtg ggcaaggaca tgaacaaatg cctttcaaaa gaagacatct    600

gcttntacag tttntgaaac aaag                                           624
```

<210> SEQ ID NO 210
<211> LENGTH: 504
<212> TYPE: DNA
<213> ORGANISM: Homo sapiens

<400> SEQUENCE: 210

```
acgcggggca gctagcagat gctttaggac ctagtatctg catgctgaag actcatgtag     60

atattttgaa tgattttact ctggatgtga tgaaggagtt gataactctg gcaaaatgcc    120

atgagttctt gatatttgaa gaccggaagt ttgcagatat aggaaacaca gtgaaaaagc    180

agtatgaagg aggtatcttt aaaatagctt cctgggcaga tctagtaaat gctcacgtgg    240

tgccaggctc aggagttgtg aaaggcctgc aagaagtggg cctgcctttg catcgggggt    300

gcctccttat tgcggaaatg agctccaccg gctccctggc cactggggac tacactagag    360

cagcggttag aatggctgag gagcactctg aatttgttgt tggttttatt tctggctccc    420

gagtaagcat gaaaccagaa tttcttcact tgactccagg agttcagttg gaagcaggag    480

gagataatct tggccaacag tacc                                           504
```

<210> SEQ ID NO 211
<211> LENGTH: 619
<212> TYPE: DNA
<213> ORGANISM: Homo sapiens
<220> FEATURE:
<221> NAME/KEY: misc_feature
<222> LOCATION: (1)...(619)
<223> OTHER INFORMATION: n = A,T,C or G

<400> SEQUENCE: 211

```
accatgaaat atccagaaca tacttatatg taaagtatta tttatttgaa tccacaaaaa     60

acaacaaata atttttaaat ataaggattt tcctagatat tgcacgggag aatatacaaa    120

tagcaaaatt gaggccaagg gccaagagaa tatccgaact ttaatttcag gaattgaatg    180

ggtttgctag aatgtgatat ttgaagcatc acataaaaat gatgggacaa taaattttgc    240

cataaagtca aatttagctg gaaatcctgg attttttttct gttaaatctg gcaaccctag    300

tctgctagcc aggatccaca agtccttgtt ccactgtgcc ttggtttctc ctttatttct    360

aagtggaaaa agtattagcc accatcttac ctcacagtga tgttgtgagg acatgtggaa    420

gcactttaag ttttttcatc ataacataaa ttattttcaa gtgtaactta ttaacctatt    480

tattatttat gnatttattt aagcatcaaa tatttgtgca agaatttgga aaaatagaag    540

atgaatcatt gattgaatag tattaagatg tatagtaaat tatttatttt ananattaaa    600

ngangtttat taganaaaan                                                619
```

<210> SEQ ID NO 212

-continued

<211> LENGTH: 479
<212> TYPE: DNA
<213> ORGANISM: Homo sapiens

<400> SEQUENCE: 212
cgaggtacaa agcagcaact gcaatactca aggttaaaac attagaaaag catttgtgtg 60
acaggtatat tacagtatta tcaaaatatt acattttcag acttacttag cagataatca 120
tccaccagag cttaaatctt taaattattt ccatagtctt aaaaaatatg taatgtcaga 180
atgcatataa aaagaatgta aaaggaaacc taaaatacaa atggaataat gtaacaaata 240
aatatttgat ttcagtaact gttaataatc agctcaacac caccattctc tctaaactca 300
atttaattct tataggaata atgaactgtc aaatgccatg gcataattat ttatttccaa 360
gctatcatca atgattagaa ctaaaaaaat tttggcataa aaaaatcaca attcagcata 420
aataaagcta tttttagctt caacactagc tagcatctct aagaattgtt gaaataagt 479

<210> SEQ ID NO 213
<211> LENGTH: 487
<212> TYPE: DNA
<213> ORGANISM: Homo sapiens

<400> SEQUENCE: 213
actgtttact gcctgggcac tatactttct atgcagatct cctttgtggg tttccagcct 60
gtcctttcat cagagcacat ggcagccttt ggggtctttg gtctctgcca gatccatgcc 120
tttgtggatt acctgcgcag caagttgaat ccacaacaat ttgaagttct tttccggagc 180
gtcatctctc tggtaggctt tgtccttctc accgtgggag ctctcctcat gctgacagga 240
aaaatatctc cctggacggg gcgtttctac tcactgctgg atccctctta tgctaagaac 300
aacatcccca tcattgcttc tgtgtctgag catcagccca caacctggtc ctcatactat 360
tttgacctgc agctcctcgt cttcatgttt ccagttggcc tctattactg ctttagcaac 420
ctgtctgatg cccggatttt tatcatcatg tatggtgtga ccagcatgta cctcggccgc 480
gacacgc 487

<210> SEQ ID NO 214
<211> LENGTH: 393
<212> TYPE: DNA
<213> ORGANISM: Homo sapiens

<400> SEQUENCE: 214
cgaggtacaa tatgctgcag cataatttgt caggccaacc ttcacaccat attttggcag 60
ttcgtgtgca tacgctgcgc agactatcat atccccctct atacgggcat aagcaatctg 120
acaaatgata tctctgtttg tcacacgaac tatcatcctg tatttgggtg tgttgtattt 180
atttttatct tgtatcacca agcgtttccg agcataataa tcagttttac cctctcgtcg 240
tcttctaaat ttcacttggt atctcttaaa gtaggcctta ttcttaacaa ctttaacaaa 300
ccccatcctg cggaacagag accggcgtcc gctgctcgac agagacctgc aggcccagcg 360
gcgctagggg gtgggaaaag ggccaccccc cgt 393

<210> SEQ ID NO 215
<211> LENGTH: 615
<212> TYPE: DNA
<213> ORGANISM: Homo sapiens
<220> FEATURE:
<221> NAME/KEY: misc_feature
<222> LOCATION: (1)...(615)
<223> OTHER INFORMATION: n = A,T,C or G -continued

<400> SEQUENCE: 215

```
ggtacagtaa caagtgttgg cattatcagt tgaactgtaa atacaaaatg cttcttccaa     60
ttagtctcta tgatgattaa gtttctaaaa tttatctgaa caccattcag aaacttgttt    120
tggggaattt gatagttatt gatgtgcatc tgttaaactg atgacagaca taactcatca    180
ttccccagaa acctttttg attacagtat ctaacatttt gcctcctctt ttttggtttt    240
gctggttata aaggtttgga ttggagaggg ctcactggat cccaatcctt ggagctggat    300
cattggattc aaatcataat gtggatagga tagggaggat gaattaccag gattcatgga    360
gcgggatcag attaccagga acataggagt ggattcctgc ccaaccaaac ccgcattcgt    420
gtggattttt ttattcaact taattggcta ttccaaagat ttttttttcc tatttttgac    480
gaatggagcc cttaagatgc acgatggaat tgggtttgcg tttttggtaa aaggaccaaa    540
ccaggcctgg agataacgct ggagcaatct cntggaagga ttagccccaa ttgatgggaa    600
catttaangg ggaag                                                     615
```

<210> SEQ ID NO 216
<211> LENGTH: 322
<212> TYPE: DNA
<213> ORGANISM: Homo sapiens
<220> FEATURE:
<221> NAME/KEY: misc_feature
<222> LOCATION: (1)...(322)
<223> OTHER INFORMATION: n = A,T,C or G

<400> SEQUENCE: 216

```
ggtacttttt tttttttttt tttttttttt ttttttggag ttgtaggcaa atgtttaatt     60
aattctgctc atatgcacat ctgaaagcat gagacacact ccacagacag cacgcactgg    120
ggctggtggg gcanatgggc actcgccgat taggtattaa tgtcaataat acgtgcataa    180
agtgctgata aaataactta agtgttacaa aaagagacag tccacggtgg ctgcaggcac    240
atgcaggcgg gactgggtca aacactccag ggctgcacat gttccagctg gcctgagtcc    300
gacacgtcat aactggcctt gt                                             322
```

<210> SEQ ID NO 217
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 217

```
acgcgggggg aagtgagcga cacactctgc gtcctcgcct caccagagtc ttgctgtgtg     60
gcccaggctg gagtgcccgg ctggtctcaa attcctgacc tcaagtgatc tccctcccaa    120
agtgttgcga ttgcaggtgt gagccactgc acctggctgc tgagaaatct ttgcctacag    180
tgagggaaac tactaaagtt cctggggaag caaagtaaga atttcataag aacaaaatgg    240
atggagagga gaaaacctat ggtggctgtg aaggacctga tgccatgtat gtcaaattga    300
tatcatctga tggccatgaa tttattgtaa aaagagaaca tgcattaaca tcaggcacga    360
taaaagccat gttgagtggc ccaagtcaat ttgctganaa cgaaaccaat gaggncaatt    420
ttagagagat ccttcacatg tgctatcgaa agtattcatg nattttacgt accttgggcc    480
gcgaccacct taaggccaat tncacacact ggcnggccgt actantggat ccnactngga    540
```

-continued

```
ccaacttggc gtaatcatgg catactggtt cctggggaaa atgtatccgt tacaattcnc    600

acacan                                                               606
```

<210> SEQ ID NO 218
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 218

```
ggtacttttt tttttttttt ttttttttga gacggagttt ggcccttgtt gcccaggctg     60

aagtgcaata gtgcgatctc ggctcactgc aacctccacc ttccgtgttc aaccgattct    120

cctgcctcag cctcctgagt agctgggatt acagatgaaa aaacatttaa agcccttaag    180

gaagaaggaa atcaatgtgt aaatgacaaa aactataaag acgccctcag taaatacagc    240

gaatgcttaa agattaacaa taaggaatgt gccatatata caaacagagc tctctgttac    300

ttgaagctgt gccagtttga agaagcaaag caggactgtg atcaggcact tcagctagct    360

gatgggaacg tgaaagcctt ctatagacga actctggctc ataaaggact caagaattat    420

cagaaaagct taattgatct caataaagtt atcctactag atccaagtat tattgaggca    480

aagatggaac tggaagangt aactagactc ctaatcttaa ggataagaca gcaccattca    540

acaaagaaaa ggagagaagg aaaatgagaa tcaagaggng aatgaaggca ngagganc ct    600

ggaaaacctg aggggagg                                                  618
```

<210> SEQ ID NO 219
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G

<400> SEQUENCE: 219

```
ggtacaaagc ggatctgagc ccggaaaatg ctaagctcct cagcacattc ctaaatcaga     60

ctggcctaga cgccttcctg ctagagctgc acgaaatgat aatcttgaaa ctaaagaacc    120

cccaaaccca aaccgaggag cgcttccgcc ctcagtggag cctgagagac actctcgtaa    180

gttacatgca aactaaagaa agtgaaattc ttcctgaaat ggtatctcag ttcccagaag    240

agatactgct cgccagctgt gtctcagtgt ggaaaacagc tgctgtgctg aaatggaatc    300

gagaaatgag atagaattat ttcctcagct atctttggat gactttggag agaagactcc    360

tctctcctcg tctgcggcgt ggacttgatc atggactggt gcctttgcat tcagaaggag    420

agctgtcagc gtagcaccga attcaagacc aaggcgtgct acctgagctg acagcttttt    480

gaaagccgag ctggttctga accatgtcct gcccnggcng gcgctcgaaa gggcgaattc    540

agccactggc ggccgtacta ntggatccga actcggacca aacttggcgt aatatgggca    600

tactggttcc tgg                                                       613
```

<210> SEQ ID NO 220
<211> LENGTH: 616
<212> TYPE: DNA
<213> ORGANISM: Homo sapiens
<220> FEATURE:
<221> NAME/KEY: misc_feature -continued
<222> LOCATION: (1)...(616)
<223> OTHER INFORMATION: n = A,T,C or G

<400> SEQUENCE: 220
ggtacgcggg ggcagccgcg gtgttgtgct gtggggaagg gagaaggatt tgtaaacccc 60
ggagcgaggt tctgcttacc cgaggccgct gctgtgcgga gacccccggg tgaagccacc 120
gtcatcatgt ctgaccagga ggcaaaacct tcaactgagg acttggggga taagaaggaa 180
ggtgaatata ttaaactcaa agtcattgga caggatagca gtgagattca cttcaaagtg 240
aaaatgacaa cacatctcaa gaaactcaaa gaatcatact gtcaaagaca gggtgttcca 300
atgaattcac tcaggtttct ctttgagggt cagagaattg ctgataatca tactccaaaa 360
gaactgggaa tggaggaaga agatgtgatt gaaagtttat cangaacaaa ccgggggtca 420
ttcaacagtt tanatattct ttttaatnnt ttcttttncc tcaatccttt tttattttta 480
aaaatagttc ttttgtaatg tggtgtcaaa acggaattga aaactggcac cccatctttt 540
gaaacatctg gtaatttgaa tctaatgctc attatcatta tggttggttt cattggcnga 600
attttgggga tcaanc 616

<210> SEQ ID NO 221
<211> LENGTH: 615
<212> TYPE: DNA
<213> ORGANISM: Homo sapiens
<220> FEATURE:
<221> NAME/KEY: misc_feature
<222> LOCATION: (1)...(615)
<223> OTHER INFORMATION: n = A,T,C or G

<400> SEQUENCE: 221
ggtacagtga tagctccccc tgggcaatac aatacaagaa cagtgggttt tgtcaaattg 60
gaacaaggaa acagaaccac agaaataaat acattggtta acatcagatt agttcaggtt 120 actttttgt aaaagttaaa gtagagggga cttctgtatt atgctaactc aagtagactg 180
gaatctcctg tgttcttttt tttttaaatt ggttttaatt ttttttaatt ggatctatct 240
tcttccttaa catttcagtt ggagtatgta gcatttagca ccactggctc aatgcgctca 300
cctaggtgag agtgtgacca aatcttaaag cattagtgct attatcagtt accaccattt 360
ggggctttta tccttcatgg gttatgatgc tctcctgatg acacatttct ctgagttttg 420
taattccagc caaagagaga ccattcacta tttgatggct ggctgcatgc agacatttaa 480
agcttttaga gaatacacta caccagggag tatgactact antatgacta ttagganggt 540
aatacccaga attggactcg caccttaggc aagatccaac cactaaattg aataagaatg 600
agtngatgag gtncc 615

<210> SEQ ID NO 222
<211> LENGTH: 617
<212> TYPE: DNA
<213> ORGANISM: Homo sapiens
<220> FEATURE:
<221> NAME/KEY: misc_feature
<222> LOCATION: (1)...(617)
<223> OTHER INFORMATION: n = A,T,C or G

<400> SEQUENCE: 222
ggtacttttt tttttttttt tttttttttt ttttaattta tgattttatt gnctttcctt 60
tgtccggcct ttaacatgtt tctgtaattt aaataaaaat ctatttactt tctccatttt 120
agcaaatggt ttctttaccc aaataggttg cactatagtc cccatatggt tttctactgn 180

-continued tccacaacca ctatttcaca aagattgaca aaactttaat aaaagttaaa tttacagaca 240
tcttaagata acttgggaaa tatgtagtaa aaaagaatcg agtccacaaa ttaagaatat 300
tttgctaata tgcccaacac caatttcagc aaatccaatc tacttaactc atatatttaa 360
tgnggtaatt tttctaacaa aatttaatgg gggtatgaat gatatattta tgcccttgac 420
aaagatgaca tgtgtgattt tggtgngact aanaaaggag aagtatgatt tctggngggt 480
atganatcac tctggctcat cgaagctcca gaatatgtaa gggtctgnca cgtccaaaaa 540
tgttaggcna atgtataaaa ggccacccgg ctnacacacg ttttatatac aaactttngn 600
agtcctttta tntcata 617

<210> SEQ ID NO 223
<211> LENGTH: 470
<212> TYPE: DNA
<213> ORGANISM: Homo sapiens
<220> FEATURE:
<221> NAME/KEY: misc_feature
<222> LOCATION: (1)...(470)
<223> OTHER INFORMATION: n = A,T,C or G

<400> SEQUENCE: 223
ggtaccacaa ctgtgccctt gataattagt aatcactcct aaaaatcttc atttggcacc 60
agatggtgtg tttaaaacac cctaggatgt tttgaatcag gcttgatttt gttagttgag 120
ttacaggaga attttaaggg tgagggtatg ggggtcaggg aagaaaagga aatgggaaat 180
ggaccagaaa aaatcttgag tcatcatcta aatcaacaaa gcactgatag ctccaaatat 240
taggtcagac actaaaacga ctgatatagg ctcaagtggt ttataaaacc tataaaaaga 300
ctacaccagc aaagtccctg tcaatctgtc agagttcaga aactaaaaca gggagtaaca 360
ttttagctta aaaccttatc tcaagagaat catatacact tcacatgaat aaaaatacct 420
gaaaccaaac atttttaaaa gctccagtcc tgcccnggcc ggccgctcga 470

<210> SEQ ID NO 224
<211> LENGTH: 622
<212> TYPE: DNA
<213> ORGANISM: Homo sapiens
<220> FEATURE:
<221> NAME/KEY: misc_feature
<222> LOCATION: (1)...(622)
<223> OTHER INFORMATION: n = A,T,C or G

<400> SEQUENCE: 224
gcgtggncgc ggccgacgtn ctcttttttt tttttttttt ttttttgcnn actaaaaatn 60
ngattgctct ttaaagcctt aggccgnatg acaaaatgan nagactgaaa tgacancggg 120
gaggaagaaa cagannaaag ataagaatga ggtggtcagg ttgggggaat taagcgaata 180
ttcncttccn nggtgagtcc tnacactggt ctcatgccca tgatgagttg cacaccaaac 240
acnggctgnt gacttncctc ctgcnctant cagtgaactt gcngacatng ggnancctca 300
cattacagnt ataanntttc cacctaaaaa atgctgcgct tttcgacngg ctcnnncagn 360
ggccggggct tgacatggng gaanggattt ctctcccatg ccaaggaatt catcacatca 420
ctgntactcc actgncaacc ttntccattg ggctcngtgc cctgtgtngg gtcatggacc 480
cantccanaa ntatgaatac tgtaccatgc tcttaaccag gaggacctaa ggatccttag 540
ncccntgagn nanacaccag gnttcaaagg ccgttttggn aagccaaatt tgnttnggnc 600
cgaattnggg ccaaacangg tt 622

-continued

<210> SEQ ID NO 225
<211> LENGTH: 619
<212> TYPE: DNA
<213> ORGANISM: Homo sapiens
<220> FEATURE:
<221> NAME/KEY: misc_feature
<222> LOCATION: (1)...(619)
<223> OTHER INFORMATION: n = A,T,C or G

<400> SEQUENCE: 225
acgcggggag ttccgccatg gcctccttgg aagtcagtcg tagtcctcgc aggtctcggc 60
gggagctgga agtgcgcagt ccacgacaga acaaatattc ggtgctttta cctacctaca 120
acgagcgcga gaacctgccg ctcatcgtgt ggctgctggt gaaaagcttc tccgagagtg 180
gaatcaacta tgaaattata atcatagatg atggaagccc agatggaaca agggatgttg 240
ctgaacagtt ggagaagatc tatgggtcag acagaattct tctaagacca cgagagaaaa 300
agttgggact aggaactgca tatattcatg gaatgaaaca tgccacagga aactacatca 360
ttattatgga tgctgatctc tcacaccatc caaaatttat tcctgaattt attagcccgt 420
ggggccaatt ttttaactca natcttgctg agaccaggag catctgattt aacaggaagt 480
ttcagattat acccgaaaaa gaagttctag agaaattaat agaaaaatgt ggttctaaag 540
gctacgtctt ncaaatggag atgattggtc nggcaagaca gttgaatatt ctattggcga 600
ggttccatat canttgngg 619

<210> SEQ ID NO 226
<211> LENGTH: 277
<212> TYPE: DNA
<213> ORGANISM: Homo sapiens

<400> SEQUENCE: 226
acgcggggcc cctcatttac ataaatatta tactagcatt taccatctca cttctaggaa 60
tactagtata tcgctcacac ctcatatcct ccctactatg cctagaagga ataatactat 120
cgctgttcat tatagctact ctcataaccc tcaacaccca ctccctctta gccaatattg 180
tgcctattgc catactagtc tttgccgcct gcgaagcagc gggggcccta gccctactag 240
tctcaatctc caacacatat ggcctagact acgtacc 277

<210> SEQ ID NO 227
<211> LENGTH: 328
<212> TYPE: DNA
<213> ORGANISM: Homo sapiens

<400> SEQUENCE: 227
ggtacatatt tttgccaatg ctatacagca aaaatgaaaa acttacagaa aggtaaacaa 60
aattgagtcc actttttttaa tttcacaagc tgctttaaac tatagaacca ccagatatct 120
gtaaaataag caaaactggt aagtgtgttt ttttaattga gggaaggagg gccagaggag 180
ttggtgcaga agcgcttcgg gtgaattcat accagagcca ccgggtgtga ctcggctacc 240
tctcccaatt accacaggga ggtcttaaaa ttgaatttca gtttcagcag atactccaga 300
tttacctgag caatatcata gacaatgt 328

<210> SEQ ID NO 228
<211> LENGTH: 609
<212> TYPE: DNA
<213> ORGANISM: Homo sapiens
<220> FEATURE:
<221> NAME/KEY: misc_feature
<222> LOCATION: (1)...(609)

-continued

<223> OTHER INFORMATION: n = A,T,C or G

<400> SEQUENCE: 228
acgcgggagt tcaagcagat gtatggctaa ccggaaacag gtgggtcacc tcctgcaaga 60
agtggggcct cgagctgtca gtcatcatgg tgctatcctc tgaacccctc agctgccact 120
gcaacagtgg gcttaagggt gtctgagcag gagaggaaag ataagctctt cgtggtgccc 180
acgatgctca ggtttggtaa cccgggagtg ttcccaggtg gccttagaaa gcaaagcttg 240
taactggcaa gggatgatgt cagattcagc ccaaggttcc tcctctccta ccaagcagga 300
ggccaggaac ttctttggac ttggaaggtg tgcggggact ggccgaggcc cctgcaccct 360
gcgcatcagg actgcttcat cgtcttggct gagaaaggga aaagacacac aagtcgcgtg 420
ggttggagaa gccagancca ttccacctcc cttccccaac atctctcana gatgtgaaac 480
cagatctcat ggcaacnaag ccctntgcaa gaagctcaag gaanctaagg aaaatggacg 540
ttttcagana atggttgtag ttcatgggtt ttncctactg ccgggtcctt tcttangacc 600 cgcanaant 609

<210> SEQ ID NO 229
<211> LENGTH: 610
<212> TYPE: DNA
<213> ORGANISM: Homo sapiens
<220> FEATURE:
<221> NAME/KEY: misc_feature
<222> LOCATION: (1)...(610)
<223> OTHER INFORMATION: n = A,T,C or G

<400> SEQUENCE: 229
ggtacttttt tttttttttt tttttttttt gcagactaaa aattttattg ctctttaaag 60
ccttaggccg tatgacaaaa tgaagagact gaaatgacag cggggaggaa gaaacagaag 120
aaagataaga atgaggtggt caggttgggg gaattaagcg aatattctct tccagggtga 180
gtcctcacac tggtctcatg cccatgatga gttgcacacc aaacacaggc tgctgacttc 240
cctcctgcac tagtcagtga acttgcagac atagggtaac ctcacattac agttataatc 300
tttccacctc agaaatgctg tgcttctcga caggctcgca cagtggccgg ggcttganat 360
ggtggaggga tttctctccc atgcaaagta attcatcaca tcactgntac tccactccca 420
accttctcca ttgggctcgg tgccctgtgt ggggtcatgg acccaatcca acgtatgant 480
actggtacca atgctnttac cagggaggac acnaaaggat cccttacccc ctgagcacag 540
acccnaggtt tcaaanggcc gttttggcag gccaaactgn atntgnccag aatttggnga 600
caaaacaagg 610

<210> SEQ ID NO 230
<211> LENGTH: 346
<212> TYPE: DNA
<213> ORGANISM: Homo sapiens

<400> SEQUENCE: 230
ggtcggccga ggtaccatgc actgagtgac tgtggggatc atgttgttat aatgaacaca 60
agacacattg cattttctgg aaacaaatgg gaacaaaaag tatactcttc gcatactggc 120
tacccaggtg gatttagaca agtaacagct gctcagcttc acctgaggga tccagtggca 180
attgtaaaac tagctattta tggcatgctg ccaaaaaacc ttcacagaag aacaatgatg 240
gaaaggttgc atctttttcc agatgagtat attccagaag atattcttaa gaatttagta 300
gaggagcttc ctcaaccacg aaaaatacct aaacgtctag atgagt 346

<210> SEQ ID NO 231
<211> LENGTH: 601
<212> TYPE: DNA
<213> ORGANISM: Homo sapiens
<220> FEATURE:
<221> NAME/KEY: misc_feature
<222> LOCATION: (1)...(601)
<223> OTHER INFORMATION: n = A,T,C or G

<400> SEQUENCE: 231
ggtacgcggg gagagcacat ccggtgttag aagcgctggt aggccttgga gaggcgggtt 60
aggaagagtg gagactgctg cacggactct ggaaccatga acatatttga tcgaaagatc 120
aactttgatg cgcttttaaa attttctcat ataaccccgt caacgcagca gcacctgaag 180
aaggtctatg caagttttgc cctttgtatg tttgtggcgg ctgcaggggc ctatgtccat 240
atggtcactc atttcattca ggctggcctg ctgtctgcct tgggctccct gatattgatg 300
atttggctga tggcaacacc tcatagccat gaaactgaac agaaaagact gggacttctt 360
gctggatttg cattccttac aggagttggc ctgggccctg cctggagttt tgnattgctg 420
tcaaccccac atccttccac tgctttcatg ggcccgcaat gatctttacc tgcttaacct 480
taatgcactc tatccaagcg ccgtactcct tttctgggag gatcttgatg tcagcctgaa 540
cttgtgcttt gcttcctggg gaatgtttct ttggatccat tggcttttca gcnaactttt 600
t 601

<210> SEQ ID NO 232
<211> LENGTH: 390
<212> TYPE: DNA
<213> ORGANISM: Homo sapiens
<220> FEATURE:
<221> NAME/KEY: misc_feature
<222> LOCATION: (1)...(390)
<223> OTHER INFORMATION: n = A,T,C or G

<400> SEQUENCE: 232 acttttttttt tttttttttt tttttttttt ttggttttaa tgtttatttc cccaagacag 60
cctagcctgc actctacttg gataaatttt acaagctagt tttctgctgc ttctagtttt 120
aaactttaac catgtttctg atgacaagga atgctgcaaa aatactctag ttcaacaaag 180
agttatgatc acaaaataat ttttatccat tctacagtgt ttcanaatta ccagttgatt 240
tttaaacaca aagtagatat agatgctaat ggtggctaat ctggtatgtt tcttatagca 300
aactgttgtt catgcaacac ttgtgctcaa aggggaaggc acaggatttc ctacaatgag 360
ccaccttata aagagttctt tttgnacctn 390

<210> SEQ ID NO 233
<211> LENGTH: 603
<212> TYPE: DNA
<213> ORGANISM: Homo sapiens
<220> FEATURE:
<221> NAME/KEY: misc_feature
<222> LOCATION: (1)...(603)
<223> OTHER INFORMATION: n = A,T,C or G

<400> SEQUENCE: 233
cgaggtacgc gggggaagag tgagggttcc aacttttctg cttatctggg aggtgttggg 60
cgcggacaat cgagatgtca gagaaaaagc agccggtaga cttaggtctg ttagaggaag 120
acgacgagtt tgaagagttc cctgccgaag actgggctgg cttagatgaa gatgaagatg 180

-continued

```
cacatgtctg ggaggataat tgggatgatg acaatgtaga ggatgacttc tctaatcagt    240

tacgagctga actagagaaa catggttata agatggagac ttcatagcat ccagaagaag    300

tgttgaagta acctaaactt gacctgctta atacattcta gggcagagaa cccaggatgg    360

gacactaaaa aaatgtgttt atttcattat ctgcttggat ttatttgtgt ttttgtaaca    420

caaaaaataa atggtttgat ataagaaaaa annnnnnnna aaaaaaaagt nctggccngg    480

cggccgttca aanggccaat tccacccact ggcggccgta ctaanggacc aacttggncc    540

aacttgggga atcanggcaa actggttcct ggngaaatgg nttcccttcc aattccccaa    600

atn                                                                  603
```

```
<210> SEQ ID NO 234
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 234

cgaggtacct tcattgcgat caaaccagat ggggtccagc ggggtcttgt gggagagatt     60

atcaagcgtt ttgagcagaa aggattccgc cttgttggtc tgaaattcat gcaagcttcc    120

gaagatcttc tcaaggaaca ctacgttgac ctgaaggacc gtccattctt tgccggcctg    180

gtgaaataca tgcactcagg gccggtagtt gccatggtct gggaggggct gaatgtggtg    240

aagacgggcc gagtcatgct cggggagacc aaccctgcag actccaagcc tgggaccatc    300

cgtggagact tctgcataca agttggcagg aacattatac atggcagtga ttctgtggag    360

agtgcagaga aggagatcgg cttgtggttt caccctgagg aactggtaga ttacacgaac    420

tgtgctcana actggatcta tgaatgacag gaaggcagac ccattgnttt tcacatncat    480

ttcccttcnt tccattgggc aaaggaccag ctttnggaaa tctantnttt accnggacct    540

tattcttaat ttgganggaa actnttggac tttgangtnt tcctntacct ngcccgggng    600

gccgtttaaa agggna                                                    616
```

```
<210> SEQ ID NO 235
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 235

acgcggggag tgcgttactt acctcgactc ttagcttgtc ggggacggta accgggaccc     60

ggtgtctgct cctgtcgcct tcgcctccta atccctagcc actatgcgtg agtgcatctc    120

catccacgtt ggccaggctg gtgtccagat tggcaatgcc tgctgggagc tctactgcct    180

ggaacacggc atccagcccg atggccagat gccaagtgac aagaccattg gggggaggaga    240

tgactccttc aacaccttct tcagtgagac gggcgctggc aagcacgtgc cccgggctgt    300

gtttgtagac ttggaaccca cagtcattga tgaagttcgc actggcacct accgccagct    360

cttcaccctg agcagctcat cacaggcaag gaagatgctg ccaataacta tgcccgangg    420

cactacacca ttggcaagga gatcattgac cttgngttgg acccaattcc aaacctggct    480

gaccatgcac cgggctttan ggnttnttgg gttttcccaa antttggggg ggaactgggt    540
```

-continued ttgggttaac ttcctgntna tggnacgntt ttaaatgaat ntgggaaaaa tccaactggn 600 gntttcc 607

<210> SEQ ID NO 236
<211> LENGTH: 608
<212> TYPE: DNA
<213> ORGANISM: Homo sapiens
<220> FEATURE:
<221> NAME/KEY: misc_feature
<222> LOCATION: (1)...(608)
<223> OTHER INFORMATION: n = A,T,C or G

<400> SEQUENCE: 236
acgcgggcat gcaacaccac acccagcctg aaacccagat ttttaatatg aaatcaaagt 60
cttcagacct tgtaggtgtc ataaaaagca cgctgaggac cactagtttg caactgccaa 120
tctaaaatat catagacatt atatcacttc aaccacgaaa aaaaagtatg tgaggcagaa 180
aatggaagca accatgccta atttattgtt gaatactttt tccgtatacc aagagcttcc 240
tttgcactag catctgaaac tatatccaga atgacactgg ttttcataaa agtgttgatc 300
ctcacacctc tttatagtct tgcacctagc acagtggagt gaaacacttt aaatagcact 360
tgntccttga gtatatatgg aaaaaagtga agtattgata aagtgctcaa ctaatatgag 420
cagcatctca ggagtctcca attcttgaat taccagggag tatttttacc attttcccca 480
ntgnaaggcc ttttttgaga nacttaccct caaatngaan gnnttaagca tgntcctttt 540
tttttccttt tttttttgan aaaagggctt gctntgtggc caggttggan tgcctacntg 600 aaaattcn 608

<210> SEQ ID NO 237
<211> LENGTH: 609
<212> TYPE: DNA
<213> ORGANISM: Homo sapiens
<220> FEATURE:
<221> NAME/KEY: misc_feature
<222> LOCATION: (1)...(609)
<223> OTHER INFORMATION: n = A,T,C or G

<400> SEQUENCE: 237
actatttcat atattgtgtg agccccacaa atgtctattt taaaaagagt atagtccctg 60
gccaggcgcg gtggctcacg cctgtaatcc cagcagtttg ggaggccgag gtgggcggat 120
cacctgaggt ctggagttcg agaccagcct gaccaatatg gtgaaacccc gtttctacta 180
aaaatacaaa attagctggg catggtggag catgcctgta atcccagcta ctcgggaggc 240
tgaggcagga gaatcacttg aacccgggag gcgaaggctg cagtgagcca agatcacgcc 300
attgcactcc agcctgagca acaagaggga cactccgtcc ccaaaaaaaa aataataaaa 360
aaaataaaaa ataaaaataa aaagagtata gttcccaatg ggttctacaa acattcctga 420
tttatactgg gggaagtgat gcctaantgg gaacattaat cattatggtt tcgaaaatta 480
aatatttctg caaacaattc ctttgcaaat gctaacttgc catgagctta ccccatttga 540
aattgngnct ttacaaagac cttggccgga ccccttangg ngaattcagn cactggnggg 600
cgttctttg 609

<210> SEQ ID NO 238
<211> LENGTH: 616
<212> TYPE: DNA
<213> ORGANISM: Homo sapiens
<220> FEATURE:

-continued

<221> NAME/KEY: misc_feature
<222> LOCATION: (1)...(616)
<223> OTHER INFORMATION: n = A,T,C or G

<400> SEQUENCE: 238
acgaggcggt gcgggaagtc ctgcacggga accagcgcaa gcgccgcaag ttcctggaga 60
cggtggagtt gcagatcagc ttgaagaact atgatcccca gaaggacaag cgcttctcgg 120
gcaccgtcag gcttaagtcc actccccgcc ctaagttctc tgtgtgtgtc ctgggggacc 180
agcagcactg tgacgaggct aaggccgtgg atatccccca catggacatc gaggcgctga 240
aaaaactcaa caagaataaa aaactggtca agaagctggc caagaagtat gatgcgtttt 300
tggcctcaga gtctctgatc aagcagattc cacgaatcct cggcccaggt ttaaataagg 360
caggaaaagt tcccttcctg ctcacacaca acgaaaacat ggtggccaaa agtggatgag 420
gtgaagtcca caatcaagtt ccaatgaaga aggggtatgt ctggcttgta acttgttggt 480
cacgtgaaga tgacngacga tgacttgngt ataacattna nctgggctgg caacttcttg 540
gggcaatgnt caanaaaact ggcaaaatgt ccgggccttt tttttagagc cccttggnaa 600
accccangcc ntttta 616

<210> SEQ ID NO 239
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 239
acagtctgtt cgagaacacc ttggtcatga aagtgacaac ctgctgtttg ttcagatcac 60
aggcaaaaaa ccaaactttg aagtgggttc ttctaggcag cttaagcttt ccatcaccaa 120
gaagtcttct ccttcagtga aacctgctgt ggaccctgct gctgccaagc tgtggaccct 180
ctcagccaac gatatggagg acgacagcat ggatctcatt gactcagatg agctgctgga 240
tccagaagat ttgaagaagc cagatccagc ttccctgcgg gctgcttctt gtggggaaag 300
ggaaaaagag gaaggcctgt aagaactgca cctgtggcct tgccgaagaa ctggaaaaag 360
agaagtcaag ggaacagatg aacttccaac ccaagtcaac ttgtggaaac tgctcctggg 420
cgatgccttt cgttgtgcca ctggccctac cttgggatgc cagcntnaaa ctggggaaaa 480
gngcttctaa tgatancatc tttattgaag cctaagaagg ttctgaattg ggacccattt 540
gttcttcaac caattctggn cttaaatcca ccttgggggt cttccacctc cttggatttg 600 ncacctt 607

<210> SEQ ID NO 240
<211> LENGTH: 615
<212> TYPE: DNA
<213> ORGANISM: Homo sapiens
<220> FEATURE:
<221> NAME/KEY: misc_feature
<222> LOCATION: (1)...(615)
<223> OTHER INFORMATION: n = A,T,C or G

<400> SEQUENCE: 240
ggtacgcggg gcttttcaca agatggcgcc gaaagcgaag aaggaagctc ctgcccctcc 60
taaagctgaa gccaaagcga aggctttaaa ggccaagaag gcagtgttga aaggtgtcca 120
cagccacaaa aagaagaaga tccgcacgtc acccaccttc cggcggccga agacactgcg 180

-continued

```
actccggaga cagcccaaat atcctcggaa gagcgctccc aggagaaaca agcttgacca    240

ctatgctatc atcaagtttc cgctgaccac tgagtctgcc atgaagaaga tagaagacaa    300

caacacactt gtgttcattg tggatgttaa agccaacaag caccagatta aacaggctgt    360

gaagaactgt atgacattga tgtggccaag gtcaacaccc tgattcggcc tgatggagag    420

aagaaggcat atgttcgact ggctcctgat tacnatgctt tggatgttgc caccaaaatt    480

gggatcattt aactgagtcc acttgctaaa tctgaatata tatatatata tatatctttt    540

cnccccaaaa aaaaaaaaaa aaaaaagtnc tncccggcgg ccgtttaaag gggaattccc    600

cacttggggg cgttt                                                     615
```

<210> SEQ ID NO 241
<211> LENGTH: 365
<212> TYPE: DNA
<213> ORGANISM: Homo sapiens
<220> FEATURE:
<221> NAME/KEY: misc_feature
<222> LOCATION: (1)...(365)
<223> OTHER INFORMATION: n = A,T,C or G

<400> SEQUENCE: 241

```
acgggggggt cgctttgctg ttcgtgatat gagacagaca gttgcggtgg gtgtcatcaa     60

agcagtggac aagaaggctg ctggagctgg caaggtcacc aagtctgccc agaaagctca    120

gaaggctaaa tgaatattat ccctaatacc tgccacccca ctcttaatca gtggtggaag    180

aacggtctca gaactgtttg tttcaattgg ccatttaagt ttagtagtaa aagactggtt    240

aatgataaca atgcatcgta aaaccttcag aaggaaagga gaatgttttg tggaccactt    300

tggttttctt ttttgcgtgt ggcaagtttt aaagttatta agtttttaaa atcaagtacc    360

tnggn                                                                365
```

<210> SEQ ID NO 242
<211> LENGTH: 625
<212> TYPE: DNA
<213> ORGANISM: Homo sapiens
<220> FEATURE:
<221> NAME/KEY: misc_feature
<222> LOCATION: (1)...(625)
<223> OTHER INFORMATION: n = A,T,C or G

<400> SEQUENCE: 242

```
natnggangg nttttccctt aacgtgggcc ncggccgagg nacttttttt tttttttttt     60

tttttttttt gcaggcagct atttaattan gntcttaana catttanaac nccaatttgn    120

gaanataaat tccattcgtc anaacaaacn cagatcgcan gtagccctgg anctgangaa    180

taactttgat ttttggnaaa atttgngagt ccncagcttt ctgatcaatc ttgcgctgct    240

cccnaatctc atatttctct ttttctgggg ccaaaatctt accttcctgg ngtctgggct    300

ttcgcaactt cttcttcttg aaagaagcct cagtaaaaat ggtttgggaa ttttacatta    360

ctgatatcca atttnggtga aatggcaatg accaatttct ngggggggtct tcgtaaaaga    420

actccantga nggnccaaag gtccagtccc aagtataggc nctnaccact gnttcaggaa    480

accacctttt gncctggggg gtccatgagg atgaccaaat ggncccgggg naagctggct    540

ccanttttttt acggcctacc gaagggtttt tgccngggta aaagttttag ggccattttc    600

ngggnaaatc taggcttttg gaaat                                          625
```

<210> SEQ ID NO 243

-continued

<211> LENGTH: 639
<212> TYPE: DNA
<213> ORGANISM: Homo sapiens
<220> FEATURE:
<221> NAME/KEY: misc_feature
<222> LOCATION: (1)...(639)
<223> OTHER INFORMATION: n = A,T,C or G

<400> SEQUENCE: 243

```
nncnaattcc nccntaaccn ggnccccgnc caagnacccc ggcncctttg gatgtatnga     60
aatnaacnta ttaatgggga cntattggag aaggaaatnc ctagacctac aactttnagc    120
naatagcngt gatgttttag gaactgaaat gtcacactta aagtcttnag cccagctact    180
tccctatttt tgtggggaga aaanggccng attagaactg ttctggttgt gtttggcggg    240
aggggaataa tttttgttca gtccttctta gtgaccaaac tttaattttt aagaataata    300
tattgactta ctgaactgaa gcattctgag ttgaaaggag ctccncagga ntggagttct    360
gtgttgctca catgttnaaa ncttgctcac cttnatagcn caaggaatac ctatcttcca    420
natnccgcca ttttcatctc ttaaatgnag tccaaagtat gacttgagaa agttgctctn    480
ggattctggg gtcttaaaac tngggattct gggattntgg ggtccnaaag ttnaccttgn    540
aaagttgcct gggnttttan aaatncnctg nattctgggg ttttaaaaaa ttttgaaaaa    600
accccncccn ncttgaaagg gaccttaaaa attaacctn                           639
```

<210> SEQ ID NO 244
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 244

```
tcgagccgnc ggcccgggcc aggtactttt tttttttttt tttttttttt gaaaatggag     60
tcttgctctg ntgccaaact ggantgcaat ggtgcganct gggctcactg naatctccac    120
ctnccgggtt caagcgattc tcctgcctca cctccgagta actgggacta caggtgcgcg    180
ccaccaagcc cagctcattt ttgnattttt agtanaaatg gggtttcacg atgttggcta    240
ngatggnctc gatctctggt caaagtcttt tctgnaaata tccttggtaa aaaaacaatt    300
ttagactgta gctgttgcaa atgctttaag gaagaaacna aacaactgca gtcttcctga    360
aatgaaaaaa ctccccaggg ctgctattna aaacaacccc accagcactt caatcatgat    420
gccnacagtg gcccactgaa aaancnggaa aagttcnaat cccaaactgg gatgctcttg    480
actntggaat tntgngggcn ntncccnant ttnanacaaa acngnctngg nccctntttt    540
ttgggggaat ttgggaanaa aaaaacttgn gngttcttgn ggttccnttg ttccccaaaa    600
nactgggggn nggg                                                      614
```

<210> SEQ ID NO 245
<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 245

```
gccgtggtcg cgggccgagg tccatttgcc tcccggcctc aagccgattc tcctgcctca     60
```

-continued

```
gccctccaag tagctgggga ttacaggcac ctgccaccat gcccggctaa tttttgnaat    120
tttagtagag acagggtttc accatgttgc ccaggctggt ttcgaactcc tgacctcagg    180
tgatccaccc gcctcggcct ccaaagtgct gggattacag gcttgagccc ccgcgcccag    240
ccatcaaaat gctttttatt tctgcatatg ttgaatactt tttacaattt aaaaaaatga    300
tctgntttga aggcaaaatt gcaaatcttg aaattaagaa ggcaaaaatg taaaggagtc    360
aaaactataa atcaagtatt tgggaaagtg aagactggaa gctaatttgc attaaattca    420
caaactttta tactctttct ggatatacat tttttttctt taaaaaacaa ctttngatca    480
gaatagcccc atttagaacc ttttggtatc agncaatatt tttaaatagt tnaaccnggc    540
ctaagctnaa agnggcttga tntgagtaaa cttttcaact ggcttgaacc ctnaaccttt    600
taaaatgacc ttccgagntt                                                620
```

<210> SEQ ID NO 246
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 246

```
acttattctt caggggttac tgagtcggca cctatgacag ctaagagagc tttcttaaag     60
actgcctcag tgtcttcttg gcttttggca ccttcactcc actctgccca ggaaatccac    120
aatggcagac aaacctgggg tttcaggtgc acaaagactt cttcaaaaag catggctatg    180
tcagggctct ttgactcgat cagcacctgc agcttcagct gccacattgt cccagagtct    240
ctaaacaatt caagttccag ctactgncac ttccagagct tcctcaggaa gttataacac    300
agcaacgaaa cactcaactg cttgtattgg cattctgaca gaagcttcaa gttcatgtgc    360
cttcctgaat acagtcatgg tctttncaac ctcttcctct aaggacccac tatttgactt    420
cttaataaat ctttccagcc aaaggngatg aacactttca catgggcctt gtggcaaaag    480
cttnatggct ttttatcncg gacagacctt tctcttcggg cgacctcaat ggtttggctt    540
ggtcgtggag ctggtntttg gctnggactc aacttnaatn ttgcttgccc naaac         595
```

<210> SEQ ID NO 247
<211> LENGTH: 364
<212> TYPE: DNA
<213> ORGANISM: Homo sapiens

<400> SEQUENCE: 247

```
gggtacacta gaaagtcttt tacaaaataa tcatcttaga tcaacagaag accaatcttc     60
aatgtcgtcc tgcaagatgg gttactttaa catctcctcc tgttttctcc aatgttctcc    120
tttagtatgg ctggtaattg ttttggtgat tgccaccccc tcgagatgcc ttgccataag    180
tgctctgttg gccactgtag tctgcatatc cctgtcccata tccatagttc ccatagttat    240
acccagtata atcatatccg ccatagccac tatagttttg atcaccacca taggcactat    300
tgtaatttcc atatccttga tcataatagt tattaaatcc ttggttccag ttttggccct    360
gacc                                                                 364
```

<210> SEQ ID NO 248
<211> LENGTH: 591
<212> TYPE: DNA

-continued

<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 248
ggtncagata tcttcaaagg aggaagaaga aagggaaacc agatggtgga cctgaatatg 60
ncccttancc aganctaatc aacccactca gccagaatag aagaagctgg aatagattcc 120
ccaacctggt ttgccagttc atcttttgac tctattaaaa tcttcaatag ttggtattct 180
gnaatttcac tctcatgant gcnactgngg cttaactaat attgcaatgn ggcttgaatg 240
taagtagcat cctttgatgc ttctttgaaa cttgnatgaa tttgggtatg aacagattgc 300
ctgctttccc ttaaataaca cttaaaatta tttggaccag tcagcacaac atgcctnggt 360
tgnattaaag cnnggatatg ctggatttta taaaattggc caaattagag aaatntagtc 420
ccatggaaat atatttcttg taaaaaagtg cttgaatctt tttggtcaag ataatgccac 480
tcttaagaat atcttcncac tnttgangga ttaaatatcg gcantggaaa agccttaaaa 540
atggggtcna cttgccttgn gcctaaaccg accctgaaat gggatttccc n 591

<210> SEQ ID NO 249
<211> LENGTH: 332
<212> TYPE: DNA
<213> ORGANISM: Homo sapiens
<220> FEATURE:
<221> NAME/KEY: misc_feature
<222> LOCATION: (1)...(332)
<223> OTHER INFORMATION: n = A,T,C or G

<400> SEQUENCE: 249
actctccgag agggtcgttt tcccgtcccc gagagcaagt ttatttacca aatgttggag 60
taataaagaa aggcagaaca aaatgagctg ggctttggaa gaatggaaag aaagggctgc 120
ctcaagagct cttcagaaaa ttcaagaact tgaaaggaca gcttgacaaa ctgaagaagg 180
aaaagcagca aaggcagttt cagctttgac agtctcgagg cttgcgcttg cagaaacnaa 240
aacagaaagg ttgaaaatga aaaaacccag ggtaccttgg nccgggacca cgcttaaggc 300
gaaattccaa cacacttggc cggccggtac ta 332

<210> SEQ ID NO 250
<211> LENGTH: 626
<212> TYPE: DNA
<213> ORGANISM: Homo sapiens
<220> FEATURE:
<221> NAME/KEY: misc_feature
<222> LOCATION: (1)...(626)
<223> OTHER INFORMATION: n = A,T,C or G

<400> SEQUENCE: 250
ggtactatta gccatggtca accccaccgt gttcttcgac attgccgtcg accggcgaag 60
ccctttggcc cgcgtcttcc tttgaactgg ttgcagacaa gggtcccaaa ganagcagaa 120
aattttcgtg ctctgagcac tggagaaaaa ggatttggtt ataagggttc ctgctttcac 180
agaattattc cagggtttat gtgtcaaggt ggtgacttca cacgccataa tggcactggt 240
ggcaaagtcc atctatgggg aagaaatttg aagatgaaga acttcatcct aaagcatacg 300
ggtcctggca tcttgtccat ggcaaatgct ggacccaaca caaatgggtc ccaatttttc 360
atctgcactg gccaagactg antggttgga tggcaaanca tgtngtgntt ggccaaagtg 420
aaagaaggca tgaatattgt ggaaggccat ggaacgcttt tgggtncnag gaatggcaag 480

-continued aaccnccagg aagaatcacc cnttnttgac tggggacaac tcnaataagt tgacttgggg 540
nttaatntaa ccccccanca attccttttg gaactcagga aacacccttc ancccanttn 600
tttcaanttc caaaannttg ggcctn 626

<210> SEQ ID NO 251
<211> LENGTH: 603
<212> TYPE: DNA
<213> ORGANISM: Homo sapiens
<220> FEATURE:
<221> NAME/KEY: misc_feature
<222> LOCATION: (1)...(603)
<223> OTHER INFORMATION: n = A,T,C or G

<400> SEQUENCE: 251
actttttttt tttttttttt tttttttttc aacagaagaa cttttngttt ctttattttc 60
aatattngtc ttattaatat ttttcttatt ttataatgca attacaacaa tttaggagac 120
aaaacantat aaacaaaaga atgttaaata gtttttttta aaaaatagct tgttgcttgc 180
aagaaagtcc atataatctt attccccccc aaatataatt ttatactttg cactaaacca 240
aaatagctta tggaaaatta ggtattaaat agctaaacac agaaaaccta cagctataaa 300
taacataaaa tacagtttaa ctttaatgng atgcttaaac aaagcaaact atgatgcant 360
atgaatcaac ttcattaatt ggacaagtcc agtgaggcnc aaattagata agcnctaaac 420
cctcatgatg ggcaagtgaa accttcaccc cagcaagggt ctttcnggtc ttggctatgc 480
caattccttc canaaaagnc ccagttttac angtctggct ttttccgggg gaacccccca 540
tttntttnnc ccaagttggt tnggatttgg cccccannaa attttttttg gngnaaaaan 600 aan 603

<210> SEQ ID NO 252
<211> LENGTH: 500
<212> TYPE: DNA
<213> ORGANISM: Homo sapiens
<220> FEATURE:
<221> NAME/KEY: misc_feature
<222> LOCATION: (1)...(500)
<223> OTHER INFORMATION: n = A,T,C or G

<400> SEQUENCE: 252
actttatttg tttttttgt tttgttttgg tttttttttt ggcttgactc aggatttaaa 60
aactggaacg gtgaaggtga cagcagtcgg ttggagcgag catcccccaa agttcacaat 120
gtggccgagg actttgattg cacattgttg tttttttaat agtcattcca aatatgagat 180
gcattgttac aggaagtccc ttgccatcct aaaagccacc ccacttctct ctaaggagaa 240
tggcccagtc ctctcccaag tccacacagg ggaggtgata gcattgcttt cgtgtaaatt 300
atgtaatgca aaattttttt aatcttcgcc ttaatacttt tttattttgt tttattttga 360
atgatgagcc ttcgtgcccc cccttccccc ttttttgtcc cccaacttga gatgtatgaa 420
ngcttttggt ctccctggga agtgggtgga ngcagccagg gcttacctgt accttggccg 480
cgaacaccta aggccaantt 500

<210> SEQ ID NO 253
<211> LENGTH: 634
<212> TYPE: DNA
<213> ORGANISM: Homo sapiens
<220> FEATURE:
<221> NAME/KEY: misc_feature
<222> LOCATION: (1)...(634)

-continued

<223> OTHER INFORMATION: n = A,T,C or G

<400> SEQUENCE: 253
tcgagcggcc ngcccgggca ggtactatta gccatggtca aaccccaccc gtgttcttcg 60
acattgcccg tcgacggcga acccttgggc ccgcgtctcc tttgagctgt ttgcagacaa 120
ggtcccaaag acagcagaaa attttcgtgc tctgagcact ggagagaaag gatttggtta 180
taagggttcc tgctttcaca gaattattcc agggtttatg tgtcaggggt ggtgacttca 240
cacgccataa tggcactggt ggcaagtcca tctatgggga gaaatttgaa gatgagaact 300
tcatcctaaa gcatacgggt cctggcatct tgtccatggc aaatgctgga cccaacacaa 360
atggttccca gtttttcatc tgcactgcca agactgantg gttggatggc aaacatgtgg 420
tgtttggcaa antgaaagaa ngcatgaata ttgtggaagc catgganccc tttnggtcca 480
ggaatggcag aacnnccagg aanacaccct tgntgactgt ggcaactcga ataaattgac 540
ttggggttat cttaaccncc caacattcct ttggacttag gaancanccc ttcancccnt 600
tggttcaant tcccaaaaat ttgggctncc tnng 634

<210> SEQ ID NO 254
<211> LENGTH: 602
<212> TYPE: DNA
<213> ORGANISM: Homo sapiens
<220> FEATURE:
<221> NAME/KEY: misc_feature
<222> LOCATION: (1)...(602)
<223> OTHER INFORMATION: n = A,T,C or G

<400> SEQUENCE: 254
nctttttttt tttttttttt ttttttaaat taattaatta aaaaataggt ggnctactgg 60
tggtccttaa gctggaantg cagtgggcac aatcatggnt cactgnagtc tnaacctncc 120
aggttcaagt gatcctccta cctcacctcc antagctggg attacaggca tatgcgacca 180
tgcccagcta attttttatt ttttgtaaaa acggggtctc actatgtcgc ccangctggn 240
cttgaactcc tgaactcaag tgacccttcc gnctnacctn caaagtgcta ggcttacagg 300
tgtgaaccac catgcctggc ctaaaaaatt tattttaaaa aagtaattta tctcttacag 360
ttgtggaggc tgagaaatcc aangncaant ggcncatttg gtgaaaacct tnttgctggt 420
ggggactctg tgaaatnccc aantggcnca tgcatnacac antganggggg cttacattcc 480 aacatgctat ctcttttaag ttttaaagta cnggccnaaa tntgaacntg aatgacttna 540
aatccacnca ttccnctttt ggacnaaaaa ccntgggcaa ttgggatctt ggcnttttna 600
aa 602

<210> SEQ ID NO 255
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 255
cgaggtacag gtaagccctg gctgcctcca cccactccca gggagaccaa aagccttcat 60
acatctcaag ttgggggaca aaaaaggggg aagggggggc acgaaggctc atcattcaaa 120
ataaaacaaa ataaaaaagt attaaggcga agattaaaaa aattttgcat tacataattt 180
acacgaaagc aatgctatca cctcccctgt gtggacttgg gagaggactg gaccattctc 240

-continued cttagagaga agtggggtgg cttttaggat ggcaagggac ttcctgtaac aatgcatctc 300
atatttggaa tgactattaa aaaaacaaca atgtgcaatc aaagtcctcg gccacattgt 360
gaactttggg ggatgctcgc tccaacccga ctgctgtcac cttcaccggt ccagtttttta 420 aatcctgagt caagccaaaa aaaaaaaacc anaccaaacn nanaaaccaa ttaagccatg 480
ccaatctcat ctggtttctg cncaagtang gttgncaaaa aagggttacc ncactaantc 540
ntagccccta aaccnttgcg ggggncantg angggccgan tttganactc cggntggtga 600
nccanttggn ggag 614

<210> SEQ ID NO 256
<211> LENGTH: 308
<212> TYPE: DNA
<213> ORGANISM: Homo sapiens
<220> FEATURE:
<221> NAME/KEY: misc_feature
<222> LOCATION: (1)...(308)
<223> OTHER INFORMATION: n = A,T,C or G

<400> SEQUENCE: 256
ncntccagca gtgggtcatt cgncaacgaa agtcntaccg tagaaaagat ggcgtgtttc 60
tttattttga agataatgca ggagtcatag tgaacaataa aggcgagatg aaagggtctg 120
ccattacagg accagtagca agggaatgtg cagacttgtg gccccggatt gcatccaatg 180
ctggcagcat tgcatgattc tccagtatat ttgtaaaaaa taaaaaaaaa ctaaacccaa 240
aaaaaaaaat nnnannnaac annnnanaaa aannnnaaaa aaaaaaagta cctnggccgn 300
gaccacgc 308

<210> SEQ ID NO 257
<211> LENGTH: 602
<212> TYPE: DNA
<213> ORGANISM: Homo sapiens
<220> FEATURE:
<221> NAME/KEY: misc_feature
<222> LOCATION: (1)...(602)
<223> OTHER INFORMATION: n = A,T,C or G

<400> SEQUENCE: 257
gcgtggtcgc nggccgaggt acgcggggga gacaaaccat accatatccc accagagagt 60
cgcagacact atgctgcctc catggccctg cccagtgtat cttggatgct gctttcctgc 120
ctcatgctgc tgtctcaggt tcaaggtgaa gaaccccaga gggaactgcc ctctgcacgg 180
atccgctgtc ccaaaggctc caaggcctat ggctcccact gctatgcctt gtttttgtca 240
ccaaaatcct ggacagatgc agatctggcc tgccagaagc ggccctctgg aaacctggtg 300
tctgtgctca ntggggctga gggatccttc gtgtcctccc tggtgaagag cattggtaac 360
agctactcat acgtctggat tgggctccat gaccccacac agggcaccga acccaatgga 420
aaangntggg antggaataa cantgatgtg atgaattact ttgcatggga gagaaatcct 480
tcancatttt naaccccggc cctgtccaac ctntcaaaaa cncacatttt taaggggaaa 540
attttactgg atggganggt accctttttnt ggaagtactg cttttcngga nggaagtacc 600
cc 602

<210> SEQ ID NO 258
<211> LENGTH: 600
<212> TYPE: DNA
<213> ORGANISM: Homo sapiens
<220> FEATURE:

-continued

<221> NAME/KEY: misc_feature
<222> LOCATION: (1)...(600)
<223> OTHER INFORMATION: n = A,T,C or G

<400> SEQUENCE: 258
ggtgtntgng ncttatntgt agcggcgcgg ntggttctga aatcgccttc agcggcgccg 60
cagtcntatt atgtgnatgt ccctaccacn aaaatncaga ttaattggna tgctcattac 120
ccacgtgaac gccaaagccc ttcgaagtag tgctgccctg cactnaatca agaagttgca 180
ttaaaattag aaccaaatcc agagtcactg gaactttctt ttaccatgcc ccanattcag 240
gatcagacac ctagtccttc cgatggaaag cactagacaa agttcacctg agcctaatag 300
tcccagtgaa tattggtttt atggggatag gtgatatggn caatgaattc aagttggaat 360
tggnagaaaa actttttgct naagacncng aagcnaagaa cccattttct actnaaggca 420
cagatttaga cttggagatg gtagcttcct atatccaatg gatgatgctt tcagtccgtn 480
cnttgatcag tgncacnttn gaaagcagtt cccaagncct gnaacccagt cctaagccaa 540
gtccggttcn gcgattaatc cgactatgta tgcccttcat ngcccctgtn ataaacnggn 600

<210> SEQ ID NO 259
<211> LENGTH: 600
<212> TYPE: DNA
<213> ORGANISM: Homo sapiens
<220> FEATURE:
<221> NAME/KEY: misc_feature
<222> LOCATION: (1)...(600)
<223> OTHER INFORMATION: n = A,T,C or G

<400> SEQUENCE: 259
gccgaggtac atgggaaagg gagtatggng agctatttcc tttttaaagg atgaagacct 60
tcataaattg gcccctcgga ttctggtgat tcccgcccgc aagcgcaaat gctccagtgn 120
gttatgaaaa tgnttgntaa tctgctctgg ttcttcactg gattcaagan tcgggaggnc 180
ttctcgaatc ttttggataa nctggtttaa aacctgaatt gntacccgca tcattttcct 240
tttcataaaa atagatatat ctgntcagaa tttctatnaa aagctgcact tgtaganang 300
ggtccatgca ctgatttgct atttttaaag cttttttttan gcactccatt accctnttgc 360
cttcgtgaaa cttcttccca tttttgnccn ggttctggcn gaccngaaga aatgtgccca 420
agtgcttaca agttnggcct gacaaggttc nttaaaantt tggatgtacc aagggccccc 480
tgggtcctca aaggtcatga atctttttac tggaaccctt atcctttnaa aaggccatgg 540
tcaagggaat gnncttcttg gctttgaaac ccggattaan tttttncaaa aaaagccngn 600

<210> SEQ ID NO 260
<211> LENGTH: 593
<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G

<400> SEQUENCE: 260
acgcgggaac tccatcctca ccacccacac caccctggag cactctgatt gtgccttcat 60
ggtagacaat gaggccatct atgacatctg tcgtagaaac ctcgatatcg agcgcccaac 120
ctacactaac cttaaccgcc ttattagcca gattgtgtcc tccatcactg cttccctgag 180
atttgatgga gccctgaatg ttgacctgac agaattccag accaacctgg tgccctaccc 240
ccgcatccac ttcctctggc cacatatgcc cctgtcatct ctgctgagaa agcctaccat 300

-continued gaacagctta ctgtagcaga gatcaccaat gcttgctttg agccagccaa ccagatggtg 360
aaatgtgacc ctcgccatgg taaatacatg gcttgctgcc tggtataccg tggtgacntg 420
ggtnccaaag atgtcaatgc tgccttggca ccattcaaac caagcgcaga ttcaatttgg 480
ggatggtgcc cactggcttt aaggtngnat naactaccag cttccactgn ggnnctggtg 540
gaaactngcc aaggnncctt ggccggaaca ccctangggg aattcanncc act 593

<210> SEQ ID NO 261
<211> LENGTH: 343
<212> TYPE: DNA
<213> ORGANISM: Homo sapiens
<220> FEATURE:
<221> NAME/KEY: misc_feature
<222> LOCATION: (1)...(343)
<223> OTHER INFORMATION: n = A,T,C or G

<400> SEQUENCE: 261
cctacctctc ttnccactgc aaatttctgg gatagaccaa aagtgaattt gattatgtgt 60
tggctgaagt tcttcattct gactgttgan gggaggtttt cctttgaaga gttttcatcc 120
cagactcagc tgtcttttca catggatgaa ataattcctg ctaccaacaa cagagcttca 180
ccaggaagtt gagttttcaa gatgccttgt tgctttgaag aagggagtga tgtcaattct 240
cttgntacat tctcccttta gcaacctgag taagagactc tctgccactg ggctgcaaaa 300
aaataaatta cttgaatctc cccttggccc angctgaggt acc 343

<210> SEQ ID NO 262
<211> LENGTH: 593
<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G

<400> SEQUENCE: 262 acttttttttt tttttttttt tttttttgtt tttttttttt tttttttttt tttttttttt 60
tttttttttt ttacagngtn ttttcatttt tattactcaa aaaagtttca tttttttnat 120
ttanctttnt gactntgggc ttgggccttn aacantttca naacgatttt ntgctcctcg 180
anaaggaaag cncccttgat cctgncacna acncntttag cncacatgga accnccatag 240
gccctgntga catgtttctt tgtttnggac aatntcataa aaactttagg nnttacagca 300
cnaacccctn naagtntgcc tgggcncaca ccanatgcaa attttggggc tttcccaacc 360
ttnttggnat aaaggtaaac aattttatta ccagggggtt cgggacaacc tantttttgtt 420 aaaggctgta ttgtaggaaa acctacctcg ggatgtcaaa cccttnacca ttttgagggn 480
ctggaaanaa ngttcccgga aanccccggg tancttnggc cggaaccccc taangggnga 540
attccnaccn cttgggggcn gtantaaggg ganccaantt gggccaaant tgg 593

<210> SEQ ID NO 263
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 263

-continued

```
accaagagtt tgctcctggc tgctttgatg tcagtgctgc tactccacct ctgcggcgaa     60

tcagaagtaa gcaactttga ctgccgtctt ggatacacag accgtattct tcatcctaaa    120

tttattgtgg gcttcacacg gcagctggcc aatgaaggct gtgacatcaa tgctatcatc    180

tttcacaaag aaaaagttgt ctgtgtgcgc aaatccaaaa cagacttggg tgaaatatat    240

tgtgcgtctc ctcagtaaaa aagtcaagaa catgtaaaaa ctgtggcttt tctggaatgg    300

aattggacat agcccaagaa cagaaagaac cttgctgggg ttggaggttt cacttgcaca    360

tcatggaggg tttaatgctt atctaatttg tgcctcactg gacttgncaa ttaatgaagt    420

gatcatattg catcataagt ttgctttggt taancttaca ttaaagttaa ctggatttta    480

agggaattat actgtaggtt ctggggtaac tatttaatac taattttcat aacnattttg    540

gttaatncca agttnaaatt tatttggggg gaanaaaatt tttggccttc t             591
```

<210> SEQ ID NO 264
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 264

```
accaagagtt tgctcctggc tgctttgatg tcagtgctgc tactccacct ctgcggcgaa     60

tcagaagtaa gcaactttga ctgccgtctt ggatacacag accgtattct tcatcctaaa    120

tttattgtgg gcttcacacg gcagctggcc aatgaaggct gtgacatcaa tgctatcatc    180

tttcacaaag aaaaagttgt ctgtgtgcgc aaatccaaaa cagacttggg tgaaatatat    240

tgtgcgtctc ctcagtaaaa aagtcaagaa catgtaaaaa ctgtggcttt tctggaatgg    300

aattggacat agcccaagaa cagaaagaac cttgctgggg ttggaggttt cacttgcaca    360

tcatggaggg gtttagtgct tatctaattt gtgcctcact ggacttgtcc aattaatgaa    420

gttgattcat attgcatcat agtttgcttt ggttaagcat cacattaaag ttaaactgga    480

ttttatggta tttatagctg nanggtttct ggggttanct atttaatact aaatttccat    540

aagctttttg ggttaangcc aagnttaaaa tttttttggg ggggaaaaaa atttt         595
```

<210> SEQ ID NO 265
<211> LENGTH: 592
<212> TYPE: DNA
<213> ORGANISM: Homo sapiens
<220> FEATURE:
<221> NAME/KEY: misc_feature
<222> LOCATION: (1)...(592)
<223> OTHER INFORMATION: n = A,T,C or G

<400> SEQUENCE: 265

```
ggtacttttt tttttttttt tttttttttt ttgaaaatta tacttttatt tgagtcacca     60

ggagaaagat tcacttgtgg ttcaagtcaa atgttcanaa tcataacagg ccanaaaggt    120

ttgatcccga gcacaagccc acgagggagg ggaccaaaac agaccaaaat gagacaacaa    180

ccccatataa aaagatgaac tggcggcttc acacactcac acacatacac atacacacgg    240

atgaaatgtt tggacagagg caaatttcac gtggtcattt ctgtttcttt ttaaatacag    300

gtttgtgggg tggtattttg ttttttccag ctataaaaaa aggcccaaaa gtgcatgtgt    360

gagggggggaa aggcagaaat taagcaataa agtcattttc cctggaggga catganaggg    420

agaaaacagg aggcaattgc tgggganaacg cactttctta acactgggct tttgggtatt    480
```

-continued cttantattg gnccncaaaa agttattttc acattctaac tttgaagnct ntttccnggg 540
attnaatggn ccttaaaacc tttgggaact ttaaaaaaac cngggcttac cc 592

<210> SEQ ID NO 266
<211> LENGTH: 594
<212> TYPE: DNA
<213> ORGANISM: Homo sapiens
<220> FEATURE:
<221> NAME/KEY: misc_feature
<222> LOCATION: (1)...(594)
<223> OTHER INFORMATION: n = A,T,C or G

<400> SEQUENCE: 266
acgcggggaa aaaaaaggca gtattccctt tttaaatgag ctttcaggaa gttgctgaga 60
aatggggtgg aatagggaac tgtaatggcc actgaagcac gtgagagacc ctcgcaaaat 120
gatgtgaaag gaccagtttc ttgaagtcca gtgtttccac ggctggatac ctgtgtgtct 180
ccataaaagt cctgtcacca aggacgttaa aggcatttta ttccagcgtc ttctagagag 240
cttagtgtat acagatgagg gtgtcccgct gctgctttcc ttcggaatcc agtgcttcca 300
cagagattag cctgtagctt atatttgaca ttcttcactg tctgttgttt acctaccgta 360
gctttttacc gttcacttcc ccttccaact atgtcccaga tgtgcaggct cctcctctct 420
ggactttctn caaaggcact tgacccttcg gnctctactt ggcccctnac ctcacccccct 480 tctggcaccg gncntgngac attcacttcn gagaagaccn cccccaagga ggcnggcgnt 540
tggnccanga aaaaaccccg gggaagggtt tnttttttttn aaagggaaat ttcc 594

<210> SEQ ID NO 267
<211> LENGTH: 598
<212> TYPE: DNA
<213> ORGANISM: Homo sapiens
<220> FEATURE:
<221> NAME/KEY: misc_feature
<222> LOCATION: (1)...(598)
<223> OTHER INFORMATION: n = A,T,C or G

<400> SEQUENCE: 267
actggccctc ggtgctggca aaggtgtagt tccactggcc gagggaatca agacatagtg 60
gtccttctgc taagccaagg gctgccacaa tgacacagta gccagatcct gcaattccaa 120
tgagagcagc caatacagaa gaaagcatcg cacatcgttt gccacagttt tcatggccac 180
agcagccaca gcagtcatcc tgttccagcc caatgaagac aaatgctggc aggagcatca 240
gcagggccac ctcctacgat gccagaaaag aaccacacga aacggctgag gtggttttcg 300
gaggcatact ttgttcccat tgggaaagta aagccaaata ttacccgcga tgcacaggaa 360
ggggcgagcc caaccagaaa atgtccgaat gcatcgtgca cacttcccat agcacatggt 420
ggtcttgcta ggtttttctc cccctctct ttggncttca acttcagtga taccccaaat 480
tagatgaaag tggtgccctt ttgggtggaa aaagcaaaca ccaaccccgg gtacctttgg 540
gccggaacac ncttaaggcc aattccannc aattggcggc ccgtacttan gggatccc 598

<210> SEQ ID NO 268
<211> LENGTH: 590
<212> TYPE: DNA
<213> ORGANISM: Homo sapiens
<220> FEATURE:
<221> NAME/KEY: misc_feature
<222> LOCATION: (1)...(590)
<223> OTHER INFORMATION: n = A,T,C or G -continued

<400> SEQUENCE: 268

```
ggacatatta tcaataggct ataagatgta acaacgaaat gatgacatct ggagaagaaa     60
catcttttcc ttataaaaat gtgttttcaa gctgttgttt taagaagcaa aagatagttc    120
tgcaaattca aagatacagt atcccttcaa aacaaatagg agttcaggga agagaaacat    180
ccttcaaagg acagtgttgt tttgaccggg agatctagag agtgctcaga attagggcct    240
ggcatttgga atcacaggat ttatcatcac agaaacaact gttttaagat tagttccatc    300
actctcatcc tgtattttta taagaaacac aagagtgcat accagaattg aatataccat    360
atgggattgg agaaagacaa atgtggaaga aatcatagag ctggagacta cttttgtgct    420
ttacaaaact gtgaaggatt gtggtcacct ggaacaggtc tncaatctat gtagcactat    480
gtggctcanc cttggtaccc cttggattat atatcaacct gnaacatgng nctgggactt    540
actttcnaaa cnaaatnttc cttntttgaa gaaaatctgg gtttttgnaa               590
```

<210> SEQ ID NO 269
<211> LENGTH: 602
<212> TYPE: DNA
<213> ORGANISM: Homo sapiens
<220> FEATURE:
<221> NAME/KEY: misc_feature
<222> LOCATION: (1)...(602)
<223> OTHER INFORMATION: n = A,T,C or G

<400> SEQUENCE: 269

```
acttgaagga agtcgaatca gagatagact ctgaagaaga acttataaat aaaaaaagaa     60
tcatagagaa agttattcat cgactcacac actatgatca tgttctaatt gagctcaccc    120
aggctggatt gaaaggctcc acagagggaa gtgagagcta tgaagaagat ccctacttgg    180
tagttaaccc taactacttg ctcgaagatt gagatagtaa aagtaactga ccagagctga    240
ggaactgtgg cacagcacct cgtggcctgg agcctggctg gagctctgct agggacagaa    300
gtgtttctgg aagtgatgct tcaggatttg ttttcagaaa caagaattga gttgatggtc    360
ctatgtgtca cattcatcac aggtttcata ccaacacagg cttcagcact tncntttggt    420
ggtggttcct ggtcccntgg aagttggaac caaattaatg gngtagtctc tatacccaat    480
acctttggtt ttcatgtgta anaaaaaggn ccattacttt taanggattg tgctggnctt    540
attgngccan taactttttt ttaaatggcc cagttacngg ttttaattct taaaannaaa    600
aa                                                                   602
```

<210> SEQ ID NO 270
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 270

```
ggtacgcggg ggtaggagcc tctctcccta ctgctgctac acaagaccct gagactgacc     60
tgcaggacga aaccatgaag agcctgatcc ttcttgccat cctggccgcc ttagcggtag    120
taactttgtg ttatgaatca catgaaagca tggaatctta tgaacttaat cccttcatta    180
acaggagaaa tgcaaatacc ttcatatccc ctcagcagag atggagagct aaagtccaag    240
agaggatccg agaacgctct aagcctgtcc acgagctcaa tagggaagcc tgtgatgact    300
acagactttg cgaacgctac gccatggttt atggatacaa tgctgcctat aatcgctact    360
```

-continued

```
tcaggaagcg ccgagggacc aaatgagact gagggaagaa aaaaaatctc tttntttctg    420
gaggctggca cctgattttg tatccccctg tagcagcatt actgaaatac ataggcttat    480
atacaatgct tctttctgga tattctcttg gcttgggtgg accccttttt ccggccccag    540
aattgttaan taatngaann nccntncann aagggnnnaa aggnaaatca ncttt         595
```

<210> SEQ ID NO 271
<211> LENGTH: 592
<212> TYPE: DNA
<213> ORGANISM: Homo sapiens
<220> FEATURE:
<221> NAME/KEY: misc_feature
<222> LOCATION: (1)...(592)
<223> OTHER INFORMATION: n = A,T,C or G

<400> SEQUENCE: 271

```
ggtacattga gatcccgcct ctacaaaatc aaaaaattag ccaggcaagg tggtgcgtgc     60
ctgtcgcccc agctacttgg caggctgagc tcaggaggtc aagcctgcct tgggccatga    120
tcatcccatg cactccagcc tgacattcag agcaagacct tgtctcaaag aaagaaaaac    180
atttttatgg tgttttcttt tttagtcttt tcaataatga aaattttcat tttacaggta    240
aaatgaaagg cctggcattt attcaagatc ctgatggcta ctggattgaa attttgaatc    300
ctaacaaaat ggcaacctta atgtagtgct gtgagaattc tcctttgaga tttcagaaga    360
aaggaaacaa tgtgattcaa gatatttaca taccagaagc atctaggact gatggatcac    420
tgtcccgatt caaattattc ttcagtccat ttccccttc tatttcagct ggtccttttc    480
acctaactgt cagtcattct ggtttcaacn atgctttatc tcatgtcctt gaatatagtt    540
ggggnacttt aatttttang gaataatnna acagnttccn ttaaaggntn ng            592
```

<210> SEQ ID NO 272
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 272

```
acattaaagt gtgatacttg gttttgaaaa cattcaaaca gtctctgtgg aaatctgaga     60
gaaattggcg gagagctgcc gtggtgcatt cctcctgtag tgcttcaagc taatgcttca    120
tcctctctaa taacttttga tagacagggg ctagtcgcac agacctctgg gaagccctgg    180
aaaacgctga tgcttgtttg aagatctcaa gcgcagagtc tgcaagttca tcccctcttt    240
cctgaggtct gttggctgga ggctgcagaa cattggtgat gacatggacc acgccatttg    300
tggccatgat gtcaggctcg gcaacaggct ccttggtgac actcaccaca ttgntttca     360
agctgacttt cagcttgnca ccttggagag actttaaccc ggaccaaggg cccgatgcct    420
tccgttaccc aggaatttca tcaccaatgg tggtanttca ggaatgttgg caagtttcct    480
tggcatnttc ccaaanagtt tgttcccgtt cttnttgggn ggcangggct tcggaaaggg    540
ttnattttgt ngggaaccna aaaactgggg tnaaactcct tnccggttna ngggtttccg    600
nnanccn                                                              607
```

<210> SEQ ID NO 273
<211> LENGTH: 398
<212> TYPE: DNA

-continued

<213> ORGANISM: Homo sapiens
<220> FEATURE:
<221> NAME/KEY: misc_feature
<222> LOCATION: (1)...(398)
<223> OTHER INFORMATION: n = A,T,C or G

<400> SEQUENCE: 273
ggtaccgcca ttattctttt gggcaccttt ggttgttttg ctacctgccg agcttctgca 60
tggatgctaa aactgtatgc aatgtttctg actctcgttt ttttggtcga actggtcgct 120
gccatcgtag gatttgtttt cagacatgag attaagaaca gctttaagaa taattatgag 180
aaggctttga agcagtataa ctctacagga gattatagaa gccatgcagt agacaagatc 240
caaaatacgt tgcattgttg tggtgtcacc gattatagag attggacaga tactaattat 300
tactcagaaa aaggatttcc taagagttgc tgtaaacttg aagattgtac ctgccccggg 360
ccgnccgctc gaaagcttaa ntggccgttt cnaanncg 398

<210> SEQ ID NO 274
<211> LENGTH: 587
<212> TYPE: DNA
<213> ORGANISM: Homo sapiens
<220> FEATURE:
<221> NAME/KEY: misc_feature
<222> LOCATION: (1)...(587)
<223> OTHER INFORMATION: n = A,T,C or G

<400> SEQUENCE: 274
actttttttt tttttttttt tttgttgaat caaaagcagg gtttattttt ctatcaaatc 60
cccaatccat gttccagcca atggatgaag ggtgaatcaa gccccacata gactcttggt 120
aaaaacaatt ctaactttct aaaaaaaaaa aaagccaaca cactttttc tttcttttca 180 aaaagctccc aggcctttgg gaacagctga aacaaattca tatcctgact aggtctgttt 240
tctcttaggt atttggatgg tccctctctg ctgccacttc tgcacagatg aggcactgat 300
aatggcctgc aggtcactca caatcctagc tccacatcac tccatggttt gataacctag 360
aaccacgtta tgatttccat ttataatgcc ctaagaacag ctgaaaagat ctgtattaaa 420
ttctgcaaat ctttattgag tgccactatt tgctgggcac angctaggcn ctggattctg 480
ctggttcttg agaaacctaa aanggnncct tnggccggaa cacccttang gcgaaatcca 540
cncactgggg ggcgtactaa ngggatccaa ctttggncca acttggg 587

<210> SEQ ID NO 275
<211> LENGTH: 588
<212> TYPE: DNA
<213> ORGANISM: Homo sapiens
<220> FEATURE:
<221> NAME/KEY: misc_feature
<222> LOCATION: (1)...(588)
<223> OTHER INFORMATION: n = A,T,C or G

<400> SEQUENCE: 275
actttttttt tttttttttt tttgccttta taagagaatt tttattgtta attatttacc 60
ttaatagttt cagaaagagg aacaaattag ctcagtccaa catgattggc agttggcata 120
ttctagtgaa gcaagtgttc tgactgctaa ggatttaatt tggataattt taatacttag 180
ccatctaaca cttcaagcat aacccagaat aaatgcacca ccttcctttc actttaatac 240
ccgnacctac ctcacttcga tataagaaat atcattcaat atgatttcca gaagggacaa 300
gtttcctgga gaatacaggc atganggaca atgcacaaaa agaaaaactc aaaatnaaac 360
tctggatgga taattactaa gctaagggaa ccaaaccttc caatttntaa agaaattaaa 420

-continued

```
tccggttcca aatgcctnat angnctatgt tnaaaaggtt ctggattaat accggaaaag    480

gnttgnttnt tacaggatnc cccaaccgtt acgggccctt ngcccagaat gggccttaaa    540

anccaaagng tcttttccgn ngaggcccca tttnanaatc cttntttt                 588


<210> SEQ ID NO 276
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 276

actttagata catcattcct caaaaagttt ttaacggaga aagtggggca attcaatggg     60

ggaaaggacg gcctttttaa caaatggtgc tggttctact gggtatctgc atccttgata    120

cacagaagtt aactcaagat ggaccacaga ctcacatgta agagctaaaa taacattctt    180

agaagaaatc atggaagtaa atcttcgtga ccttggatca ggtaatgggt actttttttt    240

tttttttttt ttttttttta tcagattaat tttactttat ttcttcaggc ctggggtttt    300

tcgatgactt caaatttggg atcttcaaat ttgaaggtgg gaaatggtat tcatgtctgc    360

attaccaaac atttgctttg acttaaaaag ctcctctcca gctcttgccg atctctgaac    420

tagcatcaac aggntcctcc agatgtctgg nccttaaatt tggattccct aatcttggcc    480

acaaagangt ttcttggata gggaacaaag ttcccttatt naaatgccan tngtngaacc    540

nccaatgttc cttcncaaaa ngggcttaaa ccggttaccc aattgacaaa ggaaa         595


<210> SEQ ID NO 277
<211> LENGTH: 597
<212> TYPE: DNA
<213> ORGANISM: Homo sapiens
<220> FEATURE:
<221> NAME/KEY: misc_feature
<222> LOCATION: (1)...(597)
<223> OTHER INFORMATION: n = A,T,C or G

<400> SEQUENCE: 277

ggtactgttc ctgttggccg agtggagact ggtgttctca aacccggtat ggtggtcacc     60

tttgctccag tcaacgttac aacggaagta aaatctgtcg aaatgcacca tgaagctttg    120

agtgaagctc ttcctgggga caatgtgggc ttcaatgtca agaatgtgtc tgtcaaggat    180

gttcgtcgtg gcaacgttgc tggtgacagc aaaaatgacc caccaatgga agcagctggc    240

ttcactgctc aggtgattat cctgaaccat ccaggccaaa taagcgccgg ctatgcccct    300

gtattggatt gccacacggc tcacattgca tgcaagtttg ctgagctgaa ggaaaagatt    360

gatcgccgtt ctggtaaaaa gcttggaaga tggccctaaa ttcttgaagt ctggtgatgc    420

tgccattggt tgatatggtt cctggcaagc ccatgtgtgt tgaaagcttc ttaaactatc    480

cacctttggg tcgctttgct ggtccngatt tgagacanac catttccgnn gggtggcaat    540

caaaccattg ggccaanaaa gnttntggac ttgcaagggn nccaaatttt ncccaaa       597


<210> SEQ ID NO 278
<211> LENGTH: 595
<212> TYPE: DNA
<213> ORGANISM: Homo sapiens
<220> FEATURE:
<221> NAME/KEY: misc_feature
<222> LOCATION: (1)...(595)
```

<223> OTHER INFORMATION: n = A,T,C or G

<400> SEQUENCE: 278

```
ggtacttttt tttttttttt tttttttttt ttagtttatt aaaatactga gttttatttc     60
acatgtatat ttttgtctcc ccaccatttc catgtctgac caccgctact actatgtcct    120
atcataacat tccatacata cttaaaacca agcaaagggt ggagttccat ctttaaaaac    180
taaacaggca ttttggacaa cacattcttg gcaatagaac ctggacaaca tttatcaaac    240
acggtaggga aagttctcac tctgcattat aaaaaggaca gccagatatc aactgttaca    300
gaaatgaaat aagacggaaa attttttaac aaattgntta aactattttc ttaaagagac    360
ttcctccact gccagagatc ttgaatagcc tcttggncag tcattccgga aacaattctt    420
ccataattga tgaatttggc tttcactttt gggaagagaa ccccctttttc tatacttggg    480
tgcattttgc ttaaaggctt ctacaaacta gggcctttgg gggtttaaga gttttccngg    540
gtcttgaagg ntcttggcct ttgaacttgg ggtnaaaang gttgngcttt tccat         595
```

<210> SEQ ID NO 279
<211> LENGTH: 586
<212> TYPE: DNA
<213> ORGANISM: Homo sapiens
<220> FEATURE:
<221> NAME/KEY: misc_feature
<222> LOCATION: (1)...(586)
<223> OTHER INFORMATION: n = A,T,C or G

<400> SEQUENCE: 279

```
ggtacgcggg gagatacgtt cgtcagcttg ctcctttctg cccgtggacg ccgccgaaga     60
agcatcgtta aagtctctct tcaccctgcc gtcatgtcta agtcagagtc tcctaaagag    120
cccgaacagc tgaggaagcc cttcattgga gggttgagct ttgaaacaac tgatgagagc    180
ctgaggagcc attttgagca atggggaacg ctcacggact gtgtggtaat gagagatcca    240
aacaccaagc gctccagggg ctttgggttt gtcacatatg ccactgtgga ggaggtggat    300
gcggctatga atgcaaggcc acacaaggtg gatggaagaa ttgtggaacc aaagagagct    360
gtctccagag aagattctca aagaccaggt gcccacttaa ctgtgaaaaa agatatttgg    420
tggtggcatt naagaagacc ttgaagaaca tcacctaaga gattattttg acagtatgga    480
aaattgaatg attgaaatca tgacttgacc aagcatggcc aaaaaagggc tttgctttga    540
accttgagac atgattcngg ataaaatgcn tcnaatncnt ntggga                   586
```

<210> SEQ ID NO 280
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 280

```
actttttttt tttttttttt ttttttcttt tttttttttt tttttttttt ttttgaaaaa     60
gtcatgaagg ccatggggtt ggcttgaaac cagctttggg aggttcgatt ccttcctttt    120
ttgtctaaat tttatgtata cggggttcttc aaatgtgtgg tagggtgggg ggcatccata    180
tagccactcc aggtttatgg agggttcttc tactattagg acttttcgct tnaaaacgaa    240
ggcttntcaa atcatgaaaa ttattaatat tactgctgtt anaaaaatga atgagcctac    300
anatgatagg atgtttcatg gggngtatgc atcggggtaa tccnaataac gtcggggcat    360
```

-continued

```
tccggatagg cccaaaaang tttntgggaa aaaaagtttn atttaccccc attaaattta    420

tnnnnaaaag ggattttgcc taaggttggg ctaagggggt ancccngaaa attgggggaa    480

atcangnaat gaaacccccct ntgatggnca aaaacagctc ctnttggttg ggccttatng    540

ggaanngggc ttcaacntan naccttnggc ggnaaaaccc ttanggngaa ttnnnnncaa    600

ntgggggggg tn                                                        612
```

<210> SEQ ID NO 281
<211> LENGTH: 593
<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G

<400> SEQUENCE: 281

```
acgctgcttc ttcagagcaa tacgccgccg tttgtgctgc aggacacgtg gagtaacaag     60

acgctgaatc ttgggtgctt tggtcctagg tttcttacct tctttattta agggctttct    120

tacaacatac tggcggacat catcttcttt agagagattg aaaagtttgc ggattctgct    180

agctcttttg gggcccaggc ggcgaggcac tgtagtatca gtcagtccag gaataccctt    240

ctctcctttt tttacaataa ccaagttgag aacgctcaga tttgcatcca caatgcaacc    300

acgaactgat tttctctttc tttctcagtt ctccttggtc tgtaacagga atgcccctta    360

ctcaatanca ggcggacacg ggcatgggtc aagacaccct gcttcatggg gaaaccttgg    420

ttgncgttcc accactggat tcggaccaca taaacctttc attcttnaac caaacgtaac    480

ancaactttt ggnggccata cnctttata naaagtccgg ggganaaagtn ttttgcagga    540

caagcctgta acnaatagtn aaatcccgga tttggattcc taanccttttt ccn          593
```

<210> SEQ ID NO 282
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 282

```
ggtacaattc aagaaactaa gtatttatgg gcattgaaga aaaaatgttg agataaaatt     60

gctgtgcaga aaaaagtgtt aatgaagccg acctgactac ttaaccttag agacctgctt    120

tacaaggttg gcccttgatt ggcatctggg aacttggagt tcagggggct tccaccattc    180

ccagaactga tcaaagtagc ttactatatc taaactgtaa aacaatatag tttctcctga    240

acacctgctt tccttctggg agtctggaat tttggtatgt gccaggcaga gactaccttt    300

gtgaccagct cccagtaaaa accccaggca ctcagtctct aacaagcttt tctggttgac    360

agtgtttcac aagtgctggt acaactggtt gctgggagaa ttaagctcat cctctgtgat    420

tccactggcc gaggattctt ggaagcttgc acttaagttt cccctgactt caccccatgg    480

gctttttttcc ttgctgattt ggtttgnatc cttcctgnat aaatcatggc ctgaaccnaa    540

cttgaaaaaa aaannnnnnn nnaaaaaaag gtncttgccc ggcggccgtt naaat         595
```

<210> SEQ ID NO 283
<211> LENGTH: 348
<212> TYPE: DNA

-continued

<213> ORGANISM: Homo sapiens
<220> FEATURE:
<221> NAME/KEY: misc_feature
<222> LOCATION: (1)...(348)
<223> OTHER INFORMATION: n = A,T,C or G

<400> SEQUENCE: 283 acttttttttt tttttttttt tttttttttt ctattttttt tttttttttgg ctntanaggg 60 ggtanagggg gtgctatagg gtaaatacgg gccctatttc aaagattttt aggggaatta 120
attntaggac gatgggcatg aaactgtggt ttgctccaca natttcanag cattgaccgt 180
agtatacccc cggtcgtgta gcggtgaaag tggtttggtt taaacgtccg ggaattgcat 240
ctgtttttaa gcctaatgtg gggacagctc atgagtgcaa nacgtnttgt gatgtaatta 300
ttatacgaat gggggcttna atcgggagta cctnggccgn naccacnc 348

<210> SEQ ID NO 284
<211> LENGTH: 563
<212> TYPE: DNA
<213> ORGANISM: Homo sapiens
<220> FEATURE:
<221> NAME/KEY: misc_feature
<222> LOCATION: (1)...(563)
<223> OTHER INFORMATION: n = A,T,C or G

<400> SEQUENCE: 284
ggtacccatt aatttgctca gatatagcag gcttaatggt tctatatttt caaaagtttt 60
taagaatggt ttctaacgta ggagagggaa aacatccacc atccctttc agaatttaaa 120 tggagggcag taaacattct ttacacccaa aacctatggc agcagttcaa atttgaccaa 180
ggtaaatgta gaatagagat gttctaaaca cagctaggac tcagcaagtc taacacacta 240
aaatcatatg attacatttt aaaagaaaat gcacaaaaac caaatagaaa ttttgagatt 300
ttttttcatt tgaaggtaat cttaatgcta ttaaattcac aaatgctaat ttaaataccc 360
aatcctattt atctaaaaca cacattgcaa acacacaaat tatctattct ctccacatgt 420
cagccgccca ttcatatcat ggtttggaaa tgggggagaa atagattncc cttaaactgc 480
aagtcaacan ggggttcttt acagttaact ttagccaaat tcataccaaa tacccgggta 540
cctgcccngg cggccgttcn aaa 563

<210> SEQ ID NO 285
<211> LENGTH: 422
<212> TYPE: DNA
<213> ORGANISM: Homo sapiens

<400> SEQUENCE: 285
acaatggact ggatactaga aattttcttt tcactcaaca gaacataggc atcctggaat 60
tcacatttct gacctttga tgtattaata aagtatggag aaatatagcc tcgatcaaac 120
ttcatgcctt caataatttc taattcatca ttcagtgttt ttccatcctt tactgtgatg 180
acaccctttc ttccaacttt tttcattgca tcagagatga tattgccaat ttctttgtct 240
ccgtttgcag aaatcgtagc aacctgtgca atttcttcag gggtggtcac aggtttagac 300
tgctttttaa gttcagcaat tacagcatca acagctaaca tcacacctct cctgatttcc 360
actggattag cacctttgct aatcttctcg aagccttctt ggctatagag cgtgccagta 420
cc 422

<210> SEQ ID NO 286
<211> LENGTH: 588

-continued

<212> TYPE: DNA
<213> ORGANISM: Homo sapiens
<220> FEATURE:
<221> NAME/KEY: misc_feature
<222> LOCATION: (1)...(588)
<223> OTHER INFORMATION: n = A,T,C or G

<400> SEQUENCE: 286
actgttcctg caggttaagg caggactgga actcctccac agcttgcaca tagttttcag 60
attcaacact aacttctccg agtttaagat gtgcctgggc agcataaagc tgtgcttctt 120
ttgtttcttg ccttttaaaa atgatctttg ctaaatccag catatcccag gcaagctcta 180
ggttcccaat ctcctcctcc tcattttctt gaagagactt gttttcaagg actgaatcat 240
ttggcatttc ttcggtctta tcattttctt tatcatcctc ttctgagcct tcagtttcat 300
ctatgttatc attattttct accagagatt catcttctgn tnttttctcc ttcttcctct 360
tncacatgca caccttccaa ggcgtttcca acacaccatt cttcatcttg ccaacttcag 420
aagtggattt ccatagaaaa agaangnttn ttcacactta ttaactgctc ttcatacttt 480
ttacctnaaa gactaactgn ttcctggaat gcattggccg ctgctnggaa atccccatan 540
cngaagttnt ggcctaancc aaagttntta gttactttcc catccgac 588

<210> SEQ ID NO 287
<211> LENGTH: 583
<212> TYPE: DNA
<213> ORGANISM: Homo sapiens
<220> FEATURE:
<221> NAME/KEY: misc_feature
<222> LOCATION: (1)...(583)
<223> OTHER INFORMATION: n = A,T,C or G

<400> SEQUENCE: 287
actggaactc caggaagcgc tggccagcct catacgggag ccatttttct ttcactgcct 60
ctgctgctga catcttcttc tttcccttca caccctcgaa gcctatgaag gctttctgag 120
caggcttcag cctggtggcc atgtcttggt caatcacacc ctgggagact gcgtcctgaa 180
gtgacagctt ctggcccgtg gttgggtgga tgatgccacc tgtgcaggcc tgagcctcca 240
gaagcctctg acccgtgatg ctgtcaacga tgccccgctc tataccttct gtaatggaga 300
ttttctccag gttttctgtg tcaaagatgg ctgcaatggg gctcgattct tncagggtgt 360
ctgaaaaaga actgctcctt atggntaaat tcctgacctg gatatggtgg aaatcttact 420
tactgattca tgtcgggagc tgctaaaaac atnatcgttg caccactggc catgctgtgn 480
ttggngccac accattttn angngacatg taacnaattg antaggttag nttccgaacg 540
gaccttggcc ggaacaccta aggngatcan ncatggggcg tnn 583

<210> SEQ ID NO 288
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 288
ggtacttttt tttttttttt tttttttgtt atttagtttt tatttcataa tcataaactt 60
aactctgcaa tccagctagg catgggaggg aacaaggaaa acatggaacc caaagggaac 120
tgcagcgaga gcacaaagat tctaggatac tgcgagcaaa tggggtggag gggtgctctc 180

-continued

```
ctgagctaca gaaggaatga tctggtggtt aagataaaac acaagtcaaa cttattcgag    240

ttgtccacag tcagcaatgg tgatcttctt gctggtcttg ccattcctgg acccaaagcg    300

ctccatggcc ttcacaatat tcatgccttc tttcactttg ccaaacacca catgcttgcc    360

atccaaccac tcagtcttgg cagtgcanat gaaaaactgg gaaccatttg gggttgggtc    420

cagcattttg catggaccan aatgccagga cccctatgct ttaaggatga anntcttatn    480

ttnaaatttc ttcccataaa nggcttgcca ccaangccat tatngcgngt gaagcaccac    540

ctgacccata accctggaat aattntnnga aaaccggacc cttntaccna atcttttttc    600

aggggnn                                                              607
```

<210> SEQ ID NO 289
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 289

```
acttttttttt ttttttttt tttgagaatg aataagcagt tctttaatgg ttatttaaat     60

atattccaga agagcgttta taattcattt acaagtgcag tattgcgcta gtaaatgtta    120

cttgacctct tgtataaata atgccgatta agaattagtc ctggaatagt tttcgaattt    180

ctaactctgt agatctaaaa cacaattgta aatggtataa agatgtaaga atcatattgt    240

gataaagtca atctcaaaaa tagagaatcc agacccttcc cagataattt aagaactgag    300

ttttcctcaa cttaaacatg atggccacac agaaaacagt aaagacactt ttcgatgtga    360

tacaactgga taaaactcga gaatatgagt atttagngac caatgnatan acattantgg    420

aattttaaaa nccctttttaa tctgaagccg aaaaaaangc cattttccaa gaattattgn    480

gccctaatca tcatcnannc nngaatanna tncnttcccn ggatagnnnn nnntccncct    540

tnggaaantg ggccnaantt ntttggtntn aaagggggnc cnttaantcc n             591
```

<210> SEQ ID NO 290
<211> LENGTH: 592
<212> TYPE: DNA
<213> ORGANISM: Homo sapiens
<220> FEATURE:
<221> NAME/KEY: misc_feature
<222> LOCATION: (1)...(592)
<223> OTHER INFORMATION: n = A,T,C or G

<400> SEQUENCE: 290

```
ggacttggaa atggttgtct ggaaagcttc cactttggtc ttgacggcat tcaccctctc     60

cagcaccttc tcctggattg ctaccccaaa atcatttcca tcttcaatct tggggatcag    120

gtgttggatc catgtaatca ccagaatgca tttctctttg agagtccaga cttctggctt    180

aaccagggca agcagggaca ggactttctc attcccaggg agaaatccac acttagggac    240

ttctttcttc tcctgcttat ctgtttccat ctcatcatcc ttgggtggag ggtctgggat    300

ggggatgtcc agtggggccc ggagggaagt caagtcagcc acattgaggg agtcctcttg    360

caagagctga ttcaggtata tgattttctg tggcaagaat ctgtagagga attcctcanc    420

ctnctggaaa agaatctgtc tgaagacctt cacctggttg cgggctttcc cgctaagcgc    480

accccacacg gtttgggcct gctgntttaa tccttaanct ctggcttccg gntagtcccc    540

cgggaccttg ccggccggcc ntcaaagggc aattcancna ctggcggccg tn            592
```

-continued

<210> SEQ ID NO 291
<211> LENGTH: 609
<212> TYPE: DNA
<213> ORGANISM: Homo sapiens
<220> FEATURE:
<221> NAME/KEY: misc_feature
<222> LOCATION: (1)...(609)
<223> OTHER INFORMATION: n = A,T,C or G

<400> SEQUENCE: 291
acagtggcat gatctcggct cactgcaacc tctgcctccc gggttcaagc aattctcctg 60
cctcagccac ccaagtagct gggactacag gtgcgtgcca ccacgcccag ctaaattttg 120
tatttttagt ggagacgggg tttcaccatg ttggccagga tggtctcaat ctcctgaccc 180
tgcgatctgc ccacctcagc ctcccaaagt gctgggatta caggcgtaag ccaccgggcc 240
tggcctgttt tatgattctt aatagttact tggtttaaat cacatttgat actatccttc 300
tgaaaagtct gagacagatc tacaaactac agtcaaaatt atagattaag aggaatgaat 360
gcacctattt ggctttaagt tgaagatgaa ttatttctca tgctcatttt cttgcngcag 420
ttatcttaga aagaccccca aaggcttgtg attgtaaagc acttgcatga tcacagaatg 480
caagcttctg gtaccttcgg ccgtgacacg ctaagggcga attcatcaca attgcgggcc 540
gtacctatgg atccannctc ggtccaactt ggcggaatca tgggcatact gnttcctggn 600 nnaaatgtn 609

<210> SEQ ID NO 292
<211> LENGTH: 568
<212> TYPE: DNA
<213> ORGANISM: Homo sapiens
<220> FEATURE:
<221> NAME/KEY: misc_feature
<222> LOCATION: (1)...(568)
<223> OTHER INFORMATION: n = A,T,C or G

<400> SEQUENCE: 292
actgcccaga aggagttcat aaagaataca aagaagaccc caaaagatgt cacgatggca 60
ctattgaatt cacgagcatc gatgcacaca atggtgtggc cccatcaaga cgtggtgatt 120
tggaaatact tggttattgc atgatccaat ggcttactgg ccatcttcct tgggaggata 180
atttgaaaga tcctaaatat gttagagatt ccaaaattag atacagagaa aatattgcaa 240
gtttgatgga caaatgtttt cctgagaaaa acaaaccagg tgaaattgcc aaatacatgg 300
aaacagtgaa attactagac tacactgaaa aacctcttta tgaaaattta cgtgacattc 360
ttttgcaagg actaaaaact ataggaagta agggtgatgg caaaatggac ctcaatggtg 420
tggaaaatgg angnttgaaa gccaaaacca tnnnnnaaaa ncttagggcg aattccannc 480
actggcggcc gtnctaangg atccagcttg gncccaactt ggggtaatca tgggcataac 540
tggtncctgg ggaaaatggt ttcccnnn 568

<210> SEQ ID NO 293
<211> LENGTH: 603
<212> TYPE: DNA
<213> ORGANISM: Homo sapiens
<220> FEATURE:
<221> NAME/KEY: misc_feature
<222> LOCATION: (1)...(603)
<223> OTHER INFORMATION: n = A,T,C or G

<400> SEQUENCE: 293

-continued

```
ggtacttttt tttttttttt tttttttttt tttttttctt tttttttttt tttttngcct     60

ttttaanaaa cttttatttg agnggntntt acaaanattg nngcaatatg aaagtcattt    120

gtttgatana aatatcaagc tgncttgtca aacacnctga agtaacccaa aaatntnttt    180

caaagctcac anagcttaaa aagagcnaag attntntgca accagacaaa acctatttnt    240

gcatttccta tttctttctn aaactgnttt gcctaccaaa ctttnacgtt taaacatttt    300

caggaaatgc agggatcatt ttgtttggaa ttttaagacc ccccngaacn cataggtntt    360

tacaaagaaa cttttcccga tcccttaatt gaaaagaacc ntccnaaata taaantttgn    420

aaactcccnt ttttggccaa ttgatcanaa tgccagaaga natgctaacc naanagccct    480

ttaactgggc tgggattcca taccctaaan ggggtttcaa aactggttaa ccttnnccca    540

attttaacct tngggaaaag ggnaaaggan ccccggggna aaaataaggt tttgaaaaat    600

aaa                                                                  603


<210> SEQ ID NO 294
<211> LENGTH: 617
<212> TYPE: DNA
<213> ORGANISM: Homo sapiens
<220> FEATURE:
<221> NAME/KEY: misc_feature
<222> LOCATION: (1)...(617)
<223> OTHER INFORMATION: n = A,T,C or G

<400> SEQUENCE: 294

ggtacgcggg gatcgcttcc tggtcctcgc cccctccgct gtctccctgg agttcttgca     60

agtcggccag gatgtctcag gctgagtttg agaaagctgc agaggaggtt aggcacctta    120

agaccaagcc atcggatgag gagatgctgt tcatctatgg ccactacaaa caagcaactg    180

tgggcgacat aaatacagaa cggcccggga tgttggactt cacgggcaag gccaagtggg    240

atgcctggaa tgagctgaaa gggacttcca aggaagatgc catgaaagct tacatcaaca    300

aaagtagaag agctaaagaa aaaatacggg atatganaga ctggatttgg ttactgtgcc    360

atgtgtttat cctaaactga gacaatgcct tgttttttttc taataccgtg gatggtggga    420

attcgggaaa ataaccagtt aaaccagcta ctcaaggctg ctcaccatac ggctctaaca    480

gattaggggc taaaacgatt actgactttc cttgagtagt tttaatctga aatcaattaa    540

aagtggattt tgtaccaaaa aaaaaaaaaa aaaaagtnct gcccggccgg ccntcaaaag    600

gcnaattcan ccccttg                                                   617


<210> SEQ ID NO 295
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 295

cgaggtactt ttaccatgaa catctctaga ctgtgattat taaatatagt gataatatac     60

atgggtttac tgggatattg aaaaataaaa gataatgaac ccaatttagt aaatcaacat    120

aaatacaaaa cagagcgaat tagccctcta caactgagct cgtcctgcgt cttgagcttg    180

ggttctttct ggaactgtct caaaccttag tgggggaagt gaccttatcc acagattgct    240

tttcccagag gttccgcttg ctggatacgt ctcctggtct caagtcagaa ggtttgggag    300

caggtgactt gtttccatct ggggttttag ttagccattc attgatgccg ctagaaaccc    360
```

-continued ctaccttcaa gccagcagtt tccttatttg gtgtgcctgc tgcantgggg gatgaaaaca 420
cattcctttc tnccacatac tcttggatgt tgcgtacctg cccnggcngg ccgttcnaaa 480
ggccaattcc acaccactgg cggccgtact aatggatcca aaactcggac cancttggcg 540
natcatnggc atactggttc ctggggnaaa tggattccgt tacattcccc caacttccag 600 ccnggg 606

<210> SEQ ID NO 296
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 296
ggtacgcggg gtgccagagg aaatcttaaa gcgcctactt aaagaacagc acctctggga 60
tgtagacctg ttggattcaa aagtgatcga aattctggac agccaaactg aaatttacca 120
gtatgtccaa aacagtatgg cacctcatcc tgctcgagac tacgttgttt taagaacctg 180
gaggactaat ttacccaaag gagcctgtgc ccttttacta acctctgtgg atcacgatcg 240
cgcacctgtg gtgggtgtga gggttaatgt gctcttgtcc aggtatttga ttgaaccctg 300
tgggccagga aaatccaaac tcacctacat gtgcagagtt gacttaaggg gccacatgcc 360
anaatggtcc cgcaggaagg ccgtcaagaa nggctcgacc cggntggtgt ttcaaggaag 420
aaacattgtg gtcttggtgt ggaaaaaaaa tcantgggcc aactggngga tgaaagacna 480
tgccggaana nctgggcttt ggatgacaac ccctgcatgg gcttttgang ccttaccgcc 540
gatccagggt tntnttaaca nggcccggtg gaatgccnaa nccccggtta ctttggagga 600
cccggtnctt gg 612

<210> SEQ ID NO 297
<211> LENGTH: 590
<212> TYPE: DNA
<213> ORGANISM: Homo sapiens
<220> FEATURE:
<221> NAME/KEY: misc_feature
<222> LOCATION: (1)...(590)
<223> OTHER INFORMATION: n = A,T,C or G

<400> SEQUENCE: 297
acgcggggga acacatccaa gcttaagacg gtgaggtcag cttcacattc tcaggaactc 60
tccttctttg ggccacggaa ttaacccgag caggcatgga ggcctctgct ctcacctcat 120
cagcagtgac cagtgtggcc aaagtggtca gggtggcctc tggctctgcc gtagttttgc 180
ccctggccag gattgctaca gttgtgattg gaggagttgt ggctgtgccc atggtgctca 240
gtgccatggg cttcactgcg gcgggaatcg cctcgtcctc catagcagcc aagatgatgt 300
ccgcggcggc cattgccaat gggggtggaa ttgcctcggg caaccttgtg gctactctgc 360
agtcactggg aacaactgga ctcttcngat tgaccaagtt catcctgggc ttcattgggt 420
ctgccattgc ggctgcattg cnaggtctac taacttcctg cccttgcctt gcaaaaaaaa 480
aaaccttgcc agggaaaaag nccccaancc ttctgaacca accanggggc ccacttttcc 540
aaaatacctn gggnggaaaa tncccaattt tgantttcnn aggaaanana 590

<210> SEQ ID NO 298

-continued

<211> LENGTH: 590
<212> TYPE: DNA
<213> ORGANISM: Homo sapiens
<220> FEATURE:
<221> NAME/KEY: misc_feature
<222> LOCATION: (1)...(590)
<223> OTHER INFORMATION: n = A,T,C or G

<400> SEQUENCE: 298
ggtactttga gccactctcg catggaaagg agtgtcttta tgcctcgacc tcaagctgtg 60
ggctcttcca attatgcttc caccagtgcc ggactgaagt atcctggaag tggggctgac 120
cttcctcctc cccaaagagc agctggagac agtggtgagg attcagacga cagtgattat 180
gaaaatttga ttgaccctac agagccttct aatagtgaat actcacattc aaaggattct 240
cgacccatgg cacatcccga cgaggacccc aggaacactc agacctccca gatttaacta 300
aacaaaagaa actctccacc tagcactgtt tttcttcatt gcttactgag agggtttttg 360
agaacttaat ctggggggag aactgctttc tcagatcctt aactcccgag aagagaagtc 420
cttgtgcaca gaacttgtgg gaaccttcat ccgntgtctt tacctttgga tccagtgtgc 480
aagtttcatg acngaatcat taagatatca aatggcctaa tttggngcna atcatggtat 540
actgggaaaa ttaggcnaat ggaacttntc accgantttg gtctttaaan 590

<210> SEQ ID NO 299
<211> LENGTH: 549
<212> TYPE: DNA
<213> ORGANISM: Homo sapiens
<220> FEATURE:
<221> NAME/KEY: misc_feature
<222> LOCATION: (1)...(549)
<223> OTHER INFORMATION: n = A,T,C or G

<400> SEQUENCE: 299
cgaggtacaa agatctgaca tgtcacccag ggacccattt cacccactgc tctgtttggc 60
cgccagtctt ttgtctctct cttcagcaat ggtgaggcgg ataccctttc ctcggggaag 120
agaaatccat ggtttgttgc ccttgccaat aacaaaaatg ttggaaagtc gagtggcaaa 180
gctgttgcca ttggcatcct tcacgtgaac cacgtcaaaa gatccagggt gcctctctct 240
gttggtgatc acaccaattc ttcctaggtt agcacctcca gtcaccatac acaggttacc 300
agtgtcgaac ttgatgaaat cagtaatctt gccagtctct aaatcaatct gaatggtatc 360
attcaccttg atgaggggat cggggtaacg gatggtgcgg gcatcatgag tcaccagatg 420
anggattcct tttgtgccca caaagatctt tctactttgc ancacacact ggcggncgta 480
ctagtggatc cacttcgnac caacttggcg tatcatgggc tnactggtnc cgggggaaat 540 ggtatccnn 549

<210> SEQ ID NO 300
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 300
actccagcct gggcgacaga gcaagactcc acctcaaaaa agaaatattt agcaaatatt 60
aaaggacaag agggaatatc tgtttaaaaa attataatgc acgttagatg aaaagtaata 120
ggatgagatg gttgttgctg aaatagcact tgctatataa attcaaacat tccttttcaa 180

-continued

```
attcagcttc tcagaggttt gacttcagat gcttgagcac tttcaacatt atctttgcct    240
ttatccttcn ttatgcggat aaacacaact gctaaaatta taccattgat tttggaaact    300
tcccagtcgt tttgtaagct tcactgccga gggaaaatgt aaaatgggga ccccgaaata    360
aagtgctgat catcatcaag tagcctcgaa aatgagactt tcaggtgcac tgaaggggat    420
ggcagaagaa caagccccgt gtagtccttg ctagcctggg aaggttggca ttcacatcct    480
taaggatcan gtggactttg acnccgaact taaaggaaga accccctatt ntggggccac    540
cacttgacct tgggccggaa cacccttaag gcgaattcca cacactgggg g             591
```

```
<210> SEQ ID NO 301
<211> LENGTH: 655
<212> TYPE: DNA
<213> ORGANISM: Homo sapiens
<220> FEATURE:
<221> NAME/KEY: misc_feature
<222> LOCATION: (1)...(655)
<223> OTHER INFORMATION: n = A,T,C or G

<400> SEQUENCE: 301

cgaggtactc tttaaaaagg gactgcaggg ctgggtgtag tggctcacac ctgtaatccc     60
agcactttgg gaggccaagg caggtgggtc acttgaggcc aggagtttga gaccagcctg    120
accaacatgg caaaaacccca tctctactaa aatacaaaaa ttagctgggc atgatggtgc    180
actcctgtaa tcccagctac ttggtaggct gaagcatgag aattgcttaa acctgggagg    240
cagaggttgc agtaagccaa gatcatgcca ctgcactcca gcctgggcaa cagagtaaga    300
ctctgtctta ataaataaat aagaaaataa aacggaactg cagtgctaac agtaatttat    360
acatttttaa atgttctgag tatgttttga ctgggctagt gtaacaatat actaccctga    420
aaagtgcagt tttgattgtt ggtggtgtct ttgggtcang aaaagtgaac tgtgccaaga    480
agtatttttc aatgacatga atggattnct gttaatgcaa ttgactgaga aaatgngctt    540
acgctttctt aactgcaaaa agagntttgt ccacatcana attgttgaaa ctggngctgt    600
ttctgttgcc tgggatctga tgactgggat ttcctcttgg acaaaanacc tgatn         655
```

```
<210> SEQ ID NO 302
<211> LENGTH: 513
<212> TYPE: DNA
<213> ORGANISM: Homo sapiens
<220> FEATURE:
<221> NAME/KEY: misc_feature
<222> LOCATION: (1)...(513)
<223> OTHER INFORMATION: n = A,T,C or G

<400> SEQUENCE: 302

actcgtcttg gtgagagcgt gagctgctga gatttgggag tctgcgctag gcccgcttgg     60
agttctgagc cgatggaaga gttcactcat gtttgcaccc gcggtgatgc gtgcttttcg    120
caagaacaag actctcggct atggagtccc catgttgatg gatcctgagc ttgaaaaaaa    180
actgaaagag aataaaatat ctttagagtc ggaatatgag aaaatcaaag actccaagtt    240
tgatgactgg aagaatattc gaggacccag gccttgggaa gatcctgacc tcctccaagg    300
aagaaatcca gaaagcctta agactaagac aacttgactc tgctgatttt tttttccttt    360
ttttttttta aataaaaata ctattaactg gacttcctaa tatatacttc tatcaagtgg    420
aaaggaaatt ccaggcccat ggaaacttgg atatgggtaa attgatgacc aataatcttc    480
acttaaagnc atgtcctttg gccgcgaaca cgc                                  513
```

<210> SEQ ID NO 303
<211> LENGTH: 610
<212> TYPE: DNA
<213> ORGANISM: Homo sapiens
<220> FEATURE:
<221> NAME/KEY: misc_feature
<222> LOCATION: (1)...(610)
<223> OTHER INFORMATION: n = A,T,C or G

<400> SEQUENCE: 303
acgcggggct tgcagagccg gctccggagg agacgcacgc agctgacttt gtcttctccg 60
cacgactgtt acagaggtct ccagagcctt ctctctcctg tgcaaaatgg caactcttaa 120
ggaaaaactc attgcaccag ttgcggaaga agaggcanca gttccaaaca ataagatcac 180
tgtagtgggt gttggacaag tnggtatggn gtgtgctatc agcattctgg gaaagtctct 240
ggctgatgaa cttgctcttg tggatgtttt ggaagataag cttaaaggag aaatgatgga 300
tctgcagcnt ggggagctta tttcttcana caccttnaaa ttgtgggcag atnaagatta 360
ttctgtgacc cgtcaattct tanattngta gttggtnact gcatggaatt cngtcagcaa 420
gaaangggaa aantctngtt caatttggtn gnataagaan tggttaatgg tcttcaaatt 480
cnttattcct tcagancggc caagtacctn ggccgnganc atgcctaagg gctaattcna 540
ctcantggng gccgntctan ntggattcca ncttggtacc aancttggng ntattnatgt 600 caatanctgg 610

<210> SEQ ID NO 304
<211> LENGTH: 596
<212> TYPE: DNA
<213> ORGANISM: Homo sapiens
<220> FEATURE:
<221> NAME/KEY: misc_feature
<222> LOCATION: (1)...(596)
<223> OTHER INFORMATION: n = A,T,C or G

<400> SEQUENCE: 304
ggtacctgga attatctaat tggccagagg tggcgcccga cccatcagtt cgaaatgtag 60
aagtaataga gttggcaaaa gaatggaccc cagcaggaaa agcaaagcaa gagaattctg 120
ctaagaagtt ttattctgaa tctgaggaag aggaggactc ttctgatagt agcagtgaca 180
gtgagagtga atctggaaag tgaaaagtgg agaacaaggc cgaaagtggg ggaggaagga 240
gacagcaatg aggacagcag tgangactcc tncagtgagc angacagtga gagtggacgg 300
gagtcaggcc tagaaaacan angaacagcc nagangaact caaaagccaa agggaaaaag 360
tgattctgaa gatggggaga aggaaaatga aaaatctaaa acttcagatt cttcaaatga 420
cgaatctagt tcaattanaa gacagttctt ccgattcttg aatcagaatc agaacctgaa 480
agtgaatctt gaatncngaa cagtcgctta ggagaaagaa agaaaccaag caggattgac 540
tccttttncc aagntgttcc ttctaaactg gatgatttaa ccngntccct cagtgn 596

<210> SEQ ID NO 305
<211> LENGTH: 629
<212> TYPE: DNA
<213> ORGANISM: Homo sapiens
<220> FEATURE:
<221> NAME/KEY: misc_feature
<222> LOCATION: (1)...(629)
<223> OTHER INFORMATION: n = A,T,C or G

<400> SEQUENCE: 305
ggtactttnt tttttttttt tttttttttt tttttttttt tggggattta ntttttattt 60

-continued

```
cataatcata aacttaactn tgcaatccan ctaggcatgg gagggaacaa ggaaaacatg    120

gaacccaaag ggaactgcag cgagagcnca aanattntng gatactgcga gcaaatgggg    180

nggaggggng ctntcctgag ctacaaaagg aatgatctgg tggntaaaat aaaacacaag    240

tcaaacttat tnnagttgtc cacagncagc aatggngatc ttcttgctgg ncttgccatt    300

cctggaccca aagcgctcca tggcctccac aanattcatg ccttctttna ctttgccaaa    360

caccacatgc ttgccatcca accactcant cttggnagng cagatgaaaa actgggaacc    420

atttttnttg ggtccnacat ttccatggca aaangccang acccnttgct ttaagaagaa    480

aatctcatct tcaaattctn ccctaaanga cttgccncan gccntntggg tgngaagcnc    540

cccctgncca taaccctgga tatttttgaa agagganect ntacnaacnt ttttccnggt    600

aanaaaaaat tttttntttg acctnccca                                     629
```

<210> SEQ ID NO 306
<211> LENGTH: 643
<212> TYPE: DNA
<213> ORGANISM: Homo sapiens
<220> FEATURE:
<221> NAME/KEY: misc_feature
<222> LOCATION: (1)...(643)
<223> OTHER INFORMATION: n = A,T,C or G

<400> SEQUENCE: 306

```
acagggagga atttgaagta gatagaaacc gacctggatt actccggtct gaactcagat     60

cacgtaggac tttaatcgtt gaacaaacga acctttaata gcggctgcac catcgggatg    120

tcctgatccc ccgcgtacat ttccttgtag actctgttaa tttcctgcag ctcctggttg    180

gttctggagc agatgatctc aatgagagag tcctcgtcgg ttcccagccc cttcatggaa    240

gcttttatct cagaagcgtc atactgagca ggtgtnttca ataggcccaa aatcaccgtc    300

tccaggtggc cagataaggc tgacttcaat gctgatgcaa gntccttttt ggtccttctc    360

tggtaggcga aggnaatatc ctgtctctgt ncattgcttg cggntgggca aaatgttgac    420

aatggtgacc tcatccacac ctttggtctt tgatggntgg ntcaatgttc aaagcatccg    480

ctcagcatca aaantaagta tangctttgc agacccatat gcacttgggg gngnngagng    540

acaccctcca actgaacttg ccaggatttn tgaaagtaan antttttaaga acttgccgnc    600

cccanactaa acnnccaatc tagcccnntn cctaacggcc aag                      643
```

<210> SEQ ID NO 307
<211> LENGTH: 643
<212> TYPE: DNA
<213> ORGANISM: Homo sapiens
<220> FEATURE:
<221> NAME/KEY: misc_feature
<222> LOCATION: (1)...(643)
<223> OTHER INFORMATION: n = A,T,C or G

<400> SEQUENCE: 307

```
cgaggtactt tttttttttt tttttttnt ttnttnttnn tttggggatt nantttttat     60

ttcataatca taaacttaac tctgcaatcc aactaggcat gggagggaac aaggaaaaca    120

tggaacccaa agggaactgc ancgagagca caaanattct nggatactgc gancaaatgg    180

ggnggagggg tgctctcctn agctacaaaa ggaatgatct ggtggttaan ataaaacaca    240

agtcaaactt attcnagttn tccacagnca gcaaagggga ncttcttgnt gggcttgcca    300

ttcctggacc caaaacgctc catggnctcc caaaatttat gccttttttt actttgccaa    360
```

-continued

```
anaccacatg ctttgccttc caccnctcan tttttgnggg ggnaaataaa aancgggaac    420

cnnttgtgtt tggnccnaca ttttccnttg gnaaaaaacc ncgacccctt tntttaagaa    480

naaaatttta nttttaaaat tttcccctaa aaaggactgg cccnaaggcn ttttgggggn    540

gaagcccncc ntccccnaaa cctggaaaaa ttttggaagc nggacccttt accaaatctt    600

tntcctggtt aaaaaaaaat ttttttttt gacctttccc aan                       643
```

<210> SEQ ID NO 308
<211> LENGTH: 653
<212> TYPE: DNA
<213> ORGANISM: Homo sapiens
<220> FEATURE:
<221> NAME/KEY: misc_feature
<222> LOCATION: (1)...(653)
<223> OTHER INFORMATION: n = A,T,C or G

<400> SEQUENCE: 308

```
cgaggtacag agagtagctt ctgtgatgca agaatatact cagtcaggtg gtgttcgtcc     60

atttggagtt tctttactta tttgtggttg gaatgaggga cgaccatatt tatttcagtc    120

agatccatct ggagcttact ttgcctggaa agctacagca atgggaaaga actatgtgaa    180

tgggaagact ttccttgaga aaagatataa tgaagatctg gaacttgaag atgccattca    240

tacagccatc ttaaccctaa aggaaagctt tgaagggcaa atgacagagg ataacataga    300

agttggaatc tgcaatgaag ctggatttag gaggcttact ccaactgaag ttaaggatta    360

cttggctgcc atagcataac aatgaaagtg actgaaaaat ccagaatttc agataatcta    420

tctacttaaa catgtttaaa agatggtttg tttgcaagac tttttgcata cttanttcta    480

catgaattaa atcactggtt tnaaatgaca cttattaatc ctaataactg gtnaacccnc    540

aaaaaaaaaa aaaaaaaaaa ntacttnccc ggcggccgtc gaanggcaat tcacncctgg    600

cggccgtcta tggatccacc cggnccacct gggnaacagg cnactggttc tgg           653
```

<210> SEQ ID NO 309
<211> LENGTH: 649
<212> TYPE: DNA
<213> ORGANISM: Homo sapiens
<220> FEATURE:
<221> NAME/KEY: misc_feature
<222> LOCATION: (1)...(649)
<223> OTHER INFORMATION: n = A,T,C or G

<400> SEQUENCE: 309

```
acttgcaaaa gcacttgaag tcattaaacc agctcatata ctgcaagaga aagaagaaca     60

gcatcagttg gctgtcactg cataccttaa aaattcacga aaagagcacc agcggatcct    120

ggctcgccgc cagacaattg aggagagaaa agagcgcctt gagagtctga atattcagcg    180

tgagaaagaa gaattggaac agagggaagc tgaactccan aaagtgcgga aggctgagga    240

agagaggctg cgccaggaag caaaggagag agagaaggag cgtatcttac aggaacatga    300

acaaatcaaa aagaaaactg tccgagagcg tttggagcag atcaagaaaa cagaactggg    360

tgccaaagca ttcaaagata ttgatattga agaccttgag gaaatggatc cagattttat    420

catggctnaa cagggtgaac aactggagaa agaaaagaaa gaacttcaga acccttaaga    480

atcagaaaag aagattgctn ttttgaagac ccacctttgg aaaaaattcct ttgttaagag    540

cctttcgagg acagaaaatt aagacatggt ctggggngcc cccgaggaga aagaattctc    600

ctgcccttga cgtgaaaggt nttgcataaa atcatgtccn atcttgaga                649
```

-continued

<210> SEQ ID NO 310
<211> LENGTH: 319
<212> TYPE: DNA
<213> ORGANISM: Homo sapiens

<400> SEQUENCE: 310
cgaggtacta gccggacttg gattttctgg aaagatttca gttgaggaac gggaacaaag 60
attatgatag ctttccgacc accaccaact tcaatttcct tagctgccgt aatattcagc 120
tccctgagct gagccttgag gtccgagttc atctccagct ccagaagagc ctgggagatg 180
ccggactcga actcgtccgg cttctcgcca ttgggcttca cgatcttggc gctcgaactg 240
aacatggctt tctcctggga gaacttgccg agcgccggct taggaagaga ccccgcgtac 300
ctgccgggcg ggcgctcga 319

<210> SEQ ID NO 311
<211> LENGTH: 646
<212> TYPE: DNA
<213> ORGANISM: Homo sapiens
<220> FEATURE:
<221> NAME/KEY: misc_feature
<222> LOCATION: (1)...(646)
<223> OTHER INFORMATION: n = A,T,C or G

<400> SEQUENCE: 311
cgaggtactg atgcaacagt tgggtagcca atctgcagac agacactggc aacattgcgg 60
acaccctcca ggaagcgaga atgcagagtt tcctctgtga tatcaagcac ttcggggttg 120
tagatgctgc cattgtcgaa cacctgctgg atgaccagcc caaaggagaa gggggagatg 180
ttgagcatgt tcagcagcgt ggcttcgctg gctcccactt tgtctccagt cttgatcaag 240
ctgcacatca ctcangattt caatggtgcc cctggagatt ttagtggtga tacctaaagc 300
ctggaaaaaa ggaggtcttn tntggcccca aaccaatgtt ctgggctggc caatgacttc 360
acatggggca atggcaccaa caccggcaga acttgnaccc tattgccaca acatgtcctt 420
atctnaatga nggncttctt tgtgaaaaca aaccccattc cccggaatta agnacaantt 480
cttcaaactt gggtggnttc aagggcctcg atngcctgcc catatngggt ttttgccata 540
aaacacaacn ttccnnaaag gaatccgant nttgttttgt tgganccat ttttgttccc 600 aagaaaattn ggtaatatcc aaattgggga attaggaaaa tgggnt 646

<210> SEQ ID NO 312
<211> LENGTH: 622
<212> TYPE: DNA
<213> ORGANISM: Homo sapiens
<220> FEATURE:
<221> NAME/KEY: misc_feature
<222> LOCATION: (1)...(622)
<223> OTHER INFORMATION: n = A,T,C or G

<400> SEQUENCE: 312
cgaggtactt ttgtgagagg gttcaatggg agagctttaa tgcagatgag acttgaagct 60
tctgaagaag atctaagtct tgatgaggtt attcaaactc aaatcttgaa tgcataatga 120
tgataggcca tggtcttcaa aaacgtggta cttttaatag caacagggtt tcaccatgtt 180
ggccaggctg gtctcaaatt cctgacctca agtgatctgc ccacttaagt gctgggatta 240
caggcatgag ccacaacatc tggccagaaa tattttttct tttctttctc tttctctctc 300
tctttttttt tttttttttt tttggagctc gctctgtccc ccagctgcaa tgcaatgggg 360
caatcttaac ttactgnaac ctccccttcc aggtcnaaag aatctttgng ctacctccta 420

-continued

```
natntnggaa tacaagggcg tccccccacct actaattttg ntttttaaga aaaggagggt    480

ttancatgtt ggtnngntga tcccaacctc cgaccttaan ganccctccgc ctaatttcca    540

aaggctggat nttggctgan cccaccccnc ttaaccaaaa ttnaaattct tttntcctgc    600

cgggggcgtt aaagggaatc aa                                              622
```

```
<210> SEQ ID NO 313
<211> LENGTH: 674
<212> TYPE: DNA
<213> ORGANISM: Homo sapiens
<220> FEATURE:
<221> NAME/KEY: misc_feature
<222> LOCATION: (1)...(674)
<223> OTHER INFORMATION: n = A,T,C or G

<400> SEQUENCE: 313

nggacttgaa atcattgaag ttctgcaaaa aggagatgga natgcacaca gaaagaaaga     60

tacagaggtc cgcagacggg agctcctaga atccatttct ccagctttgt taanctacct    120

gcntgaacac gcccaagacg tggtgctaga taagtcagcg tgtgngtagg tntctgncat    180

tccngggaac agacnaattn gaccatnagg naacctgagc ttnccaaagt ncgcaaggct    240

gaagaagana ggctnctcca ggaagccnac gagaaagana aangagccgt attttacncg    300

aacatgaaca aatcaaaaaa naaaactgtc cgaaaaccgt ttggagcaaa ncaaanaaaa    360

cagnacctgg gngcccaaag cattcnaana tatttgttat tancncaccn tgatggattc    420

naaacnttat ttttncttgg cncggctggn ccgcccggct ngngnaaaga aaagaacttt    480

nctaccnctc ccgaatcaag aaaagaanat ggctttttn taaaanncaa cccttgggaa      540

aaaattcttt gtttaananc cctccaangc ccgggaaatt aattcatgct ttgtgtgngc    600

gaccnannaa aaaanaanan atccttcctt ccccttaann gaaaagggcc ttncaaaaaa    660

tgattgccca agnc                                                      674
```

```
<210> SEQ ID NO 314
<211> LENGTH: 646
<212> TYPE: DNA
<213> ORGANISM: Homo sapiens
<220> FEATURE:
<221> NAME/KEY: misc_feature
<222> LOCATION: (1)...(646)
<223> OTHER INFORMATION: n = A,T,C or G

<400> SEQUENCE: 314

actttttttt tttttttttt tttttttttt tttgagatgg agtcttgctc tgtcgcccag     60

gctggagtgc agtgttgcga tctcagctca ttgcaacctc tgcctcccag gttcaagtga    120

ttctcctgcc tnagcctcct gagtagttgg gactacaggc acatgccacc atgcctggct    180

aattttttttg catttttaag tanagacagg gtttcatcat gttggccagg caggtntcaa   240

actcctgacc tcaagtgatc cacctgtctc agcctcccaa agtgctggga ttacaggcat    300

gagccactgn acccggccta aaaatgatta cttcttataa aaaggatttc ttccccttca    360

caacacttan cttccttttt ctttcctggn aactatgggt ntggngnccg cataaggatc    420

taccttncnc aagctggaca ntgggggttg ctncttgang gnaactcagg ccanatacng    480

accctggggg gaacnctaaa cttacttggg tanaacccgg gctaacattt ctgcttgnga    540

ngttgattcc ccncaaattt ttaaaaggnn tttcatggcc cttagggcaa ccattttaca    600

aagatgggnc acatggnctt ggccgnaacc cctangngaa ttcncn                   646
```

-continued

<210> SEQ ID NO 315
<211> LENGTH: 666
<212> TYPE: DNA
<213> ORGANISM: Homo sapiens
<220> FEATURE:
<221> NAME/KEY: misc_feature
<222> LOCATION: (1)...(666)
<223> OTHER INFORMATION: n = A,T,C or G

<400> SEQUENCE: 315
acagtctttg gatatttagg aaggggatgg ggagaaagtc agttctcaga acaaattagt 60
cagcttcagt ctcgtcagca gggtctttgg attctttgtt cttccgcact tcttcaatgt 120
gcttatcctt ctctcgcaaa cgttccagtt tggcagccat ttgtgcctct cggttctctt 180
tattagcttc cattttgtgg gtcagtttct cttctgccat tttactgaag ttgntgttct 240
cttctattgc cttctgaagc acttctttct cgtgctctcg tttctcancc agctgcttca 300
agaccttagc ttcatgggac ttgcgtcttt cttctgcagc ttctaatttc ttctgaattt 360
cctccaggga aagaccttct tctttggaag ggaaaggggg aattctggaa ccagattctt 420
ttgacccaag gctgaaaatc agcttaaaag cctggccttg angcacccnt tttcagntct 480
ttcacctgga tatcntaaag aagccctngt gattnaaaac aagccnaccg gcantnnatt 540
ntgncaanan cnnggataan gnaatccctg tnaantccna cccctnaccc cattttcccg 600
ggaccttggc ngnaacccct tanggngaat tcnnccnctn ggcggccgta ctaangggac 660
ccaccg 666

<210> SEQ ID NO 316
<211> LENGTH: 656
<212> TYPE: DNA
<213> ORGANISM: Homo sapiens
<220> FEATURE:
<221> NAME/KEY: misc_feature
<222> LOCATION: (1)...(656)
<223> OTHER INFORMATION: n = A,T,C or G

<400> SEQUENCE: 316
actcttggtt tgtcaatggg actttccagc aatccaccca agagctcttt atccccaaca 60
tcactgtgaa taatagtgga tcctatacgt gccaagccca taactcagac actggcctca 120
ataggaccac agtcacgacg atcacagtct atgcagagcc acccaaaccc ttcatcacca 180
gcaacaactc caaccccgtg gaggatgagg atgctgtagc cttaacctgt gaacctgaga 240
ttcagaacac aacctactgt gggtgggtaa ataatcagag ccttcccgnc aagtcccagg 300
cttgcagctg gccnatgacc aacaggaccc tnactctact tagtgtcaca aggaatgatg 360
ganggaccct atgaagtgtg gaaaccagaa ccaattaagt ggtgnccaca cganccaggc 420
attcttgaat ggcccttatg gnccanaaga acccaccatt tcccctnata cacctaatnc 480
cgtccagggt gaaccttaag ctntctggca tgcaancctt aaccactggc aggattcttg 540
gnttaatgaa gggaacattc nnacccnccc agaagttttt attttcaact tacttggaan 600
aacgggggct ntttactgcc ngccataact taacnggggc cnnancggac ttcgnn 656

<210> SEQ ID NO 317
<211> LENGTH: 636
<212> TYPE: DNA
<213> ORGANISM: Homo sapiens
<220> FEATURE:
<221> NAME/KEY: misc_feature
<222> LOCATION: (1)...(636)
<223> OTHER INFORMATION: n = A,T,C or G -continued

<400> SEQUENCE: 317 acttttttttt tttttttttt tttttttttt tttgnagtca gctatttaat taggttctta 60
agacatttag aacaccaatt tgngaggata aattccattc gtcagagcaa acacagatcg 120
caggtagccc tggagctgag gaatagcttt gatttttggt aaaatttgtg agtccacagc 180
tttctgatca atcttgcgct gctccgtaat ctcatatttc cctttttctg ggncgaaaan 240
cttacctttc tggggnntgg gcttncgcag cttcttcttn ttgaagtaag catnagtaan 300
aagntttggg anttttacan tgntgatann cattttggnt gaagnggnan tgacnaattt 360
ctgggggggt cttcgtaaag gaactcnant gaggcccaag ggnccgtccn agtaataagg 420
ccctnncanc tggttangga aaccccctnt tggcctgggg ggnccangag gntgatccaa 480
atggccccgg ggaaaagcng gntcaanttt tnacggctnc tnaaagggtt ttgccnggnt 540
taanctttnn ggncnttttc agnggaaana ccngctttgn nantntaccc ccggntcctc 600
ggcggaaacc nttagggnna attncncnct gggggg 636

<210> SEQ ID NO 318
<211> LENGTH: 654
<212> TYPE: DNA
<213> ORGANISM: Homo sapiens
<220> FEATURE:
<221> NAME/KEY: misc_feature
<222> LOCATION: (1)...(654)
<223> OTHER INFORMATION: n = A,T,C or G

<400> SEQUENCE: 318
cgaggtacgc ggggcctttc tgcccgtgga cgccgccgaa gaagcatcgt taaagtctct 60
cttcaccctg ccgtcatgtc taagtcagag tctcctaaag agcccgaaca gctgaggaag 120
ctcttcattg gagggttgag ctttgaaaca actgatgaga gcctgaggag ccattttgag 180
caatggggaa cgctcacgga ctgtgtggta atgagagatc caaacaccaa gcgctncagg 240
ggctttgggt ttgtcacata tgccactgtg gaagaggtgg atgcagctat gaatgcaagg 300
ncacacaagg tggatggaag aattgtggaa ccaaagaaaa ctgtcttcag agaagattct 360
taaagaccan gtgcccactt aactgtgaaa aagatatttg gtggtggcat taaagaagac 420
actgaagaac atcactaaga gantattttg aacagtatgg anaaaattgn agngattgaa 480
atnatgactg ccnangcagt ggcancaaan ggggctttgg ctttnnacct ttgacnacca 540
tgactcnngg ataaaatggn attcnnaaat ccctcntgng aatggccnca ctgggaagtt 600
ngaaancctn ncaacnagaa agggtncgnt tnntccncca aangcnaang tttc 654

<210> SEQ ID NO 319
<211> LENGTH: 659
<212> TYPE: DNA
<213> ORGANISM: Homo sapiens
<220> FEATURE:
<221> NAME/KEY: misc_feature
<222> LOCATION: (1)...(659)
<223> OTHER INFORMATION: n = A,T,C or G

<400> SEQUENCE: 319
acgcggggaa gccaactcag actcagccaa cagagattgt tgatttgcct cttaagcaag 60
agattcattg cagctcagca tggctcagac cagctcatac ttcatgctga tctcctgcct 120
gatgtttctg tctcagagcc aaggccaaga ggcccagaca gagttgcccc aggcccggat 180
cagctgccca gaaggcacca atgcctatcg ctcctactgc tactacttta atgaaagacc 240
gtgagacctg ggttgatgca anatctctat tgncagaaca tgaattnngg caacctggtg 300

-continued tctgtgctna cccangccca aggtgccctt ggggcctcac tgattaanga aantggcact 360
gatgacttca atggctggaa tggccttcat gaccccnaaa aagaacccgc gnttgcactg 420
gacagtgggt ccctngntct cttacaagtc tggggcaatt gganccccaa nccatgntaa 480
ttcnggctac tggggtgagc nnacctcagc ccaggatttn gaantggaan gcctgncttg 540
ggaanacaag ttcttctttn gctngcaagt tcaaaaccta atgcagctgg aaaatcatnt 600
ctanaactga tcagcattcn accgnttcaa attaaccggc ctttttcant tanttaccg 659

<210> SEQ ID NO 320
<211> LENGTH: 664
<212> TYPE: DNA
<213> ORGANISM: Homo sapiens
<220> FEATURE:
<221> NAME/KEY: misc_feature
<222> LOCATION: (1)...(664)
<223> OTHER INFORMATION: n = A,T,C or G

<400> SEQUENCE: 320
ggtactctgc cttttaggag atgaggtaag acatatacat agatggcttt tactagccaa 60
ggcaatgtaa atggactaag attctcatgt gacttgaggt tatctgatga atttattctc 120
ttcaaaacca cctactttta gagggcatgt ttaacccctc tctttattta aggagggaga 180
gaaaaacaca tgtaaccaga attcagagtg ggttactcaa cctaagagaa catacggagt 240
tctctttggg aaaacgacaa gactacagtg ttcacttcgc accatgaagt ggcactcctg 300
ntatggctgc agantcctct tacttcttat gaaaggatgc atctgattct gaaattactg 360
atatattcga tcagttaggg atgntttaaa aagngaaaac caatgccaca catacacttt 420
ctagctttct gaaaatnacc cgacacattn ccnaaaatng agaatttacc ctattacttt 480
tagagaaatt tccataatat tcttgggtaa agaancccng ttgggcatat tnccaatttt 540
cagnggncnt ggttttatgc ccnaganccc aataggntcc cccatttttt aaggcttttt 600
ccacngacga ttttttaaan cnttctnnan tgggggaaga ataatcttaa aagtngnctt 660 atnt 664

<210> SEQ ID NO 321
<211> LENGTH: 666
<212> TYPE: DNA
<213> ORGANISM: Homo sapiens
<220> FEATURE:
<221> NAME/KEY: misc_feature
<222> LOCATION: (1)...(666)
<223> OTHER INFORMATION: n = A,T,C or G

<400> SEQUENCE: 321
cgaggtacag tattacagtc agccacagaa gctgtgttgg gggacaagac ccaatccttc 60
cccacaccag gcaaagcagt attggacatg agttggcatg tggctgggcc cacgtcctta 120
tcccccaggc ctgaggggag accaccttct gatgataacc aacccctagc taccactctg 180
tattcatcag gggaggggta taaaccccgc atgcaagaag aacccttgcc cccagtgtca 240
aatgggatgg ggatgctaga gttatagtaa aggggaaacc ctatgtaagc tgntaacaga 300
gttcacaggg gtagggataa cccctgntct tcagctncca aatgngctca ctttccagct 360
tcttcatccg tcatcaatgc tggcaaagtt tccctnaact gnggccaggt tttcacgcat 420
gggtggctgc acctgggtca aaaaggtggn attggccntt aaggaattag caatcatntg 480
ctgggtggga ttccagtgtg taaggaactt anccaactgc atggnttgnt tgtgcanctg 540

-continued

```
cttgatggng acaagtttnt gcaccanctn aaggaaggtg gaagcatggg gctcaacctn    600

gataagttca tatacttggg gcnccttgct ttgggatctg catntttaca aggnttatcn    660

tggcan                                                               666
```

<210> SEQ ID NO 322
<211> LENGTH: 631
<212> TYPE: DNA
<213> ORGANISM: Homo sapiens
<220> FEATURE:
<221> NAME/KEY: misc_feature
<222> LOCATION: (1)...(631)
<223> OTHER INFORMATION: n = A,T,C or G

<400> SEQUENCE: 322

```
accggaaagg aagctcccat tcaaaggaaa tttatcttaa gatactgtaa atgatactaa     60

ttttttgtcc atttgaaata tataagttgt gctataacaa atcatcctgt caagtgtaac    120

cactgtccac gtagttgaac ttctgggatc aagaaagtct atttaaattg attcccatca    180

taactggtgg ggtacatcta actcaactgt gaaaagacac atcacacaat caccttgctg    240

ctgattacac ggcctggggt ctctgccttc tccccttacc cttccggctc cacccttcct    300

gcaacaacag ccctntacct gggggcttg ntagaagaga tgtgaagggt tcaaggtcgc    360

aacctgtggg actactgcta ggtgtgtggg gnggttcgcc tgcacccctg ggttctttaa    420

gncttaaagt gatgcccctt tccaaccatt attctggncc cacacttctc actccggcct    480

tggncnanca taaatgnacc ccttcacttc ctntgagaat ggccttcgng aagaatcnag    540

gctttcccaa ncttctttcc ccccnttatc angggngctg gttttctnct ctcnaaggtc    600

ntttgaccgn accaccaaac ttctgaattn t                                   631
```

<210> SEQ ID NO 323
<211> LENGTH: 647
<212> TYPE: DNA
<213> ORGANISM: Homo sapiens
<220> FEATURE:
<221> NAME/KEY: misc_feature
<222> LOCATION: (1)...(647)
<223> OTHER INFORMATION: n = A,T,C or G

<400> SEQUENCE: 323

```
actgtgggtc gaagtaatgg atacggacgt aaccatcttc gccgccgctg ctgtagctct     60

tgccatcagg atggaaggca acactgttga taggtccaaa gtgacccttg actcttccaa    120

actcttcttc aaaggccaaa tggaagaacc tggcctcaaa cttgccaatc ctggtggagg    180

ttgtggttac atccatggct tcctgaccac cgcccaggac cacatggtca tagttggggg    240

agagggcagc tgagttgaca ggacgttctg tccggaaagt cttctgatgt tcaagagttg    300

tggagtcgaa aagcttggct gtgttgtcct tggacgcggt cacaaacatg ggcatgtccc    360

tggataactg gatgtccgtg atctgcccgg agtgcttctt aacattncca acacctnttc    420

aaanttggca ctatactggg tgagctcttc actttatng gcaacgnatg atcacttccc    480

caagggtccc caaacagcac tggggaattt agagncattc cagggaactt tatgtagggt    540

tcatggtgca attggttnga tccccaggtc aaaaagttnc aaacactgga nccctttctt    600

gtccnnggag aacatgttat ttgccccaag taaaacccng nccggng                  647
```

<210> SEQ ID NO 324
<211> LENGTH: 653
<212> TYPE: DNA
<213> ORGANISM: Homo sapiens -continued
<220> FEATURE:
<221> NAME/KEY: misc_feature
<222> LOCATION: (1)...(653)
<223> OTHER INFORMATION: n = A,T,C or G

<400> SEQUENCE: 324
ggtacttttt tttttttttt tttttttttt ttgagatgga gtcttgctct gttgccagac 60
cggagtgcag tggtgcgatc tgggctcact gcaatctcca cctcccgggt tcaagcgatt 120
ctcctgcctc agcctcccga gtaactggga ctacaggtgt gcgccaccaa gcccagctca 180
tttttgtatt tttagtanag atggggtttc acgatgttgg ctaggatggt ctcgatctct 240
ggtcagagtc ttttctgtaa aaatccttgg taaagaagca attttagact gtancctgtt 300
gcaaatgcnt taaggaagaa gcaaaacaac tgntagtctt tctgaaatga aaaaactacn 360
ccagggctgg tatatnnaga gcaaccccaa ccannactnc catcntgatg cccacagggg 420
cccactgana nacccngaaa angtccnnaa gcntaaannt ngangcnttg cttttgaaat 480
attgcgccng taccnagntn nagacaaacn ngnttaaggc ccnnantntt tggccngant 540
ttgcgataaa aaaaacttgg gggtcgctnc nngatcccnn ttgtncccca naanctgggg 600
ggatgggttn aagcccntgn cnnaaggttt nngttctccc aaggtaaaan nng 653

<210> SEQ ID NO 325
<211> LENGTH: 655
<212> TYPE: DNA
<213> ORGANISM: Homo sapiens
<220> FEATURE:
<221> NAME/KEY: misc_feature
<222> LOCATION: (1)...(655)
<223> OTHER INFORMATION: n = A,T,C or G

<400> SEQUENCE: 325
ggtacgcggg gccttttggc tctctgacca gcaccatggc ggttggcaag aacaagcgcc 60
ttacgaaagg cggcaaaaag ggagccaaga agaaagtggt tgatccattt tctaagaaag 120
attggtatga tgtgaaagca cctgctatgt tcaatataag aaatattgga aagacgctcg 180
tcaccaggac ccaaggaacc aaaattgcat ctgatggtct caaggggtcg tgtgtttgaa 240
agtgagtctt gctgatttgc agaatgatga agttgcattt agaaaattca agctgattac 300
tgaagatgtt caagggtaaa aactgnctga ctaacttcca tggcatggat cttacccgtg 360
acaaaatgtg gtccatgggc aaaaaatggc agaccatgat tgaagcttac ggtgatgtca 420
agactaccga atgggtactt gcttcgtctg gtctggggtg ggtttactaa aaaacgcaca 480
atnanatacc gaagaactct tatgcttang accacangtc cngccaatcc ggagaanata 540
tggaaatctg accccaaagn gccnaccaat gacttgaaaa annggccatt aaatggttcn 600
nacacnttgg aaaagcctta aaaggttgcc aantattaac ctntcatgaa gnttc 655

<210> SEQ ID NO 326
<211> LENGTH: 657
<212> TYPE: DNA
<213> ORGANISM: Homo sapiens
<220> FEATURE:
<221> NAME/KEY: misc_feature
<222> LOCATION: (1)...(657)
<223> OTHER INFORMATION: n = A,T,C or G

<400> SEQUENCE: 326
ggtacgcggg ggaaacggga gtgaacggag agcgtagtga ccatcatgag cctcctcaac 60
aagcccaaga gtgagatgac cccagaggag ctgcagaagc gagaggagga ggaatttaac 120

-continued

```
accggtccac tctctgtgct cacacagtca gtcaagaaca atacccaagt gctcatcaac    180

tgccgcaaca ataagaaact cctgggccgc gtgaaggcct tcgataggca ctgcaacatg    240

gtgctggaga acgtgaagga gatgtggact gaggtacttt tttttttttt ttnttctttt    300

ttttgagata gggnctcact gnatnaccca ntntggaatg caattggcat gaacncagct    360

tactgnagnc ttccaaacct gggctcaagc aattatnttg nattaacctn ttgagtacct    420

gggactntcn cangcaccan ccctgctttg cttacttaaa tttttgtnaa nacnnggctt    480

gcttttttc ccaggntggn tcnaactccn gaattaaggg atccttcccc ctcaattttt    540

aaannngctg ngattntnga atangccttt ttgttngccc ttttnacctt ttnnnnggtt    600

nnttcnnggc tttaancctn ccgggggccn tttaaaggng aaatcncncc ttggggg       657
```

<210> SEQ ID NO 327
<211> LENGTH: 658
<212> TYPE: DNA
<213> ORGANISM: Homo sapiens
<220> FEATURE:
<221> NAME/KEY: misc_feature
<222> LOCATION: (1)...(658)
<223> OTHER INFORMATION: n = A,T,C or G

<400> SEQUENCE: 327

```
ggtacttttt tttttttttt tttttttttt ttttttttgg tttgaaacag aaatttattc     60

tcanaataat gcacagaagc acaggttgag gctactcttg ggaagcttcc ctccccttcc    120

tcttcctcct ctccctcctc tctgaatgcc agggagaaca cagttgaagg aaggaaacat    180

gcaatcacaa acaatgaaca actntaaaga caaaaaggtt tggtccaaaa gaactcaaca    240

taattaatcc aatgactgtg aanagcttca ctgagtagga ttaanatatt gcagatgtan    300

ngtttncaca gggtggctnt tcagtgcacc ancggggcct ncttgangga natgaggact    360

gacncatncg ggaaanatct ttggcctgct tgctaaactt ggggntaaag gcacacnnnc    420

cgggccaccc gttccactna nngcctgggg accanttgtc aatgncnttt ccnaangntt    480

tttttgntgc cttgtggttg nttttggttt ctggaactgn tcgncctgnc ttgnaaacca    540

ttnttntaac nccttaatgg cctttctttt cnnnctggtt ntgnttccaa aatnggatta    600

ngggttcang ngcccctact tnccgggggc ngttaaangg naattccncc nctggngg      658
```

<210> SEQ ID NO 328
<211> LENGTH: 644
<212> TYPE: DNA
<213> ORGANISM: Homo sapiens
<220> FEATURE:
<221> NAME/KEY: misc_feature
<222> LOCATION: (1)...(644)
<223> OTHER INFORMATION: n = A,T,C or G

<400> SEQUENCE: 328

```
acgcggacgg tggtttttgg gcccgtttct gagcagcgct tcctttttgt ccgacatctt     60

gacgaggctg cggtgtctgc tgctattctc cgagcttcgc aatgccgcct aaggacgaca    120

agaagaagaa ggacgctgga aagtcggcca agaaagacaa agacccagtg aacaaatccg    180

ggggcaaggc caaaaagaag aagtggtcca aaggcaaagt tcgggacaag ctcaataact    240

tagtcttgnt tgacaaagct acctatgata aactctgtaa ggaagttccc aactataaac    300

ttataacccc agctgtggnc tcttgagaga ctgaagattc naggctncct ggccagggca    360

gccctttagg agcttcttag taaaggactt atnaactggt tttnaancac agacctcaag    420

taattnacac cagaaatncc nnggtggaga atnctccnct gctggtnnag angcatgaat    480
```

-continued

```
aggnncaacc agctntctct gnccnnaccn cncttaggnc naattccgca ccctgcggcc    540

gttctnatgg atccnaactn ggtnccaant nggcnnacta tggcatancn tgccctgggg    600

aantggttcc nttccaatcc anaanttcta tcgnaactta acgg                     644


<210> SEQ ID NO 329
<211> LENGTH: 651
<212> TYPE: DNA
<213> ORGANISM: Homo sapiens
<220> FEATURE:
<221> NAME/KEY: misc_feature
<222> LOCATION: (1)...(651)
<223> OTHER INFORMATION: n = A,T,C or G

<400> SEQUENCE: 329

actattagcc atggtcaacc ccaccgtgtt cttcgacatt gccgtcgacg gcgagccctt     60

gggccgcgtc tcctttgagc tgtttgcaga caaggtccca aagacagcag aaaattttcg    120

tgctctgagc actggagaga aaggatttgg ttataagggt tcctgctttc acagaattat    180

tccagggttt atgtgtcagg gtggtgactt cacacgccat aatggcactg gtggcaagtc    240

catctatggg gagaaatttg aagatgagaa cttcatccta aagcatacgg gtcctggcat    300

cttgtccatg gcaaatgctg gacccaacac aaatggttcc cagtttttca tctgcactgc    360

caagactgag tggttggatg gcaagcatgt ggtgtttggc aaagtgaaaa gaaagggcat    420

gaatattgtg gaggccatgg aaccgctttg ggtccaggaa tgncnagaac agcaagaaga    480

acaccattgc tgactgngga caactcgaat aagttggact tggggttant ttaaccacca    540

gaacaattcc tttgtncnta aggagancan ccctcaccca tttgntngca tatcctanaa    600

actttgggct ttcnttngtt cctttggttc aggtttcctg gtcctccanc c             651


<210> SEQ ID NO 330
<211> LENGTH: 643
<212> TYPE: DNA
<213> ORGANISM: Homo sapiens
<220> FEATURE:
<221> NAME/KEY: misc_feature
<222> LOCATION: (1)...(643)
<223> OTHER INFORMATION: n = A,T,C or G

<400> SEQUENCE: 330

actttntttt ttttntnttt ttttttttt ctggaaggnt ctcaggtctt tatttgctnt      60

ctcaaattcc aggaatngac ttatttaatt aatccatcaa cctctcatag caaatatttg    120

agaaaacaaa tttatattca gattcttatt ttcagtaggg aagtaagaag ttgcagctca    180

ttgcacgtaa agttgagaca ganatggaga catccagccc cacctntctg gaacaagaaa    240

gatgactggg gaggaaacac aggtcancat gggaacaggg gttacagtgg acacaagggn    300

gggctgnctn ttcacctnct tacattatgc taacagggac ncaaacccat tcaggggcct    360

ttgcnaaaag aaatgccaaa agctnttgaa gtcncnaagg ggangcgtga anaaaactgc    420

atttnagtcc ccgggtcctt ngncgggaac ccctnanggn gaaatcncca cactggcggg    480

ccgtactagn ggatccagct nggncccaat tggnggaata tggnnaanac tgttcctgtg    540

ggaaaatggn atccgtccaa ttcnccactt acanncggag cctaaangna aaacntgggg    600

ngcctatggg gggctacnnn aataatgggt gcctacggcc cnt                      643


<210> SEQ ID NO 331
<211> LENGTH: 652
<212> TYPE: DNA
```

```
<213> ORGANISM: Homo sapiens
<220> FEATURE:
<221> NAME/KEY: misc_feature
<222> LOCATION: (1)...(652)
<223> OTHER INFORMATION: n = A,T,C or G

<400> SEQUENCE: 331

ggtacagatg gcactgacaa tcccctttct ggtggggatc agtatcagaa catcacagtg     60
cacagacatc tgatgctacc agattttgat ttgctggagg acactgaaag caaaatccaa    120
ccaggttctc aacaggctga cttcctggat gcactaatcg tgagcatgga tgtgattcaa    180
catgaaacaa taggaaagaa gtttgagaag aggcatattg aaatattcac tgacctcagc    240
agcccgattc agcaaaagtc agctggatat tataattcat agcttgaaga aatgtgacat    300
ctccctgcaa ttcttcttgc ctttctcact tggcaaggaa gaaggaagtg gggacagang    360
agatggccct ttcgcttang tggccatggg ccttnctttt cactaaaagg aattaccgaa    420
cagcanaaag aaagncttga gatagtgaaa atggggatga tatctttaga agggngaaga    480
tggggtggat gaaattattc attcctgnga agnttgnaaa ctgngcgnct tcnnnaaant    540
nnnaggcatt ccntnnctgg ccntgccatt gccattggnt ccanttgcta tagggatgcc    600
ccttaaancn ntttccnnna anagtnnaaa acttgcnntn ggatccaacc nn             652

<210> SEQ ID NO 332
<211> LENGTH: 648
<212> TYPE: DNA
<213> ORGANISM: Homo sapiens
<220> FEATURE:
<221> NAME/KEY: misc_feature
<222> LOCATION: (1)...(648)
<223> OTHER INFORMATION: n = A,T,C or G

<400> SEQUENCE: 332

cgaggtactt tttttttttt tttttttttt tttttttgag acagagtttc actcttgtcg     60
cccaggctgg agtgcagtgg cgcgatctcg gtccactgca acctcaccct cccaggatca    120
agcgattctc ctgcctcagc cacctgagta gctgggatta caggcgcctg ccactacacc    180
tagccaattt ttgtattttt agaagggaca gcatttcacc atgttggcca ggctggtctc    240
gaactcctga tctcaggnga tccacccacc tcagcctccc aaagtggngg gattacaggc    300
gtgagccact gaaagttctc attagttttt tggttaaatt ttaaacataa attatgttat    360
agcaaaaatt cctaagaatt gnaaaccact ttatcagaaa tatcnnaaat tcacaaataa    420
tnccaaaatt tataatagct tttttccaga ctaaaatttt aaagctactg anaagnggna    480
aacctnccta nataggattt acctaacatt nnggantaaa aggnanccan ngcctgctaa    540
anatccagan tatctaanaa tccntncctg nntctcnntc tatnttttca natccgaatt    600
tttgaaccca cnttangata nctnntttcc cccttaacnn taattccc                 648

<210> SEQ ID NO 333
<211> LENGTH: 656
<212> TYPE: DNA
<213> ORGANISM: Homo sapiens
<220> FEATURE:
<221> NAME/KEY: misc_feature
<222> LOCATION: (1)...(656)
<223> OTHER INFORMATION: n = A,T,C or G

<400> SEQUENCE: 333

cgaggtacaa gatgtccaaa tattgcgaag atctatttgg ggatctcctg ttgaaacaag     60
cacttgaatc acatccactt gaaccaggca gggctttgcc atcccccaat gacctcaaaa    120
```

gaaaaatact cataaaaaac aagcggctga aacctgaagt tgaaaaaaac agctggaagc 180
tttgagaagc atgatggaag ctggagaatc tgcctcccca gcaaacatct tagaggacga 240
taatgaagag gagatcgaaa gtgctgacca agaggaggaa gctcaccccg aattcaaatt 300
tggaaatgaa ctttctgctg atgacttggg tcacaaggaa gctgttgcaa atagcgtcaa 360
gaaggcttca gatgaccttg aacatgaaaa caacaaaaag ggcctggtca ctgtagaaga 420
tgagcangcg tggatggcat cttataaata tgtaggtgct ccactaatat ccatncatat 480
ttgtcaccat gatcaactac cccagnctgt naaggttcaa ggtttcatgt ggcanaagaa 540
ccccatattc ttttacatgg cttctttaat gaatcatcgg cttggtactg aaaccctgcc 600
attgaattgc attntacaac ggcaatgagc natttcccca gggaggccng cnttct 656

<210> SEQ ID NO 334
<211> LENGTH: 647
<212> TYPE: DNA
<213> ORGANISM: Homo sapiens
<220> FEATURE:
<221> NAME/KEY: misc_feature
<222> LOCATION: (1)...(647)
<223> OTHER INFORMATION: n = A,T,C or G

<400> SEQUENCE: 334
acgcgggcgg gaagtgcaga ggcaaatgca tttagtgttc ttcagcatgt cctcggtgct 60
gggccacatg tcaagagggg cagcaacacc gccagccatc tgcactaggc tgttgccaag 120
gcaactcagc agccatttga tgtttctgca tttaatgcca gttactcaga ttctggactc 180
tttgggattt atactatctc ccaggccaca gctgctggag atgttatcaa ggctgcctat 240
aatcaagtaa aaacaatagc tcaaggaaac ctttccaaca cagatgtcaa gctgccaaga 300
acaagctgaa agctggatac ctaatgtcaa tggagtcttc tgagtgnttc ctggaagaaa 360
gtcgggtccc aagctctaag tgctggntct tacatgccac cattcacaag tctttaacag 420
aatgattcan tggctaatgc tgatatcata aatgcgnaaa naaagtttgg ttctggcnag 480
aagtcaatgg cancaagtgg naaatttggg acatacncnt ttgtgataag tggaatactg 540
gngcncnctt acngganana cttaacgttn tttaanccaa acacaaccct tgaaagnnna 600
agctctaaan accattggct tttttcnggg ngnaaaaaag gcttaag 647

<210> SEQ ID NO 335
<211> LENGTH: 657
<212> TYPE: DNA
<213> ORGANISM: Homo sapiens
<220> FEATURE:
<221> NAME/KEY: misc_feature
<222> LOCATION: (1)...(657)
<223> OTHER INFORMATION: n = A,T,C or G

<400> SEQUENCE: 335
acaggtcaga gtcttctttt cttttctttt tgagatggag tcttgctctg ttgccagact 60
ggagtgcagt ggtgcgatct gggctcactg caatctccac ctcccgggtt caagcgattc 120
tcctgcctca gcctcccgag taactgggac tacaggtgcg cgccaccaag cccagctcat 180
ttttgtattt ttagtagaga tggggtttca cgatgttggc taggatggtc tcgatctctg 240
gtcagagtct tttctgtaaa tatccttggt aaagaagcaa ttttagactg tagctgttgc 300
aaatgcttta aggaagaagc aaaacaactg tcaagtcttc ctgaaatgaa gaaactacac 360
cagggctgct atatcagagc aaccccaacc agcacttcaa tcatgatgcc nacagtggcc 420

-continued

```
cagctgagag accnggagaa agttccagat gcanagactg ngatgctctt gactatggaa    480

atattgcggc cagtaccaag ttagagacca aacaggcata ngnncccgta ttaattggcg    540

tgaattttgc gataaganaa cttgggggg tgctgcggat nccatgatcn ccagaaaact    600

tnngggatgg ggtanaggcc catggcagaa aggttanggt ccttccaaag naaaana       657
```

<210> SEQ ID NO 336
<211> LENGTH: 649
<212> TYPE: DNA
<213> ORGANISM: Homo sapiens
<220> FEATURE:
<221> NAME/KEY: misc_feature
<222> LOCATION: (1)...(649)
<223> OTHER INFORMATION: n = A,T,C or G

<400> SEQUENCE: 336

```
ggtacgcggg caactatgga attccacagc gtgctctgcg gggtcactcc cactttgtta     60

gtgatgtggt tatctcctca gatggccagt ttgccctctc aggctcctgg gatggaaccc    120

tgcgcctctg ggatctcaca acgggcacca ccacgaggcg atttgtgggc cataccaagg    180

atgtgctgag tgtggccttc tcctctgaca accggcagat tgtctctgga tctcgagata    240

aaaccatcaa gctatggaat accctgggtg tgtgcaaata cactgtcagg atgaaaacca    300

cttaaantgg gtgncttgng ncccttntng cccaacagca acaaccctat tatcgtcttc    360

tgnggctggg acaaactggn taaaggatgg aacctggcta actgnaagct gaaaaacaac    420

cacattgggc acacangcta tntgaacacc gngactggct ttttcagang gatcctntgn    480

gcttntggag gcaaggatgg gcaagccatg ttatnggaac tcnaccaang caacaccttt    540

cacctttaan gggggacat tatnaacgcc ttgggttaac cttaacgttn ttggtttgng    600

ctgcncaggc ccacattaaa aatgggattt aanggaaana catttnann               649
```

<210> SEQ ID NO 337
<211> LENGTH: 652
<212> TYPE: DNA
<213> ORGANISM: Homo sapiens
<220> FEATURE:
<221> NAME/KEY: misc_feature
<222> LOCATION: (1)...(652)
<223> OTHER INFORMATION: n = A,T,C or G

<400> SEQUENCE: 337

```
actcttggtt tgtcaatggg actttccagc aatccaccca agagctcttt atccccaaca     60

tcactgtgaa taatagtgga tcctatacgt gccaagccca taactcagac actggcctca    120

ataggaccac agtcacgacg atcacagtct atgcagagcc acccaaaccc ttcatcacca    180

gcaacaactc caaccccgtg gaggatgagg atgctgtagc cttaacctgt gaacctgaga    240

ttcagaacac aacctacctg tggtgggtaa ataatcaaga gccttccggt cagtcccagg    300

ctgcagctgt caatgacaca ggaccctnac tctactcagt gtcacaagga atgatgnaag    360

gaccctatga atgtggaatc cagaacgaat taaagcgttg accacagcga ccangcatcc    420

tgaatgcctt tttgggccan acgaccccac cattttcccc tcataccact attaccgtcc    480

aggggtgnac cttagncttt tcttgccatg cagcctttac ccaccttgac agnattcctg    540

gctggatgtt gggaacatna gnacncacnc aagagctntt ttttccaaca tnatgggaaa    600

acanngnnct tatactgcag gccattactt ngccntngcc cagnnggctn cg            652
```

<210> SEQ ID NO 338
<211> LENGTH: 651

-continued

<212> TYPE: DNA
<213> ORGANISM: Homo sapiens
<220> FEATURE:
<221> NAME/KEY: misc_feature
<222> LOCATION: (1)...(651)
<223> OTHER INFORMATION: n = A,T,C or G

<400> SEQUENCE: 338
ggtacatttg aacacacggc tgtgttaaag atgctgctaa tgtcagtcac tgggtgcact 60
aaaggatctc ttattttatg taaaacgttg ggattgacaa gatagatctg acactctgtt 120
aagttaccct ctgaagctac ttcttgtgaa atactaatga cagcatcatc ctgccaagcg 180
aaagaggcag gcataagcaa ggacaaatta aaagggggta agagccttat catgatgagg 240
agtcttgntt tgacatcttg ggaaaagctg ccatagtgtg aaagtcgtca atttctcacc 300
atggtttgca gtttgactgn ctctagttag ggtgaagtct ctgagtggca cacaccttaa 360
gcctgaaggn tttcccttta aattttcatt gagttggccc tcttcagcat atanggcttt 420
aagaacagaa canaccttgg ttttaagtgg gtccatggga taaaatggga atggangact 480
ngaagaattc aagggctggg ccatctngca gtattctgaa tatcgaaaat ncnccaaggc 540
tgctatataa anccccctgg gcaanacttc aatcggaanc ccacggnggc ccnactnana 600
gncaggaccn ttccaantgg aacatnggan tggggccttt gaggcnnggn n 651

<210> SEQ ID NO 339
<211> LENGTH: 634
<212> TYPE: DNA
<213> ORGANISM: Homo sapiens
<220> FEATURE:
<221> NAME/KEY: misc_feature
<222> LOCATION: (1)...(634)
<223> OTHER INFORMATION: n = A,T,C or G

<400> SEQUENCE: 339
actttttttt tttttttttt ttttttctag tttcagttat ttattgattt aatcattgta 60
atctccaata gagattacaa tagagatctc caacatgatt tcatgcattt agaggagaaa 120
tatttcctgg ttaagtggaa aattgtgcgg atgtggcttc tggaanacct tcattctaaa 180
gcagcgttat agtgaaacat ttcatttana aatctggacg ttccttcttc agcttgctgt 240
aatccacatt cactgagtag aacttgtatt gatcattggg acccagtttg ttccagggct 300
ctgggttatt tctgcccaac aaacatctgg attgaacaat gccagacgca agagatcagt 360
gttgctccag tagctccagt tccaataaat acnaagaggg ggatcaaagc tcggatgctt 420
cttggcctga ccgatgatct ggcggancat gtttgcngca aagtctccga ctggaaagga 480
ganaaccgcc taccccaagc cctaagctaa aaattatntg ccccgcgacc ttggncgnga 540
cccnctaagg caattccacc actggcggcc gtctaangga tccacttggg ccaacttgng 600
naacatggca nactggtcct ggggaangta tccc 634

<210> SEQ ID NO 340
<211> LENGTH: 655
<212> TYPE: DNA
<213> ORGANISM: Homo sapiens
<220> FEATURE:
<221> NAME/KEY: misc_feature
<222> LOCATION: (1)...(655)
<223> OTHER INFORMATION: n = A,T,C or G

<400> SEQUENCE: 340
ggtactcttc cactcaggta tccgtgcggc cactccagca cacgcagtat gagcgcttca 60

-continued

```
tcccctcggc ctacccctac tacgccagcg ccttctccat gatgctgggg ctcttcatct    120

tcagcatcgt cttcttgcac atgaaggaga aggagaagtc cgactgaggg gctagagccc    180

tctccgcaca gcgtggagac ggggcaggga gggggttat taggattggt ggttttgttt     240

tgctttgttt aaagccgtgg gaaaatggca caactttacc tctgtgggag atgcaacact    300

gagagccaag ggtgggagt tgagataatt tttatataaa agaagttttt ccactttgaa     360

ttgctaaaag tggnattttt cctatgtgca gtcactcctc tcatttctaa aatagggacg    420

tggccaggca ccgtggctca tgcctgtaat ccacactttt ggaggncnng caagcggtta    480

cgaagtcagg agatcgagac tattctggtt acacgnaaaa cctgncttac taaaagtacc    540

tgcccggccg gccgntcaaa ggcgaatcca cacactggcg ggcgtactan tggatnccaa    600

cttggaccaa cttggngnaa tatggcatac tggttcctgg nggaaatggt accnn         655
```

<210> SEQ ID NO 341
<211> LENGTH: 648
<212> TYPE: DNA
<213> ORGANISM: Homo sapiens
<220> FEATURE:
<221> NAME/KEY: misc_feature
<222> LOCATION: (1)...(648)
<223> OTHER INFORMATION: n = A,T,C or G

<400> SEQUENCE: 341

```
acgaacctac agttttaact gtggatattg ttacgtagcc taaggctcct gttttgcaca     60

gccaaattta aaactgttgg aatggatttt tctttaactg ccgtaattta actttctggg    120

ttgcctttgt ttttggcgtg gctgacttac atcatgtgtt ggggaagggc ctgcccagtt    180

gcactcaggt gacatcctcc agatagtgta gctgaggagg cacctacact cacctgcact    240

aacagagtgg ccgtcctaac ctcgggcctg ctgcgcagac gtccatcacg ttagctgtcc    300

cacatcacaa gactatgcca ttggggtaag ttgtgtttca acggaaagtg ctgtcttaaa    360

ctaaatgtgc aatagaaggn gatggtgcca tcctaccgnc ttttcctggt tcctanctgn    420

gtgaatacct gctacgtcaa atgcntacca ggttcattct ncctttnact aaaacacaca    480

ggtgcaacag acttgaatgc taagtatacc taattggata tgggatttaa ttttctttct    540

tacaancatt tgtattgcta acaggccaaa atttcagtta cccttagggt ggttaacaat    600

cnaattaaac ctgggaggca tacnttgnct aaatattact gnaaaaaa                 648
```

<210> SEQ ID NO 342
<211> LENGTH: 342
<212> TYPE: DNA
<213> ORGANISM: Homo sapiens
<220> FEATURE:
<221> NAME/KEY: misc_feature
<222> LOCATION: (1)...(342)
<223> OTHER INFORMATION: n = A,T,C or G

<400> SEQUENCE: 342

```
ggtacttttt tttttttttt tttttttttt gttttttttt tttttttttt tttttttttt     60

tggctntana gggggtanag ggggtgctat agggtaaata cgggccctat ttcaaanatt    120

tttaggggaa ttaattctag gacnatgggc atgaaactgn ggtttgctcc acanatttca    180

nagcattgac cgtagtatac ccccggtcgt gtancggtga aagtggtttg gtttaaacgt    240

ccgggaattg catctgtttt taagcctaat gtggggacag ctnatgagtg caaaacgtct    300

tgngatgtaa ttattatacc aatgggggct ttaatcggga at                       342
```

<210> SEQ ID NO 343
<211> LENGTH: 484
<212> TYPE: DNA
<213> ORGANISM: Homo sapiens
<220> FEATURE:
<221> NAME/KEY: misc_feature
<222> LOCATION: (1)...(484)
<223> OTHER INFORMATION: n = A,T,C or G

<400> SEQUENCE: 343

| | | | | | |
|---|---|---|---|---|---|
| ggtacgatgc | ctagtgatga | gtttgctaat | acaatgccag | tcaggccacc | tacggtgaaa | 60 |
| agaaagatga | atcctagggc | tcagagcact | gcagcagatc | atttcatatt | gcttccgtgg | 120 |
| agtgtggcga | gtcagctaaa | tactttgacg | ccggtgggga | tagcgatgat | tatggtagcg | 180 |
| gaggtgaaat | atgctcgtgt | gtctacgtct | attcctactg | taaatatatg | gtgtgctcac | 240 |
| acgataaacc | ctaggaagcc | aattgatatc | atagctcaga | ccatacctat | gtatccaaat | 300 |
| ggttcttttt | ttccggagta | gtaagttaca | atatgggaga | ttattccgaa | cctggtagga | 360 |
| taagaatata | aacttcaggg | tgaccgaaaa | atcagaatan | gtgttggtat | agaatggggt | 420 |
| cttcttcttc | ngcggggtcn | aanaaggtgg | tggtnccgcg | tcctggccng | gcnggcgctc | 480 |
| gaan | | | | | 484 |

<210> SEQ ID NO 344
<211> LENGTH: 657
<212> TYPE: DNA
<213> ORGANISM: Homo sapiens
<220> FEATURE:
<221> NAME/KEY: misc_feature
<222> LOCATION: (1)...(657)
<223> OTHER INFORMATION: n = A,T,C or G

<400> SEQUENCE: 344

| | | | | | |
|---|---|---|---|---|---|
| cgaggtacgc | gggattgttc | tggggcttgt | cctcctttct | gttacggtcc | agggcaaggt | 60 |
| ctttgaaagg | tgtgagttgg | ccagaactct | gaaaagattg | ggaatggatg | gctacagggg | 120 |
| aatcagccta | gcaaactgga | tgtgtttggc | caaatgggag | agtggttaca | acacacgagc | 180 |
| tacaaactac | aatgctggag | acagaagcac | tgattatggg | atatttcaga | tcaatagccg | 240 |
| ctactggtgt | aatgatggca | aaaccccagg | agcagttaat | gcctgtcatt | tatcctgcag | 300 |
| tgctttgctg | caagataaca | tcgctgatgc | tgtagcttgt | gcaaaaangg | ttgtcccgtg | 360 |
| atccacaagg | cattaagagc | atgggtggca | tggagaaatc | gttgtcaaaa | cagagatgtc | 420 |
| cgcagtatgt | tcaanggtgt | ggagtgtaac | tncagaattt | tccntcttca | ctcatttggc | 480 |
| tctctacatt | aaggagtagg | aaataantga | aaggtcccct | ccattaattt | cccttcaaca | 540 |
| aataattttt | tccgaaacng | gaccaaatat | ggccttcttn | tagannataa | tgtcntaagg | 600 |
| ggnatttatt | ttaagcnnca | canttttaat | ttgcaaatna | ctatctgggg | aaaatac | 657 |

<210> SEQ ID NO 345
<211> LENGTH: 662
<212> TYPE: DNA
<213> ORGANISM: Homo sapiens
<220> FEATURE:
<221> NAME/KEY: misc_feature
<222> LOCATION: (1)...(662)
<223> OTHER INFORMATION: n = A,T,C or G

<400> SEQUENCE: 345

| | | | | | |
|---|---|---|---|---|---|
| ggtacgcggg | cgactcttag | cggtggatca | ctcggctcgt | gcgtcgatga | agaacgcagc | 60 |
| tagctgcgag | aattaatgtg | aattgcagga | cacattgatc | atcgacactt | cgaacgcact | 120 |

-continued tgcngccccg ggttcctccc ggggctacgc ctgtctgagc gtctcttgca aaaaaaaaat 180
aaannanaan acancaagta caatttaatg cntanaaagg cctctctcca taaaactcan 240
cnctttacag atgtangaat atataagcnn tgccaaaatt actaatntgc cacatacnna 300
gcatcaattc caggtgctag tnagngggaa aaaaanttgg agaattcggc cctcgangag 360
ctccanannt taanctncct tactaantnc canggttctt tcaagcatgg aaaaattaat 420
ngtgctncat ngatnaangn cttgtcattg ggccttnttt cctngacctg gcccggccgn 480
ccgttcnaaa ggctaaatcc agacactgcg gccgttntaa tggttcnnac ttgggccaag 540
cttgggnaat catgggcaaa gctgttcctg ggnnaaatnt tatccnctcc aattcncaca 600
natacgaanc tgaancttaa gtgtnanntn gggngctaaa agtggcnaan ctcccttnat 660
gg 662

<210> SEQ ID NO 346
<211> LENGTH: 654
<212> TYPE: DNA
<213> ORGANISM: Homo sapiens
<220> FEATURE:
<221> NAME/KEY: misc_feature
<222> LOCATION: (1)...(654)
<223> OTHER INFORMATION: n = A,T,C or G

<400> SEQUENCE: 346
acttcttggc cgcctcacta gcactctccg cctgcttttt aaaggcttca ttggaggcca 60
gcagcgtggc ctgctgcgaa atgagagtca ccaggcgtct aagcaggaag gacagcagcg 120
aggaaaagcc agcaatgtag agattcctct gggcacggaa aagcttcatg tggaagtgct 180
ccatggcccc gggattgttc tggaggttca ccttttccgt cacatcatca tacttccgaa 240
tttcgcgcac ggcatcgatg accaacagca caaggatgac aatgagaacc acaaagaagg 300
tgttgccata ggacactaac aactccacca gccgggactt gaaaatcttc tgccatcttt 360
taggagaaat gaagggaatg cagagaagca acacaacaaa gaccttcgca tagaggaagg 420
tggcaactgc agtccactgc agactcatcc tggtgctana agggttccac aggaagatgt 480
gaacttgttn cgagtttcca cagtcaacgt gtcccccgta ccttnggccg ngaacacnct 540
taaggcgaat tccaccactg cnggccgtct antggatcca actnggncca acttggcgaa 600
tatggcaaat tgttctnggg naaatggttc ngtcaattcc ccantacnac cgga 654

<210> SEQ ID NO 347
<211> LENGTH: 536
<212> TYPE: DNA
<213> ORGANISM: Homo sapiens
<220> FEATURE:
<221> NAME/KEY: misc_feature
<222> LOCATION: (1)...(536)
<223> OTHER INFORMATION: n = A,T,C or G

<400> SEQUENCE: 347
ggtactaatt taaggtaaca attctcgagg taaaataagg cattatagta acacaatttt 60
catgcctcag caattaacaa tgattttcgt ttaattctct tccaactcta cagacataat 120
tctgctttca ccttcatcac gctttcatat ggttttaaca ggggatacac ctcctcttct 180
aagaatctct gcacctgctg ggaggcacga ccagtgaaag aagaaggatc cagtaaatga 240
tccaactggg agtgaatggg actgaagtag gcatcaacct ggatacgctc tatgaggnca 300
ttgcaccccc ttcctgctta accacagaag ctgcctgctg agaaagcact ctgattttct 360
catggcaatc ctggcggcta ccttcacttt gaccatggcc atgatgatgg tctctgtggc 420

-continued catgaaangc agctcttgcc gaatgcgccg tcaattactt tggggtacct gcccnggccg 480
gccgntcnaa nggcgaattt cagccactgg cngncgtact agnggatcca actcgg 536

<210> SEQ ID NO 348
<211> LENGTH: 665
<212> TYPE: DNA
<213> ORGANISM: Homo sapiens
<220> FEATURE:
<221> NAME/KEY: misc_feature
<222> LOCATION: (1)...(665)
<223> OTHER INFORMATION: n = A,T,C or G

<400> SEQUENCE: 348
ggtacgcggg gagtcggcgt aggccttagg tgggttcgtg cgccttctac ctcgctgttt 60
cggttttcct ggctcctcgg cccttttctc ccctgttgca gctgggagcg gacgaagcgc 120
gaagctggga ttttttactg tctcctgaag aatttaacac aaacatggat atcagaccaa 180
atcatacaat ttatatcaac aatatgaatg acaaaattaa aaaggaagaa ttgaagagat 240
ccctatatgc cctgttttct cagtttggtc atgtggtgga cattgtggct ttaaagacca 300
tgaagatgag gggggcaggcc tttgtcatat ttaaggaact gggctcatcc acaaatgcct 360
tgagacagct accaggattt ccattttatg gtaaaccaat gccaatacag tatgcaaaaa 420
cagattcgga tataatatca aaaatgcgtg gaacttttgc ttaaaaaaaa aaannnnnna 480
naaaaaagtc ctgccnggcc gcccgttcaa anggcgaatt naccactggc ggccgttcta 540
gnggatccaa ctnggnacca acttggcgta atatggcaaa actggtnccg ngngaaatgg 600
tatccgttan aattcccaca cttcaaccgg aacctnaang taaacctggg gcctaagagn 660 gacnn 665

<210> SEQ ID NO 349
<211> LENGTH: 474
<212> TYPE: DNA
<213> ORGANISM: Homo sapiens
<220> FEATURE:
<221> NAME/KEY: misc_feature
<222> LOCATION: (1)...(474)
<223> OTHER INFORMATION: n = A,T,C or G

<400> SEQUENCE: 349
acttcgtcag tttgtaagac atgagtccga aacaactacc agtttggttc ttgaaagatc 60
cctgaatcgt gtgcacttac ttgggcgagt gggtcaggac cctgtcttga gacaggtgga 120
aggaaaaaat ccagtcacaa tattttctct agcaactaat gagatgtggc gatcagggga 180
tagtgaagtt taccaactgg gtgatgtcag tcaaaagaca acatggcaca gaatatcagt 240
attccggcca ggcctnagag acgtggcata tcaatatgtg aaaaaggggt ctcgaattta 300
tttggaaggg aaaatagact atggtgaata catggataaa aataatgtga ggcgacaagc 360
ncaaccatca tagcttgatn atattatatt tctgagtgcc agaccaaaga gaaggagtnt 420
aaanggatga tcntcttttg ggcatcattt tgggaccttn ggccgggaac accc 474

<210> SEQ ID NO 350
<211> LENGTH: 452
<212> TYPE: DNA
<213> ORGANISM: Homo sapiens
<220> FEATURE:
<221> NAME/KEY: misc_feature
<222> LOCATION: (1)...(452)
<223> OTHER INFORMATION: n = A,T,C or G -continued

<400> SEQUENCE: 350
acgcggggac cgtggagagc agagcgcggc ggctggaagc tgctaagtca gagccgcgat 60
gttccggatt gagggcctcg cgccgaagct ggacccggag gagatgaaac ggaagatgcg 120
cgaggatgtg atctcctcca tacggaactt tctcatctac gtggccctcc tgcgagtcac 180
tccatttatc ttaaagaaat tggacagcat atgaagacag gacatcacat atgaatgcac 240
gatatgaaga gcctggttac agtttcgact cctctctgca agtgaatagg cccagaaagg 300
tgtaagagac tctttgaatg gacataaaat tctgcttgtt aagaacaagt ttggctctgg 360
taactgacct tcaaagctaa aatataaaac tatttgggaa agtatgaaac gatgtcttcg 420
tgatctggtg taccttggnc gngaccacgc tt 452

<210> SEQ ID NO 351
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 351
ggtacgcggg aataattcca tagtcaagag catcacagtc tctgcatctg gaacttctcc 60
tggtctctca gctggggcca ctgtcggcat catgattgga gtgctggttg gggttgctct 120
gatatagcag ccctggtgta gtttcttcat ttcaggaaga ctgacagttg ttttgcttct 180
tccttaaagc atttgcaaca gctacagtct aaaattgctt ctttaccaag gatatttaca 240
gaaaagactc tgaccagaga tcgagaccat cctagccaac atcgtgaaac cccatctcta 300
ctaaaaatac aaaaatgagc tgggcttggt ggcgcgcacc tgtagtccca gttactnggg 360
aggctgaggc aggagaatng cttgaacccg gnaggtggag attgcagtga gccagatcgn 420
acnactgnac tcagtctggc aantgagnag gcttccatct nanaangaan aganangang 480
actntnacct ggacctgccn ggccggtcgt ttgngcaggt cnggagattt attcccttng 540
ggtggggngc nntaattggn tgntgggccn attcangttt tgggaatttc nncttggnnn 600 naaaangga aatttt 616

<210> SEQ ID NO 352
<211> LENGTH: 603
<212> TYPE: DNA
<213> ORGANISM: Homo sapiens
<220> FEATURE:
<221> NAME/KEY: misc_feature
<222> LOCATION: (1)...(603)
<223> OTHER INFORMATION: n = A,T,C or G

<400> SEQUENCE: 352
ggtacggcac ttggcgtaaa gccgcttccc tcaagagtaa ctacaatctt cccatgcaca 60
agatgattaa tacagatctt agcagaatct tgaaaagccc agagatccaa agagcccttc 120
gagcaccacg caagaagatc catcgcagag tcctaaagaa gaacccactg aaaaacttga 180
gaatcatgtt gaagctaaac ccatatgcaa agaccatgcg ccggaacacc attcttcgcc 240
aggccaggaa tcacaagctc cgggtggata aggcagctgc tgcagcagcg gcactacaag 300
ccaaatcaga tgagaaggcg gcggttgcag gcaagaagcc tgtggtaggt aagaaaggaa 360
agaaggctgc tgttggtgtt aagaagcaga agaagcctct ggtgggaaaa aaggcagcag 420
ctaccaagaa aaccagcccc tgaaaagaac ctgcagagaa gaaacctact acngaggaga 480

-continued

```
agaagcctgc tgcataactc ttaaatttga atatttcntt aagggcnaat nttttggcag    540

gttctttgga taagacntnt tttcngngtg ggaaaataan tnnnntattn nnggctntcc    600

tgg                                                                  603
```

<210> SEQ ID NO 353
<211> LENGTH: 604
<212> TYPE: DNA
<213> ORGANISM: Homo sapiens
<220> FEATURE:
<221> NAME/KEY: misc_feature
<222> LOCATION: (1)...(604)
<223> OTHER INFORMATION: n = A,T,C or G

<400> SEQUENCE: 353

```
ggtaccgact gtttttgaca actatgcagt cacagttatg attggtggag aaccatatac     60

tcttggactt tttgatactg cagggcaaga ggattatgac agattacgac cgctgagtta    120

tccacaaaca gatgtatttc tagtctgttt ttcagtggtc tctccatctt catttgaaaa    180

cgtgaaagaa aagtgggtgc ctgagataac tcaccactgt ccaaagactc ctttcttgct    240

tgttgggact caaattgatc tcagagatga cccctctact attgagaaac ttgccaagaa    300

caaacagaag cctatcactc cagagactgc tgaaaagctg gcccgtgacc tgaaggctgt    360

caagtatgtg gagtgttctg cacttacaca gaaaggccta aagaatgtat ttgacgaagc    420

aatattggct gccctggacc tncagaccga agaagacccc aagtgtgtgc tgctatgaac    480

atctttcaga gcctttcttg nacagctgga ttggcatctt cttaaagcca tgnttaaatt    540

caacttanga ttaaaattaa aattcgtttt gcannatggc caatgcctgg actaacccan    600

ggcn                                                                 604
```

<210> SEQ ID NO 354
<211> LENGTH: 631
<212> TYPE: DNA
<213> ORGANISM: Homo sapiens
<220> FEATURE:
<221> NAME/KEY: misc_feature
<222> LOCATION: (1)...(631)
<223> OTHER INFORMATION: n = A,T,C or G

<400> SEQUENCE: 354

```
ggtacttttt tttttttttt tttttttttt tttgggacgg agtcatgctc tgtcgcccag     60

gctggagtgc agtggcatga tctcggctca ctgcaagctc cgcctcccgg gctcatgcca    120

ttctcctgcc tcagcctccc gagtagctga gattataggc acctaccacc acgcccggct    180

aatttttgta tttttagtag agacggggtt tcaccatgtt gaccaggctg gtctcgaact    240

cctgacctta ggtgatccac tcgccttcat ctcccaaagt gctgggatta caggcgtgag    300

ccaccgtgcc tggccacgcc caactaattt ttgnattttt agtaagagac agggtttcac    360

catgttggcc aaggctgctc tttgaactcc tgacctcatg taatcgacct gcctttggcc    420

ttccaaaagt gctgggatta ccaggtgtga gcccacaagc cccggnacct ggccnggcng    480

gccgtttaaa agggcgaatt cagcacaatg gnnggccgta ctaaggggat ncnanctttg    540

nanccaactt tgggggaaat atggggcana actggttcct ngngnaaatg gtaaccgtta    600

caaattcccn caaanttttg nnccgggagg n                                   631
```

<210> SEQ ID NO 355
<211> LENGTH: 626
<212> TYPE: DNA

-continued

<213> ORGANISM: Homo sapiens
<220> FEATURE:
<221> NAME/KEY: misc_feature
<222> LOCATION: (1)...(626)
<223> OTHER INFORMATION: n = A,T,C or G

<400> SEQUENCE: 355
ggtacgatgc ctagtgatga gtttgctaat acaatgccag tcaggccacc tacggtgaaa 60
agaaagatga atcctagggc tcagagcact gcagcagatc atttcatatt gcttccgtgg 120
agtgtggcga gtcagctaaa tactttgacg ccggtgggga tagcgatgat tatggtagcg 180
gaggtgaaat atgctcgtgt gtctacgtct attcctactg taaatatatg gtgtgctcac 240
acgataaacc ctaggaagcc aattgatatc atagctcaga ccatacctat gtatccaaat 300
ggttcttttt ttccggagta gtaagttaca atatgggaga ttattccgaa gcctggtagg 360
ataagaatat aaacttcagg gtgaccngaa aaatcagaat aggtgtttgg tttagaatgg 420
ngtcttctnc ttcngctggg gtnnaagaan gtnggggttc nngcgtnctn gntcgggcgg 480
ntggttttaa nggccnaaat tcnngnataa ttggcggcng ttactaagng gnatctanct 540
tggtnccaaa nttggngnta atcatggtnc tagctngtnc tcngtgntaa attggntncc 600
tgttaaattn tntnnaatnt tntggc 626

<210> SEQ ID NO 356
<211> LENGTH: 617
<212> TYPE: DNA
<213> ORGANISM: Homo sapiens
<220> FEATURE:
<221> NAME/KEY: misc_feature
<222> LOCATION: (1)...(617)
<223> OTHER INFORMATION: n = A,T,C or G

<400> SEQUENCE: 356 acttttttttt tttttttttt tttttttcta gtttcagtta tttattgatt taatcattgt 60
aatctccaat agagattaca atagagatct ccaacatgat ttcatgcatt tagaggagaa 120
atatttcctg gttaagtgga aaattgtgcg gatgtggctt ctggaanacc ttcattctaa 180
agcagcgtta tagtgaaaca tttcatttan aaatctggac gttccttctt cagcttgctg 240
taatccacat tcactgagta naacttgtat tgatcattgg gacccagttt gttccagggc 300
tctgggttat ttctgtccca acaaacatct ggattgaaca atgccagacg caagagatac 360
agtgttgctc cagtagctcc agttccaata aatacnaaga gggggatcaa gctcggatgc 420
ttcttggcct gaccgatgat ctggccggaa ncatgtttgc cggcaaaagg ctccnacttg 480
ggaaagggga naacccgcct aaccnccagg gcctaagctt aaaatttttg gccccgggta 540
ccttggccgg gaccccctaa gggngnaatt ccnnccccctt gggggccgt ttaangggan 600 ccaacttggn ccaaatt 617

<210> SEQ ID NO 357
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 357
ggtacttttt tttttttttt tttttttttt ttttaggcaa agaactttat taatctttgt 60
ttcaaacttg attcccaggc ttcttcggct taattagctg caaagaatga attgngtata 120

-continued

```
agcaaaaact gaaaagagct gcagtgtcca aggggcttgg gcttaaaaat attagagatc    180

tagattttat cagatccata aacaaaaatt tcttaaaaag cagtcataat ataaaatagc    240

agctcccagt aacttcttca ggntttatct tcagaagttg actcaattca gtttgcctca    300

ttcttggaag cctcatcaaa attctccaca agatctggaa cttcatcatc atcatcctct    360

ccagtaacaa gtggngcttt tccatcccca gantggttgg gcanaacttt ngnccagctc    420

cttaacttag cagactattc ggacccaagc tnggttnaaa aanctgggaa cnatttntgn    480

naactggttt ggttnaacan ggcntgnaag ggggaaaggn gtnccctgcc caaaaaaccn    540

ggacctttag ggtgnnaaag gggacctggc cctgggttgg aaccaantcn ccttttnana    600

ccnnanaatn g                                                         611
```

<210> SEQ ID NO 358
<211> LENGTH: 619
<212> TYPE: DNA
<213> ORGANISM: Homo sapiens
<220> FEATURE:
<221> NAME/KEY: misc_feature
<222> LOCATION: (1)...(619)
<223> OTHER INFORMATION: n = A,T,C or G

<400> SEQUENCE: 358

```
ggtacttttt tttttttttt tttttttttt ttgagatgga gtctcgctct gtcgcccagg     60

ctggagtgca gtggcgcaat ctctgctcac tgcaacctcc gcctcctggg ttcaagcaat    120

tctcctgtct cagcctccca aatagctggg attacgggca tgtgtcacga cgctcggcta    180

atttttgtat ttttagtcga gacgaggttc caccatgttg gctaggctgg tctcaaactc    240

ctgacctcag gtgatccgcc tgcctcggcc tcccaaagtg ttaggattac gggtgtgagc    300

cactgcgccc agcaagcaac ctagatttta aaacaacatg agataaataa gcctaattgg    360

atttaactac atctaacatt tttactaata gttgnaatac tggtagaatt tggaaactat    420

tatatatatt atgcngaaaa gtaaataatt ctggtaaaat canttanggn ccntgaattt    480

nagcataggg gaaaaaaaga tgccntttta aatccaataa gtaaaaaccn tttaaccctn    540

tntttaaatt ggaanttccc cccaatttnt tattaatttc aacttntttt gaaaactcat    600

ntttccnaaa antnggggg                                                 619
```

<210> SEQ ID NO 359
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 359

```
ggactttttt tttttttttt tttttttttt ttttttggag gaaaacccgg taatgatgtc     60

ggggttgagg gataggagga gaatggggga taggtgtatg aacatgaggg tgctttctcg    120

tgtgaatgag ggttttatgt tgttaatgtg gtgggtgagt gagccccatt gtgttgtggt    180

aaatatgtag agggagtata gggctgtgac tagtatgttg agtcctgtaa gtagganagt    240

gatatttgat caggagaacg tggttactag cacagagagt tctcccagta ggttaatagt    300

ggggggtaag gcgaggttag cgaggcttgt tanaagtcat caaaaagcta ttagtgggag    360

tagagtttga agtccttgag agaggattat gatgccactg ngaatgcntt cctaatttga    420
```

-continued gtttgctagg cagaatagtn atgaggatgt aaacccctng gccaattatt aaaaatgact 480
gcncccgtga aacttnaggg ggtttggatt aaaaangctt gtacttccaa nggctntntg 540
gcctnattta aaaaatttcc ctnnncnaat ttagggcttn ttnncnnaag ccnanagggn 600
ccccnancct ttcccggggg ggcn 624

<210> SEQ ID NO 360
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 360
acgcggggag gcggaggctt gggtgcgttc aagattcaac ttcacccgta acccaccgcc 60
atggccgagg aaggcattgc tgctggaggt gtaatggacg ttaatactgc tttacaagag 120
gttctgaaga ctgtcctcat ccacgatggc ctagcacgtg gaattcgcga agctgccaaa 180
gccttagaca agcgccaagc ccatctttgt gtgcttgcat ccaactgtga tgagcctatg 240
tatgtcaagt tggtggaggc cctttgtgct gaacaccaaa tcaacctaat taaggttgat 300
gacaacaaga aactaggaga atgggtaggc ctttgtaaaa ttgacagaga ggggaaaccc 360
cgtaaagtgg ttggttgcag ttgtgtagta attaangact atggcaagga gtctcagcca 420
aggatgtcat tgaagagtat ttcaaatgcc agaaatgaag aaattaaatc nttggcttac 480
ttaaaaaaaa annnnnnnnn aaaaaaaagg tccttgggcg gnacaccctt aaggggnaat 540
tcnnnnccct gggggccntt ataangggnn ccnacttggg ccaaattggg naaanangggg 600 naaanttttt n 611

<210> SEQ ID NO 361
<211> LENGTH: 404
<212> TYPE: DNA
<213> ORGANISM: Homo sapiens
<220> FEATURE:
<221> NAME/KEY: misc_feature
<222> LOCATION: (1)...(404)
<223> OTHER INFORMATION: n = A,T,C or G

<400> SEQUENCE: 361
acatatttta atagaaagat acaacctttt tattttcact ccttttattt ctgctgcttg 60
gcacattttt gagttttccc acattatttg tctccatgat accactcaag cagtgtgctg 120
gacctaaaat actgacttta gttagtatcc ttggattttt agattcccag tgtctaattc 180
cctgttataa tttgcgcaaa caaaacaaaa tgttatgata atctttctcc actgttctaa 240
tatatattgt atttttattt gatagcttgg gatttaaaac atctctgttg aaggcttttg 300
atccttttga gaaataaaga tctgaaagaa atggcataat cttaaaactt gataaaaaaa 360
aaanannnnn nnnaaaaaaa aaagtacctn ggccgngacc acgc 404

<210> SEQ ID NO 362
<211> LENGTH: 322
<212> TYPE: DNA
<213> ORGANISM: Homo sapiens
<220> FEATURE:
<221> NAME/KEY: misc_feature
<222> LOCATION: (1)...(322)
<223> OTHER INFORMATION: n = A,T,C or G

<400> SEQUENCE: 362

-continued

```
ggtacttttt tttttttttt tttttttttt ttttttggag ttgtaggcaa atgtttaatt     60

aattctgctc atatgcacat ctgaaagcat gagacacact ccacagacag cacgcactgg    120

ggctggtggg gcanatgggc actcgccgat taggtattaa tgtcaataat acgtgcataa    180

agtgctgata aaataactta agtgttacaa aaagagacag tccacggtgg ctgcaggcac    240

atgcaggcgg gactgggtca gacactccag ggctgcacat gttccagctg gcctgagtcc    300

gacacgtcat agctggcctt gt                                             322


<210> SEQ ID NO 363
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 363

cgaggtacgc gggctaagca agggaaaaat aacagtttct ctgagccaga gaagacttga     60

tcacagttct ccaagcatcg tgatagcaat gcttaacccc aggaagattt caaggcaggg    120

agaagaacat ttcaaataag attcttgtta acccatttat gcctagtgtt ccattattgg    180

aatgctaagc ttgtgggagt catttacatc ctactgctca aagtcattgc caaggtctga    240

tttttcacac aaaaaattgc aacccccagc ataaatgttt agctactgtc atcagttagc    300

aaattcatcc acacaaacac aattagagtt tggttttttt ttaagctttt caaaacttac    360

taaactggca caattttata tgtatgctat ttggtgnatt tatgcttaag agcnaaaaag    420

tttgatggga ttttaaattc angccaagcc tacacgctga gacaatccct acaaccatgg    480

nagtaactaa ngaaccttta tctaagnttt taagttttaa anggagngct taatggttca    540

ngtctangtt ggaatttcct tcanaaattt cntcttttaa aaaattttcc caaaatnggt    600

ccttaaaaaa ctcann                                                    616


<210> SEQ ID NO 364
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 364

cgaggtacgc ggggcttctc gcctaacgcc gccaacatgg tgttcaggcg cttcgtggag     60

gttggccggg tggcctatgt ctcctttgga cctcatgccg gaaaattggt cgcgattgta    120

gatgttattg atcagaacag ggctttggtc gatggacctt acactcaagt gaggagacag    180

gccatgcctt tcaaatgcat gcagctcact gatttcatcc tcaagtttcc gcacagtgcc    240

caccagaagt atgtccgaca agcctggcag aaggcagaca tcaatacaaa atgggcagcc    300

acacgatggg ccaagaagat tgaagccaga gaaaggaaag ccaagatgac agattttgat    360

cgttttaaag ttatgaaggc aaagaaaatg aggaacagaa taatcaagaa tgaaagttaa    420

agaaacttca aaaggcagct nttctgaaag cttnttccca aaaaagcacc tgggtacctg    480

gccgggccgg ccgtttaaaa gggcnaattc caccactggc ggccgtctan ngggatccaa    540

cttnggacca acttggngga atatggcnaa attgttcctg gggnaaatgt ttncgttcaa    600
```

-continued attncncaaa ttacggcc 618

<210> SEQ ID NO 365
<211> LENGTH: 601
<212> TYPE: DNA
<213> ORGANISM: Homo sapiens
<220> FEATURE:
<221> NAME/KEY: misc_feature
<222> LOCATION: (1)...(601)
<223> OTHER INFORMATION: n = A,T,C or G

<400> SEQUENCE: 365
acgtcctgga ggactctatt gtggacccac agaatcagac catgactacc ttcacctgga 60
acatcaacca cgcccggctg atggtggtgg aggaacgatg tgtttactgt gtgaactctg 120
acaacagtgg ctggactgaa atccgccggg aagcctgggt ctcctctagc ttatttggtg 180
tctccagagc tgtccaggaa tttggtcttg cccggttcaa aagcaacgtg accaagacta 240
tgaagggttt tgaatatatc ttggctaagc tgcaaggcga ggccccttcc aaaacacttg 300
ttgagacagc caaggaagcc aaggagaagg caaaggagac ggcactggca gctacagaga 360
agccaaggac ctcgccagca aggcggccac caagaacagc agcagcagca acagtttgtg 420
taaccagnct accaacaaca nagnacccca nacaggtagg cttacccctt tggcctcctt 480
taatggacct tggccgggaa cacccttang gcgaattcag ncactggggg ccgtactang 540
ggatccnctt ggaccaactt ggggaaacag ggcaaaattg ttcttgggga aattntatcc 600 n 601

<210> SEQ ID NO 366
<211> LENGTH: 321
<212> TYPE: DNA
<213> ORGANISM: Homo sapiens

<400> SEQUENCE: 366
actttttttt tttttttttt tttttttgag atggagtctc actctgtcgc ccaggctgga 60
atgcagtggt gcaatctcag ctcactgcaa cttccacctc ccaggttcaa gtgattctcc 120
tgcctcagcc tcccacatat ctgggactac aggtgcacac caccatgccc agctaatttc 180
tttgtatttt ttagtagaga cggggtttca tcttattggg caggctggtc tcgaactcct 240
aaccttgtga tctgcccacc tcggccttcc aaagtgctgg gattacaggc gtgagccacc 300
gtgctcggcc acccgcgtac c 321

<210> SEQ ID NO 367
<211> LENGTH: 264
<212> TYPE: DNA
<213> ORGANISM: Homo sapiens

<400> SEQUENCE: 367
actgatcatg gagttaatca acaatgtcgc caaagcccat ggtggttact ctgtgtttgc 60
tggtgttggt gagaggaccc gtgaaggcaa tgatttatac catgaaatga ttgaatctgg 120
tgttatcaac ttaaaagatg ccacctctaa ggtagcgctg gtatatggtc aaatgaatga 180
accacctggt gctcgtgccc gggtagctct gactgggctg actgtggctg aatacttcag 240
agaccaagaa ggtcaagatg tacc 264

<210> SEQ ID NO 368
<211> LENGTH: 488
<212> TYPE: DNA
<213> ORGANISM: Homo sapiens -continued
<220> FEATURE:
<221> NAME/KEY: misc_feature
<222> LOCATION: (1)...(488)
<223> OTHER INFORMATION: n = A,T,C or G

<400> SEQUENCE: 368
ggtacagatg cacaggaggc catagggttt aggcanaggg gagcacaaan gttgaagatg 60
aggcgctgcc atcaatgctg ggacttcagg cnaagggcag gaactgagga agccacaagg 120
gaggacattt tctgcagttg ctgaancagt ancaactagg tcctgagaaa gccctntctc 180
gtggaagaat aacagccagg cnggaaagct tttcatcctg caaagctggg gaagaagatt 240
cttccttaaa ttgtcatctg cacttcagct cangaatcct gttggctgaa gtccagagtg 300
tccntttctg attcctgaag tanatnaaca gcccngnccc aangaagagn aggnntagta 360
caaagccnnc tncgcgtacc tgtncgggcg gnngttcgna aggntcaaat tccagcacaa 420
ttgnctgccg ttantagttg gattctnact ttngtactta ncttggcgta ntttatggtn 480 ataanttg 488

<210> SEQ ID NO 369
<211> LENGTH: 602
<212> TYPE: DNA
<213> ORGANISM: Homo sapiens
<220> FEATURE:
<221> NAME/KEY: misc_feature
<222> LOCATION: (1)...(602)
<223> OTHER INFORMATION: n = A,T,C or G

<400> SEQUENCE: 369
acgggggttt cactacttct cccccggact ccttggtagt ctgttagtgg gagatccttg 60
ttgccgtccc ttcgcctcct tcaccgccgc agaccccttc aagttctagt catgcgtgag 120
tgcatctcca tccacgttgg ccaggctggt gtccagattg gcaatgcctg ctgggagctc 180
tactgcctgg aacacggcat ccagcccgat ggccagatgc caagtgacaa gaccattggg 240
ggaggagatg attccttcaa caccttcttc agtgaaacgg gtgctggcaa gcatgtgccc 300
cgggcagtgt ttgtagactt ggaacccaca gtcattgatg aagttcgcac tggcacttac 360
cggcagctct tcaccctgag caactcatca caggcnagga aaaatgctgc aataactatc 420
ccgaaggcac tacaccattg gcaaggagaa taattgacct gtgttggacc gaattcgcaa 480
gctggctgac catgcaccgg cttaagggtt nttggttttc ccaacttttg gggggggaac 540
tgggtttngg gtaaccctnn tggtnatngg aacgntttta antggatttt gggaanaaan 600
cc 602

<210> SEQ ID NO 370
<211> LENGTH: 257
<212> TYPE: DNA
<213> ORGANISM: Homo sapiens
<220> FEATURE:
<221> NAME/KEY: misc_feature
<222> LOCATION: (1)...(257)
<223> OTHER INFORMATION: n = A,T,C or G

<400> SEQUENCE: 370
actttttttt tttttttttt tttagttttt ttttattttt tacaaatata ctggagaatc 60
atgcaatgct gccagcattg gatgcaatcc ggggccacaa gtctgcacac tcctttgcta 120
ctggtcctgt aatggcagaa cctttcatct cgcctttatt gntcactatg actcctgcat 180
tatcttcaaa ataaagaaac acgccatctt ttctacggta tgactttcgt tgtcgaatga 240

-continued

```
ccactgctgg atgtacc                                                257


<210> SEQ ID NO 371
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 371

actttttttt tttttttttt ttttttgct atttagtttt tatttcataa tcataaactt    60

aactctgcaa tccagctagg catgggaggg aacaaggaaa acatggaacc caaagggaac   120

tgcagcgaga gcacaaagat tctaggatac tgcgagcaaa tggggtggag gggtgctctc   180

ctgagctaca gaaggaatga tctggtggtt aagataaaac acaagtcaaa cttattcgag   240

ttgtccacag tcagcaatgg tgatcttctt gctggtcttg ccattcctgg acccaaagcg   300

ctccatggcc tccacaatat tcatgccttc tttcactttg ccaaacacca catgcttgcc   360

atccaaccac tcagtcttgg caagtgcaga tgaaaaactg ggaaccantt ggggttgggt   420

ccacatttgc catggacaag aatgccagga acccgtatgc tttaaggatg aagtctcatc   480

ttcaaaattc ttccccataa atggacttgc caccagngcc attatggcgt gtgaagtccc   540

cancctggcc cataaaccct ggaaaaatnt tggnaaaccg gaacccttt aaccaatcct    600

ttttttc                                                           607


<210> SEQ ID NO 372
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 372

acgaatgtgg gaattactca ggagcagcag aatatcttta tttttttaga gtgctggttc    60

cagcaacaga tagaaatgct ttaagttcac tctggggaaa gctggcctct gaaatcttaa   120

tgcagaattg ggatgcagcc atggaagacc ttacacggtt aaaagagacc atagataata   180

attctgtgag ttctccactt cagtctcttc agcagagaac atggctcatt cactggtctc   240

tgtttgtttt cttcaatcac cccaaaggtc gcgataatat tattgacctc ttcctttatc   300

agccacaata tcttaatgca attcagacaa tgtgtccaca cattcttcgc tatttgacta   360

cagcagtcat aacaaacaag gatgttcgaa aacgtcggca ggttctaaaa agatctaggt   420

taaaggttat tcaacangga gtcttacnca tntaagaccc cattacngga atttggtgaa   480

tggttatatg taactttgac tttaangggc tcaaaaaaag ctnaggggat gtgaatcaag   540

cttgngaagg ctttttttgg gggctngntt nngggtttnt tgnaaagncc ngttttnntt   600

ttggaat                                                           607


<210> SEQ ID NO 373
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G
```

-continued

<400> SEQUENCE: 373

```
acttttaatg tttgctgttc aaacgaaaat agattggatc ttggttaagt tcacttggtt    60
tggccaggca cagtggctca cgcctgcagt cccagcactt ggggaggtgg aggcgggccg   120
atcacctgag gtcaagagtt tgagaccagc ctggctaacg cggtgaaacc ccatttctac   180
taaaaataca aaaaattagc tgggcgtggt ggtgcgcgct tgtaatccca gctactcggg   240
aggctgaggc aggagaatcg cttgagccag agaggcaaag gttgcaataa gccaagatag   300
cgccattgta ttccagcttg gacaacaaga gcgaaactct gtctaaaaaa aaaaaaaaaa   360
cacacacaca acacaatatt ttcacgcctg taaacctagc acattgggaa gccaaggtgg   420
gaggattgct tgaggccagg agttcaaggc ttgcantgag ctatgaatgn acactgnacc   480
tttggncgng aacacnctta nggccaaatt ccngcacact tgggggccgg tactaanggg   540
atcccanctt tggnnccaaa nttggngnaa acatgggcaa aattggtncc tggngaaaat   600
ggttccgttc caaatccc                                                 618
```

<210> SEQ ID NO 374
<211> LENGTH: 605
<212> TYPE: DNA
<213> ORGANISM: Homo sapiens
<220> FEATURE:
<221> NAME/KEY: misc_feature
<222> LOCATION: (1)...(605)
<223> OTHER INFORMATION: n = A,T,C or G

<400> SEQUENCE: 374

```
acccagctgc tgcccacatt tctggtccag agtcccgaac cccgagcact gggatgcctg    60
gctactccga gcgttatcca gactagcgag tgggaggcag atgtaaaatc tggaacgcag   120
attttagttt gttggaagga gaaatgtaac atagtgaacc acgcatctct ggagggtgta   180
aagcagagac agccaagagc caaggcactg atgtttgaac tggaaacttc aaaacgttta   240
ataagagtct tcaggatggg tttgaactag acaagctaga aatttcttta gaacaccagc   300
tctagcatgc atctcccact tttggctttc ctggagagga gcttgaagag gtggttctgc   360
agacagccac agtgatactc aggaaacnca gaggaatgga tttgactttt ctgctaggaa   420
tctttggtat aagttctcct tgagttgtaa gangcatgga aatatacatg aaactgaana   480
acctgcaagg aanggaaatg ggaacntttc atctgagtgn aaactaacca agtnggcaat   540
ttngacttga aacccttgaa accttcnagt ccaantcctg gtttggggga taaangaacc   600
ggncn                                                               605
```

<210> SEQ ID NO 375
<211> LENGTH: 602
<212> TYPE: DNA
<213> ORGANISM: Homo sapiens
<220> FEATURE:
<221> NAME/KEY: misc_feature
<222> LOCATION: (1)...(602)
<223> OTHER INFORMATION: n = A,T,C or G

<400> SEQUENCE: 375

```
acggatgcta cttgtccaat gatggtaaaa gggtagctta ctggttgtcc tccgattcag    60
gttagaatga ggaggtctgc ggctaggagt caataaagtg attggcttag tgggcgaaat   120
attatgcttt gttgtttgga tatatggagg atggggatta ttgctaggat gaggatggat   180
agtaataggg caaggacgcc tcctagcttg ttagggacgg atcggagaat tgtgtaggcg   240
```

-continued

```
aataggaaat atcattcggg cttgatgtgg ggaggggtgt ttaaggggtt ggctagggta    300

taattgtctg ggtcgcctag gaggtctggt gagaatagtg ttaatgtcat taaggagaga    360

atgaanagaa gtaagccgag ggcgtctttg attgtgtagt aagggtggaa ggtgatttta    420

tcggaatggg aagtgattnc taaggggntg tttganccccc gtttgtgcca gaatangaag    480

tggaatgctt cttanggctt caataaatga anggcanaat gaattgaaag gtaaanaaac    540

cntnaagggt ggacttgtta ctgataaccn tcctaaaatc attgccccgn aacttggccg    600

gg                                                                   602
```

<210> SEQ ID NO 376
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 376

```
acgcgggatc gaagaattca caaaaaacaa tagcctcatc atccccacca tcatagccac     60

catcaccctc cttaacctct acttctacct acgcctaatc tactccacct caatcacact    120

actccccata tctaacaacg taaaaataaa atgacagttt gaacatacaa aacccacccc    180

attcctcccc acactcatcg cccttaccac gctactccta cctatctccc cttttatact    240

aataatctta taaaaaaaaa aaaaaaaaaa aaaaaaaaaa ncaaaaaaaa aaaaanaaaa    300

aaaaaaaang tncngccatt tttngtttcn ggtaaacngg aatataangn gaaagaacaa    360

acnttggaac atacttaatg gatttttata gaactttgna aaccaaagga gattcatgtt    420

ttanaagtct ggcctttttt atatcttgga agaaaattat gtntggaggc tntaaataaa    480

tcccattatt ttctcaggga atctgggtag gaattgccgg catgggaant tttnngggc     540

cggatnggaa agtttggcct aanaaatngc nctttntnaa naattttgga attttgggaa    600

gcccnaagca n                                                         611
```

<210> SEQ ID NO 377
<211> LENGTH: 367
<212> TYPE: DNA
<213> ORGANISM: Homo sapiens
<220> FEATURE:
<221> NAME/KEY: misc_feature
<222> LOCATION: (1)...(367)
<223> OTHER INFORMATION: n = A,T,C or G

<400> SEQUENCE: 377

```
acgcgggccg tttggcatct ctgccctcat cgtgggtttc gactttgatg tcactcctag     60

gctctatcag actgacccct cgggcacata ccatgcctgg aaggccaatg ccataggccg    120

gggtgccaag tcagtgcgtg agttcctgga gaagaactat actgacgaag ccattgaaac    180

agatgatctg accattaagc tggtgatcaa ggcactcctg gaagtggttc agtcaggtgg    240

caaaaacatt gaacttgctg tcatgaggcg agatcaatcc ctcaagattt taaatcctga    300

agaaattgag aagtatgttg caaaaaaaaa aananaaatn aaanaagtac ctcggccgng    360

accacgc                                                              367
```

<210> SEQ ID NO 378
<211> LENGTH: 611
<212> TYPE: DNA
<213> ORGANISM: Homo sapiens -continued
<220> FEATURE:
<221> NAME/KEY: misc_feature
<222> LOCATION: (1)...(611)
<223> OTHER INFORMATION: n = A,T,C or G

<400> SEQUENCE: 378
ggtacctgga tcctgctcct ctgggttgaa acccgggcgc cgccaagatg ccggcttacc 60
actcttctct catggatcct gataccaaac tcatcggaaa catggcactg ttgcctatca 120
gaagtcaatt caaaggacct gcccccagag agacaaaaga tacagatatt gtggatgaag 180
ccatctatta cttcaaggcc aatgtcttct tcaaaaacta tgaaattaag aatgaagctg 240
ataggacctt gatatatata actctctaca tttctgaatg tctgaagaaa ctgcaaaagt 300
gcaattccaa aagccaaggt gagaaagaaa tgtatacgct gggaatcact aattttccat 360
tcctggagag cctggttttc cacttaacgc aatttatgcc aaacctgcaa acaaacaggg 420
aagatgaagt gatgagagcc tatttacaac agcttaaggg caagaaactg gactggaact 480
ttgtgaagaa gttttcgacc cttagaatgg ttaaaccnac agtgggggga cttgcttttg 540
gaaaanaccg tttattgacn anagtttttt tggactggan atgaaaggng cccnggttng 600
ccccggtttn n 611

<210> SEQ ID NO 379
<211> LENGTH: 602
<212> TYPE: DNA
<213> ORGANISM: Homo sapiens
<220> FEATURE:
<221> NAME/KEY: misc_feature
<222> LOCATION: (1)...(602)
<223> OTHER INFORMATION: n = A,T,C or G

<400> SEQUENCE: 379
acagctggtt ggacctattc atgcatcttc accagcagct ggagcatctc caccccttggt 60 atttctggtg taaattactt gagctctgtg ctttgaaacc agtttgataa gtcctttact 120
aaggagctcc tgaagggctg ccctggccag ggagcctcga atcttcagtc tctcagagac 180
cacagctggg gttataagtt tatagttggg aacttcctta cagagtttat cataggtagc 240
tttgtcaaac aagactaagt tattgagctt gtcccgaact ttgcctttgg accacttctt 300
ctttttggcc ttgcccccgg atttgttcac tgggtctttg nctttcttgg ccgactttcc 360
agcgtccttc ttcttcttgt cgtccttagg cggcattgcc aagctcggag aatagcanca 420
gacacngnaa cctngtcaag atgtcngaca aaaagccccg ggtaccttgg gcgngaacac 480
gcttaaggcg aattccacac actggcggcc gtactanggg gatccagctt nggaccaact 540
tggnggaaac atggcnaact gnttcctngn ggaaaatgtn atccgttaaa attnccccaa 600
at 602

<210> SEQ ID NO 380
<211> LENGTH: 598
<212> TYPE: DNA
<213> ORGANISM: Homo sapiens
<220> FEATURE:
<221> NAME/KEY: misc_feature
<222> LOCATION: (1)...(598)
<223> OTHER INFORMATION: n = A,T,C or G

<400> SEQUENCE: 380
ggtacngcgg ggggtgcctg gctccgtttc ctgcttttgg ttcttacagt agtcggcgta 60
ggccttagat tttttactgt ctcctgaaga atttaacaca aacatggata tcagaccaaa 120

-continued

```
tcatacaatt tatatcaaca atatgaatga caaaattaaa aaggaagaat tgaagagatc    180

cctatatgcc ctgttttctc agtttggtca tgtggtggac attgtggctt taaagaccat    240

gaagatgagg gggcaggcct ttgtcatatt taaggaactg ggctcatcca caaatgcctt    300

gagacagcta caaggatttc cattttatgg taaaccaatg cgaatcagta tgcaaaacag    360

attccggata taatatcaaa aatgcgtgga acttttgttg ccaagaaaag aanaaagaaa    420

agaaaaagnc caaacttggg aacaactgna caaccncaac caaaaanctg ggcnngggac    480

tccaaatcac ttatacccag ggaattcacc ccnaatctta ggtcctgata ccttcaacta    540

tatttaatcc ttaaaactta nccgaagagc taatngatga tgtntcctgc cggtaacn      598
```

<210> SEQ ID NO 381
<211> LENGTH: 631
<212> TYPE: DNA
<213> ORGANISM: Homo sapiens
<220> FEATURE:
<221> NAME/KEY: misc_feature
<222> LOCATION: (1)...(631)
<223> OTHER INFORMATION: n = A,T,C or G

<400> SEQUENCE: 381

```
ggtacgcggg gagagtgtgg tcaggcggct cggactgagc aggactttcc ttatcccagt     60

tgattgtgca gaatacactg cctgtcgctt gtcttctatt caccatggct tcttctgata    120

tccaggtgaa agaactggag aagcgtgcct caggccaggc ttttgagctg attctcagcc    180

ctcggtcaaa agaatctgtt ccagaattcc ccctttcccc tccaaagaag aaggatcttt    240

ccctggagga aattcagaag aaattagaag ctgcagaaga aagacgcaag tcccatgaag    300

ctgaggtctt gaagcagctg gctgagaaac gagagcacga gaaagaagtg ctttagaagg    360

caatagaaga agaaccacaa cttcgtaaaa atggcngaan aagaaactga ccnccaaaat    420

gggagcttat taaagagaan ccagangnnc caatngnttg gccaactggg accgtttgca    480

anaagaaggg ttagccccnt tgaanaaatg ccggaagaac caaagaattc caagaccctt    540

gntgcnaaac ttgaacttgc ctaattggtc ttgagaactg ctttttttccc atcccttcta    600

aaatccaaaa atgnacctgc ccgggggccg t                                   631
```

<210> SEQ ID NO 382
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G

<400> SEQUENCE: 382

```
acattcccag atttttaagc ctccctcata aacacctgta atcagatcag agtgagaaga     60

aaagcttttt gaaactatgt tttctccagg gaagttctct ttcaacaaga tggttttcac    120

tactgataac ttaacatgct ggaaacctgg taatgtttct atgactttat tttctaacat    180

cttctttaaa tctttaggca tagcatgctc tttggcagct ctcaaggagg gctgtttcca    240

tgtggctcca agttccttga actgctggct gcactgagtg gactgtctgt gtcttgagag    300

ggagctgcat tttcattgac ttatggtccc acaagtgacc ctgaggcaan gtcnaattgg    360

tctncanaac atttttggcc ctctcttctc ctttttgact tttctgagac tgacagttct    420

tttganggaa tccagggnna angcttccnt ctctaatggg ggntaaattc attttccaaa    480

anggncggtt tttgggaaaa tnaaanttga aanggcatcc nttttattaa tgccccnanc    540
```

-continued ttttaanttc ngattntnaa cttnctgnta gaatttgtgg atccnccaaa ttggcttaat 600
attcaaatag ctt 613

<210> SEQ ID NO 383
<211> LENGTH: 628
<212> TYPE: DNA
<213> ORGANISM: Homo sapiens
<220> FEATURE:
<221> NAME/KEY: misc_feature
<222> LOCATION: (1)...(628)
<223> OTHER INFORMATION: n = A,T,C or G

<400> SEQUENCE: 383
ggtactttga ccctggaaag gtatgggtct gcttaaaaga aagaagaaac atacacgtaa 60
tcaaataaag cttaacatta tgcagggctt ataatcattt tcagcaacgg actgcaagct 120
gcactgtgaa gaaaatgcat agcagaggag aaagctgggg atctgaggaa ataggtaagg 180
aaaacagtgt caacacacag tggaagaagt gatgaagaca tctattccgg agctcacgtg 240
ccatgccctg ctagcgttcc ttaacaagcc acctgctcca gaaggccaca gcctgaccct 300
cccaagtgga atataaatgc ccaagtgcca catgaagcca ccttctncac tacctaaaaa 360
ggttgtctgg gactgagctc agaacacaca cctttctggg ctaccaaacc tttaagtgga 420
aagaattttt tnctaaatat ctanttttna tacccacttt aacgccactt ttatattgaa 480
attgggcttc taattagncc ctttcctcaa ttccttagga nggaactcat aatgggagcc 540
aaccaaccag ggattctacc cccaatngac tgnnctttaa angtattatt aattttgang 600
ggcaaaggtg tgaatggttt acaatacc 628

<210> SEQ ID NO 384
<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 384
acaggtaagc cctggctgcc tccacccact cccagggaga ccaaaagcct tcatacatct 60
caagttgggg gacaaaaaaa gggggaaggg ggggcacgaa ggctcatcat tcaaaataaa 120
acaaaataaa aaagtattaa agcgaagatt aaaaaaattt tgcattacat aatttacacg 180
aaagcaatgc tatcacctnc cctgtgtgga cttgggagag gactgggcca ttctccttag 240
agagaagtgg ggnggctttt angatggcaa gggacttcct gtaacaatgc atctcatatt 300
ttggaatgac tattaaaaaa acaacaatgt gcaatcnaaa gtctcggccc atttgcggaa 360
ctttgggggg atgcttgctt cnaccgantt ggtgncaacc tttnnccggt tccanttttt 420
naaattctta gtnnaagcnn aaaaaanntag aatancncna nancataact tannaancca 480
tttaanaggt ccctcggccg gaacnnnctt aanggtnaat cccantnnnt ggcgggcgtt 540
actncnggat ccanccttgg nnccaaantn gnggaattca tggcnnaacc gntcctgggn 600
gaantngttn ccttnaaanc 620

<210> SEQ ID NO 385
<211> LENGTH: 535
<212> TYPE: DNA
<213> ORGANISM: Homo sapiens
<220> FEATURE:

-continued

<221> NAME/KEY: misc_feature
<222> LOCATION: (1)...(535)
<223> OTHER INFORMATION: n = A,T,C or G

<400> SEQUENCE: 385
ggtacttttt tttttttttt tttttttggt atttagtttt tatttcataa tcataaactt 60
aactctgcaa tccagctagg catgggaggg aacaaggaaa acatggaacc caaagggaac 120
tgcagcgaga gcacaaagat tctaggatac tgcgagcaaa tggggtggag gggtgctctc 180
ctgagctaca gaaggaatga tctggtggtt aagataaaac acaagtcaaa cttattcgag 240
ttgtccacag tcagcaatgg tgatcttctt gctggtcttg ccattcctgg acccaaagcg 300
ctccatggcc tcacaatatt catgccttct ttcactttgc caaacaccac atgcttgcca 360
tccaaccact cagtcttggc agtgcagatg aaaaactggg aancntttgg ggtngggncn 420
acatttgcct tggccaaaat gccnggaacc ggccccgtac cttgnccngg ccggccggtt 480
caaaagggcg aattccacac acttggcggg ccgtactang gggatccaac ttcgg 535

<210> SEQ ID NO 386
<211> LENGTH: 642
<212> TYPE: DNA
<213> ORGANISM: Homo sapiens
<220> FEATURE:
<221> NAME/KEY: misc_feature
<222> LOCATION: (1)...(642)
<223> OTHER INFORMATION: n = A,T,C or G

<400> SEQUENCE: 386
acagcattgg cagtggtgcg tcagaggtgg cagaactatt tcacactaac cagttgaaga 60
ctacacaaga ttaataccat ccagcatcag gatatagctg tggattttac aaaccattct 120
tatttctaac ttcaggagtt gatgtttttc ccagtccatc ttaaaatatt actgctttaa 180
tcacagatca ggtaaaaagg acaacatgca caacctccac ctagaatcct gttgtagcct 240
agacagtgaa atgatatgac atcagaagac tttaaaattg cagctccttt tggatccccc 300
aaagtgtatc tgcactcttc ttcaaacggg ccctctttcc tcaagaagtc agaagtcacc 360
ttcacaangn ctgagaattc cattctgnnc ccaaantgca agggacactn aaggaagaca 420
tcattctttt attccgtnaa agacccttaa ttcatgggng gaaactgggt gcacccgcct 480
nagaatcttt attanactct ttgnccaatt tggttacaga agagntncan tanccccang 540
aannggtagc ctttggagtt tgantcaccc tcataagcac ccttaaacca cctgnttggg 600
gaaccttctt tcactggtcc ctaactttat tangccctaa ag 642

<210> SEQ ID NO 387
<211> LENGTH: 256
<212> TYPE: DNA
<213> ORGANISM: Homo sapiens

<400> SEQUENCE: 387
ggaccttttt tttttttttt tttttttttt tgaaaagaaa ggccttacat atttattact 60
gaatccagcc aaccaacgtg ttcataacag attcagagag gaaaacacgt cgaaatctcc 120
agatagtggt gacattttca gcttgatatg gtaacatgat cgtgaccttc agacagcata 180
aatatgtgtg ccatctcatg tgcaattcct tatagaccca gcttggttct tctccaatgt 240
ctccttttgg agttgt 256

<210> SEQ ID NO 388
<211> LENGTH: 566

-continued

<212> TYPE: DNA
<213> ORGANISM: Homo sapiens
<220> FEATURE:
<221> NAME/KEY: misc_feature
<222> LOCATION: (1)...(566)
<223> OTHER INFORMATION: n = A,T,C or G

<400> SEQUENCE: 388
ncnagcggcc gcccngncng gnactgaaca ttggtaaaaa attatatgag ggtaaaacaa 60
aagaagtcta cgaattgtta gacagtccag gaaaagtcct cctgcagncc aaggaccaga 120
ttacagcagg aaatgcagct agaaaaaaac cacctggaag gaaaagctgc natctcaaat 180
aaaatcacca gttgtatttt tcagttatta caggaagcan gtattaaaac tgccttcacc 240
agaaaatgtg gggagacagc tttcattgca ccgcagtgtg aaatgattcc aattgaatgg 300
gtttgcacaa gaatagcnac tggttctttt ctnaaaagaa atcctggngt caaggaagga 360
tataagtntt accccctaaa gtggagngtgt ttttcaagga tgatgcccat taatgaccnc 420
cagtcgggct tgaagaacna cttgattgct gcaaaaattt gcttttcttg gacttcttat 480
anggcnaacc tgaaanggat ttcatgaagt catgctacnc aggctatatt tgaaatctgg 540
gagaaatcct ggttgcccaa aattgg 566

<210> SEQ ID NO 389
<211> LENGTH: 629
<212> TYPE: DNA
<213> ORGANISM: Homo sapiens
<220> FEATURE:
<221> NAME/KEY: misc_feature
<222> LOCATION: (1)...(629)
<223> OTHER INFORMATION: n = A,T,C or G

<400> SEQUENCE: 389 acttttttttt tttttttttt ttttttgttt tttttttttt tttttttttt ttttttttgc 60
agtttctaag tcattacttt tnattttgaa agatttgnga aactnttcac atcatggtga 120
gagtttgtat gattaataan aagcagcttt ttcatgaaat gcttggaggt gaacgagttn 180
tcagcctgng anatccgacc ntcccattaa ctttgaagtt tctcttgatt aatagaagaa 240
aaaaggggag ggtgaanaaa aggaggaaca tgctaaaaac cttatgacaa tcatccaaat 300
gtgaggaaag aacaacccga ttcaccaact ccactttttc tattttacaa ctttctacat 360
ctcacncttg gattttggcc ttcntggctn aaacantcct ggcantccnt tanagcccct 420
gaaaaagagc cntggntttt ncaaaagacn ntnggnnggn gaannccttn annatgccct 480
gacccnttcn cnaagaactn nntntccggg ntcccaaaag tttgacccan cagcttantg 540
tgaannnaaa actnnccttn aaaggtaatg ggnggaanng gtgannaant gggttttttt 600
ganaagtctt ntttttctna aaaccnccg 629

<210> SEQ ID NO 390
<211> LENGTH: 596
<212> TYPE: DNA
<213> ORGANISM: Homo sapiens
<220> FEATURE:
<221> NAME/KEY: misc_feature
<222> LOCATION: (1)...(596)
<223> OTHER INFORMATION: n = A,T,C or G

<400> SEQUENCE: 390
actttaattt atttcccctt tctagtgtat taagaaatga catgcacttt aatttgccaa 60
aagcaatgct tgtattctgg cagcaacatg ctacttctat cacatagtaa agtgaatacc 120

-continued

```
agaactacaa aggcaggagg tgtaagtgaa tttttattgg gaggggaggt tggcaactta    180

aacagcagca aataaagagt gaataaggaa actccctgtt gccacagata cacaagacct    240

ccgtatgtga tacaggagcc atttcaattt gtgaccccta gacagagatg gcaagtgctt    300

ttccattcaa tctaatactt ccggattcct actaaaaagg aatcattaag agcatggaaa    360

agttgcttac tggaaaggaa acccccgaag agtaagggaa gggaatgtga aattaagaag    420

ttatgtggaa tctcttaaat tgnaattact acatttctta atttccaggt atnccaaaca    480

cagtccnttg caaaactggt cagntactta aatnccngat ccattttagg cnttacataa    540

gtgtttggga gtacctatgg tatttnaatg aacttttaaa cttttntccg ccgtcc        596
```

```
<210> SEQ ID NO 391
<211> LENGTH: 625
<212> TYPE: DNA
<213> ORGANISM: Homo sapiens
<220> FEATURE:
<221> NAME/KEY: misc_feature
<222> LOCATION: (1)...(625)
<223> OTHER INFORMATION: n = A,T,C or G

<400> SEQUENCE: 391

acacacccag gaaatttgtc atccaccctg agagtaacaa ccttattatc attgaaacgg     60

accacaatgc ctacactgag gccacgaaag ctcagagaaa gcagcagatg gcagaggaaa    120

tggtggaagc agcaggggag gatgagcggg agctggccgc agagatggca gcagcattcc    180

tcaatgaaaa cctccctgaa tccatctttg gagctcccaa ggctggcaat gggcagtggg    240

cctctgtgat ccgagtgatg aatcccattc aagggaacac actggacctt gtccagctgg    300

aacanaatga ggcagnttta gtgtggctgt gtgcaaggtt tccacactgg tgaagactgg    360

tntgtgctgg tgggtgtngn canaggacct ngntnctaaa accncgnntt tgggcaatgg    420

ggctttcgtc taattnttac aannttgntg accaatnggg gatnaactgg anntttttgn    480

tcaanactnt tttggaataa tntccctnnt gcnattngcc ntatttcctg gggaanggtg    540

ttnatatngt natggnnaaa cntntanccg nnntntaatc ttggaatata tatnaatacc    600

ttcttaaaan ntgntnatta tcctt                                          625
```

```
<210> SEQ ID NO 392
<211> LENGTH: 266
<212> TYPE: DNA
<213> ORGANISM: Homo sapiens

<400> SEQUENCE: 392

ggtacccata ttgctaatgc taggatcaag ataccacata gccagaacaa gaagttgaag     60

gtaaacatag aatattttat acaggcactc acacctgcca tttcggaaaa ggattaggaa    120

tccagatgcc gtgaatttaa ctattcgtta caggcttgtc ctgcaatatg ctctggagca    180

acttgcctgc agagatttct gtatccacgg cttcagagca gaaagagaaa gcaaagaagt    240

agagggagga ataaaaatcc ccgcgt                                         266
```

```
<210> SEQ ID NO 393
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 393
```

```
ggtacttttt tttttttttt tttttttttt tggttttacc tgtttttatt ccttaaaaga     60

aaaaaacaac ttaaatgcat acatacagaa tagaatacac ttacttaagt tttgacagtg    120

aaaaaaaata attacaggtt agatatttaa tccaaggttt aacatgggga tgatctcata    180

aggcaatttc tttcctttaa taaatattaa agtgaatatt attctggaag caaatcatct    240

cctaattctt catcagcaaa atcatcctca tcgatccttt tcttggctgc agtttttggt    300

cgttctattt gagggccaag tgggtccaca taggaggcat ctatttcttt gntactgcta    360

ctttcataag gntcatttgt cccaggtaaa agctctgagt ctggccttan tccgtcaccc    420

tttactactg gcnctatagt ctggccacta tnaacgntag ccttncttnt cnttttgnca    480

cnggagcccc caatgcannt ttngcntgac tttagcncng gnccctaatt cttcattttt    540

ccacctttna gnttttggca antcttgagc cnttttaat cnaagacttn gcanagccaa     600

ttaaaaaccc c                                                         611
```

<210> SEQ ID NO 394
<211> LENGTH: 340
<212> TYPE: DNA
<213> ORGANISM: Homo sapiens

<400> SEQUENCE: 394

```
acgagtccca ctatgcgctg cccctgggcc gcaagaaggg agccaagctg actcctgagg     60

aagaagagat tttaaacaaa aaacgatcta aaaaaattca gaagaaatat gatgaaagga    120

aaaagaatgc caaaatcagc agtctcctgg aggagcagtt ccagcagggc aagcttcttg    180

cgtgcatcgc ttcaaggccg ggacagtgtg gccgagcaga tggctatgtg ctagagggca    240

aagagttgga gttctatctt aggaaaatca aggcccgcaa aggcaaataa atccttgttt    300

tgtcttcacg caaaaaaaaa aaaaaaaaaa aaaaagtacc                          340
```

<210> SEQ ID NO 395
<211> LENGTH: 557
<212> TYPE: DNA
<213> ORGANISM: Homo sapiens
<220> FEATURE:
<221> NAME/KEY: misc_feature
<222> LOCATION: (1)...(557)
<223> OTHER INFORMATION: n = A,T,C or G

<400> SEQUENCE: 395

```
acacatcttc aaagcacttc cctttaacgg gaaacttagc tttatgggat ttaaacatta     60

gaaagtggga aaaaaaattc cattttcttg tcattataaa ccaaaacaaa atctagtgta    120

agtcaaggaa actcattcac acttcaggtc cttctcctcc aggaaccagc attgttatat    180

tatttccatt tagcaaaatc tgatgtaatt tagtaatcct tcttccttct ggtgtgattt    240

caaactcagt gacatcttcc agtactttnt tttttttttt tttttttggg gtgttgagct    300

tggacgcttt cttaattggt ggctgctttt aggcctacta tgggtgttaa atttttactc    360

tctctacaag gnttttttcct agtggccaaa agaagctggt ccctcttttg gactaccgtt   420

aaaattacca nggggattta aaangggtnt tgngggccaa attnaaagtt ngactangan    480

tctatttttg gccaaccagt nttaaccagg cttcggtang gttggccgcc cccgggtacc    540

ttgggccggg aacacnc                                                   557
```

<210> SEQ ID NO 396
<211> LENGTH: 617
<212> TYPE: DNA

-continued

<213> ORGANISM: Homo sapiens
<220> FEATURE:
<221> NAME/KEY: misc_feature
<222> LOCATION: (1)...(617)
<223> OTHER INFORMATION: n = A,T,C or G

<400> SEQUENCE: 396

```
ggtacngcgg ggccactcga gtgcgcaggc gcctggcgat taccggtctc accatggagc     60

ggaaagtgct tgcgctccag gcccgaaaga aaaggaccaa ggccaagaag gacaaagccc    120

aaaggaaatc tgaaactcag caccgaggct ctgctcccca ctctgagagt gatctaccag    180

agcaggaaga ggagattctg ggatctgatg atgatgagca agaagatcct aatgattatt    240

gtaaaggagg ttatcatctt gtgaaaattg gagatctatt caatgggaga taccatgtga    300

tccgaaagtt aggctgggga cacttttcaa cagtatggtt atcatgggat attcagggga    360

agaaatttgt ggcaatgaaa gtagttaaaa gtgctgaaca ttacacttga aaccagccta    420

gatgaaatcc ggttgcttga agtcagttcc aattcagacc ttatggatcc aaatngaaaa    480

atggttgtca actactagat gactttaaaa ttcaggagtt aatggaacac atatttgcat    540

gggatttgaa gttttggggc anattngtta agnggttctc aaatcaattn ttangggctt    600

tcctgccttg ggtnaaa                                                   617
```

<210> SEQ ID NO 397
<211> LENGTH: 594
<212> TYPE: DNA
<213> ORGANISM: Homo sapiens
<220> FEATURE:
<221> NAME/KEY: misc_feature
<222> LOCATION: (1)...(594)
<223> OTHER INFORMATION: n = A,T,C or G

<400> SEQUENCE: 397

```
acgcggggga tcaggactcc tcagttcacc ttctcacaat gaggctccct gctcagctcc     60

tggggctgct aatgctctgg gtcccagggt ccagtgggga ccgtcgtggt gactcagtct    120

ccggtctccc tgcccgtcac ccttggacag ccggcctcca tctcctgcag gtctggtgaa    180

actctccttt acgaagatgg aagcacctac ttgagttggt ttcaccagag gccaggccaa    240

tctccgaggc gcctgattta taaagtttct aaccgggact ctggggtccc agacagattc    300

agcggcagtg ggtcaggcac ttatttcacg ctgaaaatca acagggtaga ggctgatgat    360

gttgggaatt attactgcat gccanggtca aactggcccg tcacttttcg gngaaggacn    420

aaaggtggcc natcaaacca actgnggctt gaccattggc ttcatnttcc cgccatttga    480

taaccantga aatctggact gctttgtggg ngcctgctga aaacttntat nccnanaggc    540

cnaagtcatg acagtttttc natttactcg aaaaatntgg aaatgataat tttn          594
```

<210> SEQ ID NO 398
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 398

```
acagtggtcc ttttcagagt tggacttcta gactcacctg ttctcactcc ctgttttaat     60

tcaacccagc catgcaatgc caaataatag aattgctccc taccagctga acagggagga    120

gtctgtgcag tttctgacac ttgttgttga acatggctaa atacaatggg tatcgctgag    180
```

```
actaagttgt agaaattaac aaatgtgctg cttggttaaa atggctacac tcatctgact    240

cattctttat tctattttag ttggtttgta tcttgcctaa ggtgcgtagt ccaactcttg    300

gtattaccct cctaatagtc atactagtag tcatactccc tggtgtagtg tattctctaa    360

aagctttaaa tgtctgcatg cagccagcat tcaatagtga atggnctctc tttggctgga    420

attaccaaac tcagagaaat gnggcatcag agaacatct taaccccatg aanggataaa    480

agccccaaat ggngggnact tgataatagc nctaatgctt taaanatttg gtccactttt    540

tacctaaggt gagcccattg aaccannggt gctaaangct catacttcca actgaaatgg    600

ttaaggaaaa a                                                         611
```

<210> SEQ ID NO 399
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 399

```
actctgtgaa tggtgagagg ctgggcacct acatgggcca taccggagct gtgtggtgtg     60

tggacgctga ctgggacacc aagcatgtcc tcactggctc agctgacaac agctgtcgtc    120

tctgggactg tgaaacagga aagcagctgg cccttctcaa gaccaattcg gctgtccgga    180

cctgcggttt tgactttggg ggcaacatca tcatgttctc cacggacaag canatgggct    240

accagtgctt tgtgagcttt tttgacctgc gggatccgag ccagattgac aacaatgagc    300

cctacatgaa gatcccttgc aatgactcta aaatcaccag tgctgtttgg ggacccctng    360

gggagtgcat catnctggcc atgaaaagtg gagagctnaa ccagtattag tgccnnagtt    420

tnnanaaggt gttngttnaa tgttaaagga gcantttccg gnagaataac cnacnttcag    480

gttattccnn gganatgacc anngtttnga ccccttnnna gtccattaat nccnaacttt    540

tttacnctca aattttnaan tnanaaaact tttngnatna aattnttnaa ttanttgttc    600

tttttcaata tnnn                                                     614
```

<210> SEQ ID NO 400
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 400

```
acttacactg tgaaatttta tgatggagta gttcagactg tcaaacatat tcatgtcaaa     60

gcttttttcca aagatcaggc ctaaagaaac agatcacaaa agtctttcat catctcctga    120

taaacgagag aagtttaaag aacagagaaa agcaacagtg aatgtgaaga agacaaaga     180

agataaaccc ttaaagacag aaaagcgacc caagcagcct gataaagaag gaaagttaat    240

ctgttctgaa aaggggaaag tgtcagagaa aagtcttccc aagaacgaga aggaagacaa    300

ggaaaacatt tccgaaaatg acagagagta ttctggagat gcccaagtgg ataagaaacc    360

tgaaaatgac attgtgaaga gtccacaaga aaacttgagg ggaaccnaaa ngaaaacgag    420

gcagaccccc ttccatagct nctactgctg gggattnaaa ctttaaactt tggcacccat    480
```

-continued acctttggac ttnnnanaag gaaaatttca nagggtgtga agtcctttaa accgtccttg 540
gttgncaaaa ntttttncng ggaaagtcaa aaacttcttt gaaaaccttg ccnangattt 600
ttnnggngac nt 612

<210> SEQ ID NO 401
<211> LENGTH: 601
<212> TYPE: DNA
<213> ORGANISM: Homo sapiens
<220> FEATURE:
<221> NAME/KEY: misc_feature
<222> LOCATION: (1)...(601)
<223> OTHER INFORMATION: n = A,T,C or G

<400> SEQUENCE: 401
ggtacggtaa ctgactccag ggtcactcat actgtgtccg tggtaacggt aagtctgcag 60
ctccatcagg atgggcccct tcccagatct acaataggca gcagcaaacc ttgttgcctc 120
tcggacgcac aggatatcca ttccatccac tctcagccca ggaatgaaat cgcctctctt 180
gtagtaatca gtgctggctg ccgctctctc aacagacgtt cccattccat agcgattatt 240
ctcacagatg aaaatacaag gtaatttcca caaagctgcc atgttgtaag cttcgaatat 300
ctggccctgg ttagcagcac catcgccata taaagtcagg cagacctcat cttttccatt 360
atacttacag gctagagcaa tcccagcgcc caagggcacc tgcgctccta cgatgccatg 420
gccccgtana agtcttggca tacatgtgca tcgatcctcc ttcctttagc acaanctcct 480
tttgncctgt aactgcaaaa tttntcggac ggaaaggccc cggtgnaaag taaagccgtg 540
agcccggnag gctgngatna aanggcttgt ggggttnaag cccggcttca ggtcccacag 600
a 601

<210> SEQ ID NO 402
<211> LENGTH: 600
<212> TYPE: DNA
<213> ORGANISM: Homo sapiens
<220> FEATURE:
<221> NAME/KEY: misc_feature
<222> LOCATION: (1)...(600)
<223> OTHER INFORMATION: n = A,T,C or G

<400> SEQUENCE: 402
acctggagaa gatcaaacag cgactgtttg agaaccttag aatgctgccg cacgcacctg 60
gggtccaaat gcaggcgatt cctgaggacg ccatccctga ggagagtggc cgatgaggac 120
gaagacgacc ctgacaagcg catctcgatc tgctcctctg acaaacgaat tgcctgtgag 180
gaagagttct ccgattctga agaggaggga gaggggggcc gcaagaactc ttccaacttc 240
aaaaaagcca agagagtcaa aacagaggat gaaaaagaga aagacccaga ggagaagaaa 300
gaagtcaccg aagaggagaa aaccaaggag gagaagccag aagccaaagg ggtcaaggag 360
gaggtcaagt tggcctgaat ggacctnttc agctctggct ttctgctgag tccctacgtt 420
ctttcccaac cccttaaatt tataatttct attctctggg gatttatata aaaatttatt 480
naatnttaat attcccaggg cccgaaacca agggcccgaa ctnaaggnaa ntttgcttgg 540
gtgagctntt tcaagaacca ccttgcaccc atttttccgt cttaacttta accaaaangg 600

<210> SEQ ID NO 403
<211> LENGTH: 604
<212> TYPE: DNA
<213> ORGANISM: Homo sapiens
<220> FEATURE:
<221> NAME/KEY: misc_feature -continued
<222> LOCATION: (1)...(604)
<223> OTHER INFORMATION: n = A,T,C or G

<400> SEQUENCE: 403
actcagtgga tgacgagtgc ttggtgaaat tgttgaaagg cctgtgtctg aaatacctgg 60
gccgtgtcca ggaggccgag gagaatttta ggagcatctc tgccaatgaa aagaagatta 120
aatatgacca ctacttgatc ccaaacgccc tgctggagct ggccctgctg cttatggagc 180
aagacagaaa cgaagaggcc atcaaacttt tggaatctgc caagcaaaac tacaagaatt 240
actccatgga gtcaaggaca cactttcgaa tccaggcagc cacactccaa gccaagtctt 300
ccctagagaa cagcagcaga tccatggtct catcagtgtc cttgtagctt tgtgcagcag 360
ttccgggctg gaagacagag acagctggac agagctcctg aaaacatttc aaaaataccc 420
ccttcccctg gcctgccctg cctttggggt ccancggcac ttcagttgga tggcacaacc 480
tantgtatcc gtgcnnaaan cnaacctggc attttcaccc anntanccaa gggcttttgc 540
caagggnana acagtggagc ccttggcttg ncctataaac atacgggtac cttggccgnn 600 acnn 604

<210> SEQ ID NO 404
<211> LENGTH: 604
<212> TYPE: DNA
<213> ORGANISM: Homo sapiens
<220> FEATURE:
<221> NAME/KEY: misc_feature
<222> LOCATION: (1)...(604)
<223> OTHER INFORMATION: n = A,T,C or G

<400> SEQUENCE: 404
ggtactttgt ggataagaaa atggaggaac acatctgatg gagagtgggc atttgacaac 60
aatggaacag gtaaccagca tgtaaaatca aaatataagt gtctttttaa gagctgaaag 120
ctgctgctgg tcattcatta atgtgtcaga catttaatca ggatgctgga ccttcaaaat 180
aactgaaaaa agaaccaaga aaaggcgttt ttgttttcaa caaactttac taaataaccc 240
cggaaaggca atgaacgatc tgacaattta agctctaatg atttaaagct cagctagaag 300
aaagtgaggc atgacatata ctgtcaacgg agggtgaagg aggcagattt ctggaaatgc 360
aatgatccca cacatttgct tcaaggagaa acctgcagac atattttcag gtcttgctaa 420
gtaacaactg gttatttgta atcaatcatt tgggaaagtc tgctatgtag ctaanggcac 480
tgtgaccccn gacaacngat gaaaaggaaa aagcnttgac agcaggaaaa atccttccat 540
cttaaagaat ttaggggaca cctttaaagg aaaaaaattg ntccagcctc atttttacaa 600 ntnt 604

<210> SEQ ID NO 405
<211> LENGTH: 593
<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G

<400> SEQUENCE: 405
acttgcattt caaagcttat aagatataaa tggagatttt aaagtagaaa taaatatgta 60
ttccatgttt ttaaaagatt actttctact ttgtgtttca cagacattga atatattaaa 120
ttattccata ttttcttttc agtgaaaaat tttttaaatg gaagactgtt ctaaaatcac 180

-continued

```
ttttttccct aatccaattt ttagagtggc tagtagtttc ttcatttgaa attgtaagca    240

tccggtcagt aagaatgccc atccagtttt ctatatttca tagtcaaagc cttgaaagca    300

tctacaaatc tcttttttta ggttttgncc atagcatcag ttgatcctta ctaagttttc    360

atggggagac ttccttcatc acatcttatg ttgaaatcac tttctgtagt caaaggtata    420

ccaaaaccaa tttatcttga actaaattct aaagtatggg tatccaacca tatacatctg    480

ggtaccaaac ataaatgctg acattcntat attatagtna aggcttaatc nacttgcagg    540

tgaatggaaa aaaaataagc ttnaacctag gattctggaa tgaggaatgc tcn           593
```

```
<210> SEQ ID NO 406
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 406

acttttttttt tttttttttt ttttttttttg ggactgaatc ttgctctgtc gcccaggctg    60

gagtgcagtg gcgcaatctt ggctcactgc aacctctgcc tcctgggttc aagtggttct    120

catgcctcag cctcctgggt agctgggatt acagacaagc accaccacaa ccagctagtt    180

ttttttgttt tgttttttttg agacggagtc tcgctctgtc accaggctgg agtgcagtgg    240

cacaatcttg gctcactgca acctctgcct cctgggttca agagattctc ctgcttcagc    300

ctnccaagta gctgggacta caggtgcaca ccatcacacc tggctaattt ttgtattttt    360

aagtanagac ggggtttcac catgttggcc aggctggtct caaactcctg acctcaagtg    420

aaccggccgc ttancctcca aagtgctggg attacaggcg tgagcccact ggcctggctg    480

accatttggt tattaacagg gcccccaana tgcnccttta ngtgaaaggg natggcccca    540

gggaacaatt nngctgaaaa acaccaaagg ccnantccat aattcnttgg n              591
```

```
<210> SEQ ID NO 407
<211> LENGTH: 463
<212> TYPE: DNA
<213> ORGANISM: Homo sapiens
<220> FEATURE:
<221> NAME/KEY: misc_feature
<222> LOCATION: (1)...(463)
<223> OTHER INFORMATION: n = A,T,C or G

<400> SEQUENCE: 407

ggtactgatt ttaaaaacta ataacttaaa actgccacac gcaaaaaaga aaaccaaagt    60

ggtccacaaa acattctcct ttccttctga aggttttacg atgcattgtt atcattaacc    120

agtcttttac tactaaactt aaatggccaa ttgaaacaaa cagttctgag accgttcttc    180

caccactgat taagagtggg gtggcaggta ttagggataa tattcattta gccttctgag    240

ctttctgggc agacttggtg accttgccag ctccagcagc cttcttgtcc actgctttga    300

tgacacccac cgcaactgtc tgtctcatat cacgaacagc aaagcgaccc aaaggtggat    360

agtctgagaa gctctcaaca cacatgggct tgccaggaac catatcaaca atggcagcat    420

caccagactt caagaattta nggccatctt tcccgggtac ctg                      463
```

```
<210> SEQ ID NO 408
<211> LENGTH: 588
<212> TYPE: DNA
<213> ORGANISM: Homo sapiens
```

-continued

<220> FEATURE:
<221> NAME/KEY: misc_feature
<222> LOCATION: (1)...(588)
<223> OTHER INFORMATION: n = A,T,C or G

<400> SEQUENCE: 408

```
acaaatatat ataacttaca tttgattgta aggccaacgt tcaaaagtaa aaatgagatg     60

agctctctta ttgttatccg aggtcaagag gctgcaactg tcaaggggat gttctcacca    120

aaagggggtt tgggggaaga ggacacacac aaagctaata aaaccagaat ccccatcccc    180

acaaaactca tgggaacaaa atttaaagga taaaacaaaa cccaccaaga cccatattac    240

aaaccaatat ggtaacctgt gttcccttct atggtatgat tatgtcatgt taccttagtg    300

ttaaaagatt aacataagga aactgcagca atatataaaa gatatattct ctatagagca    360

tatttcgatt gattccatta aaataatgac attagaattc catcatangg ttaaaaccag    420

gacaatactg nttttncttt atttaaaaaa aactaccacc taatgactgn attggtcata    480

acctgaatgg tgtgcaatgg gctcttccat gaatggctgg cngaaacaag cttgggncct    540

gcttgagttt cagctttcct ctttaattta gtngctcaat gataaaca                 588
```

<210> SEQ ID NO 409
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 409

```
ggtacaaaga tctgacatgt cacccaggga cccatttcac ccactgctct gtttggccgc     60

cagtcttttg tctctctctt cagcaatggt gaggcggata ccctttcctc ggggaagaga    120

aatccatggt ttgttgccct tgccaataac aaaaatgttg gaaagtcgag tggcaaagct    180

gttgccattg gcatctttca cgtgaaccac gtcaaaagat ccagggtgcc tctctctgtt    240

ggtgatcaca ccaatttttc taggttagca cctncagtca ccatacacag ggtaccagtg    300

tcnaacttga tgaaaatcaa gtaatcntgg ccagtctcta aaatcaaatc ttgaatggta    360

tcaattcacc cttgatgaag gggaatcggg ggtaacccgg atgggtgccg ggccttnatg    420

aagtcancca natgaaggga ttcctttggg gcccccaaag aacttttttn attttcacaa    480

cttgnacctt gcccggcggg ccgttcaaaa gggcnaattc cagncacttg gnggccgtct    540

aanggatcca actcggacca acttggcgna anatggcaaa ctggttcctg gggaaatggt    600

atccctccaa tn                                                        612
```

<210> SEQ ID NO 410
<211> LENGTH: 353
<212> TYPE: DNA
<213> ORGANISM: Homo sapiens

<400> SEQUENCE: 410

```
acgcggaagc agtggtaaca acgcagagta acgcgggatg gcacatgcag cacaagtagg     60

tctacaagac gctacttccc ctatcataga agagcttatc acctttcatg atcacgccct    120

cataatcatt ttccttatct gcttcctagt cctgtatgcc cttttcctaa cactcacaac    180

aaaactaact aatactaaca tctcagacgc tcaggaaata gaaaccgtct gaactatcct    240

gcccgccatc atcctagtcc tcatcgccct cccatcccta cgcatccttt acataacaga    300
```

-continued

```
cgaggtcaac gatccctccc ttaccatcaa atcaattggc caccaatggt acc          353


<210> SEQ ID NO 411
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 411

ggtacgcggg gagagaaacc tggctttact atggcggttg gaggaacggc agtgatcaca     60

cgtcggctgc tgggaagatc tggattctcg tttcaggtca ccatcagaaa agctaagttt    120

gctgtatagt gaggatcagg agatctgatc ctgattgcag aaccttccct gattacagaa    180

tcttgggttg tatctcccac ttcacccttc tagaccatcc cagaagatct ataagatttc    240

atctgggaaa tcactaggag ttcttggaag ggaaagaagg aagattgttg gttggaataa    300

aaacagggtt gaatgagttc cagaaagcnn ggttctcaac ctcgtggaca gcaatctgca    360

gaagangaga acttcaaaaa accnactana agcancttgc anagaagtaa aatgagaagg    420

ggncttctna ngaaagaaga cacttggncc acagcagaaa aaactttgac cnantnttnc    480

caggaagana gggggggtcc cnctttttaaa naacccccctt taagatncng gnggaanacc    540

tcanngacca nccntaaatt nnggaaaccg aaaaggggcn gtcctttttg ntnncagntg    600

cnccnttaan nt                                                        612


<210> SEQ ID NO 412
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 412

acgcggggct ctctcgccag gcgtcctcgt ggaagtgaca tcgtctttaa accctgcgtg     60

gcaatccctg acgcaccgcc gtgatgccca gggaagacag ggcgacctgg aagtccaact    120

acttccttaa gatcatccaa ctattggatg attatccgaa atgtttcatt gtgggagcag    180

acaatgtggg ctccaagcag atgcagcaga tccgcatgtc ccttcgcggg aaggctgtgg    240

tgctgatggg caagaacacc atgatgcgca aggccatccg agggcacctg gaaaacaacc    300

cagctctgga gaaactgctg cctcatatcc gggggaatgt gggctttgtg ttcaccaagg    360

aggacctcac tgagatcagg gacatgttgc tggccaatna ggtgcccagc tgctgcccgt    420

gctggtgccc atttgcccat gtgaangtca cttgtgccca gcccaaaaca cttgtcttng    480

ggcccganaa gaacttcttt tttccaggcn ttaaaatatt cacccccttaa antttcaagg    540

ggccccattt gaaatcctgg annatnngca ttgatcaana ttganacaaa gtggnancnt    600

ccaaccc                                                              607


<210> SEQ ID NO 413
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G
```

<400> SEQUENCE: 413
acaggtcaga gtcttctttt cttttctttt tgagatggag tcttgctctg ttgccagact 60
ggagtgcagt ggtgcgatct gggctcactg caatctccac ctcccgggtt caagcgattc 120
tcctgcctca gcctcccgag taactgggac tacaggtgtg cgccaccaag cccagctcat 180
ttttgtattt ttagtagaga tggggtttca cgatgttggc taggatggtc tcgatctctg 240
gtcagagtct tttctgtaaa tatccttggt aaagaagcaa ttttagactg tagctgttgc 300
aaatgcttta aggaagaagc anaacaactg tcagtcttcc tgaaatgaag aaactacacc 360
agggctgcta tatcagagca accccaacca gcactccaat catgatgccc gacagtggcc 420
ccagcttgag aaccagagaa gttccagatg cagagactgt gagctcntga ctatgggaat 480
tttngnggcn ntaacccaan tttgagacna aacnaggcct tngncccggt tttnatttgg 540
gngggatttt gcggataaan aaacttgnng gggntnctgc ggnatccatg gaacnccaaa 600 anatng 606

<210> SEQ ID NO 414
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 414
ggtacttttt tttttttttt tttttttttg tagatgaggt ctcgctatgt tgcccaggct 60
ggagtgcagt tattcacagg tgcaaccaca gggcactgca gctttaaact cctgggctca 120
agcgatcctc ctgcctcagc ctcccaaata gttgggacta gatgcacgca cnaccacgcc 180
tgactcagga cattattctt aaaggtatta tccaggaaac agataaggtc attcataaaa 240
cacacggntt ttttctttag ctcagtgtta acaatgaaag tagattccac tattgaagca 300
caagttgcaa attggtaaca tagngaacat attgntgtag gaaaggggggt tcagtgtgnt 360 gtgttatatn agcncttgaa ctttttatgg gngtnataag ccnngttatc ttgncccaaa 420
gaaannccat tttnaggatt ngatggtttt cttannggaa nannctnggg ggnattntgt 480
ngggcatgaa cttttatgtn ggaatcagtc ccatanaggt aaggggtttn aatcccaaaa 540
ancggggnct tttatgggaa atnnccttta cttcaaaggc caaanngatn gtnggtgtca 600
cttcnaantt ccngannnca anng 624

<210> SEQ ID NO 415
<211> LENGTH: 609
<212> TYPE: DNA
<213> ORGANISM: Homo sapiens
<220> FEATURE:
<221> NAME/KEY: misc_feature
<222> LOCATION: (1)...(609)
<223> OTHER INFORMATION: n = A,T,C or G

<400> SEQUENCE: 415
acgcgggtta caacggaagt aaaatctgtc gaaatgcacc atgaagcttt gagtgaagct 60
cttcctgggg acaatgtggg cttcaatgtc aagaatgtgt ctgtcaagga tgttcgtcgt 120
ggcaacngtt gctggtgaca gcaaaaatga cccaccaatg gaagcagctg gcttcactgc 180
tcaggtgatt atcctgaacc atccaggcca aataagcgcc ggctatgccc ctgtattgga 240

-continued

```
ttgccacacg gctcacattg catgcaagtt tgctgagctg aaggaaaaga ttgatcgccg    300

ntctggtaaa aagctggaag aaggccctaa attcttgaag tctggtgatg ctgccattgt    360

tgatatgggt cctggcaagc ccatgtgttg ttgagagctt tctcagacta tccacctttg    420

ggtngctttg ctggtcgtga natgagacag acaggtgccn gtggggtggc atcaanncat    480

gggacaanaa aggcttnttg ganccttgcaa aggtncncaa nttttgncca naagcntcaa    540

aagntaattg aatttttccc ctannncctg cncccncttt tannanggnn ggaaaacggc    600

ttaaanntt                                                            609
```

```
<210> SEQ ID NO 416
<211> LENGTH: 577
<212> TYPE: DNA
<213> ORGANISM: Homo sapiens
<220> FEATURE:
<221> NAME/KEY: misc_feature
<222> LOCATION: (1)...(577)
<223> OTHER INFORMATION: n = A,T,C or G

<400> SEQUENCE: 416

ggtacgagct gattgggaac gggctccaat ggacatggct ctgcagtcaa aatagttagc     60

agatggacag gtttggaaaa tgtgagggcc catatcatca tanccagcaa taaggagacc    120

aacaccatat ggtctccggc catatccgtt gtgttggtat ctgggtcttg cttccaatta    180

gagatacaag actgagacac aggcagtggt ctatcgaata caaatctgga atncaaacac    240

tcctgacgca taaaattaca taacagncta gcatnancag taagcccccg caattgagat    300

accaatatgg ttgtcaacat ggagaatttt tttctgatga cctgccaact cttgatttgc    360

gcccttttca atgcnaaccc aaaactggca tgaagntttt gnatttcaga ccancctgnt    420

ggctgnacct tggcttaaca ggtttccatt ggcntatttc natttggatn aantcttgcc    480

cntggggggn ttcnaancta ggggccatca nttggtcaaa ctgntttnta aaccatgggg    540

gcnggctcng gccttggttg ctggcntcaa caaaaan                             577
```

```
<210> SEQ ID NO 417
<211> LENGTH: 570
<212> TYPE: DNA
<213> ORGANISM: Homo sapiens
<220> FEATURE:
<221> NAME/KEY: misc_feature
<222> LOCATION: (1)...(570)
<223> OTHER INFORMATION: n = A,T,C or G

<400> SEQUENCE: 417

ggtactaaga atattagaga actggaaatc cagttttttt gtggtttttt aagaaagaga     60

atctgactcc attgcccagc ttggagagca gtggtgcaat agctggggct acaggcgtga    120

gccaccacac caggcctgga aacccagttt taatttgtga actacaaatg gttggcaact    180

gattccttaa ttgttattgc aggagtaggc ccaacatgag tccatatgta gtccttctct    240

ggtctggtgg gaactgtggg aaatggtgat gaccgtgact tgaaatactn agaaggtgca    300

tgacaaacaa attccaagta ttccatcttc cttggaagat cttcctctgg ccctatgata    360

taggaagcng gaatcaaatt tgggctcttg ggctaagant aggggtatgg aatgagcccc    420

cgtnaantgg cttgnacttc ttcttcgcta atactgggcc ctggattaaa accttttgat    480

ttnancnata gntagggctt tccttcttgg ttaatcaatt cccagaaacc aacattccca    540

atttgggtaa natactccct tgtanaaaaa                                     570
```

-continued

<210> SEQ ID NO 418
<211> LENGTH: 570
<212> TYPE: DNA
<213> ORGANISM: Homo sapiens
<220> FEATURE:
<221> NAME/KEY: misc_feature
<222> LOCATION: (1)...(570)
<223> OTHER INFORMATION: n = A,T,C or G

<400> SEQUENCE: 418
ggtacttcta cacatctgcc taacttggga atgaatgtgg gagaaaatcg ctgctgctga 60
gatggactcc agaagaagaa actgtttctc caggcgactt tgaacccatt ttttggcagt 120
gttcatatta ttaaactagt caaaaatgct aaaataattt gggagaaaat attttttaag 180
tagtgttata gtttcatgtt tatcttttat tatgttttgt gaagttgtgt cttttcacta 240
attacctata ctatgccaat atttccttat atctatccat aacatttata ctacatttgt 300
aagagaatat gcacgtgaaa cttaacactt tataaggtaa aaatgaggtt tccaagattt 360
aataatctga tncagttctt gntatttccc aatagaatgg gactnngnnc tgttaanggc 420
ttaagganaa agggaagata agggttaaaa gttggttaat ggacccaacc ntttnaaaga 480
aatgcnntan anaatanttt natgantaaa naaaggtncc tngcccnggc cggccgtttt 540
aaangggcca atttcnagca cnctnggcgg 570

<210> SEQ ID NO 419
<211> LENGTH: 574
<212> TYPE: DNA
<213> ORGANISM: Homo sapiens
<220> FEATURE:
<221> NAME/KEY: misc_feature
<222> LOCATION: (1)...(574)
<223> OTHER INFORMATION: n = A,T,C or G

<400> SEQUENCE: 419
ggtacacctt tgactacagc tgcagaagtg ttcctttaga caaagttgtg acccatttta 60
ctctggataa gggcagaaac ggttcacatt ccattatttg taaagttacc tgctgttagc 120
tttcattatt tttgctacac tcattttatt tgnatttaaa tgttttangc aacctaagaa 180
caaatgtaaa agtaaagatg caggaaaaat gaattgcttg gtattcatta cttcatgtat 240
atcaagcaca gcagtaaaac aaaaacccat gtatttnact tttttttagg attttttgct 300
ttctgtgatt tttcttnttt tttgatactt gcctaacatg catgtgctgt anaantnagt 360
taaccaggga aataaccttg ngatnatggc ctanctttta gtttangtct tatgaanttt 420
tcattgacca attctaanca ataatggttt annaacaccg tgntntnaaa atttctggta 480
anttggaaat aaaaggtttn nttgaaatgg gccttttcca cnnactttnt ttnncagctn 540
tttcttggna aataagccct nggttcctga aacc 574

<210> SEQ ID NO 420
<211> LENGTH: 573
<212> TYPE: DNA
<213> ORGANISM: Homo sapiens
<220> FEATURE:
<221> NAME/KEY: misc_feature
<222> LOCATION: (1)...(573)
<223> OTHER INFORMATION: n = A,T,C or G

<400> SEQUENCE: 420
acctccggta gaattcggtg aatccatctg gtcctggact ctttttggtt ggtaaactat 60
tgattattgc cacaatttca gctcctgtta ttggtctatt cagagattca acttcttcct 120

-continued

```
ggtttagtct tgggagagtg tatgtgtcga ggaatttatc catttcttct agattttcta    180

gtttatttgc gtagaggtgt ttgtagtatt ctctgatggt agtttgtatt tctgtgggat    240

cggtggtgat atccccttta tcatttttta ttgngtctat ttgattcttc tctctttttt    300

tatntagtct tgctagcagt ctatcaattt ntgtngatcc ttttcanaaa aacccngctc    360

ctggaattca tttaatnttt tnaaggggtt ttttngtggc ctctaatttc cttcaagttc    420

tggctctgat ttaagttaat atncctggct ttttggctac nttttgnaan gnggttggcn    480

cntgnntttt ctanntcctn ttnaantggg gatngnttnn aangcccatt ttnggaannt    540

tcccgctttn ntttgggggg catttangtt nnn                                 573
```

<210> SEQ ID NO 421
<211> LENGTH: 582
<212> TYPE: DNA
<213> ORGANISM: Homo sapiens
<220> FEATURE:
<221> NAME/KEY: misc_feature
<222> LOCATION: (1)...(582)
<223> OTHER INFORMATION: n = A,T,C or G

<400> SEQUENCE: 421

```
ggtacgcggg ggtccgccat ttcgtggacg ccgggtgagt gagagagttg gttggtgttg     60

ggccggagga aagcgggaag actcatcgga gcgtgtggat ttgagccgcc gcattttta     120

accctagatc tcgaaatgca tcgtgatttc tgtccattgg actgtaaggt ttatgtaggc    180

aatcttggaa acaatggcaa caagacggaa ttggaacggg cttttggcta ctatggacca    240

ctccgaagtg tgtgggttgn tagaaaccca cccngctttg cttttgntga atttgaagat    300

ccccgagatg canctgatgc aatccgagag ctanattngn angaacacta tgtggcctgc    360

ccgtgtnagg aattggaact ggccgnaatg gttgaaanaa agaangttcg aaaattcgtg    420

gncctncntt ccttttggng gtcgtcngnc cttnagaatg attaatcgnn nggaaggang    480

tccttccncc ttnncccnan antttncant aaangaanaa agcttttttt ngcaacccgn    540

aancaggtcc cttttttttag attggganaa atagnngagn tc                     582
```

<210> SEQ ID NO 422
<211> LENGTH: 570
<212> TYPE: DNA
<213> ORGANISM: Homo sapiens
<220> FEATURE:
<221> NAME/KEY: misc_feature
<222> LOCATION: (1)...(570)
<223> OTHER INFORMATION: n = A,T,C or G

<400> SEQUENCE: 422

```
ggtactctga ggctttagat tcagtttggg tctttggggg ggacctctat catcacgcct     60

ataatcatcc cgagagtaat catctctgga gctccacgac cgatcatccc gtctgtcata    120

tcggtcttca tagcggtccc cgcctcctct gtagtcatca tccctgcgat acccactgcc    180

aaatgctctt ctgccactgc ctatccggga atcatagcct ctatcatagt ctctgctgcc    240

tcggtcatca tagcgatccc ggccaccata tcgatccata tcccggcgtg ggccatccga    300

tacccatccc gatacccatc ccgataccgg ctgaatcata acgatctcga tacttgnctc    360

caaagctatc atcacctctt ctaggtgggt aagtcatcaa agctgtctgg tagcaaggac    420

gaagcccttc aagtctggat ctggtttggg cagaatnccc atttttatca cnggccaaaa    480

gnaacgaatc atccctnggc tttaaccnng ngcttgatcn agcaacgtcc acntcgaaat    540

tntcctngtt acctananaa ctcttcattg                                     570
```

-continued

<210> SEQ ID NO 423
<211> LENGTH: 584
<212> TYPE: DNA
<213> ORGANISM: Homo sapiens
<220> FEATURE:
<221> NAME/KEY: misc_feature
<222> LOCATION: (1)...(584)
<223> OTHER INFORMATION: n = A,T,C or G

<400> SEQUENCE: 423

```
acccgggtgg ttaaacttcg canaatgcct agatattatc ctactgaaga tttgcctnga     60

aagctgttga nccacggcaa aaaacccttc agtcagcacg tgagaaaact gcgagccanc    120

attacccncg ggaccattct gatcatcctc actggacgcc acaggggcan gagggtggtt    180

ttnctgaagc agctggctag tggcttatta cttgtgactg gacctctggt cctnaatcga    240

gttcctctac naagaacaca ccaataaatt tgtcattgcc acttcaacca anantcngat    300

atcagcaatg taaaaatncc aaancatctt actgatgctt actttaagaa gangaagctg    360

cngaagccca anacancnng gaaggtgaga tctttcgaca canaagtatg agaanttatg    420

agatttacgg agcaangcan ggattgatca nganaagctt ngggcctcac caaatttttn    480

nccaanannt tcaaagttta ttttcntnag tttcnnnggg cttncttgcn antctggggn    540

tggctttgnc ctaatgggaa tttattnctc ccaaaaatgg nggn                     584
```

<210> SEQ ID NO 424
<211> LENGTH: 547
<212> TYPE: DNA
<213> ORGANISM: Homo sapiens
<220> FEATURE:
<221> NAME/KEY: misc_feature
<222> LOCATION: (1)...(547)
<223> OTHER INFORMATION: n = A,T,C or G

<400> SEQUENCE: 424

```
actcttggtt tgtcaatggg actttccagc aatccaccca agagctcttt atccccaaca     60

tcactgtgaa taatagtgga tcctatacgt gccaagccca taactcagac actggcctca    120

ataggaccac agtcacgacg atcacagtct atgcagagcc acccaaaccc ttcatcacca    180

gcaacaactc caaccccgtg gaggatgagg atgctgtagc cttaacctgt gaacctgaga    240

ttcagaacac aacctacctg tggtgggtaa ataatcagag cctcccggtc agtcccaggc    300

tgcagctgtc caatgacaac gggaccctca ctctactcag tgtcacaagg aatgatgtag    360

gaccctatga gtgtggaatc cagaacgaat taagtgttga ccacagcgac ccagtcattc    420

tggaatgncc tctatggncc aaacgaaccc caccatttcc cctnatacac taattaccgn    480

ccaggggtga accttaagct tttctggcat gcagccttta cccacctggc acagtattct    540

tggctgn                                                              547
```

<210> SEQ ID NO 425
<211> LENGTH: 567
<212> TYPE: DNA
<213> ORGANISM: Homo sapiens
<220> FEATURE:
<221> NAME/KEY: misc_feature
<222> LOCATION: (1)...(567)
<223> OTHER INFORMATION: n = A,T,C or G

<400> SEQUENCE: 425

```
ggtaccatcc tttaatagat ctcatacacc agaattcaga tcatgaatga ctgacagaat     60
```

-continued

```
attttgttgg gcagtcctga tttaaaacta agactggctt gtggttaaat gaatatgttc    120

agtttttgaa ttttaatagt aactccaatt cagtaaatgg tatcactgtt taccccttt     180

aaagatatga ttagacttcg ttagtaatgt tcaacttttc acaaagatgg tgagtgccat    240

cttaaaactt actggagatt ggctttatat ttagatttat ataactggtt atgtgaatat    300

atttaaatac tggggaaatt gcttcactgt cttagaacca agcaagattc acctgtgttt    360

tgtgttcatg ttcatttgcc tcttaaaggc aaggggttga agataaataa ggtagcaatg    420

tctatagttt tggccttaac ctatgccaat cctaattata attccctgga nttnaaaang    480

gttnctttta ccttatttgg aanggcnttt taaatngngg gttnntgggn naatatttaa    540

aggattattc accccttca catnttn                                          567
```

<210> SEQ ID NO 426
<211> LENGTH: 563
<212> TYPE: DNA
<213> ORGANISM: Homo sapiens
<220> FEATURE:
<221> NAME/KEY: misc_feature
<222> LOCATION: (1)...(563)
<223> OTHER INFORMATION: n = A,T,C or G

<400> SEQUENCE: 426

```
ggtacaattt gttcaaggaa tttttgtaga aaaatacgat cctacgatag aagattctta     60

tagaaagcaa gttgaagtag atgcacaaca gtgtatgctt gaaatcttgg atactgcagg    120

aacggagcaa tttacagcaa tgagggattt atacatgaaa aatggacaag gatttgcatt    180

agtttattcc atcacagcac agtccacatt taacgattta caagacctga gagaacagat    240

tcttcgagtt aaagacactg atgatgttcc aatgattctt gttggtaata agtgtgactt    300

ggaagatgaa agagttgtag ggaaggaaca aggtcaaaat ctagcaagac aatggaacaa    360

ctgtgcattc ttagaatctt ctgnaaaatc aaaaataaat ggtaatgaga attttttatg    420

acctantgcg gcaaattacc ggaaaaactt ccngngcctg ggaaggctng gcaaaaggcc    480

ttcatggtca gntgcttaat tatnctaaat gccntgganc ttttgaccag gntctgaana    540

actgttgncc aattcaacag ggg                                            563
```

<210> SEQ ID NO 427
<211> LENGTH: 567
<212> TYPE: DNA
<213> ORGANISM: Homo sapiens
<220> FEATURE:
<221> NAME/KEY: misc_feature
<222> LOCATION: (1)...(567)
<223> OTHER INFORMATION: n = A,T,C or G

<400> SEQUENCE: 427

```
ggtacttttt tttttttttt tttttttttt tttttgttaa aaaccataca tcctttttat     60

tgntaagtca taaagaggta tcaaaattaa aagcaaaaat tacagggtaa gacttaacaa    120

aactactagg agcgtcaaag gaagtgaaaa tgggactagg cgcggggcaa tatgaattaa    180

tgaacatggg aaggacaagg atggggaнaa cggtgagcat gtgctgaana tactagggga    240

gaggatctgg tgaaaaattt gatcttanac aagcgcctag gtaaagaaat aatgggataa    300

gatttctaaa ccccactatg gagcttaaga gtcatcctng ccattggcgc tgtctctgnc    360

atcctctcct tcctcaagnc tctttttcat catnctttga tccaattcca gctgggcaat    420

tcccccgatc tttnattatc atcatcattc cantanggnn cccnttctta ggaanngntn    480

ttttggnccc cccttaanat ttcaatttcc cttnnnccca ttttttttan ggagnttgtg    540
```

-continued

```
gcnntggccc ttttnggntt aaaaatn                                         567


<210> SEQ ID NO 428
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 428

ggtaccctat gaacctgact ctgtggtcat ggcagaagct cctcctgggg tagagacaga      60

tcttattgat gttggatnca cagatgatgt gaagaaagga ggccctggaa gaggagggag     120

tggtggcttc acagcaccag ttggtggacc tgatggaacg gtgccaatgc ccatgcccat     180

gcccatgcct atgccatctg naaatacngc ctttctcata tccactgcca aagggaccat     240

canatttcaa tggactgcca atggggacct atcaggcctt tnccaatatt catccacctt     300

cagataccag cnactccccc atcgnatgaa tctgnanatg acattaatgc tgataatgaa     360

tatctctttn tgcacanatt gttggtcctg gaccccagcc aanaancctt tgcaaanctt     420

nctttccaga cctggaggat tacttatnga caccnttgtc cctaaccaga agttgnccat     480

ttgngcccng aacancactt tcccaactgg canttngctg gatcccagnn ccttcnggat     540

ttggaanaac nttggctttt gatggatttt ttccccgg                             578


<210> SEQ ID NO 429
<211> LENGTH: 572
<212> TYPE: DNA
<213> ORGANISM: Homo sapiens
<220> FEATURE:
<221> NAME/KEY: misc_feature
<222> LOCATION: (1)...(572)
<223> OTHER INFORMATION: n = A,T,C or G

<400> SEQUENCE: 429

ggtaccaaga gtttgctcct ggctgctttg atgtcagtgc tgctactcca cctctgcggc      60

gaatcagaag cagcaagcaa ctttgactgc tgtcttggat acacagaccg tattcttcat     120

cctaaattta ttgtgggctt cacacggcag ctggccaatg aaggctgtga catcaatgct     180

atcatctttc acacaaagaa aaagttgtct gtgtgcgcaa atccaaaaca gacttgggtg     240

aaatatattg tgcgtctcct cagtaaaaaa gtnaagaaca tgtaaaaact gtggcttttt     300

ctggaatgga attggacata gcccangaac agaaagaacc ttgctgggct ggaggtttca     360

cttgcacatc atggaagggt ttagtgctta atctaatttg ggcctcactg gacttngncc     420

atttaatgaa gttnantcat tattgnnatc atagtttgct ttgtttnaan ccttnncatt     480

taaagttaaa actggaattt nanggtaatt tnaacttgta nggtttcctg ggtttagctt     540

tttaaatcnt aatttttcca taagcntttt tg                                   572


<210> SEQ ID NO 430
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 430
```

-continued ggtacagccc aggtaatttg ctgagcctaa tgggtgtcag ggtcagtcta agtgaaggca 60
aagagaggct gggatgaagg gtgcaaagga atagtaaaga aagcatgttt gagatccana 120
acagaataat gggtagtaga gggaggtatt gaggatagaa nagtatatgg gtttggcacc 180
acggggtgga taggcaaaac atttggttga taangcgcag attctgaact aacttgtaag 240
gcttgtctgg ttttaggaca ggtaaaatgg nggaatggta aggagaagtt tataggtttt 300
atgagcccat gctgtancan gcaagtgata actngctttt aatccctttt cnaaagcaat 360
gcctggngnt atgaagnata tttggcattt gatcngggtt tnaanggntg attagngttn 420
ctantgaaca atngnaaagg ggntgccatg atcngtnncc caaggatgng attttanggn 480
antctcntac ttgtggggtt naagggtggn gggnttttac naggngggtc cccnaagggn 540
gcctnttggn tntangnaat aaanggccng nnaatngana atccnnnttn n 591

<210> SEQ ID NO 431
<211> LENGTH: 565
<212> TYPE: DNA
<213> ORGANISM: Homo sapiens
<220> FEATURE:
<221> NAME/KEY: misc_feature
<222> LOCATION: (1)...(565)
<223> OTHER INFORMATION: n = A,T,C or G

<400> SEQUENCE: 431
accagtgatg ttttgataca agcatataat gtttaatgat caagtcagga taaatggggt 60
atccatcacc tcaagcacat ataatcattt ctttgtatta ggcatattca aattccactc 120
ttttagttat ttttaaatat ccagtaaatt agatcttatt cattctatct agatgtattt 180
ttgtacttta tttttctcaa atatttttac ttatgctttt tgtcattatc cacagtgttt 240
ttttttaaag cctgagccac tttgtggttt cagcctcaat ataataatca tccccttact 300
cttagactaa ttccttttcc cctgncactt tgcctgtata ctctgtaaaa atgangacct 360
tagaaaatca acatttcctg gtgaactttg agagactatt acaagcagtg cccaaaacag 420
tangaataag gcaggtaaaa ccagttggga tagccagatn tattattgat ctggtnggac 480
aaanggataa nttggngggc atggtttcca nggcantcgn gaattcccca ttagctttaa 540
gggtcnatnn angntggccc anggg 565

<210> SEQ ID NO 432
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 432
acgcgggggc caccgtggag agcagagcgc ggcggctgga agctgctaag tcagagccgc 60
gatgttccgg attgagggcc tcgcaccgaa gctggacccg gaggagatga aacggaagat 120
gcgcgaggat atgatctcct ccatacggaa ctttctcatc tacgtggccc tcctgcgagt 180
cactccattt atcttaaaga aattggacag catatgaaga caggacatca catatgaatg 240
caccgatatg aagagcctgg ttacagtttc gactcctctc tgnaagtgaa taggcccaga 300
aaggtgtaag agactctttg aatggacata aaattctgct tgttnagaac caagttttgg 360
ntctgggtna ctgacctttc aaaagctaaa attttaaaac tattttgggg aagtttttta 420
tttnnntatt nntcngtttn ttnataaaaa agtaccttgg tnccggnacc acccnttaag 480

-continued ggccnaattn cagncnncnt ngngggccgn ttactttnng ggatncntaa nttcgggganc 540 cnaancttgg ggggtaantc angggtcata nnctggtt 578

<210> SEQ ID NO 433
<211> LENGTH: 563
<212> TYPE: DNA
<213> ORGANISM: Homo sapiens
<220> FEATURE:
<221> NAME/KEY: misc_feature
<222> LOCATION: (1)...(563)
<223> OTHER INFORMATION: n = A,T,C or G

<400> SEQUENCE: 433
acttcttctg gccaaaggct gttccacatt cactacattt aaaaggcttc tctccaatat 60
ggattttctc atgctcagta aggttggatt tgccactgaa ggtttttcca cactccttac 120
atacaaaggg cttctctcct gtgtgagttc tctggtgtct gatgaggttt gacttctgaa 180
tgaaagcttt cccgcaatct ttacactcaa aaggtttttc tccagtgtga attttctggt 240
gcgtaaggag gttttccttc tggctaaatg attttccaca ttcattacat tcgaaaagct 300
tctcgccagt atgggtgttc tgatgtttaa tgacatactg cttttggcta aaggcttttc 360
cacactcgtt acattcaaaa gggttctctc tccgtgtgaa aatgctcatg ctcantgang 420
tttgaattgn nggcttgaag acttttccca tacccttaca ggcaaanggg gttttccccn 480
ttggaanatn tntggctgcn tnaagntggt gacatctgga tnggaaacct tttccncatt 540
tccaaaggnn tttttttcnn nag 563

<210> SEQ ID NO 434
<211> LENGTH: 563
<212> TYPE: DNA
<213> ORGANISM: Homo sapiens
<220> FEATURE:
<221> NAME/KEY: misc_feature
<222> LOCATION: (1)...(563)
<223> OTHER INFORMATION: n = A,T,C or G

<400> SEQUENCE: 434
ggtacagctg tctgcattga aaattcatgc atggagaaag ggagtaagca agggagaaac 60
ggtgcgattc acatattccg cgagatcatc aagccagcag agaaatccct ccatgaaaag 120
ttaaaacaag ataagcgctt tagcaccttc ctcagcctac ttgaagctgc agacttgaaa 180
gagctcctga cacaacctgg agactggaca ttatttgtgc caaccaatga tgcttttaag 240
ggaatgacta gtgaagaaaa agaaattctg atcgggacaa aaatgctctt caaaacatca 300
ttctttatca cctgacacca ggagttttca ttggaaaagg atttgaacct ggtgttacta 360
acattttaaa gaccacacaa ggaaacaaaa tcttttcttg aaagaaagta aatngatcca 420
cttctggtga atgaatttga aattcaaagg aatctggcct tcatgccanc aaatgggggt 480
aattcatgnt ggagaataac ctcctttatc cagccgnaca cacctgttgg aaatggatcc 540
aactgctgga aattncttaa taa 563

<210> SEQ ID NO 435
<211> LENGTH: 558
<212> TYPE: DNA
<213> ORGANISM: Homo sapiens
<220> FEATURE:
<221> NAME/KEY: misc_feature
<222> LOCATION: (1)...(558)
<223> OTHER INFORMATION: n = A,T,C or G -continued

<400> SEQUENCE: 435
ggtacgcggg ggaagatggc ggccgtgcag gcggccgagg tgaaagtgga tggcagcgag 60
ccgaaactga gcaagaatga gctgaagaga cgcctgaaag ctgagaagaa agtagcagag 120
aaggaggcca aacagaaaga gctcagtgag aaacagctaa gccaagccac tgctgctgcc 180
accaaccaca ccactgataa tggtgtgggt cctgaggaag agagcgtgga cccaaatcaa 240
tactacaaaa tccgcagtca agcaattcat cagctgaagg tcaatgggga agacccatac 300
ccacacaagt tccatgtaga catctcactc actgacttca tccaaaaata taagtcacct 360
gcagcctggg gatcacctga ctgacatcac cttaaaggtg gcaggtagga tccttccaaa 420
agancttntg ggggaaactn antcttctnt tgaactttca aggaaanggg tgaagtttgc 480
agtcatgggc caattccaga aattttaaat cagnagaaga atttttccta ttaataccaa 540
ctgggtcggg ggagactn 558

<210> SEQ ID NO 436
<211> LENGTH: 528
<212> TYPE: DNA
<213> ORGANISM: Homo sapiens
<220> FEATURE:
<221> NAME/KEY: misc_feature
<222> LOCATION: (1)...(528)
<223> OTHER INFORMATION: n = A,T,C or G

<400> SEQUENCE: 436
ggtacaaaaa aaaccttaca taaattaaga atgaatacat ttacaggcgt aaatgcaaac 6 cgcttccaac tcaaagcaag taacagccca cgatgttctg gccaaagaca tcagctaaga 12 aaggaaactg ggtcctacgg cttggacttt ccaaccctga cagacccgca agacaaaaca 18 actggttctt gccagcctct agagaaatcc cagaacactc agccctgaca cgttaatacc 24 aaggggaaca gttaactcca atacaaggtc aaaatcagca acaagttcta caatccagtg 30
ctgatatcag atacaaagct tcaagggcaa tttcttttcg aaggcttatt ccagtttcgt 36 gaggctagca tgaagtgtgt gcatttgcca ggggcaaatt tctattctca attaacccat 42 gcagcaaant gctacgcatc tggctgagtc cggtttanaa nccatttgcc ggnggaccaa 48 tggaaggggc ccgaattcgt cnnaacttgn cccgggcggg ccgttcaa 528

<210> SEQ ID NO 437
<211> LENGTH: 576
<212> TYPE: DNA
<213> ORGANISM: Homo sapiens
<220> FEATURE:
<221> NAME/KEY: misc_feature
<222> LOCATION: (1)...(576)
<223> OTHER INFORMATION: n = A,T,C or G

<400> SEQUENCE: 437 acttttttttt tttttttttt tttttttttt aggtttgagg gggaatgctg ganattgtaa 60
tgggtatgga gacatgtcat ataagtaatg ctagggtgag tggtaggaag ttttttcata 120
ggaggtgtat gggttggtcg tagcggaatc gggggtatgc tgttcgaatt cataagaaca 180
gggaggttag aantagggtc ttggtgacaa aatatgttgt gtagagttca ggggganagtg 240 cgtcatangt tgttcctagg aanattgtac nggtgagggt tgtttattat aataatgttn 300
gggtatccgg ctntgaaana atngggccaa ngggcctgcg gtgtattcga ngttnaaacc 360
tgagactagt tcggactccc ntttgcaagg ncccaaaggg ggttnggttt ggcccttgct 420
annggtgnga naataaatcn tntttattgg cccaagggtt cttaacngcn aggagtnaat 480

-continued ccaaaggggt ncntnggntt ttnnnanaaa nggttgnnaa aaggttaaag ggacccncct 540
ttntnnntaa tgntcgnaat gtcaaatnga tngcnn 576

<210> SEQ ID NO 438
<211> LENGTH: 576
<212> TYPE: DNA
<213> ORGANISM: Homo sapiens
<220> FEATURE:
<221> NAME/KEY: misc_feature
<222> LOCATION: (1)...(576)
<223> OTHER INFORMATION: n = A,T,C or G

<400> SEQUENCE: 438
ggtaccccaa ttaccagtat ggtggaccct acccccttctt ctctgcattg ggaaacagaa 60
cagagaacag aaaaaatcat tccatcttgc tcttaactct ttccacctat gtgctcagtt 120
tttcaagtag aatttctatt cctttgctgg tgcttttggt tttttccaat gtaggaatca 180
agcttttcag tgcagctttg actttgtttg caacttccag gtcacaactc tggaggaggc 240
tagaaagaat aatggcacct cgatttacac tagcccagga cttcaggttc ttcataccaa 300
catgctctac aagtgttttt gcaaaacaac cttctcttcc attntctttt catcttttta 360
tcttgctcta ttaaccactt nagaaactaa gaatgtccct gcaaggatgt tctggcaatg 420
ntgaaagctt ctccgtcctt ggccaccagg atgcaagtcc ntggttnttg ccagcttggc 480
cnatnggcat tccatnggna nggcttgaac cgttttccag ggggcagant cccaaaatgg 540
ccngacacca acccnacang cagacttntt ttagcn 576

<210> SEQ ID NO 439
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 439
cgaggtacgc gggggagaaa aaacctgcgg aaaatggtag cgatggcggc tgggccgagt 60
gggtgtctgg tgccggcgtt tgggctacgg ttgttgttgg cgactgtgct tcaagcggtg 120
tctgcttttg gggcagagtt ttcatcggag gcatgcagag agttaggctt ttctagcaac 180
ttgctttgca gctcttgtga tcttctcgga cagttcaacc tgcttcagct ggatcctgat 240
tgcagaggat gctgtcagga ggaagcacaa tttgaaacca aaaagctgta tgcaggagct 300
attcttgaag tttgnggatg aaaattggga aggttccctn aagtccaanc ttttgttang 360
agtgataaaa cccaaactgt tcagaaggac tgccaaatna aagtatgtnn cgtggtttca 420
aaccntgaat taaaaggctt ttngaccaac atngggnaca attgcttgan nacttgtcca 480
tttcttaaaa ttgggaacnc tggaccnggt nanaaaanatt tcngattgga aaantttgga 540
ccncatttta aatcttgctt aaattttggc caatcctt 578

<210> SEQ ID NO 440
<211> LENGTH: 573
<212> TYPE: DNA
<213> ORGANISM: Homo sapiens
<220> FEATURE:
<221> NAME/KEY: misc_feature
<222> LOCATION: (1)...(573)
<223> OTHER INFORMATION: n = A,T,C or G

<400> SEQUENCE: 440
ggtacttttt tttttttttg agacagggtc ttgccctgtc acccaggctc gagtgcactg 60

-continued

```
gagtgatcac agctcactgg cctcaagtga tcctcctgcc ttggcccctt aagtgccagg    120

gttacaggca tgagctacca tgcctggcag aaattcaaga tttggataaa cttacttctt    180

tgccaagcct gttcttcaag ttattcagaa ctgggtgtat accttgtcct catatgtatc    240

ttgtccctgc tgtcttttag gttagcaagg tgtatgaata cttttaagtt ttgtttgttc    300

ttttcctcgt ggtatcaagt gaaatactga tctattctct ggctagggtc aatttacaaa    360

attgccatgg aactgagcca aaaggcccca cgtgggataa aaattnctta ccatcgacgc    420

ccanccgtan tttttcaagg tattggcttt tggaagnttt accaaatttc nggtaaacca    480

aaattcnaaa agnaaaaaat tnccctggng taaccttgcc cgggcggccg ttcaaaaggg    540

cnaatttcca ncacattggg cggccgttaa tna                                 573
```

<210> SEQ ID NO 441
<211> LENGTH: 572
<212> TYPE: DNA
<213> ORGANISM: Homo sapiens
<220> FEATURE:
<221> NAME/KEY: misc_feature
<222> LOCATION: (1)...(572)
<223> OTHER INFORMATION: n = A,T,C or G

<400> SEQUENCE: 441

```
ggtacaaaat tttattaaag gtctttagag agcaacatcc agactccaga atacagctgc     60

caaggagacc ctgttatgct gtggggactg gctggggcat ggcaggcggc tctggcttcc    120

cacccttctg ttctgagatg gggtggtgg gcagtatctc atctttgggt tccacaatgc    180

tcacgtggtc aggcaggggc ttcttagggc caatcttacc agttgggtcc cagggcagca    240

tgatcttcac cttgatgccc agcacaccct gtctgagcaa cacgtggcgc acagcagtgt    300

caacgtagta gttaacaggg gtctccgctt gtggatcatc aagccatcca caaacttcat    360

ggatttagcc ctctgncctt cggaggttcc cagacaccca caanctngca agcctttggc    420

cccacttttc catgatgaaa ctgnagncac aaccatangc aagggccctt cggacannta    480

aggccttcct aaggagnttg naacncnana naacttttgc ttgggcantg ggcacaccag    540

nacctntaag nggccccctt tttaagcata aa                                  572
```

<210> SEQ ID NO 442
<211> LENGTH: 562
<212> TYPE: DNA
<213> ORGANISM: Homo sapiens
<220> FEATURE:
<221> NAME/KEY: misc_feature
<222> LOCATION: (1)...(562)
<223> OTHER INFORMATION: n = A,T,C or G

<400> SEQUENCE: 442

```
acaggtcaga gtcttctttt cttttctttt tgagatggag tcttgctctg ttgccagact     60

ggagtgcagt ggtgcgatct gggctcactg caatctccac ctcccgggtt caagcgattc    120

tcctgcctca gcctcccgag taactgggac tacaggtgcg cgccaccaag cccagctcat    180

ttttgtattt ttagtagaga tggggtttca cgatgttggc taggatggtc tcgatctctg    240

gtcagagtct tttctgtaaa tatccttggt aaagaagcaa ttttagactg tagctgttgc    300

aaatgcttta aggaagaagc aaaacaactg tcaagtcttc ctgaaatgaa gaaactncac    360

cagggctgct atatcagaac aaccncaacc aagcacttca aacatgatgc cgacaggtgg    420

ccccagctta aaaaaccagg aanaagttcn gantcccnaa actgngaatg cctcttggac    480

ttttggaatt aattgggggc cagtagccaa gttatnagac caaatcangg cntagggccc    540

cgtattattt ggcggggatt tg                                             562
```

-continued

<210> SEQ ID NO 443
<211> LENGTH: 585
<212> TYPE: DNA
<213> ORGANISM: Homo sapiens
<220> FEATURE:
<221> NAME/KEY: misc_feature
<222> LOCATION: (1)...(585)
<223> OTHER INFORMATION: n = A,T,C or G

<400> SEQUENCE: 443 actttattt tttggtggtg aaattgactg atgattttcc tttttcttcg ctggactatt 60
gtgccaactg ccaggctgcc tcctgccctt acagccctaa gtggctgcct tctttccatc 120
aactcccaac ttcttcctgt gaagtttaat tgtctcaacg cctccccctc ccccattccc 180
tccatttttc tcccaagaaa cctgactcaa ttatttgcat attttgagaa actgctgcag 240
attagttctt tttgccagtt ttccctggaa ctcctggcct tttgtggagg ggagggatgg 300
agagaatagg aatcttcact agaagccgtg ggaagaattg gaagttacat gctgtatatg 360
caatgtccag cagtctgata aactgacgat tcttaatcaa gattttttcc tgatggggaa 420
gggactttta ttttctttta nagaggggaa agtgtgagct cttcccttat tcctaatggc 480
tatttttgaa gcaaanaagg ccacaacatt ngcacatgcc acctgcnaag gaccttgagt 540
nagtgaagnc tcctaaaact gggttaanaa ccttgttttc tctnn 585

<210> SEQ ID NO 444
<211> LENGTH: 437
<212> TYPE: DNA
<213> ORGANISM: Homo sapiens
<220> FEATURE:
<221> NAME/KEY: misc_feature
<222> LOCATION: (1)...(437)
<223> OTHER INFORMATION: n = A,T,C or G

<400> SEQUENCE: 444
acgcggggac gtgactcagc actttcccca gagcccggac tgcggagaac aatatcctcc 60
tccctaacag ataaacagcc cttgttcctc gggataagga ctggcagtcc cctgacaccc 120
taagaccggc atctgtcgat gttatttccc cagcatggcc gaaacagaag ccctgtcgaa 180
gcttcgggaa gacttcagga tgcagaataa atccgtcttt attttgggcg ccagcggaga 240
aaccggcaga gtgctcttaa aggaaatcct ggagcagggc ctgttttcca aagtcacgct 300
cattggccgg aggaagctca ccttcgacga ggaagcttat aaaaatgtga atcaagaagt 360
ggtggacttt gaaaagttgg atgactacgc ctctgccttt caaggtcatg atgttggatt 420
ctgtgcctgg gtacctn 437

<210> SEQ ID NO 445
<211> LENGTH: 592
<212> TYPE: DNA
<213> ORGANISM: Homo sapiens
<220> FEATURE:
<221> NAME/KEY: misc_feature
<222> LOCATION: (1)...(592)
<223> OTHER INFORMATION: n = A,T,C or G

<400> SEQUENCE: 445 acttttttttt tttttttttt tttttttttt taaggtttga gggggaatgc tggagattgt 60
aatgggtatg gagacatatc atataagtaa tgctagggtg agtggtagga agttttttca 120
taggaggtgt atganttggn cgtagcggaa tcgggggtat gctgttcgaa ttcataagaa 180
cagggaggtt aaaagtaggg tcttggtgac aaaatatgtt gtgtanagtt caggggaaag 240

-continued tgcgtcatat gttgttccta ggaanattgt antggtgagg gtgttaatta taataatgtt 300
tgtgtattcg gctatnaana atagggccaa atgggcctgc ngcctattcn atgtttaanc 360
tgagacttnt tcggactccc cttcggcaan gtcnaantgg ggttcggttg ngcnctgcag 420
tgnggagata nntcntntta ntggccaatg gtnnngatgg ccagaataat cannanggnt 480
tcnttnntcn tnaaaaggtc naaatggttn angganaccn cttattagga attgttaatc 540
ttnaatgatn gttntggnga cnctatatgg anaatgtnag gnctactccn ng 592

<210> SEQ ID NO 446
<211> LENGTH: 599
<212> TYPE: DNA
<213> ORGANISM: Homo sapiens
<220> FEATURE:
<221> NAME/KEY: misc_feature
<222> LOCATION: (1)...(599)
<223> OTHER INFORMATION: n = A,T,C or G

<400> SEQUENCE: 446
ggtacggcaa acacaacgga cctgagcact ggcataagga cttccccatt gccaagggag 60
agcgccagtc ccctgttgac atcgacactc atacagccaa gtatgaccct tccctgaagc 120
ccctgtctgt ttcctatgat caagcaactt ccctgaggat cctcaacaat ggtcatgctt 180
tcaacgtgga gtttgatgac tctcaggaca aagcagtgct caagggagga cccctggatg 240
gcacttacag attgattcag tttcactttc actggggttc acttgatgga caaggttcat 300
agcatactgt ggataaaaag aaatatgctg cagaacttca cttggttcac tggaacacca 360
aatatgggga ttttgggaaa gctgtgcagc aacctgatgg actggccgtt ctaggtattt 420
tttttgaagg ttggcagcgc taaaccnggc cttnataaag ttgttgaatg tgctggattc 480
cattaaaaca aagggcaaga attgctgact ttcactaatt nnaatcctcg tnggccttct 540
tcctgaaatc cttggattac cggacctncc cagcttactn accanccttc tcttttngg 599

<210> SEQ ID NO 447
<211> LENGTH: 588
<212> TYPE: DNA
<213> ORGANISM: Homo sapiens
<220> FEATURE:
<221> NAME/KEY: misc_feature
<222> LOCATION: (1)...(588)
<223> OTHER INFORMATION: n = A,T,C or G

<400> SEQUENCE: 447
ggtacgcggg atgagtgtgg aatccagaac aaattaagtg ttgaccacag cgacccagtc 60
atcctgaatg tcctctatgg cccagacgac ccccaccattt ccccctcata cacctattac 120
cgtccagggg tgaacctcag cctctcctgc catgcagcct ctaacccacc tgcacagtat 180
tcttggctga ttgatgggaa catccagcaa cacacacaag agctctttat ctccaacatc 240
actgagaaga acagcggact ctatacctgc caggccaata actcagccag tggccacagc 300
aggactacag tcaagacaat cacagtctct gcggagctgc caagccctcc atctccagca 360
acaactccaa acccgtggag gacaaggatg ctgtggcctt ccctgtgaac ctgaggctca 420
gaacacaacc tacctgtggt gggtaaatgg tcagagcctc cagcagtccc aaggctggag 480
ctgtccaatg gcaacangga cctnactcta ttcaatgtca caagaaatga cncaagaacc 540
tatgnatgtg gaatccagaa ctnagtgatg caaaccgaat gaccagnn 588

<210> SEQ ID NO 448
<211> LENGTH: 593

-continued

<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G

<400> SEQUENCE: 448
accatttgtc tgacctctgt aaaaaatgtg atcctacaga agtggagctg gataatcaga 60
tagttactgc tacccagagc aatatctgtg atgaagacag tgctacagag acctgctaca 120
cttatgacag aaacaagtgc tacacagctg tggtcccact cgtatatggt ggtgagacca 180
aaatggtgga aacagcctta accccagatg cctgctatcc tgactaattt aagtcattgc 240
tgactgcata gctctttttc ttgagaggct ctccattttg attcanaaag ttagcatatt 300
tattaccaat gaatttgaaa ccagggcttt tttttttttt ttgggtgatg taaaacncaa 360
ctncctgnca ncaaaataat taaaatagnc acattgntat cttttattag gtaattcact 420
tcttaattan atggntcaat actctaagna tcaaaatntt ccaattatna tggctcacct 480
gaaagaagna tgctctttta aggaatacag cttcttcnat tnacaattta acanggggag 540
aaaattaaan tnaangantt ganatctgga ggngtannaa ngntctcgcn ttc 593

<210> SEQ ID NO 449
<211> LENGTH: 577
<212> TYPE: DNA
<213> ORGANISM: Homo sapiens
<220> FEATURE:
<221> NAME/KEY: misc_feature
<222> LOCATION: (1)...(577)
<223> OTHER INFORMATION: n = A,T,C or G

<400> SEQUENCE: 449
actgtgggtc gaagtaatgg atacggacgt aaccatcttc gccgccgctg ctgtagctct 60
tgccatcagg atggaaggca acactgttga taggtccaaa gtgacccttg actcttccaa 120
actcttcttc aaaggccaaa tggaagaacc tggcctcaaa cttgccaatc ctggtggagg 180
ttgtggttac atccatggct tcctgaccac cgcccaggac cacatggtca tagttggggg 240
agagggcagc tgagttgaca ggacgttctg tccggaaagt cttctgatgt tcaagagttg 300
tggagtcaaa aagcttggct gtgttgtcct tggacncggc acaaacatgg tcatgtccct 360
ggataactgg atgtcgttga tctgccggga gtgctcctta acattcacca acacctcttc 420
anacttggca ctatactggt tgactctcca ctcttatggc cnggatgatg cactccccca 480
aggggtncca aacagnactg gtgatttaga atcattgcan ggatcttatg tagggctcat 540
tgntgcaatc tggcttggat ccgcagtcaa aaaagnt 577

<210> SEQ ID NO 450
<211> LENGTH: 575
<212> TYPE: DNA
<213> ORGANISM: Homo sapiens
<220> FEATURE:
<221> NAME/KEY: misc_feature
<222> LOCATION: (1)...(575)
<223> OTHER INFORMATION: n = A,T,C or G

<400> SEQUENCE: 450
ggtacttgtg atcacactac gggaatctct gtggtatata cctggggcca ttctaggctc 60
tttcaagtga cttttggaaa tcaacctttt ttatttgggg gggaggatgg ggaaaagagc 120
tgagagttta tgctgaaatg gatttataga atatttgtaa atctattttt agtgtttgtt 180

-continued

```
cgttttttta actgttcatt cctttgtgca gagtgtatat ctctgcctgg gcaagagtgt    240

ggaggtgccg aggtgtcttc attctctcgc acatttccac agcacctgct aagtttgtat    300

ttaatggttt ttgtttttgt ttttgtttgt ttcttgaaaa tgagagaaga gccggagaga    360

tgatttttat taattnttnt tttttttttt tactatttat agctttaaaa agggcctncc    420

ttcccctctt ctttctttgg nctctttcat taaccccttc ccagtttttt ttaacttaaa    480

ccccgttctc atggcctngg ccttttgaag cgnttcctct tataaaaagc tttgccgaac    540

aanttttttt taccgatccc aaatttatga agggg                               575


<210> SEQ ID NO 451
<211> LENGTH: 573
<212> TYPE: DNA
<213> ORGANISM: Homo sapiens
<220> FEATURE:
<221> NAME/KEY: misc_feature
<222> LOCATION: (1)...(573)
<223> OTHER INFORMATION: n = A,T,C or G

<400> SEQUENCE: 451

actaggctaa ctagaaggat ctcatcccca tatgtggtct catttcaagt ctatggatga     60

ctaccttcat tgctgtgtgc gagatggttt caccccttga aaatatggtc acttcagcat    120

aaaatagtta aatctttata atgatcaatt catcctacct ccttttacat gcagctgaaa    180

aatgacaggc tagggacata gaatattgtg aactttatac tgttagaatc actgtccatt    240

aaatgatcac tagctaatgg tcactaaatt tacaaattaa ggaaattata tatagaatac    300

tgcaaaaaca cagtaaaaag actgaagttc gcccatttct gctcaggaag tctcttcact    360

cctaagcttc atatgttgcc ttctggcttc aaaattctgc tattattact gttttcctcc    420

tttgatcttc ctttggtccc cagtgccaga cttccaagcc ttttngttaa aaagccatct    480

tttggatgcc atttcnaaca gcttcagtga tgcctctgaa aaaaggatct gccggctaan    540

atttctcngg ttcgtgcttt ctaccggganc tcc                                573


<210> SEQ ID NO 452
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 452

acaattttat ccctaaaact ctgttgacat caaaatatga cagttgctat atccataaaa     60

tatttacata gcacggcata ttaagcttta gacacttggc aattaaacca cataaaaaga    120

ggacaagacc cccatcctac atgtttggaa tcaggtgttc accggtccct atctggcgac    180

tgtacgcggg tggggtcctt acttgtattc tgttatcagc tgattttgaa acatataata    240

atgattttct tgttcccttc tttaactagc tgcctttaga ttttgataat cacagtctta    300

aaatactagg aaagaagtgg atgggaattg taggcataga tttcatatca agggcatttc    360

aagacagaat ttttaattcc tgtagtaggc ttgctggagc naaaggaaaa tgtgctggtt    420

aaaaatcaac ttatgccatt ttaaaatttg ataaaatttg gagtggcatn ctgctaaggg    480

gagaccttgg gccggacccc cttangggca aattccngca cactgggggg cggtactang    540

gggatccgac ntcggnccan acttggcgna tcatgggctt antgttcctt gnggn         595
```

-continued

<210> SEQ ID NO 453
<211> LENGTH: 380
<212> TYPE: DNA
<213> ORGANISM: Homo sapiens
<220> FEATURE:
<221> NAME/KEY: misc_feature
<222> LOCATION: (1)...(380)
<223> OTHER INFORMATION: n = A,T,C or G

<400> SEQUENCE: 453
ggtacgcggg gagccgcctg gataccgcag ctaggaataa tggaatagga ccgcggttct 60
attttgttgg ttttcggaac tgaggccatg attaagaggg acggccgggg gcattcgtat 120
tgcgccgcta gaggtgaaat tcttggaccg gcgcaagacg gaccagagcg aaagcatttg 180
ccaagaatgt tttcattaat caagaacgaa agtcggaggt tcgaagacga tcagataccg 240
tcgtagttcc gaccataaac gatgccgacc ggcgatgcgg cggcgttatt cccatgaccc 300
gccgggcagc ttccgggaaa ccaaagtctt tgggttccgg ggggagtatg gttgcaaaaa 360
aaaaaannaa aaaaaaaagt 380

<210> SEQ ID NO 454
<211> LENGTH: 589
<212> TYPE: DNA
<213> ORGANISM: Homo sapiens
<220> FEATURE:
<221> NAME/KEY: misc_feature
<222> LOCATION: (1)...(589)
<223> OTHER INFORMATION: n = A,T,C or G

<400> SEQUENCE: 454
ggtactcttg gtttatcaat gggacgttcc agcaatccac acaagagctc tttatcccca 60
acatcactgt gaataatagc ggatcctata tgtgccaagc ccataactca gccactggcc 120
tcaataggac cacagtcacg atgatcacag tctctggaag tgctcctgtc ctctcagctg 180
tggccaccgt cggcatcacg attggagtgc tggccagggt ggctctgata tagcagccct 240
ggtgtatttt cgatatttca ggaagactgg cagattggac cagaccctga attcttctag 300
ctcctccaat cccattttat cccatggaac cactaaaaac aaggtctgct ctgctcctga 360
agccctatat gctggagatg gacaactcaa tgaaaattta aagggaaaac cctcaggcct 420
gangtgtgtg ccactcagag acttcaccta actagagaca gtcaaactgc aaccatgggt 480
gagaaattga cgacttcaca ctatggacag cttttnccaa gatgtcaaac aagactcctc 540
atcatgataa ggntcttacc cctttaattg nccttgttat gcctgccct 589

<210> SEQ ID NO 455
<211> LENGTH: 589
<212> TYPE: DNA
<213> ORGANISM: Homo sapiens
<220> FEATURE:
<221> NAME/KEY: misc_feature
<222> LOCATION: (1)...(589)
<223> OTHER INFORMATION: n = A,T,C or G

<400> SEQUENCE: 455
ggtacgcgga agagacaggg tttcaccatg ttgcccaggc tggtttcgaa ctcctgacct 60
caggtgatcc acccgcctcg gcctcccaaa gtgctgggat tacaggcttg agcccccgcg 120
cccagccatc aaaatgcttt ttatttctgc atatgttgaa tactttttac aattcaaaaa 180
aatgatctgt tttgaaggca aaattgcaaa tcttgaaatt aagaaggcaa aaatgtaaag 240
gagtcaaaac tataaatcaa gtatttggga agtgaagact ggaagctaat ttgcattaaa 300

-continued ttcacaaact tttatactct ttctgtatat acattttttt tctttaaaaa acaactatgg 360
atcagaatag ccacatttag aacacttttt gttatcaagt caatattttt agatagttag 420
aacctggtct taagcctaaa agtgggcttg attctgcagt aaatcnttta caactgcctc 480
gacacacatt aaccttttta aaaatngacc ttcccgaagt cttttggtag catggnacac 540
ctgatgctta natgttcang taattaatat ggnccagnag tnttgtnnc 589

<210> SEQ ID NO 456
<211> LENGTH: 582
<212> TYPE: DNA
<213> ORGANISM: Homo sapiens
<220> FEATURE:
<221> NAME/KEY: misc_feature
<222> LOCATION: (1)...(582)
<223> OTHER INFORMATION: n = A,T,C or G

<400> SEQUENCE: 456
acagaatgtt gatacaaagc ttaaaattct tgcatatggt catagaaaat gcatctttgg 60
ttttgtgttt ttatcacttg cttccaactt aggcttttgg ctcagaagat tattgaataa 120
tgatttgtct tagtttctgt ttcagtaagg gaattctgag gccgttgcta tgataccatc 180
attaagacat tcacatgtct tcatataata tctcttcatt tcaaatccta atcactattt 240
catactatta cagggctttg atgctgccag cactgtcttt tacataggaa attctagatt 300
tgcacagtaa tagaggaatt agaagtacct aactatacac tttgattcag cctgctaaat 360
caggggttca atactagctt ggacaaactt tgtaagtaat taattgctac cagccttatt 420
ggaaacaaat tatcaactag tttcccctgc caaattttga aattcactgn ttcacttaat 480
ctattatatt actaataatg gattaataaa gatgaattaa ttattattac ttactagtnt 540
aaatgaaaaa cagggactga aatagtctgn atccgngttg ca 582

<210> SEQ ID NO 457
<211> LENGTH: 380
<212> TYPE: DNA
<213> ORGANISM: Homo sapiens

<400> SEQUENCE: 457
ggtacttttt tttttttttt tttttggagt ttttagttta ttaatgttct tgcgaaaaat 60
ccacagtggc cacagctaac atcattgcag cacctttact ccttcggctg tgatccaatc 120
tccagctcac ttctttttgc cagcaccaac attggccttt gcagtccccc tgactttctt 180
cattctgttc ttgcgttcct ttcgttgctt tcttgaggtc tttttcttct catacaggcc 240
atgtcttgca agtctatgtt tgggttcatt tttctttgca taatccaggg aatcataaat 300
catgccaaag ccagttgtct tgccaccacc aaaatgagtt ctgaatccaa atacaaagat 360
gacatccggt gtggtcttgt 380

<210> SEQ ID NO 458
<211> LENGTH: 382
<212> TYPE: DNA
<213> ORGANISM: Homo sapiens
<220> FEATURE:
<221> NAME/KEY: misc_feature
<222> LOCATION: (1)...(382)
<223> OTHER INFORMATION: n = A,T,C or G

<400> SEQUENCE: 458
acgcggggag aacagccacc cctctctcgg gcactgctgc catgaatgcc ttcctgctct 60
ccgcactgtg cctccttggg gcctgggccg ccttggcagg aggggtcacc gtgcaggatg 120

-continued

```
gaaatttctc cttttctctg gagtcagtga agaagctcaa agacctccag gagccccagg    180

agcccagggt tgggaaactc aggaactttg cacccatccc tggtgaacct gtggttccca    240

tcctctgtag caacccgaac tttccagaag aactcaagcc tctctgcaag gagcccaatg    300

cccaggagat acttcagagg ctggaggaaa tcgctgagga cccgggcaca tgtgaaatct    360

gtgcctacgc tgcctgtacc tn                                             382
```

<210> SEQ ID NO 459
<211> LENGTH: 592
<212> TYPE: DNA
<213> ORGANISM: Homo sapiens
<220> FEATURE:
<221> NAME/KEY: misc_feature
<222> LOCATION: (1)...(592)
<223> OTHER INFORMATION: n = A,T,C or G

<400> SEQUENCE: 459

```
ggtactgagg aaatattttg taaagtgagc tttgggtata acttagcccc atcattattt     60

agagaataga ggaggaagaa agaggaagga ttttaaaggc agacaatgac agaccattca    120

ggataggtag ggttttaaag ggagataaac acagtctcat caactaagga gagatttgct    180

gcagtaaata ggatgaggga aatagtctgt gggatgcaag caaaggaagc agggtgcctt    240

agacactgag tggagccaga aagatcatgc ggccttttc caagtacatg gccaccaagt    300

aagaatggtt ggtgacaaga cagaaggcta aaacaggaag gtaatcttgt gcacctgaca    360

aatngaaaga attaaggatc aaaattgaag caggctntaa gagtttcaag aaattcttaa    420

aacccaaaag tgatttggaa gccccaaact ttccggtaat gctncccatg gcatgatggg    480

ccaaaacctt gggggttcct aagttnnaaa agccctntnc caaattttaa tggaccccct    540

acattttttc taatcaatcc cccctttcca aaaaaatngg acctcntttt tt            592
```

<210> SEQ ID NO 460
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 460

```
acgcgggcac tatcctgaat tatgtgcctg tctagataag cagagaccat gccaaagcta     60

taatggaaaa caagtttaca aagagacctg tatttctttc ataaaagact tcttggcaaa    120

aaatttgatt atagttattg gaatagcatt tggactggca gttattgaga tactgggttt    180

ggtgttttct atggtcctgt attgccagat cgggaacaaa tgaatctgtg gatgcatcaa    240

gctatcgtca gtcaaacccc tttaaaatgt tgctttggct ttgtaaattt aaatatgtaa    300

gtgctatata agtcaggagc agctgtcttt ttaaaatgtc tcggctagct agaccacaga    360

tatcttctag acatattgaa cacatttaag atttgaggga tataagggaa aatgatatga    420

atgtgtattt ttactcaaaa taaaagtaac tgttacgttg cgaaaaaaan nnnnnnnnnn    480

naaaaaaaag tnccttgggc cgggaccacg ctagggcaaa tccagcacac tggcggccgt    540

actagggatc cactnggacc agctggcgna atatggnn                            578
```

<210> SEQ ID NO 461
<211> LENGTH: 425
<212> TYPE: DNA

-continued

<213> ORGANISM: Homo sapiens
<220> FEATURE:
<221> NAME/KEY: misc_feature
<222> LOCATION: (1)...(425)
<223> OTHER INFORMATION: n = A,T,C or G

<400> SEQUENCE: 461
acgcggggct ttctggtctc ggccgcagaa gcgagatgac gaagggaacg tcatcgtttg 60
gaaagcgtcg caataagacg cacacgttgt gccgccgctg tggctctaag gcctaccacc 120
ttcagaagtc gacctgtggc aaatgtggct accctgccaa gcgcaagaga aagtataact 180
ggagtgccaa ggctaaaaga cgaaatacca ccggaactgg tcgaatgagg cacctaaaaa 240
ttgtataccg cagattcagg catggattcc gtgaaggaac aacacctaaa cccaagaggg 300
cagctgttgc agcatccagt tcatcttaag aatgtcaacg attagtcatg caataaatgt 360
tctggtttta aaaaatnnan nnnaannntn ntnnaaanaa aaaaagtnct nggccgngac 420
cacgc 425

<210> SEQ ID NO 462
<211> LENGTH: 581
<212> TYPE: DNA
<213> ORGANISM: Homo sapiens
<220> FEATURE:
<221> NAME/KEY: misc_feature
<222> LOCATION: (1)...(581)
<223> OTHER INFORMATION: n = A,T,C or G

<400> SEQUENCE: 462
ggtactattg acccagcgat gggggcttcg acatgggctt tagggagtca taagtggagt 60
ccgtaaagag gtatctttac tataaaagct attgtgtaag ctagtcatat taagttgttg 120
gctcaggagt ttgatagttc ttgggcagtg agagtgagta gtagaatgtt tagtgagcct 180
agggtgttgt gagtgtaaat tagtgcgatg agtaggggaa gggagcctac tagggtgtag 240
aataggaagt atgtgcctgc gttcaggcgt tctggctggt tgcctcatcg ggtgatgata 300
gccaaggtgg ggataagtgt ggtttcgaag aagatataaa atatgattag ttctgtggct 360
gtgaatgtta taattaagga gatttgtaag ggagattagt atanagaggt anagtttttt 420
tcgtgatagt ggntcactgg ataantggcc gttggctttg ccatgattgt gaggggtagg 480
agtcaagtag ttagtattan ganggggggtt nttaggggtc cnaggaaang ttggggaana 540 ctaaanngg t gtngtnattn gtaaaaaata nnnnanggat n 581

<210> SEQ ID NO 463
<211> LENGTH: 574
<212> TYPE: DNA
<213> ORGANISM: Homo sapiens
<220> FEATURE:
<221> NAME/KEY: misc_feature
<222> LOCATION: (1)...(574)
<223> OTHER INFORMATION: n = A,T,C or G

<400> SEQUENCE: 463
actgtgtggc gccttattct aggcacttgt tgggcagaat gtcacacctg ccgatgaaac 60
tcctgcgtaa gaagatcgag aagcggaacc tcaaattgcg gcagcggaac ctaaagtttc 120
agggggcctc aaatctgacc ctatcggaaa ctcaaaatgg agatgtatct gaagaaacaa 180
tgggaagtag aaaggttaaa aaatcaaaac aaaagcccat gaatgtgggc ttatcagaaa 240
ctcaaaatgg aggcatgtct caagaagcag tgggaaatat aaaagttaca aagtctcccc 300
agaaatccac tgtattaagc aatggagaag cagcaatgca gtcttccaat tcagaaccaa 360

-continued aaaaaaaaaa naaaaaaaag tacttttttt ttttnnnnnt tttttttttt taggtaatgg 420
gtgttgagct tgaacgcttt cttaattggn ggctgctttt angcctctat gggtgttaaa 480
ttttttactc tcttacaagg tttttcctaa gtccaaanac tgtccttttg gctacagtta 540
aatttccagg ggattaaagg gttttgggcn aatt 574

<210> SEQ ID NO 464
<211> LENGTH: 580
<212> TYPE: DNA
<213> ORGANISM: Homo sapiens
<220> FEATURE:
<221> NAME/KEY: misc_feature
<222> LOCATION: (1)...(580)
<223> OTHER INFORMATION: n = A,T,C or G

<400> SEQUENCE: 464
ggtacctagt aagctctccc tcctcccacc ctccaccctc aaggaggccc cagtgtcagt 60
tgttcccctc tgggtccatg agttcttatc atttagctcc cacttataag caagaacatg 120
cagtatttgg ttttctgttc ctgccttagt ttgctaagga taacggcctc cagctccatc 180
cagttcctgc aaaggacatg atcctgttct ttctatggct gtatagtatt ccatggtgta 240
tatttaccac attgtcttta tccagtctgt cattgatggg cttttgggtt gattagtagc 300
tttttgaatg gtaacttttc tacagaagta cgcggggctt tttttttgc tgtaggcccg 360 ggtggttgct gccgaaatgg gcangttcat gaaacctggg aaggtggtgc ttgtcctgct 420
ggacgctact ncggacgcaa agctgtcatc gtgaaagaac attgatgatg gcaccttana 480
cgccctacag ccatgctctg gtggctggaa ttgaccgcta cncccgaaag tgacagctgn 540
catgggcaag aagaagatcg ccagagatca aagataaaan 580

<210> SEQ ID NO 465
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 465
ggtacttttt tttttttttt tttttttttt ttctacatca ctttanaata tttattgtat 60
tccttaatgc atttcttaac atgtatagca ctctttaatc aagaatataa agtcatctac 120
ttagaatcac attatcttaa agatgcatac tggaatgata agtttgaaga tgtaactatc 180
aacaattctt ttcaaaatca tatcaatata ttactctcat ggaacttgca cattctaaga 240
agggtcattt tttcccccca gtaccaatat tacattattt gacagggata ataaaatgag 300
cagagactgg aaatcacaga caataacatt gctttctcaa ttaacagaaa ggattcataa 360
catattcctt aacggtagat gtgatttgta gagaatgtgg aaaagaacta ttgagaagtc 420
cacctgctgc ccaaactgag gcacattagg gtggttgtgg gangagttat atttgagggt 480
ccatttttcc ttagggttta aaagcatgtc cnggttggng gtnatttgcc attaagtctn 540
ttttcaaata aaagaattag gggagaaagt ttggaaaa 578

<210> SEQ ID NO 466
<211> LENGTH: 546
<212> TYPE: DNA
<213> ORGANISM: Homo sapiens
<220> FEATURE:

-continued

```
<221> NAME/KEY: misc_feature
<222> LOCATION: (1)...(546)
<223> OTHER INFORMATION: n = A,T,C or G

<400> SEQUENCE: 466

accaatacca ccaattttgt agacatcctg gagaggcagg cgcaagggct tgtcagttgg     60

acgagttggt ggtaggatgc agtccagagc ctcaagcagc gtggttccac tggcattgcc    120

atccttacgg gtgactttcc atcccttgaa ccaaggcatg ttagcacttg gctccagcat    180

gttgtcacca ttccaaccag aaattggcac aaatgctact gtgtcggggt tgtagccaat    240

tttcttaatg taagtgctga cttccttaac aatttcctca tatctcttct ggctgtaggg    300

tggctcagtg gaatccattt tgttaacacc gacaattagt tgtttcacac ccagtgtgta    360

agccagaang gcatgctctc gggtctgccc attcttggag ataccagctt caaattcacc    420

aacaccagca gcaacaatca ggacagnaca gtcggnctga gatgtccctg taatcatgtt    480

ttgataaaag tctctgtgtc ctggggcatc aatgatagtc acatagtacc tcggccgcga    540

ncacgc                                                               546


<210> SEQ ID NO 467
<211> LENGTH: 445
<212> TYPE: DNA
<213> ORGANISM: Homo sapiens
<220> FEATURE:
<221> NAME/KEY: misc_feature
<222> LOCATION: (1)...(445)
<223> OTHER INFORMATION: n = A,T,C or G

<400> SEQUENCE: 467

acctaaaacc cgaagaacct tctgtaagaa gtgtggcaag catcagcctc acaaagtgac     60

acagtataag aagggcaagg attctttgta tgcccaggga aggaggcgct atgatcggaa    120

gcagagtggc tatggtgggc agacaaagcc aattttccgg aagaaggcta agaccacaaa    180

gaagattgtg ctaaggctgg aatgtgttga gcctaactgc agatccaaga ggatgctggc    240

tattaagaga tgcaagcatt ttgaactggg aggagataag aagagaaagg gccaagtgat    300

ccagttctaa actttgggat atttttcttc aattttgaag agaaaatggt gaaccataga    360

aaagttaccc gagggaaaat aaatacagtg atattccaaa aaaaaaaann nnnnnaaaaa    420

aaagtncttg gccgggaccc cctaa                                          445


<210> SEQ ID NO 468
<211> LENGTH: 566
<212> TYPE: DNA
<213> ORGANISM: Homo sapiens
<220> FEATURE:
<221> NAME/KEY: misc_feature
<222> LOCATION: (1)...(566)
<223> OTHER INFORMATION: n = A,T,C or G

<400> SEQUENCE: 468

actgtgtggc gccttattct aggcacttgt tgggcagaat gtcacacctg ccgatgaaac     60

tcctgcgtaa gaagatcgag aagcggaacc tcaaattgcg gcagcggaac ctaaagtttc    120

agggggcctc aaatctgacc ctatcggaaa ctcaaaatgg agatgtatct gaagaaacaa    180

tgggaagtag aaaggttaaa aaatcaaaac aaaagcccat gaatgtgggc ttatcagaaa    240

ctcaaaatgg aggcatgtct caagaagcag tgggaaatat aaaagttaca aagtctcccc    300

agaaatccac tgtattaagc aatggagaag cagcaatgca gtcttccaat tcagaaccaa    360

aaaaaaaaaa nnaaaaaaag tacttttttt tntnnnnnnn tttttttag gaatgggtgt     420
```

-continued

```
tgaacttgac ctttcttaat gggggctggt tttaggctat atggngtaaa tttttctctt    480

ttacaaggtt tttcctagng ncaaaaactg tcctttggac taccgtaaat tacaggggtt    540

taaaggttnt ggggcaatta aanttn                                         566
```

<210> SEQ ID NO 469
<211> LENGTH: 586
<212> TYPE: DNA
<213> ORGANISM: Homo sapiens
<220> FEATURE:
<221> NAME/KEY: misc_feature
<222> LOCATION: (1)...(586)
<223> OTHER INFORMATION: n = A,T,C or G

<400> SEQUENCE: 469

```
acgcgggata ggtttggtcc tagcctttct attagctctt agtaagatta cacatgcaag     60

catccccgtt ccagtgagtt caccctctaa atcaccacga tcaaaaggga caagcatcaa    120

gcacgcagca atgcagctca aaacgcttag cctagccaca cccccacggg aaacagcagt    180

gattaacctt tagcaataaa cgaaagttta actaagctat actaacccca gggttggtca    240

atttcgtgcc agccaccgcg gtcacacgat taacccaagt caatagaagc cggcgtaaag    300

agtgttttag atcacccccct ccccaataaa gctaaaactc acctgagttg taaaaaactc    360

cagttgacac aaaatagact acgaaagtgg ctttaacata tctgaacaca caatagctaa    420

gacccaaact gggattagat accccactat gcttagccct aaacctnaca gttaaatcaa    480

caaaactgct cgccagacac tcgagccaca gcttaaaact caaggacctg cgggcttcat    540

atccctctag angacctgtc tgtaatcgat aaccccgatc aacctn                   586
```

<210> SEQ ID NO 470
<211> LENGTH: 487
<212> TYPE: DNA
<213> ORGANISM: Homo sapiens
<220> FEATURE:
<221> NAME/KEY: misc_feature
<222> LOCATION: (1)...(487)
<223> OTHER INFORMATION: n = A,T,C or G

<400> SEQUENCE: 470

```
acggccaggg ctattggttg aatgagtagg ctgatggttt cgataataac tagtatgggg     60

ataaggggtg taggtgtgcc ttgtggtaag aagtgggcta gggcattttt aatcttagag    120

cgaaagccta taatcactgc gcccgctcat aaggggatgg ccatggctag gtttatagat    180

agttgggtgg ttggtgtaaa tgagtgaggc aggagtccga ggaggttagt tgtggcaata    240

aaaatgatta aggatactag tataagagat caggttcgtc ctttagtgtt gtgtatggtt    300

atcatttgtt ttgaggttag tttgattagt cattgttggg tggtgattaa tcngttgntg    360

atgaaatatt tggaggtggg gatcaatana gggggaaata gaatgatcag tacctcgccc    420

gcgaccacgc taagggccaa tccacacact ggcggncgta ctaatggatc ccaactcgga    480

ccagctt                                                              487
```

<210> SEQ ID NO 471
<211> LENGTH: 488
<212> TYPE: DNA
<213> ORGANISM: Homo sapiens
<220> FEATURE:
<221> NAME/KEY: misc_feature
<222> LOCATION: (1)...(488)
<223> OTHER INFORMATION: n = A,T,C or G -continued

<400> SEQUENCE: 471
actgcggcgg gtaggcctag gattgtgggg gcaatgaatg aagcgaacag attttcgttc 60
attttggttc tcagggtttg ttataatttt ttatttttat gggctttggt gagggaggta 120
ggtggtagtt tgtgtttaat atttttagtt gggtgatgag gaatagtgta aggagtatgg 180
gggtaattat ggtgggccat acggtagtat ttagttgggg cattcccgcg tacctatttg 240
tatttttggt agagacaggg ttttgccatg ttggccagga tggtcttgaa ctactgacct 300
caggtgatcc tcacgccttt atctcccaaa gtgctgcgat tacaggcatg aggcaccact 360
cctggccaca ttcttatatt taaaaaaaaa gcacaactct attgtctact ggtgttcttt 420
tacctgaagt tcaaactcta gctcttcaaa aaaaaaaaaa aaaaaaagta cctngggccgc 480 naccacnc 488

<210> SEQ ID NO 472
<211> LENGTH: 586
<212> TYPE: DNA
<213> ORGANISM: Homo sapiens
<220> FEATURE:
<221> NAME/KEY: misc_feature
<222> LOCATION: (1)...(586)
<223> OTHER INFORMATION: n = A,T,C or G

<400> SEQUENCE: 472
ggtacttgat gccctccaag caattaaaac caagggcaaa cgagccccat tcacaaattt 60
tgacccctct actctccttc cttcatccct ggatttctgg acctacccctg gctctctgac 120 tcatcctcct ctttatgaga gtgtaacttg gatcatctgt aaggagagca tcagtgtcag 180
ctcagagcag ctggcacaat tcagcagcct tctatcaaat gttgaaggtg ataacgctgt 240
ccccatgcag cacaacaacc gcccaaccca acctctgaag ggcagaacag tgagagcttc 300
attttgatga ttctgagaag aaacttgtcc ttcctcaaga acacagccct gcttctgaca 360
taatccagta aaataataat ttttaagaaa taaatttatt tcaatattag caaagacagc 420
atgccttcaa atcaatctgt aaaactaaga aacttaaatt ttagttctta ctgcttaatc 480
aaataataat tagtaagcta gcaaatagta atctgtaagc ataagcttat gcttaaatca 540
gtttagtttg aggaatcttt aaaattacca ctaantgatt gnatgg 586

<210> SEQ ID NO 473
<211> LENGTH: 575
<212> TYPE: DNA
<213> ORGANISM: Homo sapiens
<220> FEATURE:
<221> NAME/KEY: misc_feature
<222> LOCATION: (1)...(575)
<223> OTHER INFORMATION: n = A,T,C or G

<400> SEQUENCE: 473
ggtacaaagg ggaaagggtg catgccaact atcgaattat aggatatgta aaaaatataa 60
gtcaagaaaa tgccccaggg cccgcacaca acggtcgaga gacaatatac cccaatggaa 120
ccctgctgat ccagaacgtc acccacaatg acgcaggaat ctatacccta cacgttataa 180
aagaaaatct tgtgaatgaa gaagtaacca gacaattcta cgtattctcg gagccaccca 240
agccctccat caccagcaac aacttcaatc cggtggagaa caaagatatt gtggttttaa 300
cctgtcaacc tgagactcag aacacaacct acctgtggtg ggtaaacaat cagagcctcc 360
tggtcagtcc caggctgctg ctctccactg acaacaggac cctcgttcta ctcacgccca 420
aagaatgaca taggacccta tgaatgtgaa atacagaacc cagtgggtgc cacccgcant 480

-continued gcccantcac cctgaatgtc cgtatgagtc aatcctgccg gcggccgttc naanggcgaa 540
ttccacacac tggcggccgt ctaatggatc cactc 575

<210> SEQ ID NO 474
<211> LENGTH: 515
<212> TYPE: DNA
<213> ORGANISM: Homo sapiens
<220> FEATURE:
<221> NAME/KEY: misc_feature
<222> LOCATION: (1)...(515)
<223> OTHER INFORMATION: n = A,T,C or G

<400> SEQUENCE: 474
ggtacgtggg ggactcaact gaaatcatgg cgtttgacag cacttggaag gtagaccgga 60
gtgaaaacta tgacaagttc atggaaaaaa tgggtgttaa tatagtgaaa aggaagcttg 120
cagctcatga caatttgaag ctgacaatta cacaagaagg aaataaattc acagtcaaag 180
aatcaagcgc ttttcgaaac attgaagttg tttttgaact tggtgtcacc tttaattaca 240
acctagcaga cggaactgaa ctcaggggga cctggagcct tgagggaaat aaacttattg 300
gaaaattcaa acggacagac aatggaaacg aactgaatac tgtccgagaa attataggtg 360
atgaactagt ccagacttat gtgtatgaag gagtagaagc caaaaggatc tttaaaaagg 420
attgaccatt attcttggcg cacagtccaa aatncaaatt ggccagaaga tctatattgn 480
acctgcccgg gcggccgttc gaaaggccaa ttcca 515

<210> SEQ ID NO 475
<211> LENGTH: 580
<212> TYPE: DNA
<213> ORGANISM: Homo sapiens
<220> FEATURE:
<221> NAME/KEY: misc_feature
<222> LOCATION: (1)...(580)
<223> OTHER INFORMATION: n = A,T,C or G

<400> SEQUENCE: 475
acaaagatct gacatgtcac ccagggaccc atttcaccca ctgctctgtt tggccgccag 60
tcttttgtct ctctcttcag caatggtgag gcggataccc tttcctcggg gaagagaaat 120
ccatggtttg ttgcccttgc caataacaaa aatgttggaa agtcgagtgg caaagctgtt 180
gccattggca tctttcacgt gaaccacgtc aaaagatcca gggtgcctct ctctgttggt 240
gatcacacca attcttccta ggttagcacc tccagtcacc atacacaggt taccagtgtc 300
gaacttgatg aaatcagtaa tcttgccagt ctctaaatca atctgaatgg tatcattcac 360
cttgatgagg ggatcggggt agcggatggt gcgggcatca tgagtcacca gatgagggat 420
tccttttgtg ccccaaagat ctttctnact ttgacaactt gaccttggnc gcgaccaccc 480
taaggcgaat tcacccactg gcggccgtct aatggatccn nctcggncca acctggntat 540
atggcntaan tnntccnggn naaatntntc cccncaatcc 580

<210> SEQ ID NO 476
<211> LENGTH: 593
<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G

<400> SEQUENCE: 476

-continued

```
ggtactatgt gggacagtat tttgcaaata caagaagagc tcagggcagc tgtggagctg     60

gatggtctgc ctggcaggcc tctgtgcagt ctgcctgctc atcctgtccc ctttttgggg    120

cttgatcctc ttctcggtgt catgcttcct catgtatact tacttatctg gccaagaatt    180

gttacctgtg gatcagaagg cagtcctggt gacaggtgtg attgcgggct tggccatgct    240

ttgtgcaagt atctggatga gctgggcttc acggtatttg ccggagtttt gaatgaaaat    300

ggcccaggag ctgaggaatt gcgaagaacc tgctctccgc gcctctcggt gctccaaatg    360

gacatcacga accagtgcag ataaaagatg cttacagcaa ggttgcaaca atgctgcagg    420

acaaaagact gtgggctgtg atcaacaatg ctngggtgct tggcttttcc actgatgggg    480

agcttnttnt tatgatgact acnaacaatc ntggccgnga actttttga actgngaggg     540

acaaaacgtt tttccttttt taaaaaancc aagggnggtg gnnaattncn nnt           593
```

<210> SEQ ID NO 477
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 477

```
actacaaggt ttagcatttg ctctgctggt cgacattccc ccagtctatg ggttgtatgc     60

atcctttttc ccagccataa tctacctttt cttcggcact tccagacaca tatccgtggg    120

tccgtttccg attctgagta tgatggtggg actagcagtt tcaggagcag tttcaaaagc    180

agtcccagat cgcaatgcaa ctactttggg attgcctaac aactcgaata attcttcact    240

actggatgac gagagggtga gggtggcggc ggcggcatca gtcacagtgc tttctggaat    300

catccagttg gcttttggga ttctgcggat tggatttgta gtgatatacc tgtctgagtc    360

cctcatcagt ggcttcacta ctgctgctgc tgttcatgtt tttggnttcc caactcaaat    420

tcatttttca agtgacagtc ccgtcacaca ctgatncagt ttnaatttta aaagtacctc    480

ggccgcganc accctaaggc gaatttnaac ccactngcgg ccgttctant ggatccaact    540

ngnnncaaac ttngngaata ngggcataac ngntcctggg gaaatnnttc ccnct          595
```

<210> SEQ ID NO 478
<211> LENGTH: 420
<212> TYPE: DNA
<213> ORGANISM: Homo sapiens
<220> FEATURE:
<221> NAME/KEY: misc_feature
<222> LOCATION: (1)...(420)
<223> OTHER INFORMATION: n = A,T,C or G

<400> SEQUENCE: 478

```
ggtacacagt atgtataaca atgcatacta tggtgtggag ttaattccaa ttaccatatt     60

ttatatttat tggtcacaac agcatacatt ttatgctcca aaatacatgg atctgacaaa    120

atggttacat ttaatgttct tttaaagaaa gatgaactaa atttaagaag aattggtttt    180

tcctaatatc tcattttcaa attactgata caaatttgcc agagaaacaa ttacatgttt    240

tacctaacat caaataatct ccagtttcta agacagatgc atttcttgtt caatttccaa    300

aagtaaataa aggctttcta actgaaaaca tttgcatccc tagctctcta aagtaattaa    360

aaagaaaatt acaaaaaatg acctctaagc ttctgaacag cccacttant tacataaagt    420
```

<210> SEQ ID NO 479

-continued

```
<211> LENGTH: 602
<212> TYPE: DNA
<213> ORGANISM: Homo sapiens
<220> FEATURE:
<221> NAME/KEY: misc_feature
<222> LOCATION: (1)...(602)
<223> OTHER INFORMATION: n = A,T,C or G

<400> SEQUENCE: 479

ggtacctagt cagatggtag acgagctgtc tgctgccgca ggagcacctc tatacaggac     60

ttagaagtag tatgttattc ctggttaagc aggcattgct ttgccctgga gcagctattt    120

taagccatct cagattctgt ctaaaggggt tttttgggaa gacgttttct ttatcgccct    180

gagaagatct accccaggga gaatctgaga catcttgcct acttttcttt attagctttc    240

tcctcatcca tttcttttat acctttcctt tttggggagt tgttatgcca tgatttttgg    300

tatttatgta aaaggattat tactaattct atttctctat gtttattcta gttaaggaaa    360

tgttgagggc aagccaccaa attacctang ctgaggttag agagattggc cagcaaaaac    420

tgtgggaaga tgaactttgt cattatgatt tcattatcac atgattatag aaggctgtct    480

taatgcaaaa aacatactta catttnanac atattccaan gggatctcnc attttgtaaa    540

aagttgacta ttactggagt aaaccctgtt ttccctaant ttaacttttt ttgggaaatt    600

at                                                                   602


<210> SEQ ID NO 480
<211> LENGTH: 600
<212> TYPE: DNA
<213> ORGANISM: Homo sapiens
<220> FEATURE:
<221> NAME/KEY: misc_feature
<222> LOCATION: (1)...(600)
<223> OTHER INFORMATION: n = A,T,C or G

<400> SEQUENCE: 480

ggtacttttt tttttttttt tttttttttc ggtttgaggg ggaatgctgg anattgtaat     60

gggtatggan acatgtcata taagtaatgc tagggtgagt ggtaggaagt tttttcatag    120

gaggtgtatg agttggtcgt agcggaatcg ggggtatgct gttcgaattc ataaaaacag    180

ggaggttana agtagggtct tggtgacaaa atatgttgtg taaagttcag gggganagtgc    240

gtcatatgtt gttcctagga aaattgtagt ggtgagggtg tttattataa taatgtttgt    300

gtattcggct atgaaaaata gggcgaaggg gcctgcggcg tattccatgt tgaagcctga    360

gactagttcg gactcccctt cggcaaggtc caaaggggtt ccggttggtc tcttctagtg    420

tggagataaa tcatattatg gccnagggtc atgatggcag gagtaatcaa aggggtcntt    480

tgttttgaaa aagggnggan aggttaaagg ancccctttt tataatggtg atantaaaaa    540

gatgcttggg ggactcnttt aaaatgttgg ctcttcttcc angcncccac aggcgtattt    600


<210> SEQ ID NO 481
<211> LENGTH: 594
<212> TYPE: DNA
<213> ORGANISM: Homo sapiens
<220> FEATURE:
<221> NAME/KEY: misc_feature
<222> LOCATION: (1)...(594)
<223> OTHER INFORMATION: n = A,T,C or G

<400> SEQUENCE: 481

cgaggtacgg ccagggctat tggttgaatg agtaggctga tggtttcgat aataactagt     60

atggggataa ggggtgtagg tgtgccttgt ggtaagaagt gggctagggc atttttaatc    120
```

ttagagcgaa agcctataat cactgcgccc gctcataagg ggatggccat ggctaggttt 180
atagatagtt gggtggttgg tgtaaatgag tgaggcagga gtccgaggag gttagttgtg 240
gcaataaaaa tgattaagga tactagtata agagatcagg ttcgtccttt agtgttgngt 300
atggttatca tttgttttga ggttagtttg attagtcatt gttgggtggt gattantccg 360
ttgttgatga gatatttgga ggtggggatc aatagagggg gaaatagaat gatcagtacc 420
tgcccnggcg gncgctcgaa anggcgaatt ccaccacact ggcgggcgnt ctaatggatn 480
cgacccngtc ccaacttgcg taatcatggc atacttgttn ctggtgaaat ggtatccctc 540
acaattccca cacatacaac ccgaacctaa atgtaaanct gggggcctat natn 594

<210> SEQ ID NO 482
<211> LENGTH: 600
<212> TYPE: DNA
<213> ORGANISM: Homo sapiens
<220> FEATURE:
<221> NAME/KEY: misc_feature
<222> LOCATION: (1)...(600)
<223> OTHER INFORMATION: n = A,T,C or G

<400> SEQUENCE: 482
accatgaaat acatatattt cataaggttc agttacaaaa tggattgttt caaatggcaa 60
tttcttacac taacctgatt atgaaaaaaa gaagtctgta tcatctgctt ccaagtctgt 120
tatgtccaaa tatattttaa ttatgcattt attttgctac ttttataaat attagagatt 180
tcaccttaaa ttatttttgt aactagttct agaacatgtt ttccaattat tatttttcta 240
atggagacat ataattgacc tatgtttatg catatatgtt ctctacacag tgaaactttt 300
tttaaaaaga atagtaaaga aaatgcggaa gctctggctc tccaaggcaa agtcaaaaaa 360
aaaaaaaaag cggggggGaa tgcgaggaac attttattac acctnctgat tttcctcctt 420
gagntttatt ttctcccctt ggntatttgt taatgctaga aactgnattc ctaanaaagc 480
atacctcttt caggngagcn tgataattgg gaanaatttt gttcctttag tntgaacatt 540
ttattaagaa gngattccta ataaaganac aangggctnt ttaattnttt gggggnngga 600

<210> SEQ ID NO 483
<211> LENGTH: 605
<212> TYPE: DNA
<213> ORGANISM: Homo sapiens
<220> FEATURE:
<221> NAME/KEY: misc_feature
<222> LOCATION: (1)...(605)
<223> OTHER INFORMATION: n = A,T,C or G

<400> SEQUENCE: 483
acagaacatc gtcagcacta gcacagttta cagaacctca cagacccaaa ggaacatcaa 60
taggcaaagc gactacagga ggcgtgtgtc cgcgtgggcg aggtaaagag ggtcagtatt 120
ggtcaagtga cagtgtcggt aatctggcaa gacagtgatg ttaagaaggt tcatagttta 180
agaattatct aaaatatttt aaaaactata aagctgcaac acatgatttt tacacctagt 240
tactagaaaa ctaaggaaag cacttattag ctctgaataa agtaacatgg aaagcacttt 300
tactaatcga caaaaaaacc ttctaatgca ttatcagaaa gattttataa tacaaggagg 360
catattgctc agtcagaagg ggttctataa gaaaagcact tactaagtta gcgactaaca 420
gaacaaccng tttaaagatg aattaaatgc cccatttggg gangcatggc aggtgttaag 480
anaaangaaa agcntaagaa aacatttnct ggttatanca aacctttntt tnttatctac 540

-continued tgnatttgac aaaaattaac cntttaaagt tttacccngg cacttnnttc nttgtcctcg 600
gcccg 605

<210> SEQ ID NO 484
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 484
ggtacgcggg tggggagacc ctggggtagc agccactgac ctcacacctg gaggaagctg 60
tgtgaccgat tcatgagctt atgcctgaag acagagcaag cactccccgc accacgacga 120
tgacgttcac ttgttttgtg tttttcgatc tcttcaacgc cttgacctgc cgctctcaga 180
ccaagctgat atttgagatc ggctttctca ggaaccacat gttcctctac tccgtcctgg 240
ggtccatcct ggggcagctg gcggtcattt acatcccccc gctgcagagg gtcttccaga 300
cggagaacct gggagcgctt gatttgctgt ttttaactgg attggcctca tccgtcttca 360
ttttgtcaga gctcctcaaa ctatgtgaaa aatactgttg cagccccaaa gagagtccag 420
atgcaccctg aaagatgtgt agtggaccgc acttccgcgg naccttccta atnatttcaa 480
ctgggtgnga ctgtggccct gccctgtttc ttcttagggg agactttang anggcgagcn 540
tcataccgga tagttttctt taggaaactn aggaaccttg gctcaggacc a 591

<210> SEQ ID NO 485
<211> LENGTH: 605
<212> TYPE: DNA
<213> ORGANISM: Homo sapiens
<220> FEATURE:
<221> NAME/KEY: misc_feature
<222> LOCATION: (1)...(605)
<223> OTHER INFORMATION: n = A,T,C or G

<400> SEQUENCE: 485
ggtacgcggg gatataaagg gagagagcaa gcagcgagtc ttgaagctct gttnggtgct 60
tnggatccat ttccatcggn ccttacagcc gctcgtcaga ctccancagc caanatggtg 120
aancagatcg agagcaagac tgcttttcan gaagccttgg acgctgcang tgataaactt 180
gtagnagttg acttctcagc cacgtggtgt gggccttgca aaatgatcaa gcctttcttt 240
cattccctct ctgaaaagta ttccaacgtg atattccttg aagtagatgt ggatgactgt 300
caggatgttg cttcagagtg tgaagtcaaa tgcatgccaa cattccagtt ttttaagaag 360
ggacaaaagg tgggtgaatt ttctggagcc aataaggaaa agctttgnag ccnccattaa 420
tgaatgagtc taatcatgtt ttctgaaaac ataacccagc catttggcta tttaaaactt 480
gnaanttttt nagntaccna aatttaaagt ctgaagacat aacccggtgc catttgcgtg 540
acaatnaaaa attatgccaa cactttttna anaanganan nnntttcctn gggaaatngt 600 anccc 605

<210> SEQ ID NO 486
<211> LENGTH: 319
<212> TYPE: DNA
<213> ORGANISM: Homo sapiens

<400> SEQUENCE: 486
ggtaccagtt gtagccataa agattctggg actcattatg gactactaga aggacctcct 60

-continued tcccttctgc gacattgaac ggcacgacat caatattggt ctgggcactg tttggcaggt 120
tccagaaggt taaaagcgag gctgtgagca ggagtccctg ccagggaatg cacactctgt 180
atggacaggc tgaaggggac cccatggtct ctgctgcctg cttgtcctct gtggagaaga 240
gcttgggctc caggaactct cttgtcaggg ctgctgtgac tgtcagctct gctgtccttc 300
ctacctctgt gtcccgcgt 319

<210> SEQ ID NO 487
<211> LENGTH: 586
<212> TYPE: DNA
<213> ORGANISM: Homo sapiens
<220> FEATURE:
<221> NAME/KEY: misc_feature
<222> LOCATION: (1)...(586)
<223> OTHER INFORMATION: n = A,T,C or G

<400> SEQUENCE: 487
acgcgggagc tgagtgtccc gcggggcccg aagcgtttac tttgaaaaaa ttagagtgtt 60
caaagcaggc ccgagccgcc tggataccgc agctaggaat aatggaatag gaccgcggtt 120
ctattttgtt ggttttcgga actgaggcca tgattaagag ggacggccgg gggcattcgt 180
attgcgccgc tagaggttaa attcttggac cggcgcaaga cggaccanag cgaaagcatt 240
tgccaagaat gttttcatta atcaagaacg aaagtcggag gttcgaagac gatcagatac 300
cgtcgtagtt ccgaccataa acgatgccga ccggcgatgc ggcggcgtta ttccatgacc 360
cgccgggcag ctttcnggaa accaaagtct ttgggttncc gggggagtat ngttcnaaaa 420
aaaaaaaaaa aaaaaaaagt cctnggccgg gancccctta nggngaaatt cagccactgg 480
nggcgttctn atggatncna gctcggncca acntggcgta atatggcata cttgttcctg 540
gngnaaatgt ttccctccaa attccccaaa tacgggcgga gcttaa 586

<210> SEQ ID NO 488
<211> LENGTH: 487
<212> TYPE: DNA
<213> ORGANISM: Homo sapiens
<220> FEATURE:
<221> NAME/KEY: misc_feature
<222> LOCATION: (1)...(487)
<223> OTHER INFORMATION: n = A,T,C or G

<400> SEQUENCE: 488
acagctggtt ggacctattc atgcatcttc accagcagct ggagcatctc caccettggt 60 atttctggtg taaattactt gagctctgtg ctttgaaacc agtttgataa gtcctttact 120
aaggagctcc tgaagggctg ccctggccag ggagcctcga atcttcagtc tctcagagac 180
cacagctggg gttataagtt tatagttggg aacttcctta cagagtttat cataggtagc 240
tttgtcaaac aagactaagt tattgagctt gtcccgaact ttgcctttgg accacttctt 300
ctttttggcc ttgcccccgg atttgttcac tgggtctttg tctttcttgg ccgactttcc 360
agcgtccttc ttcttcttgt cgtccttaag cggcattgcg aanctcggag aataagcaac 420
aaacaccgca cctcgtcnaa gatgtcggac aaaaaaaggc cccgcgtacc ttnggccgcg 480 ancacnc 487

<210> SEQ ID NO 489
<211> LENGTH: 589
<212> TYPE: DNA
<213> ORGANISM: Homo sapiens
<220> FEATURE:

-continued

<221> NAME/KEY: misc_feature
<222> LOCATION: (1)...(589)
<223> OTHER INFORMATION: n = A,T,C or G

<400> SEQUENCE: 489
acgcggggtc tctcctcagg cagcagcaac gcggaggaaa cgggagtgaa cggagagcgt 60
agtgaccatc atgagcctcc tcaacaagcc caagagtgag atgaccccag aggagctgca 120
gaagcgagag gaggaggaat ttaacaccgg tccactctct gtgctcacac agtcagtcaa 180
gaacaatacc caagtgctca tcaactgccg caacaataag aaactcctgg gccgcgtgaa 240
ggccttcgat aggcactgca acatggtgct ggagaacgtg aaggagatgt ggactgaggt 300
acaaagatta aattaagaca cggtaaattg actaaatatt tggtttttat ataaataaag 360
gtcataacca caccgttgac atgtaatact gttataatac aacagttaaa ctttgtgagt 420
ctcaacagaa gtcatctgta gttnaacagg aaacaaaagt tgaaaaaaaa catgttnaaa 480
caaaactctg ggactaacag gtcgggattg taagtacaac caacatattc ctcacttctg 540
ggtntttcaa gtttacagta cttggccgga ccccccttang ggnattcac 589

<210> SEQ ID NO 490
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 490
ggtaccggga tagtttttgc agggttttat tttataaaat ccaagcgcgc tgttgattgt 60
gttttccttg ttttcagccc cccgactcca gcccgcagca catttccgct gtccgtcagt 120
aattgtgtcc tctctttatg cttgcttggg gaatgttgtt ttctgactag gctgatcatt 180
atctaaagaa tctaattctg ttgattttta aaacttttag gaccataaac gttgtgttca 240
tatatggaca tggaaatatt tatataattt tatagaaaat aaccttttag atggtcaaag 300
tgtaaggagt tttttttgtc agataatcat ttctacttca aaaacatttc atgcaatatt 360
agaataaagt tcctgtcatt cctctnnnan aaaaannnnn nnnnnnanna nnnnnnnnnn 420
nggaanannn nnnnnnnnnn aaaaaagtac ctgcccnggc ggccgttcaa aaggcgaatt 480
ccacccactg gcggccgttc taatggatcc anctcggacc aacctggnga aacatggcat 540
acctgttcct ggngaaatgg tntcccttac aattcccaca aataaaaccg g 591

<210> SEQ ID NO 491
<211> LENGTH: 583
<212> TYPE: DNA
<213> ORGANISM: Homo sapiens
<220> FEATURE:
<221> NAME/KEY: misc_feature
<222> LOCATION: (1)...(583)
<223> OTHER INFORMATION: n = A,T,C or G

<400> SEQUENCE: 491
ggtacatata aatccttttg gtgtcacttg tagcaagcct tgcttctgca gttttcggat 60
tttcctcaaa gctttgttgc gcttgcgtag aattcgaagt ggactaaagc caacagcatc 120
gataagtttc cgcctaaaga aaccaatgtt tgcaaagtag ataggagatg gacatctgaa 180
aattttcact ccttctggct catacatatc ataataatct tttttattct tatagatgtt 240
ggttcttcca atattagcca gcgtgctgca ttttggaaat tgggtcctga acacgatggt 300
tagcagttga aatgccacac tagctgccag gcctaacccg agtcccagga caatggtgaa 360
agatgaaagg catgaaccca aataaacaat catatttggn cnttccccca atctgctatt 420
ttaaccaact gcatcaacat tcctttaagt tccaatgcta aactggcang acnggcnttt 480
gtagaagngc cangaaaaat cagngcttga cgacaatcac accatgatgn nccataancc 540
acaatctggg nttggctcnn ggcctctgaa cnnngactgg nag 583

<210> SEQ ID NO 492
<211> LENGTH: 597
<212> TYPE: DNA
<213> ORGANISM: Homo sapiens
<220> FEATURE:
<221> NAME/KEY: misc_feature
<222> LOCATION: (1)...(597)
<223> OTHER INFORMATION: n = A,T,C or G

<400> SEQUENCE: 492
acgcgggggg tggcacggag gaaccaggag cgtgccctgc gcaccgtctg gagctccgga 60
gatgacaagg agcagctggt gaagaacaca tatgtcctgt gaccgccctg tcgccaagag 120
gactggggaa gggaggggag actatgtgtg agcttttttt aaatagaggg attgactcgg 180
atttgagtga tcattagggc tgaggtctgt ttctctggga ggtaggacgg ctgcttcctg 240
gtctggcang gatgggtttg ctttggaaat cctctangag gctcctcctc gcatggcctg 300
cagnctggca acaaccccga gttgtttcct cgctgatcga tttctttcct ncaggtagag 360
ttttctttgc ttatgttgaa ttccattgcc tttttctcat cacaaaaaat gatgttggga 420
atcgnntctt ttgtttggct gaattatggg ntttttaant ataaaccaaa ntttttttatt 480 aacattctta aanaagggaa agtnnaatgt ncnttggncc cnaccncgct aanggcnaat 540
ttcancccnt ggnggccgtn nttnnggatc cnnncnngnn ccaannntgg nntantn 597

<210> SEQ ID NO 493
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 493
acggatgcta cttgtccaat gatggtaaaa gggtagctta ctggttgtcc tccgattcag 60
gttagaatga ggaggtctgc ggctaggagt caataaagtg attggcttag tgggcgaaat 120
attatgcttt gttgtttgga tatatggagg atggggatta ttgctaggat gaggatggat 180
agtaataggg caaggacgcc tcctagtttg ttagggacgg atcggagaat tgtgtaggcg 240
aataggaaat atcattcggg cttgatgtgg ggaggggtgt ttaaggggtt ggctagggta 300
taattgtctg ggtcgcctag gaggtctggt gagaatagtg ttaatgtcat taaggagaga 360
aggaagagaa gtaagccgag ggcgtctttg attgtgtagt aagggtggaa ggtgatttta 420
tcggaatggg aggtgattcc taagggggtg gttgatcccg tttcctgcca agaataagaa 480
gtggaatgct gctagggctg cattaatgaa ggccaagatg aaatgaaagg taaanaatcn 540
ngtgangggg gactgctact gatancctct caaatcatga ataggntgtc c 591

<210> SEQ ID NO 494
<211> LENGTH: 374
<212> TYPE: DNA

-continued

<213> ORGANISM: Homo sapiens
<220> FEATURE:
<221> NAME/KEY: misc_feature
<222> LOCATION: (1)...(374)
<223> OTHER INFORMATION: n = A,T,C or G

<400> SEQUENCE: 494

```
ggtacttttt tttttttttt tttttttttt ttttttagnt catgtctttt attaactcat      60

acagttactt gtcttctggt ttgttgaaac agtaagtcan acaacatttg ccacaataat     120

gtctgtcaaa gtgacttgcc ataaacaccc cagcaccaca ttcatcanaa gggcactctc     180

gacgaaggcg actaattttg ccattctcat ccaccttata atatttcagg acagccagct     240

taaccttctt tctcttgtgc ttattcttct tgggagnggt gtaagacttc ttcttccttt     300

tcttagcacc accacgaagt ctcaacacaa gatgaagagt agactccttt tgaatattgt     360

aagtcagaca aagt                                                       374
```

<210> SEQ ID NO 495
<211> LENGTH: 597
<212> TYPE: DNA
<213> ORGANISM: Homo sapiens
<220> FEATURE:
<221> NAME/KEY: misc_feature
<222> LOCATION: (1)...(597)
<223> OTHER INFORMATION: n = A,T,C or G

<400> SEQUENCE: 495

```
actgggagaa ggtgctgacg ccgacgaagt ggtggatggg cttcccgctg caggtgaacc      60

tcctggtgcc atcctgcagg gtcccccgag gattgcctag atcatttttc aagcagtagt     120

tgctttctgg gtttttacaa attctgcatt ttccacactg aggagtaaag agcgggatga     180

ctttatcacc tggtttgact gtagtcaccc cttctccaac actttccacg atgccggctg     240

cctcatggcc taaaatcaca ggaagggggg tcaccaggtt gccactaacc acatgctcat     300

ctgaacgaca gattcctgca gccaccatct taatgcgaac ttcatgagcc ttaggaggtg     360

caacctctac ctcctcaatg gaaaagggtt tctttaactc ccatagcaca actgctttgc     420

atttgattac ctgtaaactc agctacttgt gaaggctgag gcanganaat actttgaacc     480

ccggaaggca aaggttgcaa tgagccnana acaccattgn acttccanct gggcaatana     540

aaaaaactca tttttcctgc tggctcaaat gatctgcttc ttgcaaacaa gagntgn        597
```

<210> SEQ ID NO 496
<211> LENGTH: 604
<212> TYPE: DNA
<213> ORGANISM: Homo sapiens
<220> FEATURE:
<221> NAME/KEY: misc_feature
<222> LOCATION: (1)...(604)
<223> OTHER INFORMATION: n = A,T,C or G

<400> SEQUENCE: 496

```
ggacgcgggt gctgactgca tagctctttt tcttgagagg ctctccattt tgattcagaa      60

agttagcata tttattacca atgaatttga aaccagggct tttttttttt tttgggtgat     120

gtaaaaccaa ctccctgcca ccaaaataat taaaatagtc acatttatct ttattaggta     180

atcacttctt aattatatgt tcatactcta agtatcaaaa tcttccaatt atcatgctca     240

cctgaaagag gtatgctctc ttaggaatac agtttctagc attaaacaaa taaacaaggg     300

gagaaaataa aactcaagga gtgaaaatca ggaggtgtaa taaaatgttc ctcgcattcc     360

cccccgcttt tttttttttt ttgactttgc cttggaaagc cagagcttcc cgcattttct     420
```

-continued

```
ttactattct ttttaaaaaa agtttcactg ngtaaaagaa catatttgcc taaacatang    480

tcaattatat gtctccatta naaaaaaata attggnaaac attgtctana actagttcca    540

aaataattaa gggggaaatc tntaatnttt ttaaagtgcc naaanaatgc ctaanttaaa    600

antt                                                                 604
```

<210> SEQ ID NO 497
<211> LENGTH: 587
<212> TYPE: DNA
<213> ORGANISM: Homo sapiens
<220> FEATURE:
<221> NAME/KEY: misc_feature
<222> LOCATION: (1)...(587)
<223> OTHER INFORMATION: n = A,T,C or G

<400> SEQUENCE: 497

```
acattaatga aatgtttcca aagaaatact gaacaatata tactctagtt tgctgaggtt     60

ccagctcgag ttcaaaccta attcttgtgc aataaaaatc agcatggatc ttagatgatc    120

tagaatacac tgtgttttga aatccacagc tggtttcatt tttaaccatt atgaaaaacc    180

agtacttttt tttttttttt ttttttttc nctnggacca taaattttta ttggcaggtc    240

aggaaaaaag ccgggggtaa gggtcccttc cttcccatcc ctctacccan aanacaccct    300

ccaaaggaca gcagaagccc cagagcctgc tgcctcagag gaccttggag gcagacaaat    360

tgttgtagng atcttcctgt ccctcaanca ggctgcggta ggtggnaatc tnctgctcca    420

gccgcgactt gatgtccatg aaccgctggt cctcggccgc gacaccctta nggcgaattn    480

caccnactgg gnggcgttct agtggatccg actcggacca acctngcgna atcatggcan    540

actggttnct gnnggaaatg gtttccctnc aattccccaa cataccn                  587
```

<210> SEQ ID NO 498
<211> LENGTH: 354
<212> TYPE: DNA
<213> ORGANISM: Homo sapiens

<400> SEQUENCE: 498

```
acgcgggcaa taaagctaaa actcacctga gttgtaaaaa actccagttg acacaaaata     60

gactacgaaa gtggctttaa catatctgaa cacacaatag ctaagaccca aactgggatt    120

agatacccca ctatgcttag ccctaaacct caacagttaa atcaacaaaa ctgctcgcca    180

gaacactacg agccacagct taaaactcaa aggacctggc ggtgcttcat atccctctag    240

aggagcctgt tctgtaatcg ataaaccccg atcaacctca ccacctcttg ctcagcctat    300

ataccgccat cttcagcaaa ccctgatgaa ggctacaaag taagcgcaag tacc          354
```

<210> SEQ ID NO 499
<211> LENGTH: 632
<212> TYPE: DNA
<213> ORGANISM: Homo sapiens
<220> FEATURE:
<221> NAME/KEY: misc_feature
<222> LOCATION: (1)...(632)
<223> OTHER INFORMATION: n = A,T,C or G

<400> SEQUENCE: 499

```
nccgaggtac caactgcact cgttttggca ttgcagctaa atatcagttg gatcccactg     60

cttccatttc tgcaaaagtc aacaactcta gcttaattgg agtaggctat actcagactc    120

tgaggcctgg tgtgaagctt acactctctg ctctggtaga tgggaagagc attaatgctg    180
```

-continued

```
gaggccacaa ggntgggctc gccctggagt tggaggctta atccanctga aaagaaacct    240

ttgggaatgg atatcaaaag aattggcctt aatatatttc cattgngacc agcagcaggc    300

tttttttccc ccagaagatg atcaaaacaa aaggatgatc tcaacaagaa ctgtatttta    360

aagtatttaa ganagtcttt ggtaactngg ttctaagtng gtatctaatt acccaatgct    420

gcagtcctgc agtccctatt cattanttaa atgtatttaa ctggtaaatg ccctncccnc    480

cataatgaaa taganccttt ttgaaaaccc aaaaaaaaaa aaaaaaaaaa aaaaaagtcc    540

ctgcccggcc ggccctcaaa nggngaattc cannccctgg gggccgtact aanggatccn    600

cccggnccaa cttggggaat atgggntant gn                                  632
```

<210> SEQ ID NO 500
<211> LENGTH: 619
<212> TYPE: DNA
<213> ORGANISM: Homo sapiens
<220> FEATURE:
<221> NAME/KEY: misc_feature
<222> LOCATION: (1)...(619)
<223> OTHER INFORMATION: n = A,T,C or G

<400> SEQUENCE: 500

```
tccagcggnc cgccgggcng gtcatctata aaaggaaaag tgatggcatc tatatcataa     60

atctcaagan gacctgggag aagcttctgc tggcagctcg tgcaattgtt gccattgaaa    120

accctgctga tgtcagtgtt atatcctcca ngaatactgg ccaaanggct gtgctgaant    180

ttgctgctgc actggaacca ctccaattgc tggccgcttc actcctggaa ccttcactaa    240

ccagatcagg caaccttccg ggaccacggn ttnttgtggt tactgacccc aaggctgacc    300

accaacctnt cacggaggca ttttatgtta acctacctac cattgcgctg tgtaacacaa    360

gattcttctc tgcctatgtg gacattggca ttccatgcaa caaccaaggg gagctcactc    420

aatgggtttg atgtggtgga tctgctcggg naagtctgcg catgcctggc accatttccg    480

tgaacaccat ggagggatgc ctgattttac cttggccgga cacnctangg cgaattcacc    540

acttggngcc gtatantgga tccactcgga ccaacttggg naaaatggca naatnttccg    600

gggaaatgat ccctccaan                                                 619
```

<210> SEQ ID NO 501
<211> LENGTH: 605
<212> TYPE: DNA
<213> ORGANISM: Homo sapiens
<220> FEATURE:
<221> NAME/KEY: misc_feature
<222> LOCATION: (1)...(605)
<223> OTHER INFORMATION: n = A,T,C or G

<400> SEQUENCE: 501

```
accacactga gatagtgttt gccaggacct cccctcagca gaagctcatc attgtggaag     60

gctgccaaag acagggtgct atcgtggctg tgactggtga cggtgtgaat gactctccag    120

ctttgaagaa agcaaacatt ggggttgcta tggggattgc tggctcagat gtgtccaagc    180

aagctgctga catgattctt ctggatgaca actttgcctc aattgtgact ggagtagagg    240

aaggtcgtct gatctttgat aacttgaaaa aatccattgc ttatacctta accagtaaca    300

ttccccgaga tcaccccgtt cctgatattt attattgcaa acattccact accactgggg    360

actgtcacca tcctctgcat tgacttgggc actgacatgg gtnctgccat ctcctggctt    420

atgagcaggc tggagggcat catgaanaaa cagcccaaaa tccaaacaga caacttgtga    480

atgancnggt gatcacatgg ctatggcaga atggatgatc nagncctggg aggttcttac    540
```

-continued

```
ttacttggaa tctgntgaaa cggttcttcc aatacctntt ggcctccatg gntggaanac    600

cctga                                                                605


<210> SEQ ID NO 502
<211> LENGTH: 627
<212> TYPE: DNA
<213> ORGANISM: Homo sapiens
<220> FEATURE:
<221> NAME/KEY: misc_feature
<222> LOCATION: (1)...(627)
<223> OTHER INFORMATION: n = A,T,C or G

<400> SEQUENCE: 502

acatcttgct ggaaaatgct gcccagggct ctggagacgg tggctgcccg ggctcccttc     60

actgtccagg tcctgaaaga ctcttgttca tgaactgtct cttcacaaag caagtccacc    120

acttgctggg tttatcattc tgagggtcga aaactttctc acaaagtctc agtccagtct    180

cttgccttag ctgttgtaaa taggctctca tcacttcatc ttctgtttgt ttgcaggttt    240

ggcataaatt gcgttaagtg gaaaaccagg ctctccagga atgggaaaat taagtgattc    300

ccagcgtata catttctttc tcaccttggc ttttggaatt gcacttttgc agtttcttca    360

nacattcaga aatgtagaga gttatatata tcaangncct atcaacttca ttcttaattt    420

cataagtttt gaaaaaaaca ttggcccttg aagtaataaa tngntttatt cccaaaatct    480

ggatcntttg gcnctctngg ggcangnccc ttgaaatgac ttttgatagg gaacaangcc    540

ctggtttcca nnagnttggg ttcnggaccn taaaaaaaaa gggaanccgg nttttggngg    600

gcccggttta acccaagggc cggancn                                        627


<210> SEQ ID NO 503
<211> LENGTH: 629
<212> TYPE: DNA
<213> ORGANISM: Homo sapiens
<220> FEATURE:
<221> NAME/KEY: misc_feature
<222> LOCATION: (1)...(629)
<223> OTHER INFORMATION: n = A,T,C or G

<400> SEQUENCE: 503

ggtacattag tagagctctc caatcacagg cagacgccag tgtcctatga ccagggggca     60

aatatggcca aacagattgg agcagctact tatatcgaat gctcagcttt acagtcggaa    120

aatagcgtca gagacatttt tcacgttgcc accttggcat gtgtaaataa gacaaataaa    180

aacgttaagc ggaacaaatc acagagagcc acaaagcgga tttcacacat gcctagcaga    240

ccagaactct cggcagttgc tacggactta cgaaaggaca aagcgaagag ctgcactgtg    300

atgtgaatct ttcattatct ttaatgaaga caaaggaatc tagtgtaaaa aacaacagca    360

aacaaaaagg tgaagtctaa atgaagtgca cagccaaagt catgtatcca gaggcttang    420

aggcgtttga gangatactc atctttttgg aatnctgcct taggttcggc atgtanacca    480

agtgatgaga agtgaatcca tggaagagtt ttaatgtgac ttggaaaata tgccaaaaaa    540

tgagagatcc aataacttna ggaaaataag ggggatccaa tncctncccg gcggccctta    600

ggggaattca aacactnggg gcggtatan                                      629


<210> SEQ ID NO 504
<211> LENGTH: 462
<212> TYPE: DNA
<213> ORGANISM: Homo sapiens
<220> FEATURE:
```

-continued

<221> NAME/KEY: misc_feature
<222> LOCATION: (1)...(462)
<223> OTHER INFORMATION: n = A,T,C or G

<400> SEQUENCE: 504
acgcgggagc tgagtgtccc gcggggcccg aagcgtttac tttgaaaaaa ttagagtgtt 60
caaagcaggc ccgagccgcc tggataccgc agctaggaat aatggaatag gaccgcggtt 120
ctattttgtt ggttttcgga actgaggcca tgattaagag ggacggccgg gggcattcgt 180
attgcgccgc tagaggttaa attcttggac cggcgcaaga cggaccagag cgaaagcatt 240
tgccaagaat gttttcatta atcaagaacg aaagtcggag gttcgaagac gatcagatac 300
cgtcgtagtt ccgaccataa acgatgcccg accggcgatg cggcggcgtt attccatgac 360
ccgncgggca gcttccggga aaccaaagtc tttgggttcc ngggggagta tnggtgcaaa 420
aaaaaaaaaa aaaaaaaaaa gtcctnggnc gcgacccccct aa 462

<210> SEQ ID NO 505
<211> LENGTH: 628
<212> TYPE: DNA
<213> ORGANISM: Homo sapiens
<220> FEATURE:
<221> NAME/KEY: misc_feature
<222> LOCATION: (1)...(628)
<223> OTHER INFORMATION: n = A,T,C or G

<400> SEQUENCE: 505
actttttttt tttttttttt tttgggggag gttatatggg tttaatagtt tttttaattt 60
atttaggggg aatgatggtt gtctttggat atactacagc gatggctatt gaggagtatc 120
ctgaggcatg ggggtcaggg gttgaggtct tggtgagtgt tttagtgggg ttagcgatgg 180
aggtaggatt ggtgctgtgg gtgaaagant atgatggggt ggtggttgtg gtaaacttta 240
atagtgtagg aagctgaata atttatgaag gagaggggtc agggttgatt cgggaggatc 300
ctattggtgc gggggctttg tatgattatg ggcgttgatt agtantaatt actggttgaa 360
cattgtttgt tggtgtatat attgnaattg agattgctcg ggggaatang ttatgtgatt 420
aggaataggg ttangatgag tgggaagaaa aaaagaaagg aantaaaagt ttaattattc 480
cctttttggg ttgaagngat natggaaggg gaaaatttgg gccttgaaat tgtttaagta 540
atacttttct aataaggtaa gtctagaaga atagggcngg ttttggtctt aaaaaggcta 600
aaaggggatt ggcggggtgg atccncccc 628

<210> SEQ ID NO 506
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 506
acggtagaac tgctattatt catcctatgt gggtaattga ggagtatgct aagattttgc 60
cgtagctggg tttggtttaa tccacctcaa ctgcctgcta tgatggataa gattgagaga 120
gtggggagaa ggcttacgtt cagtgaggga gagatttggt atatgattga gatgggggct 180
agtttttgtc atgtgagaag aagcaggccg gatgtcagag gggtgccttg ggtaacctct 240
gggactcaga agtgaaaggg ggctattcct agttttattg ctatagccat tatgattatt 300
aatgatgagt attgattggt agtattggtt atggttcatt gccggagaag tatattgttg 360

-continued

```
aagaggatag ctattagaag gattatggat gccgttgctt gcctgaagaa atacttgatg    420

gcagcttctg tggaaccaag gtttattttt ttggntagaa ctggaataaa acctacatgt    480

ttatttctan gccactcagg taaaaaatca tgcnaactta acccttgata atgtgcctcc    540

aaaatgtaaa aaaataacgg ttggcccggg ataatcccgt ncttggccga ccccctaggn    600

aattcccccc tg                                                        612
```

<210> SEQ ID NO 507
<211> LENGTH: 632
<212> TYPE: DNA
<213> ORGANISM: Homo sapiens
<220> FEATURE:
<221> NAME/KEY: misc_feature
<222> LOCATION: (1)...(632)
<223> OTHER INFORMATION: n = A,T,C or G

<400> SEQUENCE: 507

```
ggtactacgt tgtagcccac ttccactatg tcctatcaat aggagctgta tttgccatca     60

taggaggctt cattcactga tttcccctat tctcaggcta caccctagac caaacctacg    120

ccaaaatcca tttcactatc atattcatcg gcgtaaatct aactttcttc ccacaacact    180

ttctcggcct atccggaatg ccccgacgtt actcggacta ccccgatgca tacaccacat    240

gaaacatcct atcatctgta ggctcattca tttctctaac agcagtaata ttaataattt    300

tcatgatttg agaagccttc gcttcgaagc gaaaagtcct aatagtagaa gaaccctcca    360

taaacctgga gtgactatat ggatgccccc caccctacca cacattcgaa gaacccgtat    420

acataaaatc tagacaaaaa aggaaggaat cgaacccccc aaactgggtt nagccaaccc    480

catgggcttc acgacttttt tataaaaaaa aaaaaaaaaa aaaagtcctg gcccgggngg    540

cggtcanggn gaaattcaac nactgggngg cggtctaang ggtccaactc gggnccaacc    600

tgggggaaaa tgggaaagtg gttcctgggg aa                                  632
```

<210> SEQ ID NO 508
<211> LENGTH: 336
<212> TYPE: DNA
<213> ORGANISM: Homo sapiens
<220> FEATURE:
<221> NAME/KEY: misc_feature
<222> LOCATION: (1)...(336)
<223> OTHER INFORMATION: n = A,T,C or G

<400> SEQUENCE: 508

```
cggtcctcta atgctgctcn cccggccgca ntgtgattgg atatcttgca gaattcgccc     60

ttagcgtggt cgccgggccg aggtacaact tccaaaaagg agacattgga gaanaaccaa    120

gctgggtcta taaggaattg cacatgagat ggcacacata tttatgctgt ctgaaggnca    180

cgatcatgtt accatatcaa gctgaaaatg tcaccactat ctggagattt cgaccgtgtt    240

ttcctctctg aatctgttat gaacacnttg gttggctgga ttcantaata aatatgtaag    300

gcctttcttt tcaaaaaaaa aaaaaaaaaa aaaagt                              336
```

<210> SEQ ID NO 509
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G -continued

<400> SEQUENCE: 509
ggtacttttt tttttttttt ttttttttta tagatacaat tggcttttat ttgtgattca 60
tgagtcaggg cagtttccat tctgcaaaat atagtgatag ctcctactgg gcaatacaac 120
agtanaacag tgggttttgt aaaatgggaa tccaggaaca gaagaatata aataaattga 180
tttaaataaa ctgattggtt aatttcagaa tacttcatat tactttttc taagagttaa 240 agcagaaagg actttcttac tgtgctgact canacagcct ggactctcat gtttttagga 300
aaattttgct gttctgggat ctacctgctt cctcatgttt cagtgngagt atatggcatt 360
taacatgact ggctccattc tggagtccca ggctgtccct aaatgagaag ttgactaaac 420
ataaggnatt aacactactg ncaggtacca tcattttggc ttncatcatt catanggtat 480
gatgncccnc naatcatacc tttatttgag tttttgncat tccnncccaa aaaaaaaatt 540
ttgaanttta ccaaaggntg catgccacnt ttaaagggtt anaaaatcnc cccnccnggn 600
actaatnttg ggccatcngn nggc 624

<210> SEQ ID NO 510
<211> LENGTH: 619
<212> TYPE: DNA
<213> ORGANISM: Homo sapiens
<220> FEATURE:
<221> NAME/KEY: misc_feature
<222> LOCATION: (1)...(619)
<223> OTHER INFORMATION: n = A,T,C or G

<400> SEQUENCE: 510
acggatgcta cttgtccaat gatggtaaaa gggtagctta ctggttgtcc tccgattcag 60
gttagaatga ggaggtctgc ggctaggagt caataaagtg attggcttag tgggcgaaat 120
attatgcttt gttgtttgga tatatggagg atggggatta ttgctaggat gaggatggat 180
agtaataggg caaggacgcc tcctagtttg ttagggacgg atcggagaat tgtgtaggcc 240
aataggaaat atcattcggg cttgatgtgg ggaggggtgt ttaangggtt ggctagggta 300
taattgtctg ggtcccctaa gaggtctggt gagaatagtg ttaatgtcat taangagaga 360
aagaaaaaaa ataagcccga gggcgtcttt gattgtgtan taaaggtgga angtgatttt 420
atcngaatgg gaagtgattn ctaaggggtt ggtttgatcc ctttcgtgcc aaaataagaa 480
gnggaatgct gctagggctc cataatgaag gcaanataaa atgaaagnaa aaaatctgta 540
aggnnggact gctactaata ncctcccaaa tcttgaacaa gntttnccaa ttntggatgg 600
nggtataant tnaattcnn 619

<210> SEQ ID NO 511
<211> LENGTH: 634
<212> TYPE: DNA
<213> ORGANISM: Homo sapiens
<220> FEATURE:
<221> NAME/KEY: misc_feature
<222> LOCATION: (1)...(634)
<223> OTHER INFORMATION: n = A,T,C or G

<400> SEQUENCE: 511
cgaggacgcg gggagatggc ctagaagcaa tgatagccat cactgagaac acctagcacc 60
caatcttggt tcctaatacc attctcccat caaaggaacc agagatcctt ggagaaatgg 120
ttaaggaatg aggcaggaaa tatacaagat aagcctggag catcttatag ctctagaaag 180
taagaaagta cctgcctatt ttagaatcct agagaacatt tcattgtaag aaactagccc 240
attatttaag tgtccacagt atttttcatt tcagtggtcc aagatgcgaa ggtttccaga 300

-continued

```
cacaatcttg ttctctaata ctgctccagg tgggatatca attctgtccc catgatttgc    360

aatgatgata cccgttccct ttaatgaaac attttttnca aatgtcacat cttctgaaac    420

tgngaggnga tccaattcaa gcatatctgg gntactttcc aaatcntctt agataatctt    480

gaaccttcgt aaaagaactg gctaattaan ccanggccct gnaggaaatt ccccttttcc    540

tcattggcag anancctgca ttaaantntt aagggttgnn ttnccnccan aaactgtgtg    600

gtttgnaggc aaaaaacggt cttgggcatt ancc                                634
```

<210> SEQ ID NO 512
<211> LENGTH: 623
<212> TYPE: DNA
<213> ORGANISM: Homo sapiens
<220> FEATURE:
<221> NAME/KEY: misc_feature
<222> LOCATION: (1)...(623)
<223> OTHER INFORMATION: n = A,T,C or G

<400> SEQUENCE: 512

```
ggtacgcggg cattgttcat gactttaaca agaaacttac agcctattta gatcttaacc     60

tggataagtg ctatgtgatc cctctgaaca cttccattgt tatgccaccc agaaacctac    120

tggagttact tattaacatc aaggctggaa cctatttgcc tcagtcctat ctgattcatg    180

agcacatggt tattactgat cgcattgaaa acattgatca cctgggtttc tttatttatc    240

gactgtgtca tgacaaggaa acttacaaac tgcaacgcag agaaactatt aaaggtattc    300

agaaacgtga agccagcaat tgtttcgcaa ttcggcattt tgaaaacaaa tttgccgtgg    360

aaactttaat ttgtcttgaa cagtcaagaa aaacattatt gaggaaaatt aatatcacag    420

catacccccc cctttacatt ttgngcagng gatatttttt aaagcttctt tnatgtaagt    480

agcaacangg ntttactatc tttcatttca taaatcaatt aaancnttnc ctcaaaaaaa    540

aaaaaaaaaa aaaaatacct ncccggcggc gctccaaagg ggaattcaan caccggnggc    600

cgtctttggg accaacncgg gcc                                            623
```

<210> SEQ ID NO 513
<211> LENGTH: 623
<212> TYPE: DNA
<213> ORGANISM: Homo sapiens
<220> FEATURE:
<221> NAME/KEY: misc_feature
<222> LOCATION: (1)...(623)
<223> OTHER INFORMATION: n = A,T,C or G

<400> SEQUENCE: 513

```
actgccctct ccagatcagc agttcaggag agcacaggag gcaaaacaca gattgctggg     60

cttattggtg ccatcatcgt gctgattgtc gttctagcca ttggatttct cctggcacct    120

ctacaaaagt ccgtcctggc agctttagca ttgggaaact taaagggaat gctgatgcag    180

tttgctgaaa taggcagatt gtggcgaaag gacaaatatg attgtttaat ttggatcatg    240

accttcatct tcaccattgt cctgggactc gggttaggcc tggcagctag tgtggcattt    300

caactgctaa ccatcgtgtt caggacccaa tttccaaaat gcagcacgct ggctaatatt    360

ggaagaacca acatctataa gaataaaaaa gattattatg atatgtatga gccagaagga    420

gtgaaaattt cagatgtcca tcttctatct actttgcnaa cattggnttc tttaggcngg    480

aacttatcga tgctggtngg ctttagtnca ctttgnaatt tacgcaagcc ccacaaactt    540

tgaggaaatc ccaaactgcn aancangntt nttcagtggt acccaanggt tttttttcct    600
```

-continued

```
tggcccgacn ccctangnga atn                                          623


<210> SEQ ID NO 514
<211> LENGTH: 627
<212> TYPE: DNA
<213> ORGANISM: Homo sapiens
<220> FEATURE:
<221> NAME/KEY: misc_feature
<222> LOCATION: (1)...(627)
<223> OTHER INFORMATION: n = A,T,C or G

<400> SEQUENCE: 514

ggtactcatg cccgactgtc taccaggcac acagactttg aggagagggc gtatgtcgtc     60

ttgatccgca tcaatgatgg gggtcggcca cccttggaag gcattgtttc tttaccagtt    120

acattctgca gttgtgtgga aggaagttgt ttccggccag caggtcacca gactgggata    180

cccactgtgg gcatggcagt tggtatactg ctgaccaccc ttctggtgat tggtataatt    240

ttagcagttg tgtttatccg cataaagaag gataaaggca aagataatgt tgaaagtgct    300

caagcatctg aagtcaaacc tctgagaagc tgaatttgaa aaggaatgtt tgaatttata    360

tagcaagtgc tatttcagca acaaccatct catcctatta cttttcatct aacgtgcatt    420

ataatttttt aaacagatat tccctcttgt cctttaatat ttgctaaata tttctttttt    480

gangnggagt cttgctctgt cgnccaagct ggantacctg ncccggccgg ccgtcaaagg    540

cgaattcaac aactggcggc cgtactaatg gatcgacctc ggaccaactt ggggaacatg    600

gcanactngt tcctgngnaa aggatcc                                      627


<210> SEQ ID NO 515
<211> LENGTH: 605
<212> TYPE: DNA
<213> ORGANISM: Homo sapiens
<220> FEATURE:
<221> NAME/KEY: misc_feature
<222> LOCATION: (1)...(605)
<223> OTHER INFORMATION: n = A,T,C or G

<400> SEQUENCE: 515

accattggtg gccaattgat ttgatggtaa gggagggatc gttgacctcg tctgttatgt     60

aaaggatgcc gtanggatgg gagggcgatg aggactagga tgatggcggg caggatagtt    120

cagacggttt ctatttcctg agcgtctgag atgttagtat tagttaagtt ttgttgtgag    180

tgttaggaaa agggcataca ggactaggaa gcagataagg aaaatgatta tgagggccgt    240

gatcatgaaa ggtgataagc tcttctatga taggggaaag taancgtctt gtanacctac    300

ttgcgctgca tgtgccatcc cgccgtaccc taacccgtgc aaaggtagca taatcacttg    360

ttccttaatt aagggacctg tatgaatggc ttcaccaggg ttcaactgtc tcttactttt    420

aaccagtgaa attgacctgc ccctgaanag gcggcnttac acaccagacg agaaaacctt    480

tggagcttaa ttattatcca acatacctng ccggaccccc taaggcgaat tccaccactt    540

gcggcgtcta tggatccact cggaccactt ggggaaaagg ctactgtcct ggnaatgttt    600

cctcn                                                              605


<210> SEQ ID NO 516
<211> LENGTH: 464
<212> TYPE: DNA
<213> ORGANISM: Homo sapiens
<220> FEATURE:
<221> NAME/KEY: misc_feature
<222> LOCATION: (1)...(464)
<223> OTHER INFORMATION: n = A,T,C or G
```

-continued

<400> SEQUENCE: 516
ggtacaacta atccgtgaca aattaccaga ttaattttac tttatttctt caggcctggg 60
gtttttcgat gagttcaaat ttgggatctt caaatttgaa ggtgggaaat gtattcatgt 120
ctgcattacc aaacatttgc ttgagcttaa aaagctccct ctccagctct tgctgatact 180
ctgaactagc atcaacaggt cctccagatg tctgtcgctt agatttgtat tctctaatct 240
tgtccacaaa gagtttctgt ataggatcaa gttccttatt aaatgccact gctgtaacac 300
caatgttcct ccgcaaatgg actgagacgg ctgaccgaat gacagaggag aacctgaaga 360
gcctctgaag aatcatgctg attcttgcac tcagtcccga gctgncaaag ccttcgccgc 420
caccaccttc gntctacccc cgcgtacctg cccggcgggc gctc 464

<210> SEQ ID NO 517
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 517
acccggagca cggagatctc gccggcttta cgttcacctc ggtgtctgca gcaccctccg 60
cttcctctcc taggcgacga gacccagtgg ctagaagttc accatgtcta ttctcaagat 120
ccatgccagg gagatctttg actctcgcag gaatcccact gttgaggttg atctcttcac 180
ctcaaaaggt ctcttcagag ctgctgtgcc cagtggtgct tcaactggta tctatgaggc 240
cctagagctc cgggacaatg ataagactcg ctatatgggg aagggtgtct caaaggctgt 300
tgagcacatc aataaaacta ttgcgcctgc cctggttagc aagaaactga acgtcacaga 360
acaagagaag attgacaaac tgatgatcga gatggatgga acagaaaata aatctaagtt 420
tggtgcgaac gccattctgg gggtgtcctt tgccgtctgc naaactggtg ccgttgagaa 480
gggggtcccc tgtccttggc cggacacnct aaggcgaatt ccacacactg cggccgtact 540
atggatcgac tcggnaccaa cttgggtaat atgggcatac tggtnctggn gaaatgtttc 600
cctccaatcc a 611

<210> SEQ ID NO 518
<211> LENGTH: 435
<212> TYPE: DNA
<213> ORGANISM: Homo sapiens
<220> FEATURE:
<221> NAME/KEY: misc_feature
<222> LOCATION: (1)...(435)
<223> OTHER INFORMATION: n = A,T,C or G

<400> SEQUENCE: 518
cgaggtactt tntttttttt tttttttttt ttttaagagg aaaacccggt aatgatgtcg 60
gggttgaggg ataggaggag aatgggggat aggtgtatga acatgagggt gttttctcgt 120
gtgaatgagg gttttatgtt gttaatgtgg tgggtgagtg agccccattg tgttgtggta 180
aatatgtaga gggagtatag ggctgtgact agtatgttga gtcctgtaag taggagagtg 240
atatttgatc aggagaacgt ggttactagc acagagagtt ctcccagtag gttaatagtg 300
gggggtaagg cgaggttagc gaggcttgct agaagtcatc aaaaagctat tagtgggagt 360
agagtttgaa gtccttgaaa gaggattatg atgccactgt gaatgccttc ctagtttgag 420

-continued

```
tttgctagcc cgcgt                                                   435


<210> SEQ ID NO 519
<211> LENGTH: 407
<212> TYPE: DNA
<213> ORGANISM: Homo sapiens
<220> FEATURE:
<221> NAME/KEY: misc_feature
<222> LOCATION: (1)...(407)
<223> OTHER INFORMATION: n = A,T,C or G

<400> SEQUENCE: 519

actttntttt tttttttttt tttttttttt ncagctttgc aaccatactc cccccggaac     60

ccaaagactt tggtttcccg gaagctgccc ggcgggtcat gggaataacg ccgccgcatc    120

gccggtcggc atcgtttatg gtcggaacta cnacggtntn tgatcgtntt cnaacctccg    180

actttcgttc ttgattaatg aaaacattct tggcaaatgc tttcgctctg gtccgtnttg    240

cgccggtcca anaatttcac ctctagcggc gcaatacnaa tgccccccggc cgtccctctt    300

aatcatggcc tcagttccga aaaccaacaa aataaaaccg cggtcctatt ccattatgcc    360

tagctgcggt atccaggcgg tccccggtac ctnggccgng accacgc                  407


<210> SEQ ID NO 520
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G

<400> SEQUENCE: 520

accttctggg gcatacaaca tggcagcagg gcctcgggaa gaggggtagg aggaccgagc     60

agcattctct gtagaggaag acaggaaagg agaccctctt ggcacacatt tatggagggt    120

tgtccctgaa gagaagggca ggtgggagag gttccctgtt acttaagaga aggcaccagt    180

ggcaaagagc acaatgaaga ggatgatgat aaaaacaatc acgcagataa ggacaatcat    240

cttcacgttc ttccaccaga attttcgagc caccttctgc gatgtcgtct tgaagtgctc    300

agatgtggct tccagatcct ctgtcttgtt gcggagatgt tccaagtttt ccccccgggc    360

caggatccgc tccacattct gggtcataat attcttaact ccctccacct cactttgcag    420

gttccgcaca cgatcatttc cttcaccttc actggcttnc tncatgtctc aaagcaccca    480

gccggcagta agtgaatcgc ctatcggntt cttccaggng ggcctanttn anttctggtg    540

gtcaactttc cccgcgtact tgggcggacc ccctaagggg aattcactgg cggccgtctt    600

tggatccacc cgn                                                       613


<210> SEQ ID NO 521
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 521

actgcagtaa aagctttaac aggtggaatt gcccacttat tcaaacagaa taaggttgtt     60

catgtcaatg gatatggaaa gataactggc aaaaatcaag tcactgctac gaaagctgat    120

ggcggcactc aggttattga tacaaagaac attcttatag ccacgggttc agaagttact    180
```

-continued cctttttcctg gaatcacgat agatgaagat acaatagtgt catctacagg tgctttatct 240
ttaaaaaaag ttccagaaaa gatggttgtt attggtgcag gagtaatagg tgtagaattg 300
ggttcagttt ggcaaagact tggtgcagat gtgacagcag ttgaattttt angtcatgta 360
ggtggagttg gaattgatat ggagatatct aaaaactttc aacgcatcct tcaaaaacag 420
gggtttaaat ttaaattgaa tacaanggta ctggtgctcc aagaagcana tggaaaaatt 480
gatgttctat tgaanctctt ttgngggaaa gctgaantnt acttggatgn cctnggccgn 540
acncnctagg caatccncca ctggngccnt ntttggtccn cctggtccaa ctgggnnann 600 nggctn 606

<210> SEQ ID NO 522
<211> LENGTH: 617
<212> TYPE: DNA
<213> ORGANISM: Homo sapiens
<220> FEATURE:
<221> NAME/KEY: misc_feature
<222> LOCATION: (1)...(617)
<223> OTHER INFORMATION: n = A,T,C or G

<400> SEQUENCE: 522
acttgcgctt actttgtagc cttcatcagg gtttgctgaa gatggcggta tataggctga 60
gcaagaggtg gtgaggttga tcggggttta tcgattacag aacaggctcc tctagaggga 120
tatgaagcac cgccaggtcc tttgagtttt aagctgtggc tcgtagtgtt ctggcgagca 180
gttttgttga tttaactgtt gaggtttagg gctaagcata gtggggtatc taatcccagt 240
ttgggtctta gctattgtgt gttcagatat gttaaagcca ctttcgtagt ctattttgtg 300
tcaactggag ttttttacaa ctcangtgag ttttagcttt attggggagg gggtgatcta 360
aaacactctt tacgccggct tctattgact tgggttaatc gtgtgacccg cggtggctgg 420
cacgaaattg accaaccctg gggttagtat aacttaatta aactttcntt attgctnaag 480
gtaatcctgg tggttnccct gggggngtng ntaggctaaa cgtttgaacc tcattctgcg 540
gcctganctt ggccctttta tcgggggatt aaaaggggac tncttgaacn gggngcttct 600
tggnaaatta taaaaca 617

<210> SEQ ID NO 523
<211> LENGTH: 608
<212> TYPE: DNA
<213> ORGANISM: Homo sapiens
<220> FEATURE:
<221> NAME/KEY: misc_feature
<222> LOCATION: (1)...(608)
<223> OTHER INFORMATION: n = A,T,C or G

<400> SEQUENCE: 523
cgaggtactt tttttttttt tttttttttt ttttggaana agtaagcctt tatttccttg 60
ttttgcaaat aaaactggct aagttggttg ctttttggtg attaagtcaa aganaccaaa 120
tcccatatcc tcgtccgact cctccgactc ttccttggct tcaaccttan ctggggctgc 180
agcagcagca ggagcagctg tggtggtagc aaccacaggg gcagcancca caaaggcaga 240
tggatcaacc aanaaggcct tgacctttttc aacaagtggg aaggngtaat ccgtctccca 300
aacaaagtca ggactcgttt gtctcttcaa aaaaaaaaag cganggctcg catttggtcc 360
cctttggaca ttttgcaact cttcaatggg gttncattgg tnggtgatgg tataaacctt 420
tgangnacct gcccggccgg ccgtcaaang gcaaattcac ccactggcgg ccgttctatg 480

-continued

```
gatccnaccc ggncccaact tgggtaatat ggcanactgt tcctggggga aatgtntccc    540

tnaaattccc acaaanacaa nccgaaccta aangtaancn gggggccaag agggcnaccn    600

ccttattg                                                             608


<210> SEQ ID NO 524
<211> LENGTH: 398
<212> TYPE: DNA
<213> ORGANISM: Homo sapiens

<400> SEQUENCE: 524

ggtacaggat cctctaaaga gaccgcctgg ctgggtgctc aaaccacatg ggccgaccca     60

aaagacgtca aaaccaagag ctgctcagga ggcactaaat gttgacggtc ttggccggct    120

tcacatcctc aatttcagca gacagccagc ggtaagtgcg atgacgccgc agcacctcaa    180

tggccttgag ttccagtggt gttgcctgaa taccaaggtc ttctaagcca ggcaggtgag    240

gcaatttcat gtctgtgatg tgcatccgct ccactttatc ccttgttatc cagggctcaa    300

atgggcttat ttcaaagact cttgctaccc atcgataggc aaaaagcggc aaggggaatg    360

ggaggaacaa tctgtgagcc acaacaaaga tgtacctg                            398


<210> SEQ ID NO 525
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 525

actgttcctg ttggcccgag tggagactgg tgttctcaaa cccggtatgg tggtcacctt     60

tgctccagtc aacgttacaa cggaagtaaa atctgtcgaa atgcaccatg aagctttgag    120

tgaagctctt cctggggaca atgtgggctt caatgtcaag aatgtgtctg tcaaggatgt    180

tcgtcgtggc aaccgttgct ggtgacagca aaaatgaccc accaatggaa gcagctggct    240

tcactgctca ggtgattatc ctgaaccatc caggccaaat aagcgccggc tatgcccctg    300

tattggattg ccacacggct cacattgcat gcaagtttgc tgagctgaag gaaaagattg    360

atcgccgttc tggtaaaaag ctggaaaatg gccctaaatt cttgaaatct ggtgatgctg    420

ccattggtga tatgggtcct ggcaagccca tgtgtgtttg agagcttctc aaactattca    480

ccttgggtcc tttgctgtcg tgatatgaaa aaacagtgcg ggggtgtatc aaacatggac    540

aaaagnttnt tgacttgcag gtaccaattt nccaaaacta aaaggtnaan aaatttncca    600

aaccgcc                                                              607


<210> SEQ ID NO 526
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 526

cgaggtacgc gggggaagct ctgtttggtg ctttggatcc atttccatcg gtccttacag     60

ccgctcgtca gactccagca gccaagatgg tgaagcagat cgagagcaag actgcttttc    120

aggaagcctt ggacgctgca ggtgataaac ttgtagtagt tgacttctca gccacgtggt    180
```

-continued

```
gtgggccttg caaaatgatc aagcctttct ttcattccct ctctgaaaag tattccaacg    240

tgatattcct tgaagtagat gtggatgact gtcaggatgt tgcttcagag tgtgaagtca    300

aatgcatgcc aacattccag ttttttaaga agggacaaaa ggtgggtgaa ttttctggag    360

ccaataagga aaagcttgaa gccaccatta atgaattagt ctaatcatgt tttctgaaaa    420

tataaccagc ccattggcta tttaaaactt gtaatttttt taatttacca aaatntaaaa    480

tntgaagacn taacccagtt gncatctgcg tgacaatnaa acattaatgc tacactttta    540

aaaaaaaaaa aaaaaaaaaa gtcctgccng cggccctcaa aggggaattc cacacctggg    600

ggccgtcttt nggncccacc cgnn                                           624
```

```
<210> SEQ ID NO 527
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 527

acagagtgac actgaacaga tcacaaagca cgagaaacat tagttctctc cctccccagc     60

gtctccttcg tctccctggt tttccgatgt ccacagagtg agattgtccc taagtaactg    120

catgatcaga gtgctgtctt tataagactc ttcattcagc gtatccaatt cagcaattgc    180

ttcatcaaat gccgtttttg ccaggctaca ggccttttca ggagagttta gaatctcata    240

gtaaaagact gagaaattta gtgccagacc aagacgaatt gggtgtgtag gctgcatttc    300

tttcttacta atttcaaatg cttcctggta agcctgctgg gagttcgaca cagtggtttg    360

tttgttgctc cagatgccac ttcagaaaga tcctaaaata atctcctttc attttcaagt    420

agaacacctt actttctggt tgtgtagcat tgggaataaa atatttgtcc acagcttcag    480

aacatcattg cagatgtcct gcagtctggc tntatctttt acggnacctc ggccgggaca    540

ccctanggcg aattccacac ctggcggccg tctantggac ngctnggcca cttgggnana    600

tggctactgt t                                                         611
```

```
<210> SEQ ID NO 528
<211> LENGTH: 615
<212> TYPE: DNA
<213> ORGANISM: Homo sapiens
<220> FEATURE:
<221> NAME/KEY: misc_feature
<222> LOCATION: (1)...(615)
<223> OTHER INFORMATION: n = A,T,C or G

<400> SEQUENCE: 528

ggtacttttt tttttttttt tttttttga gacggagtct tgttcagctg cccaggctgg     60

agtgcagtgg ctcgatcttc gctcactgca accaccgtct cctgggttca agcgattctc    120

ctgtctcagc ctcccaagta gctgggatta caggccacca ccatcatgcc cggctaattt    180

ttgtatattg gtagagacgg agtttcacta tgttgggcag gctggtcttg aactcctcac    240

ctcaggtgat ccgcccgtct tggcctccca aagtgctagg attacaggcg taagccacca    300

tgcctggcca gatgatgtat ttaaatatca taccaaactc tgtgtattta tataaagaaa    360

gactggtaaa agacttcctn attttaaaaa aaaccaaaac ccaaaccaaa aaaaactta    420

cccttaccat tgntgcatat tgtgcagtat aaaacacaca cttattngga catganaaaa    480
```

-continued

```
ccgnaagaaa gncccgggta aactggactt tgccgccttt aaaaataaaa tcnaataagn    540

gccttgaggc cctttttcaa tgcaattttt taacccggac ctgccnggng gcggtaaggg    600

naatccancn ctggn                                                     615
```

<210> SEQ ID NO 529
<211> LENGTH: 352
<212> TYPE: DNA
<213> ORGANISM: Homo sapiens
<220> FEATURE:
<221> NAME/KEY: misc_feature
<222> LOCATION: (1)...(352)
<223> OTHER INFORMATION: n = A,T,C or G

<400> SEQUENCE: 529

```
cgaggtactt tntttttttt tttttttttt tttttgggaa aagtcatgga ggccatgggg     60

ttggcttgaa accagctttg gggggttcga ttccttcctt ttttgtctan attttatgta    120

tacgggttct tcgaatgtgt ggtagggtgg ggggcatcca tatagtcact ccaggtttat    180

ggagggttct tctactatta ggacttttcg cttcgaagcg aaggcttctc aaatcatgaa    240

aattattaat attactgctg ttagagaaat gaatgagcct acagatgata ggatgtttca    300

tgtggtgtat gcatcggggt agtccgagta acgtcggggc attcccccgc gt            352
```

<210> SEQ ID NO 530
<211> LENGTH: 769
<212> TYPE: DNA
<213> ORGANISM: Homo sapiens
<220> FEATURE:
<221> NAME/KEY: misc_feature
<222> LOCATION: (1)...(769)
<223> OTHER INFORMATION: n = A,T,C or G

<400> SEQUENCE: 530

```
ggtactgcat agattaaaga aataaactgc agtaaagcca ctcgtaagga atgaacgcca     60

ttgccaatga taatcctctg cacataggtg gaaatagcaa agaagtatag ttgcttcaga    120

acaggtaata accaaaatga taaacaccag aaataggaag ccaaacatgt aatacatctg    180

gtgtgaccaa atactattca gaatgaagaa aagttgtata aagatgcagc caaagggcaa    240

aatccctccc atgataatac caggcaaggg cttcgtgtag aacgactgtt caggaatctg    300

acngtggaat ctgattggtt cgaactgggt gttcaatggc atcttcttaa aaccaangta    360

tgcaccaata aacgtcnnag gcacagatat gtanaccaaa gggccaatat ggcaancagt    420

gtncccaaaa gaaatactgt tgganatcct ctncccagag gtcagattnt tattaagaat    480

cnccccgcgt cttttttttg tttttttttt gctccacttt nnggtaaann acntttnttt    540

aaaaatgttt aantctantt cctaattccc atnttctttn gctncnnnnc tgctggnggn    600

ctttaaggga antcnccnnt ggnggcgtcn atganccact tgnnactggn tantagcnac    660

gttcgggang ttcccncntt ctaatatccg gnagtaannc ggctttgncn cctantggnn    720

cngcttttcg aacntgcctn anannntccg gaggtgtatn ttcttctnn                769
```

<210> SEQ ID NO 531
<211> LENGTH: 777
<212> TYPE: DNA
<213> ORGANISM: Homo sapiens
<220> FEATURE:
<221> NAME/KEY: misc_feature
<222> LOCATION: (1)...(777)
<223> OTHER INFORMATION: n = A,T,C or G

<400> SEQUENCE: 531

-continued

```
cgaggtactt tttttttttt tttttttttt tgttttttttt tttttttctt cagctaaaac      60

agcggaagag gtgatttatt atatggttgt tacactcggc cacaaataaa cacagaaata     120

gtccanaatg tcacaggtcc aggacagagg accaacatgg gcattttgtt tatgagcaag     180

gtgggtctna naggtgatcg gcgatcagag ggcgatgaag ttctagatcc attgagacaa     240

gctctagaca gtagcatgca gtcccacaac ttgtctccaa agattcaggt ttactcacgt     300

catccagcan agaatggaaa gtcaaatttc ctgaattgct atgtgtctgg gtttcatcca     360

tccgacattg aagttgactt actgaanaat ggagagagaa ttgaaaaant nggacattca     420

taactgnntt tcancaagga ctggtctttc tatctcttgg ncttnntttt tcttntattt     480

tttttntaca tngggcctta ctttaaaaac atacntttcc nnnttacncn tggatgccaa     540

tngatttcna nanatttccn agnggaatcc tttngttatt nttaaaantt gggatctntn     600

gccancactt ggctaantnt taccnncttt nggaatngtc ntatgntcat tnttggaaat     660

tncccccctn angnntttct ttnngngnta aaaattntta atnnttaaat tntttttcna     720

anattnntca aatactaana ntnntnnggg nttanannaa tnntgtanat gggnnng        777
```

```
<210> SEQ ID NO 532
<211> LENGTH: 764
<212> TYPE: DNA
<213> ORGANISM: Homo sapiens
<220> FEATURE:
<221> NAME/KEY: misc_feature
<222> LOCATION: (1)...(764)
<223> OTHER INFORMATION: n = A,T,C or G

<400> SEQUENCE: 532

actttacaag atagattgta taagaagcca aataatgaaa gcctagaaaa aactaattta      60

tacttatctg aaggttacaa attagacttt taaattttct ttgtagttgg tggtgtttga     120

gggttggcta gaaatgaaag cctggatttt gtgccatgtt tgtaatatag tttgttcctt     180

gatcaaataa tcagagaaaa gaaacttaaa gatctttgtc tgtgaagaag aaaattatct     240

ccctagttca atctgtagtg aaataagact acagaaggca ttgtttttc cttttttattt     300

tntgnattat atatttttct taaatatgtt ttattgtctt ctctaagcaa aaagttctta     360

ataaacatag tatttctctc tgcgtcctat ttcattagtg aagacatagt tcacctaaaa     420

tggcatnctg ctctgaatct agctttttat aaatggctat gtttttgatg atatgtcaca     480

ttcaaaatgg cctaattaaa tgtgttaaat gnaatggcac tcttataacc ttaaaataac     540

canaattaac cctccaaaaa aanaaaaaaa aaaaaggcct tggccgacnc ntangngant     600

caccnctgng gcntcatgga cncttggcca cttgngaann nggtnangnt ccggganatt     660

tccccatncc aattcancgg acatagnnac cnggccnaag ngnnccantg nngnnnnnct     720

tnnngaacng gccctnaacn cccggggngg tngttcnccc tcnc                      764
```

```
<210> SEQ ID NO 533
<211> LENGTH: 773
<212> TYPE: DNA
<213> ORGANISM: Homo sapiens
<220> FEATURE:
<221> NAME/KEY: misc_feature
<222> LOCATION: (1)...(773)
<223> OTHER INFORMATION: n = A,T,C or G

<400> SEQUENCE: 533

cgaggtactt tttttttttt ttttacagat acaattggct tttatttgtg attcatgagt      60
```

-continued

```
cagggcagtt tccattctgc aaaatatagt gatagctcct actgggcaat acaacagtag    120

aacagtgggt tttgtaaaat gggaatccag gaacagaaga atataaataa attgatttaa    180

ataaactgat tggttaattt cagaatactt catattactt ttttctaaga gttaaagcag    240

aaaggacttt cttactgtgc tgactcagac agcctggact ctcatgtttt taggaaaatt    300

ttgtctgttc tgggatctac ctgcttcctc atgttcagtg tgagtatatg gcatttagca    360

tgactggtcc attctggagt caccaggctt gcacctaaat gagagttgac taancatagg    420

cnttaacact actgcagtac catcatttng acttcatcat catanggtat gatgncntct    480

aatnttncat tatttgagtt tggcattcag ccacgagaga atattgcctt tgacaatgnt    540

gcatgcaact ttaaaggttt tagatncgcc nccnggnact atttnngaaa tcgggggtcc    600

cccnanttgg agtttnacct ggcngaccnn tgacnaccat taaggantgt tagantnccc    660

ttgaaccccc tttacaccnt ttgnatttcc cggcntaacc ccgggcnnta agggatccnt    720

tggcntnngg cccngcnatn gaagnacntt ngannacgcc tccncaccan nng           773
```

<210> SEQ ID NO 534
<211> LENGTH: 730
<212> TYPE: DNA
<213> ORGANISM: Homo sapiens
<220> FEATURE:
<221> NAME/KEY: misc_feature
<222> LOCATION: (1)...(730)
<223> OTHER INFORMATION: n = A,T,C or G

<400> SEQUENCE: 534

```
acacagacaa atttatgcga ccagggcaga ggctgtagat gattcatatt tccaattggg     60

agggaggact cgcttggtct tataatatcg agccaaacgg tgaatccggc tctctattag    120

aatcagacgg aatttagcat ccttatcctt tctgttcctc tcaagatgct ttcgaacagc    180

aactgctttc ttaattaaat ggtagagatc ttcaggaaga tcaggagcaa gtcccttaga    240

cttaagaatt cttaaaattt tattgcctgt cacaaaacgt acaaattgac caggctgttg    300

acggctgcct ccacgtcggt ggaataattc tgacgaatct gggagctcat ggttggttgg    360

caagaaggag ctaccacaaa aacngtgctg caggtccaga agcaggagat ggccgaaaaa    420

tgtcccgaag ttcaaccgag aggaaatcga ggcggccgag cttgaagaag tcccgattgt    480

tcgtcaacct gtgaacagaa caaccccgga ccgcnantgc ccggtnctgg ccggacacct    540

angggaatcn accctgnggc gtctangacc acttggccaa ctgggganntg gaaatntccg    600

ggaaagntcn tcaatcccaa ttaccgacna agaactgggc naagggtcnc atatgggcnc    660

gccttnnnga nctnccctta anncccccgga gggtgntggn tctcntctan nntnnngtgg    720

nggnnaanag                                                           730
```

<210> SEQ ID NO 535
<211> LENGTH: 809
<212> TYPE: DNA
<213> ORGANISM: Homo sapiens
<220> FEATURE:
<221> NAME/KEY: misc_feature
<222> LOCATION: (1)...(809)
<223> OTHER INFORMATION: n = A,T,C or G

<400> SEQUENCE: 535

```
gcgtggtcng cggccgaggt accaactgca gagccaggaa aactttgaag ccttcatgaa     60

ggcaatcggt ctgccggaag agctcatcca gaaggggaag gatgtcaagg gggtgtcgga    120

aatcgtgcag aatgggaagc acttcaagtt caccatcacc gctgggtcca aagtgatcca    180
```

-continued

```
aaacgaattc acggtggggg aggaatgtga gctggagaca atgacagggg ataaagtcaa    240
gacagtggtt canttggaag gtgacaataa actggtgaca actttcaaaa acatcaagtc    300
tgtgaccgaa ctcaacggng acataatcac caataccatg acattgggtg acattgtctt    360
caagagaatc agcangagaa tttaaacaag tctgcatttc atattatttt antgntgtaa    420
aattaatgta attaaagtga actttgttta aaaaaagann nntnntntaa atanaaaaaa    480
gtncctgcct ggcggccggt caaaggccaa ttccagcnac tngnggccnt actagtgatc    540
nactcgtcna acttgcgtaa nntggcatac ttgtnctngg taaatntatc cctcncatcn    600
ccaaattcnn ccgagcttaa atntaaactg gggcctatag gnncactcct tttggttgcn    660
ctgccnttnn acgaacttcg nccctttat antgcccccc ganagggtng tttggctttc    720
ntnntatatt ctctctctcc ttgnnggttt ttanggtngg tcatntgggn tctntanttt    780
agcttngaan ntantngntn tttnttnnt                                      809
```

<210> SEQ ID NO 536
<211> LENGTH: 755
<212> TYPE: DNA
<213> ORGANISM: Homo sapiens
<220> FEATURE:
<221> NAME/KEY: misc_feature
<222> LOCATION: (1)...(755)
<223> OTHER INFORMATION: n = A,T,C or G

<400> SEQUENCE: 536

```
actttttttt tttttttttt tttttttttt atgaggaaaa cccggtaatg atgtcggggt     60
tgagggatag gaggagaatg ggggataggt gtatgaacat gagggtgttt tctcgtgtga    120
atgagggttt tatgttgtta atgtggtggg tgagtgagcc ccattgtgtt gtggtaaata    180
tgtagaggga gtatagggct gtgactagta tgttgagtcc tgtaagtagg agagtgatat    240
ttgatcagga gaacgtggtt actagcacag agagttctcc cagtaggtta atagtggggg    300
gtaaggcgag gttagcgagg cttgctagaa gtcatcaaaa agctattant gggagtanag    360
tttgaagtcc ttgagagagg attatgatgc nacttgtaat gcnttcgant ttgagtttgc    420
tagcngaata nnatgaggat gtantccngg gccaatatna aaatactccc cgtnaacttn    480
aggggttnga taaaatgctg tctacccnng actttgccgn acaccttagg caattcanca    540
ctggngccgt ctnanggncc cacttggncc acnttggnga acatggcnnc ngtcntngga    600
aatgtttcnt caattcccnc ttcnaccgan tantgnaacn ggggcanaag cncccatatn    660
gtccctccct tctngaactt nnccnttaaa tncccccgga gggttnatgg ctttctctnc    720
taananntnt tnngnggnnt tcnataanna taann                               755
```

<210> SEQ ID NO 537
<211> LENGTH: 794
<212> TYPE: DNA
<213> ORGANISM: Homo sapiens
<220> FEATURE:
<221> NAME/KEY: misc_feature
<222> LOCATION: (1)...(794)
<223> OTHER INFORMATION: n = A,T,C or G

<400> SEQUENCE: 537

```
cgaggtacga aagggacaag agaaataagg cctacttcac aaagcgcctt cccccgtaaa     60
tgatatcatc tcaacttagt attataccca cacccaccca agaacagggt ttgttaaaaa    120
aaaaaaaaaa aaaaaaaaaa aaaaaagtac cttgactttg ttcacagcat gtagggtgat    180
```

-continued

```
gagcactcac aattgttgac taaaatgctg cttttaaaac ataggaaagt agaatggttg    240

agtgcaaatc catagcacaa gataaattga gctagttaag gcaaatcagg taaaatagtc    300

atgattctat gtaatgtaaa ccagaaaaaa taaatgttca tgatttcaag atgttatatt    360

aaagaaaaac tttaaaaatt attatatatt tatagcaaaa gttatcttaa atatgaattc    420

tgttgtaatt taatgctttt gaatacagag atntaaatga agtattatct gtaaaaatgt    480

atattagagt tgtgatacag agtatatttc attcanccat nttcatacta ataatatgga    540

tttaaanata tcctataaat tcnaattcaa nanaaannnt gntananaan aanggnctgn    600

cggcggcgca nggcaattca acaatgnggc gtctanggac nactggtcca cttgggaana    660

ggcaacttnc tgggaatgat ccttcattcc canntaccna gctanttaac nggggcaaag    720

ggcccnntta tgggnntngc ntntnnaant tgcccttaaa accccggngg gtgntggntc    780

tttnnntttn ngnt                                                      794
```

<210> SEQ ID NO 538
<211> LENGTH: 766
<212> TYPE: DNA
<213> ORGANISM: Homo sapiens
<220> FEATURE:
<221> NAME/KEY: misc_feature
<222> LOCATION: (1)...(766)
<223> OTHER INFORMATION: n = A,T,C or G

<400> SEQUENCE: 538

```
ggtacgcggg ggaaggcctt cctttttcgt ctgggctgcc aacatgccat ccagactgag     60

gaagacccgg aaacttaggg gccacgtgag ccacggccac ggccgcatag gcaagcaccg    120

gaagcacccc ggcggccgcg gtaatgctgg tggtctgcat caccaccgga tcaacttcga    180

caaataccac ccaggctact ttgggaaagt tggtatgaag cattaccact taaagaggaa    240

ccagagcttc tgcccaactg tcaaccttga caaattgtgg actttggtca gtgaacagac    300

acgggtgaat gctgctaaaa acaagactgg ggctgtccca tcattgatgt ggtgcgatcg    360

gctactacaa agttctggga aagggaaagc tccaaagcaa nctgtcatcg tgaaggccaa    420

atcttcacag aagagctgag gagaaaaata agantgttgg ggggcctgtg tctggtgctt    480

gaagcccatt ganggagttt aattaatgct actcttttga aaaaaanann aananaaaaa    540

gacctgcccg gcggcngtaa ggcaattcac cnttgngccg tctaaggacc actggccaan    600

tgggaanang gcnaanntcc tgggaatngt tcntcaattc cccaattaac caanaangna    660

acnngggcca nnnggcaccc ttatggntcc ctncctttng gaactngcct tttaatccnc    720

cngagggtnt tgctccttnt ntttntgnnt ggggtaatna aaagtn                   766
```

<210> SEQ ID NO 539
<211> LENGTH: 789
<212> TYPE: DNA
<213> ORGANISM: Homo sapiens
<220> FEATURE:
<221> NAME/KEY: misc_feature
<222> LOCATION: (1)...(789)
<223> OTHER INFORMATION: n = A,T,C or G

<400> SEQUENCE: 539

```
accattggtg gccaattgat ttgatggtaa gggagggatc gttgacctcg tctgttatgt     60

aaaggatgcg tagggatggg agggcgatga ggactaggat gatggcgggc aggatagttc    120

agacggtttc tatttcctga gcgtctgaga tgttagtatt agttagtttt gttgtgagtg    180

ttaggaaaag gcatacagga ctaggaagca gataaggaaa atgattatga gggcgtgatc    240
```

-continued

```
atgaaaggtg ataagctctt ctatgatagg ggaagtagcg tcttgtagac ctacttgcgc    300

tgcatgtgcc cccgcgtact tgactttctt ttntatttnt tttattnttt ttgactactt    360

agaattttca caattctaat aagattgttc caagtctctc atgtgcaagc tttaaaggat    420

gactcttgcc atttatgtac ctcggncgcg accacgctaa gggcaaattc agcacacttg    480

cggncgttct aagtggatcc nagctcggtc caaccttgcg tatcatggca tactggtccc    540

tngtgaaatg tatcccttac aatcncacac atcnancccg aanctaaann taaanctggg    600

gccaataata ctactncata atgctcnctn ctgccnttca ncnggaacnt gtgcncttnt    660

tatnatggca acncggaagn gtggttggcc ttcctctcta aaacntgnng gntngttgga    720

aggganctct aggnnncggt ccaattggan ncgaaattnt agctntntac naaanatntt    780

tttttcncg                                                            789
```

<210> SEQ ID NO 540
<211> LENGTH: 747
<212> TYPE: DNA
<213> ORGANISM: Homo sapiens
<220> FEATURE:
<221> NAME/KEY: misc_feature
<222> LOCATION: (1)...(747)
<223> OTHER INFORMATION: n = A,T,C or G

<400> SEQUENCE: 540

```
acttttaagg gcataataag ggttaacatt ctaggcagta taaacacacc ccataatgca     60

agtaataggt aatctagaga tgtggacttt attgctatat gggaattaca tttaaatttg    120

agggcatttt atataaagaa aaatacagac ctataaagtt tggcatattc attaagttat    180

cttttaatat ttttttctag aaaacaggtg acatttgtat ctacgataaa aatttttata    240

cagaacctac tgcctcaaac tgaatcccat caagaaaact agtttctatt gnattaagta    300

actcaaaata aattatcact tcgaaaactt gctttccaca ctaaggtaag tcagactaga    360

tgaacactcc agaattttta ctacagactg ttttaagtta gaagtgatgg caatttataa    420

attgagaata tcctccctga tgccctaact ggccaaacca aaatctaaga aagcagtgac    480

ncctcttact atnatgaact tctgaatang gtagggacct cctggcntan nnatgaaaan    540

ncctggccga ccccctaggg aatccncact gggggcctnn anggaccnan tggccaantt    600

gnnanngggn aangnncctg gnaatgtccn caattcncna atnccgncna aagtaacngg    660

gcccngggn annnnnangn ngncnnccnn nnngaannng cccttnaann ncccgngggg    720

ggngggntct nnncnnnncc nnngggg                                        747
```

<210> SEQ ID NO 541
<211> LENGTH: 773
<212> TYPE: DNA
<213> ORGANISM: Homo sapiens
<220> FEATURE:
<221> NAME/KEY: misc_feature
<222> LOCATION: (1)...(773)
<223> OTHER INFORMATION: n = A,T,C or G

<400> SEQUENCE: 541

```
cgaggtacca tgaaatacat atatttcata aggttcagtt acaaaatgga ttgtttcaaa     60

tggcaatttc ttacactaac ctgattatga aaaaaagaag tctgtatcat ctgcttccaa    120

gtctgttatg tccaaatata ttttaattat gcatttattt tgctactttt ataaatatta    180

gagatttcac cttaaattat ttttgtaact agttctagaa catgttttcc aattattatt    240
```

-continued

```
tttctaatgg agacatataa ttgacctatg tttatgcata tatgttctct acacagtgaa    300

actttttttta aaaagaatag taaagaaaat gcggaagctc tggctctcca aggcaaagtc    360

aaaaaaaaaa aaaaagcggg ggggaatgcg aggaacattt tattacacct cctgatttca    420

ctccttgagt ttattttctc ccttggttat tggttaatgc tagaaactgn attctaagag    480

agcatccttt tcaggtgacn tgataattgg aagatttgat ccttccgcga cctgnccggc    540

ggccgtcnaa nggcnattcc anccactggc ggcggtctaa nggatcnact tggnccacct    600

ggctaactgg caacnggtcc ngggngaaat gnatccttaa atccncactc nacccgacct    660

aangaactgg ggcaagggnc accctatggn gctcngcctt cnngaantnn ccnncttaan    720

aaccnggggn gntggnntct nnnnnannnn cnnnntgngg gnntaanaag ann           773
```

<210> SEQ ID NO 542
<211> LENGTH: 770
<212> TYPE: DNA
<213> ORGANISM: Homo sapiens
<220> FEATURE:
<221> NAME/KEY: misc_feature
<222> LOCATION: (1)...(770)
<223> OTHER INFORMATION: n = A,T,C or G

<400> SEQUENCE: 542

```
cgaggtactt tttttttttt tttttttttt tttttttttag aattctgaat tttattagag     60

aatatatcta aaatacaata tttattaagt tatgatatat tgnctgaatg gaaatatact    120

ctgnatcgca actctaatta taacaatttt tacagataat acttcattta tatctctgna    180

attcaaaagt cattaaatta caacagaatt catatttaag ataactttgc tataaatata    240

taataatttt taaagttttt ctttaatata acatcttgaa atcatgaaca tttatttttt    300

ctgggttaca ttcatagaat catgactatt ttacctgatt tgccttaact agctcaattt    360

atcttggcta tggatttgca ctcaccattc tactttccta tgtttaaaag cacattttag    420

tcacaattgn gagtgctcat caccctacat gctgtgacaa aggcaagggc ctgcccgggc    480

ggccgtncaa anggcgaatt ccncaactgg cggcggtcca agtggancga ctcggaccaa    540

ctngggaaca tggcaactgg tcccggggaa atggaaccgt acattcccca natcagccga    600

ncttaggtaa acngggggcn aagggggcta cncataatgg nggtccnccc ttcatngaac    660

cgngccctnn tatnatgcac cccggagggt nnttngcctc ctcntnnnnn ntcngntgtg    720

gagggagtcc ngggggggtnc canggggggna aaaantgccn ngncccggng              770
```

<210> SEQ ID NO 543
<211> LENGTH: 748
<212> TYPE: DNA
<213> ORGANISM: Homo sapiens
<220> FEATURE:
<221> NAME/KEY: misc_feature
<222> LOCATION: (1)...(748)
<223> OTHER INFORMATION: n = A,T,C or G

<400> SEQUENCE: 543

```
accgcgggat gcccctcatt tacataaata ttatactagc atttaccatc tcacttctag     60

gaatactagt atatcgctca cacctcatat cctccctact atgcctagaa ggaataatac    120

tatcgctgtt cattatagct actctcataa ccctcaacac ccactccctc ttagccaata    180

ttgtgcctat tgccatacta gtctttgccg ctgcgaagca gcggtgggcc tagccctact    240

agtctcaatc tccaacacat atggcctaga ctacgtacat atgctaggcc atatggtaac    300

tctatgttta acattttgag gaactgccaa actgttttcc aaagtgacta cactatttta    360
```

-continued

```
cattcccacc ttgaaggtcc aatttctcga cattctacca acatgggtaa tggctgcttt      420

ttatttagca accttaatgg gtgtgaagag atactcaatg ggaatttgat tgattcccta      480

angctaatga tttggnttct ttctggctga ngccagagnt atctntttgg gaaaattatt     540

naancttgnc atttaacnng cngatttatn tgatntanaa tnttntattt gganccngcc      600

tttaagnaag nttaaaattn ncaatnttgg ggcttncttt tggccatgan naannttaat      660

nntannanna attnnntncn annnggcnng tnaannannn nnnanaaana annnttnnna      720

anaannactt tttnnnnnna cntggcgg                                         748
```

```
<210> SEQ ID NO 544
<211> LENGTH: 327
<212> TYPE: DNA
<213> ORGANISM: Homo sapiens
<220> FEATURE:
<221> NAME/KEY: misc_feature
<222> LOCATION: (1)...(327)
<223> OTHER INFORMATION: n = A,T,C or G

<400> SEQUENCE: 544

cttttttttt tttttttttt tttttttttt tttttttttt ttggctctag aggggtaga       60

ggggtgcta tagggtaaat acgggcccta tttcaaagat ttttagggga attaattctg       120

gacgatggg catgaaactg tggtttgctc cacagatttc anagcattga ccgtagtata      180

ccccggtcg tgtagcggtg aaagtggttt ggtttaaacg tccgggaatt gcatctgttt      240

taagcctaa tgtggggaca gctcatgagt gcaagacgtc ttgtgatgta attattatac      300

aatgggggc ttnaatcggg agtacct                                           327
```